US011401305B2

(12) United States Patent
Binder et al.

(10) Patent No.: US 11,401,305 B2
(45) Date of Patent: Aug. 2, 2022

(54) NUCLEIC ACIDS ENCODING REPETITIVE AMINO ACID SEQUENCES RICH IN PROLINE AND ALANINE RESIDUES THAT HAVE LOW REPETITIVE NUCLEOTIDE SEQUENCES

(71) Applicants: XL-PROTEIN GMBH, Freising (DE); TECHNISCHE UNIVERSITÄT MÜNCHEN, Munich (DE)

(72) Inventors: Uli Binder, Freising (DE); Stefan Achatz, Freising (DE); Arne Skerra, Freising (DE)

(73) Assignees: XL-PROTEIN GMBH, Freising (DE); TECHNISCHE UNIVERSITÄT MÜNCHEN, Munich (DE)

( * ) Notice: Subject to any disclaimer, the term of this patent is extended or adjusted under 35 U.S.C. 154(b) by 1051 days.

(21) Appl. No.: 16/064,951

(22) PCT Filed: Dec. 22, 2016

(86) PCT No.: PCT/EP2016/082407

§ 371 (c)(1),
(2) Date: Jun. 21, 2018

(87) PCT Pub. No.: WO2017/109087

PCT Pub. Date: Jun. 29, 2017

(65) Prior Publication Data

US 2019/0010192 A1 Jan. 10, 2019

(30) Foreign Application Priority Data

Dec. 22, 2015 (EP) .................................... 15202093

(51) Int. Cl.

| | |
|---|---|
| ***C07K 14/00*** | (2006.01) |
| ***C12N 15/11*** | (2006.01) |
| ***C12N 15/62*** | (2006.01) |
| ***C12N 15/64*** | (2006.01) |
| ***C12N 15/67*** | (2006.01) |
| ***C12N 15/68*** | (2006.01) |
| ***C07K 14/575*** | (2006.01) |
| ***C07K 14/715*** | (2006.01) |
| ***A61K 38/00*** | (2006.01) |

(52) U.S. Cl.

CPC ............ *C07K 14/001* (2013.01); *C07K 14/00* (2013.01); *C07K 14/5759* (2013.01); *C07K 14/7155* (2013.01); *C12N 15/11* (2013.01); *C12N 15/62* (2013.01); *C12N 15/64* (2013.01); *C12N 15/67* (2013.01); *C12N 15/68* (2013.01); *A61K 38/00* (2013.01); *C07K 2319/00* (2013.01); *C07K 2319/31* (2013.01)

(58) Field of Classification Search

None

See application file for complete search history.

(56) References Cited

U.S. PATENT DOCUMENTS

| | | | |
|---|---|---|---|
| 8,563,521 | B2 | 10/2013 | Skerra et al. |
| 9,221,882 | B2 | 12/2015 | Skerra et al. |
| 9,260,494 | B2 | 2/2016 | Skerra et al. |
| 10,081,657 | B2 | 9/2018 | Skerra et al. |
| 10,174,302 | B1 | 1/2019 | Friedrich et al. |
| 2018/0354992 | A1 | 12/2018 | Skerra et al. |
| 2019/0169589 | A1 | 6/2019 | Friedrich et al. |

FOREIGN PATENT DOCUMENTS

| | | | | |
|---|---|---|---|---|
| EP | 3 418 383 | A1 | 12/2018 | |
| WO | WO-2008/155134 | A1 | 12/2008 | |
| WO | WO-2011/144756 | A1 | 11/2011 | |
| WO | WO-2011144756 | A1 * | 11/2011 | ................ A61P 1/16 |
| WO | WO-2018/234455 | A1 | 12/2018 | |
| WO | WO-2018/234492 | A1 | 12/2018 | |
| WO | WO-2019/096226 | A1 | 5/2019 | |

OTHER PUBLICATIONS

Ambystoma tigrinum virus, complete genome NCBI Reference Sequence: NC_005832.1, 2008.
Arthrobacter aurescens TC1, complete genome NCBI Reference Sequence: NC_008711.1, 2015.
Candidatus Puniceispirillum marinum IMCC1322, complete genome NCBI Reference Sequence: NC_014010.1, 2015.
Cercopithecine herpesvirus 1 DNA, UL region, complete sequence, GenBank: AB096160.1, 2003.
Chlamydophila pecorum isolate M14 inclusion membrane protein IncA gene, complete cds, GenBank: EU340814.1, 2008.

(Continued)

*Primary Examiner* — Nancy J Leith
(74) *Attorney, Agent, or Firm* — Foley & Lardner LLP

(57) ABSTRACT

The present invention relates to a nucleic acid molecule comprising a low repetitive nucleotide sequence encoding a proline/alanine-rich amino acid repeat sequence. The encoded polypeptide comprises a repetitive amino acid sequence that forms a random coil. The nucleic acid molecule comprising said low repetitive nucleotide sequences can further comprise a nucleotide sequence encoding a biologically or pharmacologically active protein. Further, the present invention provides for selection means and methods to identify said nucleic acid molecule comprising said low repetitive nucleotide sequence. The present invention also relates to a method for preparing said nucleic acid molecules. Also provided herein are methods for preparing the encoded polypeptide or drug conjugates with the encoded polypeptide using the herein provided nucleic acid molecules. The drug conjugate may comprise a biologically or pharmacologically active protein or a small molecule drug. Also provided herein are vectors and hosts comprising such nucleic acid molecules.

31 Claims, 22 Drawing Sheets

Specification includes a Sequence Listing.

(56) References Cited

OTHER PUBLICATIONS

Conexibacter woesei DSM 14684, complete genome, NCBI Reference Sequence: NC_013739.1, 2015.
International Preliminary Report on Patentability issued in PCT/EP2008/005020, dated Dec. 22, 2009.
International Preliminary Report on Patentability issued in PCT/EP2011/058307, dated Nov. 27, 2012.
International Search Report issued in PCT/EP2011/058307, dated Oct. 7, 2011.
International Search Report issued in PCT/EP2018/066591, dated Sep. 12, 2018.
International Search Report, issued in PCT/CN2018/115733, dated Feb. 19, 2019.
International Search Report, issued in PCT/EP2018/066647, dated Aug. 2, 2018.
Leishmania major strain Friedlin hypothetical protein, conserved (LmjF35.0290) partial mRNA, NCBI Reference Sequence: XM_838047.1, 2008.
Macacine herpesvirus 1, complete genome, NCBI Reference Sequence: NC_004812.1, 2010.
*Micromonas* sp. RCC299 chromosome 3 hypothetical protein (MICPUN_57400) mRNA,complete cds, NCBI Reference Sequence: XM_002500687.1, 2009.
*Streptomyces avermitilis* MA-4680 = NBRC 14893, complete sequence, NCBI Reference Sequence: NC_003155.4, 2015.
*Streptomyces scabiei* 87.22 complete genome, NCBI Reference Sequence: NC_013929.1, 2015.
*Streptomyces* sp. Mg1 supercont1.63 genomic scaffold, whole genome shotgun sequence, NCBI Reference Sequence: NZ_DS570446.1, 2015.
Synthetic construct pBI-SS(Tom)(AP)51-EGFP gene, complete cds, GenBank: DQ399411.1, 2006.
Written Opinion of The International Searching Authority issued in PCT/EP2008/005020, dated Dec. 21, 2009.
Written Opinion of The International Searching Authority, issued in PCT/CN2018/115733, dated Feb. 19, 2019.
Written Opinion of The International Searching Authority, issued in PCT/EP2011/058307, dated Nov. 21, 2012.
Written Opinion of The International Searching Authority, issued in PCT/EP2018/066591, dated Sep. 12, 2018.
Written Opinion of The International Searching Authority, issued in PCT/EP2018/066647, dated Aug. 2, 2018.
Harari et al., "Enhanced in Vivo Efficacy of a Type I Interferon Superagonist with Extended Plasma Half-life in a Mouse Model of Multiple Sclerosis," The Journal of Biological Chemistry, vol. 289, No. 42, 2014, pp. 29014-29029.
Mendler et al., "High contrast tumor imaging with radio-labeled antibody Fab fragments tailored for optimized pharmacokinetics via PASylation," MABS, vol. 7, No. 1, 2015, pp. 96-109.
Morath et al., "PASylation of Murine Leptin Leads to Extended Plasma Half-Life and Enhanced in Vivo Efficacy" Molecular Pharmaceutics, vol. 12, 2015, pp. 1431-1442.
Schlapschy et al., "PASylation: a biological alternative to PEGylation for extending the plasma half-life of pharmaceutically active proteins," Protein Engineering, Design, & Selection, vol. 26, No. 8, 2013, pp. 489-501.
International Search Report and Written Opinion issued in corresponding application No. PCT/EP2016/082407 dated Mar. 7, 2017.

* cited by examiner

Figure 1A
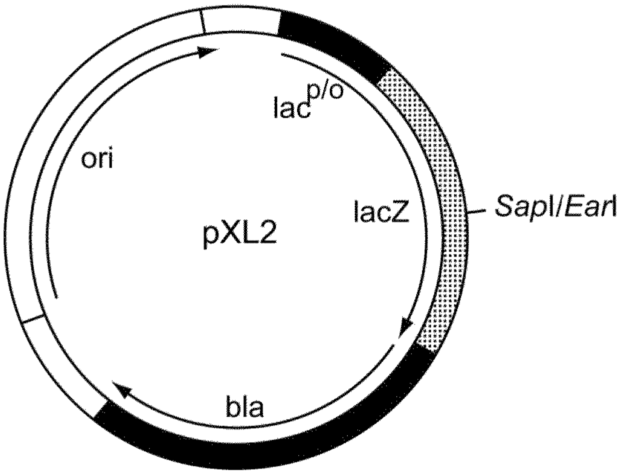
Figure 1B
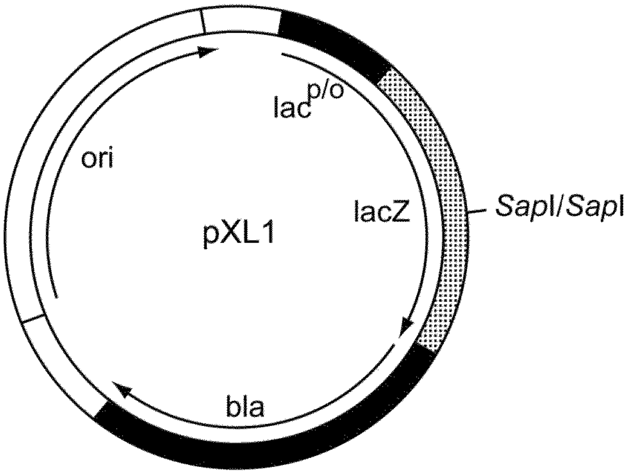
Figure 1C
```
                    SapI
5'-TACGCCAAGCTTGGCTCTTCTGCCAGAAGAGTAGAATTCACTGGCC-3'  SEQ ID NO: 59
3'-ATGCGGTTCGAACCGAGAAGACGGTCTTCTCATCTTAAGTGACCGG-5'  SEQ ID NO: 60
                                EarI
```

Figure 1D

```
             SapI
TACGCCAAGCTTGGCTCTTCTGCCAGCCCTGCCGCACCTGCGCCCGCATCACCTGCGGCA
||||||||||||||||||||||||||||||||||||||||||||||||||||||||||||
ATGCGGTTCGAACCGAGAAGACGGTCGGGACGGCGTGGACGCGGGCGTAGTGGACGCCGT
                    AlaSerProAlaAlaProAlaProAlaSerProAlaAla

CCTGCACCTTCCGCCCCGGCTGCATCTCCTGCCGCACCCGCGCCTGCCAGCCCAGCTGCA
||||||||||||||||||||||||||||||||||||||||||||||||||||||||||||
GGACGTGGAAGGCGGGGCCGACGTAGAGGACGGCGTGGGCGCGGACGGTCGGGTCGACGT
ProAlaProSerAlaProAlaAlaSerProAlaAlaProAlaProAlaSerProAlaAla

CCTGCCCCAAGTGCGCCAGCAGCATCCCCTGCCGCGCCTGCCCCCGCTAGTCCAGCGGCC
||||||||||||||||||||||||||||||||||||||||||||||||||||||||||||
GGACGGGGTTCACGCGGTCGTCGTAGGGGACGGCGCGGACGGGGGCGATCAGGTCGCCGG
ProAlaProSerAlaProAlaAlaSerProAlaAlaProAlaProAlaSerProAlaAla

CCAGCTCCATCTGCACCAGCTGCTAGCCCTGCTGCACCAGCTCCTGCTTCTCCCGCAGCC
||||||||||||||||||||||||||||||||||||||||||||||||||||||||||||
GGTCGAGGTAGACGTGGTCGACGATCGGGACGACGTGGTCGAGGACGAAGAGGGCGTCGG
ProAlaProSerAlaProAlaAlaSerProAlaAlaProAlaProAlaSerProAlaAla

CCAGCGCCTTCTGCTCCCGCAGCCTCACCTGCGGCCCCGGCACCAGCATCTCCAGCGGCA
||||||||||||||||||||||||||||||||||||||||||||||||||||||||||||
GGTCGCGGAAGACGAGGGCGTCGGAGTGGACGCCGGGGCCGTGGTCGTAGAGGTCGCCGT
ProAlaProSerAlaProAlaAlaSerProAlaAlaProAlaProAlaSerProAlaAla

CCAGCACCTTCGGCCCCTGCTGCTAGCCCAGCAGCACCTGCGCCAGCCTCACCAGCTGCT
||||||||||||||||||||||||||||||||||||||||||||||||||||||||||||
GGTCGTGGAAGCCGGGGACGACGATCGGGTCGTCGTGGACGCGGTCGGAGTGGTCGACGA
ProAlaProSerAlaProAlaAlaSerProAlaAlaProAlaProAlaSerProAlaAla

CCCGCTCCTAGTGCCCCGGCGGCCTCGCCTGCTGCTCCTGCACCAGCTTCGCCAGCGGCA
||||||||||||||||||||||||||||||||||||||||||||||||||||||||||||
GGGCGAGGATCACGGGGCCGCCGGAGCGGACGACGAGGACGTGGTCGAAGCGGTCGCCGT
ProAlaProSerAlaProAlaAlaSerProAlaAlaProAlaProAlaSerProAlaAla

CCGGCTCCTTCGGCGCCGGCTGCTTCACCAGCAGCACCTGCTCCAGCGTCCCCAGCGGCC
||||||||||||||||||||||||||||||||||||||||||||||||||||||||||||
GGCCGAGGAAGCCGCGGCCGACGAAGTGGTCGTCGTGGACGAGGTCGCAGGGGTCGCCGG
ProAlaProSerAlaProAlaAlaSerProAlaAlaProAlaProAlaSerProAlaAla

CCTGCTCCAAGTGCTCCGGCTGCATCGCCTGCCGCTCCTGCTCCTGCATCCCCAGCTGCT
||||||||||||||||||||||||||||||||||||||||||||||||||||||||||||
GGACGAGGTTCACGAGGCCGACGTAGCGGACGGCGAGGACGAGGACGTAGGGGTCGACGA
ProAlaProSerAlaProAlaAlaSerProAlaAlaProAlaProAlaSerProAlaAla

CCAGCACCAAGCGCACCTGCCGCCTCACCAGCGGCGCCAGCACCCGCCAGCCCAGCAGCG
||||||||||||||||||||||||||||||||||||||||||||||||||||||||||||
GGTCGTGGTTCGCGTGGACGGCGGAGTGGTCGCCGCGGTCGTGGGCGGTCGGGTCGTCGC
ProAlaProSerAlaProAlaAlaSerProAlaAlaProAlaProAlaSerProAlaAla

CCTGCTCCATCCGCACCGGCGGCCAGAAGAGTAGAATTCACTGGCC  SEQ ID NO: 61
||||||||||||||||||||||||||||||||||||||||||||||
GGACGAGGTAGGCGTGGCCGCCGGTCTTCTCATCTTAAGTGACCGG  SEQ ID NO: 62
ProAlaProSerAlaProAlaAla  EarI

SEQ ID NO: 63
```

Repeat window 14:

PA#3a(200)

PA#3b(200)

Repeat window 15:

PA#3a(200)

PA#3b(200)

Repeat window 14:

PAS#1a(600)

PAS#1f/1c/1b(600)

PAS#1d/1f/1c/1b(800)

Repeat window 15:

Repeat window 14:

[(AP)5]20APA glycomodule

Very large tegument protein

PA#1b(200)

Repeat window 15:

SEQ ID NO: 198 pASK75-PA#1a(600)-IL1Ra pASK75-PA#1d/1c/1b(600)-IL1Ra

SEQUENCE LISTING

```
<160> NUMBER OF SEQ ID NOS: 198

<210> SEQ ID NO 1
<211> LENGTH: 20
<212> TYPE: PRT
<213> ORGANISM: Artificial Sequence
<220> FEATURE:
<223> OTHER INFORMATION: Amino acid repeat sequence of PAS#1

<400> SEQUENCE: 1

Ala Ser Pro Ala Ala Pro Ala Pro Ala Ser Pro Ala Ala Pro Ala Pro
1               5                   10                  15

Ser Ala Pro Ala
            20


<210> SEQ ID NO 2
<211> LENGTH: 20
<212> TYPE: PRT
<213> ORGANISM: Artificial Sequence
<220> FEATURE:
<223> OTHER INFORMATION: Amino acid repeat sequence of PA#1
```

<400> SEQUENCE: 2

Ala Ala Pro Ala Ala Pro Ala Pro Ala Ala Pro Ala Ala Pro Ala Pro
1 5 10 15

Ala Ala Pro Ala
20

<210> SEQ ID NO 3
<211> LENGTH: 18
<212> TYPE: DNA
<213> ORGANISM: Artificial Sequence
<220> FEATURE:
<223> OTHER INFORMATION: Sequencing primer XLP-1

<400> SEQUENCE: 3
ccgccggggc actaggag 18

<210> SEQ ID NO 4
<211> LENGTH: 33
<212> TYPE: DNA
<213> ORGANISM: Artificial Sequence
<220> FEATURE:
<223> OTHER INFORMATION: Primer NdeI-MP-SapI-HindIIIfw

<400> SEQUENCE: 4
tatgccagcc tgaagagccg gctcttcggc cta 33

<210> SEQ ID NO 5
<211> LENGTH: 35
<212> TYPE: DNA
<213> ORGANISM: Artificial Sequence
<220> FEATURE:
<223> OTHER INFORMATION: Primer NdeI-MP-SapI-HindIIIrv

<400> SEQUENCE: 5
agcttaggcc gaagagccgg ctcttcaggc tggca 35

<210> SEQ ID NO 6
<211> LENGTH: 200
<212> TYPE: PRT
<213> ORGANISM: Artificial Sequence
<220> FEATURE:
<223> OTHER INFORMATION: Amino acid sequence of the proline/alanine-rich
sequence PAS#1(200)

<400> SEQUENCE: 6

Ala Ser Pro Ala Ala Pro Ala Pro Ala Ser Pro Ala Ala Pro Ala Pro
1 5 10 15

Ser Ala Pro Ala Ala Ser Pro Ala Ala Pro Ala Pro Ala Ser Pro Ala
20 25 30

Ala Pro Ala Pro Ser Ala Pro Ala Ala Ser Pro Ala Ala Pro Ala Pro
35 40 45

Ala Ser Pro Ala Ala Pro Ala Pro Ser Ala Pro Ala Ala Ser Pro Ala
50 55 60

Ala Pro Ala Pro Ala Ser Pro Ala Ala Pro Ala Pro Ser Ala Pro Ala
65 70 75 80

Ala Ser Pro Ala Ala Pro Ala Pro Ala Ser Pro Ala Ala Pro Ala Pro
85 90 95

Ser Ala Pro Ala Ala Ser Pro Ala Ala Pro Ala Pro Ala Ser Pro Ala
100 105 110

Ala Pro Ala Pro Ser Ala Pro Ala Ala Ser Pro Ala Ala Pro Ala Pro
115 120 125

```
Ala Ser Pro Ala Ala Pro Ala Pro Ser Ala Pro Ala Ala Ser Pro Ala
    130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala
        195                 200


<210> SEQ ID NO 7
<211> LENGTH: 200
<212> TYPE: PRT
<213> ORGANISM: Artificial Sequence
<220> FEATURE:
<223> OTHER INFORMATION: Amino acid sequence of proline/alanine-rich
      sequence PA#1(200)

<400> SEQUENCE: 7

Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Ala Pro Ala Ala Pro Ala Pro
        35                  40                  45

Ala Ala Pro Ala Ala Pro Ala Pro Ala Ala Pro Ala Ala Ala Pro Ala
    50                  55                  60

Ala Pro Ala Pro Ala Ala Pro Ala Ala Pro Ala Pro Ala Ala Pro Ala
65                  70                  75                  80

Ala Ala Pro Ala Ala Pro Ala Pro Ala Ala Pro Ala Ala Pro Ala Pro
                85                  90                  95

Ala Ala Pro Ala Ala Ala Pro Ala Ala Pro Ala Pro Ala Ala Pro Ala
            100                 105                 110

Ala Pro Ala Pro Ala Ala Pro Ala Ala Ala Pro Ala Ala Pro Ala Pro
        115                 120                 125

Ala Ala Pro Ala Ala Pro Ala Pro Ala Ala Pro Ala Ala Ala Pro Ala
    130                 135                 140

Ala Pro Ala Pro Ala Ala Pro Ala Ala Pro Ala Pro Ala Ala Pro Ala
145                 150                 155                 160

Ala Ala Pro Ala Ala Pro Ala Pro Ala Ala Pro Ala Ala Pro Ala Pro
                165                 170                 175

Ala Ala Pro Ala Ala Ala Pro Ala Ala Pro Ala Pro Ala Ala Pro Ala
            180                 185                 190

Ala Pro Ala Pro Ala Ala Pro Ala
        195                 200


<210> SEQ ID NO 8
<211> LENGTH: 200
<212> TYPE: PRT
<213> ORGANISM: Artificial Sequence
<220> FEATURE:
<223> OTHER INFORMATION: Amino acid sequence of proline/alanine-rich
      sequence PA#3(200)

<400> SEQUENCE: 8

Ala Ala Ala Pro Ala Ala Ala Pro Ala Ala Ala Pro Ala Ala Ala Pro
1               5                   10                  15
```

-continued

Ala Ala Ala Pro Ala Ala Ala Pro Ala Ala Ala Pro Ala Ala Ala Pro
20 25 30

Ala Ala Ala Pro Ala Ala Ala Pro Ala Ala Ala Pro Ala Ala Ala Pro
35 40 45

Ala Ala Ala Pro Ala Ala Ala Pro Ala Ala Ala Pro Ala Ala Ala Pro
50 55 60

Ala Ala Ala Pro Ala Ala Ala Pro Ala Ala Ala Pro Ala Ala Ala Pro
65 70 75 80

Ala Ala Ala Pro Ala Ala Ala Pro Ala Ala Ala Pro Ala Ala Ala Pro
85 90 95

Ala Ala Ala Pro Ala Ala Ala Pro Ala Ala Ala Pro Ala Ala Ala Pro
100 105 110

Ala Ala Ala Pro Ala Ala Ala Pro Ala Ala Ala Pro Ala Ala Ala Pro
115 120 125

Ala Ala Ala Pro Ala Ala Ala Pro Ala Ala Ala Pro Ala Ala Ala Pro
130 135 140

Ala Ala Ala Pro Ala Ala Ala Pro Ala Ala Ala Pro Ala Ala Ala Pro
145 150 155 160

Ala Ala Ala Pro Ala Ala Ala Pro Ala Ala Ala Pro Ala Ala Ala Pro
165 170 175

Ala Ala Ala Pro Ala Ala Ala Pro Ala Ala Ala Pro Ala Ala Ala Pro
180 185 190

Ala Ala Ala Pro Ala Ala Ala Pro
195 200

<210> SEQ ID NO 9
<211> LENGTH: 198
<212> TYPE: PRT
<213> ORGANISM: Artificial Sequence
<220> FEATURE:
<223> OTHER INFORMATION: Amino acid sequence of the proline/alanine-rich sequence PA#5(198)

<400> SEQUENCE: 9

Ala Ala Ala Ala Ala Pro Ala Ala Ala Ala Ala Pro Ala Ala Ala Ala
1 5 10 15

Ala Pro Ala Ala Ala Ala Ala Pro Ala Ala Ala Ala Ala Pro Ala Ala
20 25 30

Ala Ala Ala Pro Ala Ala Ala Ala Ala Pro Ala Ala Ala Ala Ala Pro
35 40 45

Ala Ala Ala Ala Ala Pro Ala Ala Ala Ala Ala Pro Ala Ala Ala Ala
50 55 60

Ala Pro Ala Ala Ala Ala Ala Pro Ala Ala Ala Ala Ala Pro Ala Ala
65 70 75 80

Ala Ala Ala Pro Ala Ala Ala Ala Ala Pro Ala Ala Ala Ala Ala Pro
85 90 95

Ala Ala Ala Ala Ala Pro Ala Ala Ala Ala Ala Pro Ala Ala Ala Ala
100 105 110

Ala Pro Ala Ala Ala Ala Ala Pro Ala Ala Ala Ala Ala Pro Ala Ala
115 120 125

Ala Ala Ala Pro Ala Ala Ala Ala Ala Pro Ala Ala Ala Ala Ala Pro
130 135 140

Ala Ala Ala Ala Ala Pro Ala Ala Ala Ala Ala Pro Ala Ala Ala Ala
145 150 155 160

Ala Pro Ala Ala Ala Ala Ala Pro Ala Ala Ala Ala Ala Pro Ala Ala

-continued

```
                165                 170                 175

Ala Ala Ala Pro Ala Ala Ala Ala Ala Pro Ala Ala Ala Ala Ala Pro
            180                 185                 190

Ala Ala Ala Ala Ala Pro
        195


<210> SEQ ID NO 10
<211> LENGTH: 353
<212> TYPE: PRT
<213> ORGANISM: Artificial Sequence
<220> FEATURE:
<223> OTHER INFORMATION: Amino acid sequence of the proline/alanine-rich
      sequence PA#1 after seamless fusion with IL1Ra

<400> SEQUENCE: 10

Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Ala Pro Ala Ala Pro Ala Pro
        35                  40                  45

Ala Ala Pro Ala Ala Pro Ala Pro Ala Ala Pro Ala Ala Ala Pro Ala
    50                  55                  60

Ala Pro Ala Pro Ala Ala Pro Ala Ala Pro Ala Pro Ala Ala Pro Ala
65                  70                  75                  80

Ala Ala Pro Ala Ala Pro Ala Pro Ala Ala Pro Ala Ala Pro Ala Pro
                85                  90                  95

Ala Ala Pro Ala Ala Ala Pro Ala Ala Pro Ala Pro Ala Ala Pro Ala
            100                 105                 110

Ala Pro Ala Pro Ala Ala Pro Ala Ala Ala Pro Ala Ala Pro Ala Pro
        115                 120                 125

Ala Ala Pro Ala Ala Pro Ala Pro Ala Ala Pro Ala Ala Ala Pro Ala
    130                 135                 140

Ala Pro Ala Pro Ala Ala Pro Ala Ala Pro Ala Pro Ala Ala Pro Ala
145                 150                 155                 160

Ala Ala Pro Ala Ala Pro Ala Pro Ala Ala Pro Ala Ala Pro Ala Pro
                165                 170                 175

Ala Ala Pro Ala Ala Ala Pro Ala Ala Pro Ala Pro Ala Ala Pro Ala
            180                 185                 190

Ala Pro Ala Pro Ala Ala Pro Ala Ala Arg Pro Ser Gly Arg Lys Ser
        195                 200                 205

Ser Lys Met Gln Ala Phe Arg Ile Trp Asp Val Asn Gln Lys Thr Phe
    210                 215                 220

Tyr Leu Arg Asn Asn Gln Leu Val Ala Gly Tyr Leu Gln Gly Pro Asn
225                 230                 235                 240

Val Asn Leu Glu Glu Lys Ile Asp Val Val Pro Ile Glu Pro His Ala
                245                 250                 255

Leu Phe Leu Gly Ile His Gly Gly Lys Met Cys Leu Ser Cys Val Lys
            260                 265                 270

Ser Gly Asp Glu Thr Arg Leu Gln Leu Glu Ala Val Asn Ile Thr Asp
        275                 280                 285

Leu Ser Glu Asn Arg Lys Gln Asp Lys Arg Phe Ala Phe Ile Arg Ser
    290                 295                 300

Asp Ser Gly Pro Thr Thr Ser Phe Glu Ser Ala Ala Cys Pro Gly Trp
305                 310                 315                 320
```

Phe Leu Cys Thr Ala Met Glu Ala Asp Gln Pro Val Ser Leu Thr Asn
325 330 335

Met Pro Asp Glu Gly Val Met Val Thr Lys Phe Tyr Phe Gln Glu Asp
340 345 350

Glu

<210> SEQ ID NO 11
<211> LENGTH: 600
<212> TYPE: DNA
<213> ORGANISM: Artificial Sequence
<220> FEATURE:
<223> OTHER INFORMATION: Nucleotide sequence of PAS#1a(200)

<400> SEQUENCE: 11
gcctctccag ctgcacctgc tccagcaagc cctgctgcac cagctccgtc tgctcctgct 60
gcctctccag ctgcacctgc tccagcaagc cctgctgcac cagctccgtc tgctcctgct 120
gcctctccag ctgcacctgc tccagcaagc cctgctgcac cagctccgtc tgctcctgct 180
gcctctccag ctgcacctgc tccagcaagc cctgctgcac cagctccgtc tgctcctgct 240
gcctctccag ctgcacctgc tccagcaagc cctgctgcac cagctccgtc tgctcctgct 300
gcctctccag ctgcacctgc tccagcaagc cctgctgcac cagctccgtc tgctcctgct 360
gcctctccag ctgcacctgc tccagcaagc cctgctgcac cagctccgtc tgctcctgct 420
gcctctccag ctgcacctgc tccagcaagc cctgctgcac cagctccgtc tgctcctgct 480
gcctctccag ctgcacctgc tccagcaagc cctgctgcac cagctccgtc tgctcctgct 540
gcctctccag ctgcacctgc tccagcaagc cctgctgcac cagctccgtc tgctcctgct 600

<210> SEQ ID NO 12
<211> LENGTH: 1800
<212> TYPE: DNA
<213> ORGANISM: Artificial Sequence
<220> FEATURE:
<223> OTHER INFORMATION: Nucleotide sequence of PAS#1a(600)

<400> SEQUENCE: 12
gcctctccag ctgcacctgc tccagcaagc cctgctgcac cagctccgtc tgctcctgct 60
gcctctccag ctgcacctgc tccagcaagc cctgctgcac cagctccgtc tgctcctgct 120
gcctctccag ctgcacctgc tccagcaagc cctgctgcac cagctccgtc tgctcctgct 180
gcctctccag ctgcacctgc tccagcaagc cctgctgcac cagctccgtc tgctcctgct 240
gcctctccag ctgcacctgc tccagcaagc cctgctgcac cagctccgtc tgctcctgct 300
gcctctccag ctgcacctgc tccagcaagc cctgctgcac cagctccgtc tgctcctgct 360
gcctctccag ctgcacctgc tccagcaagc cctgctgcac cagctccgtc tgctcctgct 420
gcctctccag ctgcacctgc tccagcaagc cctgctgcac cagctccgtc tgctcctgct 480
gcctctccag ctgcacctgc tccagcaagc cctgctgcac cagctccgtc tgctcctgct 540
gcctctccag ctgcacctgc tccagcaagc cctgctgcac cagctccgtc tgctcctgct 600
gcctctccag ctgcacctgc tccagcaagc cctgctgcac cagctccgtc tgctcctgct 660
gcctctccag ctgcacctgc tccagcaagc cctgctgcac cagctccgtc tgctcctgct 720
gcctctccag ctgcacctgc tccagcaagc cctgctgcac cagctccgtc tgctcctgct 780
gcctctccag ctgcacctgc tccagcaagc cctgctgcac cagctccgtc tgctcctgct 840
gcctctccag ctgcacctgc tccagcaagc cctgctgcac cagctccgtc tgctcctgct 900
gcctctccag ctgcacctgc tccagcaagc cctgctgcac cagctccgtc tgctcctgct 960

```
gcctctccag ctgcacctgc tccagcaagc cctgctgcac cagctccgtc tgctcctgct   1020

gcctctccag ctgcacctgc tccagcaagc cctgctgcac cagctccgtc tgctcctgct   1080

gcctctccag ctgcacctgc tccagcaagc cctgctgcac cagctccgtc tgctcctgct   1140

gcctctccag ctgcacctgc tccagcaagc cctgctgcac cagctccgtc tgctcctgct   1200

gcctctccag ctgcacctgc tccagcaagc cctgctgcac cagctccgtc tgctcctgct   1260

gcctctccag ctgcacctgc tccagcaagc cctgctgcac cagctccgtc tgctcctgct   1320

gcctctccag ctgcacctgc tccagcaagc cctgctgcac cagctccgtc tgctcctgct   1380

gcctctccag ctgcacctgc tccagcaagc cctgctgcac cagctccgtc tgctcctgct   1440

gcctctccag ctgcacctgc tccagcaagc cctgctgcac cagctccgtc tgctcctgct   1500

gcctctccag ctgcacctgc tccagcaagc cctgctgcac cagctccgtc tgctcctgct   1560

gcctctccag ctgcacctgc tccagcaagc cctgctgcac cagctccgtc tgctcctgct   1620

gcctctccag ctgcacctgc tccagcaagc cctgctgcac cagctccgtc tgctcctgct   1680

gcctctccag ctgcacctgc tccagcaagc cctgctgcac cagctccgtc tgctcctgct   1740

gcctctccag ctgcacctgc tccagcaagc cctgctgcac cagctccgtc tgctcctgct   1800
```

<210> SEQ ID NO 13
<211> LENGTH: 2400
<212> TYPE: DNA
<213> ORGANISM: Artificial Sequence
<220> FEATURE:
<223> OTHER INFORMATION: Nucleotide sequence of PAS#1a(800)

<400> SEQUENCE: 13

```
gcctctccag ctgcacctgc tccagcaagc cctgctgcac cagctccgtc tgctcctgct     60

gcctctccag ctgcacctgc tccagcaagc cctgctgcac cagctccgtc tgctcctgct    120

gcctctccag ctgcacctgc tccagcaagc cctgctgcac cagctccgtc tgctcctgct    180

gcctctccag ctgcacctgc tccagcaagc cctgctgcac cagctccgtc tgctcctgct    240

gcctctccag ctgcacctgc tccagcaagc cctgctgcac cagctccgtc tgctcctgct    300

gcctctccag ctgcacctgc tccagcaagc cctgctgcac cagctccgtc tgctcctgct    360

gcctctccag ctgcacctgc tccagcaagc cctgctgcac cagctccgtc tgctcctgct    420

gcctctccag ctgcacctgc tccagcaagc cctgctgcac cagctccgtc tgctcctgct    480

gcctctccag ctgcacctgc tccagcaagc cctgctgcac cagctccgtc tgctcctgct    540

gcctctccag ctgcacctgc tccagcaagc cctgctgcac cagctccgtc tgctcctgct    600

gcctctccag ctgcacctgc tccagcaagc cctgctgcac cagctccgtc tgctcctgct    660

gcctctccag ctgcacctgc tccagcaagc cctgctgcac cagctccgtc tgctcctgct    720

gcctctccag ctgcacctgc tccagcaagc cctgctgcac cagctccgtc tgctcctgct    780

gcctctccag ctgcacctgc tccagcaagc cctgctgcac cagctccgtc tgctcctgct    840

gcctctccag ctgcacctgc tccagcaagc cctgctgcac cagctccgtc tgctcctgct    900

gcctctccag ctgcacctgc tccagcaagc cctgctgcac cagctccgtc tgctcctgct    960

gcctctccag ctgcacctgc tccagcaagc cctgctgcac cagctccgtc tgctcctgct   1020

gcctctccag ctgcacctgc tccagcaagc cctgctgcac cagctccgtc tgctcctgct   1080

gcctctccag ctgcacctgc tccagcaagc cctgctgcac cagctccgtc tgctcctgct   1140

gcctctccag ctgcacctgc tccagcaagc cctgctgcac cagctccgtc tgctcctgct   1200
```

gcctctccag ctgcacctgc tccagcaagc cctgctgcac cagctccgtc tgctcctgct 1260
gcctctccag ctgcacctgc tccagcaagc cctgctgcac cagctccgtc tgctcctgct 1320
gcctctccag ctgcacctgc tccagcaagc cctgctgcac cagctccgtc tgctcctgct 1380
gcctctccag ctgcacctgc tccagcaagc cctgctgcac cagctccgtc tgctcctgct 1440
gcctctccag ctgcacctgc tccagcaagc cctgctgcac cagctccgtc tgctcctgct 1500
gcctctccag ctgcacctgc tccagcaagc cctgctgcac cagctccgtc tgctcctgct 1560
gcctctccag ctgcacctgc tccagcaagc cctgctgcac cagctccgtc tgctcctgct 1620
gcctctccag ctgcacctgc tccagcaagc cctgctgcac cagctccgtc tgctcctgct 1680
gcctctccag ctgcacctgc tccagcaagc cctgctgcac cagctccgtc tgctcctgct 1740
gcctctccag ctgcacctgc tccagcaagc cctgctgcac cagctccgtc tgctcctgct 1800
gcctctccag ctgcacctgc tccagcaagc cctgctgcac cagctccgtc tgctcctgct 1860
gcctctccag ctgcacctgc tccagcaagc cctgctgcac cagctccgtc tgctcctgct 1920
gcctctccag ctgcacctgc tccagcaagc cctgctgcac cagctccgtc tgctcctgct 1980
gcctctccag ctgcacctgc tccagcaagc cctgctgcac cagctccgtc tgctcctgct 2040
gcctctccag ctgcacctgc tccagcaagc cctgctgcac cagctccgtc tgctcctgct 2100
gcctctccag ctgcacctgc tccagcaagc cctgctgcac cagctccgtc tgctcctgct 2160
gcctctccag ctgcacctgc tccagcaagc cctgctgcac cagctccgtc tgctcctgct 2220
gcctctccag ctgcacctgc tccagcaagc cctgctgcac cagctccgtc tgctcctgct 2280
gcctctccag ctgcacctgc tccagcaagc cctgctgcac cagctccgtc tgctcctgct 2340
gcctctccag ctgcacctgc tccagcaagc cctgctgcac cagctccgtc tgctcctgct 2400

<210> SEQ ID NO 14
<211> LENGTH: 600
<212> TYPE: DNA
<213> ORGANISM: Artificial Sequence
<220> FEATURE:
<223> OTHER INFORMATION: Nucleotide sequence of PA#1a(200)

<400> SEQUENCE: 14
gccgctccag ctgcacctgc tccagcagca cctgctgcac cagctccggc tgctcctgct 60
gccgctccag ctgcacctgc tccagcagca cctgctgcac cagctccggc tgctcctgct 120
gccgctccag ctgcacctgc tccagcagca cctgctgcac cagctccggc tgctcctgct 180
gccgctccag ctgcacctgc tccagcagca cctgctgcac cagctccggc tgctcctgct 240
gccgctccag ctgcacctgc tccagcagca cctgctgcac cagctccggc tgctcctgct 300
gccgctccag ctgcacctgc tccagcagca cctgctgcac cagctccggc tgctcctgct 360
gccgctccag ctgcacctgc tccagcagca cctgctgcac cagctccggc tgctcctgct 420
gccgctccag ctgcacctgc tccagcagca cctgctgcac cagctccggc tgctcctgct 480
gccgctccag ctgcacctgc tccagcagca cctgctgcac cagctccggc tgctcctgct 540
gccgctccag ctgcacctgc tccagcagca cctgctgcac cagctccggc tgctcctgct 600

<210> SEQ ID NO 15
<211> LENGTH: 600
<212> TYPE: DNA
<213> ORGANISM: Artificial Sequence
<220> FEATURE:
<223> OTHER INFORMATION: Nucleotide sequence of PA#3a(200)

<400> SEQUENCE: 15

-continued gccgctgcac ctgctgcagc acctgctgca gctccagcag ctgctcctgc agcagctcca 60
gccgctgcac ctgctgcagc acctgctgca gctccagcag ctgctcctgc agcagctcca 120
gccgctgcac ctgctgcagc acctgctgca gctccagcag ctgctcctgc agcagctcca 180
gccgctgcac ctgctgcagc acctgctgca gctccagcag ctgctcctgc agcagctcca 240
gccgctgcac ctgctgcagc acctgctgca gctccagcag ctgctcctgc agcagctcca 300
gccgctgcac ctgctgcagc acctgctgca gctccagcag ctgctcctgc agcagctcca 360
gccgctgcac ctgctgcagc acctgctgca gctccagcag ctgctcctgc agcagctcca 420
gccgctgcac ctgctgcagc acctgctgca gctccagcag ctgctcctgc agcagctcca 480
gccgctgcac ctgctgcagc acctgctgca gctccagcag ctgctcctgc agcagctcca 540
gccgctgcac ctgctgcagc acctgctgca gctccagcag ctgctcctgc agcagctcca 600

<210> SEQ ID NO 16
<211> LENGTH: 609
<212> TYPE: DNA
<213> ORGANISM: Artificial Sequence
<220> FEATURE:
<223> OTHER INFORMATION: Nucleotide sequence of a [(AP)5]n multimer

<400> SEQUENCE: 16
gctccagcac ctgccccagc ccctgcacca gctccagcac ctgccccagc ccctgcacca 60
gctccagcac ctgccccagc ccctgcacca gctccagcac ctgccccagc ccctgcacca 120
gctccagcac ctgccccagc ccctgcacca gctccagcac ctgccccagc ccctgcacca 180
gctccagcac ctgccccagc ccctgcacca gctccagcac ctgccccagc ccctgcacca 240
gctccagcac ctgccccagc ccctgcacca gctccagcac ctgccccagc ccctgcacca 300
gctccagcac ctgccccagc ccctgcacca gctccagcac ctgccccagc ccctgcacca 360
gctccagcac ctgccccagc ccctgcacca gctccagcac ctgccccagc ccctgcacca 420
gctccagcac ctgccccagc ccctgcacca gctccagcac ctgccccagc ccctgcacca 480
gctccagcac ctgccccagc ccctgcacca gctccagcac ctgccccagc ccctgcacca 540
gctccagcac ctgccccagc ccctgcacca gctccagcac ctgccccagc ccctgcacca 600
gctccagca 609

<210> SEQ ID NO 17
<211> LENGTH: 276
<212> TYPE: DNA
<213> ORGANISM: Artificial Sequence
<220> FEATURE:
<223> OTHER INFORMATION: Synthetic gene construct encoding the glycomodule [AAPAPAPAP]10AS

<400> SEQUENCE: 17
gccgctccag cacctgcccc agcccctgca gctccagcac ctgccccagc ccctgcagct 60
ccagcacctg ccccagcccc tgcagctcca gcacctgccc cagcccctgc agctccagca 120
cctgccccag cccctgcagc tccagcacct gccccagccc ctgcagctcc agcacctgcc 180
ccagcccctg cagctccagc acctgcccca gcccctgcag ctccagcacc tgccccagcc 240
cctgcagctc cagcacctgc cccagcccct gcatcc 276

<210> SEQ ID NO 18
<211> LENGTH: 225
<212> TYPE: DNA
<213> ORGANISM: Macacine herpesvirus 1

<220> FEATURE:
<223> OTHER INFORMATION: Nucleotide sequence of a fragment of the very large tegument protein of Macacine herpesvirus [GeneBank: AAP41454.1, 8844 - 8808]

<400> SEQUENCE: 18
gcgccacccg cccctgctgc ccctgctgcc cctgctgccc ctgctgcccc tgctgcccct 60
gctgcccctg ctgcccctgc tgcccctgct gcccctgctg cccctgctgc ccctgctgcc 120
cctgctgccc ctgctgcccc tgctgcccct gctgcccctg ctgcccctgc tgcccctgct 180
gcccctgctg cccctgctgc ccctgctgcc cctgcgcccg cagca 225

<210> SEQ ID NO 19
<211> LENGTH: 600
<212> TYPE: DNA
<213> ORGANISM: Artificial Sequence
<220> FEATURE:
<223> OTHER INFORMATION: Nucleotide sequence of PAS#1b(200), codon-optimized for E. coli

<400> SEQUENCE: 19
gccagccctg ccgcacctgc gcccgcatca cctgcggcac ctgcaccttc cgccccggct 60
gcatctcctg ccgcacccgc gcctgccagc ccagctgcac ctgccccaag tgcgccagca 120
gcatcccctg ccgcgcctgc ccccgctagt ccagcggccc cagctccatc tgcaccagct 180
gctagccctg ctgcaccagc tcctgcttct cccgcagccc cagcgccttc tgctcccgca 240
gcctcacctg cggccccggc accagcatct ccagcggcac cagcaccttc ggcccctgct 300
gctagcccag cagcacctgc gccagcctca ccagctgctc ccgctcctag tgccccggcg 360
gcctcgcctg ctgctcctgc accagcttcg ccagcggcac cggctccttc ggcgccggct 420
gcttcaccag cagcacctgc tccagcgtcc ccagcggccc ctgctccaag tgctccggct 480
gcatcgcctg ccgctcctgc tcctgcatcc ccagctgctc cagcaccaag cgcacctgcc 540
gcctcaccag cggcgccagc acccgccagc ccagcagcgc ctgctccatc cgcaccggcg 600

<210> SEQ ID NO 20
<211> LENGTH: 600
<212> TYPE: DNA
<213> ORGANISM: Artificial Sequence
<220> FEATURE:
<223> OTHER INFORMATION: Nucleotide sequence of PAS#1c(200), codon-optimized for E. coli

<400> SEQUENCE: 20
gccagtcctg ctgcaccggc accggcatca ccggctgcac cagcacctag tgcaccggca 60
gcttctccgg ctgcccctgc gcctgcatca ccagctgcgc ctgcaccgtc tgcccctgca 120
gctagtccag cagctccagc tccggcttct cctgcggctc ctgcaccaag tgcgcctgca 180
gcaagtccgg ctgcgcctgc cccagctagt cctgctgctc cggcaccgtc agctccggca 240
gcatctcctg cagcaccagc ccctgcaagt ccagcagcgc cagccccatc agcaccagca 300
gcttcaccag ccgcaccagc gccagcaagc cctgctgccc cagctcctag cgcaccggca 360
gccagtcctg cagctcctgc gcctgctagt ccggcagccc cagctccaag tgcccctgcc 420
gcttcgcctg cagccccagc accagcttct ccagccgcac cggcaccttc tgccccagct 480
gcatctccgg cagctccggc accagcaagc ccggcagcac cggcaccatc tgcgcctgcc 540
gcatctccgg ctgcgccagc tccagcctct cctgcagcgc cagcaccgag cgcaccagca 600

<210> SEQ ID NO 21

<211> LENGTH: 600
<212> TYPE: DNA
<213> ORGANISM: Artificial Sequence
<220> FEATURE:
<223> OTHER INFORMATION: Nucleotide sequence of PAS#1d(200), codon-
optimized for E. coli

<400> SEQUENCE: 21
gccagccccg ccgcccctgc accggcgtct cccgccgcac cagccccttc agcgcctgca 60
gcatcacccg cggcccccgc acccgcatct ccagccgccc ctgctccttc cgccccagcc 120
gcatcgccag ccgctccagc accggcatcc cccgcggctc ccgctcccag cgcacctgcg 180
gcttcaccgg cagcaccagc gcccgcaagt ccagccgcgc cggctccttc tgcgcctgcg 240
gcctcgccgg cagctccagc ccctgcttcc ccagctgccc cggccccttc agccccagcg 300
gcgtctccag cagcaccagc tcccgcctct ccggcagcgc cagcgccctc ggcccccgcc 360
gcgtcccctg ccgccccggc acccgcatcg cccgctgccc cagccccatc cgccccagct 420
gcaagccccg ctgctccagc tcccgccagt ccagcagcac ccgccccttc tgcgccagcc 480
gcgtcaccgg ccgccccagc accggcgagc cccgctgcac ccgcccctag cgctccggcc 540
gcatctcctg cggcgcccgc acctgccagt ccagctgctc ctgctccgtc cgcccctgcc 600

<210> SEQ ID NO 22
<211> LENGTH: 600
<212> TYPE: DNA
<213> ORGANISM: Artificial Sequence
<220> FEATURE:
<223> OTHER INFORMATION: Nucleotide sequence of PAS#1e(200), codon-
optimized for Cricetulus griseus

<400> SEQUENCE: 22
gcctctcctg ctgcccctgc cccagcttct ccagctgctc ctgcaccttc tgctccagcc 60
gctagtcctg cagctccagc tcctgcttct cctgccgcac cagcacctag tgcccctgct 120
gcatcaccag cagctcccgc acccgctagc ccagctgcac cagctccaag tgctccagca 180
gcttcacccg cagcacccgc tccagcaagt ccagcagccc cagccccttc agcaccagct 240
gcatctcccg cagcccctgc tcctgccagc cctgccgctc ctgctccaag cgctcctgct 300
gctagtccag ccgcccctgc accagcaagt cctgctgctc ccgcacctag tgcaccagca 360
gcaagccctg cagctcctgc accagcatct ccagcagcac cagcaccatc agcccctgcc 420
gcttctcccg cagctccagc cccagcctcc cctgctgctc cagccccctc tgctcctgca 480
gcatctcctg ccgctcccgc ccctgcaagt cccgccgctc cagcaccatc cgctccagct 540
gcttccccag ccgctccagc tccagctagc cccgcagccc ccgcaccatc tgccccagca 600

<210> SEQ ID NO 23
<211> LENGTH: 600
<212> TYPE: DNA
<213> ORGANISM: Artificial Sequence
<220> FEATURE:
<223> OTHER INFORMATION: Nucleotide sequence of PAS#1f(200), codon-
optimized for E. coli

<400> SEQUENCE: 23
gcctcccctg ccgctccagc ccccgcctcg ccggccgctc ccgctccgtc tgcacctgct 60
gcctcaccag cagccccggc cccagcatcc ccggccgcac cagctccgtc agcacctgcc 120
gcatcgcctg ctgcccctgc cccagccagt ccagcggctc cagccccgag tgctccggcc 180
gcttcccccg cagcaccggc tcctgcctcc cctgcagccc ctgctccatc tgcccctgcg 240
gcatcccctg cggcgccagc tcctgcctct ccagctgcac cggctccctc agctcccgct 300
gcctccccag ccgcgcccgc tcctgcaagc ccagcagctc cggctccatc cgcccccgcc 360
gccagccccg cagccccggc gcctgcctct cctgctgcac ctgcaccgtc agcccctgca 420
gcatctcccg cagctcctgc accggcatct ccagcagccc ccgccccgtc agctcccgca 480
gccagcccgg ccgcacccgc ccccgcgtca ccagctgcac cagcgccatc cgctcctgct 540
gcgtctcccg ctgcgcccgc ccctgcctca cctgcagcac ctgcacctag cgccccggct 600

<210> SEQ ID NO 24
<211> LENGTH: 600
<212> TYPE: DNA
<213> ORGANISM: Artificial Sequence
<220> FEATURE:
<223> OTHER INFORMATION: Nucleotide sequence of PAS#1g(200), codon-optimized for Pichia Pastoris

<400> SEQUENCE: 24
gcctctcctg ctgcacctgc accagcttct cccgctgctc ctgctccttc agctcctgct 60
gcatcacctg ctgcacctgc tcctgcttct ccagctgcac cagctccatc tgcaccagct 120
gcttcacctg cagcacctgc acctgcttca ccagcagcac cagctccttc cgctccagcc 180
gcttcaccag ccgctccagc accagcttca ccagcagctc ctgctccatc tgctcctgct 240
gcttcccctg ctgctccagc tcctgcatca ccagctgcac ctgcaccttc tgctccagct 300
gcatctccag cagctccagc tcccgcttca cctgctgctc cagcaccatc cgctcctgca 360
gcttctccag ctgctcctgc tccagcttct cctgcagcac ctgctccatc cgctccagca 420
gcttctccag ccgctcctgc tcctgcctcc cctgctgcac cagctccttc agctccagct 480
gcttccccag ctgctccagc tccagcttct ccagcagctc ctgcaccatc tgctccagct 540
gcttctcctg ctgcaccagc cccagcatcc ccagctgctc ctgcaccttc cgctcctgct 600

<210> SEQ ID NO 25
<211> LENGTH: 600
<212> TYPE: DNA
<213> ORGANISM: Artificial Sequence
<220> FEATURE:
<223> OTHER INFORMATION: Nucleotide sequence of PAS#1h(200), codon-optimized for Cricetulus griseus

<400> SEQUENCE: 25
gcctcaccag ccgccccagc ccccgcctcc ccagccgccc ctgctccttc cgcccccgcc 60
gcttctccag ccgctcctgc ccccgcttct cccgctgccc ccgccccatc agcccccgcc 120
gcctctccag cagctccagc tcccgcctct cctgccgccc cagctccaag cgcccccgcc 180
gcatctcctg ccgcacctgc ccctgcctct cctgccgctc cagccccatc tgcccctgcc 240
gcctctccag ccgcccccgc ccctgcttct ccggctgccc ccgcaccttc agcacccgcc 300
gcttcaccag ctgcaccagc ccctgcctct cccgccgccc ccgcaccctc cgcacccgct 360
gcttcacctg ccgcccctgc acctgcctcc cctgccgcac ctgcacctag cgcccccgcc 420
gcctcacctg ccgccccagc cccagcttct cccgccgcac ccgccccttc tgcccctgca 480
gcctcccccg ctgccccagc tccagcctcc cctgccgccc ccgctccatc cgcccctgcc 540
gcttcccccg cagcccctgc ccctgcatcc cctgccgctc cagctccctc agctcccgcc 600

<210> SEQ ID NO 26
<211> LENGTH: 600
<212> TYPE: DNA
<213> ORGANISM: Artificial Sequence

```
<220> FEATURE:
<223> OTHER INFORMATION: Nucleotide sequence of PAS#1i(200), codon-
      optimized for Cricetulus griseus

<400> SEQUENCE: 26

gccagccccg ccgctcccgc acctgccagc ccagccgctc ccgctccctc cgcccccgcc     60

gccagccccg ccgcccctgc tcccgccagc cctgcagctc cagcacctag cgccccagca    120

gcatccccag ctgcacccgc acccgcctcc ccagcagcac ctgcaccatc tgctccagca    180

gcaagtccgg ctgctcctgc tcctgcatca cctgctgcac cagccccctc agctcctgca    240

gcaagcccag ctgcacctgc accagctagt ccagccgctc cagcaccttc cgctccagca    300

gcatctcctg ctgcaccagc accagcatct cctgcagctc ccgccccaag tgccccagca    360

gcatcacctg ccgcaccagc tcctgcaagc ccagcagctc cagcaccaag cgctcctgca    420

gcctccccag ctgctcctgc cccagcttcc cccgcagctc ccgcaccttc tgccccagca    480

gcaagccccg cggcaccagc accagcttca cccgccgctc ctgcaccaag cgcccccgct    540

gcaagccctg cagcacccgc accagcctca ccagccgcac cagcaccctc cgccccagca    600


<210> SEQ ID NO 27
<211> LENGTH: 600
<212> TYPE: DNA
<213> ORGANISM: Artificial Sequence
<220> FEATURE:
<223> OTHER INFORMATION: Nucleotide sequence of PAS#1j(200), codon-
      optimized for Cricetulus griseus

<400> SEQUENCE: 27

gcctcacccg ccgcaccagc cccagcatca cccgccgctc cggctccaag tgccccagcc     60

gcttctccag ctgcccctgc tccagcatca cctgctgctc ctgccccttc cgctcccgca    120

gcatctccag ctgcacctgc cccagcaagt ccagccgcac ctgctcctag tgctcctgct    180

gctagccctg ctgccccagc acctgcatca cccgcagctc ccgctccttc agctccagca    240

gcttcccctg ccgctcccgc accagcatca cccgcagccc cagctcctag cgcccctgcc    300

gccagtcccg ctgctcctgc tcccgcaagt cctgccgcac ccgcacccag tgcacctgct    360

gcatccccag ctgctccagc cccagctagt ccagcagccc ctgctccctc tgctcctgcc    420

gcttccccag cagcaccagc tcccgctagt cctgccgctc ctgccccaag tgcacccgct    480

gccagccccg cagcaccagc tccagcctca cccgctgctc ctgcacccag cgcaccagca    540

gctagcccag cagctcctgc tccagccagc ccagccgcac ctgccccatc tgcacccgct    600


<210> SEQ ID NO 28
<211> LENGTH: 600
<212> TYPE: DNA
<213> ORGANISM: Artificial Sequence
<220> FEATURE:
<223> OTHER INFORMATION: Nucleotide sequence of PA#1b(200), codon-
      optimized for E. coli

<400> SEQUENCE: 28

gccgctcctg ctgcccctgc tcccgctgcc cccgccgccc ccgccccagc tgcccccgct     60

gccgcacctg ctgccccagc tcccgctgcc ccagccgcgc cggcccccgc agctccagcc    120

gcggcaccag ctgccccagc tccagcggcg cctgctgccc cggcccccgc ggcaccggct    180

gccgcgcccg cagctccagc gcctgctgca ccggctgctc cggcacccgc cgcgccagca    240

gctgcccctg cggcaccagc tcctgctgcc cccgcggcac ctgcacccgc tgccccggcg    300

gcagctcccg ccgcgccagc ccctgcagct cctgctgcac ctgctcctgc cgcccctgct    360
```

```
gctgcccctg ctgctccagc ccctgcagca ccggccgctc cagctcctgc cgctcctgcc    420

gctgcgcccg ctgctccagc cccagctgcg ccagcagctc ctgcacctgc tgcccctgcc    480

gccgcccctg cggctccagc acctgctgca ccggccgccc cggcgcccgc tgcccccgca    540

gcagccccag ccgcacccgc tccagcagct cccgcagccc cagcacccgc agcaccagcc    600


<210> SEQ ID NO 29
<211> LENGTH: 600
<212> TYPE: DNA
<213> ORGANISM: Artificial Sequence
<220> FEATURE:
<223> OTHER INFORMATION: Nucleotide sequence of PA#1c(200), codon-
      optimized for E. coli

<400> SEQUENCE: 29

gccgcgccag cggccccggc ccctgccgcg cccgctgctc ccgcccctgc tgccccagcc     60

gccgctcctg cggcacctgc gcccgccgcg ccggcagcgc cggcaccggc agctccggcg    120

gccgcgcctg cagctcctgc accggcggct ccagcagccc cggcgccggc cgcacctgcg    180

gcggcgcccg cggcgcctgc acccgcagcg cctgcggcac cggccccagc agcccctgcc    240

gccgcaccgg ctgcgcctgc cccagcggcc cccgctgccc cggcccccggc ggctccagcc    300

gcagcgcctg ccgccccagc gcccgcagca ccggcggcac cagctccggc ggcgccggcg    360

gcggctccgg cagctccggc ccctgctgcg ccggctgcgc cggctccggc ggcccctgcg    420

gcggctccgg ccgcacctgc acctgccgcg ccggctgctc cggcccccggc tgccccagca    480

gcggcaccag cagcgcctgc tcctgcggcg cctgcagctc cggcgccggc agccccggcc    540

gccgcacccg cggctccagc cccgccgct ccagcagccc ccgcgccagc tgcacctgct    600


<210> SEQ ID NO 30
<211> LENGTH: 600
<212> TYPE: DNA
<213> ORGANISM: Artificial Sequence
<220> FEATURE:
<223> OTHER INFORMATION: Nucleotide sequence of PA#1d(200), codon-
      optimized for E. coli

<400> SEQUENCE: 30

gccgcaccgg ctgccccagc ccctgccgca ccagcagctc ccgcccctgc agcccccgcc     60

gccgctccgg ccgcaccagc cccggctgcc cctgctgccc ccgcccccggc agcacccgct    120

gcagcaccag ccgcgcctgc accggcagct cctgcagccc cggcaccggc agcacctgcc    180

gcagcacccg cagccccagc cccagcagcg cctgccgctc cagcaccagc ggcaccggcc    240

gccgcaccag ccgccccagc accggcagcc cccgcagcgc cggcaccagc cgctccagcc    300

gccgccccag cagccccggc tccggccgct cccgcggctc cagcaccagc agctccagcg    360

gccgctccgg cagcgccggc cccagcagca cctgcagccc ctgcaccagc agcgccagcc    420

gcggcgcccg cagctcccgc acctgcggct cccgcagccc ctgcacccgc ggcgccagca    480

gccgcccctg cagcgccagc tcctgcagca cctgcagctc cagcccccggc cgccccagct    540

gcagctcctg cggccccagc acctgccgcc cctgccgcac cggctccagc cgccccagcc    600


<210> SEQ ID NO 31
<211> LENGTH: 600
<212> TYPE: DNA
<213> ORGANISM: Artificial Sequence
<220> FEATURE:
<223> OTHER INFORMATION: Nucleotide sequence of PA#1e(200), codon-
      optimized for E. coli
```

<400> SEQUENCE: 31
gccgcaccgg ctgcaccagc tccggcagct ccagcagcac cggcaccagc agctccggct 60
gcagcgccag cagcaccagc gcctgctgct ccagctgctc ctgctcctgc tgcaccagca 120
gcagctccag ccgcaccagc accggcagcg cctgcagccc ctgctccggc agctcctgcc 180
gcagcaccgg cagcaccagc tccagcggca cccgctgccc ctgctcctgc agcaccggca 240
gcggcaccgg ctgctcctgc gccagctgct ccggcagccc cagcccctgc agccccagca 300
gcagcgcctg cggctccagc gccagccgca ccagcggctc cggcaccggc agcccctgcg 360
gcagctcctg ctgcgcctgc tccagcagct ccagctgccc cagcgccggc agctccggct 420
gccgcaccag ctgcgcctgc ccctgctgcg ccagccgcac cggctccggc agcaccagca 480
gctgccccag cagctcctgc cccagctgcg cctgctgcgc cagcaccagc agccccagct 540
gcagcaccag ctgcaccggc accagctgct ccagcagcac cagccccagc cgctccggca 600

<210> SEQ ID NO 32
<211> LENGTH: 600
<212> TYPE: DNA
<213> ORGANISM: Artificial Sequence
<220> FEATURE:
<223> OTHER INFORMATION: Nucleotide sequence of PA#1f(200), codon-
      optimized for Cricetulus griseus

<400> SEQUENCE: 32
gccgctcctg ctgctccagc tcctgctgcc ccagcagccc ctgccccagc tgctcctgca 60
gcagctcccg cagccccagc acccgccgca ccagcagctc cagcccctgc agcaccagct 120
gctgcccctg ccgcccctgc tccagccgca cccgctgcac ccgcaccagc tgccccagcc 180
gccgcacccg cagctccagc tcccgctgct cctgctgcac cagcccctgc cgctccagca 240
gccgcaccag cagcaccagc cccagctgct cccgctgctc cagcacccgc agccccccgca 300 gcagcaccag ccgctcctgc tcctgccgcc ccagcagctc ctgctccagc agcccctgct 360
gctgctccag cagcaccagc accagctgct ccagctgccc cagctcctgc agcacccgcc 420
gctgctcccg cagctcctgc ccctgctgca cccgcagcac ccgctccagc agcacctgca 480
gctgcaccag ctgctcccgc acctgccgct cccgcagctc ccgctcctgc agctccagcc 540
gcagctcctg ctgctcctgc accagcagct cccgccgcac cagctccagc tgcccctgct 600

<210> SEQ ID NO 33
<211> LENGTH: 600
<212> TYPE: DNA
<213> ORGANISM: Artificial Sequence
<220> FEATURE:
<223> OTHER INFORMATION: Nucleotide sequence of PA#1g(200), codon-
      optimized for Cricetulus griseus

<400> SEQUENCE: 33
gccgcaccgg ctgctcctgc tcctgccgct cctgccgcac ccgctcccgc tgcccctgcc 60
gccgcccctg cagctcctgc ccccgccgca cctgcagctc cagcacctgc agcaccagct 120
gcagcacctg ctgcaccagc tcccgccgct ccagcagctc ctgccccagc tgcaccagcc 180
gctgcacccg ccgctcccgc tcctgcagcc cccgctgcac cggcccctgc cgctcctgca 240
gctgcgccag cagcccctgc tccagctgca cctgccgcac ccgccccagc tgccccccgcc 300 gctgctccag ccgctcctgc acctgctgca cctgctgctc cagcacctgc ggctcctgct 360
gccgctccag ctgccccccgc tccagcggct cctgccgccc ctgctcccgc cgctcctgca 420
gcagcccctg ctgctccagc cccagccgct ccggcagctc ccgctccagc agcccccgcc 480
gctgcccctg ctgcaccagc cccgctgcc ccagctgccc ctgctcctgc tgcccccgcc 540
gcagcccccg ccgcacccgc accagcagca cccgcagctc cagcaccagc tgcaccagca 600

<210> SEQ ID NO 34
<211> LENGTH: 600
<212> TYPE: DNA
<213> ORGANISM: Artificial Sequence
<220> FEATURE:
<223> OTHER INFORMATION: Nucleotide sequence of PA#1h(200), codon-
optimized for Cricetulus griseus

<400> SEQUENCE: 34
gccgcccctg ctgccccagc cccagccgcc cccgccgctc ccgccccagc tgccccagcc 60
gctgcacctg cagccccagc acctgctgcc ccagccgctc cagcaccagc tgcccctgca 120
gccgctcccg ccgccccagc cccgctgcc cccgcagctc cagctcctgc cgctccagcc 180
gccgcccccg cagctcctgc cccgctgcc cctgcagccc ctgctcctgc tgcacctgcc 240
gcagcccctg ctgccccagc tccagcagca cctgctgccc ccgctcccgc cgcacccgca 300
gcagcacctg ccgctccagc tccagccgcc cccgctgccc ctgctccagc cgctccagct 360
gctgctcccg cagcccctgc cccagccgct cccgcagcac ccgctcctgc cgccccagcc 420
gcagctccag ccgctcctgc ccctgccgca ccagctgctc ccgctcccgc tgctcccgcc 480
gccgctcccg ccgcacctgc tcctgccgca cccgccgctc cagcaccagc agctccagct 540
gccgctccag ccgctcccgc acccgctgct cctgccgccc ctgcccccgc agcccctgct 600

<210> SEQ ID NO 35
<211> LENGTH: 600
<212> TYPE: DNA
<213> ORGANISM: Artificial Sequence
<220> FEATURE:
<223> OTHER INFORMATION: Nucleotide sequence of PA#1i(200), codon-
optimized for Cricetulus griseus

<400> SEQUENCE: 35
gccgctccag ccgccccagc ccctgccgcc cccgccgcac ctgcccccgc cgccccagct 60
gccgccccag ccgcccctgc tcccgctgct cctgccgcac ctgcacccgc tgcccctgct 120
gctgcccccg ctgctcctgc tcccgctgct cccgctgccc cggcccccgc tgctcccgcc 180
gctgctcccg ccgcacctgc cccagccgca ccagctgcac ctgctccagc cgctcccgct 240
gccgctccag ccgcccccgc acccgccgca cctgccgccc ctgcccctgc agcccccgcc 300
gccgctcccg cagcccccgc tcccgctgcc ccagccgccc ctgcccccgc ggctcccgcc 360
gctgctcctg ccgctcccgc ccccgccgcc cctgccgccc cggcccctgc tgcccccgct 420
gccgcacctg ctgctcccgc cccagccgct ccagctgccc ctgccccagc tgcccccgct 480
gctgcccctg ccgctcctgc ccctgctgct cctgccgccc ccgcccccgc cgctcctgcc 540
gctgcccccg ctgcacccgc tcccgccgcc cccgctgccc ccgcccctgc tgctcctgct 600

<210> SEQ ID NO 36
<211> LENGTH: 600
<212> TYPE: DNA
<213> ORGANISM: Artificial Sequence
<220> FEATURE:
<223> OTHER INFORMATION: Nucleotide sequence of PA#3b(200), codon-
optimized for E. coli

<400> SEQUENCE: 36
gccgcagcac cggcagcagc ccctgcagca gctccagctg ccgcaccagc agctgcacca 60
gctgcagcgc ctgctgctgc tcctgcagct gcgccagcag ctgctccggc agcggcaccg 120
gctgcagcac cagccgcagc cccagcagcc gctcctgctg cagctcctgc ggctgcacca 180
gcggctgccc ctgcggcagc accagcagca gcgccagcgg ctgcaccagc tgccgcaccg 240
gcagcagctc cggcagcagc accagcagcg gcaccggcag ctgcgcctgc cgctgcgcct 300
gcggcagccc ctgccgcagc tccagcagca gcaccggcag ctgctccagc ggcagctcct 360
gcagcagccc cagccgctgc gcctgccgca gcgccagcag ctgcgcctgc agcggctcca 420
gccgcagcac cagcggcagc tccagctgca gcccctgctg cagcgccagc agcagcacct 480
gcggctgccc ctgcagcggc tccggctgca gcgcctgcgg cagcacctgc agcggcacca 540
gcagcagccc ctgcggcagc gcctgctgca gccccagctg cagccccagc agcggcacca 600

<210> SEQ ID NO 37
<211> LENGTH: 594
<212> TYPE: DNA
<213> ORGANISM: Artificial Sequence
<220> FEATURE:
<223> OTHER INFORMATION: Nucleotide sequence of PA#5b(198), codon-
optimized for E. coli

<400> SEQUENCE: 37
gccgcagcag cagcaccggc agctgcagca gctccagcgg cagcagctgc ccctgcagcc 60
gcagctgcac cagcagcagc cgcagcgcct gcagcagctg ccgctccggc agcagcagcc 120
gcaccagctg ccgcagcagc tcctgccgca gccgcagccc cagccgcagc agcggctcca 180
gcagcagctg cagcaccagc cgctgcagcc gcaccggcag ctgcggcagc accagcagcg 240
gcagcagccc cagcagctgc agcagcgcct gcagccgcag cagcgccagc tgcagcagcg 300
gcaccggcag cggcagcggc tccggcagca gctgcagccc ctgccgcagc agctgcacct 360
gcagcagccg cagcaccggc tgccgcagcg gcaccagccg cagcagctgc cccagcggca 420
gcagcagcac cagcagctgc tgcagcacca gctgcagccg cagcaccagc ggctgccgca 480
gcgccagcag cggcagcggc accagcggca gcggcagcac cggcagcagc ggcagcccct 540
gcagccgctg cagctcctgc agcagcggca gcgccagccg cagccgcagc tcct 594

<210> SEQ ID NO 38
<211> LENGTH: 1800
<212> TYPE: DNA
<213> ORGANISM: Artificial Sequence
<220> FEATURE:
<223> OTHER INFORMATION: Nucleotide sequence of PAS#1f/1c/1b(600),
codon-optimized for E. coli

<400> SEQUENCE: 38
gcctcccctg ccgctccagc ccccgcctcg ccggccgctc ccgctccgtc tgcacctgct 60
gcctcaccag cagcccggc cccagcatcc ccggccgcac cagctccgtc agcacctgcc 120
gcatcgcctg ctgcccctgc cccagccagt ccagcggctc cagccccgag tgctccggcc 180
gcttcccccg cagcaccggc tcctgcctcc cctgcagccc ctgctccatc tgcccctgcg 240
gcatcccctg cggcgccagc tcctgcctct ccagctgcac cggctccctc agctcccgct 300
gcctccccag ccgcgcccgc tcctgcaagc ccagcagctc cggctccatc cgcccccgcc 360
gccagccccg cagccccggc gcctgcctct cctgctgcac ctgcaccgtc agcccctgca 420
gcatctcccg cagctcctgc accggcatct ccagcagccc ccgccccgtc agctcccgca 480
gccagcccgg ccgcacccgc ccccgcgtca ccagctgcac cagcgccatc cgctcctgct 540
gcgtctcccg ctgcgcccgc ccctgcctca cctgcagcac ctgcacctag cgccccggct 600
gccagtcctg ctgcaccggc accggcatca ccggctgcac cagcacctag tgcaccggca 660
gcttctccgg ctgcccctgc gcctgcatca ccagctgcgc ctgcaccgtc tgcccctgca 720
gctagtccag cagctccagc tccggcttct cctgcggctc ctgcaccaag tgcgcctgca 780
gcaagtccgg ctgcgcctgc cccagctagt cctgctgctc cggcaccgtc agctccggca 840
gcatctcctg cagcaccagc ccctgcaagt ccagcagcgc cagccccatc agcaccagca 900
gcttcaccag ccgcaccagc gccagcaagc cctgctgccc cagctcctag cgcaccggca 960
gccagtcctg cagctcctgc gcctgctagt ccggcagccc cagctccaag tgcccctgcc 1020
gcttcgcctg cagccccagc accagcttct ccagccgcac cggcaccttc tgccccagct 1080
gcatctccgg cagctccggc accagcaagc ccggcagcac cggcaccatc tgcgcctgcc 1140
gcatctccgg ctgcgccagc tccagcctct cctgcagcgc cagcaccgag cgcaccagca 1200
gccagccctg ccgcacctgc gcccgcatca cctgcggcac ctgcaccttc cgccccggct 1260
gcatctcctg ccgcacccgc gcctgccagc ccagctgcac ctgccccaag tgcgccagca 1320
gcatcccctg ccgcgcctgc ccccgctagt ccagcggccc cagctccatc tgcaccagct 1380
gctagccctg ctgcaccagc tcctgcttct cccgcagccc cagcgccttc tgctcccgca 1440
gcctcacctg cggccccggc accagcatct ccagcggcac cagcaccttc ggcccctgct 1500
gctagcccag cagcacctgc gccagcctca ccagctgctc ccgctcctag tgccccggcg 1560
gcctcgcctg ctgctcctgc accagcttcg ccagcggcac cggctccttc ggcgccggct 1620
gcttcaccag cagcacctgc tccagcgtcc ccagcggccc ctgctccaag tgctccggct 1680
gcatcgcctg ccgctcctgc tcctgcatcc ccagctgctc cagcaccaag cgcacctgcc 1740
gcctcaccag cggcgccagc acccgccagc ccagcagcgc ctgctccatc cgcaccggcg 1800

<210> SEQ ID NO 39
<211> LENGTH: 2400
<212> TYPE: DNA
<213> ORGANISM: Artificial Sequence
<220> FEATURE:
<223> OTHER INFORMATION: Nucleotide sequence of PAS#1d/1f/1c/1b(800), codon-optimized for E. coli

<400> SEQUENCE: 39
gccagccccg ccgcccctgc accggcgtct cccgccgcac cagccccttc agcgcctgca 60
gcatcacccg cggcccccgc acccgcatct ccagccgccc ctgctccttc cgccccagcc 120
gcatcgccag ccgctccagc accggcatcc cccgcggctc ccgctcccag cgcacctgcg 180
gcttcaccgg cagcaccagc gcccgcaagt ccagccgcgc cggctccttc tgcgcctgcg 240
gcctcgccgg cagctccagc ccctgcttcc ccagctgccc cggccccttc agccccagcg 300
gcgtctccag cagcaccagc tcccgcctct ccggcagcgc cagcgccctc ggcccccgcc 360
gcgtcccctg ccgccccggc acccgcatcg cccgctgccc cagccccatc cgccccagct 420
gcaagccccg ctgctccagc tcccgccagt ccagcagcac ccgccccttc tgcgccagcc 480
gcgtcaccgg ccgccccagc accggcgagc cccgctgcac ccgcccctag cgctccggcc 540
gcatctcctg cggcgcccgc acctgccagt ccagctgctc ctgctccgtc cgcccctgcc 600
gcctcccctg ccgctccagc ccccgcctcg ccggccgctc ccgctccgtc tgcacctgct 660
gcctcaccag cagccccggc cccagcatcc ccggccgcac cagctccgtc agcacctgcc 720
gcatcgcctg ctgcccctgc cccagccagt ccagcggctc cagccccgag tgctccggcc 780
gcttcccccg cagcaccggc tcctgcctcc cctgcagccc ctgctccatc tgcccctgcg 840
gcatcccctg cggcgccagc tcctgcctct ccagctgcac cggctccctc agctcccgct 900
gcctccccag ccgcgcccgc tcctgcaagc ccagcagctc cggctccatc cgcccccgcc 960
gccagccccg cagccccggc gcctgcctct cctgctgcac ctgcaccgtc agcccctgca 1020
gcatctcccg cagctcctgc accggcatct ccagcagccc ccgccccgtc agctcccgca 1080
gccagcccgg ccgcacccgc ccccgcgtca ccagctgcac cagcgccatc cgctcctgct 1140
gcgtctcccg ctgcgcccgc ccctgcctca cctgcagcac ctgcacctag cgccccggct 1200
gccagtcctg ctgcaccggc accggcatca ccggctgcac cagcacctag tgcaccggca 1260
gcttctccgg ctgcccctgc gcctgcatca ccagctgcgc ctgcaccgtc tgcccctgca 1320
gctagtccag cagctccagc tccggcttct cctgcggctc ctgcaccaag tgcgcctgca 1380
gcaagtccgg ctgcgcctgc cccagctagt cctgctgctc cggcaccgtc agctccggca 1440
gcatctcctg cagcaccagc ccctgcaagt ccagcagcgc cagccccatc agcaccagca 1500
gcttcaccag ccgcaccagc gccagcaagc cctgctgccc cagctcctag cgcaccggca 1560
gccagtcctg cagctcctgc gcctgctagt ccggcagccc cagctccaag tgcccctgcc 1620
gcttcgcctg cagccccagc accagcttct ccagccgcac cggcaccttc tgccccagct 1680
gcatctccgg cagctccggc accagcaagc ccggcagcac cggcaccatc tgcgcctgcc 1740
gcatctccgg ctgcgccagc tccagcctct cctgcagcgc cagcaccgag cgcaccagca 1800
gccagccctg ccgcacctgc gcccgcatca cctgcggcac ctgcaccttc cgccccggct 1860
gcatctcctg ccgcacccgc gcctgccagc ccagctgcac ctgccccaag tgcgccagca 1920
gcatcccctg ccgcgcctgc ccccgctagt ccagcggccc cagctccatc tgcaccagct 1980
gctagccctg ctgcaccagc tcctgcttct cccgcagccc cagcgccttc tgctcccgca 2040
gcctcacctg cggccccggc accagcatct ccagcggcac cagcaccttc ggcccctgct 2100
gctagcccag cagcacctgc gccagcctca ccagctgctc ccgctcctag tgccccggcg 2160
gcctcgcctg ctgctcctgc accagcttcg ccagcggcac cggctccttc ggcgccggct 2220
gcttcaccag cagcacctgc tccagcgtcc ccagcggccc ctgctccaag tgctccggct 2280
gcatcgcctg ccgctcctgc tcctgcatcc ccagctgctc cagcaccaag cgcacctgcc 2340
gcctcaccag cggcgccagc acccgccagc ccagcagcgc ctgctccatc cgcaccggcg 2400

<210> SEQ ID NO 40
<211> LENGTH: 1800
<212> TYPE: DNA
<213> ORGANISM: Artificial Sequence
<220> FEATURE:
<223> OTHER INFORMATION: Nucleotide sequence of PAS#1h/1e/1i(600), codon-optimized for Cricetulus griseus

<400> SEQUENCE: 40
gcctcaccag ccgccccagc ccccgcctcc ccagccgccc ctgctccttc cgcccccgcc 60
gcttctccag ccgctcctgc ccccgcttct cccgctgccc ccgccccatc agcccccgcc 120
gcctctccag cagctccagc tcccgcctct cctgccgccc cagctccaag cgcccccgcc 180
gcatctcctg ccgcacctgc ccctgcctct cctgccgctc cagccccatc tgcccctgcc 240
gcctctccag ccgcccccgc ccctgcttct ccggctgccc ccgcaccttc agcacccgcc 300
gcttcaccag ctgcaccagc ccctgcctct cccgccgccc ccgcaccctc cgcacccgct 360
gcttcacctg ccgcccctgc acctgcctcc cctgccgcac ctgcacctag cgcccccgcc 420
gcctcacctg ccgccccagc cccagcttct cccgccgcac ccgccccttc tgcccctgca 480
gcctcccccg ctgccccagc tccagcctcc cctgccgccc ccgctccatc cgcccctgcc 540
gcttcccccg cagcccctgc ccctgcatcc cctgccgctc cagctccctc agctcccgcc 600
gcctctcctg ctgcccctgc cccagcttct ccagctgctc ctgcaccttc tgctccagcc 660
gctagtcctg cagctccagc tcctgcttct cctgccgcac cagcacctag tgcccctgct 720
gcatcaccag cagctcccgc acccgctagc ccagctgcac cagctccaag tgctccagca 780
gcttcacccg cagcacccgc tccagcaagt ccagcagccc cagccccttc agcaccagct 840
gcatctcccg cagcccctgc tcctgccagc cctgccgctc ctgctccaag cgctcctgct 900
gctagtccag ccgcccctgc accagcaagt cctgctgctc ccgcacctag tgcaccagca 960
gcaagccctg cagctcctgc accagcatct ccagcagcac cagcaccatc agcccctgcc 1020
gcttctcccg cagctccagc cccagcctcc cctgctgctc cagccccctc tgctcctgca 1080
gcatctcctg ccgctcccgc ccctgcaagt cccgccgctc cagcaccatc cgctccagct 1140
gcttccccag ccgctccagc tccagctagc cccgcagccc ccgcaccatc tgccccagca 1200
gccagccccg ccgctcccgc acctgccagc ccagccgctc ccgctccctc cgcccccgcc 1260
gccagccccg ccgcccctgc tcccgccagc cctgcagctc cagcacctag cgccccagca 1320
gcatccccag ctgcacccgc acccgcctcc ccagcagcac ctgcaccatc tgctccagca 1380
gcaagtccgg ctgctcctgc tcctgcatca cctgctgcac cagccccctc agctcctgca 1440
gcaagcccag ctgcacctgc accagctagt ccagccgctc cagcaccttc cgctccagca 1500
gcatctcctg ctgcaccagc accagcatct cctgcagctc ccgccccaag tgccccagca 1560
gcatcacctg ccgcaccagc tcctgcaagc ccagcagctc cagcaccaag cgctcctgca 1620
gcctccccag ctgctcctgc cccagcttcc cccgcagctc ccgcaccttc tgccccagca 1680
gcaagccccg cggcaccagc accagcttca cccgccgctc ctgcaccaag cgcccccgct 1740
gcaagccctg cagcacccgc accagcctca ccagccgcac cagcaccctc cgccccagca 1800

<210> SEQ ID NO 41
<211> LENGTH: 2400
<212> TYPE: DNA
<213> ORGANISM: Artificial Sequence
<220> FEATURE:
<223> OTHER INFORMATION: Nucleotide sequence of PAS#1j/1h/1e/1i(800), codon-optimized for Cricetulus griseus

<400> SEQUENCE: 41
gcctcacccg ccgcaccagc cccagcatca cccgccgctc cggctccaag tgccccagcc 60
gcttctccag ctgcccctgc tccagcatca cctgctgctc ctgccccttc cgctcccgca 120
gcatctccag ctgcacctgc cccagcaagt ccagccgcac ctgctcctag tgctcctgct 180
gctagccctg ctgccccagc acctgcatca cccgcagctc ccgctccttc agctccagca 240
gcttcccctg ccgctcccgc accagcatca cccgcagccc cagctcctag cgcccctgcc 300
gccagtcccg ctgctcctgc tcccgcaagt cctgccgcac ccgcacccag tgcacctgct 360
gcatccccag ctgctccagc cccagctagt ccagcagccc ctgctccctc tgctcctgcc 420
gcttccccag cagcaccagc tcccgctagt cctgccgctc ctgccccaag tgcacccgct 480
gccagccccg cagcaccagc tccagcctca cccgctgctc ctgcacccag cgcaccagca 540
gctagcccag cagctcctgc tccagccagc ccagccgcac ctgccccatc tgcacccgct 600
gcctcaccag ccgccccagc ccccgcctcc ccagccgccc ctgctccttc cgcccccgcc 660

```
gcttctccag ccgctcctgc ccccgcttct cccgctgccc ccgccccatc agcccccgcc    720
gcctctccag cagctccagc tcccgcctct cctgccgccc cagctccaag cgcccccgcc    780
gcatctcctg ccgcacctgc ccctgcctct cctgccgctc cagccccatc tgcccctgcc    840
gcctctccag ccgcccccgc ccctgcttct ccggctgccc ccgcaccttc agcacccgcc    900
gcttcaccag ctgcaccagc ccctgcctct cccgccgccc ccgcaccctc cgcacccgct    960
gcttcacctg ccgcccctgc acctgcctcc cctgccgcac ctgcacctag cgcccccgcc   1020
gcctcacctg ccgccccagc cccagcttct cccgccgcac ccgccccttc tgcccctgca   1080
gcctcccccg ctgccccagc tccagcctcc cctgccgccc ccgctccatc cgcccctgcc   1140
gcttcccccg cagcccctgc ccctgcatcc cctgccgctc cagctccctc agctcccgcc   1200
gcctctcctg ctgcccctgc cccagcttct ccagctgctc ctgcaccttc tgctccagcc   1260
gctagtcctg cagctccagc tcctgcttct cctgccgcac cagcacctag tgcccctgct   1320
gcatcaccag cagctcccgc acccgctagc ccagctgcac cagctccaag tgctccagca   1380
gcttcacccg cagcacccgc tccagcaagt ccagcagccc cagccccttc agcaccagct   1440
gcatctcccg cagcccctgc tcctgccagc cctgccgctc ctgctccaag cgctcctgct   1500
gctagtccag ccgcccctgc accagcaagt cctgctgctc ccgcacctag tgcaccagca   1560
gcaagccctg cagctcctgc accagcatct ccagcagcac cagcaccatc agcccctgcc   1620
gcttctcccg cagctccagc cccagcctcc cctgctgctc cagcccccctc tgctcctgca   1680
gcatctcctg ccgctcccgc ccctgcaagt cccgccgctc cagcaccatc cgctccagct   1740
gcttccccag ccgctccagc tccagctagc cccgcagccc ccgcaccatc tgccccagca   1800
gccagccccg ccgctcccgc acctgccagc ccagccgctc ccgctccctc cgcccccgcc   1860
gccagccccg ccgcccctgc tcccgccagc cctgcagctc cagcacctag cgccccagca   1920
gcatccccag ctgcacccgc acccgcctcc ccagcagcac ctgcaccatc tgctccagca   1980
gcaagtccgg ctgctcctgc tcctgcatca cctgctgcac cagcccccctc agctcctgca   2040
gcaagcccag ctgcacctgc accagctagt ccagccgctc cagcaccttc cgctccagca   2100
gcatctcctg ctgcaccagc accagcatct cctgcagctc ccgccccaag tgccccagca   2160
gcatcacctg ccgcaccagc tcctgcaagc ccagcagctc cagcaccaag cgctcctgca   2220
gcctccccag ctgctcctgc cccagcttcc cccgcagctc ccgcaccttc tgccccagca   2280
gcaagccccg cggcaccagc accagcttca cccgccgctc ctgcaccaag cgcccccgct   2340
gcaagccctg cagcacccgc accagcctca ccagccgcac cagcaccctc cgccccagca   2400
```

<210> SEQ ID NO 42
<211> LENGTH: 1800
<212> TYPE: DNA
<213> ORGANISM: Artificial Sequence
<220> FEATURE:
<223> OTHER INFORMATION: Nucleotide sequence of PA#1d/1c/1b(600), codon-optimized for E. coli

<400> SEQUENCE: 42

```
gccgcaccgg ctgccccagc ccctgccgca ccagcagctc ccgcccctgc agcccccgcc     60
gccgctccgg ccgcaccagc cccggctgcc cctgctgccc ccgccccggc agcacccgct    120
gcagcaccag ccgcgcctgc accggcagct cctgcagccc cggcaccggc agcacctgcc    180
gcagcacccg cagccccagc cccagcagcg cctgccgctc cagcaccagc ggcaccggcc    240
gccgcaccag ccgccccagc accggcagcc cccgcagcgc cggcaccagc cgctccagcc    300
```

gccgccccag cagccccggc tccggccgct cccgcggctc cagcaccagc agctccagcg 360
gccgctccgg cagcgccggc cccagcagca cctgcagccc ctgcaccagc agcgccagcc 420
gcggcgcccg cagctcccgc acctgcggct cccgcagccc ctgcacccgc ggcgccagca 480
gccgcccctg cagcgccagc tcctgcagca cctgcagctc cagccccggc cgccccagct 540
gcagctcctg cggccccagc acctgccgcc cctgccgcac cggctccagc cgccccagcc 600
gccgcgccag cggccccggc ccctgccgcg cccgctgctc ccgcccctgc tgccccagcc 660
gccgctcctg cggcacctgc gcccgccgcg ccggcagcgc cggcaccggc agctccggcg 720
gccgcgcctg cagctcctgc accggcggct ccagcagccc cggcgccggc cgcacctgcg 780
gcggcgcccg cggcgcctgc acccgcagcg cctgcggcac cggccccagc agcccctgcc 840
gccgcaccgg ctgcgcctgc cccagcggcc cccgctgccc cggcccggc ggctccagcc 900 gcagcgcctg ccgccccagc gcccgcagca ccggcggcac cagctccggc ggcgccggcg 960
gcggctccgg cagctccggc ccctgctgcg ccggctgcgc cggctccggc ggcccctgcg 1020
gcggctccgg ccgcacctgc acctgccgcg ccggctgctc cggcccggc tgccccagca 1080 gcggcaccag cagcgcctgc tcctgcggcg cctgcagctc cggcgccggc agccccggcc 1140
gccgcacccg cggctccagc ccccgccgct ccagcagccc ccgcgccagc tgcacctgct 1200
gccgctcctg ctgcccctgc tcccgctgcc cccgccgccc ccgccccagc tgcccccgct 1260
gccgcacctg ctgccccagc tcccgctgcc ccagccgcgc cggcccccgc agctccagcc 1320
gcggcaccag ctgccccagc tccagcggcg cctgctgccc cggcccccgc ggcaccggct 1380
gccgcgcccg cagctccagc gcctgctgca ccggctgctc cggcacccgc cgcgccagca 1440
gctgcccctg cggcaccagc tcctgctgcc cccgcggcac ctgcacccgc tgccccggcg 1500
gcagctcccg ccgcgccagc ccctgcagct cctgctgcac ctgctcctgc cgcccctgct 1560
gctgcccctg ctgctccagc ccctgcagca ccggccgctc cagctcctgc cgctcctgcc 1620
gctgcgcccg ctgctccagc cccagctgcg ccagcagctc ctgcacctgc tgcccctgcc 1680
gccgcccctg cggctccagc acctgctgca ccggccgccc cggcgcccgc tgcccccgca 1740
gcagccccag ccgcacccgc tccagcagct cccgcagccc cagcacccgc agcaccagcc 1800

<210> SEQ ID NO 43
<211> LENGTH: 2400
<212> TYPE: DNA
<213> ORGANISM: Artificial Sequence
<220> FEATURE:
<223> OTHER INFORMATION: Nucleotide sequence of PA#1i/1h/1g/1f(800),
codon-optimized for Cricetulus griseus

<400> SEQUENCE: 43
gccgctccag ccgccccagc ccctgccgcc cccgccgcac ctgcccccgc cgccccagct 60
gccgccccag ccgcccctgc tcccgctgct cctgccgcac ctgcacccgc tgcccctgct 120
gctgcccccg ctgctcctgc tcccgctgct cccgctgccc cggcccccgc tgctcccgcc 180
gctgctcccg ccgcacctgc cccagccgca ccagctgcac ctgctccagc cgctcccgct 240
gccgctccag ccgcccccgc acccgccgca cctgccgccc ctgcccctgc agcccccgcc 300
gccgctcccg cagcccccgc tcccgctgcc ccagccgccc ctgcccccgc ggctcccgcc 360
gctgctcctg ccgctcccgc ccccgccgcc cctgccgccc cggcccctgc tgcccccgct 420
gccgcacctg ctgctcccgc cccagccgct ccagctgccc ctgccccagc tgcccccgct 480
gctgcccctg ccgctcctgc ccctgctgct cctgccgccc ccgcccccgc cgctcctgcc 540
gctgcccccg ctgcacccgc tcccgccgcc cccgctgccc ccgcccctgc tgctcctgct 600
gccgcccctg ctgccccagc cccagccgcc cccgccgctc ccgccccagc tgccccagcc 660
gctgcacctg cagccccagc acctgctgcc ccagccgctc cagcaccagc tgcccctgca 720
gccgctcccg ccgccccagc ccccgctgcc cccgcagctc cagctcctgc cgctccagcc 780
gccgcccccg cagctcctgc ccccgctgcc cctgcagccc ctgctcctgc tgcacctgcc 840
gcagcccctg ctgccccagc tccagcagca cctgctgccc ccgctcccgc cgcacccgca 900
gcagcacctg ccgctccagc tccagccgcc cccgctgccc ctgctccagc cgctccagct 960
gctgctcccg cagcccctgc cccagccgct cccgcagcac ccgctcctgc cgccccagcc 1020
gcagctccag ccgctcctgc ccctgccgca ccagctgctc ccgctcccgc tgctcccgcc 1080
gccgctcccg ccgcacctgc tcctgccgca cccgccgctc cagcaccagc agctccagct 1140
gccgctccag ccgctcccgc acccgctgct cctgccgccc ctgcccccgc agcccctgct 1200
gccgcaccgg ctgctcctgc tcctgccgct cctgccgcac ccgctcccgc tgcccctgcc 1260
gccgcccctg cagctcctgc ccccgccgca cctgcagctc cagcacctgc agcaccagct 1320
gcagcacctg ctgcaccagc tcccgccgct ccagcagctc ctgccccagc tgcaccagcc 1380
gctgcacccg ccgctcccgc tcctgcagcc cccgctgcac cggcccctgc cgctcctgca 1440
gctgcgccag cagcccctgc tccagctgca cctgccgcac ccgccccagc tgcccccgcc 1500
gctgctccag ccgctcctgc acctgctgca cctgctgctc cagcacctgc ggctcctgct 1560
gccgctccag ctgcccccgc tccagcggct cctgccgccc ctgctcccgc cgctcctgca 1620
gcagcccctg ctgctccagc cccagccgct ccggcagctc ccgctccagc agcccccgcc 1680
gctgcccctg ctgcaccagc ccccgctgcc ccagctgccc ctgctcctgc tgcccccgcc 1740
gcagcccccg ccgcacccgc accagcagca cccgcagctc cagcaccagc tgcaccagca 1800
gccgctcctg ctgctccagc tcctgctgcc ccagcagccc ctgccccagc tgctcctgca 1860
gcagctcccg cagccccagc acccgccgca ccagcagctc cagcccctgc agcaccagct 1920
gctgcccctg ccgcccctgc tccagccgca cccgctgcac ccgcaccagc tgccccagcc 1980
gccgcacccg cagctccagc tcccgctgct cctgctgcac cagcccctgc cgctccagca 2040
gccgcaccag cagcaccagc cccagctgct cccgctgctc cagcacccgc agcccccgca 2100
gcagcaccag ccgctcctgc tcctgccgcc ccagcagctc ctgctccagc agcccctgct 2160
gctgctccag cagcaccagc accagctgct ccagctgccc cagctcctgc agcacccgcc 2220
gctgctcccg cagctcctgc ccctgctgca cccgcagcac ccgctccagc agcacctgca 2280
gctgcaccag ctgctcccgc acctgccgct cccgcagctc ccgctcctgc agctccagcc 2340
gcagctcctg ctgctcctgc accagcagct cccgccgcac cagctccagc tgcccctgct 2400

<210> SEQ ID NO 44
<211> LENGTH: 2400
<212> TYPE: DNA
<213> ORGANISM: Artificial Sequence
<220> FEATURE:
<223> OTHER INFORMATION: Nucleotide sequence of PA#1e/1d/1c/1b(800), codon-optimized for E. coli

<400> SEQUENCE: 44
gccgcaccgg ctgcaccagc tccggcagct ccagcagcac cggcaccagc agctccggct 60
gcagcgccag cagcaccagc gcctgctgct ccagctgctc ctgctcctgc tgcaccagca 120
gcagctccag ccgcaccagc accggcagcg cctgcagccc ctgctccggc agctcctgcc 180

-continued

```
gcagcaccgg cagcaccagc tccagcggca cccgctgccc ctgctcctgc agcaccggca    240
gcggcaccgg ctgctcctgc gccagctgct ccggcagccc cagcccctgc agccccagca    300
gcagcgcctg cggctccagc gccagccgca ccagcggctc cggcaccggc agcccctgcg    360
gcagctcctg ctgcgcctgc tccagcagct ccagctgccc cagcgccggc agctccggct    420
gccgcaccag ctgcgcctgc ccctgctgcg ccagccgcac cggctccggc agcaccagca    480
gctgccccag cagctcctgc cccagctgcg cctgctgcgc cagcaccagc agccccagct    540
gcagcaccag ctgcaccggc accagctgct ccagcagcac cagccccagc cgctccggca    600
gccgcaccgg ctgccccagc ccctgccgca ccagcagctc ccgcccctgc agcccccgcc    660
gccgctccgg ccgcaccagc cccggctgcc cctgctgccc ccgccccggc agcacccgct    720
gcagcaccag ccgcgcctgc accggcagct cctgcagccc cggcaccggc agcacctgcc    780
gcagcacccg cagccccagc cccagcagcg cctgccgctc cagcaccagc ggcaccggcc    840
gccgcaccag ccgccccagc accggcagcc cccgcagcgc cggcaccagc cgctccagcc    900
gccgccccag cagccccggc tccggccgct cccgcggctc cagcaccagc agctccagcg    960
gccgctccgg cagcgccggc cccagcagca cctgcagccc ctgcaccagc agcgccagcc   1020
gcggcgcccg cagctcccgc acctgcggct cccgcagccc ctgcacccgc ggcgccagca   1080
gccgcccctg cagcgccagc tcctgcagca cctgcagctc cagccccggc cgccccagct   1140
gcagctcctg cggccccagc acctgccgcc cctgccgcac cggctccagc cgccccagcc   1200
gccgcgccag cggccccggc ccctgccgcg cccgctgctc ccgcccctgc tgccccagcc   1260
gccgctcctg cggcacctgc gcccgccgcg ccggcagcgc cggcaccggc agctccggcg   1320
gccgcgcctg cagctcctgc accggcggct ccagcagccc cggcgccggc cgcacctgcg   1380
gcggcgcccg cggcgcctgc acccgcagcg cctgcggcac cggccccagc agcccctgcc   1440
gccgcaccgg ctgcgcctgc cccagcggcc cccgctgccc cggcccccggc ggctccagcc  1500
gcagcgcctg ccgccccagc gcccgcagca ccggcggcac cagctccggc ggcgccggcg   1560
gcggctccgg cagctccggc ccctgctgcg ccggctgcgc cggctccggc ggcccctgcg   1620
gcggctccgg ccgcacctgc acctgccgcg ccggctgctc cggccccggc tgccccagca   1680
gcggcaccag cagcgcctgc tcctgcggcg cctgcagctc cggcgccggc agccccggcc   1740
gccgcacccg cggctccagc cccgccgct ccagcagccc ccgcgccagc tgcacctgct    1800
gccgctcctg ctgcccctgc tcccgctgcc cccgccgccc ccgccccagc tgcccccgct   1860
gccgcacctg ctgccccagc tcccgctgcc ccagccgcgc cggcccccgc agctccagcc   1920
gcggcaccag ctgccccagc tccagcggcg cctgctgccc cggcccccgc ggcaccggct   1980
gccgcgcccg cagctccagc gcctgctgca ccggctgctc cggcacccgc cgcgccagca   2040
gctgcccctg cggcaccagc tcctgctgcc cccgcggcac ctgcacccgc tgccccggcg   2100
gcagctcccg ccgcgccagc ccctgcagct cctgctgcac ctgctcctgc cgcccctgct   2160
gctgcccctg ctgctccagc ccctgcagca ccggccgctc cagctcctgc cgctcctgcc   2220
gctgcgcccg ctgctccagc cccagctgcg ccagcagctc ctgcacctgc tgcccctgcc   2280
gccgcccctg cggctccagc acctgctgca ccggccgccc cggcgcccgc tgcccccgca   2340
gcagccccag ccgcacccgc tccagcagct cccgcagccc cagcacccgc agcaccagcc   2400
```

<210> SEQ ID NO 45
<211> LENGTH: 4800
<212> TYPE: DNA

<213> ORGANISM: Artificial Sequence
<220> FEATURE:
<223> OTHER INFORMATION: Nucleotide sequence of
PA#1i/1h/1g/1f/1e/1d/1c/1b(1600)

<400> SEQUENCE: 45
gccgctcctg ctgcccctgc tcccgctgcc cccgccgccc ccgccccagc tgcccccgct 60
gccgcacctg ctgccccagc tcccgctgcc ccagccgcgc cggcccccgc agctccagcc 120
gcggcaccag ctgccccagc tccagcggcg cctgctgccc cggcccccgc ggcaccggct 180
gccgcgcccg cagctccagc gcctgctgca ccggctgctc cggcacccgc cgcgccagca 240
gctgcccctg cggcaccagc tcctgctgcc cccgcggcac ctgcacccgc tgccccggcg 300
gcagctcccg ccgcgccagc ccctgcagct cctgctgcac ctgctcctgc cgcccctgct 360
gctgcccctg ctgctccagc ccctgcagca ccggccgctc cagctcctgc cgctcctgcc 420
gctgcgcccg ctgctccagc cccagctgcg ccagcagctc ctgcacctgc tgcccctgcc 480
gccgcccctg cggctccagc acctgctgca ccggccgccc cggcgcccgc tgcccccgca 540
gcagccccag ccgcacccgc tccagcagct cccgcagccc cagcacccgc agcaccagcc 600
gccgcgccag cggccccggc ccctgccgcg cccgctgctc ccgcccctgc tgccccagcc 660
gccgctcctg cggcacctgc gcccgccgcg ccggcagcgc cggcaccggc agctccggcg 720
gccgcgcctg cagctcctgc accggcggct ccagcagccc cggcgccggc cgcacctgcg 780
gcggcgcccg cggcgcctgc acccgcagcg cctgcggcac cggccccagc agcccctgcc 840
gccgcaccgg ctgcgcctgc cccagcggcc cccgctgccc cggccccggc ggctccagcc 900
gcagcgcctg ccgccccagc gcccgcagca ccggcggcac cagctccggc ggcgccggcg 960
gcggctccgg cagctccggc ccctgctgcg ccggctgcgc cggctccggc ggcccctgcg 1020
gcggctccgg ccgcacctgc acctgccgcg ccggctgctc cggccccggc tgccccagca 1080
gcggcaccag cagcgcctgc tcctgcggcg cctgcagctc cggcgccggc agccccggcc 1140
gccgcacccg cggctccagc ccccgccgct ccagcagccc ccgcgccagc tgcacctgct 1200
gccgcaccgg ctgccccagc ccctgccgca ccagcagctc ccgcccctgc agcccccgcc 1260
gccgctccgg ccgcaccagc cccggctgcc cctgctgccc ccgccccggc agcacccgct 1320
gcagcaccag ccgcgcctgc accggcagct cctgcagccc cggcaccggc agcacctgcc 1380
gcagcacccg cagccccagc cccagcagcg cctgccgctc cagcaccagc ggcaccggcc 1440
gccgcaccag ccgccccagc accggcagcc cccgcagcgc cggcaccagc cgctccagcc 1500
gccgccccag cagccccggc tccggccgct cccgcggctc cagcaccagc agctccagcg 1560
gccgctccgg cagcgccggc cccagcagca cctgcagccc ctgcaccagc agcgccagcc 1620
gcggcgcccg cagctcccgc acctgcggct cccgcagccc ctgcacccgc ggcgccagca 1680
gccgcccctg cagcgccagc tcctgcagca cctgcagctc cagccccggc cgccccagct 1740
gcagctcctg cggccccagc acctgccgcc cctgccgcac cggctccagc cgccccagcc 1800
gccgcaccgg ctgcaccagc tccggcagct ccagcagcac cggcaccagc agctccggct 1860
gcagcgccag cagcaccagc gcctgctgct ccagctgctc ctgctcctgc tgcaccagca 1920
gcagctccag ccgcaccagc accggcagcg cctgcagccc ctgctccggc agctcctgcc 1980
gcagcaccgg cagcaccagc tccagcggca cccgctgccc ctgctcctgc agcaccggca 2040
gcggcaccgg ctgctcctgc gccagctgct ccggcagccc cagcccctgc agccccagca 2100
gcagcgcctg cggctccagc gccagccgca ccagcggctc cggcaccggc agcccctgcg 2160

```
gcagctcctg ctgcgcctgc tccagcagct ccagctgccc cagcgccggc agctccggct   2220
gccgcaccag ctgcgcctgc ccctgctgcg ccagccgcac cggctccggc agcaccagca   2280
gctgccccag cagctcctgc cccagctgcg cctgctgcgc cagcaccagc agccccagct   2340
gcagcaccag ctgcaccggc accagctgct ccagcagcac cagccccagc cgctccggca   2400
gccgctcctg ctgctccagc tcctgctgcc ccagcagccc ctgccccagc tgctcctgca   2460
gcagctcccg cagccccagc acccgccgca ccagcagctc cagcccctgc agcaccagct   2520
gctgcccctg ccgcccctgc tccagccgca cccgctgcac ccgcaccagc tgccccagcc   2580
gccgcacccg cagctccagc tcccgctgct cctgctgcac cagcccctgc cgctccagca   2640
gccgcaccag cagcaccagc cccagctgct cccgctgctc cagcacccgc agcccccgca   2700
gcagcaccag ccgctcctgc tcctgccgcc ccagcagctc ctgctccagc agcccctgct   2760
gctgctccag cagcaccagc accagctgct ccagctgccc cagctcctgc agcacccgcc   2820
gctgctcccg cagctcctgc ccctgctgca cccgcagcac ccgctccagc agcacctgca   2880
gctgcaccag ctgctcccgc acctgccgct cccgcagctc ccgctcctgc agctccagcc   2940
gcagctcctg ctgctcctgc accagcagct cccgccgcac cagctccagc tgcccctgct   3000
gccgcaccgg ctgctcctgc tcctgccgct cctgccgcac ccgctcccgc tgcccctgcc   3060
gccgcccctg cagctcctgc ccccgccgca cctgcagctc cagcacctgc agcaccagct   3120
gcagcacctg ctgcaccagc tcccgccgct ccagcagctc ctgccccagc tgcaccagcc   3180
gctgcacccg ccgctcccgc tcctgcagcc cccgctgcac cggcccctgc cgctcctgca   3240
gctgcgccag cagcccctgc tccagctgca cctgccgcac ccgccccagc tgcccccgcc   3300
gctgctccag ccgctcctgc acctgctgca cctgctgctc cagcacctgc ggctcctgct   3360
gccgctccag ctgcccccgc tccagcggct cctgccgccc ctgctcccgc cgctcctgca   3420
gcagcccctg ctgctccagc cccagccgct ccggcagctc ccgctccagc agcccccgcc   3480
gctgcccctg ctgcaccagc ccccgctgcc ccagctgccc ctgctcctgc tgcccccgcc   3540
gcagccccg ccgcacccgc accagcagca cccgcagctc cagcaccagc tgcaccagca   3600
gccgcccctg ctgccccagc cccagccgcc cccgccgctc ccgccccagc tgccccagcc   3660
gctgcacctg cagccccagc acctgctgcc ccagccgctc cagcaccagc tgcccctgca   3720
gccgctcccg ccgccccagc ccccgctgcc cccgcagctc cagctcctgc cgctccagcc   3780
gccgcccccg cagctcctgc ccccgctgcc cctgcagccc ctgctcctgc tgcacctgcc   3840
gcagcccctg ctgccccagc tccagcagca cctgctgccc ccgctcccgc cgcacccgca   3900
gcagcacctg ccgctccagc tccagccgcc cccgctgccc ctgctccagc cgctccagct   3960
gctgctcccg cagcccctgc cccagccgct cccgcagcac ccgctcctgc cgccccagcc   4020
gcagctccag ccgctcctgc ccctgccgca ccagctgctc ccgctcccgc tgctcccgcc   4080
gccgctcccg ccgcacctgc tcctgccgca cccgccgctc cagcaccagc agctccagct   4140
gccgctccag ccgctcccgc acccgctgct cctgccgccc ctgcccccgc agcccctgct   4200
gccgctccag ccgccccagc ccctgccgcc cccgccgcac ctgcccccgc cgccccagct   4260
gccgccccag ccgcccctgc tcccgctgct cctgccgcac ctgcacccgc tgcccctgct   4320
gctgcccccg ctgctcctgc tcccgctgct cccgctgccc cggcccccgc tgctcccgcc   4380
gctgctcccg ccgcacctgc cccagccgca ccagctgcac ctgctccagc cgctcccgct   4440
gccgctccag ccgcccccgc acccgccgca cctgccgccc ctgcccctgc agcccccgcc   4500
gccgctcccg cagcccccgc tcccgctgcc ccagccgccc ctgcccccgc ggctcccgcc   4560
```

gctgctcctg ccgctcccgc ccccgccgcc cctgccgccc cggcccctgc tgcccccgct 4620
gccgcacctg ctgctcccgc cccagccgct ccagctgccc ctgccccagc tgcccccgct 4680
gctgcccctg ccgctcctgc ccctgctgct cctgccgccc ccgcccccgc cgctcctgcc 4740
gctgcccccg ctgcacccgc tcccgccgcc cccgctgccc ccgcccctgc tgctcctgct 4800

<210> SEQ ID NO 46
<211> LENGTH: 571
<212> TYPE: DNA
<213> ORGANISM: Artificial Sequence
<220> FEATURE:
<223> OTHER INFORMATION: Synthetic gene construct for seamless fusion of a proline/alanine-rich sequence with IL1Ra

<400> SEQUENCE: 46
tctagataac gagggcaaaa aatgaaaaag acagctatcg cgattgcagt ggcactggct 60
ggtttcgcta ccgtagcgca ggccgccaga agagcgcgct cttctgcccg accctctggg 120
agaaaatcca gcaagatgca agccttcaga atctgggatg ttaaccagaa gaccttctat 180
ctgaggaaca accaactagt tgccggatac ttgcaaggac caaatgtcaa tttagaagaa 240
aagatagatg tggtacccat tgagcctcat gctctgttct tgggaatcca tggagggaag 300
atgtgcctgt cctgtgtcaa gtctggtgat gagaccagac tccagctgga ggcagttaac 360
atcactgacc tgagcgagaa cagaaagcag gacaagcgct tcgccttcat ccgctcagac 420
agtggcccca ccaccagttt tgagtctgcc gcctgccccg gttggttcct ctgcacagcg 480
atggaagctg accagcccgt cagcctcacc aatatgcctg acgaaggcgt catggtcacc 540
aaattctact tccaggagga cgagtaagct t 571

<210> SEQ ID NO 47
<211> LENGTH: 1150
<212> TYPE: DNA
<213> ORGANISM: Artificial Sequence
<220> FEATURE:
<223> OTHER INFORMATION: Expression cassette encoding the PA#1b(200) sequence seamless fused to IL1Ra

<400> SEQUENCE: 47
tctagataac gagggcaaaa aatgaaaaag acagctatcg cgattgcagt ggcactggct 60
ggtttcgcta ccgtagcgca ggccgccgct cctgctgccc ctgctcccgc tgcccccgcc 120
gcccccgccc cagctgcccc cgctgccgca cctgctgccc cagctcccgc tgccccagcc 180
gcgccggccc ccgcagctcc agccgcggca ccagctgccc cagctccagc ggcgcctgct 240
gccccggccc ccgcggcacc ggctgccgcg cccgcagctc cagcgcctgc tgcaccggct 300
gctccggcac ccgccgcgcc agcagctgcc cctgcggcac cagctcctgc tgcccccgcg 360
gcacctgcac ccgctgcccc ggcggcagct cccgccgcgc cagcccctgc agctcctgct 420
gcacctgctc ctgccgcccc tgctgctgcc cctgctgctc cagcccctgc agcaccggcc 480
gctccagctc ctgccgctcc tgccgctgcg cccgctgctc cagccccagc tgcgccagca 540
gctcctgcac ctgctgcccc tgccgccgcc cctgcggctc cagcacctgc tgcaccggcc 600
gccccggcgc ccgctgcccc cgcagcagcc ccagccgcac ccgctccagc agctcccgca 660
gccccagcac ccgcagcacc agccgcccga ccctctggga gaaaatccag caagatgcaa 720
gccttcagaa tctgggatgt taaccagaag accttctatc tgaggaacaa ccaactagtt 780
gccggatact tgcaaggacc aaatgtcaat ttagaagaaa agatagatgt ggtacccatt 840

-continued gagcctcatg ctctgttctt gggaatccat ggagggaaga tgtgcctgtc ctgtgtcaag 900
tctggtgatg agaccagact ccagctggag gcagttaaca tcactgacct gagcgagaac 960
agaaagcagg acaagcgctt cgccttcatc cgctcagaca gtggccccac caccagtttt 1020
gagtctgccg cctgccccgg ttggttcctc tgcacagcga tggaagctga ccagcccgtc 1080
agcctcacca atatgcctga cgaaggcgtc atggtcacca aattctactt ccaggaggac 1140
gagtaagctt 1150

<210> SEQ ID NO 48
<211> LENGTH: 2662
<212> TYPE: DNA
<213> ORGANISM: Artificial Sequence
<220> FEATURE:
<223> OTHER INFORMATION: Nucleotide sequence of pXL2

<400> SEQUENCE: 48
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgg 240
ctcttctgcc agaagagtag aattcactgg ccgtcgtttt acaacgtcgt gactgggaaa 300
accctggcgt tacccaactt aatcgccttg cagcacatcc ccctttcgcc agctggcgta 360
atagcgagga ggcccgcacc gatcgccctt cccaacagtt gcgcagcctg aatggcgaat 420
ggcgcctgat gcggtatttt ctccttacgc atctgtgcgg tatttcacac cgcatatggt 480
gcactctcag tacaatctgc tctgatgccg catagttaag ccagccccga cacccgccaa 540
cacccgctga cgcgccctga cgggcttgtc tgctcccggc atccgcttac agacaagctg 600
tgaccgtctc cgggagctgc atgtgtcaga ggttttcacc gtcatcaccg aaacgcgcga 660
gacgaaaggg cctcgtgata cgcctatttt tataggttaa tgtcatgata ataatggttt 720
cttagacgtc aggtggcact tttcggggaa atgtgcgcgg aacccctatt tgtttatttt 780
tctaaataca ttcaaatatg tatccgctca tgagacaata accctgataa atgcttcaat 840
aatattgaaa aaggacgagt atgagtattc aacatttccg tgtcgccctt attccctttt 900
ttgcggcatt ttgccttcct gtttttgctc acccagaaac gctggtgaaa gtaaaagatg 960
ctgaagatca gttgggtgca cgagtgggtt acatcgaact ggatctcaac agcggtaaga 1020
tccttgagag ttttcgcccc gaagaacgtt ttccaatgat gagcactttt aaagttctgc 1080
tatgtggcgc ggtattatcc cgtattgacg ccgggcaaga gcaactcggt cgccgcatac 1140
actattctca gaatgacttg gttgagtact caccagtcac agaaaagcat cttacggatg 1200
gcatgacagt aagagaatta tgcagtgctg ccataaccat gagtgataac actgcggcca 1260
acttacttct gacaacgatc ggaggaccga aggagctaac cgcttttttg cacaacatgg 1320
gggatcatgt aactcgcctt gatcgttggg aaccggagct gaatgaagcc ataccaaacg 1380
acgagcgtga caccacgatg cctgtagcaa tggcaacaac gttgcgcaaa ctattaactg 1440
gcgaactact tactctagct tcccggcaac aattaataga ctggatggag gcggataaag 1500
ttgcaggacc acttctgcgc tcggcccttc cggctggctg gtttattgct gataaatctg 1560
gagccggtga gcgtgggtct cgcggtatca ttgcagcact ggggccagat ggtaagccct 1620
cccgtatcgt agttatctac acgacgggga gtcaggcaac tatggatgaa cgaaatagac 1680
agatcgctga gataggtgcc tcactgatta agcattggta actgtcagac caagtttact 1740

```
catatatact ttagattgat ttaaaacttc atttttaatt taaaaggatc taggtgaaga   1800
tcctttttga taatctcatg accaaaatcc cttaacgtga gttttcgttc cactgagcgt   1860
cagaccccgt agaaaagatc aaaggatctt cttgagatcc tttttttctg cgcgtaatct   1920
gctgcttgca aacaaaaaaa ccaccgctac cagcggtggt ttgtttgccg gatcaagagc   1980
taccaactct ttttccgaag gtaactggct tcagcagagc gcagatacca aatactgttc   2040
ttctagtgta gccgtagtta ggccaccact tcaagaactc tgtagcaccg cctacatacc   2100
tcgctctgct aatcctgtta ccagtggctg ctgccagtgg cgataagtcg tgtcttaccg   2160
ggttggactc aagacgatag ttaccggata aggcgcagcg gtcgggctga acggggggtt   2220
cgtgcacaca gcccagcttg gagcgaacga cctacaccga actgagatac ctacagcgtg   2280
agctatgaga aagcgccacg cttcccgaag ggagaaaggc ggacaggtat ccggtaagcg   2340
gcagggtcgg aacaggagag cgcacgaggg agcttccagg gggaaacgcc tggtatcttt   2400
atagtcctgt cgggtttcgc cacctctgac ttgagcgtcg atttttgtga tgctcgtcag   2460
gggggcggag cctatggaaa aacgccagca acgcggcctt tttacggttc ctggcctttt   2520
gctggccttt tgctcacatg ttctttcctg cgttatcccc tgattctgtg gataaccgta   2580
ttaccgcctt tgagtgagct gataccgctc gccgcagccg aacgaccgag cgcagcgagt   2640
cagtgagcga ggaagcggag aa                                            2662
```

<210> SEQ ID NO 49
<211> LENGTH: 3670
<212> TYPE: DNA
<213> ORGANISM: Artificial Sequence
<220> FEATURE:
<223> OTHER INFORMATION: Nucleotide sequence of pASK75-IL1Ra:

<400> SEQUENCE: 49

```
acccgacacc atcgaatggc cagatgatta attcctaatt tttgttgaca ctctatcatt     60
gatagagtta ttttaccact ccctatcagt gatagagaaa agtgaaatga atagttcgac    120
aaaaatctag ataacgaggg caaaaaatga aaaagacagc tatcgcgatt gcagtggcac    180
tggctggttt cgctaccgta gcgcaggccg ctagccatca ccatcaccac catagctctt    240
ctgcccgacc ctctgggaga aaatccagca agatgcaagc cttcagaatc tgggatgtta    300
accagaagac cttctatctg aggaacaacc aactagttgc cggatacttg caaggaccaa    360
atgtcaattt agaagaaaag atagatgtgg tacccattga gcctcatgct ctgttcttgg    420
gaatccatgg agggaagatg tgcctgtcct gtgtcaagtc tggtgatgag accagactcc    480
agctggaggc agttaacatc actgacctga gcgagaacag aaagcaggac aagcgcttcg    540
ccttcatccg ctcagacagt ggccccacca ccagttttga gtctgccgcc tgccccggtt    600
ggttcctctg cacagcgatg gaagctgacc agcccgtcag cctcaccaat atgcctgacg    660
aaggcgtcat ggtcaccaaa ttctacttcc aggaggacga gtaagcttga cctgtgaagt    720
gaaaaatggc gcacattgtg cgacattttt tttgtctgcc gtttaccgct actgcgtcac    780
ggatctccac gcgccctgta gcggcgcatt aagcgcggcg ggtgtggtgg ttacgcgcag    840
cgtgaccgct acacttgcca gcgccctagc gcccgctcct ttcgctttct tcccttcctt    900
tctcgccacg ttcgccggct ttccccgtca agctctaaat cgggggctcc ctttagggtt    960
ccgatttagt gctttacggc acctcgaccc caaaaaactt gattagggtg atggttcacg   1020
tagtgggcca tcgccctgat agacggtttt tcgccctttg acgttggagt ccacgttctt   1080
```

-continued

```
taatagtgga ctcttgttcc aaactggaac aacactcaac cctatctcgg tctattcttt   1140
tgatttataa gggattttgc cgatttcggc ctattggtta aaaaatgagc tgatttaaca   1200
aaaatttaac gcgaatttta acaaaatatt aacgtttaca atttcaggtg gcacttttcg   1260
gggaaatgtg cgcggaaccc ctatttgttt atttttctaa atacattcaa atatgtatcc   1320
gctcatgaga caataaccct gataaatgct tcaataatat tgaaaaagga agagtatgag   1380
tattcaacat ttccgtgtcg cccttattcc cttttttgcg gcattttgcc ttcctgtttt   1440
tgctcaccca gaaacgctgg tgaaagtaaa agatgctgaa gatcagttgg gtgcacgagt   1500
gggttacatc gaactggatc tcaacagcgg taagatcctt gagagttttc gccccgaaga   1560
acgttttcca atgatgagca cttttaaagt tctgctatgt ggcgcggtat tatcccgtat   1620
tgacgccggg caagagcaac tcggtcgccg catacactat tctcagaatg acttggttga   1680
gtactcacca gtcacagaaa agcatcttac ggatggcatg acagtaagag aattatgcag   1740
tgctgccata accatgagtg ataacactgc ggccaactta cttctgacaa cgatcggagg   1800
accgaaggag ctaaccgctt ttttgcacaa catgggggat catgtaactc gccttgatcg   1860
ttgggaaccg gagctgaatg aagccatacc aaacgacgag cgtgacacca cgatgcctgt   1920
agcaatggca acaacgttgc gcaaactatt aactggcgaa ctacttactc tagcttcccg   1980
gcaacaattg atagactgga tggaggcgga taaagttgca ggaccacttc tgcgctcggc   2040
ccttccggct ggctggttta ttgctgataa atctggagcc ggtgagcgtg gctctcgcgg   2100
tatcattgca gcactggggc cagatggtaa gccctcccgt atcgtagtta tctacacgac   2160
ggggagtcag gcaactatgg atgaacgaaa tagacagatc gctgagatag gtgcctcact   2220
gattaagcat tggtaggaat taatgatgtc tcgtttagat aaaagtaaag tgattaacag   2280
cgcattagag ctgcttaatg aggtcggaat cgaaggttta acaacccgta aactcgccca   2340
gaagctaggt gtagagcagc ctacattgta ttggcatgta aaaaataagc gggctttgct   2400
cgacgcctta gccattgaga tgttagatag gcaccatact cacttttgcc ctttagaagg   2460
ggaaagctgg caagattttt tacgtaataa cgctaaaagt tttagatgtg ctttactaag   2520
tcatcgcgat ggagcaaaag tacatttagg tacacggcct acagaaaaac agtatgaaac   2580
tctcgaaaat caattagcct ttttatgcca acaaggtttt tcactagaga atgcattata   2640
tgcactcagc gcagtggggc attttacttt aggttgcgta ttggaagatc aagagcatca   2700
agtcgctaaa gaagaaaggg aaacacctac tactgatagt atgccgccat tattacgaca   2760
agctatcgaa ttatttgatc accaaggtgc agagccagcc ttcttattcg gccttgaatt   2820
gatcatatgc ggattagaaa aacaacttaa atgtgaaagt gggtcttaaa agcagcataa   2880
cctttttccg tgatggtaac ttcactagtt taaaaggatc taggtgaaga tcctttttga   2940
taatctcatg accaaaatcc cttaacgtga gttttcgttc cactgagcgt cagaccccgt   3000
agaaaagatc aaaggatctt cttgagatcc tttttttctg cgcgtaatct gctgcttgca   3060
aacaaaaaaa ccaccgctac cagcggtggt ttgtttgccg gatcaagagc taccaactct   3120
ttttccgaag gtaactggct tcagcagagc gcagatacca aatactgtcc ttctagtgta   3180
gccgtagtta ggccaccact tcaagaactc tgtagcaccg cctacatacc tcgctctgct   3240
aatcctgtta ccagtggctg ctgccagtgg cgataagtcg tgtcttaccg ggttggactc   3300
aagacgatag ttaccggata aggcgcagcg gtcgggctga acggggggtt cgtgcacaca   3360
gcccagcttg gagcgaacga cctacaccga actgagatac ctacagcgtg agctatgaga   3420
aagcgccacg cttcccgaag ggagaaaggc ggacaggtat ccggtaagcg gcagggtcgg   3480
```

aacaggagag cgcacgaggg agcttccagg gggaaacgcc tggtatcttt atagtcctgt 3540
cgggtttcgc cacctctgac ttgagcgtcg atttttgtga tgctcgtcag gggggcggag 3600
cctatggaaa aacgccagca acgcggcctt tttacggttc ctggcctttt gctggccttt 3660
tgctcacatg 3670

<210> SEQ ID NO 50
<211> LENGTH: 5470
<212> TYPE: DNA
<213> ORGANISM: Artificial Sequence
<220> FEATURE:
<223> OTHER INFORMATION: Nucleotide sequence of
pASK75-PAS#1f/1c/1b(600)-IL1Ra:

<400> SEQUENCE: 50
acccgacacc atcgaatggc cagatgatta attcctaatt tttgttgaca ctctatcatt 60
gatagagtta ttttaccact ccctatcagt gatagagaaa agtgaaatga atagttcgac 120
aaaaatctag ataacgaggg caaaaaatga aaaagacagc tatcgcgatt gcagtggcac 180
tggctggttt cgctaccgta gcgcaggccg ctagccatca ccatcaccac catagctctt 240
ctgcctcccc tgccgctcca gcccccgcct cgccggccgc tcccgctccg tctgcacctg 300
ctgcctcacc agcagccccg gccccagcat ccccggccgc accagctccg tcagcacctg 360
ccgcatcgcc tgctgcccct gccccagcca gtccagcggc tccagccccg agtgctccgg 420
ccgcttcccc cgcagcaccg gctcctgcct cccctgcagc ccctgctcca tctgcccctg 480
cggcatcccc tgcggcgcca gctcctgcct ctccagctgc accggctccc tcagctcccg 540
ctgcctcccc agccgcgccc gctcctgcaa gcccagcagc tccggctcca tccgcccccg 600
ccgccagccc cgcagccccg gcgcctgcct ctcctgctgc acctgcaccg tcagcccctg 660
cagcatctcc cgcagctcct gcaccggcat ctccagcagc ccccgccccg tcagctcccg 720
cagccagccc ggccgcaccc gccccccgcgt caccagctgc accagcgcca tccgctcctg 780
ctgcgtctcc cgctgcgccc gcccctgcct cacctgcagc acctgcacct agcgccccgg 840
ctgccagtcc tgctgcaccg gcaccggcat caccggctgc accagcacct agtgcaccgg 900
cagcttctcc ggctgcccct gcgcctgcat caccagctgc gcctgcaccg tctgcccctg 960
cagctagtcc agcagctcca gctccggctt ctcctgcggc tcctgcacca agtgcgcctg 1020
cagcaagtcc ggctgcgcct gccccagcta gtcctgctgc tccggcaccg tcagctccgg 1080
cagcatctcc tgcagcacca gcccctgcaa gtccagcagc gccagcccca tcagcaccag 1140
cagcttcacc agccgcacca gcgccagcaa gccctgctgc cccagctcct agcgcaccgg 1200
cagccagtcc tgcagctcct gcgcctgcta gtccggcagc cccagctcca agtgcccctg 1260
ccgcttcgcc tgcagcccca gcaccagctt ctccagccgc accggcacct tctgccccag 1320
ctgcatctcc ggcagctccg gcaccagcaa gcccggcagc accggcacca tctgcgcctg 1380
ccgcatctcc ggctgcgcca gctccagcct ctcctgcagc gccagcaccg agcgcaccag 1440
cagccagccc tgccgcacct gcgcccgcat cacctgcggc acctgcacct tccgccccgg 1500
ctgcatctcc tgccgcaccc gcgcctgcca gcccagctgc acctgcccca agtgcgccag 1560
cagcatcccc tgccgcgcct gcccccgcta gtccagcggc cccagctcca tctgcaccag 1620
ctgctagccc tgctgcacca gctcctgctt ctcccgcagc cccagcgcct tctgctcccg 1680
cagcctcacc tgcggccccg gcaccagcat ctccagcggc accagcacct tcggcccctg 1740
ctgctagccc agcagcacct gcgccagcct caccagctgc tcccgctcct agtgccccgg 1800

-continued

```
cggcctcgcc tgctgctcct gcaccagctt cgccagcggc accggctcct tcggcgccgg   1860
ctgcttcacc agcagcacct gctccagcgt ccccagcggc ccctgctcca agtgctccgg   1920
ctgcatcgcc tgccgctcct gctcctgcat ccccagctgc tccagcacca agcgcacctg   1980
ccgcctcacc agcggcgcca gcacccgcca gcccagcagc gcctgctcca tccgcaccgg   2040
cggcccgacc ctctgggaga aaatccagca agatgcaagc cttcagaatc tgggatgtta   2100
accagaagac cttctatctg aggaacaacc aactagttgc cggatacttg caaggaccaa   2160
atgtcaattt agaagaaaag atagatgtgg tacccattga gcctcatgct ctgttcttgg   2220
gaatccatgg agggaagatg tgcctgtcct gtgtcaagtc tggtgatgag accagactcc   2280
agctggaggc agttaacatc actgacctga gcgagaacag aaagcaggac aagcgcttcg   2340
ccttcatccg ctcagacagt ggccccacca ccagttttga gtctgccgcc tgccccggtt   2400
ggttcctctg cacagcgatg gaagctgacc agcccgtcag cctcaccaat atgcctgacg   2460
aaggcgtcat ggtcaccaaa ttctacttcc aggaggacga gtaagcttga cctgtgaagt   2520
gaaaaatggc gcacattgtg cgacattttt tttgtctgcc gtttaccgct actgcgtcac   2580
ggatctccac gcgccctgta gcggcgcatt aagcgcggcg ggtgtggtgg ttacgcgcag   2640
cgtgaccgct acacttgcca gcgccctagc gcccgctcct ttcgctttct tcccttcctt   2700
tctcgccacg ttcgccggct ttccccgtca agctctaaat cgggggctcc ctttagggtt   2760
ccgatttagt gctttacggc acctcgaccc caaaaaactt gattagggtg atggttcacg   2820
tagtgggcca tcgccctgat agacggtttt tcgccctttg acgttggagt ccacgttctt   2880
taatagtgga ctcttgttcc aaactggaac aacactcaac cctatctcgg tctattcttt   2940
tgatttataa gggattttgc cgatttcggc ctattggtta aaaaatgagc tgatttaaca   3000
aaaatttaac gcgaatttta acaaaatatt aacgtttaca atttcaggtg gcacttttcg   3060
gggaaatgtg cgcggaaccc ctatttgttt atttttctaa atacattcaa atatgtatcc   3120
gctcatgaga caataaccct gataaatgct tcaataatat tgaaaaagga agagtatgag   3180
tattcaacat ttccgtgtcg cccttattcc cttttttgcg gcattttgcc ttcctgtttt   3240
tgctcaccca gaaacgctgg tgaaagtaaa agatgctgaa gatcagttgg gtgcacgagt   3300
gggttacatc gaactggatc tcaacagcgg taagatcctt gagagttttc gccccgaaga   3360
acgttttcca atgatgagca cttttaaagt tctgctatgt ggcgcggtat tatcccgtat   3420
tgacgccggg caagagcaac tcggtcgccg catacactat tctcagaatg acttggttga   3480
gtactcacca gtcacagaaa agcatcttac ggatggcatg acagtaagag aattatgcag   3540
tgctgccata accatgagtg ataacactgc ggccaactta cttctgacaa cgatcggagg   3600
accgaaggag ctaaccgctt ttttgcacaa catgggggat catgtaactc gccttgatcg   3660
ttgggaaccg gagctgaatg aagccatacc aaacgacgag cgtgacacca cgatgcctgt   3720
agcaatggca acaacgttgc gcaaactatt aactggcgaa ctacttactc tagcttcccg   3780
gcaacaattg atagactgga tggaggcgga taaagttgca ggaccacttc tgcgctcggc   3840
ccttccggct ggctggttta ttgctgataa atctggagcc ggtgagcgtg gctctcgcgg   3900
tatcattgca gcactggggc cagatggtaa gccctcccgt atcgtagtta tctacacgac   3960
ggggagtcag gcaactatgg atgaacgaaa tagacagatc gctgagatag gtgcctcact   4020
gattaagcat tggtaggaat taatgatgtc tcgtttagat aaaagtaaag tgattaacag   4080
cgcattagag ctgcttaatg aggtcggaat cgaaggttta acaacccgta aactcgccca   4140
```

gaagctaggt gtagagcagc ctacattgta ttggcatgta aaaaataagc gggctttgct 4200
cgacgcctta gccattgaga tgttagatag gcaccatact cacttttgcc ctttagaagg 4260
ggaaagctgg caagattttt tacgtaataa cgctaaaagt tttagatgtg ctttactaag 4320
tcatcgcgat ggagcaaaag tacatttagg tacacggcct acagaaaaac agtatgaaac 4380
tctcgaaaat caattagcct ttttatgcca acaaggtttt tcactagaga atgcattata 4440
tgcactcagc gcagtggggc attttacttt aggttgcgta ttggaagatc aagagcatca 4500
agtcgctaaa gaagaaaggg aaacacctac tactgatagt atgccgccat tattacgaca 4560
agctatcgaa ttatttgatc accaaggtgc agagccagcc ttcttattcg gccttgaatt 4620
gatcatatgc ggattagaaa aacaacttaa atgtgaaagt gggtcttaaa agcagcataa 4680 ccttttttccg tgatggtaac ttcactagtt taaaaggatc taggtgaaga tcctttttga 4740
taatctcatg accaaaatcc cttaacgtga gttttcgttc cactgagcgt cagaccccgt 4800
agaaaagatc aaaggatctt cttgagatcc tttttttctg cgcgtaatct gctgcttgca 4860
aacaaaaaaa ccaccgctac cagcggtggt ttgtttgccg gatcaagagc taccaactct 4920
ttttccgaag gtaactggct tcagcagagc gcagatacca aatactgtcc ttctagtgta 4980
gccgtagtta ggccaccact tcaagaactc tgtagcaccg cctacatacc tcgctctgct 5040
aatcctgtta ccagtggctg ctgccagtgg cgataagtcg tgtcttaccg ggttggactc 5100
aagacgatag ttaccggata aggcgcagcg gtcgggctga acggggggtt cgtgcacaca 5160
gcccagcttg gagcgaacga cctacaccga actgagatac ctacagcgtg agctatgaga 5220
aagcgccacg cttcccgaag ggagaaaggc ggacaggtat ccggtaagcg gcagggtcgg 5280
aacaggagag cgcacgaggg agcttccagg gggaaacgcc tggtatcttt atagtcctgt 5340
cgggtttcgc cacctctgac ttgagcgtcg atttttgtga tgctcgtcag gggggcggag 5400
cctatggaaa aacgccagca acgcggcctt tttacggttc ctggcctttt gctggccttt 5460
tgctcacatg 5470

<210> SEQ ID NO 51
<211> LENGTH: 5470
<212> TYPE: DNA
<213> ORGANISM: Artificial Sequence
<220> FEATURE:
<223> OTHER INFORMATION: Nucleotide sequence of pASK75-PAS#1a(600)-
IL1Ra:

<400> SEQUENCE: 51
acccgacacc atcgaatggc cagatgatta attcctaatt tttgttgaca ctctatcatt 60
gatagagtta ttttaccact ccctatcagt gatagagaaa agtgaaatga atagttcgac 120
aaaaatctag ataacgaggg caaaaaatga aaaagacagc tatcgcgatt gcagtggcac 180
tggctggttt cgctaccgta gcgcaggccg ctagccatca ccatcaccac catagctctt 240
ctgcctctcc agctgcacct gctccagcaa gccctgctgc accagctccg tctgctcctg 300
ctgcctctcc agctgcacct gctccagcaa gccctgctgc accagctccg tctgctcctg 360
ctgcctctcc agctgcacct gctccagcaa gccctgctgc accagctccg tctgctcctg 420
ctgcctctcc agctgcacct gctccagcaa gccctgctgc accagctccg tctgctcctg 480
ctgcctctcc agctgcacct gctccagcaa gccctgctgc accagctccg tctgctcctg 540
ctgcctctcc agctgcacct gctccagcaa gccctgctgc accagctccg tctgctcctg 600
ctgcctctcc agctgcacct gctccagcaa gccctgctgc accagctccg tctgctcctg 660

-continued

```
ctgcctctcc agctgcacct gctccagcaa gccctgctgc accagctccg tctgctcctg    720
ctgcctctcc agctgcacct gctccagcaa gccctgctgc accagctccg tctgctcctg    780
ctgcctctcc agctgcacct gctccagcaa gccctgctgc accagctccg tctgctcctg    840
ctgcctctcc agctgcacct gctccagcaa gccctgctgc accagctccg tctgctcctg    900
ctgcctctcc agctgcacct gctccagcaa gccctgctgc accagctccg tctgctcctg    960
ctgcctctcc agctgcacct gctccagcaa gccctgctgc accagctccg tctgctcctg   1020
ctgcctctcc agctgcacct gctccagcaa gccctgctgc accagctccg tctgctcctg   1080
ctgcctctcc agctgcacct gctccagcaa gccctgctgc accagctccg tctgctcctg   1140
ctgcctctcc agctgcacct gctccagcaa gccctgctgc accagctccg tctgctcctg   1200
ctgcctctcc agctgcacct gctccagcaa gccctgctgc accagctccg tctgctcctg   1260
ctgcctctcc agctgcacct gctccagcaa gccctgctgc accagctccg tctgctcctg   1320
ctgcctctcc agctgcacct gctccagcaa gccctgctgc accagctccg tctgctcctg   1380
ctgcctctcc agctgcacct gctccagcaa gccctgctgc accagctccg tctgctcctg   1440
ctgcctctcc agctgcacct gctccagcaa gccctgctgc accagctccg tctgctcctg   1500
ctgcctctcc agctgcacct gctccagcaa gccctgctgc accagctccg tctgctcctg   1560
ctgcctctcc agctgcacct gctccagcaa gccctgctgc accagctccg tctgctcctg   1620
ctgcctctcc agctgcacct gctccagcaa gccctgctgc accagctccg tctgctcctg   1680
ctgcctctcc agctgcacct gctccagcaa gccctgctgc accagctccg tctgctcctg   1740
ctgcctctcc agctgcacct gctccagcaa gccctgctgc accagctccg tctgctcctg   1800
ctgcctctcc agctgcacct gctccagcaa gccctgctgc accagctccg tctgctcctg   1860
ctgcctctcc agctgcacct gctccagcaa gccctgctgc accagctccg tctgctcctg   1920
ctgcctctcc agctgcacct gctccagcaa gccctgctgc accagctccg tctgctcctg   1980
ctgcctctcc agctgcacct gctccagcaa gccctgctgc accagctccg tctgctcctg   2040
ctgcccgacc ctctgggaga aaatccagca agatgcaagc cttcagaatc tgggatgtta   2100
accagaagac cttctatctg aggaacaacc aactagttgc cggatacttg caaggaccaa   2160
atgtcaattt agaagaaaag atagatgtgg tacccattga gcctcatgct ctgttcttgg   2220
gaatccatgg agggaagatg tgcctgtcct gtgtcaagtc tggtgatgag accagactcc   2280
agctggaggc agttaacatc actgacctga gcgagaacag aaagcaggac aagcgcttcg   2340
ccttcatccg ctcagacagt ggccccacca ccagttttga gtctgccgcc tgccccggtt   2400
ggttcctctg cacagcgatg gaagctgacc agcccgtcag cctcaccaat atgcctgacg   2460
aaggcgtcat ggtcaccaaa ttctacttcc aggaggacga gtaagcttga cctgtgaagt   2520
gaaaaatggc gcacattgtg cgacattttt tttgtctgcc gtttaccgct actgcgtcac   2580
ggatctccac gcgccctgta gcggcgcatt aagcgcggcg ggtgtggtgg ttacgcgcag   2640
cgtgaccgct acacttgcca gcgccctagc gcccgctcct ttcgctttct tcccttcctt   2700
tctcgccacg ttcgccggct ttccccgtca agctctaaat cgggggctcc ctttagggtt   2760
ccgatttagt gctttacggc acctcgaccc caaaaaactt gattagggtg atggttcacg   2820
tagtgggcca tcgccctgat agacggtttt tcgccctttg acgttggagt ccacgttctt   2880
taatagtgga ctcttgttcc aaactggaac aacactcaac cctatctcgg tctattcttt   2940
tgatttataa gggattttgc cgatttcggc ctattggtta aaaaatgagc tgatttaaca   3000
aaaatttaac gcgaatttta acaaaatatt aacgtttaca atttcaggtg gcacttttcg   3060
```

```
gggaaatgtg cgcggaaccc ctatttgttt atttttctaa atacattcaa atatgtatcc   3120
gctcatgaga caataaccct gataaatgct tcaataatat tgaaaaagga agagtatgag   3180
tattcaacat ttccgtgtcg cccttattcc cttttttgcg gcattttgcc ttcctgtttt   3240
tgctcaccca gaaacgctgg tgaaagtaaa agatgctgaa gatcagttgg gtgcacgagt   3300
gggttacatc gaactggatc tcaacagcgg taagatcctt gagagttttc gccccgaaga   3360
acgttttcca atgatgagca cttttaaagt tctgctatgt ggcgcggtat tatcccgtat   3420
tgacgccggg caagagcaac tcggtcgccg catacactat tctcagaatg acttggttga   3480
gtactcacca gtcacagaaa agcatcttac ggatggcatg acagtaagag aattatgcag   3540
tgctgccata accatgagtg ataacactgc ggccaactta cttctgacaa cgatcggagg   3600
accgaaggag ctaaccgctt ttttgcacaa catgggggat catgtaactc gccttgatcg   3660
ttgggaaccg gagctgaatg aagccatacc aaacgacgag cgtgacacca cgatgcctgt   3720
agcaatggca acaacgttgc gcaaactatt aactggcgaa ctacttactc tagcttcccg   3780
gcaacaattg atagactgga tggaggcgga taaagttgca ggaccacttc tgcgctcggc   3840
ccttccggct ggctggttta ttgctgataa atctggagcc ggtgagcgtg gctctcgcgg   3900
tatcattgca gcactggggc cagatggtaa gccctcccgt atcgtagtta tctacacgac   3960
ggggagtcag gcaactatgg atgaacgaaa tagacagatc gctgagatag gtgcctcact   4020
gattaagcat tggtaggaat taatgatgtc tcgtttagat aaaagtaaag tgattaacag   4080
cgcattagag ctgcttaatg aggtcggaat cgaaggttta acaacccgta aactcgccca   4140
gaagctaggt gtagagcagc ctacattgta ttggcatgta aaaaataagc gggctttgct   4200
cgacgcctta gccattgaga tgttagatag gcaccatact cacttttgcc ctttagaagg   4260
ggaaagctgg caagattttt tacgtaataa cgctaaaagt tttagatgtg ctttactaag   4320
tcatcgcgat ggagcaaaag tacatttagg tacacggcct acagaaaaac agtatgaaac   4380
tctcgaaaat caattagcct ttttatgcca acaaggtttt tcactagaga atgcattata   4440
tgcactcagc gcagtggggc attttacttt aggttgcgta ttggaagatc aagagcatca   4500
agtcgctaaa gaagaaaggg aaacacctac tactgatagt atgccgccat tattacgaca   4560
agctatcgaa ttatttgatc accaaggtgc agagccagcc ttcttattcg gccttgaatt   4620
gatcatatgc ggattagaaa aacaacttaa atgtgaaagt gggtcttaaa agcagcataa   4680
cctttttccg tgatggtaac ttcactagtt taaaaggatc taggtgaaga tcctttttga   4740
taatctcatg accaaaatcc cttaacgtga gttttcgttc cactgagcgt cagaccccgt   4800
agaaaagatc aaaggatctt cttgagatcc tttttttctg cgcgtaatct gctgcttgca   4860
aacaaaaaaa ccaccgctac cagcggtggt ttgtttgccg gatcaagagc taccaactct   4920
ttttccgaag gtaactggct tcagcagagc gcagatacca aatactgtcc ttctagtgta   4980
gccgtagtta ggccaccact tcaagaactc tgtagcaccg cctacatacc tcgctctgct   5040
aatcctgtta ccagtggctg ctgccagtgg cgataagtcg tgtcttaccg ggttggactc   5100
aagacgatag ttaccggata aggcgcagcg gtcgggctga acggggggtt cgtgcacaca   5160
gcccagcttg gagcgaacga cctacaccga actgagatac ctacagcgtg agctatgaga   5220
aagcgccacg cttcccgaag ggagaaaggc ggacaggtat ccggtaagcg gcagggtcgg   5280
aacaggagag cgcacgaggg agcttccagg gggaaacgcc tggtatcttt atagtcctgt   5340
cgggtttcgc cacctctgac ttgagcgtcg atttttgtga tgctcgtcag gggggcggag   5400
```

cctatggaaa aacgccagca acgcggcctt tttacggttc ctggcctttt gctggccttt 5460
tgctcacatg 5470

<210> SEQ ID NO 52
<211> LENGTH: 3862
<212> TYPE: DNA
<213> ORGANISM: Artificial Sequence
<220> FEATURE:
<223> OTHER INFORMATION: Nucleotide sequence of pXL2-PAS#1c/1b(400):

<400> SEQUENCE: 52
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgg 240
ctcttctgcc agtcctgctg caccggcacc ggcatcaccg gctgcaccag cacctagtgc 300
accggcagct tctccggctg cccctgcgcc tgcatcacca gctgcgcctg caccgtctgc 360
ccctgcagct agtccagcag ctccagctcc ggcttctcct gcggctcctg caccaagtgc 420
gcctgcagca agtccggctg cgcctgcccc agctagtcct gctgctccgg caccgtcagc 480
tccggcagca tctcctgcag caccagcccc tgcaagtcca gcagcgccag ccccatcagc 540
accagcagct tcaccagccg caccagcgcc agcaagccct gctgccccag ctcctagcgc 600
accggcagcc agtcctgcag ctcctgcgcc tgctagtccg gcagccccag ctccaagtgc 660
ccctgccgct tcgcctgcag ccccagcacc agcttctcca gccgcaccgg caccttctgc 720
cccagctgca tctccggcag ctccggcacc agcaagcccg gcagcaccgg caccatctgc 780
gcctgccgca tctccggctg cgccagctcc agcctctcct gcagcgccag caccgagcgc 840
accagcagcc agccctgccg cacctgcgcc cgcatcacct gcggcacctg caccttccgc 900
cccggctgca tctcctgccg cacccgcgcc tgccagccca gctgcacctg ccccaagtgc 960
gccagcagca tcccctgccg cgcctgcccc cgctagtcca gcggccccag ctccatctgc 1020
accagctgct agccctgctg caccagctcc tgcttctccc gcagccccag cgccttctgc 1080
tcccgcagcc tcacctgcgg ccccggcacc agcatctcca gcggcaccag caccttcggc 1140
ccctgctgct agcccagcag cacctgcgcc agcctcacca gctgctcccg ctcctagtgc 1200
cccggcggcc tcgcctgctg ctcctgcacc agcttcgcca gcggcaccgg ctccttcggc 1260
gccggctgct tcaccagcag cacctgctcc agcgtcccca gcggcccctg ctccaagtgc 1320
tccggctgca tcgcctgccg ctcctgctcc tgcatcccca gctgctccag caccaagcgc 1380
acctgccgcc tcaccagcgg cgccagcacc cgccagccca gcagcgcctg ctccatccgc 1440
accggcggcc agaagagtag aattcactgg ccgtcgtttt acaacgtcgt gactgggaaa 1500
accctggcgt tacccaactt aatcgccttg cagcacatcc ccctttcgcc agctggcgta 1560
atagcgagga ggcccgcacc gatcgccctt cccaacagtt gcgcagcctg aatggcgaat 1620
ggcgcctgat gcggtatttt ctccttacgc atctgtgcgg tatttcacac cgcatatggt 1680
gcactctcag tacaatctgc tctgatgccg catagttaag ccagccccga cacccgccaa 1740
cacccgctga cgcgccctga cgggcttgtc tgctcccggc atccgcttac agacaagctg 1800
tgaccgtctc cgggagctgc atgtgtcaga ggttttcacc gtcatcaccg aaacgcgcga 1860
gacgaaaggg cctcgtgata cgcctatttt tataggttaa tgtcatgata ataatggttt 1920
cttagacgtc aggtggcact tttcggggaa atgtgcgcgg aacccctatt tgtttatttt 1980
tctaaataca ttcaaatatg tatccgctca tgagacaata accctgataa atgcttcaat 2040
aatattgaaa aaggacgagt atgagtattc aacatttccg tgtcgccctt attccctttt 2100
ttgcggcatt ttgccttcct gtttttgctc acccagaaac gctggtgaaa gtaaaagatg 2160
ctgaagatca gttgggtgca cgagtgggtt acatcgaact ggatctcaac agcggtaaga 2220
tccttgagag ttttcgcccc gaagaacgtt ttccaatgat gagcactttt aaagttctgc 2280
tatgtggcgc ggtattatcc cgtattgacg ccgggcaaga gcaactcggt cgccgcatac 2340
actattctca gaatgacttg gttgagtact caccagtcac agaaaagcat cttacggatg 2400
gcatgacagt aagagaatta tgcagtgctg ccataaccat gagtgataac actgcggcca 2460
acttacttct gacaacgatc ggaggaccga aggagctaac cgcttttttg cacaacatgg 2520
gggatcatgt aactcgcctt gatcgttggg aaccggagct gaatgaagcc ataccaaacg 2580
acgagcgtga caccacgatg cctgtagcaa tggcaacaac gttgcgcaaa ctattaactg 2640
gcgaactact tactctagct tcccggcaac aattaataga ctggatggag gcggataaag 2700
ttgcaggacc acttctgcgc tcggcccttc cggctggctg gtttattgct gataaatctg 2760
gagccggtga gcgtgggtct cgcggtatca ttgcagcact ggggccagat ggtaagccct 2820
cccgtatcgt agttatctac acgacgggga gtcaggcaac tatggatgaa cgaaatagac 2880
agatcgctga gataggtgcc tcactgatta agcattggta actgtcagac caagtttact 2940
catatatact ttagattgat ttaaaacttc atttttaatt taaaaggatc taggtgaaga 3000
tcctttttga taatctcatg accaaaatcc cttaacgtga gttttcgttc cactgagcgt 3060
cagaccccgt agaaaagatc aaaggatctt cttgagatcc tttttttctg cgcgtaatct 3120
gctgcttgca aacaaaaaaa ccaccgctac cagcggtggt ttgtttgccg gatcaagagc 3180
taccaactct ttttccgaag gtaactggct tcagcagagc gcagatacca aatactgttc 3240
ttctagtgta gccgtagtta ggccaccact tcaagaactc tgtagcaccg cctacatacc 3300
tcgctctgct aatcctgtta ccagtggctg ctgccagtgg cgataagtcg tgtcttaccg 3360
ggttggactc aagacgatag ttaccggata aggcgcagcg gtcgggctga acggggggtt 3420
cgtgcacaca gcccagcttg gagcgaacga cctacaccga actgagatac ctacagcgtg 3480
agctatgaga aagcgccacg cttcccgaag ggagaaaggc ggacaggtat ccggtaagcg 3540
gcagggtcgg aacaggagag cgcacgaggg agcttccagg gggaaacgcc tggtatcttt 3600
atagtcctgt cgggtttcgc cacctctgac ttgagcgtcg atttttgtga tgctcgtcag 3660
gggggcggag cctatggaaa aacgccagca acgcggcctt tttacggttc ctggcctttt 3720
gctggccttt tgctcacatg ttctttcctg cgttatcccc tgattctgtg gataaccgta 3780
ttaccgcctt tgagtgagct gataccgctc gccgcagccg aacgaccgag cgcagcgagt 3840
cagtgagcga ggaagcggag aa 3862

<210> SEQ ID NO 53
<211> LENGTH: 5520
<212> TYPE: DNA
<213> ORGANISM: Artificial Sequence
<220> FEATURE:
<223> OTHER INFORMATION: Nucleotide sequence of
pASK37-MP-PA#1d/1c/1b(600)

<400> SEQUENCE: 53
acccgacacc atcgaatggc gcaaaacctt tcgcggtatg gcatgatagc gcccggaaga 60
gagtcaattc agggtggtga atgtgaaacc agtaacgtta tacgatgtcg cagagtatgc 120

-continued

```
cggtgtctct tatcagaccg tttcccgcgt ggtgaaccag gccagccacg tttctgcgaa    180
aacgcgggaa aaagtggaag cggcgatggc ggagctgaat tacattccca accgcgtggc    240
acaacaactg gcgggcaaac agtcgttgct gattggcgtt gccacctcca gtctggccct    300
gcacgcgccg tcgcaaattg tcgcggcgat taaatctcgc gccgatcaac tgggtgccag    360
cgtggtggtg tcgatggtag aacgaagcgg cgtcgaagcc tgtaaagcgg cggtgcacaa    420
tcttctcgcg caacgcgtca gtgggctgat cattaactat ccgctggatg accaggatgc    480
cattgctgtg gaagctgcct gcactaatgt tccggcgtta tttcttgatg tctctgacca    540
gacacccatc aacagtatta ttttctccca tgaagacggt acgcgactgg gcgtggagca    600
tctggtcgca ttgggtcacc agcaaatcgc gctgttagcg ggcccattaa gttctgtctc    660
ggcgcgtctg cgtctggctg gctggcataa atatctcact cgcaatcaaa ttcagccgat    720
agcggaacgg gaaggcgact ggagtgccat gtccggtttt caacaaacca tgcaaatgct    780
gaatgagggc atcgttccca ctgcgatgct ggttgccaac gatcagatgg cgctgggcgc    840
aatgcgcgcc attaccgagt ccgggctgcg cgttggtgcg gatatctcgg tagtgggata    900
cgacgatacc gaagacagct catgttatat cccgccgtta accaccatca aacaggattt    960
tcgcctgctg gggcaaacca gcgtggaccg cttgctgcaa ctctctcagg gccaggcggt   1020
gaagggcaat cagctgttgc ccgtctcact ggtgaaaaga aaaaccaccc tggcgcccaa   1080
tacgcaaacc gcctctcccc gcgcgttggc cgattcatta atgcagctgg cacgacaggt   1140
ttcccgactg gaaagcgggc agtgagcgca acgcaattaa tgtgagttag ctcactcatt   1200
aggcacccca ggctttacac tttatgcttc cggctcgtat aatgtgtgga attgtgagcg   1260
gataacaatt tcacacagga aacagctatg accatgatta cggattcact ggaactctag   1320
aaataatttt gtttaacttt aagaaggaga tatacatatg ccagccgctc ctgctgcccc   1380
tgctcccgct gcccccgccg cccccgcccc agctgccccc gctgccgcac ctgctgcccc   1440
agctcccgct gccccagccg cgccggcccc cgcagctcca gccgcggcac cagctgcccc   1500
agctccagcg gcgcctgctg ccccggcccc cgcggcaccg gctgccgcgc ccgcagctcc   1560
agcgcctgct gcaccggctg ctccggcacc cgccgcgcca gcagctgccc ctgcggcacc   1620
agctcctgct gcccccgcgg cacctgcacc cgctgccccg gcggcagctc ccgccgcgcc   1680
agcccctgca gctcctgctg cacctgctcc tgccgcccct gctgctgccc ctgctgctcc   1740
agcccctgca gcaccggccg ctccagctcc tgccgctcct gccgctgcgc ccgctgctcc   1800
agccccagct gcgccagcag ctcctgcacc tgctgcccct gccgccgccc ctgcggctcc   1860
agcacctgct gcaccggccg ccccggcgcc cgctgccccc gcagcagccc cagccgcacc   1920
cgctccagca gctcccgcag ccccagcacc cgcagcacca gccgccgcgc cagcggcccc   1980
ggcccctgcc gcgcccgctg ctcccgcccc tgctgcccca gccgccgctc ctgcggcacc   2040
tgcgcccgcc gcgccggcag cgccggcacc ggcagctccg gcggccgcgc ctgcagctcc   2100
tgcaccggcg gctccagcag ccccggcgcc ggccgcacct gcggcggcgc ccgcggcgcc   2160
tgcacccgca gcgcctgcgg caccggcccc agcagcccct gccgccgcac cggctgcgcc   2220
tgccccagcg gcccccgctg ccccggcccc ggcggctcca gccgcagcgc ctgccgcccc   2280
agcgcccgca gcaccggcgg caccagctcc ggcggcgccg gcggcggctc cggcagctcc   2340
ggcccctgct gcgccggctg cgccggctcc ggcggcccct gcggcggctc cggccgcacc   2400
tgcacctgcc gcgccggctg ctccggcccc ggctgcccca gcagcggcac cagcagcgcc   2460
```

-continued

```
tgctcctgcg gcgcctgcag ctccggcgcc ggcagccccg gccgccgcac ccgcggctcc   2520
agccccccgcc gctccagcag cccccgcgcc agctgcacct gctgccgcac cggctgcccc   2580
agcccctgcc gcaccagcag ctcccgcccc tgcagccccc gccgccgctc cggccgcacc   2640
agccccggct gcccctgctg cccccgcccc ggcagcaccc gctgcagcac cagccgcgcc   2700
tgcaccggca gctcctgcag ccccggcacc ggcagcacct gccgcagcac ccgcagcccc   2760
agccccagca gcgcctgccg ctccagcacc agcggcaccg gccgccgcac cagccgcccc   2820
agcaccggca gcccccgcag cgccggcacc agccgctcca gccgccgccc cagcagcccc   2880
ggctccggcc gctcccgcgg ctccagcacc agcagctcca gcggccgctc cggcagcgcc   2940
ggccccagca gcacctgcag cccctgcacc agcagcgcca gccgcggcgc ccgcagctcc   3000
cgcacctgcg gctcccgcag cccctgcacc cgcggcgcca gcagccgccc ctgcagcgcc   3060
agctcctgca gcacctgcag ctccagcccc ggccgcccca gctgcagctc ctgcggcccc   3120
agcacctgcc gcccctgccg caccggctcc agccgcccca gccgcctaag cttgacctgt   3180
gaagtgaaaa atggcgcaca ttgtgcgaca tttttttgt ctgccgttta ccgctactgc   3240
gtcacggatc cccacgcgcc ctgtagcggc gcattaagcg cggcgggtgt ggtggttacg   3300
cgcagcgtga ccgctacact tgccagcgcc ctagcgcccg ctcctttcgc tttcttccct   3360
tcctttctcg ccacgttcgc cggctttccc cgtcaagctc taaatcgggg catcccttta   3420
gggttccgat ttagtgcttt acggcacctc gaccccaaaa aacttgatta gggtgatggt   3480
tcacgtagtg ggccatcgcc ctgatagacg gtttttcgcc ctttgacgtt ggagtccacg   3540
ttctttaata gtggactctt gttccaaact ggaacaacac tcaaccctat ctcggtctat   3600
tcttttgatt tataagggat tttgccgatt tcggcctatt ggttaaaaaa tgagctgatt   3660
taacaaaaat ttaacgcgaa ttttaacaaa atattaacgt ttacaatttc aggtggcact   3720
tttcggggaa atgtgcgcgg aacccctatt tgtttatttt tctaaataca ttcaaatatg   3780
tatccgctca tgagacaata accctgataa atgcttcaat aatattgaaa aaggaagagt   3840
atgagtattc aacatttccg tgtcgccctt attccctttt ttgcggcatt ttgccttcct   3900
gtttttgctc acccagaaac gctggtgaaa gtaaaagatg ctgaagatca gttgggtgca   3960
cgagtgggtt acatcgaact ggatctcaac agcggtaaga tccttgagag ttttcgcccc   4020
gaagaacgtt ttccaatgat gagcactttt aaagttctgc tatgtggcgc ggtattatcc   4080
cgtattgacg ccgggcaaga gcaactcggt cgccgcatac actattctca gaatgacttg   4140
gttgagtact caccagtcac agaaaagcat cttacggatg gcatgacagt aagagaatta   4200
tgcagtgctg ccataaccat gagtgataac actgcggcca acttacttct gacaacgatc   4260
ggaggaccga aggagctaac cgcttttttg cacaacatgg gggatcatgt aactcgcctt   4320
gatcgttggg aaccggagct gaatgaagcc ataccaaacg acgagcgtga caccacgatg   4380
cctgtagcaa tggcaacaac gttgcgcaaa ctattaactg gcgaactact tactctagct   4440
tcccggcaac aattaataga ctggatggag gcggataaag ttgcaggacc acttctgcgc   4500
tcggcccttc cggctggctg gtttattgct gataaatctg gagccggtga gcgtgggtct   4560
cgcggtatca ttgcagcact ggggccagat ggtaagccct cccgtatcgt agttatctac   4620
acgacgggga gtcaggcaac tatggatgaa cgaaatagac agatcgctga gataggtgcc   4680
tcactgatta agcattggta actgtcagac caagtttact catatatact ttagattgat   4740
ttaaaacttc atttttaatt taaaaggatc taggtgaaga tcctttttga taatctcatg   4800
accaaaatcc cttaacgtga gttttcgttc cactgagcgt cagaccccgt agaaaagatc   4860
```

aaaggatctt cttgagatcc tttttttctg cgcgtaatct gctgcttgca aacaaaaaaa 4920
ccaccgctac cagcggtggt ttgtttgccg gatcaagagc taccaactct ttttccgaag 4980
gtaactggct tcagcagagc gcagatacca aatactgtcc ttctagtgta gccgtagtta 5040
ggccaccact tcaagaactc tgtagcaccg cctacatacc tcgctctgct aatcctgtta 5100
ccagtggctg ctgccagtgg cgataagtcg tgtcttaccg ggttggactc aagacgatag 5160
ttaccggata aggcgcagcg gtcgggctga acggggggtt cgtgcacaca gcccagcttg 5220
gagcgaacga cctacaccga actgagatac ctacagcgtg agctatgaga aagcgccacg 5280
cttcccgaag ggagaaaggc ggacaggtat ccggtaagcg gcagggtcgg aacaggagag 5340
cgcacgaggg agcttccagg gggaaacgcc tggtatcttt atagtcctgt cgggtttcgc 5400
cacctctgac ttgagcgtcg atttttgtga tgctcgtcag gggggcggag cctatggaaa 5460
aacgccagca acgcggcctt tttacggttc ctggcctttt gctggccttt tgctcacatg 5520

<210> SEQ ID NO 54
<211> LENGTH: 3262
<212> TYPE: DNA
<213> ORGANISM: Artificial Sequence
<220> FEATURE:
<223> OTHER INFORMATION: Nucleotide sequence of pXL2-PA#1b(200)

<400> SEQUENCE: 54
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgg 240
ctcttctgcc gctcctgctg cccctgctcc cgctgccccc gccgcccccg ccccagctgc 300
ccccgctgcc gcacctgctg ccccagctcc cgctgcccca gccgcgccgg cccccgcagc 360
tccagccgcg gcaccagctg ccccagctcc agcggcgcct gctgccccgg cccccgcggc 420
accggctgcc gcgcccgcag ctccagcgcc tgctgcaccg gctgctccgg cacccgccgc 480
gccagcagct gcccctgcgg caccagctcc tgctgccccc gcggcacctg cacccgctgc 540
cccggcggca gctcccgccg cgccagcccc tgcagctcct gctgcacctg ctcctgccgc 600
ccctgctgct gcccctgctg ctccagcccc tgcagcaccg gccgctccag ctcctgccgc 660
tcctgccgct gcgcccgctg ctccagcccc agctgcgcca gcagctcctg cacctgctgc 720
ccctgccgcc gcccctgcgg ctccagcacc tgctgcaccg gccgccccgg cgcccgctgc 780
ccccgcagca gccccagccg cacccgctcc agcagctccc gcagccccag cacccgcagc 840
accagccgcc agaagagtag aattcactgg ccgtcgtttt acaacgtcgt gactgggaaa 900
accctggcgt tacccaactt aatcgccttg cagcacatcc ccctttcgcc agctggcgta 960
atagcgagga ggcccgcacc gatcgccctt cccaacagtt gcgcagcctg aatggcgaat 1020
ggcgcctgat gcggtatttt ctccttacgc atctgtgcgg tatttcacac cgcatatggt 1080
gcactctcag tacaatctgc tctgatgccg catagttaag ccagccccga cacccgccaa 1140
cacccgctga cgcgccctga cgggcttgtc tgctcccggc atccgcttac agacaagctg 1200
tgaccgtctc cgggagctgc atgtgtcaga ggttttcacc gtcatcaccg aaacgcgcga 1260
gacgaaaggg cctcgtgata cgcctatttt tataggttaa tgtcatgata ataatggttt 1320
cttagacgtc aggtggcact tttcggggaa atgtgcgcgg aacccctatt tgtttatttt 1380
tctaaataca ttcaaatatg tatccgctca tgagacaata accctgataa atgcttcaat 1440
aatattgaaa aaggacgagt atgagtattc aacatttccg tgtcgccctt attccctttt 1500
ttgcggcatt ttgccttcct gtttttgctc acccagaaac gctggtgaaa gtaaaagatg 1560
ctgaagatca gttgggtgca cgagtgggtt acatcgaact ggatctcaac agcggtaaga 1620
tccttgagag ttttcgcccc gaagaacgtt ttccaatgat gagcactttt aaagttctgc 1680
tatgtggcgc ggtattatcc cgtattgacg ccgggcaaga gcaactcggt cgccgcatac 1740
actattctca gaatgacttg gttgagtact caccagtcac agaaaagcat cttacggatg 1800
gcatgacagt aagagaatta tgcagtgctg ccataaccat gagtgataac actgcggcca 1860
acttacttct gacaacgatc ggaggaccga aggagctaac cgcttttttg cacaacatgg 1920
gggatcatgt aactcgcctt gatcgttggg aaccggagct gaatgaagcc ataccaaacg 1980
acgagcgtga caccacgatg cctgtagcaa tggcaacaac gttgcgcaaa ctattaactg 2040
gcgaactact tactctagct tcccggcaac aattaataga ctggatggag gcggataaag 2100
ttgcaggacc acttctgcgc tcggcccttc cggctggctg gtttattgct gataaatctg 2160
gagccggtga gcgtgggtct cgcggtatca ttgcagcact ggggccagat ggtaagccct 2220
cccgtatcgt agttatctac acgacgggga gtcaggcaac tatggatgaa cgaaatagac 2280
agatcgctga gataggtgcc tcactgatta agcattggta actgtcagac caagtttact 2340
catatatact ttagattgat ttaaaacttc atttttaatt taaaaggatc taggtgaaga 2400
tcctttttga taatctcatg accaaaatcc cttaacgtga gttttcgttc cactgagcgt 2460
cagaccccgt agaaaagatc aaaggatctt cttgagatcc tttttttctg cgcgtaatct 2520
gctgcttgca aacaaaaaaa ccaccgctac cagcggtggt ttgtttgccg gatcaagagc 2580
taccaactct ttttccgaag gtaactggct tcagcagagc gcagatacca aatactgttc 2640
ttctagtgta gccgtagtta ggccaccact tcaagaactc tgtagcaccg cctacatacc 2700
tcgctctgct aatcctgtta ccagtggctg ctgccagtgg cgataagtcg tgtcttaccg 2760
ggttggactc aagacgatag ttaccggata aggcgcagcg gtcgggctga acggggggtt 2820
cgtgcacaca gcccagcttg gagcgaacga cctacaccga actgagatac ctacagcgtg 2880
agctatgaga aagcgccacg cttcccgaag ggagaaaggc ggacaggtat ccggtaagcg 2940
gcagggtcgg aacaggagag cgcacgaggg agcttccagg gggaaacgcc tggtatcttt 3000
atagtcctgt cgggtttcgc cacctctgac ttgagcgtcg atttttgtga tgctcgtcag 3060
gggggcggag cctatggaaa aacgccagca acgcggcctt tttacggttc ctggcctttt 3120
gctggccttt tgctcacatg ttctttcctg cgttatcccc tgattctgtg gataaccgta 3180
ttaccgcctt tgagtgagct gataccgctc gccgcagccg aacgaccgag cgcagcgagt 3240
cagtgagcga ggaagcggag aa 3262

<210> SEQ ID NO 55
<211> LENGTH: 2662
<212> TYPE: DNA
<213> ORGANISM: Artificial Sequence
<220> FEATURE:
<223> OTHER INFORMATION: Nucleotide sequence of plasmid pXL1

<400> SEQUENCE: 55
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180

-continued tgtgagcgga taacaatttc acacaggaaa cagctatgac catgattacg ccaagcttgg 240
ctcttcaggc agaagagcag aattcactgg ccgtcgtttt acaacgtcgt gactgggaaa 300
accctggcgt tacccaactt aatcgccttg cagcacatcc ccctttcgcc agctggcgta 360
atagcgaaga ggcccgcacc gatcgccctt cccaacagtt gcgcagcctg aatggcgaat 420
ggcgcctgat gcggtatttt ctccttacgc atctgtgcgg tatttcacac cgcatatggt 480
gcactctcag tacaatctgc tctgatgccg catagttaag ccagccccga cacccgccaa 540
cacccgctga cgcgccctga cgggcttgtc tgctcccggc atccgcttac agacaagctg 600
tgaccgtctc cgggagctgc atgtgtcaga ggttttcacc gtcatcaccg aaacgcgcga 660
gacgaaaggg cctcgtgata cgcctatttt tataggttaa tgtcatgata ataatggttt 720
cttagacgtc aggtggcact tttcggggaa atgtgcgcgg aacccctatt tgtttatttt 780
tctaaataca ttcaaatatg tatccgctca tgagacaata accctgataa atgcttcaat 840
aatattgaaa aaggaagagt atgagtattc aacatttccg tgtcgccctt attccctttt 900
ttgcggcatt ttgccttcct gtttttgctc acccagaaac gctggtgaaa gtaaaagatg 960
ctgaagatca gttgggtgca cgagtgggtt acatcgaact ggatctcaac agcggtaaga 1020
tccttgagag ttttcgcccc gaagaacgtt ttccaatgat gagcactttt aaagttctgc 1080
tatgtggcgc ggtattatcc cgtattgacg ccgggcaaga gcaactcggt cgccgcatac 1140
actattctca gaatgacttg gttgagtact caccagtcac agaaaagcat cttacggatg 1200
gcatgacagt aagagaatta tgcagtgctg ccataaccat gagtgataac actgcggcca 1260
acttacttct gacaacgatc ggaggaccga aggagctaac cgcttttttg cacaacatgg 1320
gggatcatgt aactcgcctt gatcgttggg aaccggagct gaatgaagcc ataccaaacg 1380
acgagcgtga caccacgatg cctgtagcaa tggcaacaac gttgcgcaaa ctattaactg 1440
gcgaactact tactctagct tcccggcaac aattaataga ctggatggag gcggataaag 1500
ttgcaggacc acttctgcgc tcggcccttc cggctggctg gtttattgct gataaatctg 1560
gagccggtga gcgtgggtct cgcggtatca ttgcagcact ggggccagat ggtaagccct 1620
cccgtatcgt agttatctac acgacgggga gtcaggcaac tatggatgaa cgaaatagac 1680
agatcgctga gataggtgcc tcactgatta agcattggta actgtcagac caagtttact 1740
catatatact ttagattgat ttaaaacttc atttttaatt taaaaggatc taggtgaaga 1800
tcctttttga taatctcatg accaaaatcc cttaacgtga gttttcgttc cactgagcgt 1860
cagaccccgt agaaaagatc aaaggatctt cttgagatcc tttttttctg cgcgtaatct 1920
gctgcttgca aacaaaaaaa ccaccgctac cagcggtggt ttgtttgccg gatcaagagc 1980
taccaactct ttttccgaag gtaactggct tcagcagagc gcagatacca aatactgttc 2040
ttctagtgta gccgtagtta ggccaccact tcaagaactc tgtagcaccg cctacatacc 2100
tcgctctgct aatcctgtta ccagtggctg ctgccagtgg cgataagtcg tgtcttaccg 2160
ggttggactc aagacgatag ttaccggata aggcgcagcg gtcgggctga acggggggtt 2220
cgtgcacaca gcccagcttg gagcgaacga cctacaccga actgagatac ctacagcgtg 2280
agctatgaga aagcgccacg cttcccgaag ggagaaaggc ggacaggtat ccggtaagcg 2340
gcagggtcgg aacaggagag cgcacgaggg agcttccagg gggaaacgcc tggtatcttt 2400
atagtcctgt cgggtttcgc cacctctgac ttgagcgtcg atttttgtga tgctcgtcag 2460
gggggcggag cctatggaaa aacgccagca acgcggcctt tttacggttc ctggcctttt 2520
gctggccttt tgctcacatg ttctttcctg cgttatcccc tgattctgtg gataaccgta 2580
ttaccgcctt tgagtgagct gataccgctc gccgcagccg aacgaccgag cgcagcgagt 2640
cagtgagcga ggaagcggag aa 2662

<210> SEQ ID NO 56
<211> LENGTH: 4240
<212> TYPE: DNA
<213> ORGANISM: Artificial Sequence
<220> FEATURE:
<223> OTHER INFORMATION: Nucleotide sequence of pASK75-PA#1b(200)-IL1RA
      encoding the proline/alanine-rich sequence PA#1 seamless fused
      with IL1Ra

<400> SEQUENCE: 56
acccgacacc atcgaatggc cagatgatta attcctaatt tttgttgaca ctctatcatt 60
gatagagtta ttttaccact ccctatcagt gatagagaaa agtgaaatga atagttcgac 120
aaaaatctag ataacgaggg caaaaaatga aaaagacagc tatcgcgatt gcagtggcac 180
tggctggttt cgctaccgta gcgcaggccg ccgccgctcc tgctgcccct gctcccgctg 240
cccccgccgc ccccgcccca gctgcccccg ctgccgcacc tgctgcccca gctcccgctg 300
ccccagccgc gccggccccc gcagctccag ccgcggcacc agctgcccca gctccagcgg 360
cgcctgctgc ccccggcccc gcggcaccgg ctgccgcgcc cgcagctcca gcgcctgctg 420
caccggctgc tccggcaccc gccgcgccag cagctgcccc tgcggcacca gctcctgctg 480
cccccgcggc acctgcaccc gctgccccgg cggcagctcc cgccgcgcca gcccctgcag 540
ctcctgctgc acctgctcct gccgcccctg ctgctgcccc tgctgctcca gcccctgcag 600
caccggccgc tccagctcct gccgctcctg ccgctgcgcc cgctgctcca gccccagctg 660
cgccagcagc tcctgcacct gctgcccctg ccgccgcccc tgcggctcca gcacctgctg 720
caccggccgc cccggcgccc gctgccccg cagcagcccc agccgcaccc gctccagcag 780
ctcccgcagc cccagcaccc gcagcaccag ccgcccgacc ctctgggaga aaatccagca 840
agatgcaagc cttcagaatc tgggatgtta accagaagac cttctatctg aggaacaacc 900
aactagttgc cggatacttg caaggaccaa atgtcaattt agaagaaaag atagatgtgg 960
tacccattga gcctcatgct ctgttcttgg gaatccatgg agggaagatg tgcctgtcct 1020
gtgtcaagtc tggtgatgag accagactcc agctggaggc agttaacatc actgacctga 1080
gcgagaacag aaagcaggac aagcgcttcg ccttcatccg ctcagacagt ggccccacca 1140
ccagttttga gtctgccgcc tgccccggtt ggttcctctg cacagcgatg gaagctgacc 1200
agcccgtcag cctcaccaat atgcctgacg aaggcgtcat ggtcaccaaa ttctacttcc 1260
aggaggacga gtaagcttga cctgtgaagt gaaaaatggc gcacattgtg cgacattttt 1320
tttgtctgcc gtttaccgct actgcgtcac ggatctccac gcgccctgta gcggcgcatt 1380
aagcgcggcg ggtgtggtgg ttacgcgcag cgtgaccgct acacttgcca gcgccctagc 1440
gcccgctcct ttcgctttct tcccttcctt tctcgccacg ttcgccggct ttccccgtca 1500
agctctaaat cgggggctcc ctttagggtt ccgatttagt gctttacggc acctcgaccc 1560
caaaaaactt gattagggtg atggttcacg tagtgggcca tcgccctgat agacggtttt 1620
tcgccctttg acgttggagt ccacgttctt taatagtgga ctcttgttcc aaactggaac 1680
aacactcaac cctatctcgg tctattcttt tgatttataa gggattttgc cgatttcggc 1740
ctattggtta aaaaatgagc tgatttaaca aaaatttaac gcgaatttta acaaaatatt 1800
aacgtttaca atttcaggtg gcacttttcg gggaaatgtg cgcggaaccc ctatttgttt 1860

```
atttttctaa atacattcaa atatgtatcc gctcatgaga caataaccct gataaatgct   1920
tcaataatat tgaaaaagga agagtatgag tattcaacat ttccgtgtcg cccttattcc   1980
ctttttttgcg gcattttgcc ttcctgtttt tgctcaccca gaaacgctgg tgaaagtaaa   2040
agatgctgaa gatcagttgg gtgcacgagt gggttacatc gaactggatc tcaacagcgg   2100
taagatcctt gagagttttc gccccgaaga acgttttcca atgatgagca cttttaaagt   2160
tctgctatgt ggcgcggtat tatcccgtat tgacgccggg caagagcaac tcggtcgccg   2220
catacactat tctcagaatg acttggttga gtactcacca gtcacagaaa agcatcttac   2280
ggatggcatg acagtaagag aattatgcag tgctgccata accatgagtg ataacactgc   2340
ggccaactta cttctgacaa cgatcggagg accgaaggag ctaaccgctt ttttgcacaa   2400
catgggggat catgtaactc gccttgatcg ttgggaaccg gagctgaatg aagccatacc   2460
aaacgacgag cgtgacacca cgatgcctgt agcaatggca acaacgttgc gcaaactatt   2520
aactggcgaa ctacttactc tagcttcccg gcaacaattg atagactgga tggaggcgga   2580
taaagttgca ggaccacttc tgcgctcggc ccttccggct ggctggttta ttgctgataa   2640
atctggagcc ggtgagcgtg gctctcgcgg tatcattgca gcactggggc cagatggtaa   2700
gccctcccgt atcgtagtta tctacacgac ggggagtcag gcaactatgg atgaacgaaa   2760
tagacagatc gctgagatag gtgcctcact gattaagcat tggtaggaat taatgatgtc   2820
tcgtttagat aaaagtaaag tgattaacag cgcattagag ctgcttaatg aggtcggaat   2880
cgaaggttta acaacccgta aactcgccca gaagctaggt gtagagcagc ctacattgta   2940
ttggcatgta aaaaataagc gggctttgct cgacgcctta gccattgaga tgttagatag   3000
gcaccatact cacttttgcc ctttagaagg ggaaagctgg caagattttt tacgtaataa   3060
cgctaaaagt tttagatgtg ctttactaag tcatcgcgat ggagcaaaag tacatttagg   3120
tacacggcct acagaaaaac agtatgaaac tctcgaaaat caattagcct ttttatgcca   3180
acaaggtttt tcactagaga atgcattata tgcactcagc gcagtggggc attttacttt   3240
aggttgcgta ttggaagatc aagagcatca agtcgctaaa gaagaaaggg aaacacctac   3300
tactgatagt atgccgccat tattacgaca agctatcgaa ttatttgatc accaaggtgc   3360
agagccagcc ttcttattcg gccttgaatt gatcatatgc ggattagaaa aacaacttaa   3420
atgtgaaagt gggtcttaaa agcagcataa cctttttccg tgatggtaac ttcactagtt   3480
taaaaggatc taggtgaaga tcctttttga taatctcatg accaaaatcc cttaacgtga   3540
gttttcgttc cactgagcgt cagaccccgt agaaaagatc aaaggatctt cttgagatcc   3600
tttttttctg cgcgtaatct gctgcttgca aacaaaaaaa ccaccgctac cagcggtggt   3660
ttgtttgccg gatcaagagc taccaactct ttttccgaag gtaactggct tcagcagagc   3720
gcagatacca aatactgtcc ttctagtgta gccgtagtta ggccaccact tcaagaactc   3780
tgtagcaccg cctacatacc tcgctctgct aatcctgtta ccagtggctg ctgccagtgg   3840
cgataagtcg tgtcttaccg ggttggactc aagacgatag ttaccggata aggcgcagcg   3900
gtcgggctga acggggggtt cgtgcacaca gcccagcttg gagcgaacga cctacaccga   3960
actgagatac ctacagcgtg agctatgaga aagcgccacg cttcccgaag ggagaaaggc   4020
ggacaggtat ccggtaagcg gcagggtcgg aacaggagag cgcacgaggg agcttccagg   4080
gggaaacgcc tggtatcttt atagtcctgt cgggtttcgc cacctctgac ttgagcgtcg   4140
atttttgtga tgctcgtcag gggggcggag cctatggaaa aacgccagca acgcggcctt   4200
```

-continued tttacggttc ctggcctttt gctggccttt tgctcacatg 4240

<210> SEQ ID NO 57
<211> LENGTH: 20
<212> TYPE: PRT
<213> ORGANISM: Artificial Sequence
<220> FEATURE:
<223> OTHER INFORMATION: Amino acid sequence of a PA#3

<400> SEQUENCE: 57

Ala Ala Ala Pro Ala Ala Ala Pro Ala Ala Ala Pro Ala Ala Ala Pro
1 5 10 15

Ala Ala Ala Pro
20

<210> SEQ ID NO 58
<211> LENGTH: 18
<212> TYPE: PRT
<213> ORGANISM: Artificial Sequence
<220> FEATURE:
<223> OTHER INFORMATION: Amino acid sequence of a PA#5

<400> SEQUENCE: 58

Ala Ala Ala Ala Ala Pro Ala Ala Ala Ala Ala Pro Ala Ala Ala Ala
1 5 10 15

Ala Pro

<210> SEQ ID NO 59
<211> LENGTH: 46
<212> TYPE: DNA
<213> ORGANISM: Artificial Sequence
<220> FEATURE:
<223> OTHER INFORMATION: Upper nucleotide strand depicted in Figure 1C

<400> SEQUENCE: 59
tacgccaagc ttggctcttc tgccagaaga gtagaattca ctggcc 46

<210> SEQ ID NO 60
<211> LENGTH: 46
<212> TYPE: DNA
<213> ORGANISM: Artificial Sequence
<220> FEATURE:
<223> OTHER INFORMATION: Lower nucleotide strand depicted in Figure 1C

<400> SEQUENCE: 60
ggccagtgaa ttctactctt ctggcagaag agccaagctt ggcgta 46

<210> SEQ ID NO 61
<211> LENGTH: 646
<212> TYPE: DNA
<213> ORGANISM: Artificial Sequence
<220> FEATURE:
<223> OTHER INFORMATION: Upper nucleotide strand depicted in Figure 1D

<400> SEQUENCE: 61
tacgccaagc ttggctcttc tgccagccct gccgcacctg cgcccgcatc acctgcggca 60
cctgcacctt ccgccccggc tgcatctcct gccgcacccg cgcctgccag cccagctgca 120
cctgccccaa gtgcgccagc agcatcccct gccgcgcctg cccccgctag tccagcggcc 180
ccagctccat ctgcaccagc tgctagccct gctgcaccag ctcctgcttc tcccgcagcc 240
ccagcgcctt ctgctcccgc agcctcacct gcggccccgg caccagcatc tccagcggca 300
ccagcacctt cggcccctgc tgctagccca gcagcacctg cgccagcctc accagctgct 360

```
cccgctccta gtgccccggc ggcctcgcct gctgctcctg caccagcttc gccagcggca    420

ccggctcctt cggcgccggc tgcttcacca gcagcacctg ctccagcgtc cccagcggcc    480

cctgctccaa gtgctccggc tgcatcgcct gccgctcctg ctcctgcatc cccagctgct    540

ccagcaccaa gcgcacctgc cgcctcacca gcggcgccag cacccgccag cccagcagcg    600

cctgctccat ccgcaccggc ggccagaaga gtagaattca ctggcc                   646
```

<210> SEQ ID NO 62
<211> LENGTH: 646
<212> TYPE: DNA
<213> ORGANISM: Artificial Sequence
<220> FEATURE:
<223> OTHER INFORMATION: Lower nucleotide strand depicted in Figure 1D

<400> SEQUENCE: 62

```
ggccagtgaa ttctactctt ctggccgccg gtgcggatgg agcaggcgct gctgggctgg     60

cgggtgctgg cgccgctggt gaggcggcag gtgcgcttgg tgctggagca gctggggatg    120

caggagcagg agcggcaggc gatgcagccg gagcacttgg agcaggggcc gctggggacg    180

ctggagcagg tgctgctggt gaagcagccg gcgccgaagg agccggtgcc gctggcgaag    240

ctggtgcagg agcagcaggc gaggccgccg gggcactagg agcgggagca gctggtgagg    300

ctggcgcagg tgctgctggg ctagcagcag gggccgaagg tgctggtgcc gctggagatg    360

ctggtgccgg ggccgcaggt gaggctgcgg gagcagaagg cgctggggct gcgggagaag    420

caggagctgg tgcagcaggg ctagcagctg gtgcagatgg agctggggcc gctggactag    480

cgggggcagg cgcggcaggg gatgctgctg gcgcacttgg ggcaggtgca gctgggctgg    540

caggcgcggg tgcggcagga gatgcagccg gggcggaagg tgcaggtgcc gcaggtgatg    600

cgggcgcagg tgcggcaggg ctggcagaag agccaagctt ggcgta                   646
```

<210> SEQ ID NO 63
<211> LENGTH: 201
<212> TYPE: PRT
<213> ORGANISM: Artificial Sequence
<220> FEATURE:
<223> OTHER INFORMATION: Amino acid sequence depicted in Figure 1D

<400> SEQUENCE: 63

```
Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
                85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro
        115                 120                 125

Ala Ser Pro Ala Ala Pro Ala Pro Ser Ala Pro Ala Ala Ser Pro Ala
    130                 135                 140
```

-continued

```
Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala Ala
        195                 200
```

<210> SEQ ID NO 64
<211> LENGTH: 30
<212> TYPE: DNA
<213> ORGANISM: Artificial Sequence
<220> FEATURE:
<223> OTHER INFORMATION: Nucleic acid section depicted in Figure 6A

<400> SEQUENCE: 64
gccgccagaa gagcgcgctc ttctgcccga 30

<210> SEQ ID NO 65
<211> LENGTH: 30
<212> TYPE: DNA
<213> ORGANISM: Artificial Sequence
<220> FEATURE:
<223> OTHER INFORMATION: Nucleic acid section depicted in Figure 6A

<400> SEQUENCE: 65
tcgggcagaa gagcgcgctc ttctggcggc 30

<210> SEQ ID NO 66
<211> LENGTH: 10
<212> TYPE: DNA
<213> ORGANISM: Artificial Sequence
<220> FEATURE:
<223> OTHER INFORMATION: Nucleic acid section depicted in Figure 6

<400> SEQUENCE: 66
gagtaagctt 10

<210> SEQ ID NO 67
<211> LENGTH: 10
<212> TYPE: DNA
<213> ORGANISM: Artificial Sequence
<220> FEATURE:
<223> OTHER INFORMATION: Nucleic acid section depicted in Figure 6

<400> SEQUENCE: 67
aagcttactc 10

<210> SEQ ID NO 68
<211> LENGTH: 12
<212> TYPE: DNA
<213> ORGANISM: Artificial Sequence
<220> FEATURE:
<223> OTHER INFORMATION: Nucleic acid section of the PA#1b(200) cassette
depicted in Figure 6C

<400> SEQUENCE: 68
gccgctcctg ct 12

<210> SEQ ID NO 69
<211> LENGTH: 12
<212> TYPE: DNA
<213> ORGANISM: Artificial Sequence
<220> FEATURE:

<223> OTHER INFORMATION: Nucleic acid section of the PA#1b(200) cassette
      depicted in Figure 6C

<400> SEQUENCE: 69
ggcggctggt gc    12

<210> SEQ ID NO 70
<211> LENGTH: 12
<212> TYPE: DNA
<213> ORGANISM: Artificial Sequence
<220> FEATURE:
<223> OTHER INFORMATION: Nucleic acid section depicted in Figure 6C

<400> SEQUENCE: 70
gccgctcctg ct    12

<210> SEQ ID NO 71
<211> LENGTH: 12
<212> TYPE: DNA
<213> ORGANISM: Artificial Sequence
<220> FEATURE:
<223> OTHER INFORMATION: Nucleic acid section depicted in Figure 6C

<400> SEQUENCE: 71
agcaggagcg gc    12

<210> SEQ ID NO 72
<211> LENGTH: 14
<212> TYPE: DNA
<213> ORGANISM: Artificial Sequence
<220> FEATURE:
<223> OTHER INFORMATION: Nucleic acid section depicted in Figure 6C

<400> SEQUENCE: 72
gcaccaccgc ccga    14

<210> SEQ ID NO 73
<211> LENGTH: 15
<212> TYPE: DNA
<213> ORGANISM: Artificial Sequence
<220> FEATURE:
<223> OTHER INFORMATION: Nucleic acid section depicted in Figure 6C

<400> SEQUENCE: 73
tcgggcggct ggtcg    15

<210> SEQ ID NO 74
<211> LENGTH: 4
<212> TYPE: PRT
<213> ORGANISM: Artificial Sequence
<220> FEATURE:
<223> OTHER INFORMATION: Amino acid strech depicted in Figure 6C

<400> SEQUENCE: 74

Ala Pro Ala Ala
1

<210> SEQ ID NO 75
<211> LENGTH: 4
<212> TYPE: PRT
<213> ORGANISM: Artificial Sequence
<220> FEATURE:
<223> OTHER INFORMATION: Amino acid strech depicted in Figure 6C

<400> SEQUENCE: 75

Ala Ala Pro Ala

1

<210> SEQ ID NO 76
<211> LENGTH: 5
<212> TYPE: PRT
<213> ORGANISM: Artificial Sequence
<220> FEATURE:
<223> OTHER INFORMATION: Amino acid strech depicted in Figure 6C

<400> SEQUENCE: 76

Ala Pro Ala Ala Arg
1 5

<210> SEQ ID NO 77
<211> LENGTH: 5470
<212> TYPE: DNA
<213> ORGANISM: Artificial Sequence
<220> FEATURE:
<223> OTHER INFORMATION: Nucleotide sequence of pASK75-PA#1d/1c/1b(600)-
IL1Ra

<400> SEQUENCE: 77
acccgacacc atcgaatggc cagatgatta attcctaatt tttgttgaca ctctatcatt 60
gatagagtta ttttaccact ccctatcagt gatagagaaa agtgaaatga atagttcgac 120
aaaaatctag ataacgaggg caaaaaatga aaaagacagc tatcgcgatt gcagtggcac 180
tggctggttt cgctaccgta gcgcaggccg ctagccatca ccatcaccac catagctctt 240
ctgccgcacc ggctgcccca gcccctgccg caccagcagc tcccgcccct gcagcccccg 300
ccgccgctcc ggccgcacca gccccggctg cccctgctgc ccccgccccg gcagcacccg 360
ctgcagcacc agccgcgcct gcaccggcag ctcctgcagc cccggcaccg gcagcacctg 420
ccgcagcacc cgcagcccca gccccagcag cgcctgccgc tccagcacca gcggcaccgg 480
ccgccgcacc agccgcccca gcaccggcag cccccgcagc gccggcacca gccgctccag 540
ccgccgcccc agcagccccg gctccggccg ctcccgcggc tccagcacca gcagctccag 600
cggccgctcc ggcagcgccg gccccagcag cacctgcagc ccctgcacca gcagcgccag 660
ccgcggcgcc cgcagctccc gcacctgcgg ctcccgcagc ccctgcaccc gcggcgccag 720
cagccgcccc tgcagcgcca gctcctgcag cacctgcagc tccagccccg gccgccccag 780
ctgcagctcc tgcggcccca gcacctgccg cccctgccgc accggctcca gccgccccag 840
ccgccgcgcc agcggccccg gcccctgccg cgcccgctgc tcccgcccct gctgccccag 900
ccgccgctcc tgcggcacct gcgcccgccg cgccggcagc gccggcaccg gcagctccgg 960
cggccgcgcc tgcagctcct gcaccggcgg ctccagcagc cccggcgccg gccgcacctg 1020
cggcggcgcc cgcggcgcct gcacccgcag cgcctgcggc accggcccca gcagcccctg 1080
ccgccgcacc ggctgcgcct gccccagcgg cccccgctgc cccggccccg gcggctccag 1140
ccgcagcgcc tgccgcccca gcgcccgcag caccggcggc accagctccg gcggcgccgg 1200
cggcggctcc ggcagctccg gcccctgctg cgccggctgc gccggctccg gcggcccctg 1260
cggcggctcc ggccgcacct gcacctgccg cgccggctgc tccggccccg gctgccccag 1320
cagcggcacc agcagcgcct gctcctgcgg cgcctgcagc tccggcgccg gcagccccgg 1380
ccgccgcacc cgcggctcca gcccccgccg ctccagcagc cccgcgcca gctgcacctg 1440 ctgccgctcc tgctgcccct gctcccgctg cccccgccgc ccccgcccca gctgcccccg 1500
ctgccgcacc tgctgcccca gctcccgctg ccccagccgc gccggccccc gcagctccag 1560
ccgcggcacc agctgcccca gctccagcgg cgcctgctgc cccggccccc gcggcaccgg 1620

-continued

```
ctgccgcgcc cgcagctcca gcgcctgctg caccggctgc tccggcaccc gccgcgccag   1680
cagctgcccc tgcggcacca gctcctgctg cccccgcggc acctgcaccc gctgccccgg   1740
cggcagctcc cgccgcgcca gcccctgcag ctcctgctgc acctgctcct gccgcccctg   1800
ctgctgcccc tgctgctcca gcccctgcag caccggccgc tccagctcct gccgctcctg   1860
ccgctgcgcc cgctgctcca gccccagctg cgccagcagc tcctgcacct gctgcccctg   1920
ccgccgcccc tgcggctcca gcacctgctg caccggccgc cccggcgccc gctgcccccg   1980
cagcagcccc agccgcaccc gctccagcag ctcccgcagc cccagcaccc gcagcaccag   2040
ccgcccgacc ctctgggaga aaatccagca agatgcaagc cttcagaatc tgggatgtta   2100
accagaagac cttctatctg aggaacaacc aactagttgc cggatacttg caaggaccaa   2160
atgtcaattt agaagaaaag atagatgtgg tacccattga gcctcatgct ctgttcttgg   2220
gaatccatgg agggaagatg tgcctgtcct gtgtcaagtc tggtgatgag accagactcc   2280
agctggaggc agttaacatc actgacctga gcgagaacag aaagcaggac aagcgcttcg   2340
ccttcatccg ctcagacagt ggccccacca ccagttttga gtctgccgcc tgccccggtt   2400
ggttcctctg cacagcgatg gaagctgacc agcccgtcag cctcaccaat atgcctgacg   2460
aaggcgtcat ggtcaccaaa ttctacttcc aggaggacga gtaagcttga cctgtgaagt   2520
gaaaaatggc gcacattgtg cgacattttt tttgtctgcc gtttaccgct actgcgtcac   2580
ggatctccac gcgccctgta gcggcgcatt aagcgcggcg ggtgtggtgg ttacgcgcag   2640
cgtgaccgct acacttgcca gcgccctagc gcccgctcct ttcgctttct tcccttcctt   2700
tctcgccacg ttcgccggct ttccccgtca agctctaaat cgggggctcc ctttagggtt   2760
ccgatttagt gctttacggc acctcgaccc caaaaaactt gattagggtg atggttcacg   2820
tagtgggcca tcgccctgat agacggtttt tcgccctttg acgttggagt ccacgttctt   2880
taatagtgga ctcttgttcc aaactggaac aacactcaac cctatctcgg tctattcttt   2940
tgatttataa gggattttgc cgatttcggc ctattggtta aaaaatgagc tgatttaaca   3000
aaaatttaac gcgaatttta acaaaatatt aacgtttaca atttcaggtg gcacttttcg   3060
gggaaatgtg cgcggaaccc ctatttgttt atttttctaa atacattcaa atatgtatcc   3120
gctcatgaga caataaccct gataaatgct tcaataatat tgaaaaagga agagtatgag   3180
tattcaacat ttccgtgtcg cccttattcc cttttttgcg gcattttgcc ttcctgtttt   3240
tgctcaccca gaaacgctgg tgaaagtaaa agatgctgaa gatcagttgg gtgcacgagt   3300
gggttacatc gaactggatc tcaacagcgg taagatcctt gagagttttc gccccgaaga   3360
acgttttcca atgatgagca cttttaaagt tctgctatgt ggcgcggtat tatcccgtat   3420
tgacgccggg caagagcaac tcggtcgccg catacactat tctcagaatg acttggttga   3480
gtactcacca gtcacagaaa agcatcttac ggatggcatg acagtaagag aattatgcag   3540
tgctgccata accatgagtg ataacactgc ggccaactta cttctgacaa cgatcggagg   3600
accgaaggag ctaaccgctt ttttgcacaa catgggggat catgtaactc gccttgatcg   3660
ttgggaaccg gagctgaatg aagccatacc aaacgacgag cgtgacacca cgatgcctgt   3720
agcaatggca acaacgttgc gcaaactatt aactggcgaa ctacttactc tagcttcccg   3780
gcaacaattg atagactgga tggaggcgga taaagttgca ggaccacttc tgcgctcggc   3840
ccttccggct ggctggttta ttgctgataa atctggagcc ggtgagcgtg gctctcgcgg   3900
tatcattgca gcactggggc cagatggtaa gccctcccgt atcgtagtta tctacacgac   3960
```

```
ggggagtcag gcaactatgg atgaacgaaa tagacagatc gctgagatag gtgcctcact   4020
gattaagcat tggtaggaat taatgatgtc tcgtttagat aaaagtaaag tgattaacag   4080
cgcattagag ctgcttaatg aggtcggaat cgaaggttta acaacccgta aactcgccca   4140
gaagctaggt gtagagcagc ctacattgta ttggcatgta aaaaataagc gggctttgct   4200
cgacgcctta gccattgaga tgttagatag gcaccatact cacttttgcc ctttagaagg   4260
ggaaagctgg caagattttt tacgtaataa cgctaaaagt tttagatgtg ctttactaag   4320
tcatcgcgat ggagcaaaag tacatttagg tacacggcct acagaaaaac agtatgaaac   4380
tctcgaaaat caattagcct ttttatgcca acaaggtttt tcactagaga atgcattata   4440
tgcactcagc gcagtggggc attttacttt aggttgcgta ttggaagatc aagagcatca   4500
agtcgctaaa gaagaaaggg aaacacctac tactgatagt atgccgccat tattacgaca   4560
agctatcgaa ttatttgatc accaaggtgc agagccagcc ttcttattcg gccttgaatt   4620
gatcatatgc ggattagaaa aacaacttaa atgtgaaagt gggtcttaaa agcagcataa   4680
cctttttccg tgatggtaac ttcactagtt taaaaggatc taggtgaaga tcctttttga   4740
taatctcatg accaaaatcc cttaacgtga gttttcgttc cactgagcgt cagaccccgt   4800
agaaaagatc aaaggatctt cttgagatcc tttttttctg cgcgtaatct gctgcttgca   4860
aacaaaaaaa ccaccgctac cagcggtggt ttgtttgccg gatcaagagc taccaactct   4920
ttttccgaag gtaactggct tcagcagagc gcagatacca aatactgtcc ttctagtgta   4980
gccgtagtta ggccaccact tcaagaactc tgtagcaccg cctacatacc tcgctctgct   5040
aatcctgtta ccagtggctg ctgccagtgg cgataagtcg tgtcttaccg ggttggactc   5100
aagacgatag ttaccggata aggcgcagcg gtcgggctga acggggggtt cgtgcacaca   5160
gcccagcttg gagcgaacga cctacaccga actgagatac ctacagcgtg agctatgaga   5220
aagcgccacg cttcccgaag ggagaaaggc ggacaggtat ccggtaagcg gcagggtcgg   5280
aacaggagag cgcacgaggg agcttccagg gggaaacgcc tggtatcttt atagtcctgt   5340
cgggtttcgc cacctctgac ttgagcgtcg atttttgtga tgctcgtcag gggggcggag   5400
cctatggaaa aacgccagca acgcggcctt tttacggttc ctggcctttt gctggccttt   5460
tgctcacatg                                                         5470
```

<210> SEQ ID NO 78
<211> LENGTH: 5470
<212> TYPE: DNA
<213> ORGANISM: Artificial Sequence
<220> FEATURE:
<223> OTHER INFORMATION: Nucleotide sequence of pASK75-PA#1a(600)-IL1Ra

<400> SEQUENCE: 78

```
acccgacacc atcgaatggc cagatgatta attcctaatt tttgttgaca ctctatcatt     60
gatagagtta ttttaccact ccctatcagt gatagagaaa agtgaaatga atagttcgac    120
aaaaatctag ataacgaggg caaaaaatga aaaagacagc tatcgcgatt gcagtggcac    180
tggctggttt cgctaccgta gcgcaggccg ctagccatca ccatcaccac catagctctt    240
ctgccgctcc agctgcacct gctccagcag cacctgctgc accagctccg gctgctcctg    300
ctgccgctcc agctgcacct gctccagcag cacctgctgc accagctccg gctgctcctg    360
ctgccgctcc agctgcacct gctccagcag cacctgctgc accagctccg gctgctcctg    420
ctgccgctcc agctgcacct gctccagcag cacctgctgc accagctccg gctgctcctg    480
ctgccgctcc agctgcacct gctccagcag cacctgctgc accagctccg gctgctcctg    540
```

-continued

```
ctgccgctcc agctgcacct gctccagcag cacctgctgc accagctccg gctgctcctg    600
ctgccgctcc agctgcacct gctccagcag cacctgctgc accagctccg gctgctcctg    660
ctgccgctcc agctgcacct gctccagcag cacctgctgc accagctccg gctgctcctg    720
ctgccgctcc agctgcacct gctccagcag cacctgctgc accagctccg gctgctcctg    780
ctgccgctcc agctgcacct gctccagcag cacctgctgc accagctccg gctgctcctg    840
ctgccgctcc agctgcacct gctccagcag cacctgctgc accagctccg gctgctcctg    900
ctgccgctcc agctgcacct gctccagcag cacctgctgc accagctccg gctgctcctg    960
ctgccgctcc agctgcacct gctccagcag cacctgctgc accagctccg gctgctcctg   1020
ctgccgctcc agctgcacct gctccagcag cacctgctgc accagctccg gctgctcctg   1080
ctgccgctcc agctgcacct gctccagcag cacctgctgc accagctccg gctgctcctg   1140
ctgccgctcc agctgcacct gctccagcag cacctgctgc accagctccg gctgctcctg   1200
ctgccgctcc agctgcacct gctccagcag cacctgctgc accagctccg gctgctcctg   1260
ctgccgctcc agctgcacct gctccagcag cacctgctgc accagctccg gctgctcctg   1320
ctgccgctcc agctgcacct gctccagcag cacctgctgc accagctccg gctgctcctg   1380
ctgccgctcc agctgcacct gctccagcag cacctgctgc accagctccg gctgctcctg   1440
ctgccgctcc agctgcacct gctccagcag cacctgctgc accagctccg gctgctcctg   1500
ctgccgctcc agctgcacct gctccagcag cacctgctgc accagctccg gctgctcctg   1560
ctgccgctcc agctgcacct gctccagcag cacctgctgc accagctccg gctgctcctg   1620
ctgccgctcc agctgcacct gctccagcag cacctgctgc accagctccg gctgctcctg   1680
ctgccgctcc agctgcacct gctccagcag cacctgctgc accagctccg gctgctcctg   1740
ctgccgctcc agctgcacct gctccagcag cacctgctgc accagctccg gctgctcctg   1800
ctgccgctcc agctgcacct gctccagcag cacctgctgc accagctccg gctgctcctg   1860
ctgccgctcc agctgcacct gctccagcag cacctgctgc accagctccg gctgctcctg   1920
ctgccgctcc agctgcacct gctccagcag cacctgctgc accagctccg gctgctcctg   1980
ctgccgctcc agctgcacct gctccagcag cacctgctgc accagctccg gctgctcctg   2040
ctgcccgacc ctctgggaga aaatccagca agatgcaagc cttcagaatc tgggatgtta   2100
accagaagac cttctatctg aggaacaacc aactagttgc cggatacttg caaggaccaa   2160
atgtcaattt agaagaaaag atagatgtgg tacccattga gcctcatgct ctgttcttgg   2220
gaatccatgg agggaagatg tgcctgtcct gtgtcaagtc tggtgatgag accagactcc   2280
agctggaggc agttaacatc actgacctga gcgagaacag aaagcaggac aagcgcttcg   2340
ccttcatccg ctcagacagt ggccccacca ccagttttga gtctgccgcc tgccccggtt   2400
ggttcctctg cacagcgatg gaagctgacc agcccgtcag cctcaccaat atgcctgacg   2460
aaggcgtcat ggtcaccaaa ttctacttcc aggaggacga gtaagcttga cctgtgaagt   2520
gaaaaatggc gcacattgtg cgacattttt tttgtctgcc gtttaccgct actgcgtcac   2580
ggatctccac gcgccctgta gcggcgcatt aagcgcggcg ggtgtggtgg ttacgcgcag   2640
cgtgaccgct acacttgcca gcgccctagc gcccgctcct ttcgctttct tcccttcctt   2700
tctcgccacg ttcgccggct ttccccgtca agctctaaat cgggggctcc ctttagggtt   2760
ccgatttagt gctttacggc acctcgaccc caaaaaactt gattagggtg atggttcacg   2820
tagtgggcca tcgccctgat agacggtttt tcgccctttg acgttggagt ccacgttctt   2880
```

-continued

```
taatagtgga ctcttgttcc aaactggaac aacactcaac cctatctcgg tctattcttt   2940
tgatttataa gggattttgc cgatttcggc ctattggtta aaaaatgagc tgatttaaca   3000
aaaatttaac gcgaatttta acaaaatatt aacgtttaca atttcaggtg gcacttttcg   3060
gggaaatgtg cgcggaaccc ctatttgttt atttttctaa atacattcaa atatgtatcc   3120
gctcatgaga caataaccct gataaatgct tcaataatat tgaaaaagga agagtatgag   3180
tattcaacat ttccgtgtcg cccttattcc cttttttgcg gcattttgcc ttcctgtttt   3240
tgctcaccca gaaacgctgg tgaaagtaaa agatgctgaa gatcagttgg gtgcacgagt   3300
gggttacatc gaactggatc tcaacagcgg taagatcctt gagagttttc gccccgaaga   3360
acgttttcca atgatgagca cttttaaagt tctgctatgt ggcgcggtat tatcccgtat   3420
tgacgccggg caagagcaac tcggtcgccg catacactat tctcagaatg acttggttga   3480
gtactcacca gtcacagaaa agcatcttac ggatggcatg acagtaagag aattatgcag   3540
tgctgccata accatgagtg ataacactgc ggccaactta cttctgacaa cgatcggagg   3600
accgaaggag ctaaccgctt ttttgcacaa catgggggat catgtaactc gccttgatcg   3660
ttgggaaccg gagctgaatg aagccatacc aaacgacgag cgtgacacca cgatgcctgt   3720
agcaatggca acaacgttgc gcaaactatt aactggcgaa ctacttactc tagcttcccg   3780
gcaacaattg atagactgga tggaggcgga taaagttgca ggaccacttc tgcgctcggc   3840
ccttccggct ggctggttta ttgctgataa atctggagcc ggtgagcgtg gctctcgcgg   3900
tatcattgca gcactggggc cagatggtaa gccctcccgt atcgtagtta tctacacgac   3960
ggggagtcag gcaactatgg atgaacgaaa tagacagatc gctgagatag gtgcctcact   4020
gattaagcat tggtaggaat taatgatgtc tcgtttagat aaaagtaaag tgattaacag   4080
cgcattagag ctgcttaatg aggtcggaat cgaaggttta acaacccgta aactcgccca   4140
gaagctaggt gtagagcagc ctacattgta ttggcatgta aaaaataagc gggctttgct   4200
cgacgcctta gccattgaga tgttagatag gcaccatact cacttttgcc ctttagaagg   4260
ggaaagctgg caagattttt tacgtaataa cgctaaaagt tttagatgtg ctttactaag   4320
tcatcgcgat ggagcaaaag tacatttagg tacacggcct acagaaaaac agtatgaaac   4380
tctcgaaaat caattagcct ttttatgcca acaaggtttt tcactagaga atgcattata   4440
tgcactcagc gcagtggggc attttacttt aggttgcgta ttggaagatc aagagcatca   4500
agtcgctaaa gaagaaaggg aaacacctac tactgatagt atgccgccat tattacgaca   4560
agctatcgaa ttatttgatc accaaggtgc agagccagcc ttcttattcg gccttgaatt   4620
gatcatatgc ggattagaaa aacaacttaa atgtgaaagt gggtcttaaa agcagcataa   4680
ccttttttccg tgatggtaac ttcactagtt taaaaggatc taggtgaaga tcctttttga   4740
taatctcatg accaaaatcc cttaacgtga gttttcgttc cactgagcgt cagaccccgt   4800
agaaaagatc aaaggatctt cttgagatcc tttttttctg cgcgtaatct gctgcttgca   4860
aacaaaaaaa ccaccgctac cagcggtggt ttgtttgccg gatcaagagc taccaactct   4920
ttttccgaag gtaactggct tcagcagagc gcagatacca aatactgtcc ttctagtgta   4980
gccgtagtta ggccaccact tcaagaactc tgtagcaccg cctacatacc tcgctctgct   5040
aatcctgtta ccagtggctg ctgccagtgg cgataagtcg tgtcttaccg ggttggactc   5100
aagacgatag ttaccggata aggcgcagcg gtcgggctga acggggggtt cgtgcacaca   5160
gcccagcttg gagcgaacga cctacaccga actgagatac ctacagcgtg agctatgaga   5220
aagcgccacg cttcccgaag ggagaaaggc ggacaggtat ccggtaagcg gcagggtcgg   5280
```

aacaggagag cgcacgaggg agcttccagg gggaaacgcc tggtatcttt atagtcctgt 5340
cgggtttcgc cacctctgac ttgagcgtcg atttttgtga tgctcgtcag gggggcggag 5400
cctatggaaa aacgccagca acgcggcctt tttacggttc ctggcctttt gctggccttt 5460
tgctcacatg 5470

<210> SEQ ID NO 79
<211> LENGTH: 4462
<212> TYPE: DNA
<213> ORGANISM: Artificial Sequence
<220> FEATURE:
<223> OTHER INFORMATION: Nucleotide sequence of pXL1-PA#1d/1c/1b(600)

<400> SEQUENCE: 79
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgg 240
ctcttcaggc tggtgctgcg ggtgctgggg ctgcgggagc tgctggagcg ggtgcggctg 300
gggctgctgc gggggcagcg ggcgccgggg cggccggtgc agcaggtgct ggagccgcag 360
gggcggcggc aggggcagca ggtgcaggag ctgctggcgc agctggggct ggagcagcgg 420
gcgcagcggc aggagcggca ggagctggag cggccggtgc tgcaggggct ggagcagcag 480
gggcagcagc aggggcggca ggagcaggtg cagcaggagc tgcaggggct ggcgcggcgg 540
gagctgccgc cggggcagcg ggtgcaggtg ccgcgggggc agcaggagct ggtgccgcag 600
gggcagctgc tggcgcggcg ggtgccggag cagccggtgc agcaggcgct ggagctgcgg 660
gcgcggcagc cggtgccgcg ggggccgggg cagcaggcgc cgctggagct ggggcagctg 720
gtgccgcggc tggagctgcg ggggccggcg cggctggggc agcgggagct ggggcagcag 780
gtgcggcagc gggggcagct ggggcggggg cggcgggggc agcgggagca ggggcagcag 840
gagcggcagc aggtgcagct ggcgcggggg ctgctggagc ggcgggggct ggagccgcgg 900
gtgcggcggc cggggctgcc ggcgccggag ctgcaggcgc cgcaggagca ggcgctgctg 960
gtgccgctgc tggggcagcc ggggccggag cagccggcgc ggcaggtgca ggtgcggccg 1020
gagccgccgc aggggccgcc ggagccggcg cagccggcgc agcaggggcc ggagctgccg 1080
gagccgccgc cggcgccgcc ggagctggtg ccgccggtgc tgcgggcgct ggggcggcag 1140
gcgctgcggc tggagccgcc ggggccgggg cagcgggggc cgctggggca ggcgcagccg 1200
gtgcggcggc aggggctgct ggggccggtg ccgcaggcgc tgcgggtgca ggcgccgcgg 1260
gcgccgccgc aggtgcggcc ggcgccgggg ctgctggagc cgccggtgca ggagctgcag 1320
gcgcggccgc cggagctgcc ggtgccggcg ctgccggcgc ggcgggcgca ggtgccgcag 1380
gagcggcggc tggggcagca ggggcgggag cagcgggcgc ggcaggggcc ggggccgctg 1440
gcgcggcggc tggggcggct ggagccggtg cggcaggggc ggcaggtgct ggggccgcag 1500
gagctgcagc tggggcggcc ggggctggag ctgcaggtgc tgcaggagct ggcgctgcag 1560
gggcggctgc tggcgccgcg ggtgcagggg ctgcgggagc cgcaggtgcg ggagctgcgg 1620
gcgccgcggc tggcgctgct ggtgcagggg ctgcaggtgc tgctggggcc ggcgctgccg 1680
gagcggccgc tggagctgct ggtgctggag ccgcgggagc ggccggagcc ggggctgctg 1740
gggcggcggc tggagcggct ggtgccggcg ctgcgggggc tgccggtgct ggggcggctg 1800

-continued gtgcggcggc cggtgccgct ggtgctggag cggcaggcgc tgctggggct ggggctgcgg 1860
gtgctgcggc aggtgctgcc ggtgccgggg ctgcaggagc tgccggtgca ggcgcggctg 1920
gtgctgcagc gggtgctgcc ggggcggggg cagcaggggc agccggggct ggtgcggccg 1980
gagcggcggc gggggctgca ggggcgggag ctgctggtgc ggcaggggct ggggcagccg 2040
gtgcggcggc agaagagcag aattcactgg ccgtcgtttt acaacgtcgt gactgggaaa 2100
accctggcgt tacccaactt aatcgccttg cagcacatcc ccctttcgcc agctggcgta 2160
atagcgaaga ggcccgcacc gatcgccctt cccaacagtt gcgcagcctg aatggcgaat 2220
ggcgcctgat gcggtatttt ctccttacgc atctgtgcgg tatttcacac cgcatatggt 2280
gcactctcag tacaatctgc tctgatgccg catagttaag ccagccccga cacccgccaa 2340
cacccgctga cgcgccctga cgggcttgtc tgctcccggc atccgcttac agacaagctg 2400
tgaccgtctc cgggagctgc atgtgtcaga ggttttcacc gtcatcaccg aaacgcgcga 2460
gacgaaaggg cctcgtgata cgcctatttt tataggttaa tgtcatgata ataatggttt 2520
cttagacgtc aggtggcact tttcggggaa atgtgcgcgg aacccctatt tgtttatttt 2580
tctaaataca ttcaaatatg tatccgctca tgagacaata accctgataa atgcttcaat 2640
aatattgaaa aaggaagagt atgagtattc aacatttccg tgtcgccctt attccctttt 2700
ttgcggcatt ttgccttcct gtttttgctc acccagaaac gctggtgaaa gtaaaagatg 2760
ctgaagatca gttgggtgca cgagtgggtt acatcgaact ggatctcaac agcggtaaga 2820
tccttgagag ttttcgcccc gaagaacgtt ttccaatgat gagcactttt aaagttctgc 2880
tatgtggcgc ggtattatcc cgtattgacg ccgggcaaga gcaactcggt cgccgcatac 2940
actattctca gaatgacttg gttgagtact caccagtcac agaaaagcat cttacggatg 3000
gcatgacagt aagagaatta tgcagtgctg ccataaccat gagtgataac actgcggcca 3060
acttacttct gacaacgatc ggaggaccga aggagctaac cgcttttttg cacaacatgg 3120
gggatcatgt aactcgcctt gatcgttggg aaccggagct gaatgaagcc ataccaaacg 3180
acgagcgtga caccacgatg cctgtagcaa tggcaacaac gttgcgcaaa ctattaactg 3240
gcgaactact tactctagct tcccggcaac aattaataga ctggatggag gcggataaag 3300
ttgcaggacc acttctgcgc tcggcccttc cggctggctg gtttattgct gataaatctg 3360
gagccggtga gcgtgggtct cgcggtatca ttgcagcact ggggccagat ggtaagccct 3420
cccgtatcgt agttatctac acgacgggga gtcaggcaac tatggatgaa cgaaatagac 3480
agatcgctga gataggtgcc tcactgatta agcattggta actgtcagac caagtttact 3540
catatatact ttagattgat ttaaaacttc atttttaatt taaaaggatc taggtgaaga 3600
tcctttttga taatctcatg accaaaatcc cttaacgtga gttttcgttc cactgagcgt 3660
cagaccccgt agaaaagatc aaaggatctt cttgagatcc tttttttctg cgcgtaatct 3720
gctgcttgca aacaaaaaaa ccaccgctac cagcggtggt ttgtttgccg gatcaagagc 3780
taccaactct ttttccgaag gtaactggct tcagcagagc gcagatacca aatactgttc 3840
ttctagtgta gccgtagtta ggccaccact tcaagaactc tgtagcaccg cctacatacc 3900
tcgctctgct aatcctgtta ccagtggctg ctgccagtgg cgataagtcg tgtcttaccg 3960
ggttggactc aagacgatag ttaccggata aggcgcagcg gtcgggctga acggggggtt 4020
cgtgcacaca gcccagcttg gagcgaacga cctacaccga actgagatac ctacagcgtg 4080
agctatgaga aagcgccacg cttcccgaag ggagaaaggc ggacaggtat ccggtaagcg 4140
gcagggtcgg aacaggagag cgcacgaggg agcttccagg gggaaacgcc tggtatcttt 4200

```
atagtcctgt cgggtttcgc cacctctgac ttgagcgtcg atttttgtga tgctcgtcag   4260

gggggcggag cctatggaaa aacgccagca acgcggcctt tttacggttc ctggcctttt   4320

gctggccttt tgctcacatg ttctttcctg cgttatcccc tgattctgtg gataaccgta   4380

ttaccgcctt tgagtgagct gataccgctc gccgcagccg aacgaccgag cgcagcgagt   4440

cagtgagcga ggaagcggag aa                                            4462


<210> SEQ ID NO 80
<211> LENGTH: 1800
<212> TYPE: DNA
<213> ORGANISM: Artificial Sequence
<220> FEATURE:
<223> OTHER INFORMATION: Nucleotide sequence of PA#1a(600)

<400> SEQUENCE: 80

gccgctccag ctgcacctgc tccagcagca cctgctgcac cagctccggc tgctcctgct     60

gccgctccag ctgcacctgc tccagcagca cctgctgcac cagctccggc tgctcctgct    120

gccgctccag ctgcacctgc tccagcagca cctgctgcac cagctccggc tgctcctgct    180

gccgctccag ctgcacctgc tccagcagca cctgctgcac cagctccggc tgctcctgct    240

gccgctccag ctgcacctgc tccagcagca cctgctgcac cagctccggc tgctcctgct    300

gccgctccag ctgcacctgc tccagcagca cctgctgcac cagctccggc tgctcctgct    360

gccgctccag ctgcacctgc tccagcagca cctgctgcac cagctccggc tgctcctgct    420

gccgctccag ctgcacctgc tccagcagca cctgctgcac cagctccggc tgctcctgct    480

gccgctccag ctgcacctgc tccagcagca cctgctgcac cagctccggc tgctcctgct    540

gccgctccag ctgcacctgc tccagcagca cctgctgcac cagctccggc tgctcctgct    600

gccgctccag ctgcacctgc tccagcagca cctgctgcac cagctccggc tgctcctgct    660

gccgctccag ctgcacctgc tccagcagca cctgctgcac cagctccggc tgctcctgct    720

gccgctccag ctgcacctgc tccagcagca cctgctgcac cagctccggc tgctcctgct    780

gccgctccag ctgcacctgc tccagcagca cctgctgcac cagctccggc tgctcctgct    840

gccgctccag ctgcacctgc tccagcagca cctgctgcac cagctccggc tgctcctgct    900

gccgctccag ctgcacctgc tccagcagca cctgctgcac cagctccggc tgctcctgct    960

gccgctccag ctgcacctgc tccagcagca cctgctgcac cagctccggc tgctcctgct   1020

gccgctccag ctgcacctgc tccagcagca cctgctgcac cagctccggc tgctcctgct   1080

gccgctccag ctgcacctgc tccagcagca cctgctgcac cagctccggc tgctcctgct   1140

gccgctccag ctgcacctgc tccagcagca cctgctgcac cagctccggc tgctcctgct   1200

gccgctccag ctgcacctgc tccagcagca cctgctgcac cagctccggc tgctcctgct   1260

gccgctccag ctgcacctgc tccagcagca cctgctgcac cagctccggc tgctcctgct   1320

gccgctccag ctgcacctgc tccagcagca cctgctgcac cagctccggc tgctcctgct   1380

gccgctccag ctgcacctgc tccagcagca cctgctgcac cagctccggc tgctcctgct   1440

gccgctccag ctgcacctgc tccagcagca cctgctgcac cagctccggc tgctcctgct   1500

gccgctccag ctgcacctgc tccagcagca cctgctgcac cagctccggc tgctcctgct   1560

gccgctccag ctgcacctgc tccagcagca cctgctgcac cagctccggc tgctcctgct   1620

gccgctccag ctgcacctgc tccagcagca cctgctgcac cagctccggc tgctcctgct   1680

gccgctccag ctgcacctgc tccagcagca cctgctgcac cagctccggc tgctcctgct   1740
```

gccgctccag ctgcacctgc tccagcagca cctgctgcac cagctccggc tgctcctgct 1800

<210> SEQ ID NO 81
<211> LENGTH: 4179
<212> TYPE: DNA
<213> ORGANISM: Artificial Sequence
<220> FEATURE:
<223> OTHER INFORMATION: Nucleotide sequence of pASK37-MP-huLeptin

<400> SEQUENCE: 81
acccgacacc atcgaatggc gcaaaacctt tcgcggtatg gcatgatagc gcccggaaga 60
gagtcaattc agggtggtga atgtgaaacc agtaacgtta tacgatgtcg cagagtatgc 120
cggtgtctct tatcagaccg tttcccgcgt ggtgaaccag gccagccacg tttctgcgaa 180
aacgcgggaa aaagtggaag cggcgatggc ggagctgaat tacattccca accgcgtggc 240
acaacaactg gcgggcaaac agtcgttgct gattggcgtt gccacctcca gtctggccct 300
gcacgcgccg tcgcaaattg tcgcggcgat taaatctcgc gccgatcaac tgggtgccag 360
cgtggtggtg tcgatggtag aacgaagcgg cgtcgaagcc tgtaaagcgg cggtgcacaa 420
tcttctcgcg caacgcgtca gtgggctgat cattaactat ccgctggatg accaggatgc 480
cattgctgtg gaagctgcct gcactaatgt tccggcgtta tttcttgatg tctctgacca 540
gacacccatc aacagtatta ttttctccca tgaagacggt acgcgactgg gcgtggagca 600
tctggtcgca ttgggtcacc agcaaatcgc gctgttagcg ggcccattaa gttctgtctc 660
ggcgcgtctg cgtctggctg gctggcataa atatctcact cgcaatcaaa ttcagccgat 720
agcggaacgg gaaggcgact ggagtgccat gtccggtttt caacaaacca tgcaaatgct 780
gaatgagggc atcgttccca ctgcgatgct ggttgccaac gatcagatgg cgctgggcgc 840
aatgcgcgcc attaccgagt ccgggctgcg cgttggtgcg gatatctcgg tagtgggata 900
cgacgatacc gaagacagct catgttatat cccgccgtta accaccatca aacaggattt 960
tcgcctgctg gggcaaacca gcgtggaccg cttgctgcaa ctctctcagg gccaggcggt 1020
gaagggcaat cagctgttgc ccgtctcact ggtgaaaaga aaaaccaccc tggcgcccaa 1080
tacgcaaacc gcctctcccc gcgcgttggc cgattcatta atgcagctgg cacgacaggt 1140
ttcccgactg gaaagcgggc agtgagcgca acgcaattaa tgtgagttag ctcactcatt 1200
aggcacccca ggctttacac tttatgcttc cggctcgtat aatgtgtgga attgtgagcg 1260
gataacaatt tcacacagga aacagctatg accatgatta cggattcact ggaactctag 1320
aaataatttt gtttaacttt aagaaggaga tatacatatg ccagccagaa gagcgcgctc 1380
ttctgccgtg ccgattcaga aagttcagga tgataccaaa accctgatta aaaccattgt 1440
gacccgcatt aacgatatca gccataccca gagcgttagc agcaaacaga aagttaccgg 1500
tctggatttt attccgggtc tgcatccgat tctgaccctg agcaaaatgg atcagaccct 1560
ggcagtttat cagcagattc tgacaagcat gccgagccgt aatgttattc agattagcaa 1620
tgatctggaa aacctgcgtg atctgctgca tgttctggca tttagcaaaa gctgtcatct 1680
gccgtgggca agcggtctgg aaaccctgga tagcctgggt ggtgttctgg aagcaagcgg 1740
ttatagcacc gaagttgttg cactgagccg tctgcaaggt agtctgcaag atatgctgtg 1800
gcagctggat ctgagtccgg gttgttaagc ttgacctgtg aagtgaaaaa tggcgcacat 1860
tgtgcgacat ttttttgtc tgccgtttac cgctactgcg tcacggatcc ccacgcgccc 1920
tgtagcggcg cattaagcgc ggcgggtgtg gtggttacgc gcagcgtgac cgctacactt 1980
gccagcgccc tagcgcccgc tcctttcgct ttcttccctt cctttctcgc cacgttcgcc 2040

```
ggctttcccc gtcaagctct aaatcggggc atccctttag ggttccgatt tagtgcttta   2100
cggcacctcg accccaaaaa acttgattag ggtgatggtt cacgtagtgg gccatcgccc   2160
tgatagacgg tttttcgccc tttgacgttg gagtccacgt tctttaatag tggactcttg   2220
ttccaaactg gaacaacact caaccctatc tcggtctatt cttttgattt ataagggatt   2280
ttgccgattt cggcctattg gttaaaaaat gagctgattt aacaaaaatt taacgcgaat   2340
tttaacaaaa tattaacgtt tacaatttca ggtggcactt ttcggggaaa tgtgcgcgga   2400
acccctattt gtttattttt ctaaatacat tcaaatatgt atccgctcat gagacaataa   2460
ccctgataaa tgcttcaata atattgaaaa aggaagagta tgagtattca acatttccgt   2520
gtcgccctta ttcccttttt tgcggcattt tgccttcctg tttttgctca cccagaaacg   2580
ctggtgaaag taaaagatgc tgaagatcag ttgggtgcac gagtgggtta catcgaactg   2640
gatctcaaca gcggtaagat ccttgagagt tttcgccccg aagaacgttt tccaatgatg   2700
agcactttta aagttctgct atgtggcgcg gtattatccc gtattgacgc cgggcaagag   2760
caactcggtc gccgcataca ctattctcag aatgacttgg ttgagtactc accagtcaca   2820
gaaaagcatc ttacggatgg catgacagta agagaattat gcagtgctgc cataaccatg   2880
agtgataaca ctgcggccaa cttacttctg acaacgatcg gaggaccgaa ggagctaacc   2940
gcttttttgc acaacatggg ggatcatgta actcgccttg atcgttggga accggagctg   3000
aatgaagcca taccaaacga cgagcgtgac accacgatgc ctgtagcaat ggcaacaacg   3060
ttgcgcaaac tattaactgg cgaactactt actctagctt cccggcaaca attaatagac   3120
tggatggagg cggataaagt tgcaggacca cttctgcgct cggcccttcc ggctggctgg   3180
tttattgctg ataaatctgg agccggtgag cgtgggtctc gcggtatcat tgcagcactg   3240
gggccagatg gtaagccctc ccgtatcgta gttatctaca cgacggggag tcaggcaact   3300
atggatgaac gaaatagaca gatcgctgag ataggtgcct cactgattaa gcattggtaa   3360
ctgtcagacc aagtttactc atatatactt tagattgatt taaaacttca tttttaattt   3420
aaaaggatct aggtgaagat cctttttgat aatctcatga ccaaaatccc ttaacgtgag   3480
ttttcgttcc actgagcgtc agaccccgta gaaaagatca aaggatcttc ttgagatcct   3540
ttttttctgc gcgtaatctg ctgcttgcaa acaaaaaaac caccgctacc agcggtggtt   3600
tgtttgccgg atcaagagct accaactctt tttccgaagg taactggctt cagcagagcg   3660
cagataccaa atactgtcct tctagtgtag ccgtagttag gccaccactt caagaactct   3720
gtagcaccgc ctacatacct cgctctgcta atcctgttac cagtggctgc tgccagtggc   3780
gataagtcgt gtcttaccgg gttggactca agacgatagt taccggataa ggcgcagcgg   3840
tcgggctgaa cggggggttc gtgcacacag cccagcttgg agcgaacgac ctacaccgaa   3900
ctgagatacc tacagcgtga gctatgagaa agcgccacgc ttcccgaagg gagaaaggcg   3960
gacaggtatc cggtaagcgg cagggtcgga acaggagagc gcacgaggga gcttccaggg   4020
ggaaacgcct ggtatcttta tagtcctgtc gggtttcgcc acctctgact tgagcgtcga   4080
tttttgtgat gctcgtcagg ggggcggagc ctatggaaaa acgccagcaa cgcggccttt   4140
ttacggttcc tggccttttg ctggcctttt gctcacatg                          4179
```

<210> SEQ ID NO 82
<211> LENGTH: 5958
<212> TYPE: DNA
<213> ORGANISM: Artificial Sequence
<220> FEATURE:

<223> OTHER INFORMATION: Nucleotide sequence of pASK37-MP-huLeptin-
PA#1d/1c/1b(600)

<400> SEQUENCE: 82
acccgacacc atcgaatggc gcaaaacctt tcgcggtatg gcatgatagc gcccggaaga 60
gagtcaattc agggtggtga atgtgaaacc agtaacgtta tacgatgtcg cagagtatgc 120
cggtgtctct tatcagaccg tttcccgcgt ggtgaaccag gccagccacg tttctgcgaa 180
aacgcgggaa aaagtggaag cggcgatggc ggagctgaat tacattccca accgcgtggc 240
acaacaactg gcgggcaaac agtcgttgct gattggcgtt gccacctcca gtctggccct 300
gcacgcgccg tcgcaaattg tcgcggcgat taaatctcgc gccgatcaac tgggtgccag 360
cgtggtggtg tcgatggtag aacgaagcgg cgtcgaagcc tgtaaagcgg cggtgcacaa 420
tcttctcgcg caacgcgtca gtgggctgat cattaactat ccgctggatg accaggatgc 480
cattgctgtg gaagctgcct gcactaatgt tccggcgtta tttcttgatg tctctgacca 540
gacacccatc aacagtatta ttttctccca tgaagacggt acgcgactgg gcgtggagca 600
tctggtcgca ttgggtcacc agcaaatcgc gctgttagcg ggcccattaa gttctgtctc 660
ggcgcgtctg cgtctggctg gctggcataa atatctcact cgcaatcaaa ttcagccgat 720
agcggaacgg gaaggcgact ggagtgccat gtccggtttt caacaaacca tgcaaatgct 780
gaatgagggc atcgttccca ctgcgatgct ggttgccaac gatcagatgg cgctgggcgc 840
aatgcgcgcc attaccgagt ccgggctgcg cgttggtgcg gatatctcgg tagtgggata 900
cgacgatacc gaagacagct catgttatat cccgccgtta accaccatca aacaggattt 960
tcgcctgctg gggcaaacca gcgtggaccg cttgctgcaa ctctctcagg gccaggcggt 1020
gaagggcaat cagctgttgc ccgtctcact ggtgaaaaga aaaaccaccc tggcgcccaa 1080
tacgcaaacc gcctctcccc gcgcgttggc cgattcatta atgcagctgg cacgacaggt 1140
ttcccgactg gaaagcgggc agtgagcgca acgcaattaa tgtgagttag ctcactcatt 1200
aggcacccca ggctttacac tttatgcttc cggctcgtat aatgtgtgga attgtgagcg 1260
gataacaatt tcacacagga aacagctatg accatgatta cggattcact ggaactctag 1320
aaataatttt gtttaacttt aagaaggaga tatacatatg ccagccgcac cggctgcccc 1380
agcccctgcc gcaccagcag ctcccgcccc tgcagccccc gccgccgctc cggccgcacc 1440
agccccggct gcccctgctg cccccgcccc ggcagcaccc gctgcagcac cagccgcgcc 1500
tgcaccggca gctcctgcag ccccggcacc ggcagcacct gccgcagcac ccgcagcccc 1560
agccccagca gcgcctgccg ctccagcacc agcggcaccg gccgccgcac cagccgcccc 1620
agcaccggca gccccgcag cgccggcacc agccgctcca gccgccgccc cagcagcccc 1680
ggctccggcc gctcccgcgg ctccagcacc agcagctcca gcggccgctc cggcagcgcc 1740
ggccccagca gcacctgcag cccctgcacc agcagcgcca gccgcggcgc ccgcagctcc 1800
cgcacctgcg gctcccgcag cccctgcacc cgcggcgcca gcagccgccc ctgcagcgcc 1860
agctcctgca gcacctgcag ctccagcccc ggccgcccca gctgcagctc ctgcggcccc 1920
agcacctgcc gcccctgccg caccggctcc agccgcccca gccgccgcgc cagcggcccc 1980
ggcccctgcc gcgcccgctg ctcccgcccc tgctgcccca gccgccgctc ctgcggcacc 2040
tgcgcccgcc gcgccggcag cgccggcacc ggcagctccg gcggccgcgc ctgcagctcc 2100
tgcaccggcg gctccagcag ccccggcgcc ggccgcacct gcggcggcgc ccgcggcgcc 2160
tgcacccgca gcgcctgcgg caccggcccc agcagcccct gccgccgcac cggctgcgcc 2220

-continued

```
tgccccagcg gcccccgctg ccccggcccc ggcggctcca gccgcagcgc ctgccgcccc   2280
agcgcccgca gcaccggcgg caccagctcc ggcggcgccg gcggcggctc cggcagctcc   2340
ggcccctgct gcgccggctg cgccggctcc ggcggcccct gcggcggctc cggccgcacc   2400
tgcacctgcc gcgccggctg ctccggcccc ggctgcccca gcagcggcac cagcagcgcc   2460
tgctcctgcg gcgcctgcag ctccggcgcc ggcagccccg gccgccgcac ccgcggctcc   2520
agcccccgcc gctccagcag cccccgcgcc agctgcacct gctgccgctc ctgctgcccc   2580
tgctcccgct gcccccgccg cccccgcccc agctgccccc gctgccgcac ctgctgcccc   2640
agctcccgct gccccagccg cgccggcccc cgcagctcca gccgcggcac cagctgcccc   2700
agctccagcg gcgcctgctg ccccggcccc cgcggcaccg gctgccgcgc ccgcagctcc   2760
agcgcctgct gcaccggctg ctccggcacc cgccgcgcca gcagctgccc ctgcggcacc   2820
agctcctgct gcccccgcgg cacctgcacc cgctgccccg gcggcagctc ccgccgcgcc   2880
agcccctgca gctcctgctg cacctgctcc tgccgcccct gctgctgccc ctgctgctcc   2940
agcccctgca gcaccggccg ctccagctcc tgccgctcct gccgctgcgc ccgctgctcc   3000
agccccagct gcgccagcag ctcctgcacc tgctgcccct gccgccgccc ctgcggctcc   3060
agcacctgct gcaccggccg ccccggcgcc cgctgccccc gcagcagccc cagccgcacc   3120
cgctccagca gctcccgcag ccccagcacc cgcagcacca gccgccgtgc cgattcagaa   3180
agttcaggat gataccaaaa ccctgattaa aaccattgtg acccgcatta acgatatcag   3240
ccatacccag agcgttagca gcaaacagaa agttaccggt ctggatttta ttccgggtct   3300
gcatccgatt ctgaccctga gcaaaatgga tcagaccctg gcagtttatc agcagattct   3360
gacaagcatg ccgagccgta atgttattca gattagcaat gatctggaaa acctgcgtga   3420
tctgctgcat gttctggcat ttagcaaaag ctgtcatctg ccgtgggcaa gcggtctgga   3480
aaccctggat agcctgggtg gtgttctgga agcaagcggt tatagcaccg aagttgttgc   3540
actgagccgt ctgcaaggta gtctgcaaga tatgctgtgg cagctggatc tgagtccggg   3600
ttgttaagct tgacctgtga agtgaaaaat ggcgcacatt gtgcgacatt ttttttgtct   3660
gccgtttacc gctactgcgt cacggatccc cacgcgccct gtagcggcgc attaagcgcg   3720
gcgggtgtgg tggttacgcg cagcgtgacc gctacacttg ccagcgccct agcgcccgct   3780
cctttcgctt tcttcccttc ctttctcgcc acgttcgccg gctttccccg tcaagctcta   3840
aatcggggca tccctttagg gttccgattt agtgctttac ggcacctcga ccccaaaaaa   3900
cttgattagg gtgatggttc acgtagtggg ccatcgccct gatagacggt ttttcgccct   3960
ttgacgttgg agtccacgtt ctttaatagt ggactcttgt tccaaactgg aacaacactc   4020
aaccctatct cggtctattc ttttgattta taagggattt tgccgatttc ggcctattgg   4080
ttaaaaaatg agctgattta acaaaaattt aacgcgaatt ttaacaaaat attaacgttt   4140
acaatttcag gtggcacttt tcggggaaat gtgcgcggaa cccctatttg tttatttttc   4200
taaatacatt caaatatgta tccgctcatg agacaataac cctgataaat gcttcaataa   4260
tattgaaaaa ggaagagtat gagtattcaa catttccgtg tcgcccttat tccctttttt   4320
gcggcatttt gccttcctgt ttttgctcac ccagaaacgc tggtgaaagt aaaagatgct   4380
gaagatcagt tgggtgcacg agtgggttac atcgaactgg atctcaacag cggtaagatc   4440
cttgagagtt ttcgccccga agaacgtttt ccaatgatga gcacttttaa agttctgcta   4500
tgtggcgcgg tattatcccg tattgacgcc gggcaagagc aactcggtcg ccgcatacac   4560
tattctcaga atgacttggt tgagtactca ccagtcacag aaaagcatct tacggatggc   4620
```

atgacagtaa gagaattatg cagtgctgcc ataaccatga gtgataacac tgcggccaac 4680
ttacttctga caacgatcgg aggaccgaag gagctaaccg cttttttgca caacatgggg 4740
gatcatgtaa ctcgccttga tcgttgggaa ccggagctga atgaagccat accaaacgac 4800
gagcgtgaca ccacgatgcc tgtagcaatg gcaacaacgt tgcgcaaact attaactggc 4860
gaactactta ctctagcttc ccggcaacaa ttaatagact ggatggaggc ggataaagtt 4920
gcaggaccac ttctgcgctc ggcccttccg gctggctggt ttattgctga taaatctgga 4980
gccggtgagc gtgggtctcg cggtatcatt gcagcactgg ggccagatgg taagccctcc 5040
cgtatcgtag ttatctacac gacggggagt caggcaacta tggatgaacg aaatagacag 5100
atcgctgaga taggtgcctc actgattaag cattggtaac tgtcagacca agtttactca 5160
tatatacttt agattgattt aaaacttcat ttttaattta aaaggatcta ggtgaagatc 5220
ctttttgata atctcatgac caaaatccct taacgtgagt tttcgttcca ctgagcgtca 5280
gaccccgtag aaaagatcaa aggatcttct tgagatcctt tttttctgcg cgtaatctgc 5340
tgcttgcaaa caaaaaaacc accgctacca gcggtggttt gtttgccgga tcaagagcta 5400
ccaactcttt ttccgaaggt aactggcttc agcagagcgc agataccaaa tactgtcctt 5460
ctagtgtagc cgtagttagg ccaccacttc aagaactctg tagcaccgcc tacatacctc 5520
gctctgctaa tcctgttacc agtggctgct gccagtggcg ataagtcgtg tcttaccggg 5580
ttggactcaa gacgatagtt accggataag gcgcagcggt cgggctgaac ggggggttcg 5640
tgcacacagc ccagcttgga gcgaacgacc tacaccgaac tgagatacct acagcgtgag 5700
ctatgagaaa gcgccacgct tcccgaaggg agaaaggcgg acaggtatcc ggtaagcggc 5760
agggtcggaa caggagagcg cacgagggag cttccagggg gaaacgcctg gtatctttat 5820
agtcctgtcg ggtttcgcca cctctgactt gagcgtcgat ttttgtgatg ctcgtcaggg 5880
gggcggagcc tatggaaaaa cgccagcaac gcggcctttt tacggttcct ggccttttgc 5940
tggccttttg ctcacatg 5958

<210> SEQ ID NO 83
<211> LENGTH: 5958
<212> TYPE: DNA
<213> ORGANISM: Artificial Sequence
<220> FEATURE:
<223> OTHER INFORMATION: Nucleotide sequence of pASK37-MP-huLeptin-
PAS#1f/1c/1b(600)

<400> SEQUENCE: 83
acccgacacc atcgaatggc gcaaaacctt tcgcggtatg gcatgatagc gcccggaaga 60
gagtcaattc agggtggtga atgtgaaacc agtaacgtta tacgatgtcg cagagtatgc 120
cggtgtctct tatcagaccg tttcccgcgt ggtgaaccag gccagccacg tttctgcgaa 180
aacgcgggaa aaagtggaag cggcgatggc ggagctgaat tacattccca accgcgtggc 240
acaacaactg gcgggcaaac agtcgttgct gattggcgtt gccacctcca gtctggccct 300
gcacgcgccg tcgcaaattg tcgcggcgat taaatctcgc gccgatcaac tgggtgccag 360
cgtggtggtg tcgatggtag aacgaagcgg cgtcgaagcc tgtaaagcgg cggtgcacaa 420
tcttctcgcg caacgcgtca gtgggctgat cattaactat ccgctggatg accaggatgc 480
cattgctgtg gaagctgcct gcactaatgt tccggcgtta tttcttgatg tctctgacca 540
gacacccatc aacagtatta ttttctccca tgaagacggt acgcgactgg gcgtggagca 600
tctggtcgca ttgggtcacc agcaaatcgc gctgttagcg ggcccattaa gttctgtctc 660

```
ggcgcgtctg cgtctggctg gctggcataa atatctcact cgcaatcaaa ttcagccgat    720
agcggaacgg gaaggcgact ggagtgccat gtccggtttt caacaaacca tgcaaatgct    780
gaatgagggc atcgttccca ctgcgatgct ggttgccaac gatcagatgg cgctgggcgc    840
aatgcgcgcc attaccgagt ccgggctgcg cgttggtgcg gatatctcgg tagtgggata    900
cgacgatacc gaagacagct catgttatat cccgccgtta accaccatca aacaggattt    960
tcgcctgctg gggcaaacca gcgtggaccg cttgctgcaa ctctctcagg gccaggcggt   1020
gaagggcaat cagctgttgc ccgtctcact ggtgaaaaga aaaaccaccc tggcgcccaa   1080
tacgcaaacc gcctctcccc gcgcgttggc cgattcatta atgcagctgg cacgacaggt   1140
ttcccgactg gaaagcgggc agtgagcgca acgcaattaa tgtgagttag ctcactcatt   1200
aggcacccca ggctttacac tttatgcttc cggctcgtat aatgtgtgga attgtgagcg   1260
gataacaatt tcacacagga aacagctatg accatgatta cggattcact ggaactctag   1320
aaataatttt gtttaacttt aagaaggaga tatacatatg ccagcctccc ctgccgctcc   1380
agcccccgcc tcgccggccg ctcccgctcc gtctgcacct gctgcctcac cagcagcccc   1440
ggccccagca tccccggccg caccagctcc gtcagcacct gccgcatcgc ctgctgcccc   1500
tgccccagcc agtccagcgg ctccagcccc gagtgctccg gccgcttccc ccgcagcacc   1560
ggctcctgcc tcccctgcag cccctgctcc atctgcccct gcggcatccc ctgcggcgcc   1620
agctcctgcc tctccagctg caccggctcc ctcagctccc gctgcctccc cagccgcgcc   1680
cgctcctgca agcccagcag ctccggctcc atccgccccc gccgccagcc ccgcagcccc   1740
ggcgcctgcc tctcctgctg cacctgcacc gtcagcccct gcagcatctc ccgcagctcc   1800
tgcaccggca tctccagcag cccccgcccc gtcagctccc gcagccagcc cggccgcacc   1860
cgcccccgcg tcaccagctg caccagcgcc atccgctcct gctgcgtctc ccgctgcgcc   1920
cgcccctgcc tcacctgcag cacctgcacc tagcgccccg gctgccagtc ctgctgcacc   1980
ggcaccggca tcaccggctg caccagcacc tagtgcaccg gcagcttctc cggctgcccc   2040
tgcgcctgca tcaccagctg cgcctgcacc gtctgcccct gcagctagtc cagcagctcc   2100
agctccggct tctcctgcgg ctcctgcacc aagtgcgcct gcagcaagtc cggctgcgcc   2160
tgccccagct agtcctgctg ctccggcacc gtcagctccg gcagcatctc ctgcagcacc   2220
agcccctgca agtccagcag cgccagcccc atcagcacca gcagcttcac cagccgcacc   2280
agcgccagca agccctgctg ccccagctcc tagcgcaccg gcagccagtc ctgcagctcc   2340
tgcgcctgct agtccggcag ccccagctcc aagtgcccct gccgcttcgc ctgcagcccc   2400
agcaccagct tctccagccg caccggcacc ttctgcccca gctgcatctc cggcagctcc   2460
ggcaccagca agcccggcag caccggcacc atctgcgcct gccgcatctc cggctgcgcc   2520
agctccagcc tctcctgcag cgccagcacc gagcgcacca gcagccagcc ctgccgcacc   2580
tgcgcccgca tcacctgcgg cacctgcacc ttccgccccg gctgcatctc ctgccgcacc   2640
cgcgcctgcc agcccagctg cacctgcccc aagtgcgcca gcagcatccc ctgccgcgcc   2700
tgcccccgct agtccagcgg ccccagctcc atctgcacca gctgctagcc ctgctgcacc   2760
agctcctgct tctcccgcag ccccagcgcc ttctgctccc gcagcctcac ctgcggcccc   2820
ggcaccagca tctccagcgg caccagcacc ttcggcccct gctgctagcc cagcagcacc   2880
tgcgccagcc tcaccagctg ctcccgctcc tagtgccccg gcggcctcgc ctgctgctcc   2940
tgcaccagct tcgccagcgg caccggctcc ttcggcgccg gctgcttcac cagcagcacc   3000
```

-continued

```
tgctccagcg tccccagcgg cccctgctcc aagtgctccg gctgcatcgc ctgccgctcc   3060
tgctcctgca tccccagctg ctccagcacc aagcgcacct gccgcctcac cagcggcgcc   3120
agcacccgcc agcccagcag cgcctgctcc atccgcaccg gcggccgtgc cgattcagaa   3180
agttcaggat gataccaaaa ccctgattaa aaccattgtg acccgcatta acgatatcag   3240
ccatacccag agcgttagca gcaaacagaa agttaccggt ctggatttta ttccgggtct   3300
gcatccgatt ctgaccctga gcaaaatgga tcagaccctg gcagtttatc agcagattct   3360
gacaagcatg ccgagccgta atgttattca gattagcaat gatctggaaa acctgcgtga   3420
tctgctgcat gttctggcat ttagcaaaag ctgtcatctg ccgtgggcaa gcggtctgga   3480
aaccctggat agcctgggtg gtgttctgga agcaagcggt tatagcaccg aagttgttgc   3540
actgagccgt ctgcaaggta gtctgcaaga tatgctgtgg cagctggatc tgagtccggg   3600
ttgttaagct tgacctgtga agtgaaaaat ggcgcacatt gtgcgacatt ttttttgtct   3660
gccgtttacc gctactgcgt cacggatccc cacgcgccct gtagcggcgc attaagcgcg   3720
gcgggtgtgg tggttacgcg cagcgtgacc gctacacttg ccagcgccct agcgcccgct   3780
cctttcgctt tcttcccttc ctttctcgcc acgttcgccg gctttccccg tcaagctcta   3840
aatcggggca tccctttagg gttccgattt agtgctttac ggcacctcga ccccaaaaaa   3900
cttgattagg gtgatggttc acgtagtggg ccatcgccct gatagacggt ttttcgccct   3960
ttgacgttgg agtccacgtt ctttaatagt ggactcttgt tccaaactgg aacaacactc   4020
aaccctatct cggtctattc ttttgattta taagggattt tgccgatttc ggcctattgg   4080
ttaaaaaatg agctgattta acaaaaattt aacgcgaatt ttaacaaaat attaacgttt   4140
acaatttcag gtggcacttt tcggggaaat gtgcgcggaa cccctatttg tttatttttc   4200
taaatacatt caaatatgta tccgctcatg agacaataac cctgataaat gcttcaataa   4260
tattgaaaaa ggaagagtat gagtattcaa catttccgtg tcgcccttat tccctttttt   4320
gcggcatttt gccttcctgt ttttgctcac ccagaaacgc tggtgaaagt aaaagatgct   4380
gaagatcagt tgggtgcacg agtgggttac atcgaactgg atctcaacag cggtaagatc   4440
cttgagagtt ttcgccccga agaacgtttt ccaatgatga gcacttttaa agttctgcta   4500
tgtggcgcgg tattatcccg tattgacgcc gggcaagagc aactcggtcg ccgcatacac   4560
tattctcaga atgacttggt tgagtactca ccagtcacag aaaagcatct tacggatggc   4620
atgacagtaa gagaattatg cagtgctgcc ataaccatga gtgataacac tgcggccaac   4680
ttacttctga caacgatcgg aggaccgaag gagctaaccg cttttttgca caacatgggg   4740
gatcatgtaa ctcgccttga tcgttgggaa ccggagctga atgaagccat accaaacgac   4800
gagcgtgaca ccacgatgcc tgtagcaatg gcaacaacgt tgcgcaaact attaactggc   4860
gaactactta ctctagcttc ccggcaacaa ttaatagact ggatggaggc ggataaagtt   4920
gcaggaccac ttctgcgctc ggcccttccg gctggctggt ttattgctga taaatctgga   4980
gccggtgagc gtgggtctcg cggtatcatt gcagcactgg ggccagatgg taagccctcc   5040
cgtatcgtag ttatctacac gacggggagt caggcaacta tggatgaacg aaatagacag   5100
atcgctgaga taggtgcctc actgattaag cattggtaac tgtcagacca agtttactca   5160
tatatacttt agattgattt aaaacttcat ttttaattta aaaggatcta ggtgaagatc   5220
ctttttgata atctcatgac caaaatccct taacgtgagt tttcgttcca ctgagcgtca   5280
gaccccgtag aaaagatcaa aggatcttct tgagatcctt tttttctgcg cgtaatctgc   5340
tgcttgcaaa caaaaaaacc accgctacca gcggtggttt gtttgccgga tcaagagcta   5400
```

```
ccaactcttt ttccgaaggt aactggcttc agcagagcgc agataccaaa tactgtcctt   5460

ctagtgtagc cgtagttagg ccaccacttc aagaactctg tagcaccgcc tacatacctc   5520

gctctgctaa tcctgttacc agtggctgct gccagtggcg ataagtcgtg tcttaccggg   5580

ttggactcaa gacgatagtt accggataag gcgcagcggt cgggctgaac ggggggttcg   5640

tgcacacagc ccagcttgga gcgaacgacc tacaccgaac tgagatacct acagcgtgag   5700

ctatgagaaa gcgccacgct tcccgaaggg agaaaggcgg acaggtatcc ggtaagcggc   5760

agggtcggaa caggagagcg cacgagggag cttccagggg gaaacgcctg gtatctttat   5820

agtcctgtcg ggtttcgcca cctctgactt gagcgtcgat ttttgtgatg ctcgtcaggg   5880

gggcggagcc tatggaaaaa cgccagcaac gcggcctttt tacggttcct ggccttttgc   5940

tggccttttg ctcacatg                                                 5958
```

<210> SEQ ID NO 84
<211> LENGTH: 4454
<212> TYPE: DNA
<213> ORGANISM: Artificial Sequence
<220> FEATURE:
<223> OTHER INFORMATION: Nucleotide sequence of pXL1-PAS#1f/1c/1b(600)

<400> SEQUENCE: 84

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagcttgg    240

ccgccggtgc ggatggagca ggcgctgctg ggctggcggg tgctggcgcc gctggtgagg    300

cggcaggtgc gcttggtgct ggagcagctg gggatgcagg agcaggagcg gcaggcgatg    360

cagccggagc acttggagca ggggccgctg gggacgctgg agcaggtgct gctggtgaag    420

cagccggcgc cgaaggagcc ggtgccgctg gcgaagctgg tgcaggagca gcaggcgagg    480

ccgccggggc actaggagcg ggagcagctg gtgaggctgg cgcaggtgct gctgggctag    540

cagcaggggc cgaaggtgct ggtgccgctg gagatgctgg tgccggggcc gcaggtgagg    600

ctgcgggagc agaaggcgct ggggctgcgg gagaagcagg agctggtgca gcagggctag    660

cagctggtgc agatggagct ggggccgctg gactagcggg ggcaggcgcg gcaggggatg    720

ctgctggcgc acttggggca ggtgcagctg ggctggcagg cgcgggtgcg gcaggagatg    780

cagccggggc ggaaggtgca ggtgccgcag gtgatgcggg cgcaggtgcg gcagggctgg    840

ctgctggtgc gctcggtgct ggcgctgcag gagaggctgg agctggcgca gccggagatg    900

cggcaggcgc agatggtgcc ggtgctgccg ggcttgctgg tgccggagct gccggagatg    960

cagctggggc agaaggtgcc ggtgcggctg gagaagctgg tgctggggct gcaggcgaag   1020

cggcaggggc acttggagct ggggctgccg gactagcagg cgcaggagct gcaggactgg   1080

ctgccggtgc gctaggagct ggggcagcag ggcttgctgg cgctggtgcg gctggtgaag   1140

ctgctggtgc tgatggggct ggcgctgctg gacttgcagg ggctggtgct gcaggagatg   1200

ctgccggagc tgacggtgcc ggagcagcag gactagctgg ggcaggcgca gccggacttg   1260

ctgcaggcgc acttggtgca ggagccgcag gagaagccgg agctggagct gctggactag   1320

ctgcaggggc agacggtgca ggcgcagctg gtgatgcagg cgcaggggca gccggagaag   1380

ctgccggtgc actaggtgct ggtgcagccg gtgatgccgg tgccggtgca gcaggactgg   1440
```

```
cagccggggc gctaggtgca ggtgctgcag gtgaggcagg ggcgggcgca gcgggagacg   1500
cagcaggagc ggatggcgct ggtgcagctg gtgacgcggg ggcgggtgcg gccgggctgg   1560
ctgcgggagc tgacggggcg ggggctgctg gagatgccgg tgcaggagct gcgggagatg   1620
ctgcaggggc tgacggtgca ggtgcagcag gagaggcagg cgccggggct gcggggctgg   1680
cggcgggggc ggatggagcc ggagctgctg ggcttgcagg agcgggcgcg gctggggagg   1740
cagcgggagc tgagggagcc ggtgcagctg gagaggcagg agctggcgcc gcaggggatg   1800
ccgcaggggc agatggagca ggggctgcag gggaggcagg agccggtgct gcgggggaag   1860
cggccggagc actcggggct ggagccgctg gactggctgg ggcaggggca gcaggcgatg   1920
cggcaggtgc tgacggagct ggtgcggccg gggatgctgg ggccggggct gctggtgagg   1980
cagcaggtgc agacggagcg ggagcggccg gcgaggcggg ggctggagcg gcaggggagg   2040
caagaagagc agaattcact ggccgtcgtt ttacaacgtc gtgactggga aaaccctggc   2100
gttacccaac ttaatcgcct tgcagcacat ccccctttcg ccagctggcg taatagcgaa   2160
gaggcccgca ccgatcgccc ttcccaacag ttgcgcagcc tgaatggcga atggcgcctg   2220
atgcggtatt ttctccttac gcatctgtgc ggtatttcac accgcatatg gtgcactctc   2280
agtacaatct gctctgatgc cgcatagtta agccagcccc gacacccgcc aacacccgct   2340
gacgcgccct gacgggcttg tctgctcccg gcatccgctt acagacaagc tgtgaccgtc   2400
tccgggagct gcatgtgtca gaggttttca ccgtcatcac cgaaacgcgc gagacgaaag   2460
ggcctcgtga tacgcctatt tttataggtt aatgtcatga taataatggt ttcttagacg   2520
tcaggtggca cttttcgggg aaatgtgcgc ggaaccccta tttgtttatt tttctaaata   2580
cattcaaata tgtatccgct catgagacaa taaccctgat aaatgcttca ataatattga   2640
aaaaggaaga gtatgagtat tcaacatttc cgtgtcgccc ttattccctt ttttgcggca   2700
ttttgccttc ctgtttttgc tcacccagaa acgctggtga aagtaaaaga tgctgaagat   2760
cagttgggtg cacgagtggg ttacatcgaa ctggatctca acagcggtaa gatccttgag   2820
agttttcgcc ccgaagaacg ttttccaatg atgagcactt ttaaagttct gctatgtggc   2880
gcggtattat cccgtattga cgccgggcaa gagcaactcg gtcgccgcat acactattct   2940
cagaatgact tggttgagta ctcaccagtc acagaaaagc atcttacgga tggcatgaca   3000
gtaagagaat tatgcagtgc tgccataacc atgagtgata acactgcggc caacttactt   3060
ctgacaacga tcggaggacc gaaggagcta accgcttttt tgcacaacat gggggatcat   3120
gtaactcgcc ttgatcgttg ggaaccggag ctgaatgaag ccataccaaa cgacgagcgt   3180
gacaccacga tgcctgtagc aatggcaaca acgttgcgca aactattaac tggcgaacta   3240
cttactctag cttcccggca acaattaata gactggatgg aggcggataa agttgcagga   3300
ccacttctgc gctcggccct tccggctggc tggtttattg ctgataaatc tggagccggt   3360
gagcgtgggt ctcgcggtat cattgcagca ctggggccag atggtaagcc ctcccgtatc   3420
gtagttatct acacgacggg gagtcaggca actatggatg aacgaaatag acagatcgct   3480
gagataggtg cctcactgat taagcattgg taactgtcag accaagttta ctcatatata   3540
ctttagattg atttaaaact tcatttttaa tttaaaagga tctaggtgaa gatccttttt   3600
gataatctca tgaccaaaat cccttaacgt gagttttcgt tccactgagc gtcagacccc   3660
gtagaaaaga tcaaaggatc ttcttgagat cctttttttc tgcgcgtaat ctgctgcttg   3720
caaacaaaaa aaccaccgct accagcggtg gtttgtttgc cggatcaaga gctaccaact   3780
ctttttccga aggtaactgg cttcagcaga gcgcagatac caaatactgt tcttctagtg   3840
```

```
tagccgtagt taggccacca cttcaagaac tctgtagcac cgcctacata cctcgctctg   3900

ctaatcctgt taccagtggc tgctgccagt ggcgataagt cgtgtcttac cgggttggac   3960

tcaagacgat agttaccgga taaggcgcag cggtcgggct gaacgggggg ttcgtgcaca   4020

cagcccagct tggagcgaac gacctacacc gaactgagat acctacagcg tgagctatga   4080

gaaagcgcca cgcttcccga agggagaaag gcggacaggt atccggtaag cggcagggtc   4140

ggaacaggag agcgcacgag ggagcttcca gggggaaacg cctggtatct ttatagtcct   4200

gtcgggtttc gccacctctg acttgagcgt cgatttttgt gatgctcgtc aggggggcgg   4260

agcctatgga aaaacgccag caacgcggcc tttttacggt tcctggcctt ttgctggcct   4320

tttgctcaca tgttctttcc tgcgttatcc cctgattctg tggataaccg tattaccgcc   4380

tttgagtgag ctgataccgc tcgccgcagc cgaacgaccg agcgcagcga gtcagtgagc   4440

gaggaagcgg agaa                                                     4454
```

<210> SEQ ID NO 85
<211> LENGTH: 749
<212> TYPE: PRT
<213> ORGANISM: Artificial Sequence
<220> FEATURE:
<223> OTHER INFORMATION: Amino acid sequence of PA#1(600)-
      huLeptin(W100Q)

<400> SEQUENCE: 85

```
Met Pro Ala Ala Pro Ala Ala Pro Ala Pro Ala Ala Pro Ala Ala Pro
1               5                   10                  15

Ala Pro Ala Ala Pro Ala Ala Ala Pro Ala Ala Pro Ala Pro Ala Ala
            20                  25                  30

Pro Ala Ala Pro Ala Pro Ala Ala Pro Ala Ala Ala Pro Ala Ala Pro
        35                  40                  45

Ala Pro Ala Ala Pro Ala Ala Pro Ala Pro Ala Ala Pro Ala Ala Ala
    50                  55                  60

Pro Ala Ala Pro Ala Pro Ala Ala Pro Ala Ala Pro Ala Pro Ala Ala
65                  70                  75                  80

Pro Ala Ala Ala Pro Ala Ala Pro Ala Pro Ala Ala Pro Ala Ala Pro
                85                  90                  95

Ala Pro Ala Ala Pro Ala Ala Ala Pro Ala Ala Pro Ala Pro Ala Ala
            100                 105                 110

Pro Ala Ala Pro Ala Pro Ala Ala Pro Ala Ala Ala Pro Ala Ala Pro
        115                 120                 125

Ala Pro Ala Ala Pro Ala Ala Pro Ala Pro Ala Ala Pro Ala Ala Ala
    130                 135                 140

Pro Ala Ala Pro Ala Pro Ala Ala Pro Ala Ala Pro Ala Pro Ala Ala
145                 150                 155                 160

Pro Ala Ala Ala Pro Ala Ala Pro Ala Pro Ala Ala Pro Ala Ala Pro
                165                 170                 175

Ala Pro Ala Ala Pro Ala Ala Ala Pro Ala Ala Pro Ala Pro Ala Ala
            180                 185                 190

Pro Ala Ala Pro Ala Pro Ala Ala Pro Ala Ala Ala Pro Ala Ala Pro
        195                 200                 205

Ala Pro Ala Ala Pro Ala Ala Pro Ala Pro Ala Ala Pro Ala Ala Ala
    210                 215                 220

Pro Ala Ala Pro Ala Pro Ala Ala Pro Ala Ala Pro Ala Pro Ala Ala
225                 230                 235                 240
```

-continued

```
Pro Ala Ala Ala Pro Ala Ala Pro Ala Pro Ala Ala Pro Ala Ala Pro
                245                 250                 255

Ala Pro Ala Ala Pro Ala Ala Ala Pro Ala Ala Pro Ala Pro Ala Ala
            260                 265                 270

Pro Ala Ala Pro Ala Pro Ala Ala Pro Ala Ala Ala Pro Ala Ala Pro
        275                 280                 285

Ala Pro Ala Ala Pro Ala Ala Pro Ala Pro Ala Ala Pro Ala Ala Ala
    290                 295                 300

Pro Ala Ala Pro Ala Pro Ala Ala Pro Ala Ala Pro Ala Pro Ala Ala
305                 310                 315                 320

Pro Ala Ala Ala Pro Ala Ala Pro Ala Pro Ala Ala Pro Ala Ala Pro
                325                 330                 335

Ala Pro Ala Ala Pro Ala Ala Ala Pro Ala Ala Pro Ala Pro Ala Ala
            340                 345                 350

Pro Ala Ala Pro Ala Pro Ala Ala Pro Ala Ala Ala Pro Ala Ala Pro
        355                 360                 365

Ala Pro Ala Ala Pro Ala Ala Pro Ala Pro Ala Ala Pro Ala Ala Ala
    370                 375                 380

Pro Ala Ala Pro Ala Pro Ala Ala Pro Ala Ala Pro Ala Pro Ala Ala
385                 390                 395                 400

Pro Ala Ala Ala Pro Ala Ala Pro Ala Pro Ala Ala Pro Ala Ala Pro
                405                 410                 415

Ala Pro Ala Ala Pro Ala Ala Ala Pro Ala Ala Pro Ala Pro Ala Ala
            420                 425                 430

Pro Ala Ala Pro Ala Pro Ala Ala Pro Ala Ala Ala Pro Ala Ala Pro
        435                 440                 445

Ala Pro Ala Ala Pro Ala Ala Pro Ala Pro Ala Ala Pro Ala Ala Ala
    450                 455                 460

Pro Ala Ala Pro Ala Pro Ala Ala Pro Ala Ala Pro Ala Pro Ala Ala
465                 470                 475                 480

Pro Ala Ala Ala Pro Ala Ala Pro Ala Pro Ala Ala Pro Ala Ala Pro
                485                 490                 495

Ala Pro Ala Ala Pro Ala Ala Ala Pro Ala Ala Pro Ala Pro Ala Ala
            500                 505                 510

Pro Ala Ala Pro Ala Pro Ala Ala Pro Ala Ala Ala Pro Ala Ala Pro
        515                 520                 525

Ala Pro Ala Ala Pro Ala Ala Pro Ala Pro Ala Ala Pro Ala Ala Ala
    530                 535                 540

Pro Ala Ala Pro Ala Pro Ala Ala Pro Ala Ala Pro Ala Pro Ala Ala
545                 550                 555                 560

Pro Ala Ala Ala Pro Ala Ala Pro Ala Pro Ala Ala Pro Ala Ala Pro
                565                 570                 575

Ala Pro Ala Ala Pro Ala Ala Ala Pro Ala Ala Pro Ala Pro Ala Ala
            580                 585                 590

Pro Ala Ala Pro Ala Pro Ala Ala Pro Ala Ala Val Pro Ile Gln Lys
        595                 600                 605

Val Gln Asp Asp Thr Lys Thr Leu Ile Lys Thr Ile Val Thr Arg Ile
    610                 615                 620

Asn Asp Ile Ser His Thr Gln Ser Val Ser Ser Lys Gln Lys Val Thr
625                 630                 635                 640

Gly Leu Asp Phe Ile Pro Gly Leu His Pro Ile Leu Thr Leu Ser Lys
                645                 650                 655

Met Asp Gln Thr Leu Ala Val Tyr Gln Gln Ile Leu Thr Ser Met Pro
```

-continued

```
            660                 665                 670

Ser Arg Asn Val Ile Gln Ile Ser Asn Asp Leu Glu Asn Leu Arg Asp
        675                 680                 685

Leu Leu His Val Leu Ala Phe Ser Lys Ser Cys His Leu Pro Gln Ala
    690                 695                 700

Ser Gly Leu Glu Thr Leu Asp Ser Leu Gly Gly Val Leu Glu Ala Ser
705                 710                 715                 720

Gly Tyr Ser Thr Glu Val Val Ala Leu Ser Arg Leu Gln Gly Ser Leu
                725                 730                 735

Gln Asp Met Leu Trp Gln Leu Asp Leu Ser Pro Gly Cys
            740                 745


<210> SEQ ID NO 86
<211> LENGTH: 5958
<212> TYPE: DNA
<213> ORGANISM: Artificial Sequence
<220> FEATURE:
<223> OTHER INFORMATION: Nucleotide sequence of pASK37-MP-
      PA#1d/1c/1b(600)-huLep(W100Q)

<400> SEQUENCE: 86

acccgacacc atcgaatggc gcaaaacctt tcgcggtatg gcatgatagc gcccggaaga      60

gagtcaattc agggtggtga atgtgaaacc agtaacgtta tacgatgtcg cagagtatgc     120

cggtgtctct tatcagaccg tttcccgcgt ggtgaaccag gccagccacg tttctgcgaa     180

aacgcgggaa aaagtggaag cggcgatggc ggagctgaat tacattccca accgcgtggc     240

acaacaactg gcgggcaaac agtcgttgct gattggcgtt gccacctcca gtctggccct     300

gcacgcgccg tcgcaaattg tcgcggcgat taaatctcgc gccgatcaac tgggtgccag     360

cgtggtggtg tcgatggtag aacgaagcgg cgtcgaagcc tgtaaagcgg cggtgcacaa     420

tcttctcgcg caacgcgtca gtgggctgat cattaactat ccgctggatg accaggatgc     480

cattgctgtg gaagctgcct gcactaatgt tccggcgtta tttcttgatg tctctgacca     540

gacacccatc aacagtatta ttttctccca tgaagacggt acgcgactgg gcgtggagca     600

tctggtcgca ttgggtcacc agcaaatcgc gctgttagcg ggcccattaa gttctgtctc     660

ggcgcgtctg cgtctggctg gctggcataa atatctcact cgcaatcaaa ttcagccgat     720

agcggaacgg gaaggcgact ggagtgccat gtccggtttt caacaaacca tgcaaatgct     780

gaatgagggc atcgttccca ctgcgatgct ggttgccaac gatcagatgg cgctgggcgc     840

aatgcgcgcc attaccgagt ccgggctgcg cgttggtgcg gatatctcgg tagtgggata     900

cgacgatacc gaagacagct catgttatat cccgccgtta accaccatca aacaggattt     960

tcgcctgctg gggcaaacca gcgtggaccg cttgctgcaa ctctctcagg gccaggcggt    1020

gaagggcaat cagctgttgc ccgtctcact ggtgaaaaga aaaaccaccc tggcgcccaa    1080

tacgcaaacc gcctctcccc gcgcgttggc cgattcatta atgcagctgg cacgacaggt    1140

ttcccgactg gaaagcgggc agtgagcgca acgcaattaa tgtgagttag ctcactcatt    1200

aggcacccca ggctttacac tttatgcttc cggctcgtat aatgtgtgga attgtgagcg    1260

gataacaatt tcacacagga aacagctatg accatgatta cggattcact ggaactctag    1320

aaataatttt gtttaacttt aagaaggaga tatacatatg ccagccgcac cggctgcccc    1380

agcccctgcc gcaccagcag ctcccgcccc tgcagccccc gccgccgctc cggccgcacc    1440

agccccggct gcccctgctg cccccgcccc ggcagcaccc gctgcagcac cagccgcgcc    1500

tgcaccggca gctcctgcag ccccggcacc ggcagcacct gccgcagcac ccgcagcccc    1560
```

-continued

```
agccccagca gcgcctgccg ctccagcacc agcggcaccg gccgccgcac cagccgcccc   1620
agcaccggca gcccccgcag cgccggcacc agccgctcca gccgccgccc cagcagcccc   1680
ggctccggcc gctcccgcgg ctccagcacc agcagctcca gcggccgctc cggcagcgcc   1740
ggccccagca gcacctgcag cccctgcacc agcagcgcca gccgcggcgc ccgcagctcc   1800
cgcacctgcg gctcccgcag cccctgcacc cgcggcgcca gcagccgccc ctgcagcgcc   1860
agctcctgca gcacctgcag ctccagcccc ggccgcccca gctgcagctc ctgcggcccc   1920
agcacctgcc gcccctgccg caccggctcc agccgcccca gccgccgcgc cagcggcccc   1980
ggcccctgcc gcgcccgctg ctcccgcccc tgctgcccca gccgccgctc ctgcggcacc   2040
tgcgcccgcc gcgccggcag cgccggcacc ggcagctccg gcggccgcgc ctgcagctcc   2100
tgcaccggcg gctccagcag ccccggcgcc ggccgcacct gcggcggcgc ccgcggcgcc   2160
tgcacccgca gcgcctgcgg caccggcccc agcagcccct gccgccgcac cggctgcgcc   2220
tgccccagcg gcccccgctg ccccggcccc ggcggctcca gccgcagcgc ctgccgcccc   2280
agcgcccgca gcaccggcgg caccagctcc ggcggcgccg gcggcggctc cggcagctcc   2340
ggcccctgct gcgccggctg cgccggctcc ggcggcccct gcggcggctc cggccgcacc   2400
tgcacctgcc gcgccggctg ctccggcccc ggctgcccca gcagcggcac cagcagcgcc   2460
tgctcctgcg gcgcctgcag ctccggcgcc ggcagccccg gccgccgcac ccgcggctcc   2520
agcccccgcc gctccagcag cccccgcgcc agctgcacct gctgccgctc ctgctgcccc   2580
tgctcccgct gcccccgccg cccccgcccc agctgccccc gctgccgcac ctgctgcccc   2640
agctcccgct gccccagccg cgccggcccc cgcagctcca gccgcggcac cagctgcccc   2700
agctccagcg gcgcctgctg ccccggcccc cgcggcaccg gctgccgcgc ccgcagctcc   2760
agcgcctgct gcaccggctg ctccggcacc cgccgcgcca gcagctgccc ctgcggcacc   2820
agctcctgct gcccccgcgg cacctgcacc cgctgccccg gcggcagctc ccgccgcgcc   2880
agcccctgca gctcctgctg cacctgctcc tgccgcccct gctgctgccc ctgctgctcc   2940
agcccctgca gcaccggccg ctccagctcc tgccgctcct gccgctgcgc ccgctgctcc   3000
agccccagct gcgccagcag ctcctgcacc tgctgcccct gccgccgccc ctgcggctcc   3060
agcacctgct gcaccggccg ccccggcgcc cgctgccccc gcagcagccc cagccgcacc   3120
cgctccagca gctcccgcag ccccagcacc cgcagcacca gccgccgtgc cgattcagaa   3180
agttcaggat gataccaaaa ccctgattaa aaccattgtg acccgcatta acgatatcag   3240
ccatacccag agcgttagca gcaaacagaa agttaccggt ctggatttta ttccgggtct   3300
gcatccgatt ctgaccctga gcaaaatgga tcagaccctg gcagtttatc agcagattct   3360
gacaagcatg ccgagccgta atgttattca gattagcaat gatctggaaa acctgcgtga   3420
tctgctgcat gttctggcat ttagcaaaag ctgtcatctg ccgcaggcaa gcggtctgga   3480
aaccctggat agcctgggtg gtgttctgga agcaagcggt tatagcaccg aagttgttgc   3540
actgagccgt ctgcaaggta gtctgcaaga tatgctgtgg cagctggatc tgagtccggg   3600
ttgttaagct tgacctgtga agtgaaaaat ggcgcacatt gtgcgacatt ttttttgtct   3660
gccgtttacc gctactgcgt cacggatccc cacgcgccct gtagcggcgc attaagcgcg   3720
gcgggtgtgg tggttacgcg cagcgtgacc gctacacttg ccagcgccct agcgcccgct   3780
cctttcgctt tcttcccttc ctttctcgcc acgttcgccg gctttccccg tcaagctcta   3840
aatcggggca tccctttagg gttccgattt agtgctttac ggcacctcga ccccaaaaaa   3900
```

-continued

```
cttgattagg gtgatggttc acgtagtggg ccatcgccct gatagacggt ttttcgccct   3960

ttgacgttgg agtccacgtt ctttaatagt ggactcttgt tccaaactgg aacaacactc   4020

aaccctatct cggtctattc ttttgattta taagggattt tgccgatttc ggcctattgg   4080

ttaaaaaatg agctgattta acaaaaattt aacgcgaatt ttaacaaaat attaacgttt   4140

acaatttcag gtggcacttt tcggggaaat gtgcgcggaa cccctatttg tttatttttc   4200

taaatacatt caaatatgta tccgctcatg agacaataac cctgataaat gcttcaataa   4260

tattgaaaaa ggaagagtat gagtattcaa catttccgtg tcgcccttat tccctttttt   4320

gcggcatttt gccttcctgt ttttgctcac ccagaaacgc tggtgaaagt aaaagatgct   4380

gaagatcagt tgggtgcacg agtgggttac atcgaactgg atctcaacag cggtaagatc   4440

cttgagagtt ttcgccccga agaacgtttt ccaatgatga gcacttttaa agttctgcta   4500

tgtggcgcgg tattatcccg tattgacgcc gggcaagagc aactcggtcg ccgcatacac   4560

tattctcaga atgacttggt tgagtactca ccagtcacag aaaagcatct tacggatggc   4620

atgacagtaa gagaattatg cagtgctgcc ataaccatga gtgataacac tgcggccaac   4680

ttacttctga caacgatcgg aggaccgaag gagctaaccg cttttttgca caacatgggg   4740

gatcatgtaa ctcgccttga tcgttgggaa ccggagctga atgaagccat accaaacgac   4800

gagcgtgaca ccacgatgcc tgtagcaatg gcaacaacgt tgcgcaaact attaactggc   4860

gaactactta ctctagcttc ccggcaacaa ttaatagact ggatggaggc ggataaagtt   4920

gcaggaccac ttctgcgctc ggcccttccg gctggctggt ttattgctga taaatctgga   4980

gccggtgagc gtgggtctcg cggtatcatt gcagcactgg ggccagatgg taagccctcc   5040

cgtatcgtag ttatctacac gacggggagt caggcaacta tggatgaacg aaatagacag   5100

atcgctgaga taggtgcctc actgattaag cattggtaac tgtcagacca agtttactca   5160

tatatacttt agattgattt aaaacttcat ttttaattta aaaggatcta ggtgaagatc   5220

ctttttgata atctcatgac caaaatccct taacgtgagt tttcgttcca ctgagcgtca   5280

gaccccgtag aaaagatcaa aggatcttct tgagatcctt tttttctgcg cgtaatctgc   5340

tgcttgcaaa caaaaaaacc accgctacca gcggtggttt gtttgccgga tcaagagcta   5400

ccaactcttt ttccgaaggt aactggcttc agcagagcgc agataccaaa tactgtcctt   5460

ctagtgtagc cgtagttagg ccaccacttc aagaactctg tagcaccgcc tacatacctc   5520

gctctgctaa tcctgttacc agtggctgct gccagtggcg ataagtcgtg tcttaccggg   5580

ttggactcaa gacgatagtt accggataag gcgcagcggt cgggctgaac ggggggttcg   5640

tgcacacagc ccagcttgga gcgaacgacc tacaccgaac tgagatacct acagcgtgag   5700

ctatgagaaa gcgccacgct tcccgaaggg agaaaggcgg acaggtatcc ggtaagcggc   5760

agggtcggaa caggagagcg cacgagggag cttccagggg gaaacgcctg gtatctttat   5820

agtcctgtcg ggtttcgcca cctctgactt gagcgtcgat ttttgtgatg ctcgtcaggg   5880

gggcggagcc tatggaaaaa cgccagcaac gcggcctttt tacggttcct ggccttttgc   5940

tggccttttg ctcacatg                                                  5958
```

```
<210> SEQ ID NO 87
<211> LENGTH: 600
<212> TYPE: DNA
<213> ORGANISM: Artificial Sequence
<220> FEATURE:
<223> OTHER INFORMATION: Nucleotide sequence of PA#1j(200), codon-
      optimized for P. pastoris
```

<400> SEQUENCE: 87
gccgcacctg ccgcacctgc ccctgctgcc ccagctgccc ctgctcctgc cgcccctgcc 60
gccgctcctg ccgctcctgc tcctgccgct ccagctgctc cagctcctgc tgctccagca 120
gctgccccag ccgccccagc tcctgctgcc ccagccgcac ctgcaccagc cgctccagct 180
gctgcccctg ccgcacctgc accagctgct ccagccgcac ctgcacctgc cgccccagct 240
gccgcccctg ccgcaccagc tcctgcagcc cctgccgctc cagccccagc agctccagct 300
gccgcccctg cagcccctgc cccagccgca ccagctgccc ctgccccagc agctcctgct 360
gccgcccctg ctgctccagc accagcagct ccagccgcac ctgctccagc cgctccagct 420
gccgcacctg ccgctccagc ccctgcagcc cctgcagccc cagctccagc cgccccagcc 480
gccgcacctg cagccccagc accagctgcc cctgcagcac cagctcctgc tgctcctgct 540
gcagcaccag ccgcaccagc accagcagca ccagccgccc cagccccagc cgcaccagca 600

<210> SEQ ID NO 88
<211> LENGTH: 600
<212> TYPE: DNA
<213> ORGANISM: Artificial Sequence
<220> FEATURE:
<223> OTHER INFORMATION: Nucleotide sequence of PA#1k(200), codon-
optimized for P. pastoris

<400> SEQUENCE: 88
gccgcccctg ccgcccccgc tcctgctgca cctgctgctc ccgcacccgc cgcccctgcc 60
gctgcccctg ctgcaccagc ccctgctgct ccagccgcac cagctccagc agctcctgcc 120
gctgccccag ctgccccagc tcccgccgcc cccgccgctc ctgcacccgc tgcaccagcc 180
gccgccccag ccgctccagc cccagccgct cctgcagctc ctgctcctgc tgcccctgca 240
gccgccccgg cagctccagc tcccgcagct cctgctgcac cagctcccgc tgctcctgca 300
gccgcacctg ctgcccctgc tcctgctgct ccagctgcac ccgctcctgc cgcaccagcc 360
gctgcccctg ccgctccagc acccgccgca ccagccgctc ctgcccctgc agctccagcc 420
gccgcccctg ccgcgcctgc tccagccgct cctgcagcac ctgcacctgc agcacctgct 480
gcagcaccag cagctcctgc tcccgcagca ccagcagccc cagcaccagc cgctccagca 540
gccgctccag ctgcacctgc ccctgcagca cctgcagctc ctgctccagc ggctccagct 600

<210> SEQ ID NO 89
<211> LENGTH: 600
<212> TYPE: DNA
<213> ORGANISM: Artificial Sequence
<220> FEATURE:
<223> OTHER INFORMATION: Nucleotide sequence of PA#1l(200), codon-
optimized for P. pastoris

<400> SEQUENCE: 89
gccgcccccg ccgctccagc acctgccgca cctgcagctc cagcccctgc tgctcctgct 60
gctgcacctg ccgctcccgc accagctgct cccgcagctc ccgcccctgc cgcgccagct 120
gccgctcccg ctgcccctgc accagctgct cctgctgctc ctgcccctgc tgcacctgca 180
gctgctccag ccgcccctgc tccggcagcc ccagcagcac ccgctcctgc tgcaccagcc 240
gccgcaccag ctgctccagc tccggcagca cctgcagccc ccgctccagc cgcccctgcc 300
gcagccccag ctgcgccagc tcccgctgct ccagcagctc cagcacccgc cgctccagcc 360
gccgctcccg ctgctccagc tccggctgca cctgctgcac ctgctcctgc tgctcccgct 420
gctgcccccg cagcaccagc tcctgccgca cctgctgctc ctgctccagc agcacccgcc 480
gcagctcctg cagcaccggc tccagcagct cctgctgcac ctgcccctgc cgctcccgct 540
gcagctcccg ccgctcccgc ccctgctgca cccgctgccc cagcacctgc agcacctgca 600

<210> SEQ ID NO 90
<211> LENGTH: 600
<212> TYPE: DNA
<213> ORGANISM: Artificial Sequence
<220> FEATURE:
<223> OTHER INFORMATION: Nucleotide sequence of PA#1m(200), codon-
optimized for P. pastoris

<400> SEQUENCE: 90
gccgcacccg ctgcacctgc ccccgcagcc ccagccgccc ctgcccccgc tgcacctgca 60
gcagcccccg ctgcccctgc acccgcagca ccagctgcac ctgctcctgc cgctcccgct 120
gctgcacctg ctgccccagc ccctgctgca ccagcagctc cagctcccgc tgcccctgct 180
gcagcacccg ctgctcctgc tcctgcagct ccagctgcac cagccccagc agcacctgcc 240
gctgctcctg ctgcccccgc tccagcagcc cctgcagcac ctgctcctgc agcccccgca 300
gcagctccag ctgcccctgc ccccgccgct ccagctgctc ctgctcccgc cgcacctgcc 360
gcagctcctg cagctcctgc acctgctgct ccagccgctc ccgcaccagc agcacctgct 420
gccgctcctg cagccccagc acccgctgcc cccgcagcac ctgcacccgc cgcccctgct 480
gccgcacccg ccgcacctgc tccagctgct cccgcagccc ctgcacctgc cgctcctgcc 540
gccgctccag ccgctccagc ccccgcagct cctgccgctc cagcacctgc agctccagca 600

<210> SEQ ID NO 91
<211> LENGTH: 600
<212> TYPE: DNA
<213> ORGANISM: Artificial Sequence
<220> FEATURE:
<223> OTHER INFORMATION: Nucleotide sequence of PA#1n(200), codon-
optimized for S. cerevisiae

<400> SEQUENCE: 91
gccgctccag ctgcaccagc tccagcagct ccagccgctc ctgctcctgc tgctcccgca 60
gcagcccctg cagcacccgc tccagcagca cccgctgctc cagctccagc tgcacccgca 120
gctgctccag cagcacctgc accagccgca ccagcagctc ccgctccagc agctcctgca 180
gcagcacccg ccgcaccagc accagccgca ccagctgctc cagcaccagc cgctccagct 240
gcagccccag cagctcccgc tcctgcagct cctgctgctc ctgcaccagc agcacccgcc 300
gcagctcccg cagcaccagc tccagctgct cccgctgcac ccgctccagc cgcaccagcc 360
gctgcaccag ctgcacccgc tccagctgca cccgccgctc cagctcctgc agcaccagct 420
gctgccccag ccgctccagc accagctgct cccgccgctc ctgcaccagc agctccagct 480
gccgctcctg cagcacccgc accagctgca ccagcagcac cagcaccagc agcaccagct 540
gctgctcccg ctgctcctgc tcctgccgct cctgcagctc cagctcctgc cgctccagct 600

<210> SEQ ID NO 92
<211> LENGTH: 600
<212> TYPE: DNA
<213> ORGANISM: Artificial Sequence
<220> FEATURE:
<223> OTHER INFORMATION: Nucleotide sequence of PA#o(200), codon-
optimized for S. cerevisiae

<400> SEQUENCE: 92
gccgctccag ctgctccagc cccagctgca cctgcagcgc cagcaccagc agctccagca 60
gctgcaccag ccgctcccgc accagctgct cctgctgctc cagcgcctgc agctcctgct 120
gccgctccag ctgccccagc tccagcggct ccggcagcgc cagccccagc agcacccgcc 180
gctgcacctg ccgcaccagc tcctgccgca cctgctgctc ccgcaccagc agcaccggca 240
gctgctccag ccgcaccagc gcctgccgca cccgctgccc cagcacctgc ggcgccagca 300
gcagctcctg cggcaccggc accagctgcc cctgcagctc cggctccagc tgcgcctgcc 360
gctgcaccag ctgcgcctgc gccagccgct cctgctgcgc ctgcaccagc ggcaccagca 420
gctgcacccg ctgcaccagc gccagcagct ccggcagctc cagcgcccgc ggcgcctgct 480
gctgcccctg ccgctccagc tccagctgct cctgcagcac cagcccctgc agccccggcg 540
gccgcaccag cagcgcctgc acctgcggct ccagcagccc cagccccagc ggcccctgcc 600

<210> SEQ ID NO 93
<211> LENGTH: 600
<212> TYPE: DNA
<213> ORGANISM: Artificial Sequence
<220> FEATURE:
<223> OTHER INFORMATION: Nucleotide sequence of PA#1p(200), codon-
      optimized for S. cerevisiae

<400> SEQUENCE: 93
gccgctccag cagcaccagc tcctgcagct ccagctgcac ctgctccagc cgctcccgct 60
gcagctccgg ccgctcccgc cccagccgca cccgcagccc cagctcccgc tgctccagct 120
gcagctccag cagcacctgc gcccgcggca ccagccgctc ctgcaccggc tgcacccgct 180
gcggcgccgg cagcacccgc tcccgcagcc cccgcagcgc ccgccccagc ggccccagcc 240
gcggcgccag cagctccagc tccagcggca cccgcggcac cagctcccgc agcgccggcg 300
gcagctcctg cagccccggc ccccgccgca ccagcagctc ctgctccggc ggcaccagca 360
gcagcgccgg cggctccggc gccggcagcg ccagcggccc ctgctcccgc cgcgccggca 420
gcagcccccg ccgctccagc ccctgcggct ccggcggcgc ccgcccccgc agcacctgcg 480
gctgcgccag ccgcacctgc cccggctgca cctgctgcac ccgcgccggc tgcacccgcg 540
gctgccccgg ctgctccggc gccagcggca cctgctgcac cagcacctgc cgcgccagcg 600

<210> SEQ ID NO 94
<211> LENGTH: 600
<212> TYPE: DNA
<213> ORGANISM: Artificial Sequence
<220> FEATURE:
<223> OTHER INFORMATION: Nucleotide sequence of PA#1q(200), codon-
      optimized for K. lactis

<400> SEQUENCE: 94
gccgctccag cagcaccggc cccagccgcg cccgccgctc cagctcccgc tgcacctgca 60
gccgctcctg ctgcacctgc acctgcagcc ccagccgctc cagctcctgc cgctccagcc 120
gccgcccctg ccgcacccgc accagcagca cctgccgcgc ctgctccagc agcaccagcc 180
gcagcaccag ccgctccagc gcctgcagct ccagcagccc cagctcccgc agcaccagct 240
gcagcaccag cagctcctgc acctgcagca ccagccgcac cagcccccgc tgcccctgct 300
gccgcccctg cagcacctgc gccagccgcg ccagcagctc cagctccagc agcacccgca 360
gcagctccag cagctcccgc tcctgctgcc cctgccgctc ctgcccctgc tgcaccagcc 420
gccgctcccg cagctcctgc accagctgca cctgccgccc ccgcacctgc cgcacccgct 480
gccgctcctg ctgcccccgc acccgctgca cccgcggccc cggccccggc agctccagca 540
gcagctcctg ccgctccggc ccctgcagca ccagccgctc ccgcaccggc cgcacccgcc 600

<210> SEQ ID NO 95
<211> LENGTH: 600
<212> TYPE: DNA
<213> ORGANISM: Artificial Sequence
<220> FEATURE:
<223> OTHER INFORMATION: Nucleotide sequence of PA#1r(200), codon-optimized for K. lactis

<400> SEQUENCE: 95
gccgccccag cagctcctgc tccagctgct cccgctgctc cagcccctgc agctcccgcc 60
gcagcaccag ccgccccagc tcctgccgct cccgccgctc cagcacctgc cgcccctgct 120
gctgctcctg ccgctcctgc ccccgccgcc ccagccgccc cagccccagc agcaccagca 180 gcggccccctg cagccccagc tcctgcagca cctgccgcac ctgcaccagc tgccccagct 240
gccgccccag cagcccctgc tcctgcagca ccagctgcac ctgctccggc cgcaccagca 300
gccgcacctg cagctccagc acccgcagct cccgcagccc cagcacctgc cgctcccgct 360
gctgctcccg ccgctcctgc cccagctgct cctgccgcac ctgctcccgc agctccagcc 420
gctgcgcctg ctgcaccagc acccgcagca ccggcagcgc cagcacctgc agctcctgcc 480
gcagcgcccg cagcaccagc ccctgccgct ccagcagcac ctgctcctgc tgctccagcc 540
gccgcccccg ctgcaccagc tccagctgca ccagctgctc ccgcccctgc tgccccggcc 600

<210> SEQ ID NO 96
<211> LENGTH: 600
<212> TYPE: DNA
<213> ORGANISM: Artificial Sequence
<220> FEATURE:
<223> OTHER INFORMATION: Nucleotide sequence of PA#1s(200), codon-optimized for K. lactis

<400> SEQUENCE: 96
gccgcccccg ctgctcctgc cccagctgcc cccgccgcgc cagcccctgc tgctcctgct 60
gccgcgcctg cagctccagc cccagccgca ccagcagccc cagccccagc agctcccgcc 120
gcagctccag cagcccccgc cccagctgca ccagccgcac cagcacctgc tgctcccgcc 180
gctgccccag ccgctcctgc tccagccgcc cctgccgctc ccgccccagc agccccagca 240
gcagcgccag cagccccagc acccgctgct ccagccgccc cagctccggc cgcaccagct 300
gccgccccag ccgctcctgc accagctgcc cctgccgccc cagctcccgc cgccccagca 360
gcagctccag ccgcaccagc cccagccgcg ccagctgctc ctgcacctgc tgcacctgca 420
gcagctcccg ctgctccagc acctgctgca cctgctgctc cagccccagc agcgcccgca 480
gccgctccag cagctccagc acctgcagct ccagccgctc cagccccagc cgcgcctgcc 540
gccgctccag ctgcccctgc cccagcagca cccgccgctc cagccccagc agctccagcc 600

<210> SEQ ID NO 97
<211> LENGTH: 600
<212> TYPE: DNA
<213> ORGANISM: Artificial Sequence
<220> FEATURE:
<223> OTHER INFORMATION: Nucleotide sequence of PA#1t(200), codon-optimized for H. sapiens (HEK cells)

<400> SEQUENCE: 97
gccgctcctg ctgctccagc tccagctgca ccagccgctc cggcaccagc agcacccgct 60
gctgcccctg cagctcctgc tccggcagct cccgcagctc ctgcaccagc tgctccagct 120
gccgctccag ccgctcctgc tcctgccgct cctgcagcac ccgctccggc cgcaccagct 180
gctgctcccg ctgcacccgc tccagcagct ccggctgcac cagcaccggc tgctccagca 240 gcagccccctg cagcaccagc tccagctgct cccgcagctc cagctcctgc tgctccggcc 300
gctgctcctg ccgcaccagc accagccgct ccagctgcac ccgcaccagc tgcacccgcc 360
gctgctccag ctgctcctgc accggcagca ccagctgctc ccgctccggc tgctcccgct 420
gctgcaccgg ccgctccagc tccagcagct cctgccgctc ccgcaccagc agctcccgca 480
gcagcacccg ccgcaccggc tccggcagca ccagccgcac cagctcccgc tgcaccggct 540
gccgcaccgg ctgcaccggc accagcagct ccagccgctc cggctcctgc agctccagca 600

<210> SEQ ID NO 98
<211> LENGTH: 600
<212> TYPE: DNA
<213> ORGANISM: Artificial Sequence
<220> FEATURE:
<223> OTHER INFORMATION: Nucleotide sequence of PA#1u(200), codon-
optimized for H. sapiens (HEK cells)

<400> SEQUENCE: 98
gccgccccgg ctgctcccgc tcctgcagca ccggcagctc ccgctccagc cgcaccagca 60
gcagcacccg cagctccagc accggctgca cccgctgcac ctgctccagc cgctccagca 120
gctgccccag ccgcaccagc accggcagct ccggctgctc ctgctccagc agcacccgcc 180
gcagctccgg ccgctccagc tcctgctgca cccgcagctc ccgcaccggc agctccagcc 240
gctgcaccag cagctccggc tccagctgct ccagcagcac cagctccagc cgcacccgct 300
gcagccccag ctgcaccagc accagccgca cctgcagctc cagcaccagc tgctccggca 360
gctgcacccg ctgctcccgc accagctgca ccagcagcac ccgcaccagc cgctccggcc 420
gcagctcctg cagctcccgc ccctgcagct cctgccgctc ctgctcccgc tgctcctgcc 480
gcagctcccg ctgctccggc tcctgccgca ccagctgcac ccgctccggc agcaccagca 540
gccgcacccg cagcaccagc tccagcagct ccagctgctc ctgctcctgc tgcaccagct 600

<210> SEQ ID NO 99
<211> LENGTH: 600
<212> TYPE: DNA
<213> ORGANISM: Artificial Sequence
<220> FEATURE:
<223> OTHER INFORMATION: Nucleotide sequence of PA#1v(200), codon-
optimized for H. sapiens (HEK cells)

<400> SEQUENCE: 99
gccgccccgg cagcacccgc accggctgca ccagccgctc cagcaccggc cgcaccagcc 60
gcagctccag cagcaccggc accggcagct cccgcagcac cagctccggc agctccagcc 120
gccgctccgg ctgcaccagc tccagcagca ccagctgctc cagctccagc agcacccgca 180
gctgctccag cagctcccgc tccggccgct cctgctgcac cggctccagc tgctccggcc 240
gcagcaccag cagctccagc cccagccgct ccagcagctc ctgctcccgc agcaccggca 300
gccgcaccag ctgctccggc tccggcagct cctgctgcac cagctcccgc cgctccagct 360
gcagctccag ctgctccggc accggctgca ccggccgctc cggctcccgc cgcaccagct 420 gcagccccctg ccgctcctgc accagctgca cccgctgctc cagctccggc tgctcctgca 480
gccgctcctg cagctccggc accagctgca cctgcagctc ccgctccagc tgctcctgca 540
gcagctcccg ctgcaccagc accagcagct cccgccgcac cggctccagc tgcaccagca 600

<210> SEQ ID NO 100
<211> LENGTH: 600
<212> TYPE: DNA
<213> ORGANISM: Artificial Sequence
<220> FEATURE:
<223> OTHER INFORMATION: Nucleotide sequence of PA#1w(200), codon-
optimized for B. subtilis

<400> SEQUENCE: 100
gccgcaccgg ctgcaccggc accagctgcg cctgctgcac cagcaccggc agcaccagca 60
gccgcacccg ctgctcccgc tcctgctgcg ccagctgcac cagctccggc agcgcctgcg 120
gctgctccag cggctccggc tcctgcagct cctgccgctc cagctccagc agcaccagct 180
gcggctccgg ctgcaccggc tccagccgca ccagcagcac cggcaccggc agcgccagct 240
gcagcccctg ctgctccggc gcctgctgca ccggcagctc cggcaccagc ggcaccggca 300
gcagctccgg cagctccggc tcctgctgct ccggcagcgc cagcgccagc agctcctgca 360
gctgctcctg ctgcacctgc accggctgct ccagcagcgc cggcaccggc tgcgccggct 420
gcagctccag ctgctccagc gccagctgct ccggcagcac cggctccggc tgcgcctgca 480
gccgctcctg cagcgcctgc accagccgct ccggcggctc ctgcaccagc cgcaccggct 540
gctgcacctg ctgcgcctgc gcctgctgct cctgctgcgc ctgctccggc agctcctgca 600

<210> SEQ ID NO 101
<211> LENGTH: 600
<212> TYPE: DNA
<213> ORGANISM: Artificial Sequence
<220> FEATURE:
<223> OTHER INFORMATION: Nucleotide sequence of PA#1x(200), codon-
optimized for B. subtilis

<400> SEQUENCE: 101
gccgcacctg cagcaccagc tccggcagca ccggcagctc cagcgcctgc ggctccggct 60
gctgctcctg cagctcctgc gccagctgcg ccagcagctc cagctccagc cgctcctgct 120
gcagcccctg cggcaccggc tccggcagct ccagcggcac cagcaccggc agctccggct 180
gcagcgccag cagctccggc accagcagct ccagcagcgc cagctcctgc ggcaccagcc 240
gcagcaccag ccgctccggc tccagctgcg cctgccgcac cggctccagc ggcaccggct 300
gcggcaccag cagcaccagc gcctgcagca ccagcagcgc cagcacctgc tgctccggca 360
gctgcaccgg ctgctccggc tccagcagct ccggctgcac cagcgcctgc tgcgcctgca 420
gcagcacctg cggctccggc accggctgca ccggcggcac cggctccagc tgctccagca 480
gcggctcctg cagctccggc tcctgccgca ccggctgctc cagctccggc tgcgccagcg 540
gcagcaccgg ctgcaccagc accagcggcg ccagccgcac cagcacctgc tgcgcctgct 600

<210> SEQ ID NO 102
<211> LENGTH: 600
<212> TYPE: DNA
<213> ORGANISM: Artificial Sequence
<220> FEATURE:
<223> OTHER INFORMATION: Nucleotide sequence of PA#1y(200), codon-
optimized for B. subtilis

<400> SEQUENCE: 102
gccgcaccgg ctgcgccagc acctgcagcg cctgccgctc ctgctccggc tgctccggct 60
gctgcaccag cggcaccagc accagcagcg cctgcggcac cggcaccagc cgcaccagct 120
gccgctccag ccgctccggc accggctgct ccggcagcac cagcaccagc tgcaccagcg 180
gcagcgcctg cagcgccagc tccggcagcg ccagcagcac cagctccagc tgcaccggct 240
gctgcccctg ctgcaccagc tccagccgct ccggctgcgc ctgctcctgc agcgccagct 300
gccgctcctg cagcaccagc gccagcggca ccggcagcgc ctgctccggc tgcaccagct 360
gccgcaccgg cagcacctgc accagcagct ccagctgctc cggctccagc ggctcctgca 420
gctgcgcctg cggctcctgc accagcggct ccagctgctc ctgcgcctgc cgctccagca 480
gcagctccag ctgcgcctgc gccagcagca ccggctgcgc ctgcaccagc ggctccggca 540
gcagcaccag ctgcgccagc gcctgcagct ccggctgctc cggcaccagc tgcgccagct 600

<210> SEQ ID NO 103
<211> LENGTH: 600
<212> TYPE: DNA
<213> ORGANISM: Artificial Sequence
<220> FEATURE:
<223> OTHER INFORMATION: Nucleotide sequence of PA#1z(200), codon-optimized for E. coli

<400> SEQUENCE: 103
gccgcacctg ccgcacctgc ccctgctgcc ccagctgccc ctgctcctgc cgcccctgcc 60
gccgctcctg ccgctcctgc tccagccgct ccagctgctc cagctcctgc tgctccagct 120
gctgccccag ccgccccagc tcctgctgcc ccagccgcac ctgcaccagc cgctccagct 180
gctgcccctg ccgcacctgc accagctgct ccagccgcac ctgcacctgc tgccccagct 240
gccgcccctg ccgcaccagc tcctgcagcc cctgccgctc cagccccagc agctccagct 300
gccgctcctg cagcccctgc ccctgccgca ccagctgccc ctgccccagc cgctcctgct 360
gccgcccctg ccgctccagc accagcagct ccagccgcac ctgctccagc tgctccagct 420
gccgcacctg ccgctccagc ccctgcagcc cctgcagccc cagccccagc cgctccagcc 480
gccgcccctg cagccccagc accagctgcc cctgcagccc cagctcctgc tgctcctgct 540
gcagcaccag ccgcaccagc accagcagca ccagccgccc ctgcaccagc cgcaccagca 600

<210> SEQ ID NO 104
<211> LENGTH: 600
<212> TYPE: DNA
<213> ORGANISM: Artificial Sequence
<220> FEATURE:
<223> OTHER INFORMATION: Nucleotide sequence of PA#1aa(200), codon-optimized for E. coli

<400> SEQUENCE: 104
gccgccccag cagcaccggc tccagctgcc ccagccgcac cagcaccagc cgctccagcg 60
gccgcgcctg ccgctcccgc acccgcggct ccggccgccc ctgcgccggc ggcaccggcg 120
gcggcacccg cggcacctgc acctgccgcc cccgcggctc ctgctcccgc ggcgccagca 180
gcagcgccag cggcgcctgc tcctgccgca ccagcagcac cagcacccgc cgcgccagca 240
gcggcccctg cagctcccgc cccggcagcg cccgctgcgc cagcacccgc tgctcccgcg 300
gcagcccccg cagctccggc ccctgcggct ccagctgcac cagcaccggc agcgccggcg 360
gcggcaccag ccgcacccgc accggctgcg cccgccgcgc cagcgccagc cgctccagct 420
gccgcgccgg cagccccggc ccccgctgcc cctgctgcac ccgcgcctgc agcaccggcg 480
gcagcccctg cggcacctgc acccgcggct cccgctgccc ctgcacccgc agcgcccgcc 540
gccgcaccgg ccgctccggc acctgcagcg ccggctgcac cagcgccggc agctccagcg 600

<210> SEQ ID NO 105
<211> LENGTH: 600
<212> TYPE: DNA

<213> ORGANISM: Artificial Sequence
<220> FEATURE:
<223> OTHER INFORMATION: Nucleotide sequence of PA#1ab(200), codon-
optimized for E. coli

<400> SEQUENCE: 105
gccgcgcccg ctgcacccgc accagctgca ccagccgcac cggcaccggc ggccccagct 60
gcagcaccgg cagcccccgc gccggccgcg ccagccgcgc cggcaccggc tgctccggct 120
gcagcaccgg cagcgcctgc gccagctgct cccgcagctc ctgctccggc ggcgcctgca 180
gctgcaccgg cagctcctgc cccagcagcc ccggcggcgc cagcgcccgc cgccccagct 240
gcagcccctg cagcgccggc acccgccgcc cccgcagcac ctgcgccggc cgccccagct 300
gcggcaccgg ccgcacccgc cccggcggct ccagcagcac ctgctccagc agcaccagct 360
gcagcccctg cggcaccagc acccgcagcg ccagcggcac cagctccggc cgctcccgcc 420
gctgcaccag cctcaccggc gccggccgca ccagctgctc ccgccccagc cgctcccgcg 480
gcggcaccag cggcgccagc gcccgcagct ccggcagcac cggcgccggc tgctcctgcc 540
gccgcacctg ctgccccggc gcccgccgcc cccgccgctc ccgcgccggc tgcacctgcg 600

<210> SEQ ID NO 106
<211> LENGTH: 600
<212> TYPE: DNA
<213> ORGANISM: Artificial Sequence
<220> FEATURE:
<223> OTHER INFORMATION: Nucleotide sequence of PA#1ac(200), codon-
optimized for E. coli

<400> SEQUENCE: 106
gccgcgccag cggcgccagc tcctgccgcg cccgcagccc cagcgcccgc cgctccggcc 60
gccgcgcccg cggctcccgc acccgctgcg cccgccgctc cagcacctgc cgccccagcg 120
gcggcaccag ccgcgccagc acccgctgcg cctgcagcac ccgctccggc ggccccggcg 180
gctgctccag ccgcccctgc acccgctgct ccagctgcgc ccgccccagc cgccccggcc 240
gccgctccgg ctgcaccggc accggcagca ccggctgcgc cagccccggc tgccccggca 300
gctgctccgg cggcacctgc ccccgccgcg ccagctgccc ccgcaccggc agctccagcg 360
gcagccccgg cggcaccagc tccagcagcg ccagctgcgc ctgccccagc agcgccagcc 420
gctgctccag cagctcctgc ccctgctgcg cctgcggctc cggcgccagc tgctcctgct 480
gcagctccgg ccgccccagc accggcagcg ccagcagcac cggcgccagc tgcccctgcc 540
gccgcaccag cagcacctgc gccggcggct cccgcagcac ctgctccggc tgcccctgcc 600

<210> SEQ ID NO 107
<211> LENGTH: 600
<212> TYPE: DNA
<213> ORGANISM: Artificial Sequence
<220> FEATURE:
<223> OTHER INFORMATION: Nucleotide sequence of PA#1ad(200), codon-
optimized for E. coli

<400> SEQUENCE: 107
gccgcgcccg ctgcaccggc acctgctgcg ccggcggcgc ctgcacctgc agcaccagca 60
gcggccccgg cggctcccgc acctgccgcc ccggcagctc ccgcaccggc ggcgcctgcc 120
gcagctcccg ccgcaccagc gccagccgca ccagccgctc cggcccccgc ggctccggca 180
gcagcccccg ccgctccagc gcctgctgca cctgccgcgc ctgcgcctgc cgcacctgcc 240
gctgctcccg ctgccccagc tccagccgct ccggcggcgc ccgcacctgc tgcccctgcg 300
gccgctcccg ctgcgcccgc gcctgctgct cctgcagcac cagctcccgc cgctccggcc 360
gcagcccccg ctgccccggc gcctgcagct ccagcggcgc cggctcccgc tgcgcccgcc 420
gcagcccccg cagccccagc acctgctgct cccgctgcgc cggccccggc tgctccagct 480
gcagctccag cggcccctgc ccctgctgct cccgccgcgc cagctcctgc cgctccagct 540
gcagctcctg ctgctcccgc gccggcagct ccggctgcac cggctccagc agctcctgcg 600

<210> SEQ ID NO 108
<211> LENGTH: 300
<212> TYPE: DNA
<213> ORGANISM: Artificial Sequence
<220> FEATURE:
<223> OTHER INFORMATION: Nucleotide sequence of PA#1ae(100), codon-
optimized for E. coli

<400> SEQUENCE: 108
gccgctcctg ctgcccctgc tcccgctgcc cccgccgccc ccgccccagc tgcccccgct 60
gccgcacctg ctgccccagc tcccgctgcc ccagccgcgc cggcccccgc agctccagcc 120
gcggcaccag ctgccccagc tccagcggcg cctgctgccc cggcccccgc ggcaccggct 180
gccgcgcccg cagctccagc gcctgctgca ccggctgctc cggcacccgc cgcgccagca 240
gctgcccctg cggcaccagc tcctgctgcc cccgcggcac ctgcacccgc tgccccggcg 300

<210> SEQ ID NO 109
<211> LENGTH: 600
<212> TYPE: DNA
<213> ORGANISM: Artificial Sequence
<220> FEATURE:
<223> OTHER INFORMATION: Nucleotide sequence of PA#1af(200), codon-
optimized for C. glutamicum

<400> SEQUENCE: 109
gccgcgcccg cggctcctgc cccagcagcg cccgcggcac cagcaccggc ggccccggcc 60
gccgcccctg ctgcgcccgc gcctgcagct cccgccgccc cagcccccgc tgcaccagca 120
gccgctccag ccgcaccggc gcccgctgca cctgccgctc cggcgccggc cgctccagcc 180
gctgcaccag ccgcgccagc accagctgca cctgcggccc ctgcgccagc tgcgccagca 240
gcggcaccag cagctccagc tccagctgcg cctgcggcac ctgccccggc tgccccggcg 300
gctgcgcctg cggcccctgc accagccgcc ccagctgcac ccgcccctgc ggcgcctgcc 360
gccgcacccg ccgcgcctgc cccagccgct ccggcggcac ctgccccagc tgctcctgca 420
gcagcccctg ccgccccggc gccagccgca cccgccgcac cagcacctgc agcgccagct 480
gccgcgccag ctgcgcctgc ccccgcagcc cccgccgctc ctgctccagc cgcacccgca 540
gccgctccgg ctgctccagc cccagcagct ccagcggcac ccgcccctgc tgcaccggct 600

<210> SEQ ID NO 110
<211> LENGTH: 600
<212> TYPE: DNA
<213> ORGANISM: Artificial Sequence
<220> FEATURE:
<223> OTHER INFORMATION: Nucleotide sequence of PA#1ag(200), codon-
optimized for C. glutamicum

<400> SEQUENCE: 110
gccgctccgg ccgcccccgc acccgctgct cccgcagcgc cggcgcctgc ggcacccgca 60
gccgcccctg cagccccagc tcccgcagcc cccgctgctc ctgctccagc tgcacccgcg 120
gctgcacccg ctgcaccggc cccggcggct cctgccgccc cagcgccggc ggctcccgct 180

-continued gctgcacccg cggcccctgc gccggcagcc ccagcggcac cagcgcctgc cgcaccggca 240
gccgccccag ccgccccagc gccagctgcg ccagcggctc cggccccagc tgcgccggca 300
gcggcacctg cagctccagc tcctgctgct cccgcggcgc ccgcccccgc agcacctgct 360
gccgccccag ctgccccagc tccggccgcc cctgcggctc ctgctcctgc agcgcctgct 420
gcggctcccg cggcgccagc gccggcggcc ccagcagctc cagctcctgc agcaccggca 480
gcggcccccg cggctccagc tcctgcagct ccggctgccc cagcccctgc cgcaccggct 540
gcagcgcccg cggctcccgc tcctgcagca cctgcagcac cagcccctgc tgcaccggcg 600

<210> SEQ ID NO 111
<211> LENGTH: 600
<212> TYPE: DNA
<213> ORGANISM: Artificial Sequence
<220> FEATURE:
<223> OTHER INFORMATION: Nucleotide sequence of PA#1ah(200), codon-optimized for C. glutamicum

<400> SEQUENCE: 111
gccgctcctg cagcaccagc gccagcggct cccgccgcac cggcaccagc tgctcccgct 60
gcagcgccgg cggcacccgc tccggctgcg ccggccgcgc ctgccccggc ggcgcctgca 120
gcagcgcctg ccgcacctgc tccagccgct ccagcggcgc ccgcccccgc ggccccagca 180
gcggctccgg cggccccagc gcccgcagcc ccagccgcgc ccgcacctgc tgcgccggcc 240
gccgcacccg cggcaccggc gcccgcggcc cccgctgccc ctgcacccgc tgcccccgca 300
gccgctccag cagcaccagc accagcggct ccggcggcgc cggctcccgc tgcccccgca 360
gcagcgcccg ccgcccccgc gcctgccgca ccagcggcac cggcaccagc agcgcccgcg 420
gccgcgccag ctgcgcccgc cccagcggct cctgccgccc ccgcgccggc cgctcctgca 480
gctgcccctg ccgctccggc gccagccgct cccgccgccc ccgctcctgc ggctccggcc 540
gctgcgccgg ctgcccctgc accagcggct ccggccgctc cggcccccgc cgctccagct 600

<210> SEQ ID NO 112
<211> LENGTH: 600
<212> TYPE: DNA
<213> ORGANISM: Artificial Sequence
<220> FEATURE:
<223> OTHER INFORMATION: Nucleotide sequence of PA#1ai(200), codon-optimized for C. glutamicum

<400> SEQUENCE: 112
gccgctccag ctgcacccgc tcctgccgca ccggcggctc cagcacccgc ggcacctgcc 60
gccgcacctg ctgcacctgc accggccgct cccgccgccc cggccccggc ggctccagcc 120
gctgcgcccg cagctcctgc ccccgcagcc ccggcagcgc ccgcaccggc agcccctgcg 180
gcggcgcccg cagcaccagc tccggccgct cccgctgccc cggcaccggc tgccccagcc 240
gccgcacctg cggcgccggc gccggccgca ccggctgcgc ccgcgccggc agcccccgct 300
gcagcacctg ccgccccagc cccagccgct ccagccgctc ccgcaccggc tgcgcctgct 360
gcagccccag ccgcgccggc tccggcggcc ccggcggccc cggctccggc agccccagcc 420
gcagcccccg cagcgccagc gccagccgct ccggcagcac ctgcacctgc ggcgcccgcg 480
gcggcacctg cagcgcctgc gcccgctgcc cccgcggccc ccgctcctgc cgcgccggcg 540
gcggcaccag ccgcccctgc cccagctgca ccggcagcgc ctgcccccgc tgcgccagcc 600

<210> SEQ ID NO 113
<211> LENGTH: 600

<212> TYPE: DNA
<213> ORGANISM: Artificial Sequence
<220> FEATURE:
<223> OTHER INFORMATION: Nucleotide sequence of PA#1aj(200), codon-
optimized for P. patens

<400> SEQUENCE: 113
gccgctcccg ctgcccctgc tcctgctgcg cccgctgcac ctgcccctgc tgctcccgca 60
gctgctccag ccgcccccgc tcccgctgca ccagctgctc ccgctcctgc cgctcccgct 120
gccgcacccg ctgcacctgc gcctgcggct cccgccgctc ccgcccccgc tgcgcccgca 180
gccgcccccg cagcccccgc accagcagcc ccagccgcac cagctccagc agccccagct 240
gccgcacctg ctgcacccgc tcctgctgct cccgcagcac cagcccctgc agctcccgct 300
gccgcgcctg ccgcccctgc ccccgcagca ccagcagctc ccgccccagc tgcacctgca 360
gccgctccag cagccccagc ccctgccgct ccagctgctc ctgctccagc cgcaccagca 420
gccgcacccg ctgcaccagc acctgcagcg cccgctgcac cagcgcccgc tgccccagct 480
gccgctcccg ccgcaccagc tcctgctgca cccgctgctc cagcacccgc cgctcccgcc 540
gctgctcctg ccgctcctgc tcccgcagct cccgctgcgc ctgctccagc tgcaccagcc 600

<210> SEQ ID NO 114
<211> LENGTH: 600
<212> TYPE: DNA
<213> ORGANISM: Artificial Sequence
<220> FEATURE:
<223> OTHER INFORMATION: Nucleotide sequence of PA#1ak(200), codon-
optimized for P. patens

<400> SEQUENCE: 114
gccgcacctg ccgcaccagc ccccgcagca cccgcagcgc cagctccagc agctccagcc 60
gccgcacctg ccgctcccgc gcccgctgct cctgccgccc ctgcccctgc tgcacccgct 120
gcagctcctg ccgctcctgc acctgccgct cctgcagccc ctgctcctgc tgcccctgct 180
gccgctccag ctgcccctgc tcctgccgcg cctgctgccc cagcaccggc cgccccagca 240
gctgctcctg ctgcccccgc accagcagct ccagccgcgc ctgcgcctgc tgcccccgct 300
gccgctcctg ccgctcctgc ccctgctgct cctgctgcac ccgctcccgc tgctcctgct 360
gctgcacccg ccgcccctgc tcctgcagct ccagccgctc ccgctccagc tgcaccagcc 420
gccgccccag ccgcgccagc gccagctgcc cctgctgcac ctgctcccgc cgctcccgct 480
gccgcccccg ctgcacccgc accagctgca cccgctgctc ccgcccctgc tgctcccgct 540
gcagctccgg ccgctcccgc acctgctgct cccgctgccc ctgcgcctgc cgctcccgca 600

<210> SEQ ID NO 115
<211> LENGTH: 600
<212> TYPE: DNA
<213> ORGANISM: Artificial Sequence
<220> FEATURE:
<223> OTHER INFORMATION: Nucleotide sequence of PA#1al(200), codon-
optimized for P. patens

<400> SEQUENCE: 115
gccgcaccag ctgctcccgc acctgcagca ccagccgctc ccgcccctgc cgctccagcc 60
gccgcaccag ccgccccagc ccctgcagca cccgcagcac ctgctcccgc agctccagcc 120
gcagccccag ccgctcctgc accagccgcc cctgctgcac cggctccagc cgcgcccgct 180
gctgcgcccg ccgctcccgc cccagccgcc ccagctgccc ccgctccagc tgctcccgca 240
gctgcacccg ccgcacctgc acctgctgcc cccgctgcac ctgcacctgc cgcccctgca 300
gctgccccag ccgccccggc acccgctgcc cccgccgctc ctgctcctgc tgcaccagct 360
gccgcccctg ccgcccccgc accagcggcc ccagcagccc ccgccccagc cgctccagct 420
gctgctcccg ccgcacctgc cccagccgca cctgccgccc cagctcccgc cgctcccgcc 480
gccgctcctg ctgcacccgc ccctgctgct cctgccgctc ccgctcccgc tgctcccgct 540
gccgctcccg ccgcccccgc tcctgccgcc cccgccgcac cagcacctgc agctcctgcc 600

<210> SEQ ID NO 116
<211> LENGTH: 600
<212> TYPE: DNA
<213> ORGANISM: Artificial Sequence
<220> FEATURE:
<223> OTHER INFORMATION: Nucleotide sequence of PA#1am(200), codon-optimized for P. fluorescens

<400> SEQUENCE: 116
gccgcgccag cggcgccggc cccagccgcg ccggcagcgc cagcgcccgc cgcgccagca 60
gccgcgcctg cggcgcctgc gcctgcggcc ccagcggcgc cggcgccagc ggcaccggca 120
gccgcgcccg cagcgccggc ccctgccgcg ccggcagccc ccgcgcctgc ggccccagca 180
gccgccccgg cggctcccgc gccggccgcc cctgcggcac cggcgcctgc ggccccggcg 240
gccgcgccag ccgcgcctgc cccggccgcg ccggccgcgc cggcgcccgc cgcacctgcc 300
gccgccccgg ccgcgccggc tccggccgcg ccagcggccc ctgcgcctgc agccccagcc 360
gcggccccgg cggcgcccgc accagccgcg cctgccgcgc ccgcgccggc cgcaccggca 420
gccgcgccgg ccgcgcctgc ccctgccgcc cccgccgcgc ctgccccagc agccccggca 480
gccgccccgg cagcgcctgc gccagccgca ccggccgcgc cggcgccagc cgcaccagcc 540
gccgcaccgg ccgcccctgc gccagcggcg cccgcagcgc cggcgcctgc cgcacccgcg 600

<210> SEQ ID NO 117
<211> LENGTH: 600
<212> TYPE: DNA
<213> ORGANISM: Artificial Sequence
<220> FEATURE:
<223> OTHER INFORMATION: Nucleotide sequence of PA#1an(200), codon-optimized for P. fluorescens

<400> SEQUENCE: 117
gccgcgcccg cagccccagc cccggccgcg cccgccgcac ccgcgcccgc cgcccctgct 60
gccgcgcccg ccgccccggc cccggccgct cccgccgcgc cggccccggc cgccccggcc 120
gccgcgcctg ctgcccctgc ccctgccgcg ccggccgcgc ccgccccagc ggcccctgcc 180
gccgctcccg ccgcacctgc acccgccgcc ccagctgcgc ccgcacccgc ggcgcccgcc 240
gccgccccgg cagcgcccgc gcctgccgcg ccggccgccc ctgcccctgc tgcgcccgcc 300
gcggccccgg ccgcacccgc gcccgcggcg cccgccgctc cagccccggc cgccccggca 360
gccgcgccag ccgctcccgc cccagccgcc ccggctgcgc ccgcccctgc cgccccggcc 420
gcggctcccg ccgcgcccgc gcccgccgcg cctgccgccc cagcgcccgc cgcgcccgcc 480
gcagcgcccg ccgcgccagc ccccgccgcc ccagcagcgc ccgccccagc agccccggcc 540
gccgcgcccg ccgcgcccgc accagccgca cccgccgccc cagcccctgc agcgcctgcc 600

<210> SEQ ID NO 118
<211> LENGTH: 600
<212> TYPE: DNA
<213> ORGANISM: Artificial Sequence
<220> FEATURE:

<223> OTHER INFORMATION: Nucleotide sequence of PA#1ao(200), codon-
optimized for P. fluorescens

<400> SEQUENCE: 118
gccgccccag ccgcccctgc ccctgccgcc ccagccgcac ccgccccggc agccccagcc 60
gccgccgccg ccgcacccgc cccagcagca cccgctgcgc ccgctcctgc cgcgcccgcg 120
gccgcgcccg ccgcccctgc cccggctgcg cccgccgccc cagcgccagc tgcgcccgcc 180
gccgcccctg ccgccccagc cccggccgca cccgccgccc cggcccctgc cgcgcccgct 240
gccgcacccg ccgcacccgc cccggccgcc cctgccgccc ctgcacccgc cgcgcctgcc 300
gctgccccag ccgcaccagc cccagccgcg ccagccgcac ccgcccctgc agcccctgcc 360
gccgcgccag ccgcgcccgc cccggccgcc ccagccgccc ccgctcccgc cgccccagcc 420
gccgcgccgg cagccccagc cccagccgcc cctgcagcac ccgcacccgc cgcgcccgcc 480
gccgccccag ccgcgcccgc acccgccgcc cctgccgctc ctgccccagc cgccccagcc 540
gccgcaccag ccgcccctgc cccggccgcg cccgctgcgc ccgccccggc cgcacccgcg 600

<210> SEQ ID NO 119
<211> LENGTH: 600
<212> TYPE: DNA
<213> ORGANISM: Artificial Sequence
<220> FEATURE:
<223> OTHER INFORMATION: Nucleotide sequence of PA#1ap(200), codon-
optimized for T. thermophila

<400> SEQUENCE: 119
gccgctccag ctgctccggc tcccgctgct cctgcagctc ccgctccagc tgctcctgca 60
gcagctcctg cagcccccgc tccagctgca ccggctgcac cagctcctgc tgctcctgct 120
gctgcccctg ctgctcccgc ccctgctgct cctgcagctc cggcacctgc tgctcctgct 180
gccgcacctg cagctccagc cccagctgct cctgctgcac ctgctcctgc agcaccagct 240
gctgcacctg ctgcacccgc tccagctgct ccagctgctc ctgcccctgc agctccagct 300
gccgcacctg ccgctccagc tcctgcagct cccgccgcac ctgctccagc agctcccgca 360
gctgcacctg ctgctcctgc cccagcagct cctgcagctc cagctccagc agctcctgcc 420
gctgcacctg ctgctccagc accagctgca ccagcagctc ctgctcctgc agctcctgcc 480
gcagctcctg ctgctcccgc accagctgca cctgccgctc ccgctccagc agcaccagct 540
gccgctccag ctgctcccgc cccagctgct ccagcagctc cagcaccagc agctccagct 600

<210> SEQ ID NO 120
<211> LENGTH: 600
<212> TYPE: DNA
<213> ORGANISM: Artificial Sequence
<220> FEATURE:
<223> OTHER INFORMATION: Nucleotide sequence of PA#1aq(200), codon-
optimized for T. thermophila

<400> SEQUENCE: 120
gccgctcctg ctgcaccagc acctgctgct cctgcagcac ccgctcctgc tgcccctgct 60
gcagctcctg cagctcctgc tcctgctgct ccggcagctc ctgctcccgc tgcccctgct 120
gccgctcctg cagctcccgc acctgctgct ccagctgccc cagcacctgc tgccccagct 180
gcagctcctg cggcccctgc tcctgcagct ccggctgctc ctgctcctgc cgcaccagct 240
gctgctcctg cagccccagc tcctgctgcc ccagccgctc cagctccagc tgcaccagct 300
gcagcacctg ctgctccggc tccagctgct cccgcagcac ctgctcctgc tgcaccggca 360
gctgctcctg cagctcctgc accagctgct cctgccgccc ctgcacctgc tgcacctgct 420
gctgcacctg cagctcctgc tccggctgca cctgctgccc ctgcaccagc tgcacctgct 480
gcagcacctg ccgctcctgc cccagctgcc cctgctgctc ctgctccagc tgcacccgct 540
gctgcacctg ctgcgccagc tcctgctgca cctgcagccc ctgctcctgc tgcacctgct 600

<210> SEQ ID NO 121
<211> LENGTH: 600
<212> TYPE: DNA
<213> ORGANISM: Artificial Sequence
<220> FEATURE:
<223> OTHER INFORMATION: Nucleotide sequence of PA#1ar(200), codon-optimized for T. thermophila

<400> SEQUENCE: 121
gccgctcctg cagctccagc acctgctgca ccagctgccc ctgccccagc tgctcccgct 60
gctgctccag ctgcacctgc acccgctgca ccggctgctc cggctcctgc tgctcctgcc 120
gctgctcctg ctgcccccgc tcctgctgca cctgccgcac ctgctcctgc ggctccagcc 180
gctgctccag cagctcctgc tccagccgca ccagcagcac cagctcctgc agcacctgca 240
gctgctcctg cggcacctgc tccagctgct ccagcggctc ctgcacctgc tgctcccgca 300
gctgctccag ccgcccctgc tcctgctgcg cctgctgctc cagcccctgc agctcctgcc 360
gccgctcctg cagcccctgc tccagcagcc cctgccgctc ctgctcctgc agcgcctgca 420
gctgcaccag ccgctcctgc ccctgctgct ccagcagcac ctgctcccgc cgctccagct 480
gccgctccag cagctccagc tcctgctgct ccagcggcac cagctccagc tgctcctgct 540
gctgctcctg ctgcacccgc acctgcagca ccagcagctc ccgctcctgc tgctcccgct 600

<210> SEQ ID NO 122
<211> LENGTH: 600
<212> TYPE: DNA
<213> ORGANISM: Artificial Sequence
<220> FEATURE:
<223> OTHER INFORMATION: Nucleotide sequence of PA#1as(200), codon-optimized for T. thermophila

<400> SEQUENCE: 122
gccgcacctg cagctccagc acctgccgct cccgccgcac ctgctcctgc cgctcctgct 60
gccgctccag cagcacctgc tcctgcagct ccagcagctc ctgcccctgc tgctcctgcc 120
gcagctcctg ccgcacccgc tcccgctgct ccagctgctc ctgctccggc tgctccagct 180
gctgctcctg ctgcccctgc tcctgctgct cctgcggctc cagcacccgc agctcccgcc 240
gccgctcctg ctgctcccgc acccgctgct cctgccgctc cagcacctgc tgctcctgct 300
gcagctcccg cagctcctgc gcctgctgct cctgctgcgc ctgctcccgc tgctccagca 360
gcagctcctg ctgctccagc ccctgctgct cccgctgctc ctgcacctgc agctcctgca 420
gctgcccctg cagctccagc accagctgct cctgccgctc ccgctcctgc agctcctgcc 480
gctgcaccag ctgcacctgc accagctgcc cctgctgcac ctgcacctgc cgctcctgca 540
gcagctcctg ctgcacccgc ccctgctgct ccagctgcac ccgctcctgc tgctcctgca 600

<210> SEQ ID NO 123
<211> LENGTH: 600
<212> TYPE: DNA
<213> ORGANISM: Artificial Sequence
<220> FEATURE:
<223> OTHER INFORMATION: Nucleotide sequence of PAS#1k(200), codon-optimized for E. coli

<400> SEQUENCE: 123
gcctctcctg cagctccggc cccagcttca ccagccgctc cagccccatc tgcgccggcc 60
gcctcacctg cagcaccagc ccctgcgtcg cccgccgcgc ctgcgccctc agccccagca 120
gctagccctg ccgcacccgc cccagcaagt cctgctgctc ctgccccctc tgccccggca 180
gcttcaccgg cagcccctgc accagcttcc cccgcagccc ctgcccccag tgcacctgca 240
gctagtcctg cggccccagc accagcgtct ccagctgcgc ccgcgccttc agcaccagca 300
gcttctccgg ccgctcccgc tcccgctagc cctgcagctc cagctccctc agcgcccgca 360
gcaagccctg ccgcaccggc ccctgcctct cctgctgctc ccgcccgtc cgcacccgca 420 gcctcaccag ccgctcctgc tcccgcttcg ccagccgctc ccgcccttc cgcgcctgca 480 gcttctcccg ccgctcctgc tccggcctct cccgcggcgc ctgctccttc tgccccggcc 540
gcgtcccctg ccgcacctgc ccctgcgagc cctgcagccc cagccccgag cgctcctgcc 600

<210> SEQ ID NO 124
<211> LENGTH: 600
<212> TYPE: DNA
<213> ORGANISM: Artificial Sequence
<220> FEATURE:
<223> OTHER INFORMATION: Nucleotide sequence of PAS#1l(200), codon-
optimized for E. coli

<400> SEQUENCE: 124
gccagcccag cagctcccgc tccggcatca cccgctgctc cggccccgag tgctccagct 60
gcttctcctg ccgcacccgc ccctgcaagc ccggcagccc ccgcaccctc cgcgccggcc 120
gcgtcaccag ccgctcctgc acccgcgtca ccagcggcac cggcaccctc tgcgcccgcc 180
gcatcaccag cagcaccggc gcctgcatcc ccagcagcac ctgcaccaag cgcccccgcc 240
gcctccccgg ccgcccctgc accggcaagt cctgcagcac ccgcgccttc agctccggcc 300
gcctccccag cagctcccgc accagccagc ccagccgcac cagcgccgtc tgcaccagcc 360
gcgagcccag ccgcgcctgc accggccagc cctgccgccc cagccccctc tgcgcccgca 420
gcctcccctg cagctcctgc cccggccagt ccagccgccc ccgcgccgag tgcacctgca 480
gcatcaccag cggctcctgc acctgcatct cccgcagcac ccgctccgtc agcccctgca 540
gccagccctg ccgcgccagc acctgcgtca ccagccgccc cggccccgag tgcacctgca 600

<210> SEQ ID NO 125
<211> LENGTH: 600
<212> TYPE: DNA
<213> ORGANISM: Artificial Sequence
<220> FEATURE:
<223> OTHER INFORMATION: Nucleotide sequence of PAS#1m(200), codon-
optimized for E. coli

<400> SEQUENCE: 125
gcctcgcccg ccgctccagc accggcaagt ccagctgctc ctgcccccag cgcacctgcc 60
gcatcgccag ctgctcccgc cccggcctct ccagctgccc ccgccccgtc cgccccccgcc 120 gcaagtccag cagccccagc cccagcctca ccggccgccc cagcacccag tgcgcctgcc 180
gcttcaccag cggcgccagc accagcgtca ccagcggccc cagcgccatc tgcacctgcc 240
gcaagcccag ccgcaccagc tccagcatct ccagccgcac ccgccccgag cgctccagca 300
gcttcaccag ccgcaccggc cccggcatca ccagcagcac ccgcaccctc tgcaccagct 360
gcttctccgg ccgcccctgc tccggcttcc ccagctgccc cggccccgtc cgcccctgca 420
gcaagcccag cagctcccgc gccagcgtct cctgcagcac ctgctcccag cgcacctgct 480
gcgagtccag ccgccccagc accagcttca ccagctgccc ccgcaccaag cgccccagca 540
gctagtccag cagcccccgc tcccgcgtct ccggctgcac cggccccctc tgctccggct 600

<210> SEQ ID NO 126
<211> LENGTH: 300
<212> TYPE: DNA
<213> ORGANISM: Artificial Sequence
<220> FEATURE:
<223> OTHER INFORMATION: Nucleotide sequence of PAS#1n(100), codon-optimized for E. coli

<400> SEQUENCE: 126
gccagtccgg cagcgcccgc tccagcaagt cccgctgcac ccgcacctag cgccccggca 60
gcttccccgg ctgcgcctgc gccagcctct ccggctgccc cagcgccgtc cgcacccgcg 120
gcgtcaccag cagcccctgc gcctgcttcc ccagcagccc ctgcaccgtc agcgccagca 180
gcatcacctg ctgcccccgc acccgcaagt cctgccgcac cggccccttc agcccctgct 240
gcctctccag ccgcgccagc acccgcgtcg cccgctgcgc ctgcccccag cgcacctgca 300

<210> SEQ ID NO 127
<211> LENGTH: 600
<212> TYPE: DNA
<213> ORGANISM: Artificial Sequence
<220> FEATURE:
<223> OTHER INFORMATION: Nucleotide sequence of PAS#1o(200), codon-optimized for P. pastoris

<400> SEQUENCE: 127
gcctcaccag ccgcacccgc cccagctagt cccgcagccc ccgctccctc tgctccagca 60
gccagtccag ccgcaccagc acctgcaagt ccagctgcac ccgcaccttc tgcacctgcc 120
gcctctcccg ctgctccagc cccagcctca cctgctgccc ctgctccatc cgcacctgcc 180
gcatctcctg ccgccccggc acctgcttcc cccgctgcac ccgcccctag tgctcctgca 240
gcatcacccg ctgccccagc ccctgcatcc ccagctgctc cagcccctag tgccccccgct 300 gctagtcccg ctgcaccagc ccccgcaagt ccagctgccc ccgcccccatc tgctcccgcc 360 gcctcccccg cagctcctgc tcccgcttct cctgccgccc cagcccctag tgcacctgct 420
gcctcacctg cagctccagc acctgcctct ccagcagccc cagcacccag tgctcccgct 480
gctagtcctg cagctcccgc accagcttca cctgccgcac ccgcacccag tgctcctgct 540
gcatcaccag ctgctcccgc accagcctcc ccagcagcac cagctcccag tgcacctgct 600

<210> SEQ ID NO 128
<211> LENGTH: 600
<212> TYPE: DNA
<213> ORGANISM: Artificial Sequence
<220> FEATURE:
<223> OTHER INFORMATION: Nucleotide sequence of PAS#1p(200), codon-optimized for P. pastoris

<400> SEQUENCE: 128
gcctctcctg ctgcacccgc tcccgcatca cctgcagcac ctgctcccag tgctccagca 60
gcctcacctg ccgctccagc ccctgccagt cctgccgctc cagctcccag tgctcctgct 120
gcttctccag ccgctccagc tccagcttcc cctgcagctc ccgctccctc agctcctgca 180
gcatctccag ccgcaccagc ccctgcttct cccgcagcac ccgcaccttc cgcaccagcc 240
gcctcccccg ctgcacccgc acctgcttcc ccagcagcac ctgcacccag tgctcccgca 300
gcatcaccag cagccccagc tcctgcttca cccgccgcac cagccccctc cgctcctgct 360
gcttctcctg cagctcccgc tccagcttca cccgctgcac ctgccccctc cgcacccgca 420
gcctcaccag ctgcaccagc acccgcttct cctgcagcac ccgccccctc tgctcccgct 480
gcttctccag ccgcaccagc tcctgcatca cctgcagctc ctgcccccag tgctcccgca 540
gcttctcctg cagctcctgc tccagctagt cccgctgcac ctgccccttc cgcacctgca 600

<210> SEQ ID NO 129
<211> LENGTH: 600
<212> TYPE: DNA
<213> ORGANISM: Artificial Sequence
<220> FEATURE:
<223> OTHER INFORMATION: Nucleotide sequence of PAS#1q(200), codon-
      optimized for P. fluorescens

<400> SEQUENCE: 129
gcctcgcccg cagccccagc gcccgcctcc cctgccgccc ctgccccaag cgccccggca 60
gccagcccgg ccgcaccggc cccagcaagc ccagccgcac cagccccttc cgccccggcc 120
gcctcccctg cagcgcccgc cccggcctcg cccgccgccc cggcgccgag cgcgcccgcc 180
gcctcccctg ccgctcccgc acccgcgagc cctgcagccc cggccccgtc cgccccagcc 240
gcctcccctg ccgcgcccgc cccagctagc cccgcggccc cggccccaag cgctcctgcc 300
gctagccctg ccgccccggc gcccgccagc cctgccgctc ccgccccaag tgctcccgcc 360
gcgtccccgg ccgccccggc cccggcctca cccgcagctc cggccccttc cgcgcccgcc 420
gcgagccccg cagccccggc tcctgccagc cccgccgccc ctgcaccgtc ggcgcccgcc 480
gcctccccag ccgcccctgc cccggccagc cccgccgccc cggcaccgag cgcgccagcc 540
gcttcgcccg ccgcgccagc gcctgcctcg cccgccgcgc ccgccccttc cgcccctgcc 600

<210> SEQ ID NO 130
<211> LENGTH: 600
<212> TYPE: DNA
<213> ORGANISM: Artificial Sequence
<220> FEATURE:
<223> OTHER INFORMATION: Nucleotide sequence of PAS#1r(200), codon-
      optimized for P. fluorescens

<400> SEQUENCE: 130
gcctccccag ccgcgcccgc gcccgctagc cccgcagcgc ccgccccgtc ggcccctgcc 60
gcgtctcctg ccgcgccagc cccggccagt ccagccgcgc ccgccccgtc cgcgccggca 120
gcctcgccag ccgcccctgc acccgcaagc ccggccgcac ccgccccgag cgcaccggca 180
gcctcaccag ctgccccagc cccggcatcc gccgccgctc cagccccatc cgctcccgcc 240
gccagtccgg ccgccccggc tcctgcatcg cccgcagccc ctgccccgag tgcgccagca 300
gcgagccccg ccgcccctgc gcccgccagc ccagctgccc ccgcgccgag tgcgcccgca 360
gcgtccccgg cagccccggc gcccgcctca cccgccgccc cagccccaag cgcacccgct 420
gcgtcgcccg ccgcacctgc tcccgcctcc ccggcagctc ccgccccaag tgcccctgct 480
gcgagtccgg ctgcaccggc cccagcgagc ccggcggccc cggccccgag cgcccctgcc 540
gcaagcccag ccgcccccgc tcccgcatcc ccagccgcgc cggccccgtc cgctccggcc 600

<210> SEQ ID NO 131
<211> LENGTH: 600
<212> TYPE: DNA
<213> ORGANISM: Artificial Sequence
<220> FEATURE:
<223> OTHER INFORMATION: Nucleotide sequence of PAS#1s(200), codon-
      optimized for P. fluorescens

<400> SEQUENCE: 131
gcctcaccag cagctcccgc gcccgcatcg cccgccgccc cggcccctag cgccccggcg 60
gccagccccg ccgcgcctgc cccggcctcg ccggcagccc cagcgccaag tgcgcccgcc 120
gccagccccg ccgccccagc gcccgcctcg ccggccgccc cggccccaag tgctcccgcc 180
gcctccccgg ccgcccctgc gccagccagc cccgcagccc cggccccgtc ggcaccagcc 240
gcctctccag ccgcgcccgc cccggctagc cccgcagccc cagccccgtc cgcccctgcc 300
gcgtcccctg cagccccagc ccctgcgagc cctgccgcac ccgccccgtc cgcgcccgcc 360
gcttcgccgg cagccccggc cccggcgtcg cccgccgccc cagccccgag tgccccggcc 420
gcgagccccg ccgcccccgc cccagcctcg cccgcggccc ctgcaccatc cgcaccggcc 480
gccagcccag cggcgcccgc accggcctcc ccggcagccc ctgcgcccag tgccccggca 540
gctagcccag ccgcgcccgc cccagcgtcg cccgccgcgc ctgccccaag tgcccccgcc 600

<210> SEQ ID NO 132
<211> LENGTH: 600
<212> TYPE: DNA
<213> ORGANISM: Artificial Sequence
<220> FEATURE:
<223> OTHER INFORMATION: Nucleotide sequence of PAS#1t(200), codon-
optimized for C. glutamicum

<400> SEQUENCE: 132
gcctccccgg cggcaccagc accagcgagc ccagcagcac cagcgccgtc tgcacctgca 60
gcgtctcctg ccgctccagc tccggcaagc ccggccgcac ctgctccatc tgctcccgcg 120
gcatccccag ctgcgccagc cccagcttct cccgctgcac cggctccctc cgcaccagcc 180
gcttccccag cagctccagc tccagcatct cccgctgcac ctgcaccgtc agcaccggct 240
gctagccccg cggcgccagc tcctgcgtcc ccggcagctc cagcgccatc cgctcctgcg 300
gcatcccctg cagctccagc acctgcttca cctgctgcac cagccccaag tgctccggct 360
gcatcaccag cagctcctgc accagcgtct cctgcggccc cagcaccatc cgcgcccgca 420
gcttccccag ctgcgcctgc accagcctcc cccgctgcgc cagcgccatc agcacctgcc 480
gcttctccgg ctgctccagc gcctgcctcc ccagctgcac ccgctccatc ggctccggct 540
gcttcacctg ccgcaccagc cccagcgtca cctgcagctc ctgccccatc tgccccagct 600

<210> SEQ ID NO 133
<211> LENGTH: 600
<212> TYPE: DNA
<213> ORGANISM: Artificial Sequence
<220> FEATURE:
<223> OTHER INFORMATION: Nucleotide sequence of PAS#1u(200), codon-
optimized for C. glutamicum

<400> SEQUENCE: 133
gcctccccag cagcgcccgc tccggcatct ccagccgctc cggcccctag cgctccagct 60
gcatctcctg ctgcgcctgc ccctgctagc cctgctgctc ccgcaccttc ggctccggca 120
gcttcgccag ccgctccagc tcccgcctcc ccggccgctc cagcaccctc tgctccagct 180
gcctctccag cagcaccggc accagcttcc cccgcagccc cggctccaag cgctcctgct 240
gcaagtcctg ccgcacctgc gcctgcgtct ccagctgcac cagctcccag cgccccagcc 300
gcttcccctg ctgcacctgc gccggctagt cccgctgcac ccgctccctc cgcccctgca 360
gcatcgccag ccgcccctgc acccgcatct ccggcagcgc ctgctccatc ggctcctgcc 420
gcctccccgg cagctcctgc tcccgcctcc cccgcggcac ctgctccgag tgccccagct 480
gccagcccag ctgctccagc tcctgcctcg cctgctgctc cagccccatc cgcaccagct 540
gccagtccag cggcccccgc accagcaagc cctgccgcgc cggcacccag tgctccagcg 600

<210> SEQ ID NO 134
<211> LENGTH: 600
<212> TYPE: DNA
<213> ORGANISM: Artificial Sequence
<220> FEATURE:
<223> OTHER INFORMATION: Nucleotide sequence of PAS#1v(200), codon-optimized for C. glutamicum

<400> SEQUENCE: 134
gcctccccag ctgctccagc accagcctct cctgcagcac cagcgccatc cgctccggcc 60
gcctcccctg cagcacctgc tcctgccagt cctgctgcac cggccccgag cgcacccgca 120
gctagcccag cagcacctgc acctgcctca cctgcggcgc ctgctccctc cgccccagct 180
gcatctccag ccgcgcccgc tccagcttca ccagctgcac cagcaccgtc tgctccggca 240
gccagccctg ctgctcctgc gccagcatct cccgctgctc cggcgccatc tgcacccgcc 300
gctagtccag ccgcaccagc gcctgcaagc cccgcagcac ccgctccttc cgcacctgcg 360
gctagcccag cagctcctgc tccagcgtcc ccagccgccc ctgcaccaag tgctcctgct 420
gccagcccag ctgccccagc acctgcgagt ccagcagccc ctgcaccgag tgcaccagct 480
gcttcccctg ccgctcccgc accggcttcc ccggcagcac cagctccatc agcgcctgca 540
gcaagtccag cagctccggc cccagctagt cctgcagctc ccgccccgtc agcaccagca 600

<210> SEQ ID NO 135
<211> LENGTH: 600
<212> TYPE: DNA
<213> ORGANISM: Artificial Sequence
<220> FEATURE:
<223> OTHER INFORMATION: Nucleotide sequence of PAS#1w(200), codon-optimized for P. patens

<400> SEQUENCE: 135
gcctctcccg cagccccagc gcccgcatct cctgccgctc ctgctccttc cgctcccgca 60
gctagtccag ccgccccagc tcccgctagt cctgccgccc cagctccgag tgcccccgcc 120
gcttctcccg cagcacccgc cccagcgtca cctgccgctc cagccccctc agctcctgcc 180
gcaagccctg ctgctcctgc tcccgcttct cctgccgcac ccgcaccttc tgcccctgct 240
gcatcacccg ctgctcctgc acccgcgtct ccagcagcgc cggcacctag cgctccagcc 300
gcatcgcccg ccgctcctgc acctgctagc ccggctgccc ctgccccttc agctcccgct 360
gcaagtccag ctgcaccagc ccccgcgtct cctgcagctc ctgccccttc tgctccagcc 420
gcctctccag ctgcccccgc accagcatct ccagctgcgc cggccccctc tgctcctgca 480
gcatcaccag cagctcctgc tcccgcatct ccggctgccc ctgctcccag cgcacctgca 540
gcatcgccag ccgccccagc ccccgcgagc cccgccgctc ccgctccctc tgctccagct 600

<210> SEQ ID NO 136
<211> LENGTH: 600
<212> TYPE: DNA
<213> ORGANISM: Artificial Sequence
<220> FEATURE:
<223> OTHER INFORMATION: Nucleotide sequence of PAS#1x(200), codon-optimized for P. patens

<400> SEQUENCE: 136
gccagccccg ctgctcccgc tccagcttca cctgcagctc cagctcccag tgcccccgcc 60
gcctcccctg ccgctccagc gcccgcgtcc cccgcagctc cagcaccaag cgcacctgct 120
gccagtccag cagcacccgc tccggcgagc ccagctgcac ccgctccatc cgcacctgct 180
gcaagtccag ccgcacctgc gcctgctagc cctgctgcac ccgcccegtc tgcaccagca 240 gcgagccccg cagcacccgc cccggcttcc cccgcagcac cagctccatc ggctcctgca 300
gcttccccgg cagcccccgc gccagcatca cccgcagccc ccgctccctc cgccccagcc 360
gcgagtcctg cagcgcccgc gccagcttct ccagccgccc ctgctccatc agcccccgct 420
gcctcgccag ctgcaccagc accagcatca ccggccgcac cagccccgtc tgcccccgca 480
gcatcaccag cagcacctgc tccagcatcc ccagccgctc cagcaccttc ggccccagca 540
gctagcccgg cagctcccgc cccagccagc cctgctgctc ctgcccctag cgcccctgct 600

<210> SEQ ID NO 137
<211> LENGTH: 600
<212> TYPE: DNA
<213> ORGANISM: Artificial Sequence
<220> FEATURE:
<223> OTHER INFORMATION: Nucleotide sequence of PAS#1y(200), codon-optimized for P. patens

<400> SEQUENCE: 137
gccagtcctg ctgcacctgc ccctgcgtct ccagctgctc ccgctccgag tgctcctgca 60
gcgtctcctg ccgcaccagc cccagcgtcg cctgccgcac ccgcgccttc tgctccagct 120
gcttcaccag ctgctcctgc gcccgcatca cccgcagcgc cagccccatc cgcacccgca 180
gcttccccgg ccgctccagc accagcatct cccgcagcgc ccgctccgtc ggctcctgct 240
gcctctcctg cagcgccggc tccagcatca cctgctgctc cggctccgtc ggcccccggct 300 gcttcgcccg ccgctccagc ccctgctagc ccagccgcac ctgccccgag cgcacctgca 360
gcaagcccgg ccgcacccgc ccctgcttct ccggccgccc ccgcaccgtc cgctcctgct 420
gctagtccgg ctgctccggc ccctgcatcc cctgccgcgc ccgctccttc ggcaccggcc 480
gcgtcacccg ctgcaccagc ccccgcttcc ccggcagctc ccgcgccttc agcgccagcc 540
gctagccccg ccgcacccgc tccagcttct cccgctgctc ctgctccgtc cgcacctgct 600

<210> SEQ ID NO 138
<211> LENGTH: 600
<212> TYPE: DNA
<213> ORGANISM: Artificial Sequence
<220> FEATURE:
<223> OTHER INFORMATION: Nucleotide sequence of PAS#1z(200), codon-optimized for K. lactis

<400> SEQUENCE: 138
gcctctccgg ctgcacccgc cccggctagt ccagccgccc cggctccttc agcaccagca 60
gcttcaccag cagcaccggc tcccgcctcg ccagccgccc ctgctccttc cgccccggct 120
gcaagtccag ccgcccctgc acccgccagt cccgcagctc cagctccatc agcaccagcc 180
gcatcgccgg ctgcaccagc ccctgcatcg ccggcagccc cagccccgtc agctccggct 240
gccagtcctg cagctccggc ccccgcttca cccgccgccc ccgcaccttc cgccccagcc 300
gcaagtcctg ccgccccagc accagctagt ccggctgctc ccgccccatc cgctccagcc 360
gcttcgccag ctgcccccgc ccccgcaagt cccgcagccc ccgcaccttc tgcacccgcc 420
gcttcgccgg ccgcaccggc acccgcttca cccgcagcac ctgcaccgag tgctcccgcc 480
gcatcccctg cagcaccagc acctgcaagt ccagctgcac ctgccccttc agcaccggct 540
gcatctcccg ctgcaccggc tccggcatcg cccgccgcac ccgcacctag tgctccagct 600

<210> SEQ ID NO 139
<211> LENGTH: 600
<212> TYPE: DNA
<213> ORGANISM: Artificial Sequence
<220> FEATURE:
<223> OTHER INFORMATION: Nucleotide sequence of PAS#1aa(200), codon-
optimized for K. lactis

<400> SEQUENCE: 139
gcctctccgg ctgcaccagc tcccgcatct ccagcagctc ccgccccgtc ggcaccggca 60
gcctctccgg ccgcacctgc cccagcctcc cctgcagcac cagctcccag tgctccggct 120
gcatcacctg ctgcaccagc acctgcatca cctgccgccc cggcaccgtc agccccggct 180
gcatctcccg ccgccccagc cccagcctcg ccagcagccc ctgctcccag tgcacctgct 240
gcctcacctg cagctcctgc acccgcaagt ccggcagcac ctgccccttc tgcccctgca 300
gctagtccgg ccgctcccgc cccagccagt cccgccgcac ctgcaccaag tgctcctgct 360
gcttctcctg ctgcacctgc tccggcctca cccgccgctc cggctccatc ggcccctgca 420
gcatcaccag ctgcacccgc tcccgcctcc ccggccgcac cagcaccatc tgctcctgca 480
gcatcaccgg ccgcacctgc accagcaagt ccagccgcac ccgccccatc tgcaccggca 540
gcatcacccg ctgcccctgc tccagcttcg ccagcagcac ccgccccatc ggctcctgct 600

<210> SEQ ID NO 140
<211> LENGTH: 600
<212> TYPE: DNA
<213> ORGANISM: Artificial Sequence
<220> FEATURE:
<223> OTHER INFORMATION: Nucleotide sequence of PAS#1ab(200), codon-
optimized for K. lactis

<400> SEQUENCE: 140
gcctccccgg cagctccagc ccctgcctca ccagctgccc cggccccatc ggcccccgca 60
gcctctcccg ccgctcccgc ccctgctagt cctgcagctc ctgctccatc cgcacctgca 120
gcttcaccag ccgcaccagc tccggcctcg ccagccgcac cagcaccgtc cgcccctgct 180
gcttcaccag cagcccctgc cccggcttcc cctgcagcac ctgctccttc ggctccagct 240
gcctctccgg cagctccggc tcctgcctcc cctgccgctc cagctccgtc agcacccgct 300
gcaagtcctg ccgcacccgc tcccgcctct ccggcagccc cagctccatc cgcaccagca 360
gctagtccgg cagcaccggc tccagctagt ccagctgcac cagccccttc cgccccagca 420
gcttcaccgg ccgccccggc cccagcctct ccagcagcac ctgccccatc ggccccggcc 480
gcatctcccg ctgccccggc tcccgcatcg cctgccgcac cggctccctc ggcaccggcc 540
gcctctcctg ctgcacctgc acccgcttcc cctgccgctc ctgcccctag tgcaccagca 600

<210> SEQ ID NO 141
<211> LENGTH: 600
<212> TYPE: DNA
<213> ORGANISM: Artificial Sequence
<220> FEATURE:
<223> OTHER INFORMATION: Nucleotide sequence of PAS#1ac(200), codon-
optimized for S. cerevisiae

<400> SEQUENCE: 141
gccagtcctg ccgctccagc acctgccagt ccagcagctc cagccccttc tgccccagca 60
gcctcaccag ccgcacctgc tccagcaagc ccggcagctc ccgccccgag tgctccagca 120

```
gcatcaccag ctgctcccgc gccggctagc cctgcggctc ccgcaccgag tgccccagca    180

gcatcacctg ccgcccctgc gcccgcaagc cccgcggccc ctgctccttc cgcgcctgct    240

gcctcaccag cagcaccagc cccggcaagt ccagcggcgc cggcacccag cgcacccgcg    300

gcctctcctg cagctcctgc acctgcatct cccgcggctc ccgcaccctc agctcccgcg    360

gccagccctg ctgcaccagc acctgcaagc cctgcggctc cggcgccttc tgcccctgct    420

gcctctccgg ctgcccctgc acctgcgtcc ccggctgctc ccgctcctag tgccccggca    480

gcaagcccag ccgcaccggc cccagccagc cccgccgctc ccgctccctc cgctcccgct    540

gcgtccccag ccgctcccgc tcctgcgtca cctgcagcgc ccgcgccctc tgcacccgcc    600
```

<210> SEQ ID NO 142
<211> LENGTH: 600
<212> TYPE: DNA
<213> ORGANISM: Artificial Sequence
<220> FEATURE:
<223> OTHER INFORMATION: Nucleotide sequence of PAS#1ad(200), codon-optimized for S. cerevisiae

<400> SEQUENCE: 142

```
gcctctccag cagcgccggc accagcaagc cctgcggcac ctgctccatc tgctccggcg     60

gccagtcccg ctgcacctgc tccggcttct cctgcagcac cagcaccatc tgcccctgca    120

gctagcccgg cagcgcccgc tcccgcgagt ccagcagcgc ctgccccttc agcgccggcc    180

gcgtcacctg ccgcaccggc acccgctagc ccagcggcac cggctccgtc tgcaccagcc    240

gcttccccag cagcaccagc gccagctagc ccggctgccc cagctccctc cgctcctgct    300

gcatcccctg ctgcacccgc tcccgctagt cctgctgcgc ctgcaccctc agctccagca    360

gcgtctcccg cagcgccagc acctgcgagt ccagcggcac cagcaccctc tgctccagcc    420

gcttccccgg cagccccggc ccctgcctcc ccagctgcgc cagctccttc cgctcccgct    480

gcctcccctg ccgcacctgc cccggcgagc cctgctgctc ctgcaccctc tgctcccgcg    540

gcctctcccg ctgcaccagc gcccgcgtct cccgctgctc cggcacctag tgcaccagct    600
```

<210> SEQ ID NO 143
<211> LENGTH: 600
<212> TYPE: DNA
<213> ORGANISM: Artificial Sequence
<220> FEATURE:
<223> OTHER INFORMATION: Nucleotide sequence of PAS#1ae(200), codon-optimized for S. cerevisiae

<400> SEQUENCE: 143

```
gcctctcccg cagcacccgc acccgcgtca cctgcggcac cggctccctc tgcaccggca     60

gcctctccag ctgcaccagc ccctgcgtcc ccagcagcgc ccgcgcccag cgctccagcg    120

gcaagcccag ctgccccagc tcctgcaagc ccggctgccc cggctcctag cgccccagct    180

gcttcacccg ctgctcccgc acctgcctct ccggcggccc cagcgcccag cgctcctgca    240

gcgtcaccag cggccccagc gccagcctca cccgctgctc cggcccccatc tgcgccggca    300

gcgagtccag ccgctccagc gcctgcgtct cctgcggcac cagcaccttc agctccggca    360

gcatctccgg cggctcccgc gcctgcttcc cccgctgcac cagcacctag cgcacccgcc    420

gcttcacctg ctgcgcccgc tcctgccagc ccggcagcac ccgcgccatc cgcacccgcc    480

gctagcccag cagcacctgc ccctgcatct ccggcagctc ccgcgccatc agcccccgcg    540

gcatctccgg ctgctcctgc cccagcatca cccgccgcgc cagccccgtc cgcaccagca    600
```

<210> SEQ ID NO 144
<211> LENGTH: 600
<212> TYPE: DNA
<213> ORGANISM: Artificial Sequence
<220> FEATURE:
<223> OTHER INFORMATION: Nucleotide sequence of PAS#1af(200), codon-
optimized for T. thermophila

<400> SEQUENCE: 144
gcctctccag ccgcaccagc ccctgcttca cccgctgccc ctgctcctag tgcacctgct 60
gcaagccccg ctgcccctgc acctgcttct cctgccgctc cagccccttc tgcccctgcc 120
gcttctccag cagcccctgc acccgcttca cctgctgctc cagccccatc agctcccgct 180
gctagtcccg ccgctcctgc acctgcttct cccgctgcac ctgccccatc agcaccagcc 240
gcctcaccag ccgctcccgc cccagcctca cccgccgccc ctgcaccatc tgcacctgca 300
gcctcacccg ccgcacctgc acccgcatca cccgctgcac ctgctccatc agctcctgct 360
gcttctccag ccgcacctgc tccagcatca cctgccgctc ccgccccaag tgctccagcc 420
gcatctcctg ctgcacccgc acctgcaagc cctgctgcac ctgcaccttc agcccctgca 480
gccagccctg ctgcacctgc cccagctagt cccgctgcac ccgcccctag tgctcctgcc 540
gcaagccctg cagctcctgc ccctgcttca cctgctgccc ctgctccaag cgctcctgca 600

<210> SEQ ID NO 145
<211> LENGTH: 600
<212> TYPE: DNA
<213> ORGANISM: Artificial Sequence
<220> FEATURE:
<223> OTHER INFORMATION: Nucleotide sequence of PAS#1ag(200), codon-
optimized for T. thermophila

<400> SEQUENCE: 145
gccagtcctg ctgctcccgc tccagcaagt cctgctgctc cagcccctag tgctccagct 60
gcttcacccg ccgctcccgc acccgcatca cctgctgcac ctgctccaag cgcacctgct 120
gctagcccag ctgcccctgc accagcttct cccgccgcac cagcacctag cgcaccagct 180
gcctctcccg ctgcaccagc acccgcttca cccgcagccc cagcccctag cgcacctgcc 240
gcctcaccag ctgcacctgc tccagcaagt cctgccgccc ccgctcctag cgcaccagca 300
gcctcaccag ccgcaccagc tcccgcaagt cctgcagctc cagccccaag tgcacccgca 360
gctagccctg cagctcccgc tcccgcaagt ccagctgccc cagcaccatc tgcacccgct 420
gcttcacccg ccgcacccgc accagctagc ccagcagctc ctgctccttc agctcccgcc 480
gcttcaccag ctgctcccgc accagcctca ccagctgcac ccgctcccag cgctcctgct 540
gcttcacctg ctgctcctgc accagctagt cctgctgctc cagctccatc agccccagca 600

<210> SEQ ID NO 146
<211> LENGTH: 600
<212> TYPE: DNA
<213> ORGANISM: Artificial Sequence
<220> FEATURE:
<223> OTHER INFORMATION: Nucleotide sequence of PAS#1ah(200), codon-
optimized for T. thermophila

<400> SEQUENCE: 146
gccagtcctg ccgctcccgc acctgctagt cctgccgcac ccgccccttc tgcaccagcc 60
gcatctccag cagcacctgc tccagcctct ccagccgctc ccgctcccag cgccccagcc 120
gcaagccctg ccgctcccgc tccagctagc cccgccgctc ccgcacctag tgctcctgct 180
gcaagccctg ctgctcctgc acctgctagc cctgctgcac cagctccaag cgccccagcc 240
gctagtccag ctgctcccgc tcctgcaagc cctgcagcac ctgctccaag tgctcccgcc 300
gcttctcccg ctgcccccgc acctgccagt cctgctgcac ctgctccctc agctcccgct 360
gcttcaccag ctgcacccgc accagcttca cctgccgcac cagctcctag cgctccagct 420
gcatctcctg cagctcccgc tcctgcatca ccagcagctc ctgcacccag tgcaccagcc 480
gctagccctg cagcaccagc accagcctct cctgccgcac cagcccctag cgcaccagcc 540
gcatcacctg ccgctccagc tcctgccagc cctgctgccc cagctccatc tgctccagct 600

<210> SEQ ID NO 147
<211> LENGTH: 600
<212> TYPE: DNA
<213> ORGANISM: Artificial Sequence
<220> FEATURE:
<223> OTHER INFORMATION: Nucleotide sequence of PAS#1ai(200), codon-
optimized for H. sapiens (HEK cells)

<400> SEQUENCE: 147
gccagtcccg ctgcgccggc accagcctcc cctgctgccc cagcccctag cgcacccgct 60
gcttcccctg ccgctccagc gcctgcctct cctgcggccc ctgctcctag tgcaccagcc 120
gcttccccag cagcacctgc tcctgcaagt ccagctgctc ctgcaccctc tgctcccgcg 180
gcctctccag ctgcacccgc tcctgcttca cctgccgctc cagctccatc cgcaccagct 240
gccagtcctg ctgcgcctgc acccgcctca cctgctgctc ccgcaccttc agcacctgca 300
gcctctccgg cagcccctgc acccgcctcc ccggctgccc ccgcgcccag tgctccggcc 360
gcgtctcccg ctgctcctgc tcccgcttca cccgccgctc ctgccccttc tgcccctgcc 420
gccagccccg ctgctcccgc ccctgcctcc cctgcagctc ccgccccatc tgcgcctgct 480
gcttcaccgg ctgcgccagc accagctagc cccgcagcgc cagccccatc agcaccagcc 540
gcctctcctg ctgcacccgc ccctgcgagc cctgcggctc ccgcaccctc tgccccagca 600

<210> SEQ ID NO 148
<211> LENGTH: 600
<212> TYPE: DNA
<213> ORGANISM: Artificial Sequence
<220> FEATURE:
<223> OTHER INFORMATION: Nucleotide sequence of PAS#1aj(200), codon-
optimized for H. sapiens (HEK cells)

<400> SEQUENCE: 148
gccagtcccg cagcaccagc acccgcgtcc ccagctgcgc ctgcccctag tgctccagct 60
gcctctcccg ccgcacccgc acctgcaagt cctgcagctc cggcaccgag cgcccccgcc 120
gccagtccag ccgcacccgc gcctgcaagc ccagccgcgc ccgccccttc cgccccggcc 180
gcttctccag ccgcaccagc gcccgcatcc ccagcggctc cagctccgtc tgctcctgcc 240
gcaagccctg ctgcgcccgc ccctgcatcc cctgctgcac ctgctccgag tgctcccgcc 300
gcctccccag ccgcaccggc ccctgctagt cccgccgcgc cggccccaag tgccccagct 360
gcttctcctg ctgctccagc accggcatct cccgcggccc ctgcaccaag tgcgccagcc 420
gctagtccgg cagctcctgc tccagccagt cccgcggctc ctgctccaag cgccccagct 480
gcatcaccag cagctccagc tcctgccagc cctgcagcgc ccgcgccatc agcccctgct 540
gctagcccag cagcccccgc cccagcgagt ccagcggcac ctgctccatc tgctccagct 600

<210> SEQ ID NO 149
<211> LENGTH: 600

<212> TYPE: DNA
<213> ORGANISM: Artificial Sequence
<220> FEATURE:
<223> OTHER INFORMATION: Nucleotide sequence of PAS#1ak(200), codon-
      optimized for H. sapiens (HEK cells)

<400> SEQUENCE: 149
gccagtcctg ctgcccctgc acctgcgtct ccagctgctc ccgctccttc tgctccggct     60
gcatctcctg ccgccccagc ccctgcaagt ccagcagcgc ctgctccatc agctcctgca    120
gcttcaccag cggccccagc acccgccagt cctgcagctc ctgcgccctc agccccagcc    180
gcgagccctg ccgcgcctgc tcccgcctct cccgcagccc ctgccccatc cgctccggcc    240
gcatcacctg ctgctcctgc tcctgcctca cccgctgctc cagcgccatc tgcacccgct    300
gccagccccg ctgccccggc tcctgcatcc cctgcggcac cagctccaag cgctcctgca    360
gcaagccccg ccgctccagc tcccgcgagt cctgccgctc ctgcaccatc tgccccagca    420
gctagtcccg ctgcaccggc tcccgcatct ccagcagctc cggcaccttc ggccccagca    480
gccagtcctg cagccccagc acctgccagt cctgcggctc cggcgccatc agcacctgca    540
gcgtcacctg ccgcacctgc tcccgcaagt cctgccgcgc cagctcctag cgcaccagcc    600

<210> SEQ ID NO 150
<211> LENGTH: 600
<212> TYPE: DNA
<213> ORGANISM: Artificial Sequence
<220> FEATURE:
<223> OTHER INFORMATION: Nucleotide sequence of PAS#1al(200), codon-
      optimized for B. subtilis

<400> SEQUENCE: 150
gcctcacccg ctgcacctgc tccagcttcc ccagcagcac cagccccttc cgcacctgcc     60
gctagccccg ctgctcctgc cccagcctca cctgcggctc cagctccttc cgcaccggca    120
gcgtcgcctg cagcaccggc gcctgctagc cctgctgctc ccgccccttc ggcacctgca    180
gcgtctccgg cggctcctgc tcctgcgtct ccagcagctc ctgcaccgtc cgctcctgcc    240
gcaagccccg cagcacctgc acctgcttca ccagcggctc ctgccccgag tgcaccggca    300
gcctcccctg cagctcctgc tccggcaagc ccagctgcac cggccccaag cgcaccagct    360
gcaagccctg cagccccagc accggcctca ccggcagcac ctgcgccgtc agcacctgca    420
gccagcccag cggcccctgc acctgcatca cctgcggcgc ctgctccttc tgcccctgcg    480
gcatcccctg ctgctcctgc acccgcaagt ccggctgcac cggctccaag tgcaccagca    540
gcatcacctg ccgcaccggc acctgcgagt cctgcggcac ctgcccctag tgctccggcg    600

<210> SEQ ID NO 151
<211> LENGTH: 600
<212> TYPE: DNA
<213> ORGANISM: Artificial Sequence
<220> FEATURE:
<223> OTHER INFORMATION: Nucleotide sequence of PAS#1am(200), codon-
      optimized for B. subtilis

<400> SEQUENCE: 151
gcctcaccgg ctgccccagc acctgcttct ccggcagctc cggccccttc agcacctgca     60
gcttctccgg cagcgcccgc acccgcctct cctgcagctc cggcaccgtc agcgccagcg    120
gccagcccag cagctccggc tccagcttcg cctgccgctc cagcaccgtc ggctccggca    180
gcatctccgg ctgctcctgc tccagcgtca ccagccgcac ctgcaccgag tgctcctgca    240
gcctctccag ctgcccctgc ccctgcttcg ccagcagcac ctgcgccttc ggccccggca    300
gcaagcccag ccgctcctgc accagcaagt cctgccgccc cagccccttc tgctcctgct 360
gcttccccgg cggcaccggc acccgcgtca ccggcagcac ccgcaccgtc tgcaccagct 420
gcgagcccgg ctgcaccagc gcctgcttca cctgccgcgc ccgctccttc agctccagct 480
gcttctcccg ccgcacctgc tccggctagc ccagcagcgc cggcaccttc agcacctgct 540
gcgagtccag cagctccagc gccggcaagc cctgccgctc cagcgccgtc agcccctgca 600

<210> SEQ ID NO 152
<211> LENGTH: 600
<212> TYPE: DNA
<213> ORGANISM: Artificial Sequence
<220> FEATURE:
<223> OTHER INFORMATION: Nucleotide sequence of PAS#1an(200), codon-optimized for B. subtilis

<400> SEQUENCE: 152
gcctcacctg cagcaccggc accagcttca cccgcagccc ctgctccaag cgcaccggcg 60
gcatcccctg cagcgccagc gccggcctca ccagcagctc cagccccgag cgctcctgcg 120
gcatcaccgg cagcgcccgc tccagcatct cctgccgcac cggccccgag cgctccagct 180
gcgtccccgg cagcaccagc gccagcgagt ccggcggccc ccgcaccgtc tgctccagca 240
gcgagtcctg ccgccccggc gcccgcttct ccggcagcac ccgccccgtc agcaccagcg 300
gcatcacccg cagctcctgc ccctgcaagt ccagctgctc ctgcccccctc agctccagcc 360 gccagccctg ctgcaccagc tccggcatca cctgcagcgc cagccccttc agcgcccgcc 420
gcgagccctg ctgcacccgc tcctgcttcc cctgccgcac cagcaccctc tgcgccagcc 480
gcgtcgcctg ccgctcccgc tcccgcatca ccagcggctc ccgctccatc tgcaccagca 540
gccagtcctg cagcaccagc accagctagt ccggcagccc ccgcacctag tgcacctgct 600

<210> SEQ ID NO 153
<211> LENGTH: 900
<212> TYPE: DNA
<213> ORGANISM: Artificial Sequence
<220> FEATURE:
<223> OTHER INFORMATION: Nucleotide sequence of PA#1ae/1c(300), codon-optimized for E. coli

<400> SEQUENCE: 153
gccgctcctg ctgcccctgc tcccgctgcc cccgccgccc ccgccccagc tgcccccgct 60
gccgcacctg ctgccccagc tcccgctgcc ccagccgcgc cggcccccgc agctccagcc 120
gcggcaccag ctgccccagc tccagcggcg cctgctgccc cggcccccgc ggcaccggct 180
gccgcgcccg cagctccagc gcctgctgca ccggctgctc cggcacccgc cgcgccagca 240 gctgccccctg cggcaccagc tcctgctgcc cccgcggcac ctgcacccgc tgccccggcg 300
gccgcgccag cggccccggc ccctgccgcg cccgctgctc ccgcccctgc tgccccagcc 360
gccgctcctg cggcacctgc gcccgccgcg ccggcagcgc cggcaccggc agctccggcg 420
gccgcgcctg cagctcctgc accggcggct ccagcagccc cggcgccggc cgcacctgcg 480
gcggcgcccg cggcgcctgc acccgcagcg cctgcggcac cggccccagc agcccctgcc 540
gccgcaccgg ctgcgcctgc cccagcggcc cccgctgccc cggccccggc ggctccagcc 600
gcagcgcctg ccgccccagc gcccgcagca ccggcggcac cagctccggc ggcgccggcg 660
gcggctccgg cagctccggc ccctgctgcg ccggctgcgc cggctccggc ggcccctgcg 720
gcggctccgg ccgcacctgc acctgccgcg ccggctgctc cggccccggc tgccccagca 780
gcggcaccag cagcgcctgc tcctgcggcg cctgcagctc cggcgccggc agccccggcc 840
gccgcacccg cggctccagc ccccgccgct ccagcagccc ccgcgccagc tgcacctgct 900

<210> SEQ ID NO 154
<211> LENGTH: 900
<212> TYPE: DNA
<213> ORGANISM: Artificial Sequence
<220> FEATURE:
<223> OTHER INFORMATION: Nucleotide sequence of PA#1ae/1d(300), codon-
optimized for E. coli

<400> SEQUENCE: 154
gccgctcctg ctgcccctgc tcccgctgcc cccgccgccc ccgccccagc tgcccccgct 60
gccgcacctg ctgccccagc tcccgctgcc ccagccgcgc cggcccccgc agctccagcc 120
gcggcaccag ctgccccagc tccagcggcg cctgctgccc cggcccccgc ggcaccggct 180
gccgcgcccg cagctccagc gcctgctgca ccggctgctc cggcacccgc cgcgccagca 240
gctgcccctg cggcaccagc tcctgctgcc cccgcggcac ctgcacccgc tgccccggcg 300
gccgcaccgg ctgccccagc ccctgccgca ccagcagctc ccgcccctgc agcccccgcc 360
gccgctccgg ccgcaccagc cccggctgcc cctgctgccc ccgccccggc agcacccgct 420
gcagcaccag ccgcgcctgc accggcagct cctgcagccc cggcaccggc agcacctgcc 480
gcagcacccg cagccccagc cccagcagcg cctgccgctc cagcaccagc ggcaccggcc 540
gccgcaccag ccgccccagc accggcagcc cccgcagcgc cggcaccagc cgctccagcc 600
gccgccccag cagccccggc tccggccgct cccgcggctc cagcaccagc agctccagcg 660
gccgctccgg cagcgccggc cccagcagca cctgcagccc ctgcaccagc agcgccagcc 720
gcggcgcccg cagctcccgc acctgcggct cccgcagccc ctgcacccgc ggcgccagca 780
gccgcccctg cagcgccagc tcctgcagca cctgcagctc cagccccggc cgccccagct 840
gcagctcctg cggccccagc acctgccgcc cctgccgcac cggctccagc cgccccagcc 900

<210> SEQ ID NO 155
<211> LENGTH: 1200
<212> TYPE: DNA
<213> ORGANISM: Artificial Sequence
<220> FEATURE:
<223> OTHER INFORMATION: Nucleotide sequence of PA#1d/1c(400), codon-
optimized for E. coli

<400> SEQUENCE: 155
gccgcaccgg ctgccccagc ccctgccgca ccagcagctc ccgcccctgc agcccccgcc 60
gccgctccgg ccgcaccagc cccggctgcc cctgctgccc ccgccccggc agcacccgct 120
gcagcaccag ccgcgcctgc accggcagct cctgcagccc cggcaccggc agcacctgcc 180
gcagcacccg cagccccagc cccagcagcg cctgccgctc cagcaccagc ggcaccggcc 240
gccgcaccag ccgccccagc accggcagcc cccgcagcgc cggcaccagc cgctccagcc 300
gccgccccag cagccccggc tccggccgct cccgcggctc cagcaccagc agctccagcg 360
gccgctccgg cagcgccggc cccagcagca cctgcagccc ctgcaccagc agcgccagcc 420
gcggcgcccg cagctcccgc acctgcggct cccgcagccc ctgcacccgc ggcgccagca 480
gccgcccctg cagcgccagc tcctgcagca cctgcagctc cagccccggc cgccccagct 540
gcagctcctg cggccccagc acctgccgcc cctgccgcac cggctccagc cgccccagcc 600
gccgcgccag cggccccggc ccctgccgcg cccgctgctc ccgcccctgc tgccccagcc 660
gccgctcctg cggcacctgc gcccgccgcg ccggcagcgc cggcaccggc agctccggcg 720

```
gccgcgcctg cagctcctgc accggcggct ccagcagccc cggcgccggc cgcacctgcg    780

gcggcgcccg cggcgcctgc acccgcagcg cctgcggcac cggccccagc agcccctgcc    840

gccgcaccgg ctgcgcctgc cccagcggcc cccgctgccc cggcccccggc ggctccagcc    900

gcagcgcctg ccgccccagc gcccgcagca ccggcggcac cagctccggc ggcgccggcg    960

gcggctccgg cagctccggc ccctgctgcg ccggctgcgc cggctccggc ggcccctgcg   1020

gcggctccgg ccgcacctgc acctgccgcg ccggctgctc cggcccccggc tgccccagca   1080

gcggcaccag cagcgcctgc tcctgcggcg cctgcagctc cggcgccggc agccccggcc   1140

gccgcacccg cggctccagc ccccgccgct ccagcagccc ccgcgccagc tgcacctgct   1200
```

<210> SEQ ID NO 156
<211> LENGTH: 1800
<212> TYPE: DNA
<213> ORGANISM: Artificial Sequence
<220> FEATURE:
<223> OTHER INFORMATION: Nucleotide sequence of PA#1b/1c/1d(600), codon-optimized for E. coli

<400> SEQUENCE: 156

```
gccgctcctg ctgcccctgc tcccgctgcc cccgccgccc ccgccccagc tgcccccgct     60

gccgcacctg ctgccccagc tcccgctgcc ccagccgcgc cggcccccgc agctccagcc    120

gcggcaccag ctgccccagc tccagcggcg cctgctgccc cggcccccgc ggcaccggct    180

gccgcgcccg cagctccagc gcctgctgca ccggctgctc cggcacccgc cgcgccagca    240

gctgcccctg cggcaccagc tcctgctgcc cccgcggcac ctgcacccgc tgccccggcg    300

gcagctcccg ccgcgccagc ccctgcagct cctgctgcac ctgctcctgc cgcccctgct    360

gctgcccctg ctgctccagc ccctgcagca ccggccgctc cagctcctgc cgctcctgcc    420

gctgcgcccg ctgctccagc cccagctgcg ccagcagctc ctgcacctgc tgcccctgcc    480

gccgcccctg cggctccagc acctgctgca ccggccgccc cggcgcccgc tgcccccgca    540

gcagccccag ccgcacccgc tccagcagct cccgcagccc cagcacccgc agcaccagcc    600

gccgcgccag cggccccggc ccctgccgcg cccgctgctc ccgcccctgc tgccccagcc    660

gccgctcctg cggcacctgc gcccgccgcg ccggcagcgc cggcaccggc agctccggcg    720

gccgcgcctg cagctcctgc accggcggct ccagcagccc cggcgccggc cgcacctgcg    780

gcggcgcccg cggcgcctgc acccgcagcg cctgcggcac cggccccagc agcccctgcc    840

gccgcaccgg ctgcgcctgc cccagcggcc cccgctgccc cggcccccggc ggctccagcc    900

gcagcgcctg ccgccccagc gcccgcagca ccggcggcac cagctccggc ggcgccggcg    960

gcggctccgg cagctccggc ccctgctgcg ccggctgcgc cggctccggc ggcccctgcg   1020

gcggctccgg ccgcacctgc acctgccgcg ccggctgctc cggcccccggc tgccccagca   1080

gcggcaccag cagcgcctgc tcctgcggcg cctgcagctc cggcgccggc agccccggcc   1140

gccgcacccg cggctccagc ccccgccgct ccagcagccc ccgcgccagc tgcacctgct   1200

gccgcaccgg ctgccccagc ccctgccgca ccagcagctc ccgcccctgc agcccccgcc   1260

gccgctccgg ccgcaccagc cccggctgcc cctgctgccc ccgccccggc agcacccgct   1320

gcagcaccag ccgcgcctgc accggcagct cctgcagccc cggcaccggc agcacctgcc   1380

gcagcacccg cagccccagc cccagcagcg cctgccgctc cagcaccagc ggcaccggcc   1440

gccgcaccag ccgccccagc accggcagcc cccgcagcgc cggcaccagc cgctccagcc   1500

gccgccccag cagccccggc tccggccgct cccgcggctc cagcaccagc agctccagcg   1560
```

gccgctccgg cagcgccggc cccagcagca cctgcagccc ctgcaccagc agcgccagcc 1620
gcggcgcccg cagctcccgc acctgcggct cccgcagccc ctgcacccgc ggcgccagca 1680
gccgcccctg cagcgccagc tcctgcagca cctgcagctc cagccccggc cgccccagct 1740
gcagctcctg cggccccagc acctgccgcc cctgccgcac cggctccagc cgccccagcc 1800

<210> SEQ ID NO 157
<211> LENGTH: 1800
<212> TYPE: DNA
<213> ORGANISM: Artificial Sequence
<220> FEATURE:
<223> OTHER INFORMATION: Nucleotide sequence of PA#1d/1b/1c(600), codon-
optimized for E. coli <400> SEQUENCE: 157
gccgcaccgg ctgccccagc ccctgccgca ccagcagctc ccgcccctgc agcccccgcc 60
gccgctccgg ccgcaccagc cccggctgcc cctgctgccc ccgccccggc agcacccgct 120
gcagcaccag ccgcgcctgc accggcagct cctgcagccc cggcaccggc agcacctgcc 180
gcagcacccg cagccccagc cccagcagcg cctgccgctc cagcaccagc ggcaccggcc 240
gccgcaccag ccgccccagc accggcagcc cccgcagcgc cggcaccagc cgctccagcc 300
gccgccccag cagccccggc tccggccgct cccgcggctc cagcaccagc agctccagcg 360
gccgctccgg cagcgccggc cccagcagca cctgcagccc ctgcaccagc agcgccagcc 420
gcggcgcccg cagctcccgc acctgcggct cccgcagccc ctgcacccgc ggcgccagca 480
gccgcccctg cagcgccagc tcctgcagca cctgcagctc cagccccggc cgccccagct 540
gcagctcctg cggccccagc acctgccgcc cctgccgcac cggctccagc cgccccagcc 600
gccgctcctg ctgcccctgc tcccgctgcc cccgccgccc ccgccccagc tgcccccgct 660
gccgcacctg ctgccccagc tcccgctgcc ccagccgcgc cggcccccgc agctccagcc 720
gcggcaccag ctgccccagc tccagcggcg cctgctgccc cggcccccgc ggcaccggct 780
gccgcgcccg cagctccagc gcctgctgca ccggctgctc cggcacccgc cgcgccagca 840
gctgcccctg cggcaccagc tcctgctgcc cccgcggcac ctgcacccgc tgccccggcg 900
gcagctcccg ccgcgccagc ccctgcagct cctgctgcac ctgctcctgc cgcccctgct 960
gctgcccctg ctgctccagc ccctgcagca ccggccgctc cagctcctgc cgctcctgcc 1020
gctgcgcccg ctgctccagc cccagctgcg ccagcagctc ctgcacctgc tgcccctgcc 1080
gccgcccctg cggctccagc acctgctgca ccggccgccc cggcgcccgc tgcccccgca 1140
gcagccccag ccgcacccgc tccagcagct cccgcagccc cagcacccgc agcaccagcc 1200
gccgcgccag cggccccggc ccctgccgcg cccgctgctc ccgcccctgc tgccccagcc 1260
gccgctcctg cggcacctgc gcccgccgcg ccggcagcgc cggcaccggc agctccggcg 1320
gccgcgcctg cagctcctgc accggcggct ccagcagccc cggcgccggc cgcacctgcg 1380
gcggcgcccg cggcgcctgc acccgcagcg cctgcggcac cggccccagc agcccctgcc 1440
gccgcaccgg ctgcgcctgc cccagcggcc cccgctgccc cggcccccgc ggctccagcc 1500
gcagcgcctg ccgccccagc gcccgcagca ccggcggcac cagctccggc ggcgccggcg 1560
gcggctccgg cagctccggc ccctgctgcg ccggctgcgc cggctccggc ggcccctgcg 1620
gcggctccgg ccgcacctgc acctgccgcg ccggctgctc cggcccccgc tgccccagca 1680
gcggcaccag cagcgcctgc tcctgcggcg cctgcagctc cggcgccggc agccccggcc 1740
gccgcacccg cggctccagc cccgccgct ccagcagccc ccgcgccagc tgcacctgct 1800

<210> SEQ ID NO 158
<211> LENGTH: 1800
<212> TYPE: DNA
<213> ORGANISM: Artificial Sequence
<220> FEATURE:
<223> OTHER INFORMATION: Nucleotide sequence of PA#1c/1b/1d(600), codon-
optimized for E. coli

<400> SEQUENCE: 158
gccgcgccag cggccccggc ccctgccgcg cccgctgctc ccgcccctgc tgccccagcc 60
gccgctcctg cggcacctgc gcccgccgcg ccggcagcgc cggcaccggc agctccggcg 120
gccgcgcctg cagctcctgc accggcggct ccagcagccc cggcgccggc cgcacctgcg 180
gcggcgcccg cggcgcctgc acccgcagcg cctgcggcac cggccccagc agcccctgcc 240
gccgcaccgg ctgcgcctgc cccagcggcc cccgctgccc cggcccccggc ggctccagcc 300 gcagcgcctg ccgccccagc gcccgcagca ccggcggcac cagctccggc ggcgccggcg 360
gcggctccgg cagctccggc ccctgctgcg ccggctgcgc cggctccggc ggcccctgcg 420
gcggctccgg ccgcacctgc acctgccgcg ccggctgctc cggcccccggc tgccccagca 480 gcggcaccag cagcgcctgc tcctgcggcg cctgcagctc cggcgccggc agccccggcc 540
gccgcacccg cggctccagc cccgccgct ccagcagccc ccgcgccagc tgcacctgct 600
gccgctcctg ctgcccctgc tcccgctgcc cccgccgccc ccgcccccagc tgccccccgct 660 gccgcacctg ctgccccagc tcccgctgcc ccagccgcgc cggcccccgc agctccagcc 720
gcggcaccag ctgccccagc tccagcggcg cctgctgccc cggcccccgc ggcaccggct 780
gccgcgcccg cagctccagc gcctgctgca ccggctgctc cggcacccgc cgcgccagca 840
gctgcccctg cggcaccagc tcctgctgcc cccgcggcac ctgcacccgc tgccccggcg 900
gcagctcccg ccgcgccagc ccctgcagct cctgctgcac ctgctcctgc cgcccctgct 960
gctgcccctg ctgctccagc ccctgcagca ccggccgctc cagctcctgc cgctcctgcc 1020
gctgcgcccg ctgctccagc cccagctgcg ccagcagctc ctgcacctgc tgcccctgcc 1080
gccgcccctg cggctccagc acctgctgca ccggccgccc cggcgcccgc tgccccccgca 1140 gcagccccag ccgcacccgc tccagcagct cccgcagccc cagcacccgc agcaccagcc 1200
gccgcaccgg ctgccccagc ccctgccgca ccagcagctc ccgcccctgc agccccccgcc 1260 gccgctccgg ccgcaccagc cccggctgcc cctgctgccc ccgccccggc agcacccgct 1320
gcagcaccag ccgcgcctgc accggcagct cctgcagccc cggcaccggc agcacctgcc 1380
gcagcacccg cagccccagc cccagcagcg cctgccgctc cagcaccagc ggcaccggcc 1440
gccgcaccag ccgccccagc accggcagcc cccgcagcgc cggcaccagc cgctccagcc 1500
gccgccccag cagccccggc tccggccgct cccgcggctc cagcaccagc agctccagcg 1560
gccgctccgg cagcgccggc cccagcagca cctgcagccc ctgcaccagc agcgccagcc 1620
gcggcgcccg cagctcccgc acctgcggct cccgcagccc ctgcacccgc ggcgccagca 1680
gccgcccctg cagcgccagc tcctgcagca cctgcagctc cagccccggc cgccccagct 1740
gcagctcctg cggccccagc acctgccgcc cctgccgcac cggctccagc cgccccagcc 1800

<210> SEQ ID NO 159
<211> LENGTH: 1800
<212> TYPE: DNA
<213> ORGANISM: Artificial Sequence
<220> FEATURE:
<223> OTHER INFORMATION: Nucleotide sequence of PA#1c/1d/1b(600), codon-optimized for E. coli

<400> SEQUENCE: 159
gccgcgccag cggccccggc ccctgccgcg cccgctgctc ccgcccctgc tgccccagcc 60
gccgctcctg cggcacctgc gcccgccgcg ccggcagcgc cggcaccggc agctccggcg 120
gccgcgcctg cagctcctgc accggcggct ccagcagccc cggcgccggc cgcacctgcg 180
gcggcgcccg cggcgcctgc acccgcagcg cctgcggcac cggccccagc agcccctgcc 240
gccgcaccgg ctgcgcctgc cccagcggcc cccgctgccc cggccccggc ggctccagcc 300
gcagcgcctg ccgccccagc gcccgcagca ccggcggcac cagctccggc ggcgccggcg 360
gcggctccgg cagctccggc ccctgctgcg ccggctgcgc cggctccggc ggcccctgcg 420
gcggctccgg ccgcacctgc acctgccgcg ccggctgctc cggccccggc tgccccagca 480
gcggcaccag cagcgcctgc tcctgcggcg cctgcagctc cggcgccggc agccccggcc 540
gccgcacccg cggctccagc cccgccgct ccagcagccc ccgcgccagc tgcacctgct 600
gccgcaccgg ctgccccagc ccctgccgca ccagcagctc ccgcccctgc agcccccgcc 660
gccgctccgg ccgcaccagc cccggctgcc cctgctgccc ccgccccggc agcacccgct 720
gcagcaccag ccgcgcctgc accggcagct cctgcagccc cggcaccggc agcacctgcc 780
gcagcacccg cagccccagc cccagcagcg cctgccgctc cagcaccagc ggcaccggcc 840
gccgcaccag ccgccccagc accggcagcc cccgcagcgc cggcaccagc cgctccagcc 900
gccgccccag cagccccggc tccggccgct cccgcggctc cagcaccagc agctccagcg 960
gccgctccgg cagcgccggc cccagcagca cctgcagccc ctgcaccagc agcgccagcc 1020
gcggcgcccg cagctcccgc acctgcggct cccgcagccc ctgcacccgc ggcgccagca 1080
gccgcccctg cagcgccagc tcctgcagca cctgcagctc cagccccggc cgccccagct 1140
gcagctcctg cggccccagc acctgccgcc cctgccgcac cggctccagc cgccccagcc 1200
gccgctcctg ctgcccctgc tcccgctgcc cccgccgccc ccgccccagc tgcccccgct 1260
gccgcacctg ctgccccagc tcccgctgcc ccagccgcgc cggcccccgc agctccagcc 1320
gcggcaccag ctgccccagc tccagcggcg cctgctgccc cggcccccgc ggcaccggct 1380
gccgcgcccg cagctccagc gcctgctgca ccggctgctc cggcacccgc cgcgccagca 1440
gctgcccctg cggcaccagc tcctgctgcc cccgcggcac ctgcacccgc tgccccggcg 1500
gcagctcccg ccgcgccagc ccctgcagct cctgctgcac ctgctcctgc cgcccctgct 1560
gctgcccctg ctgctccagc ccctgcagca ccggccgctc cagctcctgc cgctcctgcc 1620
gctgcgcccg ctgctccagc cccagctgcg ccagcagctc ctgcacctgc tgcccctgcc 1680
gccgcccctg cggctccagc acctgctgca ccggccgccc cggcgcccgc tgcccccgca 1740
gcagccccag ccgcacccgc tccagcagct cccgcagccc cagcacccgc agcaccagcc 1800

<210> SEQ ID NO 160
<211> LENGTH: 1800
<212> TYPE: DNA
<213> ORGANISM: Artificial Sequence
<220> FEATURE:
<223> OTHER INFORMATION: Nucleotide sequence of PA#1b/1d/1c(600), codon-
optimized for E. coli

<400> SEQUENCE: 160
gccgctcctg ctgcccctgc tcccgctgcc cccgccgccc ccgccccagc tgcccccgct 60
gccgcacctg ctgccccagc tcccgctgcc ccagccgcgc cggcccccgc agctccagcc 120
gcggcaccag ctgccccagc tccagcggcg cctgctgccc cggcccccgc ggcaccggct 180
gccgcgcccg cagctccagc gcctgctgca ccggctgctc cggcacccgc cgcgccagca 240
gctgcccctg cggcaccagc tcctgctgcc cccgcggcac ctgcacccgc tgccccggcg 300
gcagctcccg ccgcgccagc ccctgcagct cctgctgcac ctgctcctgc cgcccctgct 360
gctgcccctg ctgctccagc ccctgcagca ccggccgctc cagctcctgc cgctcctgcc 420
gctgcgcccg ctgctccagc cccagctgcg ccagcagctc ctgcacctgc tgcccctgcc 480
gccgcccctg cggctccagc acctgctgca ccggccgccc cggcgcccgc tgcccccgca 540
gcagccccag ccgcacccgc tccagcagct cccgcagccc cagcacccgc agcaccagcc 600
gccgcaccgg ctgccccagc ccctgccgca ccagcagctc ccgcccctgc agcccccgcc 660
gccgctccgg ccgcaccagc cccggctgcc cctgctgccc ccgccccggc agcacccgct 720
gcagcaccag ccgcgcctgc accggcagct cctgcagccc cggcaccggc agcacctgcc 780
gcagcacccg cagccccagc cccagcagcg cctgccgctc cagcaccagc ggcaccggcc 840
gccgcaccag ccgccccagc accggcagcc cccgcagcgc cggcaccagc cgctccagcc 900
gccgccccag cagccccggc tccggccgct cccgcggctc cagcaccagc agctccagcg 960
gccgctccgg cagcgccggc cccagcagca cctgcagccc ctgcaccagc agcgccagcc 1020
gcggcgcccg cagctcccgc acctgcggct cccgcagccc ctgcacccgc ggcgccagca 1080
gccgcccctg cagcgccagc tcctgcagca cctgcagctc cagccccggc cgccccagct 1140
gcagctcctg cggccccagc acctgccgcc cctgccgcac cggctccagc cgccccagcc 1200
gccgcgccag cggccccggc ccctgccgcg cccgctgctc ccgcccctgc tgccccagcc 1260
gccgctcctg cggcacctgc gcccgccgcg ccggcagcgc cggcaccggc agctccggcg 1320
gccgcgcctg cagctcctgc accggcggct ccagcagccc cggcgccggc cgcacctgcg 1380
gcggcgcccg cggcgcctgc acccgcagcg cctgcggcac cggccccagc agcccctgcc 1440
gccgcaccgg ctgcgcctgc cccagcggcc cccgctgccc cggccccggc ggctccagcc 1500
gcagcgcctg ccgccccagc gcccgcagca ccggcggcac cagctccggc ggcgccggcg 1560
gcggctccgg cagctccggc ccctgctgcg ccggctgcgc cggctccggc ggcccctgcg 1620
gcggctccgg ccgcacctgc acctgccgcg ccggctgctc cggccccggc tgccccagca 1680
gcggcaccag cagcgcctgc tcctgcggcg cctgcagctc cggcgccggc agccccggcc 1740
gccgcacccg cggctccagc cccgccgct ccagcagccc ccgcgccagc tgcacctgct 1800

<210> SEQ ID NO 161
<211> LENGTH: 3000
<212> TYPE: DNA
<213> ORGANISM: Artificial Sequence
<220> FEATURE:
<223> OTHER INFORMATION: Nucleotide sequence of
PA#1aa/1e/1d/1c/1b(1000), codon-optimized for E. coli

<400> SEQUENCE: 161
gccgccccag cagcaccggc tccagctgcc ccagccgcac cagcaccagc cgctccagcg 60
gccgcgcctg ccgctcccgc acccgcggct ccggccgccc ctgcgccggc ggcaccggcg 120
gcggcacccg cggcacctgc acctgccgcc cccgcggctc ctgctcccgc ggcgccagca 180
gcagcgccag cggcgcctgc tcctgccgca ccagcagcac cagcacccgc cgcgccagca 240
gcggcccctg cagctcccgc cccggcagcg cccgctgcgc cagcacccgc tgctcccgcg 300
gcagcccccg cagctccggc ccctgcggct ccagctgcac cagcaccggc agcgccggcg 360

-continued gcggcaccag ccgcacccgc accggctgcg cccgccgcgc cagcgccagc cgctccagct 420
gccgcgccgg cagccccggc ccccgctgcc cctgctgcac ccgcgcctgc agcaccggcg 480
gcagcccctg cggcacctgc acccgcggct cccgctgccc ctgcacccgc agcgcccgcc 540
gccgcaccgg ccgctccggc acctgcagcg ccggctgcac cagcgccggc agctccagcg 600
gccgcaccgg ctgcaccagc tccggcagct ccagcagcac cggcaccagc agctccggct 660
gcagcgccag cagcaccagc gcctgctgct ccagctgctc ctgctcctgc tgcaccagca 720
gcagctccag ccgcaccagc accggcagcg cctgcagccc ctgctccggc agctcctgcc 780
gcagcaccgg cagcaccagc tccagcggca cccgctgccc ctgctcctgc agcaccggca 840
gcggcaccgg ctgctcctgc gccagctgct ccggcagccc cagcccctgc agccccagca 900
gcagcgcctg cggctccagc gccagccgca ccagcggctc cggcaccggc agcccctgcg 960
gcagctcctg ctgcgcctgc tccagcagct ccagctgccc cagcgccggc agctccggct 1020
gccgcaccag ctgcgcctgc ccctgctgcg ccagccgcac cggctccggc agcaccagca 1080
gctgccccag cagctcctgc cccagctgcg cctgctgcgc cagcaccagc agccccagct 1140
gcagcaccag ctgcaccggc accagctgct ccagcagcac cagccccagc cgctccggca 1200
gccgcaccgg ctgccccagc ccctgccgca ccagcagctc ccgcccctgc agccccccgcc 1260 gccgctccgg ccgcaccagc cccggctgcc cctgctgccc ccgcccccggc agcacccgct 1320 gcagcaccag ccgcgcctgc accggcagct cctgcagccc cggcaccggc agcacctgcc 1380
gcagcacccg cagccccagc cccagcagcg cctgccgctc cagcaccagc ggcaccggcc 1440
gccgcaccag ccgccccagc accggcagcc cccgcagcgc cggcaccagc cgctccagcc 1500
gccgccccag cagccccggc tccggccgct cccgcggctc cagcaccagc agctccagcg 1560
gccgctccgg cagcgccggc cccagcagca cctgcagccc ctgcaccagc agcgccagcc 1620
gcggcgcccg cagctcccgc acctgcggct cccgcagccc ctgcacccgc ggcgccagca 1680
gccgcccctg cagcgccagc tcctgcagca cctgcagctc cagccccggc cgccccagct 1740
gcagctcctg cggccccagc acctgccgcc cctgccgcac cggctccagc cgccccagcc 1800
gccgcgccag cggccccggc ccctgccgcg cccgctgctc ccgcccctgc tgccccagcc 1860
gccgctcctg cggcacctgc gcccgccgcg ccggcagcgc cggcaccggc agctccggcg 1920
gccgcgcctg cagctcctgc accggcggct ccagcagccc cggcgccggc cgcacctgcg 1980
gcggcgcccg cggcgcctgc acccgcagcg cctgcggcac cggccccagc agcccctgcc 2040
gccgcaccgg ctgcgcctgc cccagcggcc cccgctgccc cggccccggc ggctccagcc 2100
gcagcgcctg ccgccccagc gcccgcagca ccggcggcac cagctccggc ggcgccggcg 2160
gcggctccgg cagctccggc ccctgctgcg ccggctgcgc cggctccggc ggcccctgcg 2220
gcggctccgg ccgcacctgc acctgccgcg ccggctgctc cggccccggc tgccccagca 2280
gcggcaccag cagcgcctgc tcctgcggcg cctgcagctc cggcgccggc agccccggcc 2340
gccgcacccg cggctccagc ccccgccgct ccagcagccc ccgcgccagc tgcacctgct 2400
gccgctcctg ctgcccctgc tcccgctgcc cccgccgccc ccgccccagc tgccccccgct 2460 gccgcacctg ctgccccagc tcccgctgcc ccagccgcgc cggcccccgc agctccagcc 2520
gcggcaccag ctgccccagc tccagcggcg cctgctgccc cggcccccgc ggcaccggct 2580
gccgcgcccg cagctccagc gcctgctgca ccggctgctc cggcacccgc cgcgccagca 2640
gctgcccctg cggcaccagc tcctgctgcc cccgcggcac ctgcacccgc tgccccggcg 2700
gcagctcccg ccgcgccagc ccctgcagct cctgctgcac ctgctcctgc cgcccctgct 2760
gctgcccctg ctgctccagc ccctgcagca ccggccgctc cagctcctgc cgctcctgcc 2820
gctgcgcccg ctgctccagc cccagctgcg ccagcagctc ctgcacctgc tgcccctgcc 2880
gccgcccctg cggctccagc acctgctgca ccggccgccc cggcgcccgc tgccccc gca 2940 gcagccccag ccgcacccgc tccagcagct cccgcagccc cagcacccgc agcaccagcc 3000

<210> SEQ ID NO 162
<211> LENGTH: 3600
<212> TYPE: DNA
<213> ORGANISM: Artificial Sequence
<220> FEATURE:
<223> OTHER INFORMATION: Nucleotide sequence of
PA#1ab/1aa/1e/1d/1c/1b(1200), codon-optimized for E. coli

<400> SEQUENCE: 162
gccgcgcccg ctgcacccgc accagctgca ccagccgcac cggcaccggc ggccccagct 60
gcagcaccgg cagcccccgc gccggccgcg ccagccgcgc cggcaccggc tgctccggct 120
gcagcaccgg cagcgcctgc gccagctgct cccgcagctc ctgctccggc ggcgcctgca 180
gctgcaccgg cagctcctgc cccagcagcc ccggcggcgc cagcgcccgc cgccccagct 240
gcagcccctg cagcgccggc acccgccgcc cccgcagcac ctgcgccggc cgccccagct 300
gcggcaccgg ccgcacccgc cccggcggct ccagcagcac ctgctccagc agcaccagct 360
gcagcccctg cggcaccagc acccgcagcg ccagcggcac cagctccggc cgctcccgcc 420
gctgcaccag cctcaccggc gccggccgca ccagctgctc ccgccccagc cgctcccgcg 480
gcggcaccag cggcgccagc gcccgcagct ccggcagcac cggcgccggc tgctcctgcc 540
gccgcacctg ctgccccggc gcccgccgcc cccgccgctc ccgcgccggc tgcacctgcg 600
gccgccccag cagcaccggc tccagctgcc ccagccgcac cagcaccagc cgctccagcg 660
gccgcgcctg ccgctcccgc acccgcggct ccggccgccc ctgcgccggc ggcaccggcg 720
gcggcacccg cggcacctgc acctgccgcc cccgcggctc ctgctcccgc ggcgccagca 780
gcagcgccag cggcgcctgc tcctgccgca ccagcagcac cagcacccgc cgcgccagca 840
gcggcccctg cagctcccgc cccggcagcg cccgctgcgc cagcacccgc tgctcccgcg 900
gcagcccccg cagctccggc ccctgcggct ccagctgcac cagcaccggc agcgccggcg 960
gcggcaccag ccgcacccgc accggctgcg cccgccgcgc cagcgccagc cgctccagct 1020
gccgcgccgg cagccccggc ccccgctgcc cctgctgcac ccgcgcctgc agcaccggcg 1080
gcagcccctg cggcacctgc acccgcggct cccgctgccc ctgcacccgc agcgcccgcc 1140
gccgcaccgg ccgctccggc acctgcagcg ccggctgcac cagcgccggc agctccagcg 1200
gccgcaccgg ctgcaccagc tccggcagct ccagcagcac cggcaccagc agctccggct 1260
gcagcgccag cagcaccagc gcctgctgct ccagctgctc ctgctcctgc tgcaccagca 1320
gcagctccag ccgcaccagc accggcagcg cctgcagccc ctgctccggc agctcctgcc 1380
gcagcaccgg cagcaccagc tccagcggca cccgctgccc ctgctcctgc agcaccggca 1440
gcggcaccgg ctgctcctgc gccagctgct ccggcagccc cagcccctgc agccccagca 1500
gcagcgcctg cggctccagc gccagccgca ccagcggctc cggcaccggc agcccctgcg 1560
gcagctcctg ctgcgcctgc tccagcagct ccagctgccc cagcgccggc agctccggct 1620
gccgcaccag ctgcgcctgc ccctgctgcg ccagccgcac cggctccggc agcaccagca 1680
gctgccccag cagctcctgc cccagctgcg cctgctgcgc cagcaccagc agccccagct 1740
gcagcaccag ctgcaccggc accagctgct ccagcagcac cagccccagc cgctccggca 1800
gccgcaccgg ctgccccagc ccctgccgca ccagcagctc ccgcccctgc agcccccgcc 1860
gccgctccgg ccgcaccagc cccggctgcc cctgctgccc ccgccccggc agcacccgct 1920
gcagcaccag ccgcgcctgc accggcagct cctgcagccc cggcaccggc agcacctgcc 1980
gcagcacccg cagccccagc cccagcagcg cctgccgctc cagcaccagc ggcaccggcc 2040
gccgcaccag ccgccccagc accggcagcc cccgcagcgc cggcaccagc cgctccagcc 2100
gccgccccag cagccccggc tccggccgct cccgcggctc cagcaccagc agctccagcg 2160
gccgctccgg cagcgccggc cccagcagca cctgcagccc ctgcaccagc agcgccagcc 2220
gcggcgcccg cagctcccgc acctgcggct cccgcagccc ctgcacccgc ggcgccagca 2280
gccgcccctg cagcgccagc tcctgcagca cctgcagctc cagccccggc cgccccagct 2340
gcagctcctg cggccccagc acctgccgcc cctgccgcac cggctccagc cgccccagcc 2400
gccgcgccag cggccccggc ccctgccgcg cccgctgctc ccgcccctgc tgccccagcc 2460
gccgctcctg cggcacctgc gcccgccgcg ccggcagcgc cggcaccggc agctccggcg 2520
gccgcgcctg cagctcctgc accggcggct ccagcagccc cggcgccggc cgcacctgcg 2580
gcggcgcccg cggcgcctgc acccgcagcg cctgcggcac cggccccagc agcccctgcc 2640
gccgcaccgg ctgcgcctgc cccagcggcc cccgctgccc cggcccccggc ggctccagcc 2700 gcagcgcctg ccgccccagc gcccgcagca ccggcggcac cagctccggc ggcgccggcg 2760
gcggctccgg cagctccggc ccctgctgcg ccggctgcgc cggctccggc ggcccctgcg 2820
gcggctccgg ccgcacctgc acctgccgcg ccggctgctc cggcccccggc tgccccagca 2880 gcggcaccag cagcgcctgc tcctgcggcg cctgcagctc cggcgccggc agccccggcc 2940
gccgcacccg cggctccagc ccccgccgct ccagcagccc ccgcgccagc tgcacctgct 3000
gccgctcctg ctgcccctgc tcccgctgcc cccgccgccc ccgccccagc tgcccccgct 3060
gccgcacctg ctgccccagc tcccgctgcc ccagccgcgc cggcccccgc agctccagcc 3120
gcggcaccag ctgccccagc tccagcggcg cctgctgccc cggcccccgc ggcaccggct 3180
gccgcgcccg cagctccagc gcctgctgca ccggctgctc cggcacccgc cgcgccagca 3240
gctgcccctg cggcaccagc tcctgctgcc cccgcggcac ctgcacccgc tgccccggcg 3300
gcagctcccg ccgcgccagc ccctgcagct cctgctgcac ctgctcctgc cgcccctgct 3360
gctgcccctg ctgctccagc ccctgcagca ccggccgctc cagctcctgc cgctcctgcc 3420
gctgcgcccg ctgctccagc cccagctgcg ccagcagctc ctgcacctgc tgcccctgcc 3480
gccgcccctg cggctccagc acctgctgca ccggccgccc cggcgcccgc tgcccccgca 3540
gcagccccag ccgcacccgc tccagcagct cccgcagccc cagcacccgc agcaccagcc 3600

<210> SEQ ID NO 163
<211> LENGTH: 4200
<212> TYPE: DNA
<213> ORGANISM: Artificial Sequence
<220> FEATURE:
<223> OTHER INFORMATION: Nucleotide sequence of
PA#1ac/1ab/1aa/1e/1d/1c/1b(1400), codon-optimized for E. coli

<400> SEQUENCE: 163
gccgcgccag cggcgccagc tcctgccgcg cccgcagccc cagcgcccgc cgctccggcc 60
gccgcgcccg cggctcccgc acccgctgcg cccgccgctc cagcacctgc cgccccagcg 120
gcggcaccag ccgcgccagc acccgctgcg cctgcagcac ccgctccggc ggccccggcg 180
gctgctccag ccgcccctgc acccgctgct ccagctgcgc ccgccccagc cgccccggcc 240
gccgctccgg ctgcaccggc accggcagca ccggctgcgc cagccccggc tgccccggca 300
gctgctccgg cggcacctgc ccccgccgcg ccagctgccc ccgcaccggc agctccagcg 360
gcagccccgg cggcaccagc tccagcagcg ccagctgcgc ctgccccagc agcgccagcc 420
gctgctccag cagctcctgc ccctgctgcg cctgcggctc cggcgccagc tgctcctgct 480
gcagctccgg ccgccccagc accggcagcg ccagcagcac cggcgccagc tgcccctgcc 540
gccgcaccag cagcacctgc gccggcggct cccgcagcac ctgctccggc tgcccctgcc 600
gccgcgcccg ctgcacccgc accagctgca ccagccgcac cggcaccggc ggccccagct 660
gcagcaccgg cagcccccgc gccggccgcg ccagccgcgc cggcaccggc tgctccggct 720
gcagcaccgg cagcgcctgc gccagctgct cccgcagctc ctgctccggc ggcgcctgca 780
gctgcaccgg cagctcctgc cccagcagcc ccggcggcgc cagcgcccgc cgccccagct 840
gcagcccctg cagcgccggc acccgccgcc cccgcagcac ctgcgccggc cgccccagct 900
gcggcaccgg ccgcacccgc cccggcggct ccagcagcac ctgctccagc agcaccagct 960
gcagcccctg cggcaccagc acccgcagcg ccagcggcac cagctccggc cgctcccgcc 1020
gctgcaccag cctcaccggc gccggccgca ccagctgctc ccgccccagc cgctcccgcg 1080
gcggcaccag cggcgccagc gcccgcagct ccggcagcac cggcgccggc tgctcctgcc 1140
gccgcacctg ctgccccggc gcccgccgcc cccgccgctc ccgcgccggc tgcacctgcg 1200
gccgccccag cagcaccggc tccagctgcc ccagccgcac cagcaccagc cgctccagcg 1260
gccgcgcctg ccgctcccgc acccgcggct ccggccgccc ctgcgccggc ggcaccggcg 1320
gcggcacccg cggcacctgc acctgccgcc cccgcggctc ctgctcccgc ggcgccagca 1380
gcagcgccag cggcgcctgc tcctgccgca ccagcagcac cagcacccgc cgcgccagca 1440
gcggcccctg cagctcccgc cccggcagcg cccgctgcgc cagcacccgc tgctcccgcg 1500
gcagcccccg cagctccggc ccctgcggct ccagctgcac cagcaccggc agcgccggcg 1560
gcggcaccag ccgcacccgc accggctgcg cccgccgcgc cagcgccagc cgctccagct 1620
gccgcgccgg cagccccggc cccgctgcc cctgctgcac ccgcgcctgc agcaccggcg 1680
gcagcccctg cggcacctgc acccgcggct cccgctgccc ctgcacccgc agcgcccgcc 1740
gccgcaccgg ccgctccggc acctgcagcg ccggctgcac cagcgccggc agctccagcg 1800
gccgcaccgg ctgcaccagc tccggcagct ccagcagcac cggcaccagc agctccggct 1860
gcagcgccag cagcaccagc gcctgctgct ccagctgctc ctgctcctgc tgcaccagca 1920
gcagctccag ccgcaccagc accggcagcg cctgcagccc ctgctccggc agctcctgcc 1980
gcagcaccgg cagcaccagc tccagcggca cccgctgccc ctgctcctgc agcaccggca 2040
gcggcaccgg ctgctcctgc gccagctgct ccggcagccc cagcccctgc agccccagca 2100
gcagcgcctg cggctccagc gccagccgca ccagcggctc cggcaccggc agcccctgcg 2160
gcagctcctg ctgcgcctgc tccagcagct ccagctgccc cagcgccggc agctccggct 2220
gccgcaccag ctgcgcctgc ccctgctgcg ccagccgcac cggctccggc agcaccagca 2280
gctgccccag cagctcctgc cccagctgcg cctgctgcgc cagcaccagc agccccagct 2340
gcagcaccag ctgcaccggc accagctgct ccagcagcac cagccccagc cgctccggca 2400
gccgcaccgg ctgccccagc ccctgccgca ccagcagctc ccgcccctgc agcccccgcc 2460
gccgctccgg ccgcaccagc cccggctgcc cctgctgccc ccgcccccggc agcacccgct 2520 gcagcaccag ccgcgcctgc accggcagct cctgcagccc cggcaccggc agcacctgcc 2580
gcagcacccg cagccccagc cccagcagcg cctgccgctc cagcaccagc ggcaccggcc 2640
gccgcaccag ccgccccagc accggcagcc cccgcagcgc cggcaccagc cgctccagcc 2700
gccgccccag cagccccggc tccggccgct cccgcggctc cagcaccagc agctccagcg 2760
gccgctccgg cagcgccggc cccagcagca cctgcagccc ctgcaccagc agcgccagcc 2820
gcggcgcccg cagctcccgc acctgcggct cccgcagccc ctgcacccgc ggcgccagca 2880
gccgcccctg cagcgccagc tcctgcagca cctgcagctc cagccccggc cgccccagct 2940
gcagctcctg cggccccagc acctgccgcc cctgccgcac cggctccagc cgccccagcc 3000
gccgcgccag cggccccggc ccctgccgcg cccgctgctc ccgcccctgc tgccccagcc 3060
gccgctcctg cggcacctgc gcccgccgcg ccggcagcgc cggcaccggc agctccggcg 3120
gccgcgcctg cagctcctgc accggcggct ccagcagccc cggcgccggc cgcacctgcg 3180
gcggcgcccg cggcgcctgc acccgcagcg cctgcggcac cggccccagc agcccctgcc 3240
gccgcaccgg ctgcgcctgc cccagcggcc cccgctgccc cggccccggc ggctccagcc 3300
gcagcgcctg ccgccccagc gcccgcagca ccggcggcac cagctccggc ggcgccggcg 3360
gcggctccgg cagctccggc ccctgctgcg ccggctgcgc cggctccggc ggcccctgcg 3420
gcggctccgg ccgcacctgc acctgccgcg ccggctgctc cggccccggc tgccccagca 3480
gcggcaccag cagcgcctgc tcctgcggcg cctgcagctc cggcgccggc agccccggcc 3540
gccgcacccg cggctccagc ccccgccgct ccagcagccc ccgcgccagc tgcacctgct 3600
gccgctcctg ctgcccctgc tcccgctgcc cccgccgccc ccgccccagc tgcccccgct 3660
gccgcacctg ctgccccagc tcccgctgcc ccagccgcgc cggcccccgc agctccagcc 3720
gcggcaccag ctgccccagc tccagcggcg cctgctgccc cggcccccgc ggcaccggct 3780
gccgcgcccg cagctccagc gcctgctgca ccggctgctc cggcacccgc cgcgccagca 3840
gctgcccctg cggcaccagc tcctgctgcc cccgcggcac ctgcacccgc tgccccggcg 3900
gcagctcccg ccgcgccagc ccctgcagct cctgctgcac ctgctcctgc cgcccctgct 3960
gctgcccctg ctgctccagc ccctgcagca ccggccgctc cagctcctgc cgctcctgcc 4020
gctgcgcccg ctgctccagc cccagctgcg ccagcagctc ctgcacctgc tgcccctgcc 4080
gccgcccctg cggctccagc acctgctgca ccggccgccc cggcgcccgc tgcccccgca 4140
gcagccccag ccgcacccgc tccagcagct cccgcagccc cagcacccgc agcaccagcc 4200

<210> SEQ ID NO 164
<211> LENGTH: 4800
<212> TYPE: DNA
<213> ORGANISM: Artificial Sequence
<220> FEATURE:
<223> OTHER INFORMATION: Nucleotide sequence of
PA#1ad/1ac/1ab/1aa/1e/1d/1c/1b(1600), codon-optimized for E. coli

<400> SEQUENCE: 164
gccgcgcccg ctgcaccggc acctgctgcg ccggcggcgc ctgcacctgc agcaccagca 60
gcggccccgg cggctcccgc acctgccgcc ccggcagctc ccgcaccggc ggcgcctgcc 120
gcagctcccg ccgcaccagc gccagccgca ccagccgctc cggcccccgc ggctccggca 180
gcagcccccg ccgctccagc gcctgctgca cctgccgcgc ctgcgcctgc cgcacctgcc 240
gctgctcccg ctgccccagc tccagccgct ccggcggcgc ccgcacctgc tgcccctgcg 300
gccgctcccg ctgcgcccgc gcctgctgct cctgcagcac cagctcccgc cgctccggcc 360
gcagcccccg ctgccccggc gcctgcagct ccagcggcgc cggctcccgc tgcgcccgcc 420

-continued

```
gcagccccg cagccccagc acctgctgct cccgctgcgc cggccccggc tgctccagct    480

gcagctccag cggcccctgc ccctgctgct cccgccgcgc cagctcctgc cgctccagct    540

gcagctcctg ctgctcccgc gccggcagct ccggctgcac cggctccagc agctcctgcg    600

gccgcgccag cggcgccagc tcctgccgcg cccgcagccc cagcgcccgc cgctccggcc    660

gccgcgcccg cggctcccgc acccgctgcg cccgccgctc cagcacctgc cgccccagcg    720

gcggcaccag ccgcgccagc acccgctgcg cctgcagcac ccgctccggc ggccccggcg    780

gctgctccag ccgcccctgc acccgctgct ccagctgcgc ccgccccagc cgccccggcc    840

gccgctccgg ctgcaccggc accggcagca ccggctgcgc cagccccggc tgccccggca    900

gctgctccgg cggcacctgc ccccgccgcg ccagctgccc ccgcaccggc agctccagcg    960

gcagccccgg cggcaccagc tccagcagcg ccagctgcgc ctgccccagc agcgccagcc   1020

gctgctccag cagctcctgc ccctgctgcg cctgcggctc cggcgccagc tgctcctgct   1080

gcagctccgg ccgccccagc accggcagcg ccagcagcac cggcgccagc tgcccctgcc   1140

gccgcaccag cagcacctgc gccggcggct cccgcagcac ctgctccggc tgcccctgcc   1200

gccgcgcccg ctgcacccgc accagctgca ccagccgcac cggcaccggc ggccccagct   1260

gcagcaccgg cagcccccgc gccggccgcg ccagccgcgc cggcaccggc tgctccggct   1320

gcagcaccgg cagcgcctgc gccagctgct cccgcagctc ctgctccggc ggcgcctgca   1380

gctgcaccgg cagctcctgc cccagcagcc ccggcggcgc cagcgcccgc cgccccagct   1440

gcagcccctg cagcgccggc acccgccgcc cccgcagcac ctgcgccggc cgccccagct   1500

gcggcaccgg ccgcacccgc cccggcggct ccagcagcac ctgctccagc agcaccagct   1560

gcagcccctg cggcaccagc acccgcagcg ccagcggcac cagctccggc cgctcccgcc   1620

gctgcaccag cctcaccggc gccggccgca ccagctgctc ccgccccagc cgctcccgcg   1680

gcggcaccag cggcgccagc gcccgcagct ccggcagcac cggcgccggc tgctcctgcc   1740

gccgcacctg ctgccccggc gcccgccgcc cccgccgctc ccgcgccggc tgcacctgcg   1800

gccgccccag cagcaccggc tccagctgcc ccagccgcac cagcaccagc cgctccagcg   1860

gccgcgcctg ccgctcccgc acccgcggct ccggccgccc ctgcgccggc ggcaccggcg   1920

gcggcacccg cggcacctgc acctgccgcc cccgcggctc ctgctcccgc ggcgccagca   1980

gcagcgccag cggcgcctgc tcctgccgca ccagcagcac cagcacccgc cgcgccagca   2040

gcggcccctg cagctcccgc cccggcagcg cccgctgcgc cagcacccgc tgctcccgcg   2100

gcagccccg cagctccggc ccctgcggct ccagctgcac cagcaccggc agcgccggcg   2160

gcggcaccag ccgcacccgc accggctgcg cccgccgcgc cagcgccagc cgctccagct   2220

gccgcgccgg cagccccggc ccccgctgcc cctgctgcac ccgcgcctgc agcaccggcg   2280

gcagcccctg cggcacctgc acccgcggct cccgctgccc ctgcacccgc agcgcccgcc   2340

gccgcaccgg ccgctccggc acctgcagcg ccggctgcac cagcgccggc agctccagcg   2400

gccgcaccgg ctgcaccagc tccggcagct ccagcagcac cggcaccagc agctccggct   2460

gcagcgccag cagcaccagc gcctgctgct ccagctgctc ctgctcctgc tgcaccagca   2520

gcagctccag ccgcaccagc accggcagcg cctgcagccc ctgctccggc agctcctgcc   2580

gcagcaccgg cagcaccagc tccagcggca cccgctgccc ctgctcctgc agcaccggca   2640

gcggcaccgg ctgctcctgc gccagctgct ccggcagccc cagcccctgc agccccagca   2700

gcagcgcctg cggctccagc gccagccgca ccagcggctc cggcaccggc agcccctgcg   2760

gcagctcctg ctgcgcctgc tccagcagct ccagctgccc cagcgccggc agctccggct   2820
```

gccgcaccag ctgcgcctgc ccctgctgcg ccagccgcac cggctccggc agcaccagca 2880
gctgccccag cagctcctgc cccagctgcg cctgctgcgc cagcaccagc agccccagct 2940
gcagcaccag ctgcaccggc accagctgct ccagcagcac cagccccagc cgctccggca 3000
gccgcaccgg ctgccccagc ccctgccgca ccagcagctc ccgcccctgc agccccegcc 3060 gccgctccgg ccgcaccagc cccggctgcc cctgctgccc ccgcccggc agcacccgct 3120 gcagcaccag ccgcgcctgc accggcagct cctgcagccc cggcaccggc agcacctgcc 3180
gcagcacccg cagccccagc cccagcagcg cctgccgctc cagcaccagc ggcaccggcc 3240
gccgcaccag ccgccccagc accggcagcc cccgcagcgc cggcaccagc cgctccagcc 3300
gccgccccag cagccccggc tccggccgct cccgcggctc cagcaccagc agctccagcg 3360
gccgctccgg cagcgccggc cccagcagca cctgcagccc ctgcaccagc agcgccagcc 3420
gcggcgcccg cagctcccgc acctgcggct cccgcagccc ctgcacccgc ggcgccagca 3480
gccgcccctg cagcgccagc tcctgcagca cctgcagctc cagccccggc cgccccagct 3540
gcagctcctg cggccccagc acctgccgcc cctgccgcac cggctccagc cgccccagcc 3600
gccgcgccag cggccccggc ccctgccgcg cccgctgctc ccgcccctgc tgccccagcc 3660
gccgctcctg cggcacctgc gcccgccgcg ccggcagcgc cggcaccggc agctccggcg 3720
gccgcgcctg cagctcctgc accggcggct ccagcagccc cggcgccggc cgcacctgcg 3780
gcggcgcccg cggcgcctgc acccgcagcg cctgcggcac cggccccagc agcccctgcc 3840
gccgcaccgg ctgcgcctgc cccagcggcc cccgctgccc cggccccggc ggctccagcc 3900
gcagcgcctg ccgccccagc gcccgcagca ccggcggcac cagctccggc ggcgccggcg 3960
gcggctccgg cagctccggc ccctgctgcg ccggctgcgc cggctccggc ggcccctgcg 4020
gcggctccgg ccgcacctgc acctgccgcg ccggctgctc cggccccggc tgccccagca 4080
gcggcaccag cagcgcctgc tcctgcggcg cctgcagctc cggcgccggc agccccggcc 4140
gccgcacccg cggctccagc cccgccgct ccagcagccc ccgcgccagc tgcacctgct 4200
gccgctcctg ctgcccctgc tcccgctgcc cccgccgccc ccgccccagc tgccccgct 4260 gccgcacctg ctgccccagc tcccgctgcc ccagccgcgc cggcccccgc agctccagcc 4320
gcggcaccag ctgccccagc tccagcggcg cctgctgccc cggcccccgc ggcaccggct 4380
gccgcgcccg cagctccagc gcctgctgca ccggctgctc cggcacccgc cgcgccagca 4440
gctgcccctg cggcaccagc tcctgctgcc cccgcggcac ctgcacccgc tgccccggcg 4500
gcagctcccg ccgcgccagc ccctgcagct cctgctgcac ctgctcctgc cgcccctgct 4560
gctgcccctg ctgctccagc ccctgcagca ccggccgctc cagctcctgc cgctcctgcc 4620
gctgcgcccg ctgctccagc cccagctgcg ccagcagctc ctgcacctgc tgcccctgcc 4680
gccgcccctg cggctccagc acctgctgca ccggccgccc cggcgcccgc tgcccccgca 4740
gcagccccag ccgcacccgc tccagcagct cccgcagccc cagcacccgc agcaccagcc 4800

<210> SEQ ID NO 165
<211> LENGTH: 1800
<212> TYPE: DNA
<213> ORGANISM: Artificial Sequence
<220> FEATURE:
<223> OTHER INFORMATION: Nucleotide sequence of PA#1ao/1an/1am(600),
codon-optimized for P. fluorescens

<400> SEQUENCE: 165
gccgccccag ccgcccctgc ccctgccgcc ccagccgcac ccgccccggc agccccagcc 60

-continued gccgccgccg ccgcacccgc cccagcagca cccgctgcgc ccgctcctgc cgcgcccgcg 120
gccgcgcccg ccgcccctgc cccggctgcg cccgccgccc cagcgccagc tgcgcccgcc 180
gccgcccctg ccgccccagc cccggccgca cccgccgccc cggcccctgc cgcgcccgct 240
gccgcacccg ccgcacccgc cccggccgcc cctgccgccc ctgcacccgc cgcgcctgcc 300
gctgccccag ccgcaccagc cccagccgcg ccagccgcac ccgcccctgc agcccctgcc 360
gccgcgccag ccgcgcccgc cccggccgcc ccagccgccc ccgctcccgc cgccccagcc 420
gccgcgccgg cagccccagc cccagccgcc cctgcagcac ccgcacccgc cgcgcccgcc 480
gccgccccag ccgcgcccgc acccgccgcc cctgccgctc ctgccccagc cgccccagcc 540
gccgcaccag ccgcccctgc cccggccgcg cccgctgcgc ccgccccggc cgcacccgcg 600
gccgcgcccg cagccccagc cccggccgcg cccgccgcac ccgcgcccgc cgcccctgct 660
gccgcgcccg ccgccccggc cccggccgct cccgccgcgc cggccccggc cgccccggcc 720
gccgcgcctg ctgcccctgc ccctgccgcg ccggccgcgc ccgccccagc ggcccctgcc 780
gccgctcccg ccgcacctgc acccgccgcc ccagctgcgc ccgcacccgc ggcgcccgcc 840
gccgccccgg cagcgcccgc gcctgccgcg ccggccgccc ctgcccctgc tgcgcccgcc 900
gcggccccgg ccgcacccgc gcccgcggcg cccgccgctc cagccccggc cgccccggca 960
gccgcgccag ccgctcccgc cccagccgcc ccggctgcgc ccgcccctgc cgccccggcc 1020
gcggctcccg ccgcgcccgc gcccgccgcg cctgccgccc cagcgcccgc cgcgcccgcc 1080
gcagcgcccg ccgcgccagc ccccgccgcc ccagcagcgc ccgccccagc agccccggcc 1140
gccgcgcccg ccgcgcccgc accagccgca cccgccgccc cagcccctgc agcgcctgcc 1200
gccgcgccag cggcgccggc cccagccgcg ccggcagcgc cagcgcccgc cgcgccagca 1260
gccgcgcctg cggcgcctgc gcctgcggcc ccagcggcgc cggcgccagc ggcaccggca 1320
gccgcgcccg cagcgccggc ccctgccgcg ccggcagccc ccgcgcctgc ggccccagca 1380
gccgccccgg cggctcccgc gccggccgcc cctgcggcac cggcgcctgc ggccccggcg 1440
gccgcgccag ccgcgcctgc cccggccgcg ccggccgcgc cggcgcccgc cgcacctgcc 1500
gccgccccgg ccgcgccggc tccggccgcg ccagcggccc ctgcgcctgc agccccagcc 1560
gcggccccgg cggcgcccgc accagccgcg cctgccgcgc ccgcgccggc cgcaccggca 1620
gccgcgccgg ccgcgcctgc ccctgccgcc cccgccgcgc ctgccccagc agccccggca 1680
gccgccccgg cagcgcctgc gccagccgca ccggccgcgc cggcgccagc cgcaccagcc 1740
gccgcaccgg ccgcccctgc gccagcggcg cccgcagcgc cggcgcctgc cgcacccgcg 1800

<210> SEQ ID NO 166
<211> LENGTH: 2400
<212> TYPE: DNA
<213> ORGANISM: Artificial Sequence
<220> FEATURE:
<223> OTHER INFORMATION: Nucleotide sequence of PA#1ai/1ah/1ag/1af(800), codon-optimized for C. glutamicum

<400> SEQUENCE: 166
gccgctccag ctgcacccgc tcctgccgca ccggcggctc cagcacccgc ggcacctgcc 60
gccgcacctg ctgcacctgc accggccgct cccgccgccc cggccccggc ggctccagcc 120
gctgcgcccg cagctcctgc ccccgcagcc ccggcagcgc ccgcaccggc agcccctgcg 180
gcggcgcccg cagcaccagc tccggccgct cccgctgccc cggcaccggc tgccccagcc 240
gccgcacctg cggcgccggc gccggccgca ccggctgcgc ccgcgccggc agccccccgct 300

```
gcagcacctg ccgccccagc cccagccgct ccagccgctc ccgcaccggc tgcgcctgct    360

gcagccccag ccgcgccggc tccggcggcc ccggcggccc cggctccggc agccccagcc    420

gcagcccccg cagcgccagc gccagccgct ccggcagcac ctgcacctgc ggcgcccgcg    480

gcggcacctg cagcgcctgc gcccgctgcc cccgcggccc ccgctcctgc cgcgccggcg    540

gcggcaccag ccgcccctgc cccagctgca ccggcagcgc ctgcccccgc tgcgccagcc    600

gccgctcctg cagcaccagc gccagcggct cccgccgcac cggcaccagc tgctcccgct    660

gcagcgccgg cggcacccgc tccggctgcg ccggccgcgc ctgccccggc ggcgcctgca    720

gcagcgcctg ccgcacctgc tccagccgct ccagcggcgc ccgcccccgc ggccccagca    780

gcggctccgg cggccccagc gcccgcagcc ccagccgcgc ccgcacctgc tgcgccggcc    840

gccgcacccg cggcaccggc gcccgcggcc cccgctgccc ctgcacccgc tgcccccgca    900

gccgctccag cagcaccagc accagcggct ccggcggcgc cggctcccgc tgcccccgca    960

gcagcgcccg ccgcccccgc gcctgccgca ccagcggcac cggcaccagc agcgcccgcg   1020

gccgcgccag ctgcgcccgc cccagcggct cctgccgccc ccgcgccggc cgctcctgca   1080

gctgcccctg ccgctccggc gccagccgct cccgccgccc ccgctcctgc ggctccggcc   1140

gctgcgccgg ctgcccctgc accagcggct ccggccgctc cggcccccgc cgctccagct   1200

gccgctccgg ccgcccccgc acccgctgct cccgcagcgc cggcgcctgc ggcacccgca   1260

gccgcccctg cagccccagc tcccgcagcc cccgctgctc ctgctccagc tgcacccgcg   1320

gctgcacccg ctgcaccggc cccggcggct cctgccgccc cagcgccggc ggctcccgct   1380

gctgcacccg cggcccctgc gccggcagcc ccagcggcac cagcgcctgc cgcaccggca   1440

gccgccccag ccgccccagc gccagctgcg ccagcggctc cggccccagc tgcgccggca   1500

gcggcacctg cagctccagc tcctgctgct cccgcggcgc ccgcccccgc agcacctgct   1560

gccgccccag ctgccccagc tccggccgcc cctgcggctc ctgctcctgc agcgcctgct   1620

gcggctcccg cggcgccagc gccggcggcc ccagcagctc cagctcctgc agcaccggca   1680

gcggcccccg cggctccagc tcctgcagct ccggctgccc cagcccctgc cgcaccggct   1740

gcagcgcccg cggctcccgc tcctgcagca cctgcagcac cagcccctgc tgcaccggcg   1800

gccgcgcccg cggctcctgc cccagcagcg cccgcggcac cagcaccggc ggccccggcc   1860

gccgcccctg ctgcgcccgc gcctgcagct cccgccgccc cagcccccgc tgcaccagca   1920

gccgctccag ccgcaccggc gcccgctgca cctgccgctc cggcgccggc cgctccagcc   1980

gctgcaccag ccgcgccagc accagctgca cctgcggccc ctgcgccagc tgcgccagca   2040

gcggcaccag cagctccagc tccagctgcg cctgcggcac ctgccccggc tgccccggcg   2100

gctgcgcctg cggcccctgc accagccgcc ccagctgcac ccgcccctgc ggcgcctgcc   2160

gccgcacccg ccgcgcctgc cccagccgct ccggcggcac ctgccccagc tgctcctgca   2220

gcagcccctg ccgccccggc gccagccgca cccgccgcac cagcacctgc agcgccagct   2280

gccgcgccag ctgcgcctgc ccccgcagcc cccgccgctc ctgctccagc cgcacccgca   2340

gccgctccgg ctgctccagc cccagcagct ccagcggcac ccgcccctgc tgcaccggct   2400
```

<210> SEQ ID NO 167
<211> LENGTH: 1800
<212> TYPE: DNA
<213> ORGANISM: Artificial Sequence
<220> FEATURE:
<223> OTHER INFORMATION: Nucleotide sequence of PA#1y/1x/1w(600), codon-
optimized for B. subtilis

<400> SEQUENCE: 167
gccgcaccgg ctgcaccggc accagctgcg cctgctgcac cagcaccggc agcaccagca 60
gccgcacccg ctgctcccgc tcctgctgcg ccagctgcac cagctccggc agcgcctgcg 120
gctgctccag cggctccggc tcctgcagct cctgccgctc cagctccagc agcaccagct 180
gcggctccgg ctgcaccggc tccagccgca ccagcagcac cggcaccggc agcgccagct 240
gcagcccctg ctgctccggc gcctgctgca ccggcagctc cggcaccagc ggcaccggca 300
gcagctccgg cagctccggc tcctgctgct ccggcagcgc cagcgccagc agctcctgca 360
gctgctcctg ctgcacctgc accggctgct ccagcagcgc cggcaccggc tgcgccggct 420
gcagctccag ctgctccagc gccagctgct ccggcagcac cggctccggc tgcgcctgca 480
gccgctcctg cagcgcctgc accagccgct ccggcggctc ctgcaccagc cgcaccggct 540
gctgcacctg ctgcgcctgc gcctgctgct cctgctgcgc ctgctccggc agctcctgca 600
gccgcacctg cagcaccagc tccggcagca ccggcagctc cagcgcctgc ggctccggct 660
gctgctcctg cagctcctgc gccagctgcg ccagcagctc cagctccagc cgctcctgct 720
gcagcccctg cggcaccggc tccggcagct ccagcggcac cagcaccggc agctccggct 780
gcagcgccag cagctccggc accagcagct ccagcagcgc cagctcctgc ggcaccagcc 840
gcagcaccag ccgctccggc tccagctgcg cctgccgcac cggctccagc ggcaccggct 900
gcggcaccag cagcaccagc gcctgcagca ccagcagcgc cagcacctgc tgctccggca 960
gctgcaccgg ctgctccggc tccagcagct ccggctgcac cagcgcctgc tgcgcctgca 1020
gcagcacctg cggctccggc accggctgca ccggcggcac cggctccagc tgctccagca 1080
gcggctcctg cagctccggc tcctgccgca ccggctgctc cagctccggc tgcgccagcg 1140
gcagcaccgg ctgcaccagc accagcggcg ccagccgcac cagcacctgc tgcgcctgct 1200
gccgcaccgg ctgcgccagc acctgcagcg cctgccgctc ctgctccggc tgctccggct 1260
gctgcaccag cggcaccagc accagcagcg cctgcggcac cggcaccagc cgcaccagct 1320
gccgctccag ccgctccggc accggctgct ccggcagcac cagcaccagc tgcaccagcg 1380
gcagcgcctg cagcgccagc tccggcagcg ccagcagcac cagctccagc tgcaccggct 1440
gctgcccctg ctgcaccagc tccagccgct ccggctgcgc ctgctcctgc agcgccagct 1500
gccgctcctg cagcaccagc gccagcggca ccggcagcgc ctgctccggc tgcaccagct 1560
gccgcaccgg cagcacctgc accagcagct ccagctgctc cggctccagc ggctcctgca 1620
gctgcgcctg cggctcctgc accagcggct ccagctgctc ctgcgcctgc cgctccagca 1680
gcagctccag ctgcgcctgc gccagcagca ccggctgcgc ctgcaccagc ggctccggca 1740
gcagcaccag ctgcgccagc gcctgcagct ccggctgctc cggcaccagc tgcgccagct 1800

<210> SEQ ID NO 168
<211> LENGTH: 2400
<212> TYPE: DNA
<213> ORGANISM: Artificial Sequence
<220> FEATURE:
<223> OTHER INFORMATION: Nucleotide sequence of PA#1j/1k/1l/1m(800),
codon-optimized for P. pastoris

<400> SEQUENCE: 168
gccgcacctg ccgcacctgc ccctgctgcc ccagctgccc ctgctcctgc cgcccctgcc 60
gccgctcctg ccgctcctgc tcctgccgct ccagctgctc cagctcctgc tgctccagca 120
gctgccccag ccgccccagc tcctgctgcc ccagccgcac ctgcaccagc cgctccagct 180

```
gctgcccctg ccgcacctgc accagctgct ccagccgcac ctgcacctgc cgccccagct    240
gccgcccctg ccgcaccagc tcctgcagcc cctgccgctc cagccccagc agctccagct    300
gccgcccctg cagcccctgc cccagccgca ccagctgccc ctgccccagc agctcctgct    360
gccgcccctg ctgctccagc accagcagct ccagccgcac ctgctccagc cgctccagct    420
gccgcacctg ccgctccagc ccctgcagcc cctgcagccc cagctccagc cgccccagcc    480
gccgcacctg cagccccagc accagctgcc cctgcagcac cagctcctgc tgctcctgct    540
gcagcaccag ccgcaccagc accagcagca ccagccgccc cagccccagc cgcaccagca    600
gccgcccctg ccgcccccgc tcctgctgca cctgctgctc ccgcacccgc cgcccctgcc    660
gctgcccctg ctgcaccagc ccctgctgct ccagccgcac cagctccagc agctcctgcc    720
gctgccccag ctgccccagc tcccgccgcc cccgccgctc ctgcacccgc tgcaccagcc    780
gccgccccag ccgctccagc cccagccgct cctgcagctc ctgctcctgc tgcccctgca    840
gccgccccgg cagctccagc tcccgcagct cctgctgcac cagctcccgc tgctcctgca    900
gccgcacctg ctgcccctgc tcctgctgct ccagctgcac ccgctcctgc cgcaccagcc    960
gctgcccctg ccgctccagc acccgccgca ccagccgctc ctgcccctgc agctccagcc   1020
gccgcccctg ccgcgcctgc tccagccgct cctgcagcac ctgcacctgc agcacctgct   1080
gcagcaccag cagctcctgc tcccgcagca ccagcagccc cagcaccagc cgctccagca   1140
gccgctccag ctgcacctgc ccctgcagca cctgcagctc ctgctccagc ggctccagct   1200
gccgcccccg ccgctccagc acctgccgca cctgcagctc cagcccctgc tgctcctgct   1260
gctgcacctg ccgctcccgc accagctgct cccgcagctc ccgcccctgc cgcgccagct   1320
gccgctcccg ctgcccctgc accagctgct cctgctgctc ctgcccctgc tgcacctgca   1380
gctgctccag ccgcccctgc tccggcagcc ccagcagcac ccgctcctgc tgcaccagcc   1440
gccgcaccag ctgctccagc tccggcagca cctgcagccc ccgctccagc cgcccctgcc   1500
gcagccccag ctgcgccagc tcccgctgct ccagcagctc cagcacccgc cgctccagcc   1560
gccgctcccg ctgctccagc tccggctgca cctgctgcac ctgctcctgc tgctcccgct   1620
gctgcccccg cagcaccagc tcctgccgca cctgctgctc ctgctccagc agcacccgcc   1680
gcagctcctg cagcaccggc tccagcagct cctgctgcac ctgcccctgc cgctcccgct   1740
gcagctcccg ccgctcccgc ccctgctgca cccgctgccc cagcacctgc agcacctgca   1800
gccgcacccg ctgcacctgc ccccgcagcc ccagccgccc ctgcccccgc tgcacctgca   1860
gcagccccg ctgcccctgc acccgcagca ccagctgcac ctgctcctgc cgctcccgct   1920
gctgcacctg ctgccccagc ccctgctgca ccagcagctc cagctcccgc tgcccctgct   1980
gcagcacccg ctgctcctgc tcctgcagct ccagctgcac cagccccagc agcacctgcc   2040
gctgctcctg ctgcccccgc tccagcagcc cctgcagcac ctgctcctgc agcccccgca   2100
gcagctccag ctgcccctgc ccccgccgct ccagctgctc ctgctcccgc cgcacctgcc   2160
gcagctcctg cagctcctgc acctgctgct ccagccgctc ccgcaccagc agcacctgct   2220
gccgctcctg cagccccagc acccgctgcc cccgcagcac ctgcacccgc cgcccctgct   2280
gccgcacccg ccgcacctgc tccagctgct cccgcagccc ctgcacctgc cgctcctgcc   2340
gccgctccag ccgctccagc cccgcagct cctgccgctc cagcacctgc agctccagca   2400
```

<210> SEQ ID NO 169
<211> LENGTH: 1800
<212> TYPE: DNA

<213> ORGANISM: Artificial Sequence
<220> FEATURE:
<223> OTHER INFORMATION: Nucleotide sequence of PA#1p/1o/1n(600), codon-optimized for S. cerevisiae

<400> SEQUENCE: 169

```
gccgctccag cagcaccagc tcctgcagct ccagctgcac ctgctccagc cgctcccgct     60

gcagctccgg ccgctcccgc cccagccgca cccgcagccc cagctcccgc tgctccagct    120

gcagctccag cagcacctgc gcccgcggca ccagccgctc ctgcaccggc tgcacccgct    180

gcggcgccgg cagcacccgc tcccgcagcc cccgcagcgc ccgccccagc ggccccagcc    240

gcggcgccag cagctccagc tccagcggca cccgcggcac cagctcccgc agcgccggcg    300

gcagctcctg cagccccggc ccccgccgca ccagcagctc ctgctccggc ggcaccagca    360

gcagcgccgg cggctccggc gccggcagcg ccagcggccc ctgctcccgc cgcgccggca    420

gcagcccccg ccgctccagc ccctgcggct ccggcggcgc ccgcccccgc agcacctgcg    480

gctgcgccag ccgcacctgc cccggctgca cctgctgcac ccgcgccggc tgcacccgcg    540

gctgccccgg ctgctccggc gccagcggca cctgctgcac cagcacctgc cgcgccagcg    600

gccgctccag ctgctccagc cccagctgca cctgcagcgc cagcaccagc agctccagca    660

gctgcaccag ccgctcccgc accagctgct cctgctgctc cagcgcctgc agctcctgct    720

gccgctccag ctgccccagc tccagcggct ccggcagcgc cagccccagc agcacccgcc    780

gctgcacctg ccgcaccagc tcctgccgca cctgctgctc ccgcaccagc agcaccggca    840

gctgctccag ccgcaccagc gcctgccgca cccgctgccc cagcacctgc ggcgccagca    900

gcagctcctg cggcaccggc accagctgcc cctgcagctc cggctccagc tgcgcctgcc    960

gctgcaccag ctgcgcctgc gccagccgct cctgctgcgc ctgcaccagc ggcaccagca   1020

gctgcacccg ctgcaccagc gccagcagct ccggcagctc cagcgcccgc ggcgcctgct   1080

gctgcccctg ccgctccagc tccagctgct cctgcagcac cagcccctgc agccccggcg   1140

gccgcaccag cagcgcctgc acctgcggct ccagcagccc cagccccagc ggcccctgcc   1200

gccgctccag ctgcaccagc tccagcagct ccagccgctc ctgctcctgc tgctcccgca   1260

gcagcccctg cagcacccgc tccagcagca cccgctgctc cagctccagc tgcacccgca   1320

gctgctccag cagcacctgc accagccgca ccagcagctc ccgctccagc agctcctgca   1380

gcagcacccg ccgcaccagc accagccgca ccagctgctc cagcaccagc cgctccagct   1440

gcagccccag cagctcccgc tcctgcagct cctgctgctc ctgcaccagc agcacccgcc   1500

gcagctcccg cagcaccagc tccagctgct cccgctgcac ccgctccagc cgcaccagcc   1560

gctgcaccag ctgcacccgc tccagctgca cccgccgctc cagctcctgc agcaccagct   1620

gctgccccag ccgctccagc accagctgct cccgccgctc ctgcaccagc agctccagct   1680

gccgctcctg cagcacccgc accagctgca ccagcagcac cagcaccagc agcaccagct   1740

gctgctcccg ctgctcctgc tcctgccgct cctgcagctc cagctcctgc cgctccagct   1800
```

<210> SEQ ID NO 170
<211> LENGTH: 1800
<212> TYPE: DNA
<213> ORGANISM: Artificial Sequence
<220> FEATURE:
<223> OTHER INFORMATION: Nucleotide sequence of PA#1s/1r/1q(600), codon-optimized for K. lactis

<400> SEQUENCE: 170

```
gccgcccccg ctgctcctgc cccagctgcc cccgccgcgc cagcccctgc tgctcctgct     60
```

gccgcgcctg cagctccagc cccagccgca ccagcagccc cagccccagc agctcccgcc 120
gcagctccag cagcccccgc cccagctgca ccagccgcac cagcacctgc tgctcccgcc 180
gctgccccag ccgctcctgc tccagccgcc cctgccgctc ccgccccagc agccccagca 240
gcagcgccag cagccccagc acccgctgct ccagccgccc cagctccggc cgcaccagct 300
gccgccccag ccgctcctgc accagctgcc cctgccgccc cagctcccgc cgccccagca 360
gcagctccag ccgcaccagc cccagccgcg ccagctgctc ctgcacctgc tgcacctgca 420
gcagctcccg ctgctccagc acctgctgca cctgctgctc cagccccagc agcgcccgca 480
gccgctccag cagctccagc acctgcagct ccagccgctc cagccccagc cgcgcctgcc 540
gccgctccag ctgcccctgc cccagcagca cccgccgctc cagccccagc agctccagcc 600
gccgccccag cagctcctgc tccagctgct cccgctgctc cagcccctgc agctcccgcc 660
gcagcaccag ccgccccagc tcctgccgct cccgccgctc cagcacctgc cgcccctgct 720
gctgctcctg ccgctcctgc ccccgccgcc ccagccgccc cagccccagc agcaccagca 780
gcggcccctg cagccccagc tcctgcagca cctgccgcac ctgcaccagc tgccccagct 840
gccgccccag cagcccctgc tcctgcagca ccagctgcac ctgctccggc cgcaccagca 900
gccgcacctg cagctccagc acccgcagct cccgcagccc cagcacctgc cgctcccgct 960
gctgctcccg ccgctcctgc cccagctgct cctgccgcac ctgctcccgc agctccagcc 1020
gctgcgcctg ctgcaccagc acccgcagca ccggcagcgc cagcacctgc agctcctgcc 1080
gcagcgcccg cagcaccagc ccctgccgct ccagcagcac ctgctcctgc tgctccagcc 1140
gccgcccccg ctgcaccagc tccagctgca ccagctgctc ccgcccctgc tgccccggcc 1200
gccgctccag cagcaccggc cccagccgcg cccgccgctc cagctcccgc tgcacctgca 1260
gccgctcctg ctgcacctgc acctgcagcc ccagccgctc cagctcctgc cgctccagcc 1320
gccgcccctg ccgcacccgc accagcagca cctgccgcgc ctgctccagc agcaccagcc 1380
gcagcaccag ccgctccagc gcctgcagct ccagcagccc cagctcccgc agcaccagct 1440
gcagcaccag cagctcctgc acctgcagca ccagccgcac cagcccccgc tgcccctgct 1500
gccgcccctg cagcacctgc gccagccgcg ccagcagctc cagctccagc agcacccgca 1560
gcagctccag cagctcccgc tcctgctgcc cctgccgctc ctgcccctgc tgcaccagcc 1620
gccgctcccg cagctcctgc accagctgca cctgccgccc ccgcacctgc cgcacccgct 1680
gccgctcctg ctgcccccgc acccgctgca cccgcggccc cggccccggc agctccagca 1740
gcagctcctg ccgctccggc ccctgcagca ccagccgctc ccgcaccggc cgcacccgcc 1800

<210> SEQ ID NO 171
<211> LENGTH: 2400
<212> TYPE: DNA
<213> ORGANISM: Artificial Sequence
<220> FEATURE:
<223> OTHER INFORMATION: Nucleotide sequence of PA#1as/1ar/1aq/1ap(800),
codon-optimized for T. thermophila

<400> SEQUENCE: 171
gccgcacctg cagctccagc acctgccgct cccgccgcac ctgctcctgc cgctcctgct 60
gccgctccag cagcacctgc tcctgcagct ccagcagctc ctgcccctgc tgctcctgcc 120
gcagctcctg ccgcacccgc tcccgctgct ccagctgctc ctgctccggc tgctccagct 180
gctgctcctg ctgcccctgc tcctgctgct cctgcggctc cagcacccgc agctcccgcc 240
gccgctcctg ctgctcccgc acccgctgct cctgccgctc cagcacctgc tgctcctgct 300

```
gcagctcccg cagctcctgc gcctgctgct cctgctgcgc ctgctcccgc tgctccagca    360
gcagctcctg ctgctccagc ccctgctgct cccgctgctc ctgcacctgc agctcctgca    420
gctgcccctg cagctccagc accagctgct cctgccgctc ccgctcctgc agctcctgcc    480
gctgcaccag ctgcacctgc accagctgcc cctgctgcac ctgcacctgc cgctcctgca    540
gcagctcctg ctgcacccgc ccctgctgct ccagctgcac ccgctcctgc tgctcctgca    600
gccgctcctg cagctccagc acctgctgca ccagctgccc ctgccccagc tgctcccgct    660
gctgctccag ctgcacctgc acccgctgca ccggctgctc cggctcctgc tgctcctgcc    720
gctgctcctg ctgcccccgc tcctgctgca cctgccgcac ctgctcctgc ggctccagcc    780
gctgctccag cagctcctgc tccagccgca ccagcagcac cagctcctgc agcacctgca    840
gctgctcctg cggcacctgc tccagctgct ccagcggctc ctgcacctgc tgctcccgca    900
gctgctccag ccgcccctgc tcctgctgcg cctgctgctc cagcccctgc agctcctgcc    960
gccgctcctg cagcccctgc tccagcagcc cctgccgctc ctgctcctgc agcgcctgca   1020
gctgcaccag ccgctcctgc ccctgctgct ccagcagcac ctgctcccgc cgctccagct   1080
gccgctccag cagctccagc tcctgctgct ccagcggcac cagctccagc tgctcctgct   1140
gctgctcctg ctgcacccgc acctgcagca ccagcagctc ccgctcctgc tgctcccgct   1200
gccgctcctg ctgcaccagc acctgctgct cctgcagcac ccgctcctgc tgcccctgct   1260
gcagctcctg cagctcctgc tcctgctgct ccggcagctc ctgctcccgc tgcccctgct   1320
gccgctcctg cagctcccgc acctgctgct ccagctgccc cagcacctgc tgccccagct   1380
gcagctcctg cggcccctgc tcctgcagct ccggctgctc ctgctcctgc cgcaccagct   1440
gctgctcctg cagccccagc tcctgctgcc ccagccgctc cagctccagc tgcaccagct   1500
gcagcacctg ctgctccggc tccagctgct cccgcagcac ctgctcctgc tgcaccggca   1560
gctgctcctg cagctcctgc accagctgct cctgccgccc ctgcacctgc tgcacctgct   1620
gctgcacctg cagctcctgc tccggctgca cctgctgccc ctgcaccagc tgcacctgct   1680
gcagcacctg ccgctcctgc cccagctgcc cctgctgctc ctgctccagc tgcacccgct   1740
gctgcacctg ctgcgccagc tcctgctgca cctgcagccc ctgctcctgc tgcacctgct   1800
gccgctccag ctgctccggc tcccgctgct cctgcagctc ccgctccagc tgctcctgca   1860
gcagctcctg cagcccccgc tccagctgca ccggctgcac cagctcctgc tgctcctgct   1920
gctgcccctg ctgctcccgc ccctgctgct cctgcagctc cggcacctgc tgctcctgct   1980
gccgcacctg cagctccagc cccagctgct cctgctgcac ctgctcctgc agcaccagct   2040
gctgcacctg ctgcacccgc tccagctgct ccagctgctc ctgcccctgc agctccagct   2100
gccgcacctg ccgctccagc tcctgcagct cccgccgcac ctgctccagc agctcccgca   2160
gctgcacctg ctgctcctgc cccagcagct cctgcagctc cagctccagc agctcctgcc   2220
gctgcacctg ctgctccagc accagctgca ccagcagctc ctgctcctgc agctcctgcc   2280
gcagctcctg ctgctcccgc accagctgca cctgccgctc ccgctccagc agcaccagct   2340
gccgctccag ctgctcccgc cccagctgct ccagcagctc cagcaccagc agctccagct   2400
```

<210> SEQ ID NO 172
<211> LENGTH: 1800
<212> TYPE: DNA
<213> ORGANISM: Artificial Sequence
<220> FEATURE:
<223> OTHER INFORMATION: Nucleotide sequence of PA#1v/1u/1t(600), codon-
optimized for H. sapiens (HEK cells)

<400> SEQUENCE: 172
gccgccccgg cagcacccgc accggctgca ccagccgctc cagcaccggc cgcaccagcc 60
gcagctccag cagcaccggc accggcagct cccgcagcac cagctccggc agctccagcc 120
gccgctccgg ctgcaccagc tccagcagca ccagctgctc cagctccagc agcacccgca 180
gctgctccag cagctcccgc tccggccgct cctgctgcac cggctccagc tgctccggcc 240
gcagcaccag cagctccagc cccagccgct ccagcagctc ctgctcccgc agcaccggca 300
gccgcaccag ctgctccggc tccggcagct cctgctgcac cagctcccgc cgctccagct 360
gcagctccag ctgctccggc accggctgca ccggccgctc cggctcccgc cgcaccagct 420
gcagcccctg ccgctcctgc accagctgca cccgctgctc cagctccggc tgctcctgca 480
gccgctcctg cagctccggc accagctgca cctgcagctc ccgctccagc tgctcctgca 540
gcagctcccg ctgcaccagc accagcagct cccgccgcac cggctccagc tgcaccagca 600
gccgccccgg ctgctcccgc tcctgcagca ccggcagctc ccgctccagc cgcaccagca 660
gcagcacccg cagctccagc accggctgca cccgctgcac ctgctccagc cgctccagca 720
gctgccccag ccgcaccagc accggcagct ccggctgctc ctgctccagc agcacccgcc 780
gcagctccgg ccgctccagc tcctgctgca cccgcagctc ccgcaccggc agctccagcc 840
gctgcaccag cagctccggc tccagctgct ccagcagcac cagctccagc cgcacccgct 900
gcagccccag ctgcaccagc accagccgca cctgcagctc cagcaccagc tgctccggca 960
gctgcacccg ctgctcccgc accagctgca ccagcagcac ccgcaccagc cgctccggcc 1020
gcagctcctg cagctcccgc ccctgcagct cctgccgctc ctgctcccgc tgctcctgcc 1080
gcagctcccg ctgctccggc tcctgccgca ccagctgcac ccgctccggc agcaccagca 1140
gccgcacccg cagcaccagc tccagcagct ccagctgctc ctgctcctgc tgcaccagct 1200
gccgctcctg ctgctccagc tccagctgca ccagccgctc cggcaccagc agcacccgct 1260
gctgcccctg cagctcctgc tccggcagct cccgcagctc ctgcaccagc tgctccagct 1320
gccgctccag ccgctcctgc tcctgccgct cctgcagcac ccgctccggc cgcaccagct 1380
gctgctcccg ctgcacccgc tccagcagct ccggctgcac cagcaccggc tgctccagca 1440
gcagcccctg cagcaccagc tccagctgct cccgcagctc cagctcctgc tgctccggcc 1500
gctgctcctg ccgcaccagc accagccgct ccagctgcac ccgcaccagc tgcacccgcc 1560
gctgctccag ctgctcctgc accggcagca ccagctgctc ccgctccggc tgctcccgct 1620
gctgcaccgg ccgctccagc tccagcagct cctgccgctc ccgcaccagc agctcccgca 1680
gcagcacccg ccgcaccggc tccggcagca ccagccgcac cagctcccgc tgcaccggct 1740
gccgcaccgg ctgcaccggc accagcagct ccagccgctc cggctcctgc agctccagca 1800

<210> SEQ ID NO 173
<211> LENGTH: 1800
<212> TYPE: DNA
<213> ORGANISM: Artificial Sequence
<220> FEATURE:
<223> OTHER INFORMATION: Nucleotide sequence of PA#1al/1ak/1j(600), codon-optimized for P. patens

<400> SEQUENCE: 173
gccgcaccag ctgctcccgc acctgcagca ccagccgctc ccgcccctgc cgctccagcc 60
gccgcaccag ccgccccagc ccctgcagca cccgcagcac ctgctcccgc agctccagcc 120
gcagccccag ccgctcctgc accagccgcc cctgctgcac cggctccagc cgcgcccgct 180

```
gctgcgcccg ccgctcccgc cccagccgcc ccagctgccc ccgctccagc tgctcccgca    240

gctgcacccg ccgcacctgc acctgctgcc cccgctgcac ctgcacctgc cgcccctgca    300

gctgccccag ccgccccggc acccgctgcc cccgccgctc ctgctcctgc tgcaccagct    360

gccgcccctg ccgcccccgc accagcggcc ccagcagccc ccgccccagc cgctccagct    420

gctgctcccg ccgcacctgc cccagccgca cctgccgccc cagctcccgc cgctcccgcc    480

gccgctcctg ctgcacccgc ccctgctgct cctgccgctc ccgctcccgc tgctcccgct    540

gccgctcccg ccgcccccgc tcctgccgcc cccgccgcac cagcacctgc agctcctgcc    600

gccgcacctg ccgcaccagc ccccgcagca cccgcagcgc cagctccagc agctccagcc    660

gccgcacctg ccgctcccgc gcccgctgct cctgccgccc ctgcccctgc tgcacccgct    720

gcagctcctg ccgctcctgc acctgccgct cctgcagccc ctgctcctgc tgcccctgct    780

gccgctccag ctgcccctgc tcctgccgcg cctgctgccc cagcaccggc cgccccagca    840

gctgctcctg ctgcccccgc accagcagct ccagccgcgc ctgcgcctgc tgcccccgct    900

gccgctcctg ccgctcctgc ccctgctgct cctgctgcac ccgctcccgc tgctcctgct    960

gctgcacccg ccgcccctgc tcctgcagct ccagccgctc ccgctccagc tgcaccagcc   1020

gccgccccag ccgcgccagc gccagctgcc cctgctgcac ctgctcccgc cgctcccgct   1080

gccgcccccg ctgcacccgc accagctgca cccgctgctc ccgcccctgc tgctcccgct   1140

gcagctccgg ccgctcccgc acctgctgct cccgctgccc ctgcgcctgc cgctcccgca   1200

gccgctcccg ctgcccctgc tcctgctgcg cccgctgcac ctgcccctgc tgctcccgca   1260

gctgctccag ccgcccccgc tcccgctgca ccagctgctc ccgctcctgc cgctcccgct   1320

gccgcacccg ctgcacctgc gcctgcggct cccgccgctc ccgcccccgc tgcgcccgca   1380

gccgcccccg cagcccccgc accagcagcc ccagccgcac cagctccagc agccccagct   1440

gccgcacctg ctgcacccgc tcctgctgct cccgcagcac cagcccctgc agctcccgct   1500

gccgcgcctg ccgcccctgc ccccgcagca ccagcagctc ccgccccagc tgcacctgca   1560

gccgctccag cagccccagc ccctgccgct ccagctgctc ctgctccagc cgcaccagca   1620

gccgcacccg ctgcaccagc acctgcagcg cccgctgcac cagcgcccgc tgccccagct   1680

gccgctcccg ccgcaccagc tcctgctgca cccgctgctc cagcacccgc cgctcccgcc   1740

gctgctcctg ccgctcctgc tcccgcagct cccgctgcgc ctgctccagc tgcaccagcc   1800
```

<210> SEQ ID NO 174
<211> LENGTH: 900
<212> TYPE: DNA
<213> ORGANISM: Artificial Sequence
<220> FEATURE:
<223> OTHER INFORMATION: Nucleotide sequence of PAS#1n/1b(300), codon-optimized for E. coli

<400> SEQUENCE: 174

```
gccagtccgg cagcgcccgc tccagcaagt cccgctgcac ccgcacctag cgccccggca     60

gcttccccgg ctgcgcctgc gccagcctct ccggctgccc cagcgccgtc cgcacccgcg    120

gcgtcaccag cagcccctgc gcctgcttcc ccagcagccc ctgcaccgtc agcgccagca    180

gcatcacctg ctgcccccgc acccgcaagt cctgccgcac cggcccccttc agcccctgct   240

gcctctccag ccgcgccagc acccgcgtcg cccgctgcgc ctgcccccag cgcacctgca    300

gccagccctg ccgcacctgc gcccgcatca cctgcggcac ctgcaccttc cgccccggct    360

gcatctcctg ccgcacccgc gcctgccagc ccagctgcac ctgccccaag tgcgccagca    420
```

gcatcccctg ccgcgcctgc cccgctagt ccagcggccc cagctccatc tgcaccagct 480
gctagccctg ctgcaccagc tcctgcttct cccgcagccc cagcgccttc tgctcccgca 540
gcctcacctg cggccccggc accagcatct ccagcggcac cagcaccttc ggcccctgct 600
gctagcccag cagcacctgc gccagcctca ccagctgctc ccgctcctag tgccccggcg 660
gcctcgcctg ctgctcctgc accagcttcg ccagcggcac cggctccttc ggcgccggct 720
gcttcaccag cagcacctgc tccagcgtcc ccagcggccc ctgctccaag tgctccggct 780
gcatcgcctg ccgctcctgc tcctgcatcc ccagctgctc cagcaccaag cgcacctgcc 840
gcctcaccag cggcgccagc acccgccagc ccagcagcgc ctgctccatc cgcaccggcg 900

<210> SEQ ID NO 175
<211> LENGTH: 900
<212> TYPE: DNA
<213> ORGANISM: Artificial Sequence
<220> FEATURE:
<223> OTHER INFORMATION: Nucleotide sequence of PAS#1n/1c(300), codon-
      optimized for E. coli

<400> SEQUENCE: 175
gccagtccgg cagcgcccgc tccagcaagt cccgctgcac ccgcacctag cgccccggca 60
gcttccccgg ctgcgcctgc gccagcctct ccggctgccc cagcgccgtc cgcacccgcg 120
gcgtcaccag cagcccctgc gcctgcttcc ccagcagccc ctgcaccgtc agcgccagca 180
gcatcacctg ctgcccccgc acccgcaagt cctgccgcac cggccccttc agcccctgct 240
gcctctccag ccgcgccagc acccgcgtcg cccgctgcgc ctgcccccag cgcacctgca 300
gccagtcctg ctgcaccggc accggcatca ccggctgcac cagcacctag tgcaccggca 360
gcttctccgg ctgcccctgc gcctgcatca ccagctgcgc ctgcaccgtc tgcccctgca 420
gctagtccag cagctccagc tccggcttct cctgcggctc ctgcaccaag tgcgcctgca 480
gcaagtccgg ctgcgcctgc cccagctagt cctgctgctc cggcaccgtc agctccggca 540
gcatctcctg cagcaccagc ccctgcaagt ccagcagcgc cagcccccatc agcaccagca 600 gcttcaccag ccgcaccagc gccagcaagc cctgctgccc cagctcctag cgcaccggca 660
gccagtcctg cagctcctgc gcctgctagt ccggcagccc cagctccaag tgcccctgcc 720
gcttcgcctg cagccccagc accagcttct ccagccgcac cggcaccttc tgccccagct 780
gcatctccgg cagctccggc accagcaagc ccggcagcac cggcaccatc tgcgcctgcc 840
gcatctccgg ctgcgccagc tccagcctct cctgcagcgc cagcaccgag cgcaccagca 900

<210> SEQ ID NO 176
<211> LENGTH: 1800
<212> TYPE: DNA
<213> ORGANISM: Artificial Sequence
<220> FEATURE:
<223> OTHER INFORMATION: Nucleotide sequence of PAS#1b/1f/1c(600),
      codon-optimized for E. coli

<400> SEQUENCE: 176
gccagccctg ccgcacctgc gcccgcatca cctgcggcac ctgcaccttc cgccccggct 60
gcatctcctg ccgcacccgc gcctgccagc ccagctgcac ctgccccaag tgcgccagca 120
gcatcccctg ccgcgcctgc cccgctagt ccagcggccc cagctccatc tgcaccagct 180
gctagccctg ctgcaccagc tcctgcttct cccgcagccc cagcgccttc tgctcccgca 240
gcctcacctg cggccccggc accagcatct ccagcggcac cagcaccttc ggcccctgct 300

```
gctagcccag cagcacctgc gccagcctca ccagctgctc ccgctcctag tgccccggcg    360

gcctcgcctg ctgctcctgc accagcttcg ccagcggcac cggctccttc ggcgccggct    420

gcttcaccag cagcacctgc tccagcgtcc ccagcggccc ctgctccaag tgctccggct    480

gcatcgcctg ccgctcctgc tcctgcatcc ccagctgctc cagcaccaag cgcacctgcc    540

gcctcaccag cggcgccagc acccgccagc ccagcagcgc ctgctccatc cgcaccggcg    600

gcctcccctg ccgctccagc ccccgcctcg ccggccgctc ccgctccgtc tgcacctgct    660

gcctcaccag cagccccggc cccagcatcc ccggccgcac cagctccgtc agcacctgcc    720

gcatcgcctg ctgcccctgc cccagccagt ccagcggctc cagccccgag tgctccggcc    780

gcttcccccg cagcaccggc tcctgcctcc cctgcagccc ctgctccatc tgcccctgcg    840

gcatcccctg cggcgccagc tcctgcctct ccagctgcac cggctccctc agctcccgct    900

gcctccccag ccgcgcccgc tcctgcaagc ccagcagctc cggctccatc cgcccccgcc    960

gccagccccg cagccccggc gcctgcctct cctgctgcac ctgcaccgtc agcccctgca   1020

gcatctcccg cagctcctgc accggcatct ccagcagccc ccgcccccgtc agctcccgca   1080

gccagcccgg ccgcacccgc ccccgcgtca ccagctgcac cagcgccatc cgctcctgct   1140

gcgtctcccg ctgcgcccgc ccctgcctca cctgcagcac ctgcacctag cgccccggct   1200

gccagtcctg ctgcaccggc accggcatca ccggctgcac cagcacctag tgcaccggca   1260

gcttctccgg ctgcccctgc gcctgcatca ccagctgcgc ctgcaccgtc tgcccctgca   1320

gctagtccag cagctccagc tccggcttct cctgcggctc ctgcaccaag tgcgcctgca   1380

gcaagtccgg ctgcgcctgc cccagctagt cctgctgctc cggcaccgtc agctccggca   1440

gcatctcctg cagcaccagc ccctgcaagt ccagcagcgc cagccccatc agcaccagca   1500

gcttcaccag ccgcaccagc gccagcaagc cctgctgccc cagctcctag cgcaccggca   1560

gccagtcctg cagctcctgc gcctgctagt ccggcagccc cagctccaag tgcccctgcc   1620

gcttcgcctg cagccccagc accagcttct ccagccgcac cggcaccttc tgccccagct   1680

gcatctccgg cagctccggc accagcaagc ccggcagcac cggcaccatc tgcgcctgcc   1740

gcatctccgg ctgcgccagc tccagcctct cctgcagcgc cagcaccgag cgcaccagca   1800
```

<210> SEQ ID NO 177
<211> LENGTH: 1800
<212> TYPE: DNA
<213> ORGANISM: Artificial Sequence
<220> FEATURE:
<223> OTHER INFORMATION: Nucleotide sequence of PAS#1b/1c/1f(600), codon-optimized for E. coli

<400> SEQUENCE: 177

```
gccagccctg ccgcacctgc gcccgcatca cctgcggcac ctgcaccttc cgccccggct     60

gcatctcctg ccgcacccgc gcctgccagc ccagctgcac ctgccccaag tgcgccagca    120

gcatcccctg ccgcgcctgc ccccgctagt ccagcggccc cagctccatc tgcaccagct    180

gctagccctg ctgcaccagc tcctgcttct cccgcagccc cagcgccttc tgctcccgca    240

gcctcacctg cggccccggc accagcatct ccagcggcac cagcaccttc ggcccctgct    300

gctagcccag cagcacctgc gccagcctca ccagctgctc ccgctcctag tgccccggcg    360

gcctcgcctg ctgctcctgc accagcttcg ccagcggcac cggctccttc ggcgccggct    420

gcttcaccag cagcacctgc tccagcgtcc ccagcggccc ctgctccaag tgctccggct    480

gcatcgcctg ccgctcctgc tcctgcatcc ccagctgctc cagcaccaag cgcacctgcc    540
```

gcctcaccag cggcgccagc acccgccagc ccagcagcgc ctgctccatc cgcaccggcg 600
gccagtcctg ctgcaccggc accggcatca ccggctgcac cagcacctag tgcaccggca 660
gcttctccgg ctgcccctgc gcctgcatca ccagctgcgc ctgcaccgtc tgcccctgca 720
gctagtccag cagctccagc tccggcttct cctgcggctc ctgcaccaag tgcgcctgca 780
gcaagtccgg ctgcgcctgc cccagctagt cctgctgctc cggcaccgtc agctccggca 840
gcatctcctg cagcaccagc ccctgcaagt ccagcagcgc cagccccatc agcaccagca 900
gcttcaccag ccgcaccagc gccagcaagc cctgctgccc cagctcctag cgcaccggca 960
gccagtcctg cagctcctgc gcctgctagt ccggcagccc cagctccaag tgcccctgcc 1020
gcttcgcctg cagccccagc accagcttct ccagccgcac cggcaccttc tgccccagct 1080
gcatctccgg cagctccggc accagcaagc ccggcagcac cggcaccatc tgcgcctgcc 1140
gcatctccgg ctgcgccagc tccagcctct cctgcagcgc cagcaccgag cgcaccagca 1200
gcctcccctg ccgctccagc ccccgcctcg ccggccgctc ccgctccgtc tgcacctgct 1260
gcctcaccag cagccccggc cccagcatcc ccggccgcac cagctccgtc agcacctgcc 1320
gcatcgcctg ctgcccctgc cccagccagt ccagcggctc cagccccgag tgctccggcc 1380
gcttcccccg cagcaccggc tcctgcctcc cctgcagccc ctgctccatc tgcccctgcg 1440
gcatcccctg cggcgccagc tcctgcctct ccagctgcac cggctccctc agctcccgct 1500
gcctccccag ccgcgcccgc tcctgcaagc ccagcagctc cggctccatc cgcccccgcc 1560
gccagccccg cagccccggc gcctgcctct cctgctgcac ctgcaccgtc agcccctgca 1620
gcatctcccg cagctcctgc accggcatct ccagcagccc ccgccccgtc agctcccgca 1680
gccagcccgg ccgcacccgc ccccgcgtca ccagctgcac cagcgccatc cgctcctgct 1740
gcgtctcccg ctgcgcccgc ccctgcctca cctgcagcac ctgcacctag cgcccccggct 1800

<210> SEQ ID NO 178
<211> LENGTH: 1800
<212> TYPE: DNA
<213> ORGANISM: Artificial Sequence
<220> FEATURE:
<223> OTHER INFORMATION: Nucleotide sequence of PAS#1c/1b/1f(600),
codon-optimized for E. coli

<400> SEQUENCE: 178
gccagtcctg ctgcaccggc accggcatca ccggctgcac cagcacctag tgcaccggca 60
gcttctccgg ctgcccctgc gcctgcatca ccagctgcgc ctgcaccgtc tgcccctgca 120
gctagtccag cagctccagc tccggcttct cctgcggctc ctgcaccaag tgcgcctgca 180
gcaagtccgg ctgcgcctgc cccagctagt cctgctgctc cggcaccgtc agctccggca 240
gcatctcctg cagcaccagc ccctgcaagt ccagcagcgc cagccccatc agcaccagca 300
gcttcaccag ccgcaccagc gccagcaagc cctgctgccc cagctcctag cgcaccggca 360
gccagtcctg cagctcctgc gcctgctagt ccggcagccc cagctccaag tgcccctgcc 420
gcttcgcctg cagccccagc accagcttct ccagccgcac cggcaccttc tgccccagct 480
gcatctccgg cagctccggc accagcaagc ccggcagcac cggcaccatc tgcgcctgcc 540
gcatctccgg ctgcgccagc tccagcctct cctgcagcgc cagcaccgag cgcaccagca 600
gccagccctg ccgcacctgc gcccgcatca cctgcggcac ctgcaccttc cgcccccggct 660 gcatctcctg ccgcacccgc gcctgccagc ccagctgcac ctgccccaag tgcgccagca 720
gcatcccctg ccgcgcctgc ccccgctagt ccagcggccc cagctccatc tgcaccagct 780
gctagccctg ctgcaccagc tcctgcttct cccgcagccc cagcgccttc tgctcccgca 840
gcctcacctg cggccccggc accagcatct ccagcggcac cagcaccttc ggcccctgct 900
gctagcccag cagcacctgc gccagcctca ccagctgctc ccgctcctag tgccccggcg 960
gcctcgcctg ctgctcctgc accagcttcg ccagcggcac cggctccttc ggcgccggct 1020
gcttcaccag cagcacctgc tccagcgtcc ccagcggccc ctgctccaag tgctccggct 1080
gcatcgcctg ccgctcctgc tcctgcatcc ccagctgctc cagcaccaag cgcacctgcc 1140
gcctcaccag cggcgccagc acccgccagc ccagcagcgc ctgctccatc cgcaccggcg 1200
gcctcccctg ccgctccagc cccgcctcg ccggccgctc ccgctccgtc tgcacctgct 1260
gcctcaccag cagccccggc cccagcatcc ccggccgcac cagctccgtc agcacctgcc 1320
gcatcgcctg ctgcccctgc cccagccagt ccagcggctc cagccccgag tgctccggcc 1380 gcttccccg cagcaccggc tcctgcctcc cctgcagccc ctgctccatc tgcccctgcg 1440
gcatcccctg cggcgccagc tcctgcctct ccagctgcac cggctccctc agctcccgct 1500
gcctccccag ccgcgcccgc tcctgcaagc ccagcagctc cggctccatc cgcccccgcc 1560
gccagccccg cagccccggc gcctgcctct cctgctgcac ctgcaccgtc agcccctgca 1620
gcatctcccg cagctcctgc accggcatct ccagcagccc ccgccccgtc agctcccgca 1680
gccagcccgg ccgcacccgc ccccgcgtca ccagctgcac cagcgccatc cgctcctgct 1740
gcgtctcccg ctgcgcccgc ccctgcctca cctgcagcac ctgcacctag cgccccggct 1800

<210> SEQ ID NO 179
<211> LENGTH: 1800
<212> TYPE: DNA
<213> ORGANISM: Artificial Sequence
<220> FEATURE:
<223> OTHER INFORMATION: Nucleotide sequence of PAS#1f/1b/1c(600), codon-optimized for E. coli

<400> SEQUENCE: 179
gcctcccctg ccgctccagc cccgcctcg ccggccgctc ccgctccgtc tgcacctgct 60
gcctcaccag cagccccggc cccagcatcc ccggccgcac cagctccgtc agcacctgcc 120
gcatcgcctg ctgcccctgc cccagccagt ccagcggctc cagccccgag tgctccggcc 180 gcttccccg cagcaccggc tcctgcctcc cctgcagccc ctgctccatc tgcccctgcg 240
gcatcccctg cggcgccagc tcctgcctct ccagctgcac cggctccctc agctcccgct 300
gcctccccag ccgcgcccgc tcctgcaagc ccagcagctc cggctccatc cgcccccgcc 360
gccagccccg cagccccggc gcctgcctct cctgctgcac ctgcaccgtc agcccctgca 420
gcatctcccg cagctcctgc accggcatct ccagcagccc ccgccccgtc agctcccgca 480
gccagcccgg ccgcacccgc ccccgcgtca ccagctgcac cagcgccatc cgctcctgct 540
gcgtctcccg ctgcgcccgc ccctgcctca cctgcagcac ctgcacctag cgccccggct 600
gccagccctg ccgcacctgc gcccgcatca cctgcggcac ctgcaccttc cgccccggct 660
gcatctcctg ccgcacccgc gcctgccagc ccagctgcac ctgccccaag tgcgccagca 720
gcatcccctg ccgcgcctgc ccccgctagt ccagcggccc cagctccatc tgcaccagct 780
gctagccctg ctgcaccagc tcctgcttct cccgcagccc cagcgccttc tgctcccgca 840
gcctcacctg cggccccggc accagcatct ccagcggcac cagcaccttc ggcccctgct 900
gctagcccag cagcacctgc gccagcctca ccagctgctc ccgctcctag tgccccggcg 960
gcctcgcctg ctgctcctgc accagcttcg ccagcggcac cggctccttc ggcgccggct 1020
gcttcaccag cagcacctgc tccagcgtcc ccagcggccc ctgctccaag tgctccggct 1080
gcatcgcctg ccgctcctgc tcctgcatcc ccagctgctc cagcaccaag cgcacctgcc 1140
gcctcaccag cggcgccagc acccgccagc ccagcagcgc ctgctccatc cgcaccggcg 1200
gccagtcctg ctgcaccggc accggcatca ccggctgcac cagcacctag tgcaccggca 1260
gcttctccgg ctgcccctgc gcctgcatca ccagctgcgc ctgcaccgtc tgcccctgca 1320
gctagtccag cagctccagc tccggcttct cctgcggctc ctgcaccaag tgcgcctgca 1380
gcaagtccgg ctgcgcctgc cccagctagt cctgctgctc cggcaccgtc agctccggca 1440
gcatctcctg cagcaccagc ccctgcaagt ccagcagcgc cagcccccatc agcaccagca 1500 gcttcaccag ccgcaccagc gccagcaagc cctgctgccc cagctcctag cgcaccggca 1560
gccagtcctg cagctcctgc gcctgctagt ccggcagccc cagctccaag tgcccctgcc 1620
gcttcgcctg cagccccagc accagcttct ccagccgcac cggcaccttc tgccccagct 1680
gcatctccgg cagctccggc accagcaagc ccggcagcac cggcaccatc tgcgcctgcc 1740
gcatctccgg ctgcgccagc tccagcctct cctgcagcgc cagcaccgag cgcaccagca 1800

<210> SEQ ID NO 180
<211> LENGTH: 1800
<212> TYPE: DNA
<213> ORGANISM: Artificial Sequence
<220> FEATURE:
<223> OTHER INFORMATION: Nucleotide sequence of PAS#1c/1f/1b(600), codon-optimized for E. coli

<400> SEQUENCE: 180
gccagtcctg ctgcaccggc accggcatca ccggctgcac cagcacctag tgcaccggca 60
gcttctccgg ctgcccctgc gcctgcatca ccagctgcgc ctgcaccgtc tgcccctgca 120
gctagtccag cagctccagc tccggcttct cctgcggctc ctgcaccaag tgcgcctgca 180
gcaagtccgg ctgcgcctgc cccagctagt cctgctgctc cggcaccgtc agctccggca 240
gcatctcctg cagcaccagc ccctgcaagt ccagcagcgc cagcccccatc agcaccagca 300 gcttcaccag ccgcaccagc gccagcaagc cctgctgccc cagctcctag cgcaccggca 360
gccagtcctg cagctcctgc gcctgctagt ccggcagccc cagctccaag tgcccctgcc 420
gcttcgcctg cagccccagc accagcttct ccagccgcac cggcaccttc tgccccagct 480
gcatctccgg cagctccggc accagcaagc ccggcagcac cggcaccatc tgcgcctgcc 540
gcatctccgg ctgcgccagc tccagcctct cctgcagcgc cagcaccgag cgcaccagca 600
gcctcccctg ccgctccagc ccccgcctcg ccggccgctc ccgctccgtc tgcacctgct 660
gcctcaccag cagccccggc cccagcatcc ccggccgcac cagctccgtc agcacctgcc 720
gcatcgcctg ctgcccctgc cccagccagt ccagcggctc cagccccgag tgctccggcc 780
gcttcccccg cagcaccggc tcctgcctcc cctgcagccc ctgctccatc tgcccctgcg 840
gcatcccctg cggcgccagc tcctgcctct ccagctgcac cggctccctc agctcccgct 900
gcctccccag ccgcgcccgc tcctgcaagc ccagcagctc cggctccatc cgcccccgcc 960
gccagccccg cagccccggc gcctgcctct cctgctgcac ctgcaccgtc agcccctgca 1020
gcatctcccg cagctcctgc accggcatct ccagcagccc ccgcccccgtc agctcccgca 1080 gccagcccgg ccgcacccgc ccccgcgtca ccagctgcac cagcgccatc cgctcctgct 1140
gcgtctcccg ctgcgcccgc ccctgcctca cctgcagcac ctgcacctag cgcccccggct 1200 gccagccctg ccgcacctgc gcccgcatca cctgcggcac ctgcaccttc cgcccccggct 1260

-continued

```
gcatctcctg ccgcacccgc gcctgccagc ccagctgcac ctgccccaag tgcgccagca   1320

gcatcccctg ccgcgcctgc ccccgctagt ccagcggccc cagctccatc tgcaccagct   1380

gctagccctg ctgcaccagc tcctgcttct cccgcagccc cagcgccttc tgctcccgca   1440

gcctcacctg cggccccggc accagcatct ccagcggcac cagcaccttc ggcccctgct   1500

gctagcccag cagcacctgc gccagcctca ccagctgctc ccgctcctag tgccccggcg   1560

gcctcgcctg ctgctcctgc accagcttcg ccagcggcac cggctccttc ggcgccggct   1620

gcttcaccag cagcacctgc tccagcgtcc ccagcggccc ctgctccaag tgctccggct   1680

gcatcgcctg ccgctcctgc tcctgcatcc ccagctgctc cagcaccaag cgcacctgcc   1740

gcctcaccag cggcgccagc acccgccagc ccagcagcgc ctgctccatc cgcaccggcg   1800
```

<210> SEQ ID NO 181
<211> LENGTH: 3000
<212> TYPE: DNA
<213> ORGANISM: Artificial Sequence
<220> FEATURE:
<223> OTHER INFORMATION: Nucleotide sequence of
      PAS#1k/1d/1f/1c/1b(1000), codon-optimized for E. coli

<400> SEQUENCE: 181

```
gcctctcctg cagctccggc cccagcttca ccagccgctc cagccccatc tgcgccggcc     60

gcctcacctg cagcaccagc ccctgcgtcg cccgccgcgc ctgcgccctc agccccagca    120

gctagccctg ccgcacccgc cccagcaagt cctgctgctc ctgccccctc tgccccggca    180

gcttcaccgg cagcccctgc accagcttcc cccgcagccc ctgcccccag tgcacctgca    240

gctagtcctg cggccccagc accagcgtct ccagctgcgc ccgcgccttc agcaccagca    300

gcttctccgg ccgctcccgc tcccgctagc cctgcagctc cagctccctc agcgcccgca    360

gcaagccctg ccgcaccggc ccctgcctct cctgctgctc ccgccccgtc cgcacccgca    420

gcctcaccag ccgctcctgc tcccgcttcg ccagccgctc ccgccccttc cgcgcctgca    480

gcttctcccg ccgctcctgc tccggcctct cccgcggcgc ctgctccttc tgccccggcc    540

gcgtcccctg ccgcacctgc ccctgcgagc cctgcagccc cagccccgag cgctcctgcc    600

gccagccccg ccgcccctgc accggcgtct cccgccgcac cagccccttc agcgcctgca    660

gcatcacccg cggcccccgc acccgcatct ccagccgccc ctgctccttc cgccccagcc    720

gcatcgccag ccgctccagc accggcatcc cccgcggctc ccgctcccag cgcacctgcg    780

gcttcaccgg cagcaccagc gcccgcaagt ccagccgcgc cggctccttc tgcgcctgcg    840

gcctcgccgg cagctccagc ccctgcttcc ccagctgccc cggccccttc agccccagcg    900

gcgtctccag cagcaccagc tcccgcctct ccggcagcgc cagcgccctc ggcccccgcc    960

gcgtcccctg ccgccccggc acccgcatcg cccgctgccc cagccccatc cgccccagct   1020

gcaagccccg ctgctccagc tcccgccagt ccagcagcac ccgccccttc tgcgccagcc   1080

gcgtcaccgg ccgccccagc accggcgagc cccgctgcac ccgcccctag cgctccggcc   1140

gcatctcctg cggcgcccgc acctgccagt ccagctgctc ctgctccgtc cgcccctgcc   1200

gcctcccctg ccgctccagc ccccgcctcg ccggccgctc ccgctccgtc tgcacctgct   1260

gcctcaccag cagccccggc cccagcatcc ccggccgcac cagctccgtc agcacctgcc   1320

gcatcgcctg ctgcccctgc cccagccagt ccagcggctc cagccccgag tgctccggcc   1380

gcttcccccg cagcaccggc tcctgcctcc cctgcagccc ctgctccatc tgcccctgcg   1440

gcatcccctg cggcgccagc tcctgcctct ccagctgcac cggctccctc agctcccgct   1500
```

-continued gcctccccag ccgcgcccgc tcctgcaagc ccagcagctc cggctccatc cgcccccgcc 1560
gccagccccg cagccccggc gcctgcctct cctgctgcac ctgcaccgtc agcccctgca 1620
gcatctcccg cagctcctgc accggcatct ccagcagccc ccgccccgtc agctcccgca 1680
gccagcccgg ccgcacccgc ccccgcgtca ccagctgcac cagcgccatc cgctcctgct 1740
gcgtctcccg ctgcgcccgc ccctgcctca cctgcagcac ctgcacctag cgccccggct 1800
gccagtcctg ctgcaccggc accggcatca ccggctgcac cagcacctag tgcaccggca 1860
gcttctccgg ctgcccctgc gcctgcatca ccagctgcgc ctgcaccgtc tgcccctgca 1920
gctagtccag cagctccagc tccggcttct cctgcggctc ctgcaccaag tgcgcctgca 1980
gcaagtccgg ctgcgcctgc cccagctagt cctgctgctc cggcaccgtc agctccggca 2040
gcatctcctg cagcaccagc ccctgcaagt ccagcagcgc cagccccatc agcaccagca 2100
gcttcaccag ccgcaccagc gccagcaagc cctgctgccc cagctcctag cgcaccggca 2160
gccagtcctg cagctcctgc gcctgctagt ccggcagccc cagctccaag tgcccctgcc 2220
gcttcgcctg cagccccagc accagcttct ccagccgcac cggcaccttc tgccccagct 2280
gcatctccgg cagctccggc accagcaagc ccggcagcac cggcaccatc tgcgcctgcc 2340
gcatctccgg ctgcgccagc tccagcctct cctgcagcgc cagcaccgag cgcaccagca 2400
gccagccctg ccgcacctgc gcccgcatca cctgcggcac ctgcaccttc cgccccggct 2460
gcatctcctg ccgcacccgc gcctgccagc ccagctgcac ctgccccaag tgcgccagca 2520
gcatcccctg ccgcgcctgc ccccgctagt ccagcggccc cagctccatc tgcaccagct 2580
gctagccctg ctgcaccagc tcctgcttct cccgcagccc cagcgccttc tgctcccgca 2640
gcctcacctg cggccccggc accagcatct ccagcggcac cagcaccttc ggcccctgct 2700
gctagcccag cagcacctgc gccagcctca ccagctgctc ccgctcctag tgccccggcg 2760
gcctcgcctg ctgctcctgc accagcttcg ccagcggcac cggctccttc ggcgccggct 2820
gcttcaccag cagcacctgc tccagcgtcc ccagcggccc ctgctccaag tgctccggct 2880
gcatcgcctg ccgctcctgc tcctgcatcc ccagctgctc cagcaccaag cgcacctgcc 2940
gcctcaccag cggcgccagc acccgccagc ccagcagcgc ctgctccatc cgcaccggcg 3000

<210> SEQ ID NO 182
<211> LENGTH: 3600
<212> TYPE: DNA
<213> ORGANISM: Artificial Sequence
<220> FEATURE:
<223> OTHER INFORMATION: Nucleotide sequence
PAS#1l/1k/1d/1f/1c/1b(1200), codon-optimized for E. coli

<400> SEQUENCE: 182
gccagcccag cagctcccgc tccggcatca cccgctgctc cggcccccgag tgctccagct 60 gcttctcctg ccgcacccgc ccctgcaagc ccggcagccc ccgcaccctc cgcgccggcc 120
gcgtcaccag ccgctcctgc acccgcgtca ccagcggcac cggcaccctc tgcgcccgcc 180
gcatcaccag cagcaccggc gcctgcatcc ccagcagcac ctgcaccaag cgcccccgcc 240
gcctccccgg ccgcccctgc accggcaagt cctgcagcac ccgcgccttc agctccggcc 300
gcctccccag cagctcccgc accagccagc ccagccgcac cagcgccgtc tgcaccagcc 360
gcgagcccag ccgcgcctgc accggccagc cctgccgccc cagccccctc tgcgcccgca 420
gcctcccctg cagctcctgc cccggccagt ccagccgccc ccgcgccgag tgcacctgca 480
gcatcaccag cggctcctgc acctgcatct cccgcagcac ccgctccgtc agcccctgca 540

```
gccagccctg ccgcgccagc acctgcgtca ccagccgccc cggccccgag tgcacctgca    600
gcctctcctg cagctccggc cccagcttca ccagccgctc cagccccatc tgcgccggcc    660
gcctcacctg cagcaccagc ccctgcgtcg cccgccgcgc ctgcgccctc agccccagca    720
gctagccctg ccgcacccgc cccagcaagt cctgctgctc ctgccccctc tgccccggca    780
gcttcaccgg cagcccctgc accagcttcc cccgcagccc ctgcccccag tgcacctgca    840
gctagtcctg cggccccagc accagcgtct ccagctgcgc ccgcgccttc agcaccagca    900
gcttctccgg ccgctcccgc tcccgctagc cctgcagctc cagctccctc agcgcccgca    960
gcaagccctg ccgcaccggc ccctgcctct cctgctgctc ccgccccgtc cgcacccgca   1020
gcctcaccag ccgctcctgc tcccgcttcg ccagccgctc ccgccccttc cgcgcctgca   1080
gcttctcccg ccgctcctgc tccggcctct cccgcggcgc ctgctccttc tgccccggcc   1140
gcgtcccctg ccgcacctgc ccctgcgagc cctgcagccc cagccccgag cgctcctgcc   1200
gccagccccg ccgcccctgc accggcgtct cccgccgcac cagccccttc agcgcctgca   1260
gcatcacccg cggccccgc acccgcatct ccagccgccc ctgctccttc cgccccagcc    1320
gcatcgccag ccgctccagc accggcatcc cccgcggctc ccgctcccag cgcacctgcg   1380
gcttcaccgg cagcaccagc gcccgcaagt ccagccgcgc cggctccttc tgcgcctgcg   1440
gcctcgccgg cagctccagc ccctgcttcc ccagctgccc cggccccttc agccccagcg   1500
gcgtctccag cagcaccagc tcccgcctct ccggcagcgc cagcgccctc ggccccgcc    1560
gcgtcccctg ccgccccggc acccgcatcg cccgctgccc cagccccatc cgccccagct   1620
gcaagccccg ctgctccagc tcccgccagt ccagcagcac ccgccccttc tgcgccagcc   1680
gcgtcaccgg ccgccccagc accggcgagc cccgctgcac ccgcccctag cgctccggcc   1740
gcatctcctg cggcgcccgc acctgccagt ccagctgctc ctgctccgtc cgcccctgcc   1800
gcctcccctg ccgctccagc ccccgcctcg ccggccgctc ccgctccgtc tgcacctgct   1860
gcctcaccag cagccccggc cccagcatcc ccggccgcac cagctccgtc agcacctgcc   1920
gcatcgcctg ctgcccctgc cccagccagt ccagcggctc cagccccgag tgctccggcc   1980
gcttcccccg cagcaccggc tcctgcctcc cctgcagccc ctgctccatc tgcccctgcg   2040
gcatcccctg cggcgccagc tcctgcctct ccagctgcac cggctccctc agctcccgct   2100
gcctccccag ccgcgcccgc tcctgcaagc ccagcagctc cggctccatc cgcccccgcc   2160
gccagccccg cagccccggc gcctgcctct cctgctgcac ctgcaccgtc agcccctgca   2220
gcatctcccg cagctcctgc accggcatct ccagcagccc ccgccccgtc agctcccgca   2280
gccagcccgg ccgcacccgc cccegcgtca ccagctgcac cagcgccatc cgctcctgct   2340
gcgtctcccg ctgcgcccgc ccctgcctca cctgcagcac ctgcacctag cgccccggct   2400
gccagtcctg ctgcaccggc accggcatca ccggctgcac cagcacctag tgcaccggca   2460
gcttctccgg ctgcccctgc gcctgcatca ccagctgcgc ctgcaccgtc tgcccctgca   2520
gctagtccag cagctccagc tccggcttct cctgcggctc ctgcaccaag tgcgcctgca   2580
gcaagtccgg ctgcgcctgc cccagctagt cctgctgctc cggcaccgtc agctccggca   2640
gcatctcctg cagcaccagc ccctgcaagt ccagcagcgc cagccccatc agcaccagca   2700
gcttcaccag ccgcaccagc gccagcaagc cctgctgccc cagctcctag cgcaccggca   2760
gccagtcctg cagctcctgc gcctgctagt ccggcagccc cagctccaag tgcccctgcc   2820
gcttcgcctg cagccccagc accagcttct ccagccgcac cggcaccttc tgccccagct   2880
gcatctccgg cagctccggc accagcaagc ccggcagcac cggcaccatc tgcgcctgcc   2940
```

```
gcatctccgg ctgcgccagc tccagcctct cctgcagcgc cagcaccgag cgcaccagca   3000

gccagccctg ccgcacctgc gcccgcatca cctgcggcac ctgcaccttc cgccccggct   3060

gcatctcctg ccgcacccgc gcctgccagc ccagctgcac ctgccccaag tgcgccagca   3120

gcatcccctg ccgcgcctgc ccccgctagt ccagcggccc cagctccatc tgcaccagct   3180

gctagccctg ctgcaccagc tcctgcttct cccgcagccc cagcgccttc tgctcccgca   3240

gcctcacctg cggccccggc accagcatct ccagcggcac cagcaccttc ggcccctgct   3300

gctagcccag cagcacctgc gccagcctca ccagctgctc ccgctcctag tgccccggcg   3360

gcctcgcctg ctgctcctgc accagcttcg ccagcggcac cggctccttc ggcgccggct   3420

gcttcaccag cagcacctgc tccagcgtcc ccagcggccc ctgctccaag tgctccggct   3480

gcatcgcctg ccgctcctgc tcctgcatcc ccagctgctc cagcaccaag cgcacctgcc   3540

gcctcaccag cggcgccagc acccgccagc ccagcagcgc ctgctccatc cgcaccggcg   3600
```

<210> SEQ ID NO 183
<211> LENGTH: 1800
<212> TYPE: DNA
<213> ORGANISM: Artificial Sequence
<220> FEATURE:
<223> OTHER INFORMATION: Nucleotide sequence PAS#1s/1q/1r(600), codon-
      optimized for P. fluorescens

<400> SEQUENCE: 183

```
gcctcaccag cagctcccgc gcccgcatcg cccgccgccc cggcccctag cgccccggcg     60

gccagccccg ccgcgcctgc cccggcctcg ccggcagccc cagcgccaag tgcgcccgcc    120

gccagccccg ccgccccagc gcccgcctcg ccggccgccc cggccccaag tgctcccgcc    180

gcctccccgg ccgcccctgc gccagccagc cccgcagccc cggccccgtc ggcaccagcc    240

gcctctccag ccgcgcccgc cccggctagc cccgcagccc cagccccgtc cgcccctgcc    300

gcgtcccctg cagccccagc ccctgcgagc cctgccgcac ccgccccgtc cgcgcccgcc    360

gcttcgccgg cagccccggc cccggcgtcg cccgccgccc cagccccgag tgccccggcc    420

gcgagccccg ccgcccccgc cccagcctcg cccgcggccc ctgcaccatc cgcaccggcc    480

gccagcccag cggcgcccgc accggcctcc ccggcagccc ctgcgcccag tgccccggca    540

gctagcccag ccgcgcccgc cccagcgtcg cccgccgcgc ctgccccaag tgcccccgcc    600

gcctccccag ccgcgcccgc gcccgctagc cccgcagcgc ccgccccgtc ggcccctgcc    660

gcgtctcctg ccgcgccagc cccggccagt ccagccgcgc ccgccccgtc cgcgccggca    720

gcctcgccag ccgcccctgc acccgcaagc ccggccgcac ccgccccgag cgcaccggca    780

gcctcaccag ctgccccagc cccggcatcc gccgccgctc cagccccatc cgctcccgcc    840

gccagtccgg ccgccccggc tcctgcatcg cccgcagccc ctgccccgag tgcgccagca    900

gcgagccccg ccgcccctgc gcccgccagc ccagctgccc ccgcgccgag tgcgcccgca    960

gcgtccccgg cagccccggc gcccgcctca cccgccgccc cagccccaag cgcacccgct   1020

gcgtcgcccg ccgcacctgc tcccgcctcc ccggcagctc ccgccccaag tgcccctgct   1080

gcgagtccgg ctgcaccggc cccagcgagc ccggcggccc cggccccgag cgcccctgcc   1140

gcaagcccag ccgcccccgc tcccgcatcc ccagccgcgc cggccccgtc cgctccggcc   1200

gcctcgcccg cagccccagc gcccgcctcc cctgccgccc ctgccccaag cgccccggca   1260

gccagcccgg ccgcaccggc cccagcaagc ccagccgcac cagccccttc cgccccggcc   1320

gcctcccctg cagcgcccgc cccggcctcg cccgccgccc cggcgccgag cgcgcccgcc   1380
```

gcctcccctg ccgctcccgc acccgcgagc cctgcagccc cggccccgtc cgccccagcc 1440
gcctcccctg ccgcgcccgc cccagctagc cccgcggccc cggccccaag cgctcctgcc 1500
gctagccctg ccgccccggc gcccgccagc cctgccgctc ccgccccaag tgctcccgcc 1560
gcgtccccgg ccgccccggc cccggcctca cccgcagctc cggccccttc cgcgcccgcc 1620
gcgagccccg cagccccggc tcctgccagc cccgccgccc ctgcaccgtc ggcgcccgcc 1680
gcctccccag ccgcccctgc cccggccagc cccgccgccc cggcaccgag cgcgccagcc 1740
gcttcgcccg ccgcgccagc gcctgcctcg cccgccgcgc ccgccccttc cgcccctgcc 1800

<210> SEQ ID NO 184
<211> LENGTH: 1800
<212> TYPE: DNA
<213> ORGANISM: Artificial Sequence
<220> FEATURE:
<223> OTHER INFORMATION: Nucleotide sequence PAS#1v/1t/1u(600), codon-
optimized for C. glutamicum

<400> SEQUENCE: 184
gcctccccag ctgctccagc accagcctct cctgcagcac cagcgccatc cgctccggcc 60
gcctcccctg cagcacctgc tcctgccagt cctgctgcac cggccccgag cgcacccgca 120
gctagcccag cagcacctgc acctgcctca cctgcggcgc ctgctccctc cgccccagct 180
gcatctccag ccgcgcccgc tccagcttca ccagctgcac cagcaccgtc tgctccggca 240
gccagccctg ctgctcctgc gccagcatct cccgctgctc cggcgccatc tgcacccgcc 300
gctagtccag ccgcaccagc gcctgcaagc cccgcagcac ccgctccttc cgcacctgcg 360
gctagcccag cagctcctgc tccagcgtcc ccagccgccc ctgcaccaag tgctcctgct 420
gccagcccag ctgccccagc acctgcgagt ccagcagccc ctgcaccgag tgcaccagct 480
gcttcccctg ccgctcccgc accggcttcc ccggcagcac cagctccatc agcgcctgca 540
gcaagtccag cagctccggc cccagctagt cctgcagctc ccgccccgtc agcaccagca 600
gcctccccag cagcgcccgc tccggcatct ccagccgctc cggcccctag cgctccagct 660
gcatctcctg ctgcgcctgc ccctgctagc cctgctgctc ccgcaccttc ggctccggca 720
gcttcgccag ccgctccagc tcccgcctcc ccggccgctc cagcaccctc tgctccagct 780
gcctctccag cagcaccggc accagcttcc cccgcagccc cggctccaag cgctcctgct 840
gcaagtcctg ccgcacctgc gcctgcgtct ccagctgcac cagctcccag cgccccagcc 900
gcttcccctg ctgcacctgc gccggctagt cccgctgcac ccgctccctc cgcccctgca 960
gcatcgccag ccgcccctgc acccgcatct ccggcagcgc ctgctccatc ggctcctgcc 1020
gcctccccgg cagctcctgc tcccgcctcc cccgcggcac ctgctccgag tgccccagct 1080
gccagcccag ctgctccagc tcctgcctcg cctgctgctc cagccccatc cgcaccagct 1140
gccagtccag cggcccccgc accagcaagc cctgccgcgc cggcacccag tgctccagcg 1200
gcctccccgg cggcaccagc accagcgagc ccagcagcac cagcgccgtc tgcacctgca 1260
gcgtctcctg ccgctccagc tccggcaagc ccggccgcac ctgctccatc tgctcccgcg 1320
gcatccccag ctgcgccagc cccagcttct cccgctgcac cggctccctc cgcaccagcc 1380
gcttccccag cagctccagc tccagcatct cccgctgcac ctgcaccgtc agcaccggct 1440
gctagccccg cggcgccagc tcctgcgtcc ccggcagctc cagcgccatc cgctcctgcg 1500
gcatcccctg cagctccagc acctgcttca cctgctgcac cagccccaag tgctccggct 1560
gcatcaccag cagctcctgc accagcgtct cctgcggccc cagcaccatc cgcgcccgca 1620

```
gcttccccag ctgcgcctgc accagcctcc cccgctgcgc cagcgccatc agcacctgcc   1680

gcttctccgg ctgctccagc gcctgcctcc ccagctgcac ccgctccatc ggctccggct   1740

gcttcacctg ccgcaccagc cccagcgtca cctgcagctc ctgccccatc tgccccagct   1800
```

<210> SEQ ID NO 185
<211> LENGTH: 1800
<212> TYPE: DNA
<213> ORGANISM: Artificial Sequence
<220> FEATURE:
<223> OTHER INFORMATION: Nucleotide sequence PAS#1an/am/1l(600), codon-
optimized for B. subtilis

<400> SEQUENCE: 185

```
gcctcacctg cagcaccggc accagcttca cccgcagccc ctgctccaag cgcaccggcg     60

gcatcccctg cagcgccagc gccggcctca ccagcagctc cagccccgag cgctcctgcg    120

gcatcaccgg cagcgcccgc tccagcatct cctgccgcac cggccccgag cgctccagct    180

gcgtccccgg cagcaccagc gccagcgagt ccggcggccc ccgcaccgtc tgctccagca    240

gcgagtcctg ccgccccggc gcccgcttct ccggcagcac ccgccccgtc agcaccagcg    300

gcatcacccg cagctcctgc ccctgcaagt ccagctgctc ctgccccctc agctccagcc    360

gccagccctg ctgcaccagc tccggcatca cctgcagcgc cagccccttc agcgcccgcc    420

gcgagccctg ctgcacccgc tcctgcttcc cctgccgcac cagcaccctc tgcgccagcc    480

gcgtcgcctg ccgctcccgc tcccgcatca ccagcggctc ccgctccatc tgcaccagca    540

gccagtcctg cagcaccagc accagctagt ccggcagccc ccgcacctag tgcacctgct    600

gcctcaccgg ctgccccagc acctgcttct ccggcagctc cggccccttc agcacctgca    660

gcttctccgg cagcgcccgc acccgcctct cctgcagctc cggcaccgtc agcgccagcg    720

gccagcccag cagctccggc tccagcttcg cctgccgctc cagcaccgtc ggctccggca    780

gcatctccgg ctgctcctgc tccagcgtca ccagccgcac ctgcaccgag tgctcctgca    840

gcctctccag ctgcccctgc ccctgcttcg ccagcagcac ctgcgccttc ggccccggca    900

gcaagcccag ccgctcctgc accagcaagt cctgccgccc cagccccttc tgctcctgct    960

gcttccccgg cggcaccggc acccgcgtca ccggcagcac ccgcaccgtc tgcaccagct   1020

gcgagcccgg ctgcaccagc gcctgcttca cctgccgcgc ccgctccttc agctccagct   1080

gcttctcccg ccgcacctgc tccggctagc ccagcagcgc cggcaccttc agcacctgct   1140

gcgagtccag cagctccagc gccggcaagc cctgccgctc cagcgccgtc agcccctgca   1200

gcctcacccg ctgcacctgc tccagcttcc ccagcagcac cagccccttc cgcacctgcc   1260

gctagccccg ctgctcctgc cccagcctca cctgcggctc cagctccttc cgcaccggca   1320

gcgtcgcctg cagcaccggc gcctgctagc cctgctgctc ccgccccttc ggcacctgca   1380

gcgtctccgg cggctcctgc tcctgcgtct ccagcagctc ctgcaccgtc cgctcctgcc   1440

gcaagccccg cagcacctgc acctgcttca ccagcggctc ctgccccgag tgcaccggca   1500

gcctcccctg cagctcctgc tccggcaagc ccagctgcac cggccccaag cgcaccagct   1560

gcaagccctg cagccccagc accggcctca ccggcagcac ctgcgccgtc agcacctgca   1620

gccagcccag cggcccctgc acctgcatca cctgcggcgc ctgctccttc tgcccctgcg   1680

gcatcccctg ctgctcctgc acccgcaagt ccggctgcac cggctccaag tgcaccagca   1740

gcatcacctg ccgcaccggc acctgcgagt cctgcggcac ctgcccctag tgctccggcg   1800
```

<210> SEQ ID NO 186
<211> LENGTH: 1800
<212> TYPE: DNA
<213> ORGANISM: Artificial Sequence
<220> FEATURE:
<223> OTHER INFORMATION: Nucleotide sequence PAS#1p/1o/1g(600), codon-
optimized for P. pastoris

<400> SEQUENCE: 186

```
gcctctcctg ctgcacccgc tcccgcatca cctgcagcac ctgctcccag tgctccagca     60

gcctcacctg ccgctccagc ccctgccagt cctgccgctc cagctcccag tgctcctgct    120

gcttctccag ccgctccagc tccagcttcc cctgcagctc ccgctccctc agctcctgca    180

gcatctccag ccgcaccagc ccctgcttct cccgcagcac ccgcaccttc cgcaccagcc    240

gcctcccccg ctgcacccgc acctgcttcc ccagcagcac ctgcacccag tgctcccgca    300

gcatcaccag cagccccagc tcctgcttca cccgccgcac cagccccctc cgctcctgct    360

gcttctcctg cagctcccgc tccagcttca cccgctgcac ctgccccctc cgcacccgca    420

gcctcaccag ctgcaccagc acccgcttct cctgcagcac ccgccccctc tgctcccgct    480

gcttctccag ccgcaccagc tcctgcatca cctgcagctc ctgcccccag tgctcccgca    540

gcttctcctg cagctcctgc tccagctagt cccgctgcac ctgcccctte cgcacctgca    600

gcctcaccag ccgcacccgc cccagctagt cccgcagccc ccgctccctc tgctccagca    660

gccagtccag ccgcaccagc acctgcaagt ccagctgcac ccgcaccttc tgcacctgcc    720

gcctctcccg ctgctccagc cccagcctca cctgctgccc ctgctccatc cgcacctgcc    780

gcatctcctg ccgcccccgc acctgcttcc cccgctgcac ccgcccctag tgctcctgca    840

gcatcacccg ctgccccagc ccctgcatcc ccagctgctc cagcccctag tgcccccgct    900

gctagtcccg ctgcaccagc ccccgcaagt ccagctgccc ccgccccatc tgctcccgcc    960

gcctcccccg cagctcctgc tcccgcttct cctgccgccc cagcccctag tgcacctgct   1020

gcctcacctg cagctccagc acctgcctct ccagcagccc cagcacccag tgctcccgct   1080

gctagtcctg cagctcccgc accagcttca cctgccgcac ccgcacccag tgctcctgct   1140

gcatcaccag ctgctcccgc accagcctcc ccagcagcac cagctcccag tgcacctgct   1200

gcctctcctg ctgcacctgc accagcttct cccgctgctc ctgctccttc agctcctgct   1260

gcatcacctg ctgcacctgc tcctgcttct ccagctgcac cagctccatc tgcaccagct   1320

gcttcacctg cagcacctgc acctgcttca ccagcagcac cagctccttc cgctccagcc   1380

gcttcaccag ccgctccagc accagcttca ccagcagctc ctgctccatc tgctcctgct   1440

gcttcccctg ctgctccagc tcctgcatca ccagctgcac ctgcaccttc tgctccagct   1500

gcatctccag cagctccagc tcccgcttca cctgctgctc cagcaccatc cgctcctgca   1560

gcttctccag ctgctcctgc tccagcttct cctgcagcac ctgctccatc cgctccagca   1620

gcttctccag ccgctcctgc tcctgcctcc cctgctgcac cagctccttc agctccagct   1680

gcttccccag ctgctccagc tccagcttct ccagcagctc ctgcaccatc tgctccagct   1740

gcttctcctg ctgcaccagc cccagcatcc ccagctgctc ctgcaccttc cgctcctgct   1800
```

<210> SEQ ID NO 187
<211> LENGTH: 1800
<212> TYPE: DNA
<213> ORGANISM: Artificial Sequence
<220> FEATURE:
<223> OTHER INFORMATION: Nucleotide sequence PAS#1ae/1ad/1ac(600),
codon-optimized for S. cerevisiae

<400> SEQUENCE: 187
gcctctcccg cagcacccgc acccgcgtca cctgcggcac cggctccctc tgcaccggca 60
gcctctccag ctgcaccagc ccctgcgtcc ccagcagcgc ccgcgcccag cgctccagcg 120
gcaagcccag ctgccccagc tcctgcaagc ccggctgccc cggctcctag cgccccagct 180
gcttcacccg ctgctcccgc acctgcctct ccggcggccc cagcgcccag cgctcctgca 240
gcgtcaccag cggccccagc gccagcctca cccgctgctc cggcccccatc tgcgccggca 300 gcgagtccag ccgctccagc gcctgcgtct cctgcggcac cagcaccttc agctccggca 360
gcatctccgg cggctcccgc gcctgcttcc cccgctgcac cagcacctag cgcacccgcc 420
gcttcacctg ctgcgcccgc tcctgccagc ccggcagcac ccgcgccatc cgcacccgcc 480
gctagcccag cagcacctgc ccctgcatct ccggcagctc ccgcgccatc agcccccgcg 540
gcatctccgg ctgctcctgc cccagcatca cccgccgcgc cagccccgtc cgcaccagca 600
gcctctccag cagcgccggc accagcaagc cctgcggcac ctgctccatc tgctccggcg 660
gccagtcccg ctgcacctgc tccggcttct cctgcagcac cagcaccatc tgcccctgca 720
gctagcccgg cagcgcccgc tcccgcgagt ccagcagcgc ctgccccttc agcgccggcc 780
gcgtcacctg ccgcaccggc acccgctagc ccagcggcac cggctccgtc tgcaccagcc 840
gcttccccag cagcaccagc gccagctagc ccggctgccc cagctccctc cgctcctgct 900
gcatcccctg ctgcacccgc tcccgctagt cctgctgcgc ctgcaccctc agctccagca 960
gcgtctcccg cagcgccagc acctgcgagt ccagcggcac cagcaccctc tgctccagcc 1020
gcttccccgg cagccccggc ccctgcctcc ccagctgcgc cagctccttc cgctcccgct 1080
gcctcccctg ccgcacctgc cccggcgagc cctgctgctc ctgcaccctc tgctcccgcg 1140
gcctctcccg ctgcaccagc gcccgcgtct cccgctgctc cggcacctag tgcaccagct 1200
gccagtcctg ccgctccagc acctgccagt ccagcagctc cagccccttc tgccccagca 1260
gcctcaccag ccgcacctgc tccagcaagc ccggcagctc ccgccccgag tgctccagca 1320
gcatcaccag ctgctcccgc gccggctagc cctgcggctc ccgcaccgag tgccccagca 1380
gcatcacctg ccgcccctgc gcccgcaagc cccgcggccc ctgctccttc cgcgcctgct 1440
gcctcaccag cagcaccagc cccggcaagt ccagcggcgc cggcacccag cgcacccgcg 1500
gcctctcctg cagctcctgc acctgcatct cccgcggctc ccgcaccctc agctcccgcg 1560
gccagccctg ctgcaccagc acctgcaagc cctgcggctc cggcgccttc tgcccctgct 1620
gcctctccgg ctgcccctgc acctgcgtcc ccggctgctc ccgctcctag tgccccggca 1680
gcaagcccag ccgcaccggc cccagccagc cccgccgctc ccgctccctc cgctcccgct 1740
gcgtccccag ccgctcccgc tcctgcgtca cctgcagcgc ccgcgccctc tgcacccgcc 1800

<210> SEQ ID NO 188
<211> LENGTH: 1800
<212> TYPE: DNA
<213> ORGANISM: Artificial Sequence
<220> FEATURE:
<223> OTHER INFORMATION: Nucleotide sequence PAS#1ab/1aa/1z(600), codon-optimized for K. lactis

<400> SEQUENCE: 188
gcctccccgg cagctccagc ccctgcctca ccagctgccc cggccccatc ggcccccgca 60
gcctctcccg ccgctcccgc ccctgctagt cctgcagctc ctgctccatc cgcacctgca 120
gcttcaccag ccgcaccagc tccggcctcg ccagccgcac cagcaccgtc cgcccctgct 180

-continued

```
gcttcaccag cagcccctgc cccggcttcc cctgcagcac ctgctccttc ggctccagct    240
gcctctccgg cagctccggc tcctgcctcc cctgccgctc cagctccgtc agcacccgct    300
gcaagtcctg ccgcacccgc tcccgcctct ccggcagccc cagctccatc cgcaccagca    360
gctagtccgg cagcaccggc tccagctagt ccagctgcac cagccccttc cgccccagca    420
gcttcaccgg ccgccccggc cccagcctct ccagcagcac ctgccccatc ggccccggcc    480
gcatctcccg ctgccccggc tcccgcatcg cctgccgcac cggctccctc ggcaccggcc    540
gcctctcctg ctgcacctgc acccgcttcc cctgccgctc ctgcccctag tgcaccagca    600
gcctctccgg ctgcaccagc tcccgcatct ccagcagctc ccgccccgtc ggcaccggca    660
gcctctccgg ccgcacctgc cccagcctcc cctgcagcac cagctcccag tgctccggct    720
gcatcacctg ctgcaccagc acctgcatca cctgccgccc cggcaccgtc agccccggct    780
gcatctcccg ccgccccagc cccagcctcg ccagcagccc ctgctcccag tgcacctgct    840
gcctcacctg cagctcctgc acccgcaagt ccggcagcac ctgccccttc tgcccctgca    900
gctagtccgg ccgctcccgc cccagccagt cccgccgcac ctgcaccaag tgctcctgct    960
gcttctcctg ctgcacctgc tccggcctca cccgccgctc cggctccatc ggcccctgca   1020
gcatcaccag ctgcacccgc tcccgcctcc ccggccgcac cagcaccatc tgctcctgca   1080
gcatcaccgg ccgcacctgc accagcaagt ccagccgcac ccgccccatc tgcaccggca   1140
gcatcacccg ctgcccctgc tccagcttcg ccagcagcac ccgccccatc ggctcctgct   1200
gcctctccgg ctgcacccgc cccggctagt ccagccgccc cggctccttc agcaccagca   1260
gcttcaccag cagcaccggc tcccgcctcg ccagccgccc ctgctccttc cgccccggct   1320
gcaagtccag ccgcccctgc acccgccagt cccgcagctc cagctccatc agcaccagcc   1380
gcatcgccgg ctgcaccagc ccctgcatcg ccggcagccc cagccccgtc agctccggct   1440
gccagtcctg cagctccggc ccccgcttca cccgccgccc ccgcaccttc cgccccagcc   1500
gcaagtcctg ccgccccagc accagctagt ccggctgctc ccgccccatc cgctccagcc   1560
gcttcgccag ctgcccccgc ccccgcaagt cccgcagccc ccgcaccttc tgcacccgcc   1620
gcttcgccgg ccgcaccggc acccgcttca cccgcagcac ctgcaccgag tgctcccgcc   1680
gcatcccctg cagcaccagc acctgcaagt ccagctgcac ctgccccttc agcaccggct   1740
gcatctcccg ctgcaccggc tccggcatcg cccgccgcac ccgcacctag tgctccagct   1800
```

<210> SEQ ID NO 189
<211> LENGTH: 1800
<212> TYPE: DNA
<213> ORGANISM: Artificial Sequence
<220> FEATURE:
<223> OTHER INFORMATION: Nucleotide sequence PAS#1ah/1ag/1af(600), codon-optimized for T. thermophila

<400> SEQUENCE: 189

```
gccagtcctg ccgctcccgc acctgctagt cctgccgcac ccgccccttc tgcaccagcc     60
gcatctccag cagcacctgc tccagcctct ccagccgctc ccgctcccag cgccccagcc    120
gcaagccctg ccgctcccgc tccagctagc cccgccgctc ccgcacctag tgctcctgct    180
gcaagccctg ctgctcctgc acctgctagc cctgctgcac cagctccaag cgccccagcc    240
gctagtccag ctgctcccgc tcctgcaagc cctgcagcac ctgctccaag tgctcccgcc    300
gcttctcccg ctgcccccgc acctgccagt cctgctgcac ctgctccctc agctcccgct    360
gcttcaccag ctgcacccgc accagcttca cctgccgcac cagctcctag cgctccagct    420
```

-continued

```
gcatctcctg cagctcccgc tcctgcatca ccagcagctc ctgcacccag tgcaccagcc    480

gctagccctg cagcaccagc accagcctct cctgccgcac cagcccctag cgcaccagcc    540

gcatcacctg ccgctccagc tcctgccagc cctgctgccc cagctccatc tgctccagct    600

gccagtcctg ctgctcccgc tccagcaagt cctgctgctc cagcccctag tgctccagct    660

gcttcacccg ccgctcccgc acccgcatca cctgctgcac ctgctccaag cgcacctgct    720

gctagcccag ctgcccctgc accagcttct cccgccgcac cagcacctag cgcaccagct    780

gcctctcccg ctgcaccagc acccgcttca cccgcagccc cagcccctag cgcacctgcc    840

gcctcaccag ctgcacctgc tccagcaagt cctgccgccc ccgctcctag cgcaccagca    900

gcctcaccag ccgcaccagc tcccgcaagt cctgcagctc cagccccaag tgcacccgca    960

gctagccctg cagctcccgc tcccgcaagt ccagctgccc cagcaccatc tgcacccgct   1020

gcttcacccg ccgcacccgc accagctagc ccagcagctc ctgctccttc agctcccgcc   1080

gcttcaccag ctgctcccgc accagcctca ccagctgcac ccgctcccag cgctcctgct   1140

gcttcacctg ctgctcctgc accagctagt cctgctgctc cagctccatc agccccagca   1200

gcctctccag ccgcaccagc ccctgcttca cccgctgccc ctgctcctag tgcacctgct   1260

gcaagccccg ctgcccctgc acctgcttct cctgccgctc cagccccttc tgcccctgcc   1320

gcttctccag cagcccctgc acccgcttca cctgctgctc cagccccatc agctcccgct   1380

gctagtcccg ccgctcctgc acctgcttct cccgctgcac ctgccccatc agcaccagcc   1440

gcctcaccag ccgctcccgc cccagcctca cccgccgccc ctgcaccatc tgcacctgca   1500

gcctcacccg ccgcacctgc acccgcatca cccgctgcac ctgctccatc agctcctgct   1560

gcttctccag ccgcacctgc tccagcatca cctgccgctc ccgccccaag tgctccagcc   1620

gcatctcctg ctgcacccgc acctgcaagc cctgctgcac ctgcaccttc agcccctgca   1680

gccagccctg ctgcacctgc cccagctagt cccgctgcac ccgcccctag tgctcctgcc   1740

gcaagccctg cagctcctgc ccctgcttca cctgctgccc ctgctccaag cgctcctgca   1800
```

<210> SEQ ID NO 190
<211> LENGTH: 1800
<212> TYPE: DNA
<213> ORGANISM: Artificial Sequence
<220> FEATURE:
<223> OTHER INFORMATION: Nucleotide sequence PAS#1ak/aj/ah(600), codon-
optimized for HEK cells

<400> SEQUENCE: 190

```
gccagtcctg ctgcccctgc acctgcgtct ccagctgctc ccgctccttc tgctccggct     60

gcatctcctg ccgccccagc ccctgcaagt ccagcagcgc ctgctccatc agctcctgca    120

gcttcaccag cggccccagc acccgccagt cctgcagctc ctgcgccctc agccccagcc    180

gcgagccctg ccgcgcctgc tcccgcctct cccgcagccc ctgccccatc cgctccggcc    240

gcatcacctg ctgctcctgc tcctgcctca cccgctgctc cagcgccatc tgcacccgct    300

gccagccccg ctgccccggc tcctgcatcc cctgcggcac cagctccaag cgctcctgca    360

gcaagccccg ccgctccagc tcccgcgagt cctgccgctc ctgcaccatc tgccccagca    420

gctagtcccg ctgcaccggc tcccgcatct ccagcagctc cggcaccttc ggccccagca    480

gccagtcctg cagccccagc acctgccagt cctgcggctc cggcgccatc agcacctgca    540

gcgtcacctg ccgcacctgc tcccgcaagt cctgccgcgc cagctcctag cgcaccagcc    600

gccagtcccg cagcaccagc acccgcgtcc ccagctgcgc ctgcccctag tgctccagct    660
```

-continued gcctctcccg ccgcacccgc acctgcaagt cctgcagctc cggcaccgag cgccccccgcc 720 gccagtccag ccgcacccgc gcctgcaagc ccagccgcgc ccgccccttc cgccccggcc 780
gcttctccag ccgcaccagc gcccgcatcc ccagcggctc cagctccgtc tgctcctgcc 840
gcaagccctg ctgcgcccgc ccctgcatcc cctgctgcac ctgctccgag tgctcccgcc 900
gcctccccag ccgcaccggc ccctgctagt cccgccgcgc cggccccaag tgccccagct 960
gcttctcctg ctgctccagc accggcatct cccgcggccc ctgcaccaag tgcgccagcc 1020
gctagtccgg cagctcctgc tccagccagt cccgcggctc ctgctccaag cgccccagct 1080
gcatcaccag cagctccagc tcctgccagc cctgcagcgc ccgcgccatc agcccctgct 1140
gctagcccag cagcccccgc cccagcgagt ccagcggcac ctgctccatc tgctccagct 1200
gccagtcccg ctgcgccggc accagcctcc cctgctgccc cagcccctag cgcacccgct 1260
gcttcccctg ccgctccagc gcctgcctct cctgcggccc ctgctcctag tgcaccagcc 1320
gcttccccag cagcacctgc tcctgcaagt ccagctgctc ctgcaccctc tgctcccgcg 1380
gcctctccag ctgcacccgc tcctgcttca cctgccgctc cagctccatc cgcaccagct 1440
gccagtcctg ctgcgcctgc acccgcctca cctgctgctc ccgcaccttc agcacctgca 1500
gcctctccgg cagcccctgc acccgcctcc ccggctgccc ccgcgcccag tgctccggcc 1560
gcgtctcccg ctgctcctgc tcccgcttca cccgccgctc ctgccccttc tgcccctgcc 1620
gccagccccg ctgctcccgc ccctgcctcc cctgcagctc ccgccccatc tgcgcctgct 1680
gcttcaccgg ctgcgccagc accagctagc cccgcagcgc cagccccatc agcaccagcc 1740
gcctctcctg ctgcacccgc ccctgcgagc cctgcggctc ccgcaccctc tgccccagca 1800

<210> SEQ ID NO 191
<211> LENGTH: 1800
<212> TYPE: DNA
<213> ORGANISM: Artificial Sequence
<220> FEATURE:
<223> OTHER INFORMATION: Nucleotide sequence PAS#1y/1x/1w(600), codon-
optimized for P. patens

<400> SEQUENCE: 191
gccagtcctg ctgcacctgc ccctgcgtct ccagctgctc ccgctccgag tgctcctgca 60
gcgtctcctg ccgcaccagc cccagcgtcg cctgccgcac ccgcgccttc tgctccagct 120
gcttcaccag ctgctcctgc gcccgcatca cccgcagcgc cagccccatc cgcacccgca 180
gcttccccgg ccgctccagc accagcatct cccgcagcgc ccgctccgtc ggctcctgct 240
gcctctcctg cagcgccggc tccagcatca cctgctgctc cggctccgtc ggccccggct 300
gcttcgcccg ccgctccagc ccctgctagc ccagccgcac ctgccccgag cgcacctgca 360
gcaagcccgg ccgcacccgc ccctgcttct ccggccgccc ccgcaccgtc cgctcctgct 420
gctagtccgg ctgctccggc ccctgcatcc cctgccgcgc ccgctccttc ggcaccggcc 480
gcgtcacccg ctgcaccagc ccccgcttcc ccggcagctc ccgcgccttc agcgccagcc 540
gctagccccg ccgcacccgc tccagcttct cccgctgctc ctgctccgtc cgcacctgct 600
gccagccccg ctgctcccgc tccagcttca cctgcagctc cagctcccag tgccccccgcc 660 gcctcccctg ccgctccagc gcccgcgtcc cccgcagctc cagcaccaag cgcacctgct 720
gccagtccag cagcacccgc tccggcgagc ccagctgcac ccgctccatc cgcacctgct 780
gcaagtccag ccgcacctgc gcctgctagc cctgctgcac ccgccccgtc tgcaccagca 840
gcgagccccg cagcacccgc cccggcttcc cccgcagcac cagctccatc ggctcctgca 900
gcttccccgg cagcccccgc gccagcatca cccgcagccc ccgctccctc cgccccagcc 960
gcgagtcctg cagcgcccgc gccagcttct ccagccgccc ctgctccatc agcccccgct 1020
gcctcgccag ctgcaccagc accagcatca ccggccgcac cagccccgtc tgcccccgca 1080
gcatcaccag cagcacctgc tccagcatcc ccagccgctc cagcaccttc ggccccagca 1140
gctagcccgg cagctcccgc cccagccagc cctgctgctc ctgcccctag cgcccctgct 1200
gcctctcccg cagccccagc gcccgcatct cctgccgctc ctgctccttc cgctcccgca 1260
gctagtccag ccgccccagc tcccgctagt cctgccgccc cagctccgag tgcccccgcc 1320
gcttctcccg cagcacccgc cccagcgtca cctgccgctc cagccccctc agctcctgcc 1380
gcaagccctg ctgctcctgc tcccgcttct cctgccgcac ccgcaccttc tgcccctgct 1440
gcatcacccg ctgctcctgc acccgcgtct ccagcagcgc cggcacctag cgctccagcc 1500
gcatcgcccg ccgctcctgc acctgctagc ccggctgccc ctgccccttc agctcccgct 1560
gcaagtccag ctgcaccagc ccccgcgtct cctgcagctc ctgccccttc tgctccagcc 1620
gcctctccag ctgcccccgc accagcatct ccagctgcgc cggccccctc tgctcctgca 1680
gcatcaccag cagctcctgc tcccgcatct ccggctgccc ctgctcccag cgcacctgca 1740
gcatcgccag ccgccccagc ccccgcgagc cccgccgctc ccgctccctc tgctccagct 1800

<210> SEQ ID NO 192
<211> LENGTH: 600
<212> TYPE: DNA
<213> ORGANISM: Artificial Sequence
<220> FEATURE:
<223> OTHER INFORMATION: Nucleotide sequence of PA#1at(200), codon-
      optimized for E. coli

<400> SEQUENCE: 192
gccgcaccgg cagcaccggc accggcagca ccggcggcac cggcaccggc agcgccggca 60
gcagcaccgg cagcaccggc gccggcagca ccggcagcac cggctccggc agcaccggca 120
gcagcaccgg cagcgccggc accggcagca ccggcagcac cggcaccggc ggcaccggca 180
gcagcaccgg cagcaccggc accggctgca ccggcagcac cggcaccggc agcgccggcg 240
gcagcaccgg cagcaccggc accggccgca ccggcagcac cggcaccggc agctccggca 300
gcagcaccgg cagcaccggc cccggcagca ccggcagcac cggcaccggc agccccggca 360
gcagcaccgg cagcaccggc accagcagca ccggcagcac cggcaccggc agcgccagca 420
gcagcaccgg cagcaccggc accggcagca ccagcagcac cggcaccggc agcaccggca 480
gcagcaccgg cggcaccggc accggcggca ccggcagcgc cggcaccggc agcgccggca 540
gcagcgccgg cagcaccggc accggcagca ccggcagcgc cggcaccggc ggcaccggca 600

<210> SEQ ID NO 193
<211> LENGTH: 600
<212> TYPE: DNA
<213> ORGANISM: Artificial Sequence
<220> FEATURE:
<223> OTHER INFORMATION: Nucleotide sequence of PA#1au(200), codon-
      optimized for E. coli

<400> SEQUENCE: 193
gcctctccgg cagcaccggc accggcatct ccggcggcac cggcaccgag tgcaccggca 60
gcatctccgg cagcgccggc accggcaagt ccggcagcac cggcgccgtc tgcaccggca 120
gcaagtccgg cagcgccggc gccggcatct ccggcagcac cggctccgag tgcaccggca 180
gcgagtccgg cagcaccggc accggcgtct ccggcagcac cggcaccgtc tgcaccggca 240
gcgtctccgg cagcaccggc gccggcaagt ccggcagcac cggcaccgag cgcaccggca 300
gcatctccgg cggcaccggc gccggcatct ccggcggcgc cggcaccgag tgcaccggcg 360
gcatctccgg cagcaccggc gccggcgagc ccggcagcac cggcaccgag tgcgccggca 420
gcatctccgg cagcaccggc accagcatct ccggcagcac cggcgccatc tgcaccggca 480
gcatctccgg cagcaccggc cccggcatct ccggcagcac cggcaccgag tgcaccggcg 540
gcgagtccgg cagcaccggc accggcaagc ccggcagcac cggcaccgtc tgcgccggca 600

<210> SEQ ID NO 194
<211> LENGTH: 600
<212> TYPE: DNA
<213> ORGANISM: Artificial Sequence
<220> FEATURE:
<223> OTHER INFORMATION: Nucleotide sequence of PAS#1ao(200), codon-optimized for E. coli

<400> SEQUENCE: 194
gcctctccgg cagcaccggc accggcatct ccggcagcac cggcgccgag tgcaccggca 60
gcatctccgg cagcaccggc tccggcatct ccggcagcac cggcaccgtc tgcaccggca 120
gcaagtccgg cagcaccggc accggcgagt ccggcagcac cggcaccgag tgcaccggca 180
gcaagtccgg cggcaccggc accggcaagt ccggcagcac cggcaccgtc tgcgccggca 240
gcatctccgg cagcaccggc accggcgtct ccggcagcac cggcaccgag cgcaccggca 300
gcatctccgg cagcaccggc gccggcatct ccggcagcac cggcaccgag tgcgccggca 360
gcatctccgg cagcaccggc gccggcgagt ccggcagcac cggcaccgtc tgcaccggcg 420
gcatctccgg cagcaccggc accggcaagc ccggcagcac cggcaccgag tgcaccggcg 480
gcatctccgg cagcaccggc gccggcaagt ccggcagcac cggcaccgag tgcaccggct 540
gcatctccgg cagcaccggc accggcaagt ccggcagcac cggcgccgtc tgcaccggca 600

<210> SEQ ID NO 195
<211> LENGTH: 600
<212> TYPE: DNA
<213> ORGANISM: Artificial Sequence
<220> FEATURE:
<223> OTHER INFORMATION: Nucleotide sequence of PAS#1ap(200), codon-optimized for E. coli

<400> SEQUENCE: 195
gcctctccgg cagcaccggc accggcatct ccggcggcac cggcaccgag tgcaccggca 60
gcatctccgg cagcgccggc accggcaagt ccggcagcac cggcgccgtc tgcaccggca 120
gcaagtccgg cagcgccggc gccggcatct ccggcagcac cggctccgag tgcaccggca 180
gcgagtccgg cagcaccggc accggcgtct ccggcagcac cggcaccgtc tgcaccggca 240
gcgtctccgg cagcaccggc gccggcaagt ccggcagcac cggcaccgag cgcaccggca 300
gcatctccgg cggcaccggc gccggcatct ccggcggcgc cggcaccgag tgcaccggcg 360
gcatctccgg cagcaccggc gccggcgagc ccggcagcac cggcaccgag tgcgccggca 420
gcatctccgg cagcaccggc accagcatct ccggcagcac cggcgccatc tgcaccggca 480
gcatctccgg cagcaccggc cccggcatct ccggcagcac cggcaccgag tgcaccggcg 540
gcgagtccgg cagcaccggc accggcaagc ccggcagcac cggcaccgtc tgcgccggca 600

<210> SEQ ID NO 196
<211> LENGTH: 4641
<212> TYPE: DNA

<213> ORGANISM: Artificial Sequence
<220> FEATURE:
<223> OTHER INFORMATION: Nucleotide sequence

<400> SEQUENCE: 196
atgggcagca gccatcatca tcaccatcat ggtagcctgg ttccgcgtag ctcttctgca 60
agtccggcag caccggcacc ggcttcacca gctgcaccag cacctagcgc accggcagca 120
tctccagcag cccctgcacc ggcaagccct gcagctccag caccgtcagc accagcagca 180
agcccagctg ctcctgctcc agcgagccca gcagcgccag ctcctagtgc ccctgctgcc 240
tctcctgctg ctccggcacc agcaagtcct gctgcgcctg caccgagtgc tccggctgct 300
agtcctgccg caccagctcc ggctagtcca gctgctccag ccccttcagc tccggcagct 360
tcccctgcag cgcctgcccc tgccagtcca gcggctcctg cacctagtgc gcctgcagct 420
tcaccggctg cccctgcgcc agcttctcct gcggctccag ctccatctgc cccagccgca 480
tccccagcgg caccagctcc agcttctccg gcagcgccag caccttctgc gcctgccgca 540
tctcctgcag caccagcgcc tgcgagtcct gcagctcctg ctccttcagc ccctgcggca 600
agtccagcag caccagcccc agcaagccca gccgcaccag caccatctgc ccctgcagca 660
ccatttgtga acaagcagtt taactataag gacccggtga acggtgtgga tatcgcgtat 720
atcaaaatcc cgaatgcggg ccagatgcaa ccagtcaagg cgttcaagat tcataacaag 780
atttgggtta ttccggaacg tgataccttc accaatccgg aagaaggcga cttaaacccg 840
ccgccagaag ccaaacaagt gccggtgagc tactatgata gcacgtatct tagcaccgat 900
aatgaaaaag acaattacct gaagggcgtg accaagttgt tcgagcgcat ctacagtacc 960
gacttaggcc gcatgttgtt gacgagcatc gttcgcggta tcccgttctg ggcggctcg 1020 accattgata ccgagttgaa agtcattgac acgaactgta tcaatgttat ccaaccggac 1080
ggcagttatc gcagcgagga gttaaatttg gtcatcatcg gtccaagcgc agatattatt 1140
cagttcgaat gcaagagctt cggccatgag gtcttgaatt tgacgcgcaa cggttacggc 1200
agcacccaat acatccgctt tagcccggat ttcacctttg gcttcgagga gagcttggag 1260
gtggacacca acccgctgtt aggtgccggc aaattcgcaa ccgacccggc agtgacgttg 1320
gcgcacgaat tgattcatgc gggtcaccgc ttatacggta tcgcgatcaa tccgaatcgc 1380
gtctttaaag tcaataccaa cgcgtactac gaaatgagcg gcttagaggt tagctttgaa 1440
gaattacgca ccttcggtgg ccacgacgcc aagttcatcg acagcctgca ggaaaatgag 1500
ttccgcttgt actattacaa taaattcaag gacatcgcga gcaccttaaa taaagcaaag 1560
agcattgtgg gcaccaccgc aagcttgcag tacatgaaga acgtatttaa ggaaaaatat 1620
ttgttgtcgg aggataccag cgggaaattc agcgtcgata agctgaaatt cgacaaattg 1680
tataaaatgc tgaccgagat ttacaccgag gataacttcg tcaagttttt taaggtgtta 1740
aatcgtaaga cctatttaaa ctttgataaa gcggtgttta aaattaatat cgtgccgaag 1800
gtgaattaca ccatctacga tggtttcaat ttacgcaaca cgaatctggc ggcgaatttt 1860
aatggccaaa acaccgaaat taacaacatg aactttacga agttaaagaa tttcacgggc 1920
ttattcgaat tctacaagtt attatgcgtg cgcggcatca ttaccagcaa ggcaggtgcg 1980
ggcaagtcct tggttccgcg tggcagcgcc ggcgccggcg cgctcaatga tctgtgtatt 2040
aaagtcaata actgggacct gttcttcagc ccgagcgagg ataactttac caacgactta 2100
aacaaaggcg aggagatcac gagcgatacg aacatcgagg cggcggagga aaatattagc 2160
ctggacctca ttcagcagta ctatctgacg ttcaattttg acaatgagcc ggagaacatc 2220

```
agcattgaaa atctcagcag cgacatcatc ggtcagttgg aactgatgcc gaacattgaa   2280
cgctttccga acggcaaaaa atatgaactg gacaagtata ccatgttcca ttacttacgc   2340
gcacaggaat ttgagcacgg caagagccgc attgcgctga ccaatagcgt taacgaggcc   2400
ttgttaaatc cgagccgtgt ctacacgttc ttcagcagcg attatgtcaa aaaagtgaac   2460
aaggcgaccg aagccgcgat gtttttgggc tgggtcgagc aattggttta cgattttacc   2520
gacgaaacca gcgaggtgag cacgaccgac aaaattgcag atatcaccat catcattccg   2580
tacatcggtc cggcgctcaa tatcggcaat atgttataca aggacgactt tgtgggcgcg   2640
ctgatcttta gcggcgcggt tatcttatta gaattcatcc cggagatcgc aatcccggtc   2700
ttgggcacct ttgcgttggt gagctatatc gcgaataaag tgctcacggt ccaaaccatc   2760
gataacgcgc tcagcaagcg taatgagaaa tgggacgagg tttataagta tatcgtgacc   2820
aactggttag caaaagtcaa tacgcagatc gatctcatcc gcaaaaaaat gaaagaagcc   2880
ttggaaaatc aagcggaggc aaccaaagcc atcattaatt accagtataa ccaatatacc   2940
gaagaagaaa aaaacaatat caacttcaat atcgatgatt tgagcagcaa actgaacgag   3000
agcattaaca aagcgatgat taacatcaac aagttcttga atcaatgcag cgtgagctat   3060
ctcatgaaca gcatgatccc gtatggcgtc aaacgcttgg aagattttga cgccagcctg   3120
aaagatgcgc tcctcaagta tatttatgac aaccgcggca ccctcattgg ccaggtggac   3180
cgcttgaagg ataaagtgaa caatacgctc agcacggata tcccgttcca gctgagcaag   3240
tacgtcgaca accagcgctt actgagcacc tttaccgagt atatcaagaa catcattaat   3300
accagcatcc tcaacttgcg ctatgagagc aatcacctga tcgacctcag ccgctacgcc   3360
agcaagatca acatcggcag caaggtcaat ttcgacccga tcgataagaa tcagatccaa   3420
ttgtttaacc tggaaagcag caagatcgag gttatcttga agaacgcgat tgtgtacaac   3480
agcatgtacg agaactttag cacgagcttc tggattcgta tcccgaagta tttcaatagc   3540
attagcctga ataacgaata taccattatc aactgcatgg aaaataatag cggctggaag   3600
gtgagcttaa attacggcga gatcatttgg accttacagg atacccaaga aatcaaacag   3660
cgcgtcgtct ttaagtatag ccagatgatc aacatcagcg attacatcaa ccgctggatc   3720
ttcgtgacca tcaccaataa tcgcttgaat aatagcaaga tttacatcaa tggtcgcttg   3780
attgatcaaa aaccgatcag caatctcggt aatatccatg ccagcaataa catcatgttt   3840
aagttagacg gttgccgcga tacccaccgc tatatctgga tcaagtattt taacttattt   3900
gataaggaac tcaacgaaaa ggaaattaaa gacttatatg acaatcagag caatagcggc   3960
atcctgaagg atttctgggg cgactacctg cagtacgata agccgtacta tatgttgaac   4020
ttgtatgacc cgaacaaata tgtcgatgtg aacaatgtgg gtattcgtgg ctatatgtac   4080
ttaaagggcc cgcgtggtag cgtgatgacc acgaatattt acttaaacag cagcttatac   4140
cgcggcacga agtttattat caagaagtat gccagcggca acaaggacaa tatcgtccgc   4200
aacaacgacc gtgtgtatat taacgtggtg gtgaagaata aagagtaccg cttggccacg   4260
aatgcgagcc aggcgggcgt ggaaaaaatc ttgagcgcgt tggagatccc ggacgtcggc   4320
aacctcagcc aggttgtggt gatgaagtct aaaaacgacc agggcatcac gaacaagtgc   4380
aaaatgaatt tgcaagataa caacggcaac gacatcggct ttattggttt tcaccagttc   4440
aataacatcg ccaaactcgt ggccagcaat tggtataacc gccaaattga acgcagcagc   4500
cgcacgctcg gctgtagctg ggagttcatc ccggtggacg atggctgggg cgagcgcccg   4560
```

ctcggagatc tggtgccacg cggttccgcg aattcgagct ccgtcgacaa gctttggagc 4620
cacccgcagt tcgaaaaata a 4641

<210> SEQ ID NO 197
<211> LENGTH: 4341
<212> TYPE: DNA
<213> ORGANISM: Artificial Sequence
<220> FEATURE:
<223> OTHER INFORMATION: Nucleotide sequence

<400> SEQUENCE: 197
atgggtagca gccatcatca tcaccatcat ggtagcctgg ttccgcgtag ctcttctgca 60
agtccggcag caccggcacc ggcttcacca gctgcaccag cacctagcgc accggcagca 120
tctccagcag cccctgcacc ggcaagccct gcagctccag caccgtcagc accagcagca 180
agcccagctg ctcctgctcc agcgagccca gcagcgccag ctcctagtgc ccctgctgcc 240
tctcctgctg ctccggcacc agcaagtcct gctgcgcctg caccgagtgc tccggctgct 300
agtcctgccg caccagctcc ggctagtcca gctgctccag ccccttcagc ccctgcagca 360
ccatttgtga acaagcagtt taactataag gacccggtga acggtgtgga tatcgcgtat 420
atcaaaatcc cgaatgcggg ccagatgcaa ccagtcaagg cgttcaagat tcataacaag 480
atttgggtta ttccggaacg tgataccttc accaatccgg aagaaggcga tttaaatccg 540
ccgccagaag ccaaacaagt gccggtgagc tactatgata gcacgtatct tagcaccgat 600
aatgaaaaag acaattacct gaagggcgtg accaagttgt tcgagcgcat ctacagtacc 660
gacttaggcc gcatgttgtt gacgagcatc gttcgcggta tcccgttctg gggcggctcg 720
accattgata ccgagttgaa agtcattgac acgaactgta tcaatgttat ccaaccggac 780
ggcagttatc gcagcgagga gttaaatttg gtcatcatcg gtccaagcgc agatattatt 840
cagttcgaat gcaagagctt cggccatgag gtcttgaatt tgacgcgcaa cggttacggc 900
agcacccaat acatccgctt tagcccggat ttcacctttg gcttcgagga gagcttggag 960
gtggacacca acccgctgtt aggtgccggc aaattcgcaa ccgacccggc agtgacgttg 1020
gcgcacgaat tgattcatgc gggtcaccgc ttatacggta tcgcgatcaa tccgaatcgc 1080
gtctttaaag tcaataccaa cgcgtactac gaaatgagcg gcttagaggt tagctttgaa 1140
gaattacgca ccttcggtgg ccacgacgcc aagttcatcg acagcctgca ggaaaatgag 1200
ttccgcttgt actattacaa taaattcaag gacatcgcga gcaccttaaa taaagcaaag 1260
agcattgtgg gcaccaccgc aagcttgcag tacatgaaga acgtatttaa ggaaaaatat 1320
ttgttgtcgg aggataccag cgggaaattc agcgtcgata agctgaaatt cgacaaattg 1380
tataaaatgc tgaccgagat ttacaccgag gataacttcg tcaagttttt taaggtgtta 1440
aatcgtaaga cctatttaaa ctttgataaa gcggtgttta aaattaatat cgtgccgaag 1500
gtgaattaca ccatctacga tggtttcaat ttacgcaaca cgaatctggc ggcgaatttt 1560
aatggccaaa acaccgaaat taacaacatg aactttacga agttaaagaa tttcacgggc 1620
ttattcgaat tctacaagtt attatgcgtg cgcggcatca ttaccagcaa ggcaggtgcg 1680
ggcaagtcct tggttccgcg tggcagcgcc ggcgccggcg cgctcaatga tctgtgtatt 1740
aaagtcaata actgggacct gttcttcagc ccgagcgagg ataactttac caacgactta 1800
aacaaaggcg aggagatcac gagcgatacg aacatcgagg cggcggagga aaatattagc 1860
ctggacctca ttcagcagta ctatctgacg ttcaattttg acaatgagcc ggagaacatc 1920
agcattgaaa atctcagcag cgacatcatc ggtcagttgg aactgatgcc gaacattgaa 1980

```
cgctttccga acggcaaaaa atatgaactg gacaagtata ccatgttcca ttacttacgc   2040
gcacaggaat ttgagcacgg caagagccgc attgcgctga ccaatagcgt taacgaggcc   2100
ttgttaaatc cgagccgtgt ctacacgttc ttcagcagcg attatgtcaa aaaagtgaac   2160
aaggcgaccg aagccgcgat gtttttgggc tgggtcgagc aattggttta cgattttacc   2220
gacgaaacca gcgaggtgag cacgaccgac aaaattgcag atatcaccat catcattccg   2280
tacatcggtc cggcgctcaa tatcggcaat atgttataca aggacgactt tgtgggcgcg   2340
ctgatcttta gcggcgcggt tatcttatta gaattcatcc cggagatcgc aatcccggtc   2400
ttgggcacct ttgcgttggt gagctatatc gcgaataaag tgctcacggt ccaaaccatc   2460
gataacgcgc tcagcaagcg taatgagaaa tgggacgagg tttataagta tatcgtgacc   2520
aactggttag caaaagtcaa tacgcagatc gatctcatcc gcaaaaaaat gaaagaagcc   2580
ttggaaaatc aagcggaggc aaccaaagcc atcattaatt accagtataa ccaatatacc   2640
gaagaagaaa aaaacaatat caacttcaat atcgatgatt tgagcagcaa actgaacgag   2700
agcattaaca aagcgatgat taacatcaac aagttcttga atcaatgcag cgtgagctat   2760
ctcatgaaca gcatgatccc gtatggcgtc aaacgcttgg aagattttga cgccagcctg   2820
aaagatgcgc tcctcaagta tatttatgac aaccgcggca ccctcattgg ccaggtggac   2880
cgcttgaagg ataaagtgaa caatacgctc agcacggata tcccgttcca gctgagcaag   2940
tacgtcgaca accagcgctt actgagcacc tttaccgagt atatcaagaa catcattaat   3000
accagcatcc tcaacttgcg ctatgagagc aatcacctga tcgacctcag ccgctacgcc   3060
agcaagatca acatcggcag caaggtcaat ttcgacccga tcgataagaa tcagatccaa   3120
ttgtttaacc tggaaagcag caagatcgag gttatcttga agaacgcgat tgtgtacaac   3180
agcatgtacg agaactttag cacgagcttc tggattcgta tcccgaagta tttcaatagc   3240
attagcctga ataacgaata taccattatc aactgcatgg aaaataatag cggctggaag   3300
gtgagcttaa attacggcga gatcatttgg accttacagg atacccaaga aatcaaacag   3360
cgcgtcgtct ttaagtatag ccagatgatc aacatcagcg attacatcaa ccgctggatc   3420
ttcgtgacca tcaccaataa tcgcttgaat aatagcaaga tttacatcaa tggtcgcttg   3480
attgatcaaa aaccgatcag caatctcggt aatatccatg ccagcaataa catcatgttt   3540
aagttagacg gttgccgcga tacccaccgc tatatctgga tcaagtattt taacttattt   3600
gataaggaac tcaacgaaaa ggaaattaaa gacttatatg acaatcagag caatagcggc   3660
atcctgaagg atttctgggg cgactacctg cagtacgata agccgtacta tatgttgaac   3720
ttgtatgacc cgaacaaata tgtcgatgtg aacaatgtgg gtattcgtgg ctatatgtac   3780
ttaaagggcc cgcgtggtag cgtgatgacc acgaatattt acttaaacag cagcttatac   3840
cgcggcacga agtttattat caagaagtat gccagcggca acaaggacaa tatcgtccgc   3900
aacaacgacc gtgtgtatat taacgtggtg gtgaagaata aagagtaccg cttggccacg   3960
aatgcgagcc aggcgggcgt ggaaaaaatc ttgagcgcgt tggagatccc ggacgtcggc   4020
aacctcagcc aggttgtggt gatgaagtct aaaaacgacc agggcatcac gaacaagtgc   4080
aaaatgaatt tgcaagataa caacggcaac gacatcggct ttattggttt tcaccagttc   4140
aataacatcg ccaaactcgt ggccagcaat tggtataacc gccaaattga acgcagcagc   4200
cgcacgctcg gctgtagctg ggagttcatc ccggtggacg atggctgggg cgagcgcccg   4260
ctcggagatc tggtgccacg cggttccgcg aattcgagct ccgtcgacaa gctttggagc   4320
```

-continued

```
cacccgcagt tcgaaaaata a                                            4341


<210> SEQ ID NO 198
<211> LENGTH: 917
<212> TYPE: DNA
<213> ORGANISM: Artificial Sequence
<220> FEATURE:
<223> OTHER INFORMATION: Nucleotide sequence

<400> SEQUENCE: 198

agggcacaat tttgagctgg cgcaggtgct gctgggctag cagcaggggc cgaaggtgct     60

ggtgccgctg gagatgctgg tgccggggcc gcaggtgagg ctgcgggagc agaaggcgct    120

ggggctgcgg gagaagcagg agctggtgca gcagggctag cagctggtgc agatggagct    180

ggggccgctg gactagcggg ggcaggcgcg gcaggggatg ctgctggcgc acttggggca    240

ggtgcagctg ggctggcagg cgcgggtgcg gcaggagatg cagccggggc ggaaggtgca    300

ggtgccgcag gtgatgcggg cgcaggtgcg gcagggctgg ctgctggtgc gctcggtgct    360

ggcgctgcag gagaggctgg agctggcgca gccggagatg cggcaggcgc agatggtgcc    420

ggtgctgccg ggcttgctgg tgccggagct gccggagatg cagctggggc agaaggtgcc    480

ggtgcggctg gagaagctgg tgctggggct gcaggcgaag cggcaggggc acttggagct    540

ggggctgccg gactagcagg cgcaggagct gcaggactgg ctgccggtgc gctaggagct    600

ggggcagcag ggcttgctgg cgctggtgcg gctggtgaag ctgctggtgc tgatggggct    660

ggcgctgctg gacttgcagg ggctggtgct gcaggagatg ctgccggagc tgacggtgcc    720

ggagcagcag gactagctgg ggcaggcgca gccggacttg ctgcaggcgc acttggtgca    780

ggagccgcag gagaagccgg agctggagct gctggactag ctgcaggggc agacggtgca    840

ggcgcagctg gtgatgcagg cgcaggggca gccggagaag ctgccggtgc actaggtgct    900

ggtgcagccg gtgatgc                                                   917
```

NUCLEIC ACIDS ENCODING REPETITIVE AMINO ACID SEQUENCES RICH IN PROLINE AND ALANINE RESIDUES THAT HAVE LOW REPETITIVE NUCLEOTIDE SEQUENCES

CROSS REFERENCE TO RELATED APPLICATIONS

The present application is a national stage entry of International Application no. PCT/EP201/082407, filed Dec. 22, 2016, which claims the benefit of priority from European Patent Application no. 12202093.9, filed Dec. 22, 2015; the entire contents of which are incorporated herein by reference.

SEQUENCE LISTING

The instant application contains a Sequence Listing which has been filed electronically in ASCII format and is hereby incorporated by reference in its entirety, Said ASCII copy, created on Feb. 4, 2022, is named 028622-0306_SL.txt and is 376,415 bytes in size.

BACKGROUND

The present invention relates to a nucleic acid molecule comprising a low repetitive nucleotide sequence encoding a proline/alanine-rich amino acid repeat sequence. The encoded polypeptide comprises a repetitive amino acid sequence that forms a random coil. The nucleic acid molecule comprising said low repetitive nucleotide sequences can further comprise a nucleotide sequence encoding a biologically or pharmacologically active protein. Further, the present invention provides for selection means and methods to identify said nucleic acid molecule comprising said low repetitive nucleotide sequence. The present invention also relates to a method for preparing said nucleic acid molecule(s). Also provided herein are methods for preparing the encoded polypeptide or drug conjugate(s) with the encoded polypeptide using the herein provided nucleic acid molecules. The drug conjugate may comprise a biologically or pharmacologically active protein or a small molecule drug. Also provided herein are vectors and hosts comprising such nucleic acid molecules.

Polypeptides that form random coils are known in the prior art. For example, WO 2008/155134 discloses proteins comprising an amino acid sequence of at least about 100 amino acid residues and consisting of proline, alanine and serine (PAS) residues. The amino acid sequence forming the random coil conformation can comprise a plurality of amino acid repeats. These repeats may consist of at least 3 to 30 or more amino acid residues. WO 2011/144756 discloses polypeptides comprising repetitive amino acid sequences consisting solely of proline and alanine (PA) residues. These polypeptides also form random coils and consist of at least 50 proline and alanine residues. WO 2015/132004 discloses a recombinant clostridial neurotoxin comprising a random coil domain consisting of PAS. US 2006/0252120 A1 discloses hydroxyproline-rich glycoproteins, which contain segments encoded as proline-rich glycomodules with the amino acid sequence motif $[(AP)_5]_n$. Also naturally occurring polypeptides encompass sequences rich in proline and alanine, such as the very large tegument protein of the Macacine herpesvirus 1 gene published under the gene bank accession number (AAP41454.1). Methods for codon optimization are disclosed in WO 2007/142954.

Repetitive prior art polypeptides, like PAS or PA sequences, are typically encoded by corresponding repetitive nucleic acids. Accordingly, the prior art nucleic acids reflect the repetitive structure of the amino acid sequences they encode also in their nucleotide sequence. Thus, the prior art nucleic acids are highly repetitive on their sequence level. The repetitiveness of prior art nucleic acids can lead to caveats such as partial genetic instability, in particular when encoding long PAS or PA sequences, for example 300 residues or longer.

The technical problem underlying the present invention is therefore the provision of means and methods for the convenient and reliable preparation of polypeptides containing amino acid repeats, in particular polypeptides containing amino acid repeats that consist of proline, alanine and, optionally, serine.

The technical problem is solved by provision of the embodiments provided herein below and as characterized in the appended claims.

SUMMARY

The present invention relates to the following items:

1. A nucleic acid molecule, wherein said nucleic acid molecule comprises a nucleotide sequence encoding a polypeptide consisting of proline, alanine and, optionally, serine,
   wherein the nucleotide sequence of said nucleic acid has a length of at least 300 nucleotides,
   wherein said nucleotide sequence has a Nucleotide Repeat Score (NRS) lower than 50,000,
   wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}},$$

wherein
   $N_{tot}$ is the length of said nucleotide sequence,
   n is the length of a repeat within said nucleotide sequence, and
   $f_i(n)$ is the frequency of said repeat of length n,
   wherein, if there is more than one repeat of length n, k(n) is the number of said different sequences of said repeat of length n, otherwise k(n) is 1 for said repeat of length n.
2. The nucleic acid molecule of item 1, wherein said encoded polypeptide consists of proline and alanine.
3. The nucleic acid molecule of item 2, wherein said proline residues constitute more than about 10% and less than about 75% of said encoded polypeptide.
4. The nucleic acid molecule of item 1, wherein said encoded polypeptide consists of proline, alanine and serine.
5. The nucleic acid molecule of item 4, wherein said proline residues constitute more than 4% and less than 40% of said encoded polypeptide.
6. The nucleic acid molecule of any one of items 1 to 5, wherein said Nucleotide Repeat Score (NRS) is lower than 100.
7. The nucleic acid molecule of any one of items 1 to 6, wherein said nucleic acid molecule has an enhanced genetic stability.

8. The nucleic acid molecule of any one of items 1 to 7, wherein said nucleotide sequence comprises said repeats, wherein said repeats have a maximum length $n_{max}$, wherein $n_{max}$ is determined according to the formula:

$$n_{max} \leq 17 + \frac{N_{tot}}{600}$$

and wherein $N_{tot}$ is the length of said nucleotide sequence.
9. The nucleic acid molecule of any one of items 1 to 8, wherein said repeats have a maximum length of about 14, 15, 16, or 17 nucleotides to about 55 nucleotides.
10. The nucleic acid molecule of any one of items 1 to 9, wherein said repeats have a maximum length corresponding to 50% of the length of said nucleotide sequence.
11. The nucleic acid molecule of any one of items 1 to 10, wherein said encoded polypeptide comprises a repetitive amino acid sequence with a plurality of amino acid repeats, wherein no more than 9 consecutive amino acid residues are identical and wherein said polypeptide forms a random coil.
12. The nucleic acid molecule of any one of items 1 to 11, wherein said nucleic acid molecule is selected from the group consisting of:
   (a) the nucleic acid molecule comprising at least one nucleotide sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27;
   (b) the nucleic acid molecule comprising at least one nucleotide sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.
   (c) the nucleic acid molecule comprising the nucleotide sequence selected from the group consisting of SEQ ID NO: 38, SEQ ID NO: 39, SEQ ID NO: 40 and SEQ ID NO: 41;
   (d) the nucleic acid molecule comprising the nucleotide sequence consisting of SEQ ID NO: 42, SEQ ID NO: 43, SEQ ID NO: 44, and/or SEQ ID NO: 45;
   (e) the nucleic acid molecule hybridizing under stringent conditions to the complementary strand of the nucleotide sequence as defined in (a) or (b);
   (f) the nucleic acid molecule comprising the nucleotide sequence having at least 56% identity to the nucleotide sequence as defined in any one of (a), (c) and (e);
   (g) the nucleic acid molecule comprising the nucleotide sequence having at least 66.7% identity to the nucleotide sequence as defined in any one of (b), (d) and (e); and
   (h) the nucleic acid molecule being degenerate as a result of the genetic code to the nucleotide sequence as defined in any one of (a) to (d).
13. The nucleic acid molecule of any one of items 1 to 12, wherein said nucleic acid molecule comprises two complementary 5'-overhangs, wherein the 5'-overhang on the coding strand is 5'-GCC, and wherein the 5'-overhang on the non-coding strand is 5'-GGC.
14. The nucleic acid molecule of any one of items 1 to 13 operably linked in the same reading frame to a nucleic acid encoding a biologically active protein.
15. The nucleic acid molecule of item 14, wherein said biologically active protein is a therapeutically effective protein.
16. The nucleic acid molecule of item 14 or 15, wherein said biologically active protein is selected from the group consisting of a binding protein, an antibody fragment, a cytokine, a growth factor, a hormone, an enzyme, a protein vaccine, a peptide vaccine, a peptide which consists of up to 50 amino acid residues or a peptidomimetic.
17. The nucleic acid molecule of item 16, wherein said binding protein is selected from the group consisting of antibodies, Fab fragments, Fab' fragments, $F(ab')_2$ fragments, single chain variable fragments (scFv), (single) domain antibodies, isolated variable regions of antibodies (VL and/or VH regions), CDRs, immunoglobulin domains, CDR-derived peptidomimetics, lectins, protein scaffolds, fibronectin domains, tenascin domains, protein A domains, SH3 domains, ankyrin repeat domains, and lipocalins.
18. The nucleic acid molecule of any one of items 14 to 17, wherein said biologically active protein is selected from the group consisting of interleukin 1 receptor antagonist, leptin, acid sphingomyelinase, adenosine deaminase, agalsidase alfa, alpha-1 antitrypsin, alpha atrial natriuretic peptide, alpha-galactosidase, alpha-glucosidase, alpha-N-acetylglucosaminidase, alteplase, amediplase, amylin, amylin analog, anti-HIV peptide fusion inhibitor, arginine deiminase, asparaginase, B domain deleted factor VIII, bone morphogenetic protein, bradykinin antagonist, B-type natriuretic peptide, bouganin, growth hormone, chorionic gonadotropin, CD3 receptor antagonist, CD19 antagonist, CD20 antagonist, CD40 antagonist, CD40L antagonist, cerebroside sulfatase, coagulation factor VIIa, coagulation factor XIII, coagulation factor IX, coagulation factor X, complement component C3 inhibitor, complement component 5a antagonist, C-peptide, CTLA-4 antagonist, C-type natriuretic peptide, defensin, deoxyribonuclease I, EGFR receptor antagonist, epidermal growth factor, erythropoietin, exendin-4, ezrin peptide 1, FcγIIB receptor antagonist, fibroblast growth factor 21, follicle-stimulating hormone, gastric inhibitory polypeptide (GIP), GIP analog, glucagon, glucagon receptor agonist, glucagon-like peptide 1 (GLP-1), GLP-1 analog, glucagon-like peptide 2 (GLP-2), GLP-2 analog, gonadorelin, gonadotropin-releasing hormone agonist, gonadotropin-releasing hormone antagonist, gp120, gp160, granulocyte colony stimulating factor (G-CSF), granulocyte macrophage colony stimulating factor (GM-CSF), grehlin, grehlin analog, growth hormone, growth hormone-releasing hormone, hematide, hepatocyte growth factor, hepatocyte growth factor receptor (HGFR) antagonist, hepcidin antagonist, hepcidin mimetic, Her2/neu receptor antagonist, histrelin, hirudin, hsp70 antagonist, humanin, hyaluronidase, hydrolytic lysosomal glucocerebroside-specific enzyme, iduronate-2-sulfatase, IgE antagonists, insulin, insulin analog, insulin-like growth factor 1, insulin-like growth factor 2, interferon-alpha, interferon-alpha antagonist, interferon-alpha superagonist, interferon-alpha-n3, interferon-beta, interferon-gamma, interferon-lambda, interferon tau, interleukin, interleukin 2 fusion protein, interleukin-22 receptor subunit alpha (IL-22ra) antagonist, irisin, islet neogenesis associated protein, keratinocyte growth factor, Kv1.3 ion channel antagonists, lanthipeptide, lipase, luteinizing hormone, lutropin alpha, lysostaphin, mannosidase, N-acetylgalactosamine-6-sulfatase, N-acetylglucosaminidase, neutrophil gelatinase-associated lipocalin, octreotide, ω-conotoxin, *Ornithodoros moubata* complement inhibitor, osteogenic protein-1, osteoprotegerin, oxalate decarboxylase, P128, parathyroid hormone, Phylomer, PD-1 antagonist, PDGF antagonist, phenylalanine ammonia lyase, platelet derived growth factor, proinsulin, protein C, relaxin, relaxin analog, secretin, RGD peptide, ribonuclease, senrebotase, serine protease inhibitor, soluble complement receptor type 1, soluble DCC receptor, soluble TACI receptor, soluble tumor necrosis factor I receptor (sTNF-RI), soluble tumor necrosis factor II receptor (sTNF-RII), soluble VEGF receptor Flt-1, soluble FcγIIB receptor, somatostatin, somatostatin analog, streptokinase, T-cell receptor ligand, tenecteplase, teriparatide, thrombomodulin alpha, thymosin alpha 1, toll like receptor inhibitor, tumor necrosis factor (TNFα), tumor necrosis factor α antagonist, uricase, vasoactive intestinal peptide, vasopressin, vasopressin analog, VEGF antagonist, von Willebrand factor.

19. A vector comprising the nucleic acid molecule of any one of items 1 to 18.
20. The vector of item 19, wherein said vector comprises an upstream recognition sequence that is recognized by an endonuclease restriction enzyme and a downstream recognition sequence that is recognized by an endonuclease restriction enzyme, and wherein said upstream recognition sequence and said downstream recognition sequence are in a reverse complementary orientation.
21. The vector of item 20, wherein said endonuclease restriction enzyme recognizing said downstream recognition sequence is different from the endonuclease restriction enzyme recognizing the upstream recognition sequence.
22. The vector of item 20 or 21, wherein said upstream recognition sequence comprises two recognition sequences for two different restriction enzymes.
23. The vector of any one of items 20 to 22, wherein said downstream recognition sequence is comprised in the upstream recognition sequence.
24. The vector of any one of items 20 to 23, wherein said upstream recognition sequence and/or said downstream recognition sequence are recognition sequences for restriction enzymes producing nucleotide overhangs.
25. The vector of any one of items 20 to 24, wherein said upstream recognition sequence and/or said downstream recognition sequence are recognition sites for restriction enzymes that cleave outside of the recognition sequence.
26. The vector of any one of items 20 to 25, wherein said restriction enzyme is a type IIS restriction enzyme.
27. The vector of any one of items 20 to 26, wherein said upstream recognition sequence has the nucleotide sequence “5'-GCTCTTC-3” and/or wherein said downstream recognition sequence has the nucleotide sequence “5'-CTCTTC-3'”.
28. The vector of any one of items 20 to 27, wherein said upstream recognition sequence is recognized by SapI and EarI and/or wherein said downstream recognition sequence is recognized by EarI.
29. The vector of any one of items 20 to 28, wherein said vector has a sequence given in SEQ ID NO: 48 or SEQ ID NO: 55.
30. A host comprising the nucleic acid molecule of any one of items 1 to 18 or transformed with the vector of any one of items 19 to 29.
31. The host of item 30, wherein the host is selected from the group consisting of a bacterium, a mammalian cell, an insect cell, an algal cell, a ciliate, a yeast and a plant cell.
32. The host of item 30 or 31, wherein the bacterium belongs to the genus *Escherichia, Corynebacterium, Pseudomonas* or *Bacillus.*
33. The host of item 32, wherein said bacterium is *Escherichia coli, Corynebacterium glutamicum, Pseudomonas fluorescens* or *Bacillus megaterium.*
34. The host of item 31, wherein said mammalian cell is a hamster cell.
35. The host of item 34, wherein said mammalian cell is a CHO cell.
36. The host of item 31, wherein said yeast belongs to the genus *Saccharomyces, Pichia, Hansenula* or *Kluyveromyces.*
37. The host of item 36, wherein said yeast is *Saccharomyces cerevisiae, Schizosaccharomyces pombe, Pichia pastoris, Pichia methanolica, Hansenula polymorpha*, or *Kluyveromyces lactis.*
38. A method for preparing said nucleic acid molecule of any one of items 1 to 18, or said vector of any one of items 19 to 29, wherein the method comprises culturing/raising the host of any one of items 30 to 37 and optionally isolating the produced nucleic acid molecule and/or vector.
39. A method for preparing a polypeptide encoded by the nucleic acid molecule of any one of items 1 to 18, wherein the method comprises culturing/raising the host of any one of items 30 to 37 comprising the nucleic acid molecule of any one of items 1 to 18 and optionally isolating the produced polypeptide.
40. A method for preparing a drug conjugate, wherein said drug conjugate comprises the polypeptide encoded by the nucleic acid molecule of any one of items 1 to 18 and further comprises (i) a biologically active protein and/or (ii) a small molecule and/or (iii) a carbohydrate.
41. The method for preparing the drug conjugate of item 40, wherein said nucleic acid molecule has an enhanced genetic stability.
42. The method for preparing the drug conjugate of item 40 or 41, wherein said biologically active protein is a therapeutically effective protein.
43. The method for preparing the drug conjugate of any one of items 40 to 42, wherein said polypeptide mediates an enhanced in vivo and/or in vitro stability of said drug conjugate.
44. The method for preparing the drug conjugate of any one of items 40 to 43, wherein said biologically active protein is selected from the group consisting of a binding protein, an antibody fragment, a cytokine, a growth factor, a hormone, an enzyme, a protein vaccine, a peptide vaccine, a peptide which consists of up to 50 amino acid residues or a peptidomimetic.
45. The method for preparing the drug conjugate of any one of items 40 to 44, wherein said binding protein is selected from the group consisting of antibodies, Fab fragments, Fab' fragments, $F(ab')_2$ fragments, single chain variable fragments (scFv), (single) domain antibodies, isolated variable regions of antibodies (VL and/or VH regions), CDRs, immunoglobulin domains, CDR-derived peptidomimetics, lectins, protein scaffolds, fibronectin domains, tenascin domains, protein A domains, SH3 domains, ankyrin repeat domains, and lipocalins.
46. The method for preparing the drug conjugate of any one of items 40 to 45, wherein said biologically active protein is selected from the group consisting of interleukin 1 receptor antagonist, leptin, acid sphingomyelinase, adenosine deaminase, agalsidase alfa, alpha-1 antitrypsin, alpha atrial natriuretic peptide, alpha-galactosidase, alpha-glucosidase, alpha-N-acetylglucosaminidase, alteplase, amediplase, amylin, amylin analog, anti-HIV peptide fusion inhibitor, arginine deiminase, asparaginase, B domain deleted factor VIII, bone morphogenetic protein, bradykinin antagonist, B-type natriuretic peptide, bouganin, growth hormone, chorionic gonadotropin, CD3 receptor antagonist, CD19 antagonist, CD20 antagonist, CD40 antagonist, CD40L antagonist, cerebroside sulfatase, coagulation factor VIIa, coagulation factor XIII, coagulation factor IX, coagulation factor X, complement component C3 inhibitor, complement component 5a antagonist, C-peptide, CTLA-4 antagonist, C-type natriuretic peptide, defensin, deoxyribonuclease I, EGFR receptor antagonist, epidermal growth factor, erythropoietin, exendin-4, ezrin peptide 1, FcγIIB receptor antagonist, fibroblast growth factor 21, follicle-stimulating hormone, gastric inhibitory polypeptide (GIP), GIP analog, glucagon, glucagon receptor agonist, glucagon-like peptide 1 (GLP-1), GLP-1 analog, glucagon-like peptide 2 (GLP-2), GLP-2 analog, gonadorelin, gonadotropin-releasing hormone agonist, gonadotropin-releasing hormone antagonist, gp120, gp160, granulocyte colony stimulating factor (G-CSF), granulocyte macrophage colony stimulating factor (GM-CSF), grehlin, grehlin analog, growth hormone, growth hormone-releasing hormone, hematide, hepatocyte growth factor, hepatocyte growth factor receptor (HGFR) antagonist, hepcidin antagonist, hepcidin mimetic, Her2/neu receptor antagonist, histrelin, hirudin, hsp70 antagonist, humanin, hyaluronidase, hydrolytic lysosomal glucocerebroside-specific enzyme, iduronate-2-sulfatase, IgE antagonists, insulin, insulin analog, insulin-like growth factor 1, insulin-like growth factor 2, interferon-alpha, interferon-alpha antagonist, interferon-alpha superagonist, interferon-alpha-n3, interferon-beta, interferon-gamma, interferon-lambda, interferon tau, interleukin, interleukin 2 fusion protein, interleukin-22 receptor subunit alpha (IL-22ra) antagonist, irisin, islet neogenesis associated protein, keratinocyte growth factor, Kv1.3 ion channel antagonists, lanthipeptide, lipase, luteinizing hormone, lutropin alpha, lysostaphin, mannosidase, N-acetylgalactosamine-6-sulfatase, N-acetylglucosaminidase, neutrophil gelatinase-associated lipocalin, octreotide, ω-conotoxin, *Ornithodoros moubata* complement inhibitor, osteogenic protein-1, osteoprotegerin, oxalate decarboxylase, P128, parathyroid hormone, Phylomer, PD-1 antagonist, PDGF antagonist, phenylalanine ammonia lyase, platelet derived growth factor, proinsulin, protein C, relaxin, relaxin analog, secretin, RGD peptide, ribonuclease, senrebotase, serine protease inhibitor, soluble complement receptor type 1, soluble DCC receptor, soluble TACI receptor, soluble tumor necrosis factor I receptor (sTNF-RI), soluble tumor necrosis factor II receptor (sTNF-RII), soluble VEGF receptor Flt-1, soluble FcγIIB receptor, somatostatin, somatostatin analog, streptokinase, T-cell receptor ligand, tenecteplase, teriparatide, thrombomodulin alpha, thymosin alpha 1, toll like receptor inhibitor, tumor necrosis factor (TNFα), tumor necrosis factor α antagonist, uricase, vasoactive intestinal peptide, vasopressin, vasopressin analog, VEGF antagonist, von Willebrand factor.

47. The method for preparing the drug conjugate of any one of items 40 to 46, wherein said small molecule is selected from the group consisting of angiogenesis inhibitors, anti-allergic drugs, anti-emetic drugs, anti-depressant drugs, anti-hypertensive drugs, anti-inflammatory drugs, anti-infective drugs, anti-psychotic drugs, anti-proliferative (cytotoxic and cytostatic) drugs, calcium antagonists and other circulatory organ drugs, cholinergic agonists, drugs acting on the central nervous system, drugs acting on the respiratory system, hormones, steroids, polyketides, carbohydrates, oligosaccharides, nucleic acids, nucleic acid derivatives, antisense nucleic acids, small interference RNAs (siRNAs), micro RNA (miR) inhibitors, microRNA mimetics, DNA aptamers and RNA aptamers.

48. A polypeptide as obtained or obtainable by the method of item 39, a drug conjugate as obtained by the method of any one of items 40 to 47.

49. Method for sequencing of the nucleic acid molecule of any one of items 1 to 18.

50. Method for amplification of the nucleic acid molecule of any one of items 1 to 18.

51. Method for cloning of the nucleic acid molecule of any one of items 1 to 18.

52. A method for selecting a genetically stable nucleic acid molecule, wherein said nucleic acid molecule comprises a nucleotide sequence encoding a polypeptide consisting of proline, alanine and, optionally, serine, wherein said nucleotide sequence has a length of at least 300 nucleotides, the method comprising a step of selecting a nucleic acid molecule comprising a nucleotide sequence having a Nucleotide Repeat Score (NRS) lower than 50,000, wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}},$$

wherein $N_{tot}$ is the length of said nucleotide sequence, n is the length of a repeat within said nucleotide sequence, and $f_i(n)$ is the frequency of said repeat of length n, wherein if there is more than one repeat of length n, k(n) is the number of said different sequences of said repeat of length n, otherwise k(n) is 1 for said repeat of length n.

In certain aspects the present application relates to the following items:

1. A nucleic acid molecule, wherein said nucleic acid molecule comprises a nucleotide sequence encoding a polypeptide consisting of proline, alanine and, optionally, serine, wherein the nucleotide sequence of said nucleic acid has a length of at least 300 nucleotides, wherein said nucleotide sequence has a Nucleotide Repeat Score (NRS) lower than 50,000, wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}},$$

wherein $N_{tot}$ is the length of said nucleotide sequence, n is the length of a repeat within said nucleotide sequence, and $f_i(n)$ is the frequency of said repeat of length n, wherein if there is more than one repeat of length n, k(n) is the number of said different sequences of said repeat of length n, otherwise k(n) is 1 for said repeat of length n.

2. The nucleic acid molecule of item 1, wherein said encoded polypeptide consists of proline and alanine, wherein said proline residues constitute more than about 10% and less than about 75% of said encoded polypeptide.

3. The nucleic acid molecule of item 1, wherein said encoded polypeptide consists of proline, alanine and serine, wherein said proline residues constitute more than 4% and less than 40% of said encoded polypeptide.

4. The nucleic acid molecule of any one of items 1 to 3, wherein said Nucleotide Repeat Score (NRS) is lower than 100.

5. The nucleic acid molecule of any one of items 1 to 4, wherein said nucleic acid molecule has an enhanced genetic stability.

6. The nucleic acid molecule of any one of items 1 to 5, wherein said nucleotide sequence comprises said repeats, wherein said repeats have a maximum length $n_{max}$, wherein $n_{max}$ is determined according to the formula:

$$n_{max} \leq 17 + \frac{N_{tot}}{600}$$

and wherein $N_{tot}$ is the length of said nucleotide sequence.

7. The nucleic acid molecule of any one of items 1 to 6, wherein said repeats have a maximum length of about 14, 15, 16, or 17 nucleotides to about 55 nucleotides.

8. The nucleic acid molecule of any one of items 1 to 7, wherein said encoded polypeptide comprises a repetitive amino acid sequence with a plurality of amino acid repeats, wherein no more than 9 consecutive amino acid residues are identical and wherein said polypeptide forms a random coil.

9. The nucleic acid molecule of any one of items 1 to 8, wherein said nucleic acid molecule is selected from the group consisting of:

(a) the nucleic acid molecule comprising at least one nucleotide sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27;

(b) the nucleic acid molecule comprising at least one nucleotide sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37;

(c) the nucleic acid molecule comprising the nucleotide sequence selected from the group consisting of SEQ ID NO: 38, SEQ ID NO: 39, SEQ ID NO: 40 and SEQ ID NO: 41;

(d) the nucleic acid molecule comprising the nucleotide sequence consisting of SEQ ID NO: 42, SEQ ID NO: 43 SEQ ID NO: 44 and/or SEQ ID NO: 45

(e) the nucleic acid molecule hybridizing under stringent conditions to the complementary strand of the nucleotide sequence as defined in (a) or (b);

(f) the nucleic acid molecule comprising the nucleotide sequence having at least 56% identity to the nucleotide sequence as defined in any one of (a), (c) and (e);

(g) the nucleic acid molecule comprising the nucleotide sequence having at least 66.7% identity to the nucleotide sequence as defined in any one of (b), (d) and (e); and (h) the nucleic acid molecule being degenerate as a result of the genetic code to the nucleotide sequence as defined in any one of (a) to (d).

10. The nucleic acid molecule of any one of items 1 to 9 operably linked in the same reading frame to a nucleic acid encoding a biologically active protein.

11. The nucleic acid molecule of item 10, wherein said biologically active protein is selected from the group consisting of a binding protein, an antibody fragment, a cytokine, a growth factor, a hormone, an enzyme, a protein vaccine, a peptide vaccine, a peptide which consists of up to 50 amino acid residues or a peptidomimetic, wherein said binding protein is selected from the group consisting of antibodies, Fab fragments, Fab' fragments, $F(ab')_2$ fragments, single chain variable fragments (scFv), (single) domain antibodies, isolated variable regions of antibodies (VL and/or VH regions), CDRs, immunoglobulin domains, CDR-derived peptidomimetics, lectins, protein scaffolds, fibronectin domains, tenascin domains, protein A domains, SH3 domains, ankyrin repeat domains, and lipocalins.

12. The nucleic acid molecule of item 10 or 11, wherein said biologically active protein is selected from the group consisting of acid sphingomyelinase, adenosine deaminase, agalsidase alfa, alpha-1 antitrypsin, alpha atrial natriuretic peptide, alpha-galactosidase, alpha-glucosidase, alpha-N-acetylglucosaminidase, alteplase, amediplase, amylin, amylin analog, anti-HIV peptide fusion inhibitor, arginine deiminase, asparaginase, B domain deleted factor VIII, bone morphogenetic protein, bradykinin antagonist, B-type natriuretic peptide, bouganin, growth hormone, chorionic gonadotropin, CD3 receptor antagonist, CD19 antagonist, CD20 antagonist, CD40 antagonist, CD40L antagonist, cerebroside sulfatase, coagulation factor VIIa, coagulation factor XIII, coagulation factor IX, coagulation factor X, complement component C3 inhibitor, complement component 5a antagonist, C-peptide, CTLA-4 antagonist, C-type natriuretic peptide, defensin, deoxyribonuclease I, EGFR receptor antagonist, epidermal growth factor, erythropoietin, exendin-4, ezrin peptide 1, FcγIIB receptor antagonist, fibroblast growth factor 21, follicle-stimulating hormone, gastric inhibitory polypeptide (GIP), GIP analog, glucagon, glucagon receptor agonist, glucagon-like peptide 1 (GLP-1), GLP-1 analog, glucagon-like peptide 2 (GLP-2), GLP-2 analog, gonadorelin, gonadotropin-releasing hormone agonist, gonadotropin-releasing hormone antagonist, gp120, gp160, granulocyte colony stimulating factor (G-CSF), granulocyte macrophage colony stimulating factor (GM-CSF), grehlin, grehlin analog, growth hormone, growth hormone-releasing hormone, hematide, hepatocyte growth factor, hepatocyte growth factor receptor (HGFR) antagonist, hepcidin antagonist, hepcidin mimetic, Her2/neu receptor antagonist, histrelin, hirudin, hsp70 antagonist, humanin, hyaluronidase, hydrolytic lysosomal glucocerebroside-specific enzyme, iduronate- 2-sulfatase, IgE antagonists, insulin, insulin analog, insulin-like growth factor 1, insulin-like growth factor 2, interferon-alpha, interferon-alpha antagonist, interferon-alpha superagonist, interferon-alpha-n3, interferon-beta, interferon-gamma, interferon-lambda, interferon tau, interleukin, interleukin 1 receptor antagonist, interleukin 2 fusion protein, interleukin-22 receptor subunit alpha (IL-22ra) antagonist, irisin, islet neogenesis associated protein, keratinocyte growth factor, Kv1.3 ion channel antagonists, lanthipeptide, leptin, lipase, luteinizing hormone, lutropin alpha, lysostaphin, mannosidase, N-acetylgalactosamine-6-sulfatase, N-acetylglucosaminidase, neutrophil gelatinase-associated lipocalin, octreotide, ω-conotoxin, *Ornithodoros moubata* complement inhibitor, osteogenic protein-1, osteoprotegerin, oxalate decarboxylase, P128, parathyroid hormone, Phylomer, PD-1 antagonist, PDGF antagonist, phenylalanine ammonia lyase, platelet derived growth factor, proinsulin, protein C, relaxin, relaxin analog, secretin, RGD peptide, ribonuclease, senrebotase, serine protease inhibitor, soluble complement receptor type 1, soluble DCC receptor, soluble TACI receptor, soluble tumor necrosis factor I receptor (sTNF-RI), soluble tumor necrosis factor II receptor (sTNF-RII), soluble VEGF receptor Flt-1, soluble FcγIIB receptor, somatostatin, somatostatin analog, streptokinase, T-cell receptor ligand, tenecteplase, teriparatide, thrombomodulin alpha, thymosin alpha 1, toll like receptor inhibitor, tumor necrosis factor (TNFα), tumor necrosis factor α antagonist, uricase, vasoactive intestinal peptide, vasopressin, vasopressin analog, VEGF antagonist, von Willebrand factor.

13. A host comprising the nucleic acid molecule of any one of items 1 to 12 or transformed with a vector comprising the nucleic acid molecule of any one of items 1 to 12.
14. A method for preparing a polypeptide encoded by the nucleic acid molecule of any one of items 1 to 12, wherein the method comprises culturing/raising the host of item 13 and optionally isolating the produced polypeptide.
15. A method for preparing a drug conjugate, wherein said drug conjugate comprises the polypeptide encoded by the nucleic acid molecule of any one of items 1 to 12 and further comprises (i) a biologically active protein and/or (ii) a small molecule and/or (iii) a carbohydrate.

DETAILED DESCRIPTION

The present invention relates to nucleic acid molecules with low repetitive nucleotide sequences encoding polypeptides consisting of proline, alanine and, optionally, serine. Such polypeptides are also termed herein PA-rich or proline/alanine-rich polypeptides. The inventive nucleic acid molecules provided herein have few or no nucleotide repeats of a certain maximum length, such as a maximum length of about 14, 15, 16 or 17 nucleotides per nucleotide repeat sequence. Furthermore, the PA-rich coding nucleotide sequence has an overall length of at least 300 nucleotides and the individual nucleotide repeats within this coding sequence have an individual maximal length of 14, 15, 16, 17, about 20, about 25, about 30, about 35, about 40, about 45, about 50 or about 55 nucleotides.

In one aspect, the nucleic acid molecule of the invention comprises a nucleotide sequence encoding a repetitive amino acid sequence (e.g. a PA-rich polypeptide), wherein said nucleotide sequence of said nucleic acid molecule has a length of at least 300 nucleotides, wherein said nucleotide sequence has a Nucleotide Repeat Score (NRS) lower than 50,000, and wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}}.$$

In this formula, $N_{tot}$ is the length of said nucleotide sequence, n is the length of a repeat within said nucleotide sequence, and $f_i(n)$ is the frequency of said repeat of length n, and wherein, if there is more than one repeat of length n, k(n) is the number of said different sequences of said repeat of length n, otherwise k(n) is 1 for said repeat of length n. A definition follows below.

In a certain aspect, the nucleic acid molecule of the invention encodes a polypeptide consisting of proline, alanine and, optionally, serine, wherein a nucleotide sequence stretch which repeatedly occurs within the nucleotide sequence of said nucleic acid molecule (i.e. a "repeat") has maximally a length of 14, 15, 16, 17, about 20, about 25, about 30, about 35, about 40, about 45, about 50 or about 55 nucleotides. In other words, the nucleic acid molecule comprises a nucleotide sequence encoding a PA-rich polypeptide, wherein said coding nucleotide sequence comprises nucleotide repeats having a maximum length of 14, 15, 16, 17, about 20, about 25, about 30, about 35, about 40, about 45, about 50 or about 55 nucleotides. The inventive nucleic acid molecules/sequences can also comprise additional coding sequences, like inter alia biologically or pharmacologically active proteins.

It is demonstrated in the appended examples that the low repetitive nucleic acid molecules of the invention are advantageous compared to highly repetitive nucleic acid molecules of the prior art. In particular, the genetic stability of the low repetitive nucleic acid molecules provided herein is improved as documented herein and shown in the appended examples. In order to assess the genetic stability of prior art repetitive nucleic acid molecules encoding PA-rich polypeptides, a vector was constructed comprising a prior art repetitive nucleic acid molecule encoding a repetitive proline/alanine-rich sequence (PAS #1a(600); SEQ ID NO: 12; Example 6, FIGS. 2B-2C) which is composed of multiple 60mer nucleotide sequence units as disclosed in WO 2008/155134. The vector is termed herein "pASK75-PAS #1a(600)-IL1Ra" (SEQ ID NO: 51). The host (*E. coli*) was transformed with the vector and cultivated for several days, e.g., 7 days. On day 7 after a continuous growth over approximately 70 generations, cells were plated on LB/Amp agar, clones were picked, and plasmid preparations were performed. Plasmids were analysed using restriction enzymes and subsequent agarose gel electrophoresis (FIG. 5). Four of five analyzed clones of pASK75-PAS #1a(600)-IL1Ra showed shortened nucleic acid fragments encoding the proline/alanine-rich sequences (FIG. 5 lanes 1-5).

Accordingly, prior art repetitive nucleic acid molecules encoding repetitive proline/alanine-rich sequences are genetically unstable. In other words, prior art nucleic acid molecules have a low in vivo stability. Without being bound by theory the genetic instability might be a result of homologous recombination. Due to the genetic instability and shortening of the gene cassette, the resulting proline/alanine-rich amino acid sequence will be altered, too. Thus, the proline/alanine-rich amino acid sequence encoded by the unstable plasmids during long-term cultivation will be different from that encoded by the original plasmid. Therefore, there is considerable risk that the polypeptides obtained during long-term cultivation using prior art repetitive nucleic acid molecules will not be the desired polypeptides.

Moreover, there is a risk that the resulting polypeptide composition may comprise a variety of different polypeptides (e.g. proline/alanine-rich polypeptides of various sizes, lengths and/or sequences) which is contrary to the desired conformity of biological products, particularly for biopharmaceutical use. Thus, genetic instability of repetitive prior art nucleic acid molecules encoding proline/alanine-rich polypeptides can lead to decreased quality of the biological end-product, rendering the production thereof inconvenient and unreliable, especially under regulatory aspects for therapeutic application.

In the present invention, the problem of genetic instability is solved by designing nucleic acid molecules with low internal nucleotide repeats. However, given the low number of nucleotide triplet codons available to encode proline/alanine-rich amino acid sequences, this was not a trivial task.

As shown in the appended non-limiting examples, the nucleic acid molecules of the invention avoid the above recited disadvantages; see e.g. Examples 5 and 6 and FIG. 4 and FIG. 5 lane 6-10. Nevertheless, like the prior art nucleic acid molecules, the nucleic acid molecules of the invention encode proline/alanine-rich polypeptides containing a plurality of proline/alanine-rich repeats. Yet, in strong contrast to the prior art nucleic acid molecules, the nucleic acid molecules of the present invention have a low repetitive nucleotide sequence (i.e. they contain few and/or only short nucleotide repeats).

Illustrative Example 5 shows the preparation of an exemplary vector of the invention comprising a low repetitive nucleotide sequence encoding a proline/alanine-rich polypeptide. The low repetitive nucleotide sequence termed “PAS #1f/1c/1b(600)” as used in the exemplary vector is shown in SEQ ID NO: 38. The resulting plasmid was designated “pASK75-PAS #1f/1c/1b(600)-IL1Ra” (SEQ ID NO: 50) and is shown in FIG. 4.

The plasmid of the invention, “pASK75-PAS #1f/1c/1b(600)-IL1Ra” was subjected to the same cultivation as described above in relation to the vector “pASK75-PAS #1a(600)-IL1Ra”, the latter vector comprising a prior art repetitive nucleic acid molecule encoding a repetitive proline/alanine-rich sequence (PAS #1a(600); SEQ ID NO: 12), which is composed of multiple 60mer nucleotide sequence units as disclosed in WO 2008/155134 (FIG. 1A). In contrast to “pASK75-PAS #1a(600)-IL1Ra”, the plasmid of the invention, “pASK75-PAS #1f/1c/1b(600)-IL1Ra”, showed high genetic stability: all analysed clones of “pASK75-PAS #1f/1c/1b(600)” only showed the expected bands at 3093 bp and 2377 bp (FIG. 5 lanes 6-10), indicating a high genetic stability of the low repetitive PAS #1f/1c/1b(600) gene cassette comprising 1800 base pairs and encoding the proline/alanine-rich sequence PAS #1. Due to this high genetic stability, the disadvantages of prior art nucleic acid molecules are avoided. This clearly demonstrates that the nucleic acid molecules of the invention comprising a low repetitive nucleotide sequence are useful for the convenient and reliable biosynthesis of proline/alanine-rich polypeptides and/or corresponding fusion proteins.

Illustrative Example 4 demonstrates a further advantage of the nucleic acid molecules provided in accordance with the present invention. Here, the exemplary nucleic acid molecule comprising a low repetitive nucleotide sequence of the invention (termed PAS #1f/1c/1b(600) cassette; SEQ ID NO: 38; see e.g. Example 1) was subjected to automated DNA sequencing. As result, a clearly defined and error-free electropherogram comprising more than 900 base pairs (FIG. 3) was obtained, which showed no signs of unspecific primer binding. Thus, in contrast to repetitive nucleotide sequences, which can only be reliably sequenced with primers that hybridize upstream or downstream of a corresponding cloned gene cassette, long low repetitive DNA fragments encoding proline/alanine-rich sequences can be fully sequenced in a facile way. In this case, internally binding primers can also be applied, thus generating multiple overlapping sequence reads if desired; notably, the use of such internally hybridizing primers does not result in unique sequencing patterns in the case of repetitive nucleotide sequences. Accordingly, the nucleic acid molecules of the invention comprising the low repetitive nucleotide sequence circumvent these sequencing problems.

In summary, the present invention has, inter alia, the following advantages over prior art nucleic acid molecules that comprise highly repetitive sequences. The advantageous low repetitive nucleotide sequences of the present invention can be fully sequenced without further ado in contrast to nucleic acid molecules of the prior art. A further advantage of the nucleic acid molecules of the present invention is that they have improved amplification properties, e.g. via the polymerase chain reaction PCR), due to the low repetitiveness. Furthermore, the nucleic acid molecules of the invention improve the cloning procedure compared to nucleotide sequences comprising repeated/repetitive sequences. A particular advantage of the herein provided nucleic acid molecules is that they have an improved genetic stability compared to the highly repetitive nucleic acid molecules of the prior art. This allows a reliable production of proline/alanine-rich polypeptides and/or fusion proteins thereof.

The characterizing feature of the nucleic acid molecules of the present invention is that the nucleotide sequences encoding a polypeptide consisting of proline, alanine and, optionally, serine are “low repetitive nucleotide sequences”, which confers the advantageous technical effects described above. In the appended Examples, methods are demonstrated that can be employed to analyze whether a nucleic acid molecule comprises a low repetitive nucleotide sequence according to the invention. In particular, the appended Examples provide a score termed herein “Nucleotide Repeat Score (NRS)”. This Nucleotide Repeat Score (NRS) is herein determined according to the formula as discussed above:

$$NRS = \frac{\sum_{n=4}^{N_{tot}-1} n^2 \sqrt{\sum_{i=1}^{k(n)} f_i(n)}}{N_{tot}},$$

wherein $N_{tot}$ is the length of said nucleotide sequence, n is the length of a repeat within said nucleotide sequence, and $f_i(n)$ is the frequency of said repeat of length n, and wherein, if there is more than one repeat of length n, k(n) is the number of said different sequences of said repeat of length n, otherwise k(n) is 1 for said repeat of length n. This score is described in detail below and is illustrated in the appended examples.

The NRS allows the skilled person to select low repetitive nucleotide sequences for use in the present invention. In other words, the NRS provides a tool for determining the degree of repetitiveness of a nucleotide sequence. In order to automatically identify repeats and to calculate the NRS, the algorithm termed NRS-Calculator provided herein can be employed.

As demonstrated in the appended illustrative Examples, e.g., Example 13, several prior art nucleic acids encoding proline/alanine-rich sequences were compared to low repetitive nucleic acids encoding proline/alanine-rich sequences according to this invention using the NRS-Calculator described in Example 14. For example, the NRS of the following prior art sequences was determined: PAS #1a (200) disclosed in WO 2008/155134, PA #1a(200) disclosed in WO2011144756, $[(AP)_5]_{20}$APA disclosed in US 20060252120, $[AAPAPAPAP]_{10}$AS published under GenBank accession number DQ399411a, the large tegument protein of the macacine herpesvirus 1 published under GenBank accession number NP 851896. In addition, histograms showing the frequencies of the nucleotide repeats plotted against the respective length were determined for these prior art nucleotide sequences and for the low repetitive nucleotide sequences of the present invention such as PAS #1b(200) (SEQ ID NO: 19) or PA #1e/1d/1c/1b(800) (SEQ ID NO: 44) (FIG. 9). The histograms of the prior art nucleotide sequences revealed a highly repetitive nature. In contrast, the histograms of the low repetitive nucleotide sequences of the invention, e.g., PAS #1b(200) and PA #1e/1d/1c/1b(800), demonstrate only a few repeats with a maximum length of 14 nucleotides; see e.g. FIG. 9F-I.

The difference in repetitiveness between the prior art nucleotide sequences and the inventive nucleotide sequences becomes even more evident when comparing their Nucleotide Repeat Scores. The prior art sequences analyzed herein reveal an NRS above 80000 (Table 2). In contrast, the exemplary inventive nucleotide sequences demonstrate low Nucleotide Repeat Scores, e.g., below 34; see Table 1. Consequently, it is clearly proven herein that the repeat quality of the nucleotide sequences encoding proline/alanine-rich sequences of the invention is much higher compared to prior art sequences, with both fewer and shorter nucleotide sequence repeats. Accordingly, the nucleic acid molecules of the present invention have low repetitive sequences.

As indicated above, the skilled person is aware of several alternatives to analyze the degree of repetitiveness of a nucleic acid molecule. It is shown in the appended examples that the repetitiveness of the nucleic acid molecules of the invention and of those in the prior art was also analyzed by dot plot analysis; see e.g. Example 3. The dot plot analysis was performed for nucleic acids encoding the repetitive proline/alanine-rich sequence PA #3a (SEQ ID NO: 15; FIG. 2A) disclosed in WO 2011/144756, PAS #1 (SEQ ID NO: 11; FIGS. 2B-2C) disclosed in WO 2008/155134, an encoded $[(AP)_5]_n$ multimer (SEQ ID NO: 16) disclosed in US2006/0252120 and a repetitive proline/alanine-rich region of the very large tegument protein of Macacine herpesvirus 1 gene, published under the GenBank Accession Number AAP41454.1 (SEQ ID NO: 18; FIGS. 2D-2E). In the appended Examples, the "dottup" tool of the Geneious software package version 8.1 (Biomatters, Auckland, New Zealand) was employed. The algorithm aligns the respective sequence to itself and applies a repeat window of, e.g., 14 or 15 nucleotides. The dot plots of the prior art nucleotide sequences were compared to dot plots of the low repetitive nucleotide sequences of the invention, e.g., the units PA #3b(200) (SEQ ID NO: 36), PA #1b (SEQ ID NO: 28) or the assembled low repetitive nucleotide sequences PAS #1f/1c/1b(600) (SEQ ID NO: 38) and PAS #1d/1f/1c/1b(800) (SEQ ID NO: 39). Whereas all analyzed prior art sequences revealed a highly repetitive nature on the nucleotide sequence level as illustrated by black parallel diagonal lines (FIGS. 2A-2E), dot plots of the exemplary nucleotide sequences according to the invention show no or only a few scattered repeats of a maximal length of 14 nucleotides (black lines) within the entire nucleotide sequence of 600 nucleotides (FIGS. 2A, 2D, 2E), 1800 nucleotides or 2400 nucleotides, respectively (FIGS. 2B-2C). Accordingly, it is proven herein that the nucleotide sequences provided herein are low repetitive nucleotide sequences comprising no or only few short repeats.

In summary, the appended examples clearly demonstrate that the nucleic acid molecules of the invention have low repetitive nucleotide sequences while encoding a proline/alanine-rich amino acid repeat sequence. It is further demonstrated herein that the "low repetitivity" or "low repetitiveness" of the nucleic acid molecules provided herein can readily be assessed by alternative strategies, e.g., the Nucleotide Repeat Score provided herein or methods known to the skilled person such as dot plot analysis. Alternatively, a skilled person can identify nucleotide sequence repeats and, thus, the degree of repetitiveness of the nucleotide sequence either manually or with the aid of generic software programs such as the Visual Gene Developer (Jung (2011) BMC Bioinformatics 12:340), or the Repfind tool (Betley (2002) Curr Biol 12:1756-1761). Thereby, the nucleic acid molecules of the invention having unexpected advantageous properties can easily be distinguished from prior art nucleic acid molecules lacking these characteristics.

As described above, the low repetitive nucleotide sequence of the invention can either have an NRS of lower than 50,000 or it can have repeats with a maximum length of about 17, about 20, about 25, about 30, about 35, about 40, about 45, about 50 or about 55 nucleotides. The low repetitive nucleotide sequence of the invention has a length of at least 100 nucleotides, preferably of at least 150, more preferably of at least 200, even more preferably of at least 300 nucleotides, even more preferably of at least 350 nucleotides, even more preferably of at least 600 nucleotides, even more preferably of at least 900, even more preferably of at least 1200, even more preferably of at least 1500 nucleotides, or most preferably of at least 1800 nucleotides. In other words, the nucleic acid molecule of the invention comprises or consists of a nucleotide sequence encoding a polypeptide consisting of proline, alanine and, optionally, serine, wherein the nucleotide sequence of said nucleic acid has a length of at least 100 nucleotides, preferably of at least 150, more preferably of at least 200, even more preferably of at least 300 nucleotides, even more preferably of at least 350 nucleotides, even more preferably of at least 400 or 500 nucleotides, even more preferably of at least 600 nucleotides, even more preferably of at least 700 or 800 nucleotides, even more preferably of at least 900 nucleotides, even more preferably of at least 1000 or 1100, even more preferably of at least 1200 nucleotides (e.g. 1203 nucleotides), even more preferably of at least 1300 or 1400 nucleotides, even more preferably of at least 1500 nucleotides, even more preferably of at least 1600 or 1700 nucleotides, or most preferably of at least 1800 nucleotides.

The nucleic acid molecule of the invention can comprise or consist of a nucleotide sequence encoding a polypeptide consisting of proline, alanine and, optionally, serine, wherein the nucleotide sequence of said nucleic acid has a length of maximally 5000 nucleotides, preferably maximally 4800 nucleotides, 3600 nucleotides, or 2400 nucleotides. The nucleic acid molecule of the invention can comprise or consist of a nucleotide sequence encoding a polypeptide consisting of proline, alanine and, optionally, serine, wherein the nucleotide sequence of said nucleic acid has a length of maximally 5000 nucleotides, 4900 nucleotides, 4800 nucleotides, 4700 nucleotides, 4600 nucleotides, 4500 nucleotides, 4400 nucleotides, 4300 nucleotides, 4200 nucleotides, 4100 nucleotides, 4000 nucleotides, 3900 nucleotides, 3800 nucleotides, 3700 nucleotides, 3600 nucleotides, 3500 nucleotides, 3400 nucleotides, 3300 nucleotides, 3200 nucleotides, 3100 nucleotides, 3000 nucleotides, 2900 nucleotides, 2800 nucleotides, 2700 nucleotides, 2600 nucleotides, 2500 nucleotides, 2400 nucleotides, 2300 nucleotides, 2200 nucleotides, 2100 nucleotides, 2000 nucleotides, or maximally 1900 nucleotides.

In a particularly preferred aspect, the nucleic acid molecule of the invention can comprise or consist of a nucleotide sequence encoding a polypeptide consisting of proline, alanine and, optionally, serine, wherein the nucleotide sequence of said nucleic acid has a length of 1200 to 3600 nucleotides.

Furthermore, the low repetitive nucleotide sequence has a Nucleotide Repeat Score (NRS) that is lower than 50,000, preferably lower than 40,000, more preferably lower than 30,000, more preferably lower than 20,000, more preferably lower than 10,000, more preferably lower than 1000, more preferably lower than 500, even more preferably lower than 100. Particularly preferred are low repetitive nucleotide sequences having a Nucleotide Repeat Score (NRS) of lower than 50, more preferably lower than 48, more preferably lower than 45, more preferably lower than 43, more preferably lower than 40, more preferably lower than 38, or most preferably lower than 35. In other words, the nucleic acid molecule of the invention comprises a nucleotide sequence encoding a polypeptide consisting of proline, alanine and, optionally, serine, wherein said nucleotide sequence has a Nucleotide Repeat Score (NRS) lower than 50,000, preferably lower than 40,000, more preferably lower than 30,000, more preferably lower than 20,000, more preferably lower than 10,000, more preferably lower than 1000, more preferably lower than 500, even more preferably lower than 400, 300, 200, and even more preferably lower than 100. Particularly preferred are nucleic acid molecules comprising a nucleotide sequence encoding a polypeptide consisting of proline, alanine and, optionally, serine, wherein said nucleotide sequence has a Nucleotide Repeat Score (NRS) lower than 90, 80, 70, 60, more preferably lower than 50, more preferably lower than 48, more preferably an NRS score of 45 or lower than 45, more preferably lower than 43, more preferably lower than 40, more preferably an NRS score of 39, 38, 37, or 36 or lower than 39, 38, 37, or 36, or most preferably an NRS score of 35 or lower than 35. Even more particularly preferred are nucleic acid molecules comprising a nucleotide sequence encoding a polypeptide consisting of proline, alanine and, optionally, serine, wherein said nucleotide sequence has a Nucleotide Repeat Score (NRS) of 34, 32, 31, 30, 29, 28, 27, 26, 25, 24, 23, 22, 21, 20, 19, 18, 17, 16, 15, 14, 13, 12, 11, 10, 9, or 8 or an NRS lower than 34, 32, 31, 30, 29, 28, 27, 26, 25, 24, 23, 22, 21, 20, 19, 18, 17, 16, 15, 14, 13, 12, 11, 10, 9, or 8.

As discussed above, the "Nucleotide Repeat Score" or "NRS" can be determined according to the following formula:

$$NRS = \frac{\sum_{n=4}^{N_{tot}-1} n^2 \sqrt{\sum_{i=1}^{k(n)} f_i(n)}}{N_{tot}}.$$

Accordingly, the NRS is defined as the sum, over all possible repeat lengths (from n=4 up to $N_{tot}-1$), of each squared repeat length (n) multiplied with the square root of its overall frequency, divided through the total length of the analyzed nucleotide sequence ($N_{tot}$). In other words, the NRS is the sum of the squared length of repeats within said nucleotide sequence multiplied with the square root of the sum of the frequency of said repeat of length n ($f_i(n)$), wherein, if there is more than one repeat of length n, k(n) is the number of said different sequences of said repeat of length n, otherwise k(n) is 1 for said repeat of length n; and wherein said sum is divided by the total length of said nucleotide sequence.

As used herein, "$N_{tot}$" is the overall length of said nucleotide sequence encoding the polypeptide consisting of proline, alanine and, optionally, serine. The length $N_{tot}$ is also the number of nucleotides of said nucleotide sequence. Thus, $N_{tot}$ is the total length of the nucleotide sequence analyzed.

As used herein, "n" is the length of a repeat within said nucleotide sequence encoding the polypeptide consisting of proline, alanine and, optionally, serine. The length n is also the number of nucleotides of said repeat. Hence, n is the length of a repeat within the nucleotide sequence analyzed. By definition, the longest possible repeat may have a length that is by one nucleotide shorter than the total length of the nucleotide sequence analyzed ($N_{tot}$), i.e. n=$N_{tot}-1$. On the other hand, the shortest length of a repeat considered for the NRS analysis is n=4, which corresponds to the shortest stretch of nucleotides that is longer than a single triplet codon for an amino acid. As such codons occur multiple times just as a consequence of the encoded amino acid sequence they should not be regarded as nucleotide sequence repeats with regard to the technical problem to be solved.

The term "repeat" as used herein means that the nucleotide sequence comprises an identical contiguous sequence of nucleotides of a length n (i.e., the repeat) more than once. In other words, the nucleotide sequence comprises a contiguous part/stretch/sequence of a certain length of nucleotides in at least two or multiple copies. In other words, the term repeat refers to sequences of nucleotides of length n that are present in the nucleotide sequence more than once. It is contemplated herein that there may be just one type of repeat of a length n or there may be more than one different repeats of the same length n within the total length of the nucleotide sequence analyzed. Thus, a nucleotide sequence can, for example, have a repeat of a length n, whose occurrences all have the same sequence; it is understood that said repeat occurs at least twice but may also occur multiple times within the total length of the nucleotide sequence analyzed. Alternatively, there are repeats of the same length n that have different sequences, i.e., the repeats share the same length (n) but are not identical on the sequence level. In this instance, each different repeat sequence constitutes another type of repeat.

As used herein, "$f_i(n)$" is the frequency of a repeat of length n. In other words, $f_i(n)$ is the number of occurrences of the repeat of length n. If there is only one type of repeat of length n, k(n) is 1. Alternatively, if there are more than one different repeats of length n, k(n) is the number of different sequences of said repeats of length n. In other words, if there is more than one repeat of length n with different sequences, k(n) is the number of said different sequences of said repeats of length n. Thus, if there are two or more repeats of length n of different type, k(n) is the number of said different sequences of said repeats of length n. Otherwise, if the repeats of a length n all have the same (i.e., identical) sequence, k(n) is 1 for said repeat of length n.

For example, the frequency of a repeat of a length of 14 nucleotides (n=14) may be five within a nucleotide sequence (of length $N_{tot}$). This can mean that the five repeats with a length of 14 nucleotides all have an identical sequence (belonging to the same type), i.e., the sequence of the repeat occurs five times within the nucleotide sequence. In this case, k(n) is 1 and $f_i(n)=5$. In another scenario, the five repeats of 14 nucleotides length may have different sequences. In this scenario, it is envisaged that two of the five repeats share an identical sequence (constituting one type) and three of the five repeats share another identical sequence (constituting a second type), whereby the sequence of the former two repeats sharing one sequence and the sequence of the latter three repeats sharing another sequence are different from each other. Therefore, in this scenario, the number of said different sequences of length n is 2, i.e., k(n) is 2, and $f_i(n)=2$ and $f_2(n)=3$. The index "i" in the term $f_i(n)$ can be understood to represent the type of repeat within a set of different repeats having the name length n.

The formula to determine the NRS comprises the sum of the squared length of repeats ($n^2$), wherein n is the index of summation, 4 is the lower bound of summation and $N_{tot}-1$ is the upper bound of summation. Hence, the length of the repeat that is considered minimally is 4. A repeat of a length of 4 nucleotides includes all sequences longer than one amino acid codon triplet. The index, n, is incremented by 1 for each successive term, stopping when $n=N_{tot}-1$.

Furthermore, the formula to determine the NRS comprises the square root of the sum of the frequencies of said repeats of length n ($f_i(n)$), wherein i is the index of the summation, $f_i(n)$ is an indexed variable representing each successive term in the series, 1 is the lower bound of summation and k(n) is the upper bound of summation. The index, i, is incremented by 1 for each successive term, stopping when i=k(n). Thus, if there is only one type of repeat of a length n, i.e. all repeats of length n have identical sequence, k(n) is 1 for said repeat of length n and, instead of a sum, just the frequency $f_i(n)$ of this repeat of length n within the total length of the nucleotide sequence ($N_{tot}$) is analyzed.

For example, the following NRS-Calculator script may be used in accordance with the invention to determine an NRS:

```
import math
import sys
class NRSCalculator:
    def __init__(self):
        self.repeats = dict( )
        self.sums = dict( )
        self.seq = None
        self.range_min = None
        self.range_max = None
    def _match_at(self, row, column):
        return self.seq[row] == self.seq[column]
    def _get_repeats_at(self, row, column):
        length = 1
        search_row = row
        search_column = column
        while True:
            if not 0 <= search_row < len(self.seq):
                break
            if not 0 <= search_column < search_row:
                break
            if length > self.range_max:
                break
```

-continued

```
            if not self._match_at(search_row, search_column):
                break
            if length >= self.range_min:
                repeats =
self.repeats.setdefault(self.seq[row:row + length], set( ))
                repeats.add(row)
                repeats.add(column)
            search_row += 1
            search_column += 1
            length += 1
    def _get_repeats(self):
        self.repeats = dict( )
        for row in xrange(len(self.seq)):
            for column in xrange(row):
                self._get_repeats_at(row, column)
    def _get_sums(self):
        self.sums = dict( )
        for (seq, repeats) in self.repeats.iteritems( ):
            length = len(seq)
            self.sums[length] = self.sums.get(length, 0) +
len(repeats)
    def set_range(self, range_min, range_max):
        self.range_min = range_min
        self.range_max = range_max
    def set_sequence(self, seq):
        self.seq = seq
    def work(self):
        if not self.seq and not self.range_min and not
self.range_max:
            raise RuntimeError(‘Can not work without
initialization’)
        self._get_repeats( )
        self._get_sums( )
    def print_repeats(self):
        print(‘Sequence (Length bp) : NumRepeats
(Positions)’)
        for seq, repeats in sorted(self.repeats.iteritems( ),
key=lambda t: len(t[0])):
            list = [seq, len(seq), len(repeats)]
            list.extend(map(lambda value: value + 1,
sorted(repeats)))
            print(‘%s Ntot = %u : %u (%s)’ % (seq, len(seq),
len(repeats), ‘, ’.join(map(lambda value: str(value + 1),
sorted(repeats)))))
    def print_sums(self):
        print(‘Length\tFrequency’)
        for item in self.sums.iteritems( ):
            print(‘%u\t%u’ % item)
    def print_score(self):
        sum = 0
        for length, count in self.sums.iteritems( ):
            sum += (length ** 2) * math.sqrt(count)
        print(‘NRS = %.0f’ % (sum / len(self.seq)))
def handle_sequence(finder, name, sequence):
    finder.set_range(4 , len(sequence))
    finder.set_sequence(sequence)
    finder.work( )
    print(‘%s: Ntot = %u’ % (name, len(sequence)))
    #finder.print_repeats( )
    finder.print_sums( )
    finder.print_score( )
if len(sys.argv) != 2:
    print(‘Usage: %s FILENAME’ % sys.argv[0])
    sys.exit(1)
finder = NRSCalculator( )
with open(sys.argv[1], ‘r’) as infile:
    name = ‘Unnamed’
    seq = ‘ ’
    for line in infile:
        line = line.strip( )
        if line.startswith(‘>’):
            if len(seq) > 0:
                handle_sequence(finder, name, seq)
            name = line
            seq = ‘ ’
            continue
        seq += line.upper( )
    handle_sequence(finder, name, seq)
```

Furthermore, the invention also relates to a nucleotide sequence that comprises nucleotide repeats, wherein said repeats have a maximum length $n_{max}$, wherein $n_{max}$ is determined according to the formula $$n_{max} \leq 17 + \frac{N_{tot}}{600}$$

and wherein $N_{tot}$ is the total length of said nucleotide sequence. The term "maximum length" or "maximal length" or "$n_{max}$" as used herein defines the number of nucleotides of the longest contiguous part/stretch/sequence of nucleotides that is present in at least two copies within said nucleotide sequence or nucleic acid molecule. In other words, the term "maximum length" or "maximal length" or "$n_{max}$" as used herein means that the nucleotide sequence of the nucleic acid molecule according to this invention has no repeats which are longer than this length.

It is demonstrated in the appended examples that exemplary nucleic acid molecules of the invention comprise only few repeats, e.g. of a length of 14 nucleotides; see e.g. appended Example 2. As explained above, the repeat analysis can be performed with any suitable tool such as the NRS analysis provided herein, manually or with the aid of generic software programs such as the dot plot analysis, for example using Visual Gene Developer (Jung (2011) loc. cit) or the Repfind tool (Betley (2002) loc. cit). A dot plot is a visual representation of the similarities between two sequences.

In the appended examples the nucleotide sequences provided herein were aligned to themselves. Each axis of a rectangular array represents one of the two (overall identical) nucleotide sequences to be compared. All positions from the first input sequence are compared with all positions from the second input sequence and scored, using a specified substitution matrix. This produces a matrix of scores from which local regions of similarity/identity (corresponding to diagonals in the dot plot) are identified. A repeat window/threshold of user-specified length is moved along all possible diagonals. Each position in the repeat window/threshold corresponds to a pair-wise score from the scoring matrix. The score for the entire window is the sum of the scores for individual positions within it. If the window score is above the user-defined threshold, then a line is plotted in the dot plot corresponding to the window (see e.g., emboss.sourceforge.net/apps/cvs/emboss/apps/dotmatcher.html).

The dot plot analysis is employed in the appended examples, e.g. Example 3, in order to analyze the repetitiveness of the nucleotide sequences of the nucleic acid molecules. It is proven therein that the inventive nucleic acid molecules, e.g., SEQ ID NO: 36 (termed PA #3b(200) herein) or SEQ ID NO: 28 (termed PA #1b herein), have only a few scattered 14 nucleotide repeats within the entire length of 600 nucleotides in case a repeat window/threshold of 14 is applied. An increase of the repeat window/threshold of 14 by one nucleotide, i.e., a repeat window/threshold of 15 nucleotides, reveals no further repeats within the whole nucleotide sequence analyzed (see FIGS. 2A-2E and Example 3). This means that the maximal length of the repeat within the entire nucleic acid sequence investigated has a length of 14 nucleotides (also including shorter repeats). Generally, one can assume that the shorter such nucleotide repeats are, the less they play a detrimental role for genetic stability.

Yet, nucleic acid molecules encoding proline/alanine-rich sequences disclosed in the prior art show longer and/or more repeat sequences if a repeat window/threshold of, for example, 14 or 15 nucleotides is applied as used in the appended Examples (see Example 3). For example, the proline/alanine-rich sequence disclosed in WO 2011/144756 (SEQ ID NO: 15; termed PA #3a(200) herein) possesses multiple nucleotide repeats of length 60, which are consecutive and even overlapping and thus give rise to the large number of long parallel lines. Further nucleic acid molecules disclosed in the prior art such as PAS #1a(600) as shown in SEQ ID NO: 12 and as disclosed in WO 2008/155134, an $[(AP)_5]_n$ multimer as shown in SEQ ID NO: 16 and as disclosed in US2006/0252120, or the large tegument protein of Macacine herpesvirus 1 as shown in SEQ ID NO: 18 and as disclosed in GenBank entry AAP41454.1 also document the highly repetitive nature of these nucleotide sequences.

This is in stark contrast to the nucleic acid molecules of the present invention, which demonstrate low repetitiveness on the nucleotide sequence level. When, for example, the number of repeats of the prior art sequence PA #3a(200) (SEQ ID NO: 15) is compared, using a repeat window/threshold of 14 nucleotides, to the number of repeats of a low repetitive nucleotide sequence of the invention, PA #3b(200) (SEQ ID NO: 36), it can be observed that the sequence of the invention has 29 repeats (per 600 nucleotide residues) compared to many more than 100 repeats (per 600 nucleotide residues) of the prior art sequence. If a window of 15 nucleotides is applied, the exemplary analyzed nucleic acid molecule or the nucleotide sequence of the invention does not comprise any repeats. In contrast, the nucleic acid molecules of the prior art reveal numerous repeats with a length of 15 nucleotides and more. As proven in the appended examples, a repeat window/threshold of 14 to 20, e.g. 14, 15, 16, 17, 18, 19 or 20 nucleotides, in particular, is suitable to confirm that a nucleic acid molecule of the invention has a low repetitive nucleotide sequence. It is appreciated that the length of the repeat window/threshold inversely correlates with the number of repeats that will be identified in a specific nucleotide sequence. For example, if the repeat window/threshold is "1" the number of repeats may equal the number of all nucleotide residues (A, T, G and/or C) in a nucleotide sequence (provided that each type of nucleotide occurring in the analyzed sequence is present in at least two copies). If the length of the repeat window/threshold increases, the number of repeats in the analyzed nucleotide sequence will decrease in a sequence-specific manner. Consequently, also the "low repetitive" nucleotide sequences of the invention can contain repeats; yet, compared to prior art sequences these are shorter and fewer if the same parameters are applied for analysis.

Therefore, the nucleic acid molecule(s) provided herein comprise(s) repeats of a maximum length of 14, 15, 16, 17, about 18, about 19, about 20, about 21, about 25, about 30, about 35, about 40, about 45, about 50 or about 55 nucleotides. Furthermore, the nucleic acid molecule provided herein comprises repeats of a maximum length of about 17 nucleotides to a maximum length of about 55 nucleotides. In the context of the maximum length of the repeat, the term "about" means that the maximal repeat length is +/−4 nucleotides of the indicated repeat length. In other words, in this context, "about" refers to a range, wherein the length of the repeat can be 4 nucleotides longer or shorter than the indicated repeat length. For example, a maximum repeat length of about 55 nucleotides refers to a nucleotide sequence comprising repeats of a maximum length of 51 to 59 nucleotides. Furthermore, a maximum repeat length of about 17 nucleotides refers to a nucleotide sequence comprising repeats of a maximum length of 13 to 21 nucleotides.

Furthermore, the invention relates to a nucleic acid molecule comprising repeats of a maximum length of 59 nucleotides, preferably 54 nucleotides, more preferably 50 nucleotides, more preferably 48 nucleotides, more preferably 40 nucleotides, more preferably 36 nucleotides, more preferably 35 nucleotides, more preferably 30 nucleotides, more preferably 25 nucleotides, more preferably 24 nucleotides, more preferably 21 nucleotides, more preferably 20 nucleotides, more preferably 19 nucleotides, more preferably 18 nucleotides, more preferably 16 nucleotides, more preferably 15 nucleotides, more preferably 14 nucleotides, or most preferably 17 nucleotides.

As used herein, a nucleic acid molecule comprising repeats of a maximum length of, for example, 17 nucleotides relates to a nucleic acid molecule comprising repeat sequences with lengths of 1, 2, 3, 4, 5, 6, 7, 8, 9, 10, 11, 12, 13, 14, 15, 16 or 17 nucleotides. Likewise, the nucleic acid molecule comprising repeats of a maximum length of 14 nucleotides relates to a nucleic acid molecule comprising repeats up to 14 nucleotides, i.e., "≤14 nucleotides" or "1, 2, 3, 4, 5, 6, 7, 8, 9, 10, 11, 12, 13 or 14 nucleotides". In other words, the nucleic acid molecule comprising repeats of a maximum length of 14 nucleotides does not comprise repeats that are longer than 14 nucleotides, i.e., ">14 nucleotides".

The invention furthermore relates to a low repetitive nucleic acid molecule, wherein low repetitive means that a nucleotide sequence stretch which repeatedly occurs within a longer nucleotide sequence encoding a repetitive amino acid sequence corresponds to maximally 0.05%, preferably 0.1%, more preferably 0.5%, more preferably 1%, more preferably 2%, more preferably 3%, more preferably 4%, more preferably 5%, more preferably 6%, more preferably 7%, more preferably 8%, more preferably 9%, more preferably 10%, more preferably 15%, more preferably 20%, more preferably 25%, more preferably 30%, more preferably 40%, or most preferably 50% of the length of the nucleotide sequence that encodes the repeated amino acid sequence stretch. In other words, the nucleic acid of the present invention comprises repeats, wherein said repeats have a maximum length corresponding to 0.05%, preferably 0.1%, more preferably 0.5%, more preferably 1%, more preferably 2%, more preferably 3%, more preferably 4%, more preferably 5%, more preferably 6%, more preferably 7%, more preferably 8%, more preferably 9%, more preferably 10%, more preferably 15%, more preferably 20%, more preferably 25%, more preferably 30%, more preferably 40%, or most preferably 50% of the length of said nucleotide sequence encoding the amino acid sequence repeat in the polypeptide consisting of proline, alanine and, optionally, serine.

It is evident that the present invention does not only provide novel and inventive nucleotide sequences encoding PA-rich sequences and having a length of at least 300 nucleotides (corresponding to 100 amino acid residues) but the present invention also provides for selection means and methods for recombinant and/or synthetic nucleic acid molecules leading to genetically stable sequences and/or allowing convenient cloning, sequencing and/or amplification. This selection method is based on the NRS provided herein and/or the maximal repeat length described herein. Accordingly, the present invention relates to a method for selecting a genetically stable nucleic acid molecule, wherein said nucleic acid molecule comprises a nucleotide sequence encoding a polypeptide consisting of proline, alanine and, optionally, serine, wherein said nucleotide sequence has a length of at least 300 nucleotides, the method comprising a step of selecting a nucleic acid molecule comprising a nucleotide sequence having a Nucleotide Repeat Score (NRS) lower than 50,000, wherein said Nucleotide Repeat Score (NRS) is determined according to the formula provided herein above. Furthermore, the present invention relates to a method for selecting a genetically stable nucleic acid molecule, wherein said nucleic acid molecule comprises a nucleotide sequence encoding a polypeptide consisting of proline, alanine and, optionally, serine, the method comprising a step of selecting said nucleotide sequence comprising repeats having a maximum length of $n_{max}$. Furthermore, the present invention relates to a method for selecting a genetically stable nucleic acid molecule, wherein said nucleic acid molecule comprises a nucleotide sequence encoding a polypeptide consisting of proline, alanine and, optionally, serine, the method comprising a step of selecting said nucleotide sequence comprising repeats of a maximum length of about 17 nucleotides to a maximum length of about 55 nucleotides. The embodiments and the parameters of the NRS formula and the low repetitive nucleotide sequences provided herein above in the context of the inventive nucleic acids encoding PA-rich sequences apply, mutatis mutandis, for the herein provided and illustrated selection methods for genetically stable nucleic acid molecules encoding PA-rich sequences as well as for the further embodiments.

Herein, it was surprisingly found and demonstrated that the inventive nucleic acid molecules have an enhanced in vivo stability. As shown in the appended illustrative examples, e.g., Example 6, the nucleic acid molecules provided herein are more stable than nucleic acid molecules comprising more repetitive nucleotide sequences. Example 6 compares nucleic acid molecules encoding polypeptides consisting of proline, alanine and serine that differ in the repetitivity of the nucleotide sequences. The inventive nucleic acid molecules comprising low repetitive nucleotide sequences provided herein (see also FIGS. 2B-2C), e.g., as given in SEQ ID NO: 50, have a higher genetic stability compared to highly repetitive nucleotide sequences such as given in the prior art, e.g., SEQ ID NO: 51. Thus, the term "in vivo stability" as used herein refers particularly to "genetic stability". The term "genetic stability" as used herein means that the nucleic acid is stably maintained in the host cell and that the sequence is not genetically modified, e.g., by mutation, insertion or deletion. As used herein, mutations refer to changes in the nucleotide sequence, e.g., substitutions, deletions, insertions or extensions. It is shown in the appended examples that nucleic acid molecules comprising highly repetitive nucleotide sequences are prone to deletions or shortening; see, e.g., Example 6. The nucleic acid molecules comprising highly repetitive nucleotide sequences/repetitive gene cassettes have thus an inferior genetic stability, which may arise from recombination events during cell division, for example. The parameters NRS or $n_{max}$ defined herein provide objective means to distinguish highly repetitive nucleotide sequences such as those from the prior art, having high numbers for NRS and/or $n_{max}$, from low repetitive nucleotide sequences of the invention, which have low numbers for NRS and/or $n_{max}$.

The nucleic acid molecules provided herein encode polypeptides comprising repetitive amino acid sequences. Notably, the encoded repetitive amino acid sequence may also be part/fragment of a fusion protein. For example, the nucleic acid molecule disclosed herein can encode a polypeptide consisting of proline/alanine-rich repeats, e.g. repeats consisting of proline, alanine and, optionally, serine. The proline/alanine-rich polypeptide can form a random coil. In certain aspects, the nucleic acid molecule disclosed herein encodes a polypeptide consisting of proline, alanine and serine, wherein said polypeptide forms a random coil. In certain aspects, the nucleic acid molecule disclosed herein encodes a polypeptide consisting of proline and alanine, wherein said polypeptide forms a random coil.

In particular, the nucleotide sequence encodes a polypeptide consisting of proline, alanine and, optionally, serine. This encoded polypeptide forms a random coil. The nucleotide sequence is comprised in the nucleic acid molecule provided herein. Thus, in certain aspects, the nucleic acid molecule disclosed herein encodes a polypeptide comprising a repetitive amino acid sequence and consisting of proline, alanine and, optionally, serine, wherein said polypeptide forms a random coil. In certain aspects, the nucleic acid molecule disclosed herein encodes a polypeptide comprising a repetitive amino acid sequence and consisting of proline, alanine and serine, wherein said polypeptide forms a random coil. In certain aspects, the nucleic acid molecule disclosed herein encodes a polypeptide comprising a repetitive amino acid sequence and consisting of proline and alanine, wherein said polypeptide forms a random coil.

As used herein, the term "random coil" relates to any conformation of a polymeric molecule, including amino acid polymers, in particular polypeptides made of L-amino acids, in which the individual monomeric elements that form said polymeric structure are essentially randomly oriented towards the adjacent monomeric element or elements while still being chemically linked. In particular, the encoded polypeptide or amino acid polymer adopting/having/forming "random coil conformation" substantially lacks a defined secondary and tertiary structure. The nature of the encoded polypeptide random coils and their methods of experimental identification are known to the person skilled in the art and have been described in the scientific literature (Cantor (1980) Biophysical Chemistry, 2nd ed., W. H. Freeman and Company, New York; Creighton (1993) Proteins—Structures and Molecular Properties, 2nd ed., W. H. Freeman and Company, New York; Smith (1996) Fold. Des. 1:R95-R106) and patent literature, e.g., WO2011/144756 and WO2008/155134.

The encoded random coil polypeptides of the present invention adopt/form a random coil conformation, for example, in aqueous solution and/or at physiological conditions. The term "physiological conditions" is known in the art and relates to those conditions in which proteins usually adopt their native, folded conformation. More specifically, the term "physiological conditions" relates to the environmental biophysical parameters as they are typically valid for higher forms of life and, particularly, for mammals, most preferably human beings. The term "physiological conditions" may relate to the biochemical and biophysical parameters as they are normally found in the body, in particular in body fluids, of mammals and in particular in humans. Said "physiological conditions" may relate to the corresponding parameters found in the healthy body as well as the parameters found under disease conditions or in human patients. For example, a sick mammal or human patient may have a higher, yet "physiological" body temperature (i.e., temperature condition) when said mammal or said human suffers from fever. With respect to "physiological conditions" at which proteins adopt their native conformation/state, the most important parameters are temperature (37° C. for the healthy human body), pH (7.35-7.45 for human blood), osmolarity (280-300 mmol/kg $H_2O$), and, if necessary, general protein content (66-85 g/l serum).

Yet, the person skilled in the art is aware that at physiological conditions these parameters may vary, e.g. the temperature, pH, osmolarity, and protein content may be different in given body or tissue fluids such as blood, liquor cerebrospinalis, peritoneal fluid and lymph (Klinke (2005) Physiologie, 4th edition, Georg Thieme Verlag, Stuttgart). For example, in the liquor cerebrospinalis the osmolarity may be around 290 mmol/kg $H_2O$ and the protein concentration may be between 0.15 g/l and 0.45 g/l while in the lymph the pH may be around 7.4 and the protein content may be between 3 g/l and 5 g/l. When determining whether an encoded polypeptide/amino acid sequence forms/adopts random coil conformation under experimental conditions, the biophysical parameters such as temperature, pH, osmolarity and protein content may be different from the physiological conditions normally found in vivo. Temperatures between 1° C. and 42° C. or preferably 4° C. to 25° C. may be considered useful to test and/or verify the biophysical properties and biological activity of a protein under physiological conditions in vitro.

Several buffers, which may include solvents and/or excipients for pharmaceutical compositions, are considered to represent "physiological solutions"/"physiological conditions" in vitro, in particular, in experimental settings, for example in the context of CD measurements or other methods that allow the person skilled in the art to determine the structural properties of a protein/amino acid sequence. Examples of such buffers are, e.g., phosphate-buffered saline (PBS, e.g.: 115 mM NaCl, 4 mM $KH_2PO_4$, 16 mM $Na_2HPO_4$ pH 7.4), Tris buffers, acetate buffers, citrate buffers or similar buffers. Generally, the pH of a buffer representing "physiological solution conditions" should lie in a range from 6.5 to 8.5, preferably in a range from 7.0 to 8.0, most preferably in a range from 7.2 to 7.7, and the osmolarity should lie in a range from 10 to 1000 mmol/kg $H_2O$, more preferably in a range from 50 to 500 mmol/kg $H_2O$ and most preferably in a range from 200 to 350 mmol/kg $H_2O$. Optionally, the protein content of a physiological solution may lie in a range from 0 to 100 g/1, neglecting the investigated protein adopting random coil conformation itself; furthermore, typical stabilizing proteins may be present, for example human or bovine serum albumin.

The polypeptides encoded by the nucleic acid molecules of the invention not only form random coil conformation under physiological conditions but, more generally, in aqueous solution; e.g., c.f. WO2011/144756. The term "aqueous solution" is well known in the art. An "aqueous solution" may be a solution with a water ($H_2O$) content of at least about 20%, of at least about 30%, of at least about 40%, of at least about 50%, of at least about 60%, of at least about 70%, of at least about 80% or of at least about 90% $H_2O$ (weight/weight). Accordingly, the encoded polypeptides provided in the present invention may form random coil conformation in aqueous solution, possibly containing other miscible solvents, or in aqueous dispersions with a wider range of temperatures, pH values, osmolarities or protein content. This is particularly relevant for applications of the random coil polypeptide outside medical therapy or in vivo diagnostics, for example in cosmetics, nutrition or food technology.

It is also envisaged in the context of this invention that the random coil conformation of the encoded polypeptide is maintained in pharmaceutical compositions like liquid pharmaceuticals/biologicals or lyophilized pharmaceutical compositions. This is particularly important in the context of the encoded biologically active proteins or the drug conjugates provided herein comprising, inter alia, the random coil polypeptide. Preferably, "physiological conditions" are to be used in corresponding buffer systems, solvents and/or excipients. Yet, for example, in lyophilized or dried compositions (like, e.g., pharmaceutical compositions/biologicals), it is envisaged that the random coil conformation of the herein provided encoded random coil polypeptide may transiently not be present and/or cannot be detected. However, said encoded random coil polypeptide will adopt/form its random coil again after reconstitution in corresponding buffers/solutions/excipients/solvents or after administration to the body of a patient or of an animal.

In certain aspects of the present invention, the nucleic acid molecules disclosed herein encode polypeptides that (mainly or exclusively) consist of proline, alanine and, optionally, serine, wherein no more than 9 consecutive amino acid residues are identical. Such encoded polypeptides form a random coil. In a certain aspect, the encoded amino acid sequences/polypeptides adopting random coil conformation may comprise a plurality of amino acid repeats, wherein said "amino acid repeats" mainly or exclusively consist of proline, alanine and, optionally, serine amino acid residues, wherein no more than 9 consecutive amino acid residues are identical. In a certain aspect, the encoded amino acid sequences/polypeptides adopting random coil conformation (the random coil polypeptide as defined herein) may comprise a plurality of amino acid repeats, wherein said "amino acid repeats" mainly or exclusively consist of proline, alanine and serine amino acid residues, wherein no more than 9 consecutive amino acid residues are identical. In a certain aspect, the encoded amino acid sequences/polypeptides adopting random coil conformation may comprise a plurality of amino acid repeats, wherein said "amino acid repeats" mainly or exclusively consist of proline and alanine amino acid residues, wherein no more than 9 consecutive amino acid residues are identical.

In preferred aspects, the nucleic acid molecule disclosed herein encodes a polypeptide comprising a repetitive amino acid sequence with a plurality of amino acid repeats, wherein no more than 8 consecutive amino acid residues are identical and wherein said polypeptide forms a random coil. Preferably, the nucleic acid molecule disclosed herein encodes a polypeptide comprising a repetitive amino acid sequence with a plurality of amino acid repeats, wherein no more than 7 consecutive amino acid residues are identical and wherein said polypeptide forms a random coil. More preferably, the nucleic acid molecule disclosed herein encodes a polypeptide comprising a repetitive amino acid sequence with a plurality of amino acid repeats, wherein no more than 6 consecutive amino acid residues are identical and wherein said polypeptide forms a random coil. Particularly preferably, the nucleic acid molecule disclosed herein encodes a polypeptide comprising a repetitive amino acid sequence with a plurality of amino acid repeats, wherein no more than 5 consecutive amino acid residues are identical and wherein said polypeptide forms a random coil. More particularly preferably, the nucleic acid molecule disclosed herein encodes a polypeptide comprising a repetitive amino acid sequence with a plurality of amino acid repeats, wherein no more than 4 consecutive amino acid residues are identical and wherein said polypeptide forms a random coil. Most preferably, the nucleic acid molecule disclosed herein encodes a polypeptide comprising a repetitive amino acid sequence with a plurality of amino acid repeats, wherein no more than 3 consecutive amino acid residues are identical and wherein said polypeptide forms a random coil.

A non-limiting example of an amino acid repeat consisting exclusively of proline, alanine and serine residues is provided herein below; see, e.g. SEQ ID NO: 6. A non-limiting example of an encoded amino acid repeat consisting exclusively of proline and alanine residues is provided herein below; see, e.g. SEQ ID NO: 8. The encoded polypeptide may comprise multiple copies of the same sequence or different sequences.

The nucleic acid molecule disclosed herein encodes a polypeptide consisting mainly or exclusively of the three amino acid residues proline (Pro, P), alanine (Ala, A) and, optionally, serine (Ser, S). The term "optionally" as used herein means that the encoded polypeptide of the present invention either consists mainly or exclusively of proline, alanine and serine or consists mainly or exclusively of proline and alanine. The encoded polypeptide consisting mainly or exclusively of the three amino acid residues proline, alanine and serine is referred to herein as "PAS" polypeptide. The encoded polypeptide consisting mainly or exclusively of the two amino acid residues proline and alanine is referred to herein as "PA" polypeptide. A non-limiting example of an encoded polypeptide consisting of proline and alanine is given in SEQ ID NO: 8. A non-limiting example of an encoded polypeptide consisting of proline, alanine and serine is given in SEQ ID NO: 6. The term "mainly" as used herein means that preferably at least about 90% or at least about 95% of the encoded amino acids are proline, alanine and, optionally, serine, whereby proline, alanine and serine in sum constitute the majority but may not be the only amino acid residues; therefore, the encoded amino acid sequences are not necessarily 100% proline, alanine and, optionally, serine. Hence, the encoded polypeptides/amino acid sequences may also comprise other amino acids than proline, alanine and, optionally, serine as minor constituents as long as the amino acid sequence forms/adopts/has the random coil conformation. Such a random coil conformation can be easily determined by means and methods described herein. Accordingly, the present invention relates in one embodiment to a nucleic acid molecule that encodes a random coil polypeptide whereby the amino acid sequence consists mainly of proline, alanine and, optionally, serine.

In case the encoded polypeptide consists of proline and alanine, said proline residues constitute more than about 10% and less than about 75% of said encoded amino acid sequence. Accordingly, the encoded random coil polypeptide consists mainly of proline and alanine, wherein the proline residues constitute more than about 10% and less than 75% of the amino acid sequence. The alanine residues comprise the remaining at least 25% to 90% of said amino acid sequence.

Preferably, the encoded amino acid sequence comprises more than about 10%, preferably more than about 12%, more preferably more than about 14%, 18%, 20%, more preferably more than about 22%, 23%, 24%, or 25%, more preferably more than about 27%, 29%, or 30%, more preferably more than about 32%, 33%, or 34% and most preferably more than about 35% proline residues. The amino acid sequence preferably comprises less than about 75%, more preferably less than 70%, more preferably less than 65%, more preferably less than 60%, more preferably less than 55%, more preferably less than 50% proline residues, wherein the lower values are preferred. Even more preferably, the amino acid sequence comprises less than about 48%, 46%, 44%, 42% proline residues. More preferred are amino acid sequences comprising less than about 41%, 40%, 39% 38%, 37% or 36% proline residues, whereby lower values are preferred. More preferred are amino acid sequences comprising less than about 34%, 32%, or 30%. More preferred are amino acid sequences comprising less than about 28%, 26% or 25%. Most preferably, the amino acid sequences comprise less than about 35% proline residues.

Vice versa, the amino acid sequence preferably comprises less than about 90%, more preferably less than 88%, 86%, 84%, 82% or 80% alanine residues, wherein the lower values are preferred. More preferably, the amino acid sequence comprises less than about 79%, 78%, 77%, 76% alanine residues, whereby lower values are preferred. More preferably, the amino acid sequence comprises less than about 74%, 72%, or 70% alanine residues, whereby lower values are preferred. More preferably, the amino acid sequence comprises less than about 69%, 67%, or 65% alanine residues, whereby lower values are preferred. Most preferably, the amino acid sequence comprises less than about 75% alanine residues. Also preferred herein is an amino acid sequence comprising more than about 25%, preferably more than about 30%, more preferably more than about 35%, more preferably more than about 40%, more preferably more than about 45%, more preferably more than about 50%, more preferably more than about 52%, 54%, 56%, 58% or 59% alanine residues, wherein the higher values are preferred. Even more preferably, the amino acid sequence comprises more than about 60%, 61%, 62%, 63% or 64% alanine residues. More preferably, the amino acid sequence comprises more than about 66%, 67%, 69%, or 70% alanine residues. More preferably, the amino acid sequence comprises more than about 72%, 74%, or 75%, alanine residues. Most preferably the amino acid sequence comprises more than about 65% alanine residues.

Accordingly, the random coil polypeptide may comprise an amino acid sequence consisting of about 25% or 30% proline residues and about 75% or 70%, respectively, alanine residues. Alternatively, the random coil polypeptide may comprise an amino acid sequence consisting of about 35% proline residues and about 65% alanine residues. The term “about X %” as used herein above is not limited to the concise number of the percentage, but also comprises values of 10% to 20% additional or 10% to 20% less residues. For example, the term 10% may also relate to 11% or 12% and to 9% or 8%, respectively.

In case the encoded polypeptide consists of proline, alanine and serine, said proline residues constitute more than about 4% and less than about 40% of said encoded amino acid sequence. The alanine and the serine residues constitute the remaining amount of said amino acid sequence.

Preferably, the encoded amino acid sequence comprises more than about 4%, preferably more than about 6%, more preferably more than about 10%, more preferably more than about 15%, more preferably more than about 20%, more preferably more than about 22%, 23% or 24%, more preferably more than about 26%, 29%, or 30%, more preferably more than about 31%, 32%, 33%, 34% or 35% and most preferably more than about 25% proline residues. The encoded amino acid sequence preferably comprises less than about 40%, more preferably less than 38%, 35%, 30%, 26% proline residues, wherein the lower values are preferred.

The encoded amino acid sequence preferably comprises less than about 95%, more preferably less than 90%, 86%, 84%, 82% or 80% alanine residues, wherein the lower values are preferred. More preferably, the encoded amino acid sequence comprises less than about 79%, 78%, 77%, 76% alanine residues, whereby lower values are preferred. More preferably, the encoded amino acid sequence comprises less than about 75%, 73%, 71%, or 70% alanine residues, whereby lower values are preferred. More preferably, the encoded amino acid sequence comprises less than about 69%, 67%, 66%, or 65% alanine residues, whereby lower values are preferred. More preferably, the encoded amino acid sequence comprises less than about 64%, 63%, 62%, or 60% alanine residues, whereby lower values are preferred. More preferably, the encoded amino acid sequence comprises less than about 59%, 57%, 56%, or 55% alanine residues, whereby lower values are preferred. More preferably, the encoded amino acid sequence comprises less than about 54%, 53%, or 51%, alanine residues, whereby lower values are preferred. Most preferably, the encoded amino acid sequence comprises less than about 50% alanine residues.

Also preferred herein is an encoded amino acid sequence comprising more than about 10%, preferably more than about 15%, 17%, 19%, or 20%, more preferably more than about 22%, 24%, or 25%, more preferably more than about 27%, 29%, or 30%, more preferably more than about 32%, 34% or 35%, more preferably more than about 37%, 39%, or 40%, more preferably more than about 42%, 44% or 45%, more preferably more than about 46%, 47% or 49% alanine residues, wherein the higher values are preferred. Most preferably, the encoded amino acid sequence comprises more than about 50 alanine residues. As mentioned above, the serine residues comprise the remaining amount of said amino acid sequence.

Accordingly, the encoded random coil polypeptide may comprise an amino acid sequence consisting of about 35% proline residues, about 50% alanine and 15% serine residues. Exemplary nucleotide sequences and the encoded polypeptides thereof can be found in Table 1. The term “about X %” as used herein above is not limited to the concise number of the percentage, but also comprises values of 10% to 20% additional or 10% to 20% less residues. For example, the term 10% may also relate to 11% or 12% or to 9% and 8%, respectively.

However, as mentioned above and further detailed herein below said encoded random coil polypeptide, and, in particular, the amino acid sequence may also comprise additional amino acids differing from proline, alanine and, optionally, serine as minor constituents. As already discussed herein above, said minor constituent(s), i.e. amino acid(s) different from proline, alanine or, optionally, serine, may comprise less than about 10% or less than about 5% of the encoded random coil polypeptide of this invention.

The skilled person is aware that the encoded amino acid sequence/polypeptide may also form random coil conformation when other residues than proline, alanine and, optionally, serine are comprised as a minor constituent in said amino acid sequence/polypeptide (polypeptide fragment). The term “minor constituent” as used herein means that maximally 5% or maximally 10% amino acid residues are different from proline, alanine or serine in the encoded random coil polypeptides of this invention. This means that maximally 10 of 100 amino acids may be different from proline, alanine and, optionally, serine, preferably maximally 8%, i.e. maximally 8 of 100 amino acids may be different from proline, alanine and, optionally, serine, more preferably maximally 6%, i.e. maximally 6 of 100 amino acids may be different from proline, alanine and, optionally, serine, even more preferably maximally 5%, i.e. maximally 5 of 100 amino acids may be different from proline, alanine and, optionally, serine, particularly preferably maximally 4%, i.e. maximally 4 of 100 amino acids may be different from proline, alanine and, optionally, serine, more particularly preferably maximally 3%, i.e. maximally 3 of 100 amino acids may be different from proline, alanine and, optionally, serine, even more particularly preferably maximally 2%, i.e. maximally 2 of 100 amino acids may be different from proline, alanine and, optionally, serine and most preferably maximally 1%, i.e. maximally 1 of 100 of the amino acids that are comprised in the random coil polypeptide may be different from proline, alanine and, optionally, serine. Said amino acids different from proline, alanine and, optionally, serine may be selected from the group consisting of Arg, Asn, Asp, Cys, Gln, Glu, Gly, His, Ile, Leu, Lys, Met, Phe, Thr, Trp, Tyr, and Val, including posttranslationally modified amino acids or non-natural amino acids (see, e.g., Budisa (2004) Angew Chem Int Ed Engl 43:6426-6463; Young (2010) J Biol Chem 285:11039-11044; Liu (2010) Annu Rev Biochem 79:413-444; Wagner (1983) AngewChem Int Ed Engl 22:816-828; Walsh (2010) Drug Discov Today 15: 773-780. In certain cases PA-rich sequences can also comprise Ser as a minor constuent. For example, in case the encoded random coil polypeptide consists of proline and alanine, serine can also be considered as minor constituent.

Generally, it is preferred herein that these “minor” amino acids (other than proline, alanine and, optionally, serine) are not present in the encoded random coil polypeptide as described herein or the encoded random coil polypeptide as part/fragment of a fusion protein. In accordance with the invention, the encoded random coil polypeptide/amino acid sequence may, in particular, consist exclusively of proline, alanine and, optionally, serine residues (i.e. no other amino acid residues are present in the encoded random coil polypeptide or in the amino acid sequence).

In the context of the present invention, the nucleic acid molecule encoding the polypeptide consisting of proline, alanine and, optionally, serine or the nucleotide sequence encoding the polypeptide consisting of proline, alanine and, optionally, serine may consist of at least 300 nucleotides. However, it is evident for a person skilled in the art that the length of the nucleotide sequence provided herein is not limited as long as the encoded polypeptide forms a random coil. The appended examples document that the nucleic acid molecules provided herein comprising low repetitive nucleotide sequences can surprisingly be synthesized regardless of their lengths. It is proven herein that, for example, nucleotide sequences having a length of about 600 nucleotides can be synthesized. Such nucleotide sequences can be employed to assemble even longer nucleotide sequences. In other words, these nucleotide sequences can be employed as units/modules/building blocks to combine/assemble longer nucleotide sequences encompassed in the nucleic acid molecule of the invention. In one embodiment, a single nucleotide sequence unit/module/building block also corresponds to a nucleic acid molecule of the invention.

According to this invention, identical or non-identical nucleotide sequence units/modules/building blocks can be combined with each other as long as the assembled nucleotide sequence encodes a polypeptide consisting of proline, alanine and, optionally, serine. Furthermore, according to this invention, identical or non-identical nucleotide sequence units/modules/building blocks can be combined with each other as long as the assembled nucleotide sequence encoding a polypeptide with repetitive amino acid sequence forms a random coil. As mentioned above, it is particularly advantageous to assemble the nucleic acid molecules provided herein comprising low repetitive nucleotide sequences by employing these units/modules/building blocks. It is documented herein below that long nucleotide sequences with at least a length of 2400 nucleotides can be assembled. The inventive nucleotide sequences can be combined with each other or with additional non-identical nucleotide sequences. Thus, the nucleic acid molecule provided herein may be assembled from identical or non-identical nucleotide sequences, wherein said nucleotide sequences are low repetitive nucleotide sequences. In certain aspects, the nucleic acid molecule provided herein comprises at least one nucleotide sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO:37, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 192, SEQ ID NO: 193, SEQ ID NO: 194 and SEQ ID NO: 195. As these exemplary nucleotide sequences can be employed to assemble longer nucleotide sequences, these nucleotide sequences can be termed units or modules or building blocks. Thus, it is understood herein that the nucleic acid molecules of the invention may comprise a plurality of these nucleotide modules or nucleotide sequences that are assembled into a longer nucleotide sequence, wherein said longer nucleotide sequence itself is a low repetitive nucleotide sequence as described herein above. The person skilled in the art understands that the nucleic acid molecule of the invention may also comprise fragments of the given nucleotide sequence modules. In other words, the nucleic acid molecule provided herein comprises or is at least one nucleotide sequence, or fragment thereof, selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 192, SEQ ID NO: 193, SEQ ID NO: 194 and SEQ ID NO: 195.

It is understood herein that the low repetitive nucleotide sequences or the units or modules or building blocks provided herein can be permutated or combined with each other in any combination as long as the assembled nucleotide sequence comprises a low repetitive nucleotide sequence according to the present invention. Exemplary assembled nucleotide sequences are presented herein below, e.g., SEQ ID NO: 38 or herein depicted as PAS #1f/1c/1b(600), SEQ ID NO: 39 or herein depicted as PAS #1d/1f/1c/1b(800), SEQ ID NO: 40 or herein depicted as PAS #1h/1e/1i(600), SEQ ID NO: 41 or herein depicted as PAS #1j/1h/1e/1i (800), SEQ ID NO: 42 herein depicted as PA #1d/1c/1b (600), SEQ ID NO: 43 or herein depicted as PA #1i/1h/1g/1f(800), SEQ ID NO: 44 or herein depicted as PA #1e/1d/1c/1b(800), SEQ ID NO: 45 or herein depicted as PA #1i/1h/1g/1f/1e/1d/1c/1b(1600), SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173; SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 184, SEQ ID NO: 185, SEQ ID NO: 186, SEQ ID NO: 187, SEQ ID NO: 188, SEQ ID NO: 189, SEQ ID NO: 190, and/or SEQ ID NO: 191.

Therefore, the nucleic acid molecule provided herein has, comprises or is said assembled nucleotide sequence in preferred aspects of the invention.

As documented in the appended examples (see Example 1), a long nucleotide sequence according to the invention may be assembled in a step-wise manner. The assembled nucleotide sequence maintains the low repetitivity. It is demonstrated in the appended examples how an exemplary nucleotide sequence as given in SEQ ID NO: 39 or herein depicted as PAS #1d/1f/1c/1b(800) comprising 2400 nucleotides and encoding 800 amino acids is assembled.

It is understood herein that these assembled nucleotide sequences are low repetitive nucleotide sequences. For example, the appended examples document that the exemplary nucleotide sequence as given in SEQ ID NO: 39 or depicted herein as PAS #1d/1f/1c/1b(800) sequence shows no repeats in case of a repeat window of 15, or only one single 14 nucleotide repeat, within the entire nucleotide sequence of 2400 nucleotides; see FIGS. 2B-2C. For comparison, the long nucleotide sequence as disclosed in the prior art comprises repetitive nucleotide sequences as demonstrated exemplarily in case of PAS #1a(600) given herein as SEQ ID NO: 12. Accordingly, the long nucleic acid molecules according to the present invention have low repetitive nucleotide sequences and thus overcome technical challenges associated with repeated nucleotide stretches as mentioned above.

Nucleic acid molecules and related nucleic acid molecules (like variants, fragments, nucleic acid molecules having an identity of at least 66%, e.g. at least 66.6% to the specific nucleotide sequences encoding a polypeptide consisting of proline and alanine; or like variants, fragments, nucleic acid molecules having an identity of at least 56%, e.g. at least 56.6% to the specific nucleotide sequences encoding a polypeptide consisting of proline, alanine and serine as provided and defined herein, and the like) comprise or are low repetitive nucleotide sequences encoding the polypeptide, which forms the random coil conformation increasing the in vivo/vitro stability.

Nucleic acid molecules and related nucleic acid molecules have, comprise or are low repetitive nucleotide sequences encoding polypeptides that form random coil conformation and increase the in vivo/vitro stability of a biologically or pharmacologically active protein or drug. Said related nucleic acid molecules comprise or are variants and fragments of said nucleic acid molecules. Said related nucleic acid molecules have an identity of at least 66%, e.g. at least 66.6%, to a specific nucleotide sequence encoding a polypeptide consisting of proline and alanine or having an identity of at least 56%, e.g. at least 56.6%, to a specific nucleotide sequence encoding a polypeptide consisting of proline, alanine and serine as provided and defined herein, and the like.

In certain aspects, the nucleic acid molecule comprising an orthologous/homologous/identical/similar (and thus related) nucleotide sequence encoding a polypeptide consisting of proline and alanine is at least 66%, e.g. at least 66.6% homologous/identical to the nucleotide sequence as, inter alia, shown in SEQ ID NOs: 28, 29, 30, 31, 32, 33, 34, 35, 36, 37, 42, 43, 44, 45, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 153, 154, 155, 156, 157, 158, 159, 160, 161, 162, 163, 164, 165, 166, 167, 168, 169, 170, 171, 172, 173, 192 and 193. More preferably, the nucleic acid molecule comprising the orthologous/homologous/identical/similar (and thus related) nucleotide sequence encoding a polypeptide consisting of proline and alanine is at least 68%, 70%, 75%, 80%, 85%, 90%, 92%, 93%, 94%, 95%, 96%, 97% or 98% homologous/identical to the nucleotide sequence as, inter alia, shown in 28, 29, 30, 31, 32, 33, 34, 35, 36, 37, 42, 43, 44, 45, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 153, 154, 155, 156, 157, 158, 159, 160, 161, 162, 163, 164, 165, 166, 167, 168, 169, 170, 171, 172, 173, 192 and 193, wherein the higher values are preferred. Most preferably, the nucleic acid molecule comprising the orthologous/homologous/identical/similar (and thus related) nucleotide sequence encoding a polypeptide consisting of proline and alanine is at least 99% homologous/identical/similar to the nucleotide sequence as, inter alia, shown in 28, 29, 30, 31, 32, 33, 34, 35, 36, 37, 42, 43, 44, 45, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 153, 154, 155, 156, 157, 158, 159, 160, 161, 162, 163, 164, 165, 166, 167, 168, 169, 170, 171, 172, 173, 192 and 193.

In further aspects, the nucleic acid molecule comprising an orthologous/homologous/identical/similar (and thus related) nucleotide sequence encoding a polypeptide consisting of proline, alanine and serine is at least 56%, e.g at least 56.6% homologous/identical/similar to the nucleotide sequence as, inter alia, shown in SEQ ID NOs: 19, 20, 21, 22, 23, 24, 25, 26, 27, 38, 39, 40, 41, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 174, 175, 176, 177, 178, 179, 180, 181, 182, 184, 185, 186, 187, 188, 189, 190, 191, 194 and 195. More preferably, the nucleic acid molecule comprising the orthologous/homologous/identical/similar (and thus related) nucleotide sequence encoding a polypeptide consisting of proline, alanine and serine is at least 58%, 60%, 65%, 70%, 75%, 80%, 85%, 90%, 91%, 92%, 93%, 94%, 95%, 96%, 97% or 98% homologous/identical to the nucleotide sequence as, inter alia, shown in 19, 20, 21, 22, 23, 24, 25, 26, 27, 38 39, 40, 41, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 174, 175, 176, 177, 178, 179, 180, 181, 182, 184, 185, 186, 187, 188, 189, 190, 191, 194 and 195. Most preferably, the nucleic acid molecule comprising the orthologous/homologous/identical/similar (and thus related) nucleotide sequence encoding a polypeptide consisting proline, alanine and serine is at least 99% homologous/identical/similar to the nucleotide sequence as, inter alia, shown in SEQ ID NOs: 19, 20, 21, 22, 23, 24, 25, 26, 27, 38, 39, 40, 41, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 174, 175, 176, 177, 178, 179, 180, 181, 182, 184, 185, 186, 187, 188, 189, 190, 191, 194 and 195. The above defined related nucleotide sequences can also be encompassed in longer or shorter isoforms, spliced variants or fusion constructs.

In certain aspects, the nucleic acid molecule provided herein may hybridize under stringent conditions to the complementary strand of the nucleotide sequence as, inter alia, shown in SEQ ID NOs: 19, 20, 21, 22, 23, 24, 25, 26, 27, 28, 29, 30, 31, 32, 33, 34, 35, 36, 37, 38, 39, 40, 41, 42, 43, 44, 45, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 184, 185, 186, 187, 188, 189, 190, 191, 192, 193, 194 and 195. The term "hybridization" or "hybridizes" as used herein may relate to hybridizations under stringent or non-stringent conditions. If not further specified, the conditions are preferably stringent. Said hybridization conditions may be established according to conventional protocols described, e.g., in Sambrook (2001) Molecular Cloning: A Laboratory Manual, Cold Spring Harbor Laboratory Press, 3rd ed., New York; Ausubel (1989) Current Protocols in Molecular Biology, Green Publishing Associates and Wiley Interscience, New York, or Higgins(1985)Nucleic acid hybridization, a practical approach, IRL Press Oxford, Washington D.C. The setting of suitable conditions is well within the skill of the artisan and can be determined according to protocols described in the art. Thus, the detection of only specifically hybridizing sequences will usually require stringent hybridization and washing conditions such as, for example, 0.1× saline sodium citrate buffer (SSC), 0.1% w/v SDS at 65° C. or 2×SSC, 60° C., 0.1% w/v SDS. Low stringent hybridization conditions for the detection of homologous or not exactly complementary sequences may, for example, be set at 6×SSC, 1% w/v SDS at 65° C. As is well known, the length of the nucleic acid probe and the composition of the nucleic acid to be determined constitute further parameters of the hybridization conditions.

In accordance with the present invention, the term "homology" or "percent homology" or "identical" or "percent identity" or "percentage identity" or "sequence identity" in the context of two or more nucleotide sequences refers to two or more sequences or subsequences that are the same, or that have a specified percentage of nucleotides that are the same (preferably at least 66%, e.g., at least 66.6% identity in case of the nucleic acid molecule encoding the polypeptide consisting of proline and alanine, more preferably at least 68%, 70%, 75%, 80%, 85%, 90%, 91%, 92%, 93%, 94%, 95%, 96%, 97% or 98% identity, most preferably at least 99% identity; or preferably at least 56%, e.g., at least 56.6% identity in case of the nucleic acid molecule encoding proline, alanine and serine, more preferably at least 58%, 60%, 65%, 70%, 75%, 80%, 85%, 90%, 91%, 92%, 93%, 94%, 95%, 96%, 97% or 98% identity, most preferably at least 99% identity) when compared and aligned for maximum correspondence over a window of comparison (preferably over the full length), or over a designated region as measured using a sequence comparison algorithm as known in the art, or by manual alignment and visual inspection.

Sequences having, for example, 70% to 90% or greater sequence identity may be considered to be substantially identical or similar. Such a definition also applies to the complement of a test nucleic acid sequence. Preferably, the described identity exists over a region that is at least about 15 to 25 nucleotides in length, more preferably, over a region that is at least about 50 to 100 nucleotides in length, more preferably over a region that is at least about 125 to 200 nucleotides in length, more preferably over a region that is at least about 225 to 300 nucleotides in length, even more preferably over a region that is at least about 325 to 600 nucleotides in length, even more preferably over a region that is at least about 625 to 800 nucleotides in length, and most preferably, over a region that is at least about 825 to 1200 nucleotides in length. Those having skill in the art will know how to determine percent identity between/among sequences using, for example, algorithms such as those based on CLUSTALW computer program (Thompson (1994) Nucl. Acids Res. 2:4673-4680), CLUSTAL Omega (Sievers (2014) Curr. Protoc. Bioinformatics 48:3.13.1-3.13.16) or FASTDB (Brutlag (1990) Comp App Biosci 6: 237-245). Also available to those having skill in this art are the BLAST, which stands for Basic Local Alignment Search Tool, and BLAST 2.0 algorithms (Altschul, (1997) Nucl. Acids Res. 25:3389-3402; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1992) Proc. Natl. Acad. Sci. U.S.A. 89:10915-10919) uses alignments (B) of 50, expectation (E) of 10, M=5, N=4, and a comparison of both strands.

In order to determine whether a nucleotide residue in a given nucleotide sequence corresponds to a certain position in the nucleotide sequence of, e.g., SEQ ID NOs: 19, 20, 21, 22, 23, 24, 25, 26, 27, 28, 29, 30, 31, 32, 33, 34, 35, 36, 37, 38, 39, 40, 41, 42, 43, 44, 45, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 184, 185, 186, 187, 188, 189, 190, 191, 192, 193, 194 and 195, respectively, the skilled person can use means and methods well known in the art, e.g., alignments, either manually or by using computer programs such as those mentioned herein. For example, BLAST 2.0 can be used to search for local sequence alignments. BLAST or BLAST 2.0, as discussed above, produces alignments of nucleotide sequences to determine sequence similarity. Because of the local nature of the alignments, BLAST or BLAST 2.0 is especially useful in determining exact matches or in identifying similar or identical sequences.

As shown in the appended examples, means and methods are provided herein to quickly and easily clone the long low repetitive nucleotide sequences or long low repetitive nucleic acid molecules comprising said nucleotide sequences; see, e.g., Examples 1, 2, 5, 7 and 10. As demonstrated in the appended examples, exemplary vectors are provided herein that are particularly suitable to assemble nucleotide sequences of the invention into longer constructs. As mentioned above, the nucleic acid molecules or nucleotide sequences provided herein can be assembled in a step-wise manner to build up long nucleic acid molecules or long nucleotide sequences. It is envisaged herein that the size of the assembled nucleic acid molecule or nucleotide sequence is not limited or is limited by practical circumstances, such as plasmid size or transformation/transfection efficiency, at best.

An exemplary assembly of a nucleic acid molecule comprising a low repetitive nucleotide sequence or a nucleic acid molecule encoding a repetitive amino acid sequence of proline, alanine and serine of a length of about 2400 nucleotides (encoding a polypeptide with a length of 800 amino acid residues) is demonstrated in the appended Example 2. It is shown therein that first the nucleotide sequence unit (building block) PAS #1b(200) as given in SEQ ID NO: 19, then the nucleotide sequence unit PAS #1c(200) as given in SEQ ID NO: 20, and subsequently the nucleotide sequence unit PAS #1f(200) as given in SEQ ID NO: 23, and finally the nucleotide sequence unit PAS #1d(200) as given in SEQ ID NO: 21 is cloned and assembled in the exemplary pXL2 vector. This exemplary assembled nucleic acid molecule or assembled nucleotide sequence is herein depicted as PAS #1d/1f/1c/1b(800) and is given in SEQ ID NO: 39. In addition, it is proven herein that these assembled inventive nucleic acid molecules have or comprise low repetitive nucleotide sequences. In particular, it is shown in Example 2 that this exemplary assembled nucleotide sequence as given in SEQ ID NO: 39 possesses only repeat sequences of a maximum length of 14 nucleotides.

The invention also relates to a method for providing the inventive nucleic acid molecules; see, for example, FIG. 1E, which illustrates an exemplary procedure to assemble longer nucleotide sequences. Further, the invention relates to a vector that is particularly suitable to assemble the low repetitive nucleic acid molecules encoding the PA-rich polypeptides.

In accordance with the above, the nucleic acid molecule provided herein can encode a polypeptide consisting of proline and alanine.

Accordingly, the nucleic acid molecule provided herein can be selected from the group consisting of:

(a) the nucleic acid molecule comprising at least one nucleotide sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 192 and SEQ ID NO: 193;
(b) the nucleic acid molecule comprising the nucleotide sequence consisting of SEQ ID NO: 42, SEQ ID NO: 43, SEQ ID NO: 44, SEQ ID NO: 45, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, and/or SEQ ID NO: 173;
(c) the nucleic acid molecule hybridizing under stringent conditions to the complementary strand of the nucleotide sequence as defined in (a) or (b);
(d) the nucleic acid molecule comprising the nucleotide sequence having at least 66.7% identity to the nucleotide sequence as defined in any one of (a), (b) and (c); and
(e) the nucleic acid molecule being degenerate as a result of the genetic code to the nucleotide sequence as defined in (a) or (b).

In accordance with the above, the nucleic acid molecule provided herein can encode a polypeptide consisting of proline, alanine and serine.

Accordingly, the nucleic acid molecule provided herein can be selected from the group consisting of:

(a) the nucleic acid molecule comprising at least one nucleotide sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152; SEQ ID NO: 194 and SEQ ID NO: 195;
(b) the nucleic acid molecule comprising the nucleotide sequence selected from the group consisting of SEQ ID NO: 38, SEQ ID NO: 39, SEQ ID NO: 40, SEQ ID NO: 41, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 184, SEQ ID NO: 185, SEQ ID NO: 186, SEQ ID NO: 187, SEQ ID NO: 188, SEQ ID NO: 189, SEQ ID NO: 190, and SEQ ID NO: 191;
(c) the nucleic acid molecule hybridizing under stringent conditions to the complementary strand of the nucleotide sequence as defined in (a) or (b);
(d) the nucleic acid molecule comprising the nucleotide sequence having at least 56% identity to the nucleotide sequence as defined in any one of (a), (b) and (c);
(e) the nucleic acid molecule being degenerate as a result of the genetic code to the nucleotide sequence as defined in (a) or (b).

In certain aspects, the invention relates to a method for preparing a nucleic acid molecule comprising the low repetitive nucleotide sequence of the invention, wherein the method comprises:

(a) providing a vector comprising an upstream recognition sequence that is recognized by an endonuclease restriction enzyme and a downstream recognition sequence that is recognized by an endonuclease restriction enzyme,
  - wherein optionally said endonuclease restriction enzyme recognizing said downstream recognition sequence is different from the endonuclease restriction enzyme recognizing the upstream recognition sequence,
  - wherein said upstream recognition sequence and said downstream recognition sequence are in a reverse complementary orientation,
  - wherein said upstream recognition sequence comprises two recognition sequences for two different restriction enzymes,
  - wherein said downstream recognition sequence is comprised in the upstream recognition sequence, and/or
  - wherein said upstream recognition sequence and/or said downstream recognition sequence are recognition sites for restriction enzymes cleaving outside of the recognition sequence;

(b) cleaving said vector of (a) with the restriction enzyme(s) recognizing said upstream and/or said downstream recognition sequence;

(c) optionally, dephosphorylating said vector of (b) to prevent hybridization of the complementary sticky ends;

(d) providing a nucleic acid molecule encoding a polypeptide consisting of proline, alanine and, optionally, serine, wherein the ends of the nucleotide sequence hybridize to the cleaved ends of the vector of (b) or (c); and (e) inserting said nucleic acid molecule of (d) into said cleaved vector in the presence of a DNA ligase.

In certain aspects of the invention, the method provided herein can be used for preparing longer nucleic acid molecules, wherein the nucleic acid molecule comprises an assembled low repetitive nucleotide sequence, wherein the method for preparing the nucleic acid molecule as described above additionally comprises:

(f) cleaving said vector of (e) with a restriction enzyme recognizing either said upstream or said downstream recognition sequence;

(g) optionally, dephosphorylating said vector of (f) to prevent hybridization of the complementary sticky ends;

(h) providing a nucleic acid molecule encoding a polypeptide consisting of proline, alanine and, optionally, serine, wherein the ends of the nucleotide sequence hybridize to the cleaved ends of the vector of (f) or (g);

(i) inserting said nucleotide sequence of (h) into said cleaved vector in the presence of a DNA ligase, (j) repeating steps (f) to (i) until the desired length of the nucleotide sequence is reached.

The person skilled in the art understands that the steps of this method can be iteratively repeated until the desired length of the assembled nucleotide sequence or the assembled nucleic acid molecule encoding the PA-rich polypeptide is obtained.

In order to provide means and methods to advantageously clone the nucleic acid molecules provided herein, a suitable cloning vector comprises an upstream recognition sequence that is recognized by an endonuclease restriction enzyme and a downstream recognition sequence that is recognized by an endonuclease restriction enzyme, wherein optionally said endonuclease restriction enzyme recognizing said downstream recognition sequence is different from said endonuclease restriction enzyme recognizing said upstream recognition sequence, wherein said upstream recognition sequence and said downstream recognition sequence are in a reverse complementary orientation. Further, said upstream recognition sequence can comprise two recognition sequences for two different restriction enzymes. Further, said downstream recognition sequence can be comprised in the upstream recognition sequence. Thus, said downstream recognition sequence can be comprised in one of the upstream recognition sequences. The appended illustrative examples show the exemplary vectors and nucleic acids molecules as well as methods to provide those, in particular, FIGS. 1, 4, 6 and 8.

It is documented in the appended examples that it is particularly beneficial that the downstream recognition sequence is comprised in the upstream recognition sequence. By using such a strategy, the upstream recognition site may be employed to assemble further nucleotide sequences into the vector provided herein. Of course, the positions of the upstream and downstream restriction sites on such a vector are interchangeable. An exemplary cloning region with an inserted inventive nucleotide sequence is shown in FIG. 1D. In this instance, the restriction enzyme recognizing the downstream recognition sequence also recognizes and cleaves the upstream recognition sequence. Therefore, the inventive nucleotide sequence or the nucleic acid molecule encoding the polypeptide consisting of proline, alanine and, optionally, serine may be excised from the vector provided herein by employing the restriction enzyme recognizing the downstream and upstream recognition sequence, thus allowing use for ligation with other nucleic acids or vectors, e.g. to allow gene expression or to create a coding region for a fusion protein. An example for this cloning strategy to achieve assembly of a long low repetitive nucleotide sequence is illustrated herein below; see e.g. FIG. 1E.

In certain aspects, the first overhang may comprise a nucleotide triplet/codon encoding alanine, in particular GCC, but also GCT, GCA or GCG. In a preferred aspect, the nucleic acid molecule of the invention comprises two complementary 5'-overhangs, i.e., one 5'-overhang is on the coding strand and the other 5'-overhang is on the non-coding strand. In a particularly preferred embodiment, the 5'-overhang on the coding strand is GCC, and the 5'-overhang on the non-coding strand is GGC.

In certain further aspects, the first overhang may also comprise nucleotide triplets/codons encoding proline or serine, e.g., CCT, CCC, CCA, CCG, TCT, TCC, TCA, TCG, AGT or AGC. However, the person skilled in the art knows that the method for preparing the nucleic acid molecule provided herein is not limited to overhangs but that the nucleic acid molecule or the nucleotide sequence can, for example, also be ligated via blunt ends. As used herein, the term "overhang" relates to an end-portion of a nucleic acid strand as part of the double-stranded DNA molecule with no attached complement, also known as a sticky end. As used herein, the term "blunt end" relates to an end-portion of a DNA strand with no overhang. It is envisaged that the length of the overhang is not limited; however, an overhang comprising 1 to 10 nucleotides seems to be particularly suitable. In the appended examples, an overhang of 3 nucleotides encoding the amino acid alanine was employed. This kind of triplet overhang offers the advantage that it is directly compatible with the reading frame for amino acid translation of the nucleic acid molecule according to this invention.

Notably, the overhang introduces one additional triplet to the nucleotide sequence or the nucleic acid molecule encoding the polypeptide consisting of proline, alanine and, optionally, serine. Accordingly, the inventive cloning strategy introduces one additional amino acid, e.g., alanine. This additional amino acid or the corresponding triplet/codon can be considered as part of the polypeptide consisting of proline, alanine and, optionally, serine or the encoding nucleic acid, respectively. Consequently, as the skilled person in the art is aware, when employing the cloning strategy described above for a nucleotide sequence comprising, e.g., 300 nucleotides, the excised nucleic acid molecule comprises 303 nucleotides if also counting both three-nucleotide 5'-overhangs. It is envisaged herein that depending on the length of the overhangs employed herein even more triplets/codons or, accordingly, more amino acid residues can be introduced by this cloning procedure.

Furthermore, when cloned on a vector, or as part of a longer synthetic DNA fragment (e.g., a string), the nucleic acid molecule or the nucleotide sequence provided herein comprises said upstream recognition sequence and/or said downstream recognition sequence, wherein said upstream recognition sequence and/or said downstream recognition sequence are recognition sites for restriction enzymes that cleave outside of the recognition sequence. The restriction enzymes employed herein, e.g. those of the type IIS class preferably cleave outside of their recognition sequence to one side, which results in a cleaved nucleic acid molecule or nucleotide sequence that does not comprise the recognition site(s), depending on the proper orientation of the asymmetric recognition sequence.

Also, in the vector provided herein the cleavage with such restriction enzymes maintains the recognition sequences for the restriction enzymes. The cloning site of the exemplary vector pXL2 is shown in FIG. 1C. A nucleic acid molecule or a nucleotide sequence excised from this vector lacks the recognition sites of the restriction enzymes used for its cloning or excision, which is particularly advantageous for the assembly of longer nucleic acid molecules or longer nucleotide sequences, e.g., according to the procedure described herein, for the cloning on an expression vector or for creating a coding region for a fusion protein.

In a further embodiment, the exemplary vector pXL1 is provided (SEQ ID NO: 55) (and shown in FIG. 1B. In this case, the cloned/inserted nucleic acid molecule or nucleotide sequence according to this invention is flanked by two SapI restriction sites. Hence, the nucleic acid molecule encoding the polypeptide consisting of proline, alanine and, optionally, serine can be simply excised from this vector by digest/cleavage with a single restriction enzyme, i.e. SapI (or also EarI), which is particularly advantageous for subsequent cloning on an expression vector and/or for creating a coding region for a fusion protein.

As it is shown in the appended examples, the nucleic acid molecules or the nucleotide sequences provided herein are assembled in the vector pXL2 (SEQ ID NO: 48) in an iterative manner; see, e.g., Example 2. Therefore, one or both of the recognition sites in the vector may be employed to insert a further nucleotide sequence into the vector (on one side of an insert present) or, alternatively, to excise the entire (assembled) nucleotide sequence or nucleic acid molecule from the vector.

As a further advantage, in the method for producing the inventive nucleic acid molecule provided herein, the absence of the recognition sites for the restriction enzymes within the nucleic acid molecule according to this invention (i) prevents that an assembled longer nucleotide sequence provided herein is cleaved internally, e.g., between the units/modules of the assembled nucleotide sequences and (ii) leads to an unbiased transition between the encoded amino acid sequences on neighboring units/modules of the assembled nucleotide sequences or between the encoded amino acid sequences on the nucleotide sequence of the invention and the nucleotide sequence for a biologically active protein. This strategy can be termed "traceless" or "seamless" assembly or cloning.

It is demonstrated in the appended examples that restriction enzymes of the type IIS can be employed; see Examples 1 and 2. Restriction enzymes of this class have recognition sites separate from their cleavage sites and some of them, for example SapI and EarI, cleave outside of their recognition sequence on one side. It is shown herein below that said upstream recognition sequence on pXL2 is recognized by SapI and EarI and said downstream recognition sequence is recognized by EarI. Thus, said upstream recognition sequence has the nucleotide sequence 5'-GCTCTTC-3' and said downstream recognition sequence has the nucleotide sequence 5'-CTCTTC-3'. The skilled person in the art knows that the restriction enzymes are not particularly limited herein as long as they fulfill the purpose or limitations defined herein.

As used herein, the term "endonuclease restriction enzyme" relates to an endonuclease enzyme cutting/cleaving/hydrolyzing oligo/polynucleotides at the phosphodiester bond connecting certain nucleotides within a nucleic acid molecule or nucleotide sequence, e.g., DNA, at or near a specific recognition sequence comprising a stretch of nucleotides. Thus, restriction enzymes catalyze the hydrolysis of phosphodiester bonds within a nucleotide sequence or nucleic acid molecule. Restriction enzymes are commonly classified into three types which differ in their structure and whether they cut/cleave their substrate at their recognition sequence or at a separate site. To cut/cleave double-stranded DNA, restriction enzymes usually cleave two phosphodiester bonds, one in each sugar-phosphate backbone (i.e. each strand) of the DNA double helix.

As used herein, the term "recognition sequence" relates to a specific sequence of nucleotides, e.g., 4 to 8 specific base pairs in length, which are recognized by a restriction enzyme.

As used herein, the term "cleaving" means that the nucleic acid molecule and/or the vector is cut/digested/hydrolyzed with a restriction enzyme. As mentioned above, the restriction enzyme cleaves a phosphodiester bond within a polynucleotide chain.

As used herein, the term "inserting" refers to ligation of the nucleic acid molecule into the vector through the action of an enzyme. Thereby, the ends of the polynucleotides are joined together by the formation of phosphodiester bonds between the 3'-hydroxyl group at the terminus of one polynucleotide with the 5'-phosphoryl group of another. The nucleic acid molecule encoding the polypeptide consisting of proline, alanine and, optionally, serine or the nucleotide sequence has ends that can hybridize to the cleaved ends of the vector. In preferred aspects of the invention, such ends are overhangs that are able to hybridize to the respective overhangs of the vector cleaved.

For the insertion of the nucleic acid molecule into the vector, it is preferable to dephosphorylate the vector to avoid a high background of recircularized vector DNA with no insert. An exemplary enzyme for dephosphorylation may be calf-intestinal alkaline phosphatase (CIP or CIAP) or shrimp alkaline phosphatase which both remove the phosphate group from the 5' end of digested polynucleotides.

As used herein, the terms "upstream" and "downstream" both refer to a relative position on a nucleic acid molecule or nucleotide sequence. Each strand of the nucleic acid molecule or the nucleotide sequence has a 5' end and a 3' end, so named for the carbon atoms on the deoxyribose (or ribose) sugar. In general, upstream and downstream relate to the 5' to 3' direction of the coding strand in which RNA transcription takes place. When considering double-stranded DNA, upstream is toward the 5' end of the coding strand for the gene or reading frame in question and downstream is toward the 3' end. Due to the anti-parallel nature of double-stranded DNA, this means that the 3' end of the non-coding strand is upstream of the gene and its 5' end is downstream.

As used herein, the term "nucleic acid molecule" or "nucleotide sequence" is intended to include nucleic acid molecules such as DNA molecules and RNA molecules. It is herein understood that the term "nucleotide sequence" is equal to the term "nucleic acid sequence" and that these terms can be used interchangeably herein. Said nucleic acid molecule or said nucleotide sequence may be single-stranded or double-stranded, but preferably is double-stranded DNA. The skilled person in the art knows that double-stranded DNA actually comprises two different nucleic acid molecules, with largely complementary nucleotide sequences (neglecting sticky ends if present), which are non-covalently associated/hybridized to form a double strand.

In one aspect of the invention, the nucleotide sequence or the nucleic acid molecule encoding the polypeptide consisting of proline, alanine and, optionally, serine is operably linked in the same reading frame to a nucleic acid encoding a biologically or pharmacologically active protein. In preferred aspects of the invention, the nucleotide sequence or the nucleic acid molecule encoding the polypeptide consisting of proline, alanine and, optionally, serine is operably linked in the same reading frame to a nucleic acid encoding a biologically or pharmacologically active protein. Thus, the nucleic acid molecule encodes a heterologous drug conjugate comprising the polypeptide consisting of proline, alanine and, optionally, serine and the biologically or pharmacologically active protein. As used herein, heterologous means that the nucleic acid molecule encoding the polypeptide consisting of proline, alanine and, optionally, serine and the biologically or pharmacologically active protein is not found in nature.

As used herein, the term "operably linked" refers to a juxtaposition, wherein the components in question are in a relationship permitting them to both function in their intended manner.

The nucleotide sequence encoding the polypeptide consisting of proline, alanine and, optionally, serine can be conjugated to the nucleotide sequence encoding the biologically or pharmacologically active protein seamlessly, i.e., no linkers intersperse these two sequences. Alternatively, a linker or a spacer structure is comprised between the random coil polypeptide and the biologically or pharmacologically active protein. Thus, in certain aspects of the invention, a nucleotide sequence encoding an amino acid linker is inserted between the nucleotide sequence encoding the proline/alanine-rich polypeptide and the nucleotide sequence encoding the biologically or pharmacologically active protein. An exemplary linker can be a protease sensitive cleavage site, a serine/glycine-linker, an affinity tag such as the $His_6$-tag or the Strep-tag II, a signal peptide, retention peptide, a targeting peptide like a membrane translocation peptide or additional effector domains, e.g., antibody fragments for tumour targeting associated with an anti-tumour toxin or an enzyme for prodrug activation etc. The polypeptide comprising a linker/spacer can have a plasma protease cleavage site that allows the controlled release of said biologically active protein. Linkers/spacers of different types or lengths may be identified without undue burden to obtain optimal biological activity of specific proteins.

Linkers/spacers can cause an immune response in the subject receiving the fusion protein that carries a linker or spacer structure. Therefore, in preferred aspects of the invention, the nucleotide sequence encoding the proline/alanine-rich polypeptide is conjugated to the nucleotide sequence encoding the biologically or pharmacologically active protein seamlessly. As used herein, "seamless" means that the nucleotide sequence encoding the random coil polypeptide is directly conjugated to the nucleotide sequence encoding the biologically or pharmacologically active protein. Thus, no additional nucleotides are introduced that encode amino acid residues other than proline, alanine or, optionally, serine. As demonstrated in the appended examples, a seamless cloning was accomplished by using overhangs that encode the amino acid residue alanine; see e.g. Example 7. Therefore, the present invention furthermore relates to a method for preparing the nucleic acid molecule, wherein said nucleic acid molecule comprises a nucleotide sequence encoding proline, alanine and, optionally, serine and a nucleotide sequence encoding the biologically or pharmacologically active protein or peptide, and wherein said nucleotide sequence is conjugated seamlessly to said nucleotide sequence encoding the biologically or pharmacologically active protein. It is also demonstrated in the appended examples and herein above that the seamless cloning can be used to assemble longer nucleotide sequences encoding PA-rich polypeptides. Thus, if the seamless cloning method is applied, the resulting nucleotide sequence encoding the polypeptide consisting of proline, alanine and, optionally, serine is a low repetitive nucleotide sequence as described herein.

As used herein, the term "biological activity" describes the biological effect of a substance on living matter, for example an organism. Accordingly, the term "biologically active protein" or "biologically active peptide" as used herein relates to proteins or peptides that are capable of inducing a biological effect in living cells/organisms that are exposed to said protein or polypeptide or peptide. In the context of the invention, the nucleotide sequence or the nucleic acid molecule encoding the polypeptide consisting of proline, alanine and, optionally, serine is operably linked in the same reading frame to a heterologous nucleic acid encoding a biologically active protein.

It is herein understood, that the encoded biologically active protein or peptide is an "amino acid sequence having and/or mediating biological activity" or is an "amino acid sequence with biological activity" and/or is an amino acid sequence having and/or mediating a pharmacological activity. Also comprised in the terms "biologically active protein", "amino acid sequence having and/or mediating biological activity" or "amino acid sequence with biological activity" and/or "amino acid sequence having and/or mediating a pharmacological activity" are any proteins or peptides of interest (and functional fragments thereof, such as antibody fragments, fragments comprising extracellular or intracellular domain(s) of a membrane receptor, truncated forms of a growth factor or cytokine and the like) for which prolongation of the half-life, either in vivo or in vitro, is beneficial. The skilled person in the art knows that the random coil conformation of the polypeptide consisting of proline, alanine and, optionally, serine mediates increased in vivo and/or in vitro stability to the biologically/pharmacologically active ("functional") protein(s) or peptide(s), in particular, an increased plasma half-life.

In one embodiment of this invention, the encoded amino acid sequence having and/or mediating biological activity in accordance with the present invention may be deduced from any "protein of interest", i.e., any protein of pharmaceutical or biological interest or any protein that is useful as a therapeutically effective protein. Accordingly, said biologically active protein or peptide may be a pharmacologically active or therapeutically effective protein or peptide. Pharmacologically active or therapeutically effective proteins or peptides are any proteins or peptides that have a desired pharmacological, pharmaceutical and/or physiological effect. The effect may be (i) prophylactic in terms of completely or partially preventing and/or ameliorating a disease/medical condition/disorder or symptom thereof; and/or may be (ii) therapeutic in terms of partially or completely inhibiting the disease/medical condition/disorder, i.e., arresting its development, or relieving the disease/medical condition/disorder, i.e., causing regression of the disease/medical condition/disorder. Most preferably, said biologically active protein is a therapeutically effective protein, e.g. for use as a vaccine. Thus, said biologically active protein can also be used in vaccination.

Furthermore, said biologically active protein can be a diagnostically relevant protein. As used herein, a "diagnostically relevant protein" relates to a protein or polypeptide that is employed in diagnosis. In the context of the present invention, diagnosis relates to the recognition and (early) detection of a disease, e.g. cancer and tumor, or a clinical condition in a subject. It may also comprise differential diagnosis. Also, the assessment of the severity of a disease or clinical condition may in certain embodiments be encompassed by the term "diagnosis". In particular, the polypeptides and/or drug conjugates encoded by the nucleic acid molecules of the present invention can be used for in vitro or in vivo diagnostics. For example, the encoded polypeptides and/or drug conjugates can be used in methods for medical imaging. The encoded PA-rich polypeptides and/or drug conjugates are in particular suitable for these methods as they have an improved uptake into tumor cells. Furthermore, the encoded PA-rich polypeptides and/or drug conjugates show a higher contrast between tumor cells and blood or healthy cells/tissue.

The encoded biologically active protein is selected from the group consisting of a binding protein, an antibody fragment, a cytokine, a growth factor, a hormone, an enzyme, a protein vaccine, a peptide vaccine, or a peptide or a peptidomimetic. As used herein, a "peptide" preferably comprises/consists of up to 50 amino acid residues, whereas a "protein" preferably comprises/consists of 50 or more amino acid residues.

As used herein, the term "binding protein" relates to a molecule that is able to specifically interact with (a) potential binding partner(s) so that it is able to discriminate between said potential binding partner(s) and a plurality of molecules different from said potential binding partner(s) to such an extent that, from a pool of said plurality of different molecules as potential binding partner(s), only said potential binding partner(s) is/are bound, or is/are significantly bound. Methods for the measurement of binding activity between a binding protein and a potential binding partner are known in the art and can be routinely performed, e.g., by using enzyme-linked immunosorbent assay (ELISA), isothermal titration calorimetry (ITC), equilibrium dialysis, pull down assays, microscale thermophoresis, fluorescence titration or surface plasmon resonance (SPR) spectroscopy using, e.g., a Biacore instrument.

Exemplary binding proteins/binding molecules which are useful in the context of the present invention include, but are not limited to antibodies, antibody fragments such as Fab fragments, Fab' fragments, $F(ab')_2$ fragments, single chain variable fragments (scFv), (single) domain antibodies, in particular those derived from camelids, llamas or sharks, isolated variable regions of antibodies (VL and/or VH regions), in particular those from humans or primates, CDRs, immunoglobulin domains, CDR-derived peptidomimetics, lectins, fibronectin domains, tenascin domains, protein A domains, SH3 domains, ankyrin repeat domains, and lipocalins or various types of scaffold-derived binding proteins as described, for example, in Skerra (2000) J. Mol. Recognit. 13:167-187, Gebauer (2009) Curr. Opin. Chem. Biol. 13:245-255 or Binz (2005) Nat. Biotechnol. 23:1257-1268.

Other exemplary encoded biologically, pharmacologically active proteins or therapeutically effective proteins of interest that are useful in the context of the present invention include, but are not limited to, interleukin receptor antagonist, interleukin-1 receptor antagonist like EBI-005 or anakinra, leptin, acetylcholinesterase, activated protein C (drotrecogin), activin receptor IIB antagonist, adenosine deaminase, agalsidase alfa, agonist of toll-like receptor 5 like entolimod, alpha-1 antitrypsin, alpha-1 proteinase inhibitor, alpha-galactosidase, alpha-human atrial natriuretic peptide, alpha-N-acetylglucosaminidase, alteplase, amediplase, amylin, amylin analogue, ANF-Rho, angiotensin (1-7), angiotensin II, angiotensin-converting-enzyme 2, anti-epithelial cell adhesion molecule single-chain antibody fragment, antithrombin alfa, antithrombin III, apoptosis inducing enzyme mi-APO, arginine deiminase, asparaginases like calaspargase, pegaspargase, crisantaspase, B domain deleted factor VIII like beroctocog alfa or octofactor, bectumomab (Lymphoscan), bile salt stimulated lipases like bucelipase alfa, binding protein directed against the respiratory syncytial virus like pavlizumab, bone morphogenetic proteins like BMP-2 (dibotermin alfa) or BMP-6, bouganin, bovine carboxyhemoglobin, bovine growth hormone, C1-Esterase-Inhibitor, C3 exoenzyme protein, carboxyhemoglobin, CD19 antagonist, CD20 antagonist like rituxan, CD3 receptor antagonist, CD40 antagonist, CD40L antagonist like dapirolizumab or Antova, cerebroside sulfatase, cethrin like VGX-210, chondroitin lyase, coagulation factor IX like nonacog gamma, conacog beta, albutrepenonacog alfa, coagulation factor VIIa like eptacog alfa, marzeptacog alfa, vatreptacog alfa, oreptacog alfa, coagulation factor VIII like susoctocog alfa, damoctocog alfa, turoctocog alfa, rurioctocog alfa, efmoroctocog alfa, efraloctocog alfa, simoctocog alfa, coagulation factor X, coagulation factor XIII like catridecacog, collagenase of clostridium histolyticum, complement factor C3 inhibitor, complement receptor 5a antagonist, corticotrophin releasing factor, CSF1 receptor antagonists like FPA008, CSF1R antagonist, CTLA-4 antagonist like ipilimumab, cyanovirin-N, deoxyribonuclease I like dornase alfa, EGFR receptor antagonist, elastases like human type I pancreatic elastase like vonapanitase, endostatin, enkastim, epidermal growth factor, erythropoietin alfa, erythropoietin zeta, FcγIIB receptor antagonists, fibrinogenase, fibrinolytic enzyme like brinase, fibroblast growth factor 1 (human acidic fibroblast growth factor), fibroblast growth factor 18, fibroblast growth factor 2 (human basic fibroblast growth factor), fibroblast growth factor 21, fibroblast growth factor receptor 2 antagonists like FPA144, Fms-like tyrosine kinase 3 ligand, follicle-stimulating hormones like follitropin alfa or follitropin beta, fragment of human bactericidal/permeability-increasing protein 21 (opebacan/rBPI 21), gelonin, glucagon receptor agonist, glycoprotein IIb/IIIa antagonist like abciximab, glycosaminoglycan-degrading enzymes like condoliase, gp120/gp160, granulocyte colony stimulating factor (G-CSF), granulocyte macrophage colony stimulating factor (GM-C SF), heat-shock protein hsp 65 from Mycobacterium BCG fused with transcription factor E7 (verpasep caltespen), hepatocyte growth factor, hepatocyte growth factor receptor (HGFR) antagonist, hepcidin antagonist, Her2/neu receptor antagonist like herceptin, heterodimeric 15:IL-15Ra (hetIL-15), hirudin, hsp70 antagonist, human acid sphingomyelinase, human chorionic gonadotropin like choriogonadotropin alfa, human enzyme acid α-glucosidases like reveglucosidase alfa or alglucosidase alfa, human growth hormone, human keratinocyte growth factor (KGF), human matrix metalloproteinase, human myelin basic protein fragment, human osteogenic protein 1, human osteogenic protein-1, human parathyroid hormone, human thrombomodulin alpha, hyaluronidase like rHuPH20, hyaluronidases like human hyaluronidase PH-20 (vorhyaluronidase alfa), hyalosidase or bovhyaluronidase, hydrolytic lysosomal glucocerebroside-specific enzymes like glucocerebrosidase, velaglucerase alfa or taliglucerase alfa, iduronate-2-sulfatase, IgE antagonists like omalizumab, ilroquois homeobox protein 2 (IRX-2), insulin, insulin analog, integrin α4β1 antagonist, interferon tau, interferon-alpha, interferon-alpha antagonist, interferon-alpha super-agonist, interferon-alpha-n3 (Alferon N Injection), interferon-beta, interferon-gamma, interferon-lambda, interleukin 2 fusion proteins like DAB(389)IL-2, interleukin-11 like oprelevkin, interleukin-12, interleukin-17 receptor antagonist, interleukin-18 binding protein, interleukin-2, interleukin-22, interleukin-4 like pitrakinra, interleukin-4 mutein, interleukin-6 receptor antagonist, interleukin-7, interleukin-22 receptor subunit alpha (IL-22ra) antagonist, irisin, islet neogenesis associated protein, kallidinogenase, lactoferrin, lactoferrin fragment, lanoteplase, lipase enzymes like burlulipase, rizolipase, epafipase or sebelipase alfa, luteinizing hormone, lutropin alpha, lymphocyte expansion molecule, lysostaphin, mammalian gastric lipase enzyme (merispace), mannosidases like velmanase alfa, melanocortin-4 receptor agonist, MEPE-derived 23-amino acid peptide, methionyl human stem cell factor (ancestim), microplasmin, N-acetylgalactosamine-6-sulfatase like elosulfase alfa, N-acetylglucosaminidase, nasaruplase beta, nerve growth factor, neuregulin-1, neurotoxin (e.g. a clostridial neurotoxin, like a Clostridium botulinum neurotoxin (such as Clostridium botulinum neurotoxin serotype A, B, C, D, E, F or G, particularly Clostridium botulinum neurotoxin serotype A), neutrophil gelatinase-associated lipocalin, ocriplasmin, *Ornithodoros moubata* complement inhibitor (OmCI/Coversin), osteoprotegerin, P128 (StaphTAME), pamiteplase, parathormone (PTH), PD-1 antagonist, PDGF antagonist, pentraxin-2 protein, phage lysin like HY133, phenylalanine ammonia lyase like valiase, phosphatases like tissue-nonspecific alkaline phosphatase or asfotase alfa, plasminogen, plasminogen variant like V10153, platelet derived growth factor-BB, porcine growth hormone, prohibitin-targeting peptide 1, proinsulin, protein A, protein C like drotrecognin, protein binding fibroblast growth factor receptor ligands like FP-1039, recombinant tissue factor pathway inhibitor (tifacogin), relaxin, relaxin analog like serelaxin, reteplase, rhPDGF-BB, ribonuclease like onconase or amphinase, senrebotase, serine protease inhibitors like conestat alfa, sfericase, sialidase, soluble complement receptor type 1, soluble DCC (deleted in colorectal cancer) receptor, soluble TACI receptor (atacicept), soluble tumor necrosis factor I receptor (sTNF-RI), soluble tumor necrosis factor II receptor (sTNF-RII), soluble VEGF receptor Flt-1, soluble, human FcγIIB receptor, staphylokinase, streptokinase, sulfamidase, T-cell receptor ligand, tenecteplase, thrombopoiesis-stimulating protein (AMG-531), thrombopoietin, thrombospondin-1, thyroid hormone, thyrotropin-releasing hormone (TRH) analog like taltirelin, tissue plasminogen activator, tissue-type plasminogen activator like pamiteplase, tripeptidyl peptidase I, tumor necrosis factor (TNFalpha), tumour necrosis factor α antagonist, uricase like rasburicase or pegadricase, urodilatin, urofollitropin, urokinase, uteroglobin, VEGF antagonist like ranbizumab or bevacizumab, VEGF/PDGF antagonist, VEGF/PDGF antagonist like a multi-VEGF/PDGF DARPin or a fusion protein, viscumin, von Willebrand factors like vonicog alfa. Interleukin receptor antagonist, especially interleukin-1 receptor antagonists, like EBI-005 or anakinra, and leptin, especially human leptin, or a mutant human leptin (huLeptin(W100Q), a human leptin mutant with a tryptophan to glutamine substitution at position 100 in the mature polypeptide chain), are preferred herein. The amino acid sequence of human leptin is disclosed e.g. in UniProtKB accession code P41159. Mutant huLeptin(W100Q) is described by Ricci (2006) Mutational approach to improve physical stability of protein therapeutics susceptible to aggregation, In Murphy (ed.) Misbehaving proteins: protein (mis)folding, aggregation, and stability, Springer, 1st edition, New York.

Exemplary peptides and peptidomimetics include but are not limited to adrenocorticotropic hormone (ACTH), afamelanotide, alarelin, alpha 4 integrin inhibitor, anti-HIV fusion inhibitor (like enfurvitide, V2o, SC34EK, SC35EK, IQN17 or IZN17), angiotensin II type 2 (AT2) receptor agonist (like LT2), anti-idiotypic p53 peptide, amylin, amylin analog, astressin, atosiban, bacterial peptide fragment with anticancer and anti HIV activity (like ATP-01), bicyclic peptide (like TG-758), bivalirudin, bradykinin antagonist (like icatibant), bremelanotide, B-type natriuretic peptide, calcitonin, carbetocin, carfilzomib, chrysalin, cilengitide, C-type natriuretic peptide, colostrinin, corticotrophin releasing factor (like Xerecept, coysnthropin), CNGRCG tumor homing peptide, ω-conotoxin peptide (like ziconotide), C-peptide, danegaptide, defensin, ecallantide, elcatonin, eledoisin, exendin-4, exendin-4 analog (like exendin 9-39), ezrin peptide 1, fragments from the human matrix extracellular phosphoglycoprotein (like AC-100), galanin, gastric inhibitory polypeptide (GIP), GIP analog, glatiramer, glucagon, glucagon analog, glucagon-like peptide 1 (GLP-1), GLP-1 analog (like lixisenatide, liraglutide or semiglutide), glucagon-like peptide 2 (GLP-2), GLP-2 analog (like teduglutide), gonadorelin, gonadotropin-releasing hormone agonist (like goserelin, buserelin, triptorelin, leuprolide, protirelin, lecirelin, fertirelin or desiorelin), gonadotropin-releasing hormone antagonist (like abarelix, cetrorelix, degarelix, ganirelix or teverelix), grehlin, grehlin analog (like AZP-531), growth hormone-releasing hormone, growth hormone-releasing hormone analog (like sermorelin or tesamorelin), hematide, hepcidin mimetic peptide, histrelin, indolicidin, indolicidin analog (like omiganan), IgE down-regulating peptide (like SC-01), INGAP peptide (exsulin), insulin-like growth factor 1, insulin-like growth factor 2, Kv1.3 ion channel antagonist (like cgtxA, cgtxE or cgtxF), lanreotide, lectin binding peptide (like sv6B, sv6D, svC2, svH1C, svH1D or svL4), lanthipeptide, larazotide, linaclotide, lusupultide, melanocortin-4 receptor agonist (like AZD2820), MEPE-derived 23-amino acid peptide, mitochondrial-derived peptide (like MOTS-c, humanin, SHLP-6 or SHLP-2), mutant of the insulin-like growth factor binding protein-2 (like I-HBD1), Nav ion channel modulators (like GTx1-15 or VSTx3), octreotide, proprotein convertase subtilisin/kexin type 9 (PCSK9) inhibitory peptide, peptide fragment of azurin, Phylomer, peptide antagonist to the MHC Class II-associated invariant peptide (CLIP) (like VG1177), peptide derived from a heat shock protein (like enkastim), pexiganan, plovamer, pramlintide, prohibitin-targeting peptide 1, pro-islet peptide, peptide tyrosine tyrosine (PYY 3-36), RGD peptide or peptidomimetic, ramoplanin, secretin, sinapultide, somatostatin, somatostatin analog (like pasireotide or CAP-232), specifically targeted antimicrobial peptide (STAMP) (like C16G2), receptor agonist of the bone morphogenetic protein (like THR-184 or THR-575), stresscopin, surfaxin, Tc99m apcitide, teriparatide (PTH 1-34), tetracosactide, thymosin alpha 1, TLR2 inhibitory peptide, TLR3 inhibitory peptide, TLR4 inhibitory peptide, thymosin B4, thymosin B15, vasoactive intestinal peptide, vasopressin, vasopressin analog like (desompressin, felypressin or terlypressin).

Exemplary biologically active proteins of interest that are useful in the context of vaccination include but are not limited to AE37 peptide, bombesin-gastrin-releasing peptide, carcinoembryonic antigen (CEA), the capsid protein open reading frame 2 (ORF2) protein of hepatitis E virus, cholera toxin B, clumping factor A of *Staphylococcus aureus*, diphtheria toxin, diphtheria toxin mutant (like CRM 197), *E. coli* heat labile enterotoxin, exotoxin A of *Pseudomonas aeruginosa*, F protein of measles virus, glycoprotein E of japanese encephalitis (JE) virus, GPC3-derived peptide, hepatitis A polyprotein, HER2-derived peptide GP2, herregulin, Her2neu peptid, hepatitis B virus surface antigen (HbSAg), human glutamic acid decarboxylase protein isoform 65 kDa (rhGAD65), influenza hemagglutinin antigens (HA), influenza neuraminidase (NA), L1 protein of human papilloma virus, li-Key/HER2/neu hybrid peptide, lipoprotein on outer surface of *Borrelia burgdorferi* (OspA), major outer capsid protein of rota virus, mucin-1 (MUC-1) peptide, Norwalk virus (rNVP) capsid protein, Parvovirus B19 VLP, peptide derived from granulocyte-macrophage colony-stimulating factor, porcine circovirus 2 capsid (PCV2 ORF2) protein, protein C of tick-borne encephalitis virus, protein E of tick-borne encephalitis virus, protein E of yellow fever virus, protein E-1 of rubella virus, protein G of rhabdoviridae, protein H of measles virus, protein H of paramyxoviridae, protein NS of yellow fever virus, protein N of paramyxoviridae, prostate-specific antigen E2 protein of the swine fever virus, protein VP6 of rota virus, protein VP7 of rota virus, spike protein from the SARS virus (D3252), protein VP1 of polio virus, protein VP4 of polio virus, Ras oncoprotein, sperm derived peptides (like YLP12, P10G, A9D, mFA-12-19, SP56 and or mFA-1117-136), tetanus toxin, tuberculin, tumor-associated peptides (TUMAPs) (like IMA901, IMA910 or IMA950), and the like.

In one aspect, the present invention relates to a nucleic acid molecule as disclosed herein, for example, a nucleic acid molecule comprising a nucleotide sequence encoding a polypeptide consisting of proline, alanine and serine, wherein the nucleotide sequence of said nucleic acid has a length of at least 300 nucleotides; or the present invention relates in one aspect to a nucleic acid molecule disclosed herein that is operably linked in the same reading frame to a nucleic acid encoding a biologically active protein, for example a nucleic acid molecule comprising a nucleotide sequence encoding a polypeptide consisting of proline, alanine and serine, wherein the nucleotide sequence of said nucleic acid has a length of at least 300 nucleotides, wherein the nucleic acid molecule is operably linked in the same reading frame to a nucleic acid encoding a biologically active protein;

wherein said nucleotide sequence is not (SEQ ID No. 196)

```
ATGGGCAGCAGCCATCATCATCACCATCATGGTAGCCTGGTTCCGCGTAG
CTCTTCTGCAAGTCCGGCAGCACCGGCACCGGCTTCACCAGCTGCACCAG
CACCTAGCGCACCGGCAGCATCTCCAGCAGCCCCTGCACCGGCAAGCCCT
GCAGCTCCAGCACCGTCAGCACCAGCAGCAAGCCCAGCTGCTCCTGCTCC
AGCGAGCCCAGCAGCGCCAGCTCCTAGTGCCCCTGCTGCCTCTCCTGCTG
CTCCGGCACCAGCAAGTCCTGCTGCGCCTGCACCGAGTGCTCCGGCTGCT
AGTCCTGCCGCACCAGCTCCGGCTAGTCCAGCTGCTCCAGCCCCTTCAGC
TCCGGCAGCTTCCCCTGCAGCGCCTGCCCCTGCCAGTCCAGCGGCTCCTG
CACCTAGTGCGCCTGCAGCTTCACCGGCTGCCCCTGCGCCAGCTTCTCCT
GCGGCTCCAGCTCCATCTGCCCCAGCCGCATCCCCAGCGGCACCAGCTCC
AGCTTCTCCGGCAGCGCCAGCACCTTCTGCGCCTGCCGCATCTCCTGCAG
CACCAGCGCCTGCGAGTCCTGCAGCTCCTGCTCCTTCAGCCCCTGCGGCA
AGTCCAGCAGCACCAGCCCCAGCAAGCCCAGCCGCACCAGCACCATCTGC
CCCTGCAGCACCATTTGTGAACAAGCAGTTTAACTATAAGGACCCGGTGA
ACGGTGTGGATATCGCGTATATCAAAATCCCGAATGCGGGCCAGATGCAA
CCAGTCAAGGCGTTCAAGATTCATAACAAGATTTGGGTTATTCCGGAACG
TGATACCTTCACCAATCCGGAAGAAGGCGACTTAAACCCGCCGCCAGAAG
CCAAACAAGTGCCGGTGAGCTACTATGATAGCACGTATCTTAGCACCGAT
AATGAAAAAGACAATTACCTGAAGGGCGTGACCAAGTTGTTCGAGCGCAT
CTACAGTACCGACTTAGGCCGCATGTTGTTGACGAGCATCGTTCGCGGTA
TCCCGTTCTGGGGCGGCTCGACCATTGATACCGAGTTGAAAGTCATTGAC
ACGAACTGTATCAATGTTATCCAACCGGACGGCAGTTATCGCAGCGAGGA
GTTAAATTTGGTCATCATCGGTCCAAGCGCAGATATTATTCAGTTCGAAT
GCAAGAGCTTCGGCCATGAGGTCTTGAATTTGACGCGCAACGGTTACGGC
AGCACCCAATACATCCGCTTTAGCCCGGATTTCACCTTTGGCTTCGAGGA
GAGCTTGGAGGTGGACACCAACCCGCTGTTAGGTGCCGGCAAATTCGCAA
CCGACCCGGCAGTGACGTTGGCGCACGAATTGATTCATGCGGGTCACCGC
TTATACGGTATCGCGATCAATCCGAATCGCGTCTTTAAAGTCAATACCAA
CGCGTACTACGAAATGAGCGGCTTAGAGGTTAGCTTTGAAGAATTACGCA
CCTTCGGTGGCCACGACGCCAAGTTCATCGACAGCCTGCAGGAAAATGAG
TTCCGCTTGTACTATTACAATAAATTCAAGGACATCGCGAGCACCTTAAA
TAAAGCAAAGAGCATTGTGGGCACCACCGCAAGCTTGCAGTACATGAAGA
ACGTATTTAAGGAAAAATATTTGTTGTCGGAGGATACCAGCGGGAAATTC
AGCGTCGATAAGCTGAAATTCGACAAATTGTATAAAATGCTGACCGAGAT
TTACACCGAGGATAACTTCGTCAAGTTTTTTAAGGTGTTAAATCGTAAGA
```

-continued

CCTATTTAAACTTTGATAAAGCGGTGTTTAAAATTAATATCGTGCCGAAG

GTGAATTACACCATCTACGATGGTTTCAATTTACGCAACACGAATCTGGC

GGCGAATTTTAATGGCCAAAACACCGAAATTAACAACATGAACTTTACGA

AGTTAAAGAATTTCACGGGCTTATTCGAATTCTACAAGTTATTATGCGTG

CGCGGCATCATTACCAGCAAGGCAGGTGCGGGCAAGTCCTTGGTTCCGCG

TGGCAGCGCCGGCGCCGGCGCGCTCAATGATCTGTGTATTAAAGTCAATA

ACTGGGACCTGTTCTTCAGCCCGAGCGAGGATAACTTTACCAACGACTTA

AACAAAGGCGAGGAGATCACGAGCGATACGAACATCGAGGCGGCGGAGGA

AAATATTAGCCTGGACCTCATTCAGCAGTACTATCTGACGTTCAATTTTG

ACAATGAGCCGGAGAACATCAGCATTGAAAATCTCAGCAGCGACATCATC

GGTCAGTTGGAACTGATGCCGAACATTGAACGCTTTCCGAACGGCAAAAA

ATATGAACTGGACAAGTATACCATGTTCCATTACTTACGCGCACAGGAAT

TTGAGCACGGCAAGAGCCGCATTGCGCTGACCAATAGCGTTAACGAGGCC

TTGTTAAATCCGAGCCGTGTCTACACGTTCTTCAGCAGCGATTATGTCAA

AAAAGTGAACAAGGCGACCGAAGCCGCGATGTTTTTGGGCTGGGTCGAGC

AATTGGTTTACGATTTTACCGACGAAACCAGCGAGGTGAGCACGACCGAC

AAAATTGCAGATATCACCATCATCATTCCGTACATCGGTCCGGCGCTCAA

TATCGGCAATATGTTATACAAGGACGACTTTGTGGGCGCGCTGATCTTTA

GCGGCGCGGTTATCTTATTAGAATTCATCCCGGAGATCGCAATCCCGGTC

TTGGGCACCTTTGCGTTGGTGAGCTATATCGCGAATAAAGTGCTCACGGT

CCAAACCATCGATAACGCGCTCAGCAAGCGTAATGAGAAATGGGACGAGG

TTTATAAGTATATCGTGACCAACTGGTTAGCAAAAGTCAATACGCAGATC

GATCTCATCCGCAAAAAAATGAAAGAAGCCTTGGAAAATCAAGCGGAGGC

AACCAAAGCCATCATTAATTACCAGTATAACCAATATACCGAAGAAGAAA

AAAACAATATCAACTTCAATATCGATGATTTGAGCAGCAAACTGAACGAG

AGCATTAACAAAGCGATGATTAACATCAACAAGTTCTTGAATCAATGCAG

CGTGAGCTATCTCATGAACAGCATGATCCCGTATGGCGTCAAACGCTTGG

AAGATTTTGACGCCAGCCTGAAAGATGCGCTCCTCAAGTATATTTATGAC

AACCGCGGCACCCTCATTGGCCAGGTGGACCGCTTGAAGGATAAAGTGAA

CAATACGCTCAGCACGGATATCCCGTTCCAGCTGAGCAAGTACGTCGACA

ACCAGCGCTTACTGAGCACCTTTACCGAGTATATCAAGAACATCATTAAT

ACCAGCATCCTCAACTTGCGCTATGAGAGCAATCACCTGATCGACCTCAG

CCGCTACGCCAGCAAGATCAACATCGGCAGCAAGGTCAATTTCGACCCGA

TCGATAAGAATCAGATCCAATTGTTTAACCTGGAAAGCAGCAAGATCGAG

GTTATCTTGAAGAACGCGATTGTGTACAACAGCATGTACGAGAACTTTAG

CACGAGCTTCTGGATTCGTATCCCGAAGTATTTCAATAGCATTAGCCTGA

ATAACGAATATACCATTATCAACTGCATGGAAAATAATAGCGGCTGGAAG

GTGAGCTTAAATTACGGCGAGATCATTTGGACCTTACAGGATACCCAAGA

AATCAAACAGCGCGTCGTCTTTAAGTATAGCCAGATGATCAACATCAGCG

ATTACATCAACCGCTGGATCTTCGTGACCATCACCAATAATCGCTTGAAT

-continued

AATAGCAAGATTTACATCAATGGTCGCTTGATTGATCAAAAACCGATCAG

CAATCTCGGTAATATCCATGCCAGCAATAACATCATGTTTAAGTTAGACG

GTTGCCGCGATACCCACCGCTATATCTGGATCAAGTATTTTAACTTATTT

GATAAGGAACTCAACGAAAAGGAAATTAAAGACTTATATGACAATCAGAG

CAATAGCGGCATCCTGAAGGATTTCTGGGGCGACTACCTGCAGTACGATA

AGCCGTACTATATGTTGAACTTGTATGACCCGAACAAATATGTCGATGTG

AACAATGTGGGTATTCGTGGCTATATGTACTTAAAGGGCCCGCGTGGTAG

CGTGATGACCACGAATATTTACTTAAACAGCAGCTTATACCGCGGCACGA

AGTTTATTATCAAGAAGTATGCCAGCGGCAACAAGGACAATATCGTCCGC

AACAACGACCGTGTGTATATTAACGTGGTGGTGAAGAATAAAGAGTACCG

CTTGGCCACGAATGCGAGCCAGGCGGGCGTGGAAAAAATCTTGAGCGCGT

TGGAGATCCCGGACGTCGGCAACCTCAGCCAGGTTGTGGTGATGAAGTCT

AAAAACGACCAGGGCATCACGAACAAGTGCAAAATGAATTTGCAAGATAA

CAACGGCAACGACATCGGCTTTATTGGTTTTCACCAGTTCAATAACATCG

CCAAACTCGTGGCCAGCAATTGGTATAACCGCCAAATTGAACGCAGCAGC

CGCACGCTCGGCTGTAGCTGGGAGTTCATCCCGGTGGACGATGGCTGGGG

CGAGCGCCCGCTCGGAGATCTGGTGCCACGCGGTTCCGCGAATTCGAGCT

CCGTCGACAAGCTTTGGAGCCACCCGCAGTTCGAAAAATAA

In one aspect, the present invention relates to a nucleic acid molecule as disclosed herein, for example, a nucleic acid molecule comprising a nucleotide sequence encoding a polypeptide consisting of proline, alanine and serine, wherein the nucleotide sequence of said nucleic acid has a length of at least 300 nucleotides; or the present invention relates in one aspect to a nucleic acid molecule disclosed herein that is operably linked in the same reading frame to a nucleic acid encoding a biologically active protein, for example a nucleic acid molecule comprising a nucleotide sequence encoding a polypeptide consisting of proline, alanine and serine, wherein the nucleotide sequence of said nucleic acid has a length of at least 300 nucleotides, wherein the nucleic acid molecule is operably linked in the same reading frame to a nucleic acid encoding a biologically active protein;

wherein said nucleotide sequence is not (SEQ ID No. 197)

ATGGGTAGCAGCCATCATCATCACCATCATGGTAGCCTGGTTCCGCGTAG

CTCTTCTGCAAGTCCGGCAGCACCGGCACCGGCTTCACCAGCTGCACCAG

CACCTAGCGCACCGGCAGCATCTCCAGCAGCCCCTGCACCGGCAAGCCCT

GCAGCTCCAGCACCGTCAGCACCAGCAGCAAGCCCAGCTGCTCCTGCTCC

AGCGAGCCCAGCAGCGCCAGCTCCTAGTGCCCCTGCTGCCTCTCCTGCTG

CTCCGGCACCAGCAAGTCCTGCTGCGCCTGCACCGAGTGCTCCGGCTGCT

AGTCCTGCCGCACCAGCTCCGGCTAGTCCAGCTGCTCCAGCCCCTTCAGC

CCCTGCAGCACCATTTGTGAACAAGCAGTTTAACTATAAGGACCCGGTGA

ACGGTGTGGATATCGCGTATATCAAAATCCCGAATGCGGGCCAGATGCAA

CCAGTCAAGGCGTTCAAGATTCATAACAAGATTTGGGTTATTCCGGAACG

-continued

```
TGATACCTTCACCAATCCGGAAGAAGGCGATTTAAATCCGCCGCCAGAAG
CCAAACAAGTGCCGGTGAGCTACTATGATAGCACGTATCTTAGCACCGAT
AATGAAAAAGACAATTACCTGAAGGGCGTGACCAAGTTGTTCGAGCGCAT
CTACAGTACCGACTTAGGCCGCATGTTGTTGACGAGCATCGTTCGCGGTA
TCCCGTTCTGGGGCGGCTCGACCATTGATACCGAGTTGAAAGTCATTGAC
ACGAACTGTATCAATGTTATCCAACCGGACGGCAGTTATCGCAGCGAGGA
GTTAAATTTGGTCATCATCGGTCCAAGCGCAGATATTATTCAGTTCGAAT
GCAAGAGCTTCGGCCATGAGGTCTTGAATTTGACGCGCAACGGTTACGGC
AGCACCCAATACATCCGCTTTAGCCCGGATTTCACCTTTGGCTTCGAGGA
GAGCTTGGAGGTGGACACCAACCCGCTGTTAGGTGCCGGCAAATTCGCAA
CCGACCCGGCAGTGACGTTGGCGCACGAATTGATTCATGCGGGTCACCGC
TTATACGGTATCGCGATCAATCCGAATCGCGTCTTTAAAGTCAATACCAA
CGCGTACTACGAAATGAGCGGCTTAGAGGTTAGCTTTGAAGAATTACGCA
CCTTCGGTGGCCACGACGCCAAGTTCATCGACAGCCTGCAGGAAAATGAG
TTCCGCTTGTACTATTACAATAAATTCAAGGACATCGCGAGCACCTTAAA
TAAAGCAAAGAGCATTGTGGGCACCACCGCAAGCTTGCAGTACATGAAGA
ACGTATTTAAGGAAAAATATTTGTTGTCGGAGGATACCAGCGGGAAATTC
AGCGTCGATAAGCTGAAATTCGACAAATTGTATAAAATGCTGACCGAGAT
TTACACCGAGGATAACTTCGTCAAGTTTTTTAAGGTGTTAAATCGTAAGA
CCTATTTAAACTTTGATAAAGCGGTGTTTAAAATTAATATCGTGCCGAAG
GTGAATTACACCATCTACGATGGTTTCAATTTACGCAACACGAATCTGGC
GGCGAATTTTAATGGCCAAAACACCGAAATTAACAACATGAACTTTACGA
AGTTAAAGAATTTCACGGGCTTATTCGAATTCTACAAGTTATTATGCGTG
CGCGGCATCATTACCAGCAAGGCAGGTGCGGGCAAGTCCTTGGTTCCGCG
TGGCAGCGCCGGCGCCGGCGCGCTCAATGATCTGTGTATTAAAGTCAATA
ACTGGGACCTGTTCTTCAGCCCGAGCGAGGATAACTTTACCAACGACTTA
AACAAAGGCGAGGAGATCACGAGCGATACGAACATCGAGGCGGCGGAGGA
AAATATTAGCCTGGACCTCATTCAGCAGTACTATCTGACGTTCAATTTTG
ACAATGAGCCGGAGAACATCAGCATTGAAAATCTCAGCAGCGACATCATC
GGTCAGTTGGAACTGATGCCGAACATTGAACGCTTTCCGAACGGCAAAAA
ATATGAACTGGACAAGTATACCATGTTCCATTACTTACGCGCACAGGAAT
TTGAGCACGGCAAGAGCCGCATTGCGCTGACCAATAGCGTTAACGAGGCC
TTGTTAAATCCGAGCCGTGTCTACACGTTCTTCAGCAGCGATTATGTCAA
AAAAGTGAACAAGGCGACCGAAGCCGCGATGTTTTTGGGCTGGGTCGAGC
AATTGGTTTACGATTTTACCGACGAAACCAGCGAGGTGAGCACGACCGAC
AAAATTGCAGATATCACCATCATCATTCCGTACATCGGTCCGGCGCTCAA
TATCGGCAATATGTTATACAAGGACGACTTTGTGGGCGCGCTGATCTTTA
GCGGCGCGGTTATCTTATTAGAATTCATCCCGGAGATCGCAATCCCGGTC
TTGGGCACCTTTGCGTTGGTGAGCTATATCGCGAATAAAGTGCTCACGGT
CCAAACCATCGATAACGCGCTCAGCAAGCGTAATGAGAAATGGGACGAGG
TTTATAAGTATATCGTGACCAACTGGTTAGCAAAAGTCAATACGCAGATC
```

-continued

```
GATCTCATCCGCAAAAAAATGAAAGAAGCCTTGGAAAATCAAGCGGAGGC
AACCAAAGCCATCATTAATTACCAGTATAACCAATATACCGAAGAAGAAA
AAAACAATATCAACTTCAATATCGATGATTTGAGCAGCAAACTGAACGAG
AGCATTAACAAAGCGATGATTAACATCAACAAGTTCTTGAATCAATGCAG
CGTGAGCTATCTCATGAACAGCATGATCCCGTATGGCGTCAAACGCTTGG
AAGATTTTGACGCCAGCCTGAAAGATGCGCTCCTCAAGTATATTTATGAC
AACCGCGGCACCCTCATTGGCCAGGTGGACCGCTTGAAGGATAAAGTGAA
CAATACGCTCAGCACGGATATCCCGTTCCAGCTGAGCAAGTACGTCGACA
ACCAGCGCTTACTGAGCACCTTTACCGAGTATATCAAGAACATCATTAAT
ACCAGCATCCTCAACTTGCGCTATGAGAGCAATCACCTGATCGACCTCAG
CCGCTACGCCAGCAAGATCAACATCGGCAGCAAGGTCAATTTCGACCCGA
TCGATAAGAATCAGATCCAATTGTTTAACCTGGAAAGCAGCAAGATCGAG
GTTATCTTGAAGAACGCGATTGTGTACAACAGCATGTACGAGAACTTTAG
CACGAGCTTCTGGATTCGTATCCCGAAGTATTTCAATAGCATTAGCCTGA
ATAACGAATATACCATTATCAACTGCATGGAAAATAATAGCGGCTGGAAG
GTGAGCTTAAATTACGGCGAGATCATTTGGACCTTACAGGATACCCAAGA
AATCAAACAGCGCGTCGTCTTTAAGTATAGCCAGATGATCAACATCAGCG
ATTACATCAACCGCTGGATCTTCGTGACCATCACCAATAATCGCTTGAAT
AATAGCAAGATTTACATCAATGGTCGCTTGATTGATCAAAAACCGATCAG
CAATCTCGGTAATATCCATGCCAGCAATAACATCATGTTTAAGTTAGACG
GTTGCCGCGATACCCACCGCTATATCTGGATCAAGTATTTTAACTTATTT
GATAAGGAACTCAACGAAAAGGAAATTAAAGACTTATATGACAATCAGAG
CAATAGCGGCATCCTGAAGGATTTCTGGGGCGACTACCTGCAGTACGATA
AGCCGTACTATATGTTGAACTTGTATGACCCGAACAAATATGTCGATGTG
AACAATGTGGGTATTCGTGGCTATATGTACTTAAAGGGCCCGCGTGGTAG
CGTGATGACCACGAATATTTACTTAAACAGCAGCTTATACCGCGGCACGA
AGTTTATTATCAAGAAGTATGCCAGCGGCAACAAGGACAATATCGTCCGC
AACAACGACCGTGTGTATATTAACGTGGTGGTGAAGAATAAAGAGTACCG
CTTGGCCACGAATGCGAGCCAGGCGGGCGTGGAAAAAATCTTGAGCGCGT
TGGAGATCCCGGACGTCGGCAACCTCAGCCAGGTTGTGGTGATGAAGTCT
AAAAACGACCAGGGCATCACGAACAAGTGCAAAATGAATTTGCAAGATAA
CAACGGCAACGACATCGGCTTTATTGGTTTTCACCAGTTCAATAACATCG
CCAAACTCGTGGCCAGCAATTGGTATAACCGCCAAATTGAACGCAGCAGC
CGCACGCTCGGCTGTAGCTGGGAGTTCATCCCGGTGGACGATGGCTGGGG
CGAGCGCCCGCTCGGAGATCTGGTGCCACGCGGTTCCGCGAATTCGAGCT
CCGTCGACAAGCTTTGGAGCCACCCGCAGTTCGAAAAATAA
```

In one aspect, the present invention relates to a nucleic acid molecule, wherein said nucleic acid molecule consists of a nucleotide sequence encoding a polypeptide consisting of proline, alanine and, optionally, serine, wherein the nucleotide sequence of said nucleic acid has a length of at least 300 nucleotides, wherein said nucleotide sequence has a Nucleotide Repeat Score (NRS) lower than 50,000, wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}},$$

wherein $N_{tot}$ is the length of said nucleotide sequence, n is the length of a repeat within said nucleotide sequence, and $f_i(n)$ is the frequency of said repeat of length n, wherein if there is more than one repeat of length n, k(n) is the number of said different sequences of said repeat of length n, otherwise k(n) is 1 for said repeat of length n.

Furthermore, the present invention also relates to a vector comprising the nucleic acid molecule or the nucleotide sequence of the invention. The vector can also be employed in order to provide a nucleic acid molecule comprising (i) a nucleotide sequence encoding a polypeptide consisting of alanine, proline and, optionally, serine and (ii) a nucleotide sequence encoding a biologically active protein; see, e.g., FIG. 4 and Example 7.

Such a vector can be employed as an expression vector in order to express fusion proteins comprising the encoded random coil polypeptides and biologically active proteins. Accordingly, the encoded fusion protein encompasses (i) a random coil polypeptide, which is encoded by the low repetitive nucleotide sequence, coupled to (ii) a biologically active protein. Preferably, the random coil polypeptide consists of alanine, proline and, optionally, serine. An exemplary vector is given in SEQ ID NO: 56. In the appended examples, an exemplary method is demonstrated in order to provide such a vector or nucleic acid molecule; see e.g. FIG. 6 and Example 7.

In this inventive method, the vector provided herein comprises the nucleotide sequence encoding the biologically active protein and, in a second step, the nucleotide sequence encoding the PA-rich polypeptide is introduced into the vector. In order to introduce the nucleotide sequence encoding the proline/alanine-rich sequence into the vector comprising the nucleotide sequence encoding the biologically active protein, overhangs can be employed that comprise at least one nucleotide triplet/codon encoding e.g. alanine, proline and/or optionally serine; see above. Accordingly, such a triplet or codon can encode an amino acid that is considered part of the proline/alanine-rich sequence, in particular alanine.

Consequently, the method and vector provided herein avoid the introduction of additional amino acid linkers that may be introduced by utilizing conventional restriction sites. Therefore, the means and methods provided herein allow a seamless cloning of the inventive nucleic acid molecule comprising (i) the nucleotide sequence encoding the polypeptide consisting of alanine, proline and, optionally, serine and (ii) the nucleotide sequence encoding the biologically active protein.

Many suitable vectors are known to those skilled in molecular biology. The choice of a suitable vector depends on the function desired, including plasmids, cosmids, viruses, bacteriophages and other vectors used conventionally in genetic engineering.

Preferably, the vector is a plasmid, more preferably a plasmid based on the generic *E. coli* expression vector pASK37, pASK75 or pXL2.

Methods which are well known to those skilled in the art can be used to construct various plasmids; see, for example, the techniques described in Sambrook (2001) loc cit. and Ausubel (1989) loc. cit. Typical plasmid vectors include, e.g., pQE-12, the pUCseries of plasmids, pBluescript (Stratagene), the pET series of expression vectors (Novagen) or pCRTOPO (Invitrogen), lambda gt11, pJOE, the pBBR1-MCS series, pJB861, pBSMuL, pBC2, pUCPKS, pTACT1. Typical vectors compatible with expression in mammalian cells include E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen).

Generally, vectors can contain one or more origins of replication (ori) and inheritance systems for cloning or expression, one or more markers for selection in the host, e.g., antibiotic resistance, and one or more expression cassettes. Examples of suitable origins of replication include, for example, the full length ColE1, its truncated versions such as those present on the pUC plasmids, the SV40 viral and the M13 phage origins of replication. Non-limiting examples of selectable markers include ampicillin, chloramphenicol, tetracycline, kanamycin, dhfr, gpt, neomycin, hygromycin, blasticidin or geneticin.

Further, said vector comprises a regulatory sequence that is operably linked to said nucleotide sequence or the nucleic acid molecule defined herein.

The coding sequence(s), e.g., said nucleotide sequence encoding the PA-rich polypeptide, comprised in the vector can be linked to (a) transcriptional regulatory element(s) and/or to other amino acid encoding sequences using established methods. Such regulatory sequences are well known to those skilled in the art and include, without being limiting, regulatory sequences ensuring the initiation of transcription, internal ribosomal entry sites (IRES) and, optionally, regulatory elements ensuring termination of transcription and stabilization of the transcript. Non-limiting examples for such regulatory sequences ensuring the initiation of transcription comprise promoters, a translation initiation codon, enhancers, insulators and/or regulatory elements ensuring transcription termination. Further examples include Kozak sequences and intervening sequences flanked by donor and acceptor sites for RNA splicing, nucleic acid sequences encoding secretion signals or, depending on the expression system used, signal sequences capable of directing the expressed protein to a cellular compartment or to the culture medium.

Examples of suitable promoters include, without being limiting, the cytomegalovirus (CMV) promoter, SV40 promoter, RSV (Rous sarcome virus) promoter, the lacZ promoter, chicken β-actin promoter, CAG promoter (a combination of chicken β-actin promoter and cytomegalovirus immediate-early enhancer), human elongation factor 1α promoter, AOX1 promoter, GAL1 promoter, CaM-kinase promoter, the lac, trp or tac promoter, the lacUV5 promoter, the T7 or T5 promoter, the *Autographa californica* multiple nuclear polyhedrosis virus (AcMNPV) polyhedral promoter or a globin intron in mammalian and other animal cells. One example of an enhancer is, e.g., the SV40 enhancer. Non-limiting additional examples for regulatory elements/sequences ensuring transcription termination include the SV40 poly-A site, the tk poly-A site or the AcMNPV polyhedral polyadenylation signals.

Furthermore, depending on the expression system, leader sequences capable of directing the polypeptide to a cellular compartment or secreting it into the medium may be added to the coding sequence of the nucleic acid molecule provided herein. The leader sequence(s) is (are) assembled in frame with translation, initiation and termination sequences, and preferably, a leader sequence is capable of directing secretion of translated protein, or a portion thereof, into the periplasmic space or into the extracellular medium. Suitable leader sequences are, for example, the signal sequences of BAP (bacterial alkaline phosphatase), CTB (cholera toxin subunit B), DsbA, ENX, OmpA, PhoA, stII, OmpT, PelB, Tat (Twin-arginine translocation) in *E. coli*, and the signal sequences of bovine growth hormone, human chymotrypsinogen, human factor VIII, human ig-kappa, human insulin, human interleukin-2, luciferase from Metrida or *Vargula*, human trypsinogen-2, inulinase from *Kluyveromyces marxianus*, mating factor alpha-1 from *Saccharomyces cerevisiae*, mellitin, human azurocidin and the like in eukaryotic cells.

The vectors may also contain an additional expressible nucleic acid sequence coding for one or more chaperones to facilitate correct protein folding.

Preferably, the vector of the present invention is an expression vector. An expression vector according to this invention is capable of directing the replication and the expression of the nucleic acid molecule of the invention, e.g., the nucleic acid molecule comprising the nucleotide sequence encoding the proline/alanine-rich polypeptide and the nucleotide sequence encoding the biologically active protein. In the appended examples, an expression vector comprising (i) a nucleotide sequence encoding a polypeptide consisting of proline, alanine and serine and (ii) a biologically active protein, such as IL-1Ra, was constructed; see Example 6. An exemplary expression vector comprising the nucleic acid molecule encoding a polypeptide consisting of proline and alanine is shown in Example 10.

Suitable bacterial expression hosts comprise, e.g., strains derived from *Escherichia coli* JM83, W3110, KS272, TG1, BL21 (such as BL21(DE3), BL21(DE3)PlysS, BL21(DE3) RIL, BL21(DE3)PRARE), Origami (K-12), Origami B or Rosetta. For vector modification, PCR amplification and ligation techniques, see methods described in Sambrook (2001) loc. cit.

Additionally, baculoviral systems can also be used as a vector in order to express the nucleic acid molecules of the invention in eukaryotic expression systems. In these aspects, the pFBDM vector can be used as an expression vector. The insertion into the MultiBac baculoviral DNA is mediated via the Tn7 transposition sequence upon transformation of DH10 MultiBac *E. coli* cells (Berger (2013) J. Vis. Exp. 77:50159, Fitzgerald (2006) Nat. Methods. 2006 3:1021-1032.). Virus amplification and expression can be performed in Sf21 (*Spodoptera frugiperda*) or High Five (*Trichoplusia ni*) cells.

The nucleic acid molecules and/or vectors of the invention as described herein above may be designed for introduction into cells by, e.g., non-chemical methods (electroporation, sonoporation, optical transfection, gene electrotransfer, hydrodynamic delivery or naturally occurring transformation upon contacting cells with the nucleic acid molecule of the invention), chemical-based methods (calcium phosphate, DMSO, PEG, liposomes, DEAE-dextrane, polyethylenimine, nucleofection etc.), particle-based methods (gene gun, magnetofection, impalefection), phage or phagemid vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into a targeted cell population.

Preferably, the nucleic acid molecules and/or vectors of the invention are designed for transformation of electrocompetent *E. coli* by electroporation or for stable transfection of CHO cells by calcium phosphate, polyethylenimine or lipofectaminetransfection (Pham (2006) Mol. Biotechnol. 34:225-237; Geisse (2012) Methods Mol. Biol. 899:203-219; Hacker (2013) Protein Expr. Purif. 92:67-76).

The present invention also relates to a host cell or a non-human host transformed with a vector or the nucleic acid molecule of this invention. It will be appreciated that the term "host cell or a non-human host transformed with the vector of the invention", in accordance with the present invention, relates to a host cell or a non-human host that comprises the vector or the nucleic acid molecule of invention. Host cells for the expression of polypeptides are well known in the art and comprise prokaryotic cells as well as eukaryotic cells. Thus, the host can be selected from the group consisting of a bacterium, a mammalian cell, an algal cell, a ciliate, yeast and a plant cell.

Typical bacteria include *Escherichia, Corynebacterium* (*glutamicum*), *Pseudomonas* (*fluorescens*), *Lactobacillus, Streptomyces, Salmonella Bacillus* (such as *Bacillus megaterium* or *Bacillus subtilis*), or *Corynebacterium* (like *Corynebacterium glutamicum*). The most preferred bacterium host herein is *E. coli*. An exemplary ciliate to be used herein is *Tetrahymena*, e.g. *Tetrahymena thermophila.*

Typical mammalian cells include, Hela, HEK293, HEK293T, H9, Per.C6 and Jurkat cells, mouse NIH3T3, NS0 and C127 cells, COS 1, COS 7 and CV1, quail QC1-3 cells, mouse L cells, mouse sarcoma cells, Bowes melanoma cells and Chinese hamster ovary (CHO) cells. Most preferred mammalian host cells in accordance with the present invention are CHO cells. An exemplary host to be used herein is *Cricetulus*, e.g. *Cricetulus griseus* (Chinese hamster). Also, human embryonic kidney (HEK) cells are preferred.

Other suitable eukaryotic host cells are e.g. yeasts such as *Pichia pastoris, Kluyveromyces lactis, Saccharomyces cerevisiae* and *Schizosaccharomyces pombe* or chicken cells, such as e.g. DT40 cells. Insect cells suitable for expression are e.g. *Drosophila* S2, *Drosophila* Kc, *Spodoptera* Sf9 and Sf21 or *Trichoplusia* Hi5 cells. Preferable algal cells are *Chlamydomonas reinhardtii* or *Synechococcus elongatus* cells and the like. An exemplary plant is *Physcomitrella*, for example *Physcomitrella patens*. An exemplary plant cell is a *Physcomitrella* plant cell, e.g. a *Physcomitrella patens* plant cell.

Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells), human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, human leucocytes such as B-cells, T-cells, NK-cells or dendritic cells and stable, immortalized cell lines derived thereof (for example hTERT or oncogene immortalized cells). Appropriate culture media and conditions for the above described host cells are known in the art.

The host cells may e.g. be employed to produce large amounts of the nucleic acid molecule provided herein, the encoded polypeptide provided herein, and/or said drug conjugate provided herein. Hence, the host cells may be employed to produce large amounts of the nucleic acid molecule provided herein, the polypeptide encoded by the nucleic acid molecule comprising the nucleotide sequence encoding the PA-rich polypeptide and/or the polypeptide encoded by the nucleic acid molecule comprising the nucleotide sequence encoding the PA-rich polypeptide and the biologically active protein.

Accordingly, the present invention also relates to a method for preparing the nucleic acid molecule or the vector provided herein, the method comprising culturing the host or host cell of the invention under suitable conditions and optionally isolating the produced nucleic acid molecule and/or vector.

Furthermore, the present invention relates to a method for preparing a polypeptide encoded by the nucleic acid molecule or the nucleotide sequence provided herein, the method comprising culturing the host or host cell of the invention under suitable conditions and optionally isolating the produced polypeptide.

Furthermore, the present invention relates to a method for preparing a drug conjugate, the method comprising culturing the host cell of the invention under suitable conditions and optionally isolating the produced said drug conjugate. Preferably, the present invention relates to a method for preparing a drug conjugate, wherein said drug conjugate is encoded by the nucleic acid molecule, wherein said nucleic acid molecule comprises a nucleotide sequence encoding a polypeptide consisting of proline, alanine and, optionally, serine and a biologically active protein.

Thus, the present invention relates in one aspect to a method for preparing a drug conjugate, wherein said drug conjugate comprises the polypeptide encoded by the nucleic acid molecule as defined herein and further comprises (i) a biologically active protein and/or (ii) a small molecule and/or (iii) a carbohydrate, wherein the method further comprises culturing the host or host cell as provided herein and optionally isolating the produced polypeptide and/or drug conjugate. For example, if the drug conjugate is a fusion protein comprising the polypeptide encoded by the nucleic acid molecule as defined herein and further comprising a biologically active protein, the method can further comprise culturing the host or host cell as provided herein (i.e. a host or host cell comprising a nucleic acid encoding a polypeptide consisting of proline, alanine and, optionally, serine, as provided herein and the nucleic acid encoding a biologically active protein as defined herein, particularly a therapeutically active protein), and optionally isolating the produced fusion protein (drug conjugate). Of course, if the drug conjugate is a protein, the method can also comprise culturing the host or host cell as provided herein (i.e. a host or host cell comprising a nucleic acid encoding a polypeptide consisting of proline, alanine and, optionally, serine, as provided herein) and/or culturing the host or host cell comprising a nucleic acid encoding a biologically active protein as defined herein, particularly a therapeutically active protein, and optionally isolating the produced polypeptide consisting of proline, alanine and, optionally, serine and/or isolating the produced biologically active protein, and further optionally conjugating the polypeptide and the biologically active protein (e.g. by chemical coupling) to produce the drug conjugate.

For example, if the drug conjugate is a conjugate of a polypeptide encoded by the nucleic acid molecule as defined herein (i.e. a nucleic acid encoding a polypeptide consisting of proline, alanine and, optionally, serine, as provided herein) and of a small molecule and/or of a carbohydrate, the method can further comprise culturing the host or host cell as provided herein (i.e. a host or host cell comprising a nucleic acid encoding a polypeptide consisting of proline, alanine and, optionally, serine, as provided herein), and optionally isolating the produced polypeptide, and further optionally conjugating the polypeptide to the small molecule and/or carbohydrate (e.g. by chemical coupling).

"Culturing the host or host cell" includes in this context expression of the polypeptide as defined herein and/or of the biologically active protein in the host or host cell.

It is demonstrated in the appended examples that such a nucleic acid molecule comprising (i) a nucleotide sequence encoding a polypeptide consisting of proline, alanine and serine and (ii) a biologically active protein, such as IL-1Ra, can be bacterially expressed and, subsequently, be purified; see Example 8 and FIG. 7. Furthermore, it is shown herein that a polypeptide consisting of proline and alanine encoded by the nucleic acid molecule provided herein can be expressed and purified; see e.g. Example 11 and FIG. 8. By conjugation of the encoded polypeptide consisting of proline, alanine and, optionally, serine to a small molecule drug, a carbohydrate and/or a biologically active protein, the plasma half-life and/or solubility of the small molecule/small molecule drug and/or biologically active protein may be increased, unspecific toxicity may be decreased, and the prolonged exposure of the active drug to target cells or structures in the body may result in enhanced pharmacodynamics.

The vector present in the host of the invention is either an expression vector, or the vector mediates the stable integration of the nucleic acid molecule of the present invention into the genome of the host cell in such a manner that expression of the protein is ensured. Means and methods for selecting a host cell in which the nucleic acid molecule of the present invention has been successfully introduced such that expression of the protein is ensured are well known in the art and have been described (Browne (2007) Trends Biotechnol. 25:425-432; Matasci (2008) Drug Discov. Today: Technol. 5:e37-e42; Wurm (2004) Nat. Biotechnol. 22:1393-1398).

Suitable conditions for culturing prokaryotic or eukaryotic host cells are well known to the person skilled in the art. For example, bacteria such as e.g. *E. coli* can be cultured under aeration in Luria Bertani (LB) medium, typically at a temperature from 4 to about 37° C. To increase the yield and the solubility of the expression product, the medium can be buffered or supplemented with suitable additives known to enhance or facilitate both. In those cases where an inducible promoter controls the nucleic acid molecule of the invention in the vector present in the host cell, expression of the polypeptide can be induced by addition of an appropriate inducing agent, such as, e.g., isopropyl-β-D-thiogalactopyranoside (IPTG) or anhydrotetracycline (aTc) as employed in the appended examples. Suitable expression protocols and strategies have been described in the art, e.g. in Sambrook (2001) loc. cit., (Gebauer (2012) Meth. Enzymol. 503:157-188) and can be adapted to the needs of the specific host cells and the requirements of the protein to be expressed, if required.

Depending on the cell type and its specific requirements, mammalian cell culture can, e.g., be carried out in RPMI, Williams' E or medium DMEM containing 10% (v/v) FCS, 2 mM L-glutamine and 100 U/ml penicillin/streptomycin. The cells can be kept, e.g., at 37° C., or at 41° C. for DT40 chicken cells, in a 5% $CO_2$, water-saturated atmosphere. A suitable medium for insect cell culture is, e.g., TNM+10% FCS, SF900 or HyClone SFX-Insect medium. Insect cells are usually grown at 27° C. as adhesion or suspension cultures. Suitable expression protocols for eukaryotic or vertebrate cells are well known to the skilled person and can be retrieved, e.g., from Sambrook (2001) (loc. cit).

Preferably, the method for preparing the nucleic acid molecule, the vector, the polypeptide and/or the drug conjugate of the invention is carried out using either bacterial cells, such as, e.g., E. coli cells, or mammalian cells, such as, e.g., CHO cells. More preferably, the method is carried out using E. coli cells or CHO cells and most preferably, the method is carried out using E. coli cells.

Methods for the isolation of the encoded polypeptides produced comprise, without limitation, purification steps such as affinity chromatography (preferably using a fusion tag such as the Strep-tag II or the $His_6$-tag), gel filtration (size exclusion chromatography), anion exchange chromatography, cation exchange chromatography, hydrophobic interaction chromatography, high pressure liquid chromatography (HPLC), reversed phase HPLC, ammonium sulfate precipitation or immunoprecipitation. These methods are well known in the art and have been generally described, e.g., in Sambrook (2001) loc. cit. and are also described in the appended examples, see e.g. Examples 8 and 11. Such methods provide substantially pure polypeptides. Said pure polypeptides have a homogeneity of, preferably, at least about 90 to 95% (on the protein level), more preferably, at least about 98 to 99%. Most preferably, these pure polypeptides are suitable for pharmaceutical use/applications. Also, the application in food or cosmetic industry is envisaged herein. Depending upon the host cell/organism employed in the production procedure, the encoded polypeptides of the present invention may be glycosylated or may be non-glycosylated. Preferably, the polypeptide consisting of proline, alanine and, optionally, serine encoded by the nucleic acid molecule of the invention is not glycosylated. Most preferably, the polypeptide consisting of proline, alanine and, optionally, serine encoded by the nucleic acid molecule of the invention is not posttranslationally modified in its side chains such as, for example, by proline hydroxylation.

The encoded random coil polypeptide consists predominantly of alanine, proline and, optionally, serine residues, whereas serine, threonine or asparagine, which is required for O- or N-glycosylation, is preferably absent. Thus, the production of the polypeptide itself or of a biologically active protein comprising the encoded random coil polypeptide can result in a monodisperse product preferably devoid of post-translational modifications within the Pro/Ala/Ser or Pro/Ala sequence. This is an advantage for recombinant protein production in eukaryotic cells, like chinese hamster ovarian cells (CHO), HEK cells, or yeast, which are often chosen for the biosynthesis of complex proteins.

The invention also relates to a method for preparing a drug conjugate, wherein said drug conjugate comprises the polypeptide encoded by the inventive nucleic acid molecule provided herein and further comprises (i) a biologically active protein and/or (ii) a small molecule and/or (iii) a carbohydrate. Such carbohydrate conjugates may be particularly useful as vaccines.

As described above, a drug conjugate comprising the PA-rich polypeptide and the biologically active protein can be prepared by expressing the nucleic acid molecule comprising the nucleotide sequence encoding the PA-rich polypeptide and the nucleic acid sequence encoding the biologically active protein. The expressed drug conjugate can be isolated. Alternatively, the drug conjugate can be prepared by culturing/raising the host comprising the nucleotide sequence or the nucleic acid molecule encoding said polypeptide consisting of proline, alanine and, optionally serine. Thus, the nucleic acid molecule is expressed in the host. Optionally, said produced polypeptide is isolated. The produced polypeptide consisting of proline, alanine and, optionally, serine can be conjugated to the biologically active protein, e.g., via a peptide bond or a non-peptide bond.

It is demonstrated in the illustrative examples that the PA-rich polypeptide encoded by the nucleic acid molecule provided herein can be expressed in bacteria and can be purified therefrom; see e.g. Example 11 and FIG. 8. In particular, it was surprisingly shown that the start methionine (N-terminal methionine) of the prepared polypeptide is cleaved off and is thus missing in the produced polypeptide; see e.g. Example 12 and FIG. 8D. The missing start methionine in the prepared polypeptide allows the seamless conjugation of the primary amino group of the following amino acid (after the start methionine) at the N-terminus to a biologically active protein, a small molecule and/or a carbohydrate. Therefore, the nucleic acid molecules of the invention and the prepared polypeptides thereof are particularly advantageous for the conjugation to, e.g., the biologically active proteins.

In particular, the biologically active protein can be site-specifically conjugated, e.g., in the presence of an activating agent such as N-(3-dimethylaminopropyl)-N'-ethylcarbodiimide (EDC) or as an N-hydroxysuccinimide (NETS) ester (Hermanson (1996) Bioconjugate Techniques, 1st edition, Academic Press, San Diego, Calif.) to the N-terminus of the produced random coil polypeptide. Alternatively, the biologically active protein can be site-specifically conjugated to the C-terminus of the produced random coil polypeptide consisting of proline, alanine and, optionally, serine, e.g., in the presence of an activating agent such as EDC or after activation as an NHS ester.

Furthermore, the produced polypeptide consisting of proline, alanine and, optionally, serine can be conjugated to the small molecule and/or to the carbohydrate via a non-peptide bond. Non-peptide bonds that are useful for cross-linking proteins are known in the art and may include disulfide bonds, e.g., between two Cys side chains and/or thiol groups, thioether bonds and amide bonds between carboxyl groups and amino groups. Non-peptide covalent bonds may also be provided by chemical cross-linkers, such as disuccinimidyl suberate (DSS), N-β-maleimidopropyl-oxysuccinimide ester (BMP S) or sulfosuccinimidyl 4-[p-maleimidophenyl]butyrate (Sulfo-SMPB), metal-chelating/complexing groups as well as non-covalent protein-protein or protein-peptide interactions.

Furthermore, a small molecule drug can be site-specifically conjugated to the polypeptide forming the random coil. Optionally, the N-terminus of the polypeptide can be modified with a suitable protective group, for example an acetyl group or a pyroglutamyl group, and after activation of the C-terminal carboxylate group, e.g. using the common reagents EDC and NETS (Hermanson (1996) loc. cit.), site-specific coupling of the drug to the C-terminus of the random coil polypeptide can be achieved. In this manner uniform drug conjugates can be easily obtained.

As an alternative to a single site-specific conjugation the random coil polypeptide consisting of proline, alanine and, optionally, serine may be equipped with additional side chains, at the N- or the C-terminus or internally, suitable for chemical modification, such as lysine residues with their ε-amino groups, cysteine residues with their thiol groups, or even non-natural amino acids, allowing the conjugation of one, two or multiple small molecules using, for example, NHS or maleimide active groups.

Apart from stable conjugation, a prodrug may be linked transiently to the random coil polypeptide. The linkage can be designed to be cleaved in vivo, in a predictable fashion, either via an enzymatic mechanism or by slow hydrolysis initiated at physiological pH similarly as, for example, the poorly soluble antitumor agent camptothecin was conjugated to a PEG polymer, thus achieving increased biodistribution, decreased toxicity, enhanced efficacy and tumor accumulation (Conover (1998) Cancer Chemother. Pharmacol. 42:407-414). Examples for further prodrugs are chemotherapeutic agents like docetaxel (Liu (2008) J. Pharm. Sci. 97:3274-3290), doxorubicin (Veronese (2005) Bioconjugate Chem. 16: 775-784) or paclitaxel (Greenwald (2001) J. Control Release 74:159-171).

It is also envisaged herein that the small molecule may be coupled to a fusion protein, e.g., the polypeptide forming the random coil consisting of proline, alanine and, optionally, serine genetically fused to a targeting domain, e.g. an antibody fragment, thus resulting in specific delivery of the small molecule drug. The immunotoxin generated in the latter case by conjugation with a cytotoxic small molecule is particularly useful if the targeting domain is directed against a cell-surface receptor which undergoes internalization, for example.

As used herein, the term “drug” refers to a small molecule, a biologically active protein, a peptide or a carbohydrate. As used herein, the term “small molecule” can refer to an (organic) low molecular weight (<900 Daltons) compound. Small molecules can help to regulate a biological process and have usually a size in the order of nanometer. It is envisaged herein that the small molecule is used in a method of therapy, diagnosis or is used in the food or cosmetic industry. For example, the drug conjugate with the produced polypeptide that is encoded by the nucleotide sequence or the nucleic acid molecule provided herein can comprise (a) small molecule(s) that is/are selected from the group consisting of angiogenesis inhibitors, anti-allergic drugs, anti-emetic drugs, anti-depressant drugs, anti-hypertensive drugs, anti-inflammatory drugs, anti-infective drugs, anti-psychotic drugs, anti-proliferative (cytotoxic and cytostatic) drugs, calcium antagonists and other circulatory organ drugs, cholinergic agonists, drugs acting on the central nervous system, drugs acting on the respiratory system, steroids, antisense nucleic acids, small interference RNAs (siRNAs), micro RNA (miR) inhibitors, microRNA mimetics, DNA aptamers and RNA aptamers.

Exemplary angiogenesis inhibitors include but are not limited to MetAP2 inhibitors (like fumagillin, fumagillin derivatives, 2-{3-[3,5-bis[4-nitrobenzylidene]-4-oxopiperidin-1-yl]-3-oxopropylsulfanyl} ethanesulfonic acid), VGFR inhibitors (like axitinib, brivanib, cabozantinib, tivozanib and motesanib), placenta growth factor (PIGF) inhibitors, platelet-derived growth factor receptor inhibitors (like AC 710, sorafenib, sunitinib, and vatalanib) and the like.

Exemplary anti-allergic drugs include but are not limited to antihistaminics (like diphenhydramine (benadryl), dimenhydrinate (dramamine, driminate), hydroxyzine hydrochloride (restall, vistacot), promethazine (phenergan)) and the like.

Exemplary anti-depressant drugs include but are not limited to granisetron, palonosetron, and the like.

Exemplary anti-depressant drugs include but are not limited to cis-flupenthixol, imipramine hydrochloride, mianserin and the like.

Exemplary anti-hypertensive drugs include but are not limited to alprostadil, diazoxide, nicardipine and the like.

Exemplary anti-inflammatory drugs include but are not limited to, cortisone, hyaluronic acid, ketorolac and the like.

Exemplary anti-infective drugs include but are not limited to aminoglycosides, amadovir, amoxicillin, ampicillin, benzylpenicillin, carbapenems, cephalosporin, ceftiofur, chloramphenicol, cefepime, ceftazidime, ceftobiprole, clindamycin, draxxin, dalbavancin, daptomycin, dihydrostreptomycin, erythromycin, florfenicol, fluoroquinolones, flunixin meglumine, linezolid, marbofloxacin, micafungin, nitrofurazone, oritavancin, oxytetracycline, penicillin, piperacillin, procain, rupintrivir, spiramycin, streptogramins, sulfadimethoxin, sulfamethazine, tedizolid, telavancin, ticarcillin, tilmicosin, tigecycline, tildipirosin, tylosin, vancomycin, and the like.

Exemplary anti-psychotic drugs include but are not limited to amisulprid, ariprazole, benperidol, bromperidol, clorpromazin, chlorprothixen, clopenthixol, clozapine, flupentixol, fluphenazin, fluspirilen, haloperidol, levomepromazin, melperon, olanzapine, perazin, perphenazin, pimozid, pipamperon, promazin, promethazine, prothipendyl, quetiapine, risperido, sulpirid, thioridazin, trifluoperazin, triflupromazin, zuclopenthixol, and the like.

Exemplary anti-tumor drugs include but are not limited to anthracyclins (like doxorubicin, epirubicin, idarubicin, and daunorubicin), alkylating agents (like calicheamicins, dactinomycines, mitromycines, and pyrrolobenzodiazepines), AKT inhibitors (like AT7867), amatoxins (like ax-amanitins, P-amanitins, y-amanitins, c-amanitins, amanullin, amanullic acid, amaninamide, amanin, and proamanullin, SN-38, and camptothecin), ATM inhibitors, auristatins (like auristatin EB (AEB), auristatins EFP (AEFP), monomethyl auristatin E (MMAE), monomethyl auristatin F (MMAF), auristatin F, and dolastatin), cryptophycins, cyclin-dependent kinases inhibitors (like BMS-387032, PD0332991, GSK429286, AZD7762; AZD 1152, MLN8054 and MLN8237; BI 2536, B16727, GSK461364, ON-01910, SB 743921, SB 715992, MK-0731, AZD8477, AZ3146, and ARRY-520), duocarmycins, DNA-PK inhibitors, epothilones (like epothilone A, B, C, D, E or F, and derivatives), GSK-3 inhibitors, HDAC inhibitors (like belinostat, CUDC-101, droxinostat, ITF2357, JNJ-26481585, LAQ824, and panobinostat MC1568, mocetinostat, entinostat, PCI-24781, pyroxamide, trichostatin A, and vorinostat), hsp70 inhibitors, hsp90 inhibitors (like 17AAG derivatives, B11B021, B11B028, SNX-5422, NVP-AUY-922, KW-2478, and geldanamycin), MAPK signaling pathway inhibitors (like MEK, Racs, JNK, B-Raf), maytansinoids, maytansinoid analogs (like maytansinol, maytansinol analogs, maytansine, DM-1, and DM-4), p38 MAPK inhibitors (like GDC-0973, GSK1 120212, MSC1936369B, AS703026, R05126766 and R04987655, PD0325901, AZD6244, AZD 8330, GDC-0973, CDC-0879, PLX-4032, SB590885, BIRB 796, LY2228820, SB 202190, AEE788, BIBW2992, afatinib, lapatinib, erlotinib, and gefitinib), PARP inhibitors (like iniparib, olaparib, veliparib, AG014699, CEP 9722, MK 4827, KU-0059436, LT-673, 3 aminobenzamide, A-966492, and AZD2461), PDK-1 inhibitors, platinum compounds (like cisplatin, carboplatin, oxaliplatin, iproplatin, ormaplatin or tetraplatin), taxans (like paclitaxel, and ordocetaxel), tubulysins (like tubulysin A, tubulysin B and tubulysin derivatives), vinca alkaloids (like vinblastine, vindesine and navelbine), Wnt/Hedgehog signaling pathway inhibitors like (vismodegib, GDC-0449, cyclopamine, and XAV-939), and the like.

Exemplary drugs acting on the central nervous system include but are not limited to buprenorphin, cryostatin, naltroxrexone, naloxone, and the like.

Exemplary vitamins include but are not limited to vitamin B-12 (cyanocobalamin), vitamin A, and the like.

Exemplary steroids include but are not limited to androgenic steriods (like fluoxymesterone, methyltestosterone, testosterone, trenbolone), estrogens (like beta-estradiol, diethylstilbestrol, estrone, estriol, equilin, estropipate equilin, mestranol), progestational compounds (like 19-norprogesterone, alfaprostol, chlormadinone, demegestone, dydrogesterone, dimethisterone, ethisterone, ethynodiol diacetate, norethindrone, norethindrone acetate, medroxyprogesterone, melengestrolprogesterone, norgestrel, promegestone, zeranol), and the like.

Exemplary antisense nucleic acids include but are not limited to antisense nucleic acids targeting the androgen receptor (like ISIS-AR, AZD5312), angiopoietin-like 3 protein (like ISIS-ANGPTL3), apolipoprotein B100 (like mipomersen), apolipoprotein CIII (like ISIS-APOCIII, volanesorsen), the connective tissue growth factor (CTGF) (like EXC 001, PF-06473871), clusterin (like custirsen, OGX-011), C-reactive protein (like ISIS-CRP), diacylglycerol acyltransferase (like ISIS-DGAT2), factor VII (like ISIS-FVII), fibroblast growth factor receptor 4 (like ISIS-FGFR4), hepcidin (like XEN701), Hsp27 (like apatorsen, OGX-427), the HTT gene (like ISIS-HTT), ICAM-1 (like alicaforsen), prekallikren (like ISIS-PKK), SMN2 (like ISIS-SMN), STAT3 (like ISIS-STAT3-2.5, AZD9150), the transthyretin gene (like ISIS-TTR), and the like.

Exemplary small interference RNAs (siRNAs) include but are not limited to siRNAs targeting the alpha-1-antitrypsin mutant Z-AAT (like ALN-AAT), aminolevulinate synthase 1 (ALAS-1) (like ALN-AS1, ALN-AS2), antithrombin III (like ALN-AT3), the complement component C5 (like ALN-CC5), the complement component C6 (like ALN-CC6), the connective tissue growth factor (like RXI-109), exon 8 of the dystrophin gene (like SRP-4008), exon 44 of the dystrophin gene (like SRP-4044), exon 45 of the dystrophin gene (like SRP-4045), exon 50 of the dystrophin gene (like SRP-4050), the ebola virus (like AVI-7537), exon 51 of the dystrophin gene (like eteplirsen, AVI-4658), exon 52 of the dystrophin gene (like SRP-4052), exon 53 of the dystrophin gene (like SRP-4053), the influenza virus (like AVI-7100), the kinesin spindle protein (KSP), lung diseases (like Atu111), the marburg virus (like AVI-7288), multi-targeted small interfering RNA (siRNA) cocktails (like STP503, STP523, STP601, STP702, STP705, STP801, STP805, STP900, STP902, STP911, STP916, siPOOLs), the nucleocapsid N of the virus genome (like ALN-RSV01), PCSK9 (like ALN-PCS01, ALN-PCSsc), the pro-apoptotic protein caspase 2 (like QPI-1007), the pro-apoptotic protein p53 (like QPI-1002), RTP801 (like PF-655), SERPINC1 (like ALN-AT4), the transmembrane protease serine 6 (Tmprss6) (like ALN-TMP), transthyretin (like ALN-TTRsc, ALN-TTR02), PCSK10 (like ALN-PCS02), PKN3 (like Atu027), the vascular endothelial growth factor (VEGF) (like ALN-VSP), and the like.

Exemplary microRNA inhibitors include but are not limited to inhibitors of miR-10b, miR-15, miR-21, miR-29, miR-33, miR-92, miR-145, miR195, miR-208, miR-221, miR-451, miR-499 and the like.

Exemplary microRNA mimetics include but are not limited to an analog of miR-34 (like MRX34), miR-Rx06, miR-Rx07, miR-Rx16, an analog of 1et7 (like miR-Rx1et-7), and the like. Exemplary DNA aptamers include but are not limited to nucleolin inhibitor (like AS1411), pGDF inhibitor (like E10030), thrombin inhibitor (like NU172), vWF inhibitor (like ARC1779), and the like.

Exemplary RNA aptamers include but are not limited to C5a inhibitor (like NOX-D21 or ARC1905), calcitonin gene-related peptide inhibitor (like NOX-L41), C-C chemokine ligand 2 inhibitor (like NOX-E36), CXCL12 inhibitor (like NOX-A12), glucagon inhibitor (like NOX-G16), hepcidin antagonist (like NOX-H94), pathogen recognition receptor agonist (like a RIG-I agonist), sphingosine-1-phosphate inhibitor (like NOX-S93), VEGF antagonist (like NX1838), and the like.

Exemplary carbohydrates that are potentially useful for the preparation of vaccines include but are not limited carbohydrate epitopes specifically bound by lectins, *E. coli* O 121 O-antigen, *E. coli* O 121 O-antigen derivatives, Man9 from HIV-I gp120, *Shigella flexneri* 2a O-polysaccharides, *Staphylococcus aureus* polysaccharide capsular polysaccharide 5, *Staphylococcus aureus* polysaccharide capsular polysaccharide 8, tumor-associated carbohydrate antigens (TACA) (like Tn antigens (e.g. α-GalNAc-O-Ser/Thr), sialyl Tn antigens (e.g. NeuAcα(2,6)-GalNAcα-O-Ser/Thr), Thomsen-Friedenreich antigen (Galβ1-3GalNAcα1), LewisY (e.g. Fucα(1,2)-Galβ(1,4)-[Fucα(1,3)]-GalNAc), sialyl LewisX and sialyl LewisA, LewisX (stage-specific embryonic antigen-1/SSEA-1), Globo H antigen (e.g. Fucα (1,2)-Galβ(1,3)-GalNAcβ(1,3)-Galβ(1,4)-Galβ(1,4)-Glc), T antigen (e.g. Galβ(1,3)-GalNAcα-O-Ser/Thr), glycosphingolipid stage-specific embryonic antigen-3 (SSEA-3), sialic acid containing glycosphingolipids, ganglioside GD2, GD3, ganglioside GM2, ganglioside fucosyl GM and ganglioside Neu5GcGM3), and the like.

The drug conjugate comprising the polypeptide encoded by the inventive nucleic acid molecule provided herein comprising a biologically active protein and/or a small molecule and/or a carbohydrate may be used for the treatment of inflammatory diseases, infectious diseases, respiratory diseases, endocrine disorders, diseases of the central nervous system, musculoskeletal diseases, cardiovascular diseases, oncological diseases, urogenital diseases and metabolic diseases.

Exemplary inflammatory diseases include but are not limited to ankylosing spondylitis, arthritis, atherosclerosis, atypical hemolytic uremic syndrome (aHUS), fibromyalgia, Guillain Barré syndrome (GBS), irritable bowel syndrome (IBS), Crohn's disease, colitis, dermatitis, diverticulitis, osteoarthritis, psoriatic arthritis, Lambert-Eaton fmyasthenic syndrom, systemic lupus erythematous (SLE), nephritis, Parkinson's disease, multiple sclerosis, paroxysmal nocturnal hemoglobinuria (PNH), rheumatoid arthritis (RA), Sjögren's syndrome, ulcerative colitis, and the like.

Exemplary infectious diseases include but are not limited to african trypanosomiasis, borreliosis, cholera, cryptosporidiosis, dengue fever, hepatitis A, hepatitis B, hepatitis C, HIV/AIDS, influenza, Japanese encephalitis, leishmaniasis, malaria, measles, meningitis, onchocerciasis, pneumonia, rotavirus infection, schistosomiasis, sepsis, shigellosis, streptococcal tonsillitis, tuberculosis, typhoid, yellow fever, and the like.

Exemplary respiratory diseases include but are not limited to asthma, chronic obstructive pulmonary disease (COPD), cystic fibrosis, and the like.

Exemplary endocrine disorders include but are not limited to acromegaly, type I diabetes, type II diabetes, gestational diabetes, Graves' disease, growth hormone deficiency, hyperglycemia, hyperparathyroidism, hyperthyroidism, hypoglycemia, infertility, obesity, parathyroid diseases, Morquio A syndrome, mucopolysaccharidosis, and the like.

Exemplary diseases of the central nervous system include but are not limited to Alzheimer's disease, catalepsy, Huntington's disease, Parkinson's disease, and the like.

Exemplary musculoskeletal diseases include but are not limited to osteoporosis, muscular dystrophy, and the like.

Exemplary cardiovascular diseases include but are not limited to acute heart failure, cerebrovascular disease (stroke), ischemic heart disease, and the like.

Exemplary oncological diseases include but are not limited to adrenal cancer, bladder cancer, breast cancer, colon and rectal cancer, endometrial cancer, kidney cancer, acute lymphoblastic leukemia (ALL) and other types of leukemia, lung cancer, melanoma, Non-Hodgkin lymphoma, pancreatic cancer, prostate cancer, thyroid cancer, and the like.

Exemplary urogenital diseases include but are not limited to benign prostatic hyperplasia (BPH), hematuria, neurogenic bladder, Peyronie's disease, and the like.

Exemplary metabolic diseases include but are not limited to Gaucher disease, Fabry disease, Growth hormone deficiency, Hurler syndrome, Hunter syndrome, hyperoxaluria, neuronal ceroid lipofuscinosis, Maroteaux-Lamy syndrome, Morquio syndrome, Noonan syndrome, SHOX gene haploinsufficiency, Turner syndrome, Prader-Willi syndrome, phenylketonuria, Sanfilippo syndrome, and the like.

As described above, the nucleic acid molecule provided herein can also be employed alone or as part of a vector for gene therapy purposes. Gene therapy, which is based on introducing therapeutic genes into cells by ex vivo or in vivo techniques, is one of the most important applications of gene transfer. Suitable vectors, methods or gene delivery systems for in vivo gene therapy are described in the literature and are known to the person skilled in the art; see, e.g., Giordano (1996) Nat. Med. 2:534-539; Schaper (1996) Circ. Res. 79:911-919; Anderson (1992) Science 256:808-813; Verma (1997) Nature 389:239-249; Isner (1996) Lancet 348:370-374; Muhlhauser (1995) Circ. Res. 77:1077-1086; Onodera (1998) Blood 91:30-36; Verma (1998) Gene Ther. 5:692-699; Nabel (1997) Ann. N.Y. Acad. Sci. 811:289-292; Verzeletti (1998) Hum. Gene Ther. 9:2243-2251; Wang (1996) Nat. Med. 2:714-716; WO 94/29469; WO 97/00957, U.S. Pat. Nos. 5,580,859; 5,589,466; or Schaper (1996) Curr. Opin. Biotechnol. 7:635-640. The nucleic acid molecules and vectors provided herein may be designed for direct introduction or for introduction via liposomes or viral vectors (e.g., adenoviral, retroviral) into the cell. For example, the vector can be an adeno-associated-virus (AAV) vector, in particular, an AAV8 vector. AAV vectors are attractive for gene therapy. The AAV system has several advantages including long-term gene expression, the inability to autonomously replicate without a helper virus, transduction of dividing and nondividing cells, and the lack of pathogenicity from wild-type infections. Preferably, said cell in which the nucleic acid molecule or vector is introduced is a germ line cell, embryonic cell or egg cell or derived therefrom, most preferably said cell is a stem cell. An example for an embryonic stem cell can be, inter alia, a stem cell as described in Nagy (1993) Proc. Natl. Acad. Sci. USA 90:8424-8428.

The terms "polypeptide", "peptide" and "protein" are used herein interchangeably and refer to a polymer of two or more amino acids linked via amide or peptide bonds that are formed between an amino group of one amino acid and a carboxyl group of another amino acid. Preferably, a peptide bond is formed between the α-amino group of one amino acid and the α-carboxyl group of another amino acid. The amino acids comprised in the peptide or protein, which are also referred to as amino acid residues, may be selected from the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val) but also from non-proteinogenic and/or non-standard α-amino acids (such as, e.g., ornithine, citrulline, homolysine, pyrrolysine, or 4-hydroxyproline) as well as β-amino acids (e.g., β-alanine), γ-amino acids and δ-amino acids. Preferably, the amino acid residues comprised in the peptide or protein are selected from α-amino acids, more preferably from the 20 standard proteinogenic α-amino acids (which can be present as the L-isomer or the D-isomer, and are preferably all, except for Gly, are present as the L-isomer).

The encoded polypeptide or protein may be unmodified or may be modified, e.g., at its N-terminus, at its C-terminus and/or at the side chain of any of its amino acid residues (particularly at the side chain functional group of one or more Lys, His, Ser, Thr, Tyr, Cys, Asp, Glu, and/or Arg residues). Such modifications may include, e.g., the attachment of any of the protecting groups described for the corresponding functional groups in: Wuts (2006) Greene's protective groups in organic synthesis, John Wiley & Sons, $4^{th}$ edition, Hoboken, N.J. Such modifications may also include glycosylation and/or acylation with one or more fatty acids (e.g., one or more $C_{8-30}$ alkanoic or alkenoic acids; forming a fatty acid acylated peptide or protein). The encoded polypeptide is preferably not hydroxylated, in particular does not comprise hydroxyproline.

The amino acid residues comprised in the encoded peptide or protein may, e.g., be present as a linear molecular chain (forming a linear peptide or protein) or may form one or more rings (corresponding to a cyclic peptide or protein), e.g., circularized via a peptide or isopeptide bond or a disulfide bridge. The peptide or protein may also form oligomers consisting of two or more identical or different molecules. As used herein, the term "domain" relates to any region/part of an amino acid sequence that is capable of autonomously adopting a specific structure and/or function. In the context of the present invention, accordingly, a "domain" may represent a functional domain or a structural domain, which may for example form part of a larger polypeptide.

As used herein, the terms "comprising" and "including" or grammatical variants thereof are to be taken as specifying the stated features, integers, steps or components but do not preclude the addition of one or more additional features, integers, steps, components or groups thereof. These terms encompass the terms "consisting of" and "consisting essentially of."

Thus, the terms "comprising"/"including"/"having" mean that any further component (or likewise features, integers, steps and the like) can/may be present. Thus, whenever the terms "comprising"/"including"/"having" are used herein, they can be replaced by "consisting essentially of" or, preferably, by "consisting of".

The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means that specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures, by practitioners of the chemical, biological and biophysical arts.

As used herein and if not indicated otherwise, the term "about" preferably refers to ±10% of the indicated numerical value, more preferably to ±5% of the indicated numerical value, and in particular to the exact numerical value indicated.

The present invention is further described by reference to the following non-limiting figures and examples. Unless otherwise indicated, established methods of recombinant gene technology were used as described, for example, in Sambrook (2001) loc. cit. which is incorporated herein by reference in its entirety.

BRIEF DESCRIPTION OF THE FIGURES

The present invention is further described by reference to the following non-limiting figures and examples. The figures show:

FIGS. 1A-1E: Assembly of Low Repetitive Nucleic Acids Encoding Proline/Alanine-Rich Sequences Using the Plasmid pXL2.

FIG. 1A Plasmid map of pXL2 (SEQ ID NO: 48). A SapI recognition site (5'-GCTCTTC-3') and an EarI recognition site (5'-CTCTTC-3') are inserted into the selectable marker gene lacZ, which is under transcriptional control of the lac promoter/operator)($lac^{p/o}$). The SapI restriction site allows the consecutive insertion of one or more units (building blocks) of low repetitive nucleic acid molecules encoding proline/alanine-rich sequences. Cutting with EarI, a restriction enzyme whose recognition sequence overlaps with/is a subset of the SapI recognition sequence, allows the excision and/or isolation of the assembled low repetitive nucleic acid molecule (gene cassette) encoding a proline/alanine-rich sequence. The plasmid backbone is identical with that of the generic cloning vector pUC19 (Yanisch-Perron (1985) Gene 33:103-119), except for deletion of additional SapI and EarI restriction sites via silent mutation. FIG. 1B Plasmid map of pXL1 (SEQ ID NO: 55). Two SapI recognition sites (5'-GCTCTTC-3') in opposite orientation are inserted into the selectable marker gene lacZ, which is under transcriptional control of the lac promoter/operator)($lac^{p/o}$). The SapI restriction site allows the insertion/cloning as well as propagation/amplification and the subsequent excision and/or isolation of a low repetitive nucleic acid molecule (gene cassette) encoding a proline/alanine-rich sequence. The plasmid backbone is identical with that of pUC19, except for deletion of an additional SapI restriction site via silent mutation. Note that the inserted gene cassette has reverse orientation compared with pXL2. FIG. 1C Nucleotide sequence stretch of and around the cloning site of pXL2 useful for the cloning and assembly of low repetitive nucleic acid molecules. The nucleotide sequence contains a SapI restriction site and an EarI restriction site in reverse orientation. As the EarI recognition sequence is also part of the SapI recognition sequence, EarI cuts at both recognition sites. Regardless of the restriction enzyme used, SapI or EarI; digest leads to protruding GCC/CGG ends (encoding Ala), which are compatible with the GCC/CGG overhangs of low repetitive nucleic acid molecules encoding proline/alanine-rich sequences and thus allow efficient ligation. Recognition sequences are underlined. FIG. 1D Nucleotide sequence and encoded amino acid sequence of the cloning site of pXL2 after insertion of one low repetitive nucleic acid unit/building block, PAS #1b(200) (SEQ ID NO: 19). The SapI and EarI restriction sites flanking the cloned low repetitive nucleic acid unit/building block are labelled (recognition sequences are underlined). FIG. 1E Assembly of low repetitive nucleic acid sequence units to obtain longer cloned nucleotide sequences (nucleic acid molecules) encoding proline/alanine-rich amino acid repeat sequences. In the first step, pXL2 is digested with SapI, dephosphorylated and ligated with the first sequence unit, PAS #1b(200). In the second step, the resulting plasmid is opened/linearized upstream of the cloned sequence unit by singular SapI restriction digest, followed by dephosphorylation and ligation with the second nucleotide sequence unit, PAS #1c (200). The resulting plasmid pXL2-PAS #1c/1b(400) contains an inserted gene/DNA cassette comprising in total 1200 base pairs in length. Overall, the resulting cloned low repetitive nucleotide sequence encoding a proline/alanine-rich amino acid repeat sequence contains only nucleotide repeats with a maximum length of 14 nucleotides (SEQ ID NO: 52). The entire assembled gene cassette/nucleic acid molecule can be easily excised via digestion with EarI and subsequently used for subcloning on expression vectors, for example in the same reading frame with a nucleotide sequence encoding a biologically active protein, and the like. Notably, by repeating the second step, gene cassettes with successively increasing length can be assembled and cloned on pXL2 in a systematic fashion. If different suitable nucleotide sequence units are used, the resulting long low repetitive nucleic acid molecule encoding a proline/alanine-rich amino acid repeat sequence contains only few or short nucleotide repeats.

FIG. 2A Dot plots of the prior art proline/alanine-rich sequence PA #3a(200) (SEQ ID NO: 15) are compared to dot plots of a low repetitive nucleotide sequence according to this invention, PA #3b(200) (SEQ ID NO: 36), both generated using the dot plot tool "dottup" included in the Geneious V8.1 software package (Biomatters, Auckland, New Zealand), applying a repeat window of 14 or 15. By comparing the analyzed nucleotide sequence to itself on the x- and y-axes, respectively, of a two-dimensional graph the "dottup" tool identifies all regions where an identical sequence of specified length (repeat window) occurs and draws a diagonal line, thus indicating the positions of a repeat sequence on the x- and y-axis (if represented by a diagonal line different from the central diagonal line, the latter indicating self-identity). Successive repeats extend a diagonal line. The PA #3a(200) nucleotide sequence analyzed here reveals a highly repetitive nature as illustrated by the many and/or long diagonal lines. In this case, the nucleotide sequence shows numerous repeats of 60 base pairs each. By applying a repeat window of 14, even a shorter 14 bp repeat within the 60 bp repeat appears. In contrast, the PA #3b(200) nucleotide sequence shows only a few scattered 14 bp repeats within the entire analyzed nucleotide sequence of 600 bp whereas no repeat is detectable when applying a slightly larger repeat window of 15 for analysis. FIGS. 2B-2C Dot plots of the nucleic acid PAS #1a(600) (SEQ ID NO: 12) disclosed in WO2008155134 encoding a proline/alanine-rich sequence are compared to dot plots of the assembled low repetitive nucleotide sequences encoding proline/alanine-rich amino acid repeat sequences according to this invention, PAS #1d/1f/1c/1b (800) (SEQ ID NO: 39) and PAS #1f/1c/1b(600) (SEQ ID NO: 38), using repeat windows of 14 and 15 base pairs. Whereas the nucleotide sequence PAS #1a(600) reveals a composition of 60 base pair repeats, the PAS #1d/1f/1c/1b (800) and the PAS #1f/1c/1b(600) nucleotide sequences show no or, in the case of the 14 nucleotide repeat window, only one single 14 nucleotide repeat (diagonal line) within the entire analyzed nucleotide sequences of 2400 or 1800 bp, respectively. FIGS. 2D-2E Dot plot analysis of a synthetic DNA sequence encoding an $[(AP)_5]_n$ multimer (SEQ ID NO: 16) disclosed in US2006/0252120 and of a natural DNA sequence encoding a repetitive proline/alanine-rich region of the very large tegument protein of Macacine herpesvirus 1 (GenBank AAP41454.1) (SEQ ID NO: 18) in comparison with the low repetitive nucleotide sequence according to this invention, PA #3a(200) (SEQ ID NO: 15), applying repeat windows of 14 and 15 nucleotides. Dot plots of the DNA sequences encoding the $[(AP)_5]_n$ multimer and the proline/alanine-rich region of the very large tegument protein of Macacine herpesvirus 1 illustrate the highly repetitive nature of these nucleotide sequences. In contrast, the dot plot of the PA #1b(200) nucleotide sequence shows only a few scattered 14 nucleotide repeats (14 nucleotide repeat window) or no repeat at all (15 nucleotide repeat window) within the entire analyzed nucleotide sequence of 600 bp.

Electropherogram from DNA sequencing of pXL2-PAS #1f/1c/1b(600) (SEQ ID NO: 38) having a low repetitive nucleotide sequence encoding a proline/alanine-rich sequence according to this invention. Double-stranded plasmid DNA was sequenced using the primer XLP-1 (SEQ ID NO: 3), which specifically hybridizes within the coding region of the PAS #1b(200) nucleotide sequence unit (SEQ ID NO: 19). In this electropherogram more than 900 bases are readable and correspond to the known nucleotide sequence of pXL2-PAS #1f/1c/1b(600). Notably, the electropherogram shows no signs of unspecific or multiple primer hybridization.

Figure 4A:
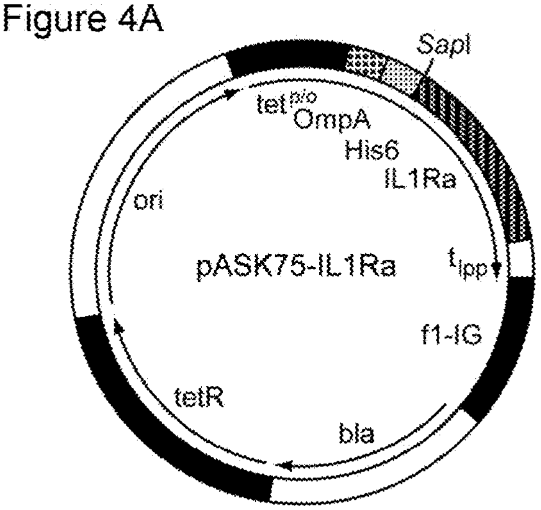
Figure 4B:
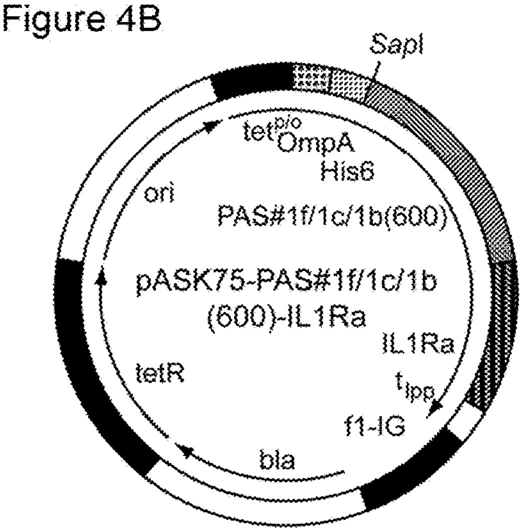

FIGS. 4A-4B: pASK75-PAS #1f/1c/1b(600)-IL1Ra, a Genetically Stable Expression Vector for Bacterial Production of the PAS #1(600)-IL1Ra Fusion Protein Having Therapeutic Relevance.

FIG. 4A Plasmid map of pASK75-IL1Ra (SEQ ID NO: 49) and FIG. 4B of its derivative pASK75-PAS #1f/1c/1b (600)-IL1Ra (SEQ ID NO: 50) after insertion of a PAS #1f/1c/1b(600) gene cassette. The structural gene for the biologically/pharmacologically active (pre)protein PAS #1(600)-IL1Ra comprising the low repetitive nucleotide sequence encoding a PAS #1 polypeptide with 601 amino acid residues and the structural gene for human IL-1Ra as well as coding regions for the bacterial OmpA signal sequence and a $His_6$-tag is cloned under transcriptional control of the tet promoter/operator ($tet^{p/o}$). The plasmid backbone outside the expression cassette flanked by the XbaI and HindIII restriction sites is identical with that of the generic expression vector pASK75 (Skerra (1994) Gene 151:131-135). The singular SapI restriction site that was retained after insertion of the low repetitive nucleic acid molecule encoding a proline/alanine-rich amino acid repeat sequence according to this invention is indicated.

Figure 5:
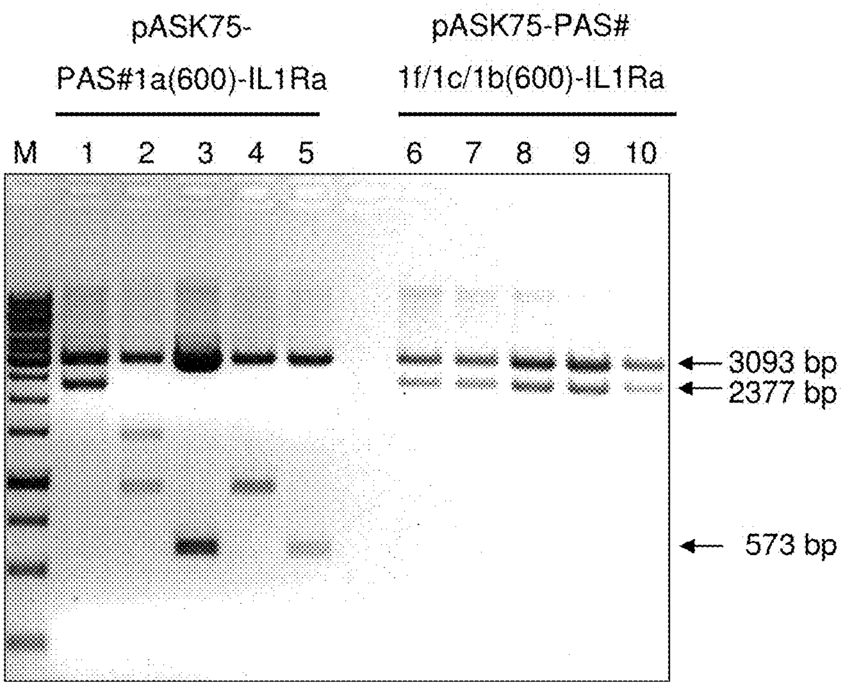

FIG. 5: Analysis of the Genetic Stability of the Low Repetitive Nucleic Acid Molecule Encoding a Proline/Alanine-Rich Amino Acid Repeat Sequence, PAS #1f/1c/1b (600), in Comparison with the Prior Art Nucleotide Sequence PAS #1a(600)

Agarose gel electrophoresis after XbaI/HindIII restriction analysis of 10 plasmid preparations of *E. coli* JM83 clones transformed with pASK75-PAS #1a(600)-IL1Ra (lanes 1-5) (SEQ ID NO: 51) or pASK75-PAS #1f/1c/1b(600)-IL1Ra (lanes 1-10) (SEQ ID NO: 50) cultivated over 7 days, which corresponds to approximately 70 generations of bacterial cell division. 4 of 5 analyzed clones of pASK75-PAS #1a(600)-IL1Ra revealed shortened DNA fragments comprising the nucleic acid insert encoding the proline/alanine-rich amino acid repeat sequence (FIG. 5), clearly indicating genetic instability. In contrast, all 5 clones of pASK75-PAS #1f/1c/1b(600)-IL1Ra showed only the expected bands corresponding to 3093 bp and 2377 bp, respectively, indicating an intact nucleic acid insert encoding the proline/alanine-rich amino acid repeat sequences and high genetic plasmid stability. Thus, low repetitive nucleotide sequences encoding proline/alanine-rich amino acid repeat sequences according to this invention offer a clear advantage over the repetitive nucleotide sequences of the prior art.

Figures 6A, 6B, 6C:
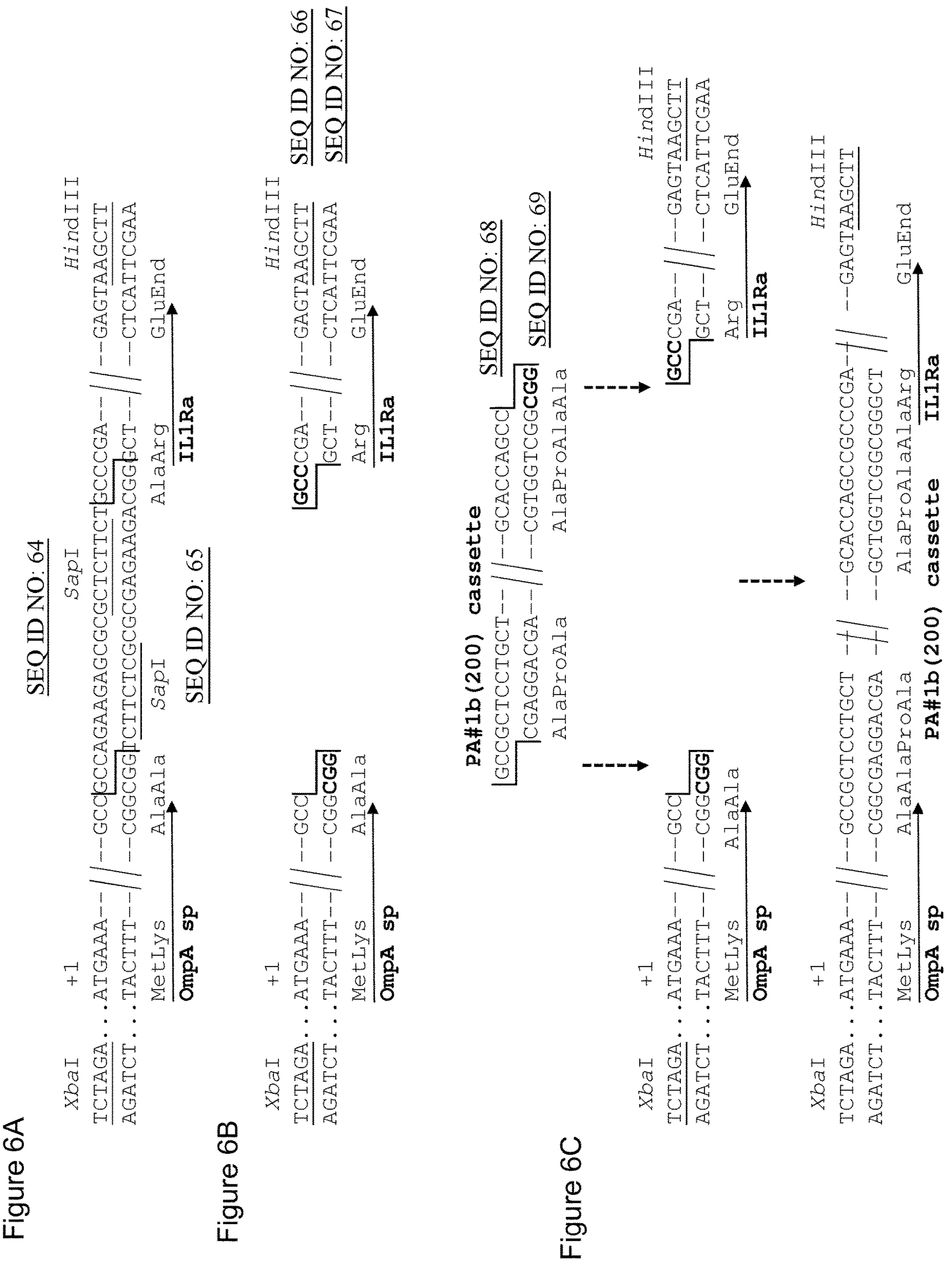

FIGS. 6A-6C: Seamless Cloning of a Low Repetitive Nucleotide Sequence Encoding Proline/Alanine-Rich Amino Acid Repeat Sequences on an Expression Plasmid Encoding the Biologically Active Protein IL-1Ra.

FIG. 6A Schematic illustration of a coding region for a fusion protein comprising the OmpA signal sequence gene followed by a GCC alanine codon, a first SapI recognition sequence GCTCTTC on the non-coding strand, a GC dinucleotide spacer, and a second SapI recognition in reverse orientation, with its recognition sequence GCTCTTC on the coding strand, finally followed by a GCC alanine codon and the coding sequence for mature IL-1Ra (UniProt ID P18510). The entire sequence shown was cloned via XbaI/HindIII restriction sites on the generic expression vector pASK75. FIG. 6B Schematic illustration of the DNA cassette described in FIG. 6A after SapI cleavage and excision of the short 24 bp insert flanked by the two SapI restriction sites. Of note, due to the two 5'-overhangs only the middle 18 nucleotides form a DNA double strand and thus comprise base pairs in the true sense. FIG. 6C Seamless insertion in a unidirectional manner of the DNA fragment comprising the low repetitive nucleotide sequence PA #1b(200), e.g., excised from pXL2-PA #1b(200) (SEQ ID NO: 54), via compatible sticky GCC/CGG ends generated by EarI restriction digest (cf. FIG. 1). The resulting expression cassette comprising the low repetitive nucleotide sequence encoding a proline/alanine-rich amino acid repeat sequence according to this invention is shown as SEQ ID NO: 47 herein further below.

Figure 7A:
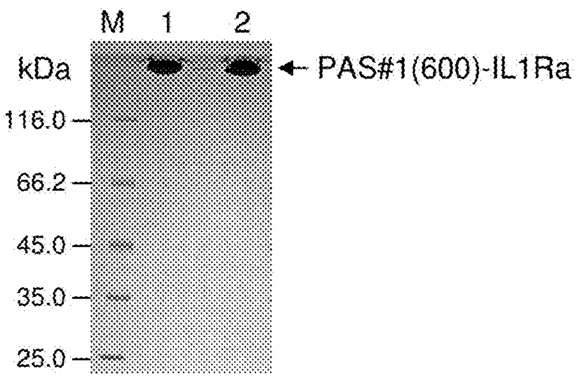
Figure 7B:
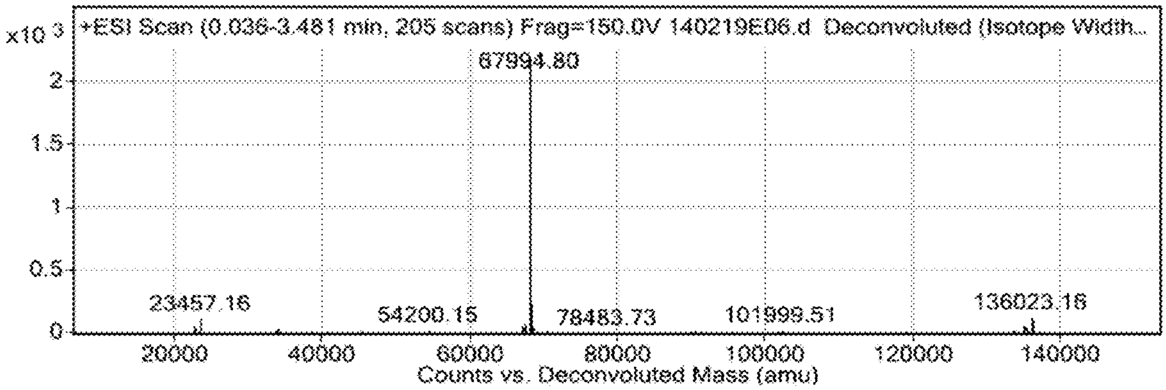

FIGS. 7A-7B: Characterization of the PAS #1(600)-IL1Ra fusion protein produced in *E. coli* using the genetically stable expression vector pASK75-PAS #1f/1c/1b(600)-IL1Ra FIG. 7A Analysis of the PAS #1(600)-IL1Ra fusion protein purified via IMAC, AEX, CEX and SEC by 10% SDS-PAGE. The gel shows 2 μg samples of PAS #1(600)-IL1Ra reduced with 2-mercaptoethanol (lane 1) and also not reduced (lane 2). Sizes of the protein marker proteins (M) are indicated on the left. The PAS #1(600)-IL1Ra fusion protein appears as a single homogeneous band with an apparent molecular size above 116 kDa. Due to poor SDS binding, PAS fusion proteins generally show significantly larger sizes (Schlapschy (2013) Protein Eng Des Sel. 26:489-501) than, e.g., the calculated mass of 68 kDa for PAS #1(600)-IL1Ra. FIG. 7B Characterization of the PAS #1(600) fusion protein via Electrospray ionisation Mass Spectrometry (ESI-MS). A deconvoluted ESI-MS spectrum of the purified PAS #1(600)-IL1Ra fusion protein reveals a measured mass of 67994.8 Da, which almost perfectly corresponds to the calculated mass of 67994.9 Da.

FIGS. 8A-8D: Characterization of a pure PA #1(600/) polypeptide produced in *E. coli* using the genetically stable expression vector pASK37-MP-PA #1d/1c/1b(600)

Figure 8A:
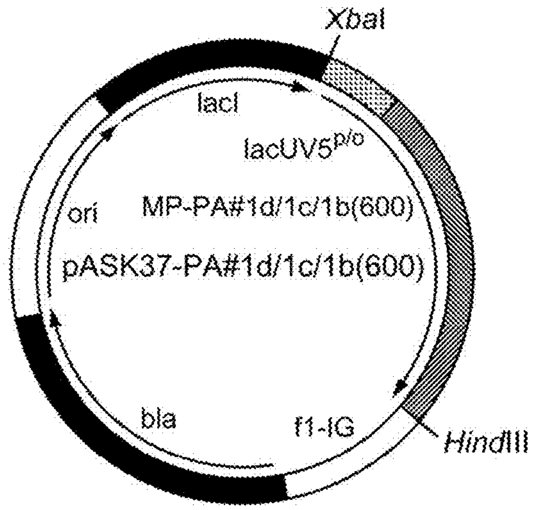
Figure 8B:
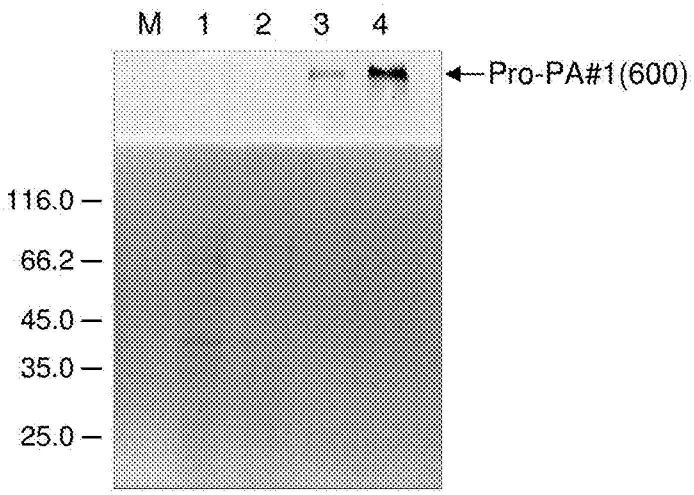
Figure 8C:
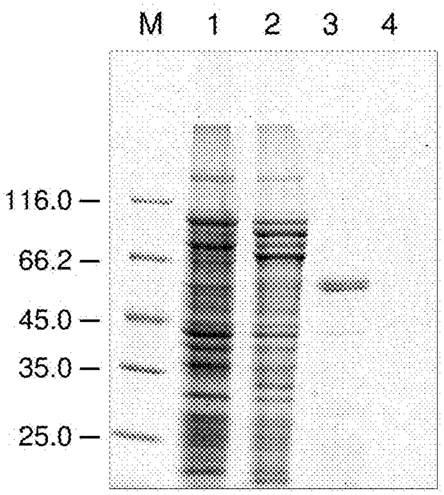
Figure 8D:
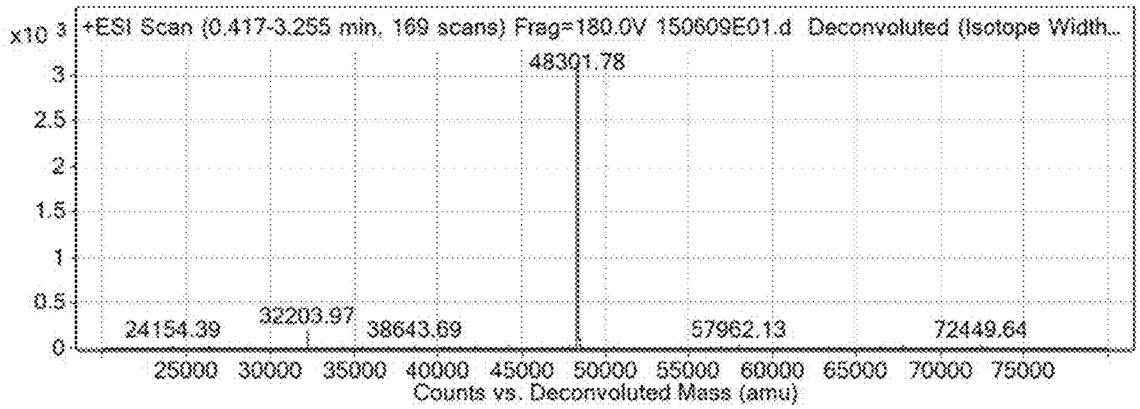

FIG. 8A Plasmid map of pASK37-MP-PA #1d/1c/1b(600) (SEQ ID NO: 53). The low repetitive nucleotide sequence encoding the PA #1(600) polypeptide was cloned under transcriptional control of the lacUV5 promoter/operator) (lacUV5$^{p/o}$) preceded by codons for a start Met residue and a Pro residue. The plasmid backbone outside the expression cassette flanked by the XbaI and HindIII restriction sites is identical with that of the generic expression vector pASK37 (Skerra (1991) Protein Eng. 4:971-979). FIG. 8B Analysis of the recombinant PA #1(600) polypeptide by 10% SDS-PAGE, followed by staining with barium iodide. Loaded samples are lysed cells after 3 h expression (lane 1), protein precipitated with 20% w/v $(NH_4)_2SO_4$ (lane 2), the supernatant of the $(NH_4)_2SO_4$ precipitate dissolved in 20 mM Tris/HCl after centrifugation for 20 min at 17.000 rpm and a subsequent treatment with 1% v/v AcOH (lane 3) and the flow through of subsequent subtractive cation exchange chromatography of the PA #1(600) polypeptide treatment (lane 4). The PA #1(600) polypeptide poorly binds SDS; thus, the PA #1(600) polypeptide appears as a red/yellow iodine-stained band within the stacking gel, indicating homogeneous composition. FIG. 8C The gel shown in FIG. 8B after destaining with water and staining with Coomassie brilliant blue. The PA #1(600) polypeptide poorly binds SDS and does not stain by the Coomassie dye; thus, only impurities (host cell proteins) are visible on the Coomassie stained gel. FIG. 8D Characterization of the pure PA #1(600) polypeptide via Electros pray ionisation Mass Spectrometry (ESI-MS). The deconvoluted spectrum reveals a measured mass of 48301.78 Da, which almost perfectly matches the calculated mass for the recombinant PA #1(600) polypeptide, carrying an additional Pro residue at the N-terminus as explained above and an additional Ala residue at the C-terminus due to the SapI restriction site that was employed for gene cloning (48301.4 Da). Note that this recombinant polypeptide no longer carries the start Met residue, most likely resulting from the intracellular action of methionine aminopeptidase (Giglione (2015) Biochimie 114:134-46).

FIGS. 9A-9I: Automated Repeat Analysis of Nucleotide Sequences Encoding Proline/Alanine-Rich Amino Acid Sequences.

Figure 9A:
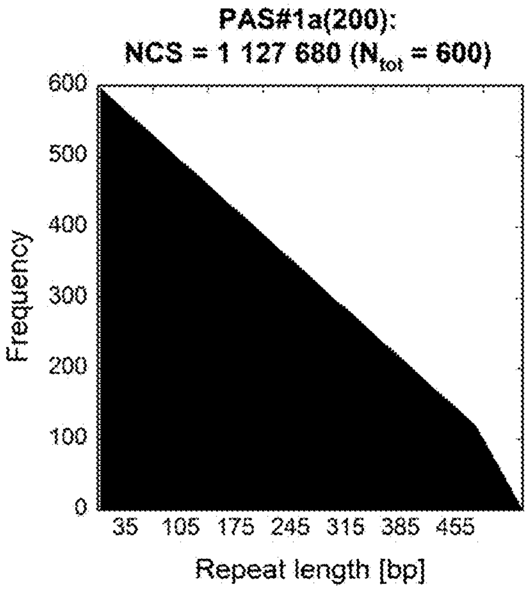
Figure 9B:
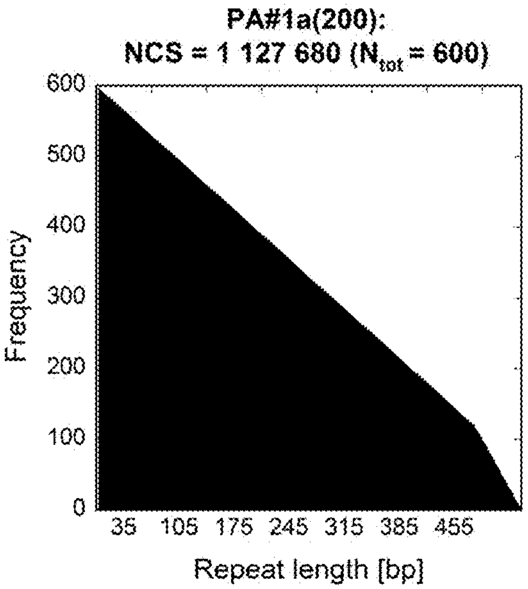
Figure 9C:
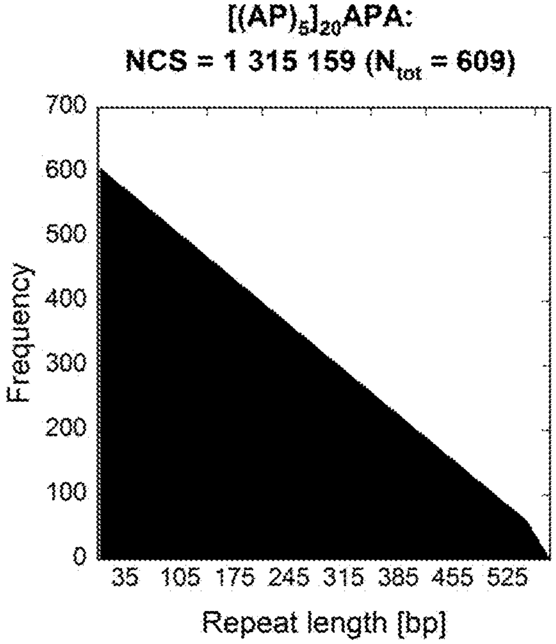
Figure 9D:
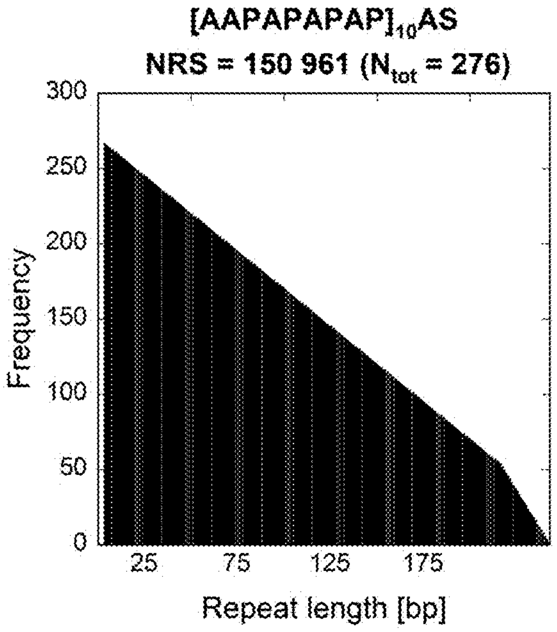
Figure 9E:
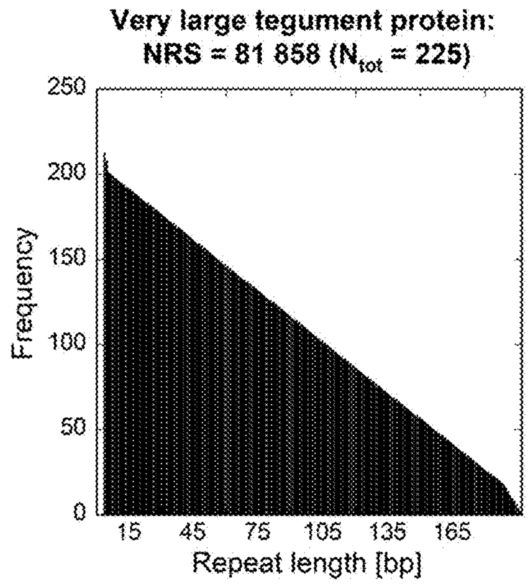
Figure 9F:
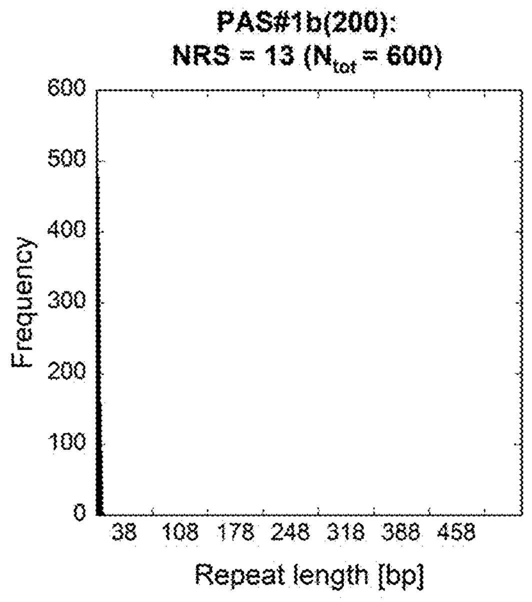
Figure 9G:
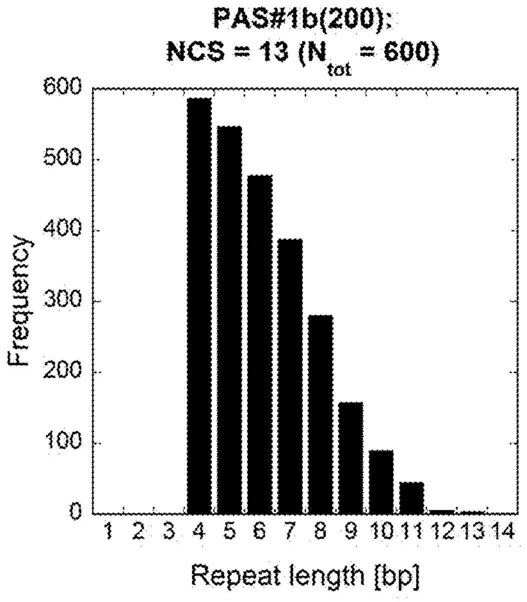
Figure 9H:
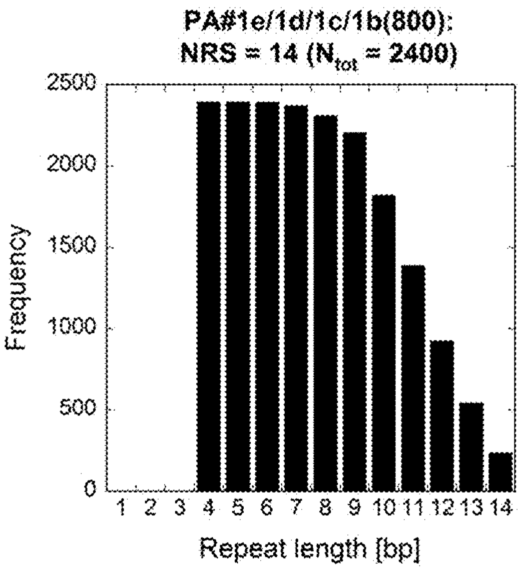
Figure 9I:
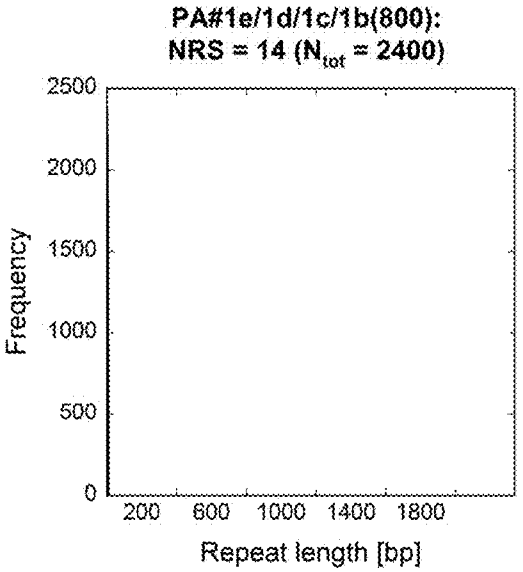

Repeats of natural as well as synthetic nucleotide sequences encoding proline/alanine-rich amino acid sequences of the prior art were analyzed as described in Example 13 using the Python script NRS-Calculator (see Example 14) and compared here to the low repetitive nucleotide sequences PAS #1b(200) and PA #1e/1d/1c/1b (800) according to this invention. The frequency (number of occurrences) of all repeats of a certain length within the analyzed nucleotide sequence was plotted against the repeat length. FIG. 9A Histogram of the prior art nucleotide sequence PAS #1a(200) (SEQ ID NO: 11). FIG. 9B Histogram of the nucleotide sequence PA #1a(200) (SEQ ID NO: 14) FIG. 9C Histogram of the nucleotide sequence encoding the glycomodule $[(AlaPro)_5]_{20}$APA (SEQ ID NO: 16). FIG. 9D Histogram of the nucleotide sequence encoding the glycomodule $[AAPAPAPAP]_{10}$AS (SEQ ID NO: 17). FIG. 9E Histogram of the nucleotide sequence encoding a proline/alanine-rich stretch within the large tegument protein of the macacine herpesvirus 1 (SEQ ID NO: 18). FIG. 9F Histogram of the low repetitive nucleotide sequence PAS #1b(200) (SEQ ID NO: 19). FIG. 9G Close-up view of the PAS #1b(200) data illustrated in (F). FIG. 9H Histogram of the low repetitive nucleotide sequence PA #1e/1d/1c/1b (800) according to this invention (SEQ ID NO: 44). FIG. 9I Close-up view of the PA #1e/1d/1c/1b(800) data illustrated in (H). The total length of the analyzed nucleotide sequence ($N_{tot}$) and its Nucleotide Repeat Score (NRS), which is a measure to assess the quality of nucleic acid molecules encoding proline/alanine-rich amino acid sequences with regard to the frequency and lengths of repeats, are summarized for the different nucleotide sequences in Tables 1 and 2.

Figure 10:
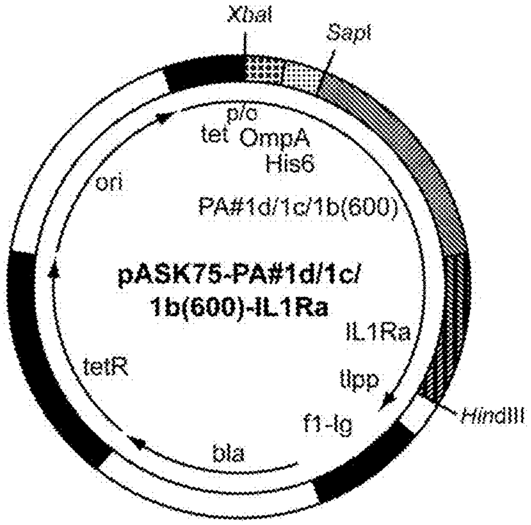

FIG. 10: pASK75-PA #1d/1c/1b(600)-IL1Ra, a Genetically Stable Expression Vector for Bacterial Production of the PA #1(600)-IL1Ra Fusion Protein Having Therapeutic Relevance.

Plasmid map of pASK75-PA #1d/1c/1b(600)-IL1Ra (SEQ ID NO: 77). The structural gene for the biologically/pharmacologically active (pre)protein PA #1(600)-IL1Ra comprising the low repetitive nucleotide sequence encoding a PA #1 polypeptide with 601 amino acid residues and the structural gene for human IL-1Ra as well as coding regions for the bacterial OmpA signal sequence and a His6-tag is cloned under transcriptional control of the tet promoter/operator (tet$^{p/o}$). The plasmid backbone outside the expression cassette flanked by the XbaI and HindIII restriction sites is identical with that of the generic expression vector pASK75 (Skerra (1994) Gene 151:131-135). The singular SapI restriction site that was retained after insertion of the low repetitive nucleic acid molecule encoding a proline/alanine-rich amino acid repeat sequence according to this invention is indicated.

Figure 11A:
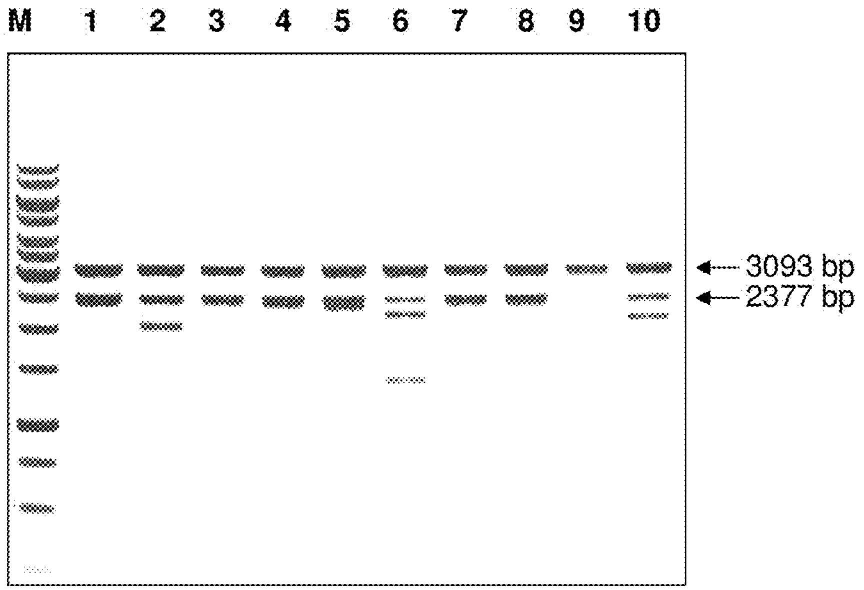
Figure 11B:
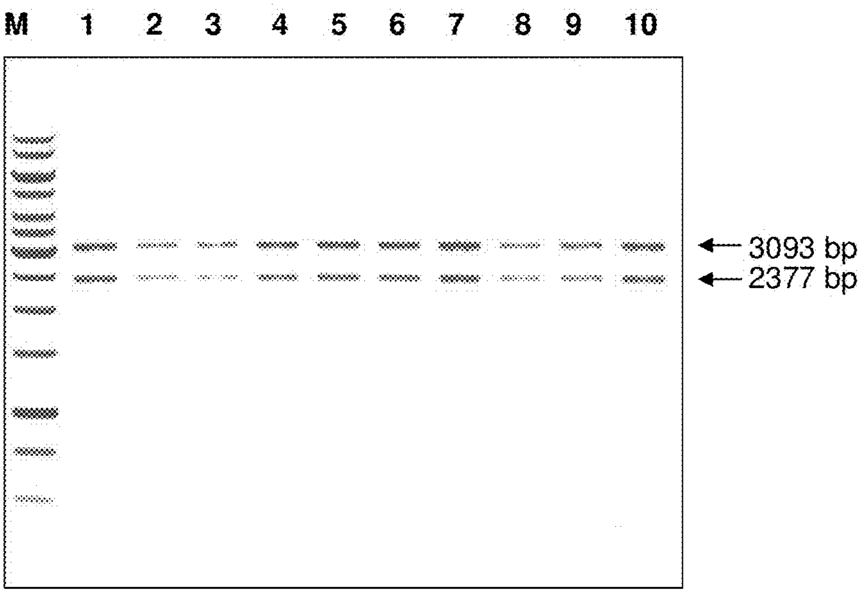

FIGS. 11A-11B: Analysis of Genetic Stability of the Low Repetitive Nucleic Acid Molecule PA #1d/1c/1b(600), Encoding a Proline/Alanine-Rich Amino Acid Repeat Sequence, in Comparison with the Prior Art Nucleotide Sequence PA #1a(600)

Agarose gel electrophoresis after XbaI/HindIII restriction analysis of 10 plasmid preparations of *E. coli* JM83 clones transformed with pASK75-PA #1d/1c/1b(600)-IL1Ra (FIG. 10) (SEQ ID NO: 77) or 10 plasmid preparations of pASK75-PA #1a(600)-IL1Ra (SEQ ID NO: 78) cultivated over 7 days, which corresponds to approximately 70 generations of bacterial cell division. Lanes: M, molecular size standard (GeneRuler 1 kb DNA Ladder: 500, 750, 1000, 1500, 2000, 2500, 3000, 3500, 4000, 5000, 6000, 8000 and 10000 bp); 1 to 10: plasmid samples from individual clones after restriction digest. At least 4 of 10 analyzed clones of pASK75-PA #1a(600)-IL1Ra revealed shortened DNA fragments comprising the nucleic acid insert encoding the proline/alanine-rich amino acid repeat sequence (FIG. 11A), clearly indicating genetic instability. In contrast, all 10 clones of pASK75-PA #1d/1c/1b(600)-IL1Ra (FIG. 11B) showed only the expected bands corresponding to 3093 bp and 2377 bp, respectively, indicating an intact nucleic acid insert encoding the proline/alanine-rich amino acid repeat sequences and high genetic plasmid stability. Thus, low repetitive nucleotide sequences encoding proline/alanine-rich amino acid repeat sequences according to this invention offer a clear advantage over the repetitive nucleotide sequences of the prior art.

Figure 12A:
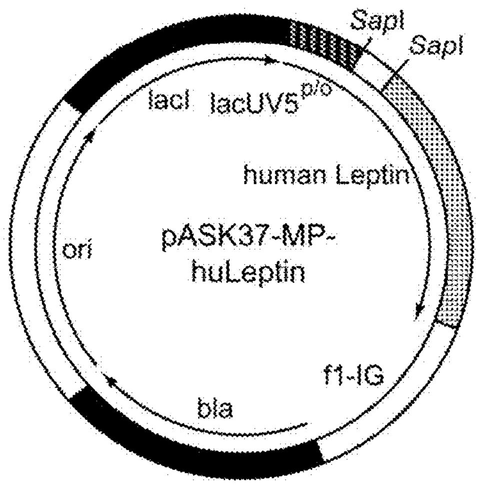
Figure 12B:
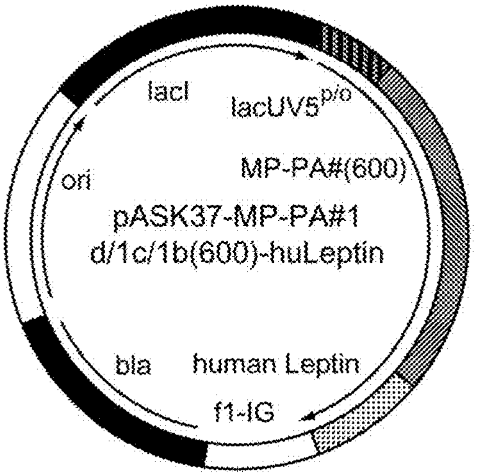
Figure 12C:
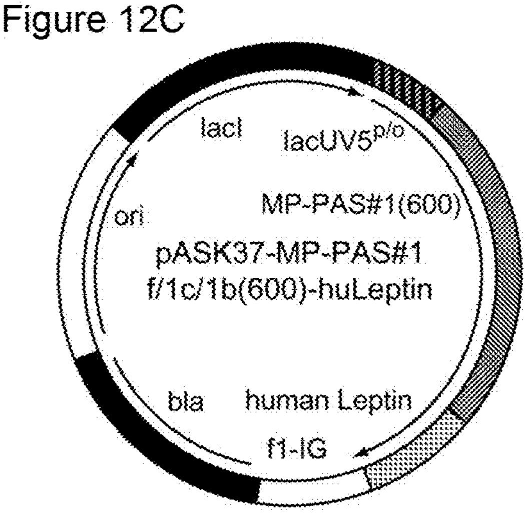

FIGS. 12A-12C: Construction of Genetically Stable Expression Vectors for Bacterial Production of Human Leptin Fused with Proline/Alanine-Rich Amino Acid Sequences FIG. 12A Plasmid map of pASK37-MP-huLeptin (SEQ ID NO: 81) containing a seamless cloning cassette flanked by SapI restriction sites to allow seamless and directed cloning of a low repetitive nucleotide sequence encoding proline/alanine-rich amino acid repeat sequences in frame with the structural gene of human Leptin. FIG. 12B Plasmid map of pASK37-MP-huLeptin-PA #1d/1c/1b(600) (SEQ ID NO: 82), a derivative of pASK37-MP-huLeptin with the insertion of a PA #1d/1c/1b(600) gene cassette (SEQ ID NO: 42). FIG. 12C Plasmid map of pASK37-MP-huLeptin-PAS #1f/1c/1b(600) (SEQ ID NO: 83), a derivative of pASK37-MP-huLeptin with the insertion of a PAS #1f/1c/1b(600) gene cassette (SEQ ID NO: 38). The structural genes for the biologically/pharmacologically active human protein Leptin, the human Leptin fused to the low repetitive nucleotide sequence encoding the PA #1(600) and the human Leptin fused to the low repetitive nucleotide sequence encoding the PAS #1(600) polypeptide were cloned under transcriptional control of the lacUV5 promoter/operator)(lacUV5$^{p/o}$), all preceded by codons for a start Met residue and a Pro residue. The plasmid backbone outside the expression cassette flanked by the XbaI and HindIII restriction sites is identical with that of the generic expression vector pASK37 (Skerra (1991) Protein Eng. 4:971-979).

Figure 13A:
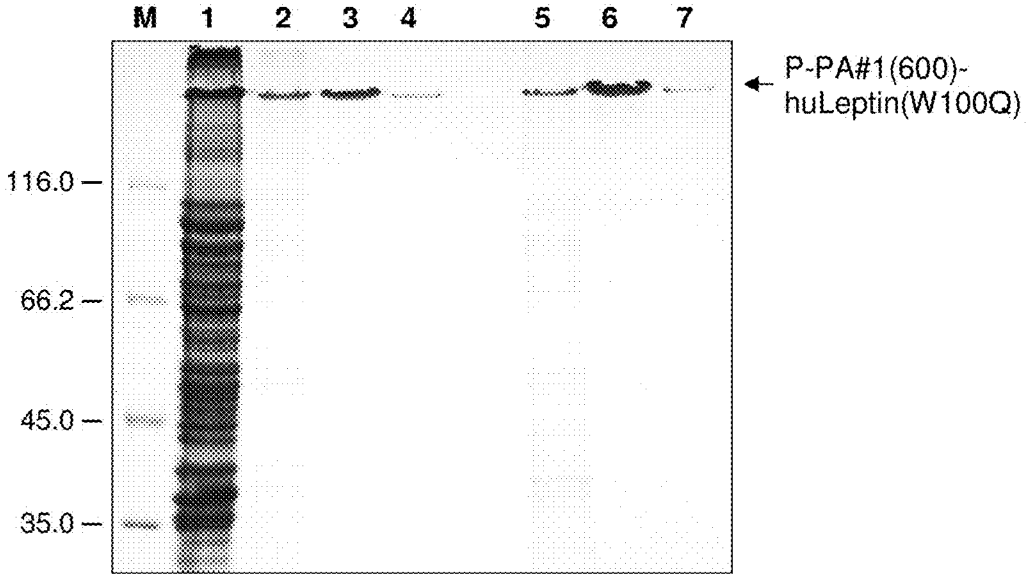
Figure 13B:
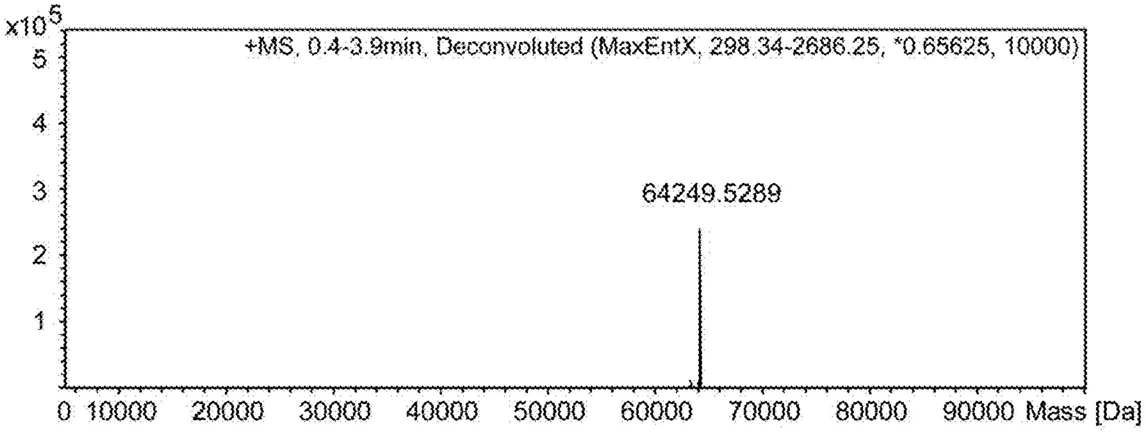

FIGS. 13A-13B: Characterization of a Human Leptin Variant Fused with a PA #1(600) Polypeptide and Produced in *E. coli* Using the Genetically Stable Expression Vector pASK37-MP-PA #1d/1c/1b(600)-huLeptin(W100Q)

FIG. 13A SDS-PAGE analysis of the PA #1(600)-huLeptin(W100Q) fusion protein using a 10% polyacrylamide gel followed by staining with Coomassie brilliant blue R-250. The gel shows a protein molecular weight (MW) marker (lane M; Thermo Fisher Scientific, Waltham, Mass.), *E. coli* whole cell extract after 19 h expression under reducing sample conditions (lane 1), protein precipitated with 1 M $(NH_4)_2SO_4$ reduced (lane 2) and not reduced (lane 5), the protein after anion exchange chromatography reduced (lane 3) and not reduced (lane 6), and the protein after size exclusion chromatography reduced (lane 4) and not reduced (lane 7). PA #1(600)-huLeptin(W100Q) appears as a single band, indicating homogeneous composition. FIG. 13B Characterization of the PA #1(600)-huLeptin(W100Q) fusion protein via Electrospray ionisation Mass Spectrometry (ESI-MS). The deconvoluted spectrum reveals a measured mass of 64249.5 Da, which matches the calculated mass for the recombinant fusion protein (64249.8 Da), indicating the successful cleavage of the start Met residue by the bacterial methionine aminopeptidase.

EXAMPLES

The present invention is additionally described by way of the following illustrative non-limiting examples that provide a better understanding of the present invention and of its many advantages.

Example 1

Synthesis of Low Repetitive Nucleotide Sequence Units Encoding Proline/Alanine-Rich Amino Acid Repeat Sequences A set of different nucleotide sequences, each encoding a proline/alanine-rich amino acid repeat sequence of 200 residues were optimized, including manual adjustment, with regard to low repetitivity on the nucleotide level, low GC content, low RNA secondary structure, preferred codon-usage for expression in *E. coli* and avoidance of antiviral motifs as well as CIS-acting elements. To this end, established algorithms such as the condition-specific codon optimization approach (Lanza (2014) BMC Syst Biol 8:33) or the GeneOptimizer algorithm (Raab (2010) Syst Synth Biol 4:215-225) were applied. The initial sequences obtained thereof were manually adjusted in the following manner.

Repeats longer than a given threshold (e.g., 14 nucleotides) were identified using the Visual Gene Developer software version 1.2, which is freely available at visualgenedeveloper.net. Subsequently, codons within identified repeats were stepwise substituted. In particular, GC-rich codons within the identified repeats were replaced by AT-rich codons prevalent in highly expressed genes in a host organism of choice (e.g., *E. coli, P. pastoris* or CHO). After each substitution, the entire nucleotide sequence was again analyzed for repeats. In case the substitution led to a new repeat longer than the given threshold, the nucleotide exchange(s) was rejected and a different codon within the previously identified repeat was substituted. If this approach failed, two codons within the identified long repeat were substituted in parallel. In this way, all identified repeats above a given threshold were iteratively eliminated while maintaining the encoded proline/alanine-rich amino acid sequence.

In a second step, the codon adaptation index (CAI), GC content and stable mRNA structures of the optimized nucleotide sequence was analyzed using the Visual Gene Developer software and compared to the start sequence. Additional manual adjustments, again by codon substitution/silent mutation, were performed until the optimized nucleotide sequence reached a CAI, GC content or mRNA structure equal or better than the start sequence. The repeat analysis from step 1 was carried out again, and, if necessary, other codons were exchanged in order to meet the objectives, which were repeat threshold, CAI, GC content and mRNA structures (secondary structures).

In a third step, different individually optimized nucleotide sequences, each encoding the same 200-residue proline/alanine-rich amino acid repeat sequence were combined, i.e. appended to each other, and the resulting longer nucleotide sequence was optimized in the same manner as in steps 1 and 2. Finally, the resulting long acid sequence was divided into shorter, e.g., DNA cassettes of 600 nucleotides lengths. For example, the 2400 nucleotide sequence PAS #1d/1f/1c/1b (SEQ ID NO: 39) was divided into four shorter cassettes (SEQ ID NO: 19, 20, 21, 23). Similarly, the 2400 nucleotide sequence PA #1e/1d/1c/1b (SEQ ID NO: 44) was divided into four shorter cassettes (SEQ ID NO: 28, 29, 30, 31), each comprising 600 nucleotides.

Flanked by two SapI recognition sites (5'-GCTCTTC-3') in reverse complementary orientation, resulting in 5'-GCC/5'-GGC nucleotide overhangs after restriction enzyme digest, these optimized nucleotide sequence units were individually synthesized by different commercial vendors. Of note, due to the presence of the two GCC/GGC nucleotide overhangs, only the middle 597 nucleotides form a DNA double strand after excision and, hence, comprise base pairs (bp). Also, the optimized 600 nucleotide sequence is extended by an additional Ala codon due to the presence of the second SapI restriction site, thus leading to a cloned DNA cassette of overall 603 nucleotides encoding a proline/alanine-rich amino acid sequence. The presence of the two flanking SapI restriction sites enables precise excision and subcloning, e.g., on pXL2, of the entire DNA cassette of the invention.

Further sets of nucleotide sequence units encoding proline/alanine-rich amino acid repeat sequences, codon-optimized for expression in *Escherichia coli, Pichia pastoris*, human embryonic kidney (HEK) cells, *Pseudomonas fluorescens, Corynebacterium glutamicum, Bacillus subtilis, Tetrahymena thermophila, Saccharomyces cerevisiae, Kluyveromyces lactis, Physcomitrella patens* or *Cricetulus griseus*, were designed and synthesized in the same manner. Codon preference tables for these organisms are available for download at kazusa.or.jp/codon. The synthesized nucleic acid molecules according to the invention and their nucleotide sequence characteristics are summarized in Table 1.

Example 2

Figure 1E:
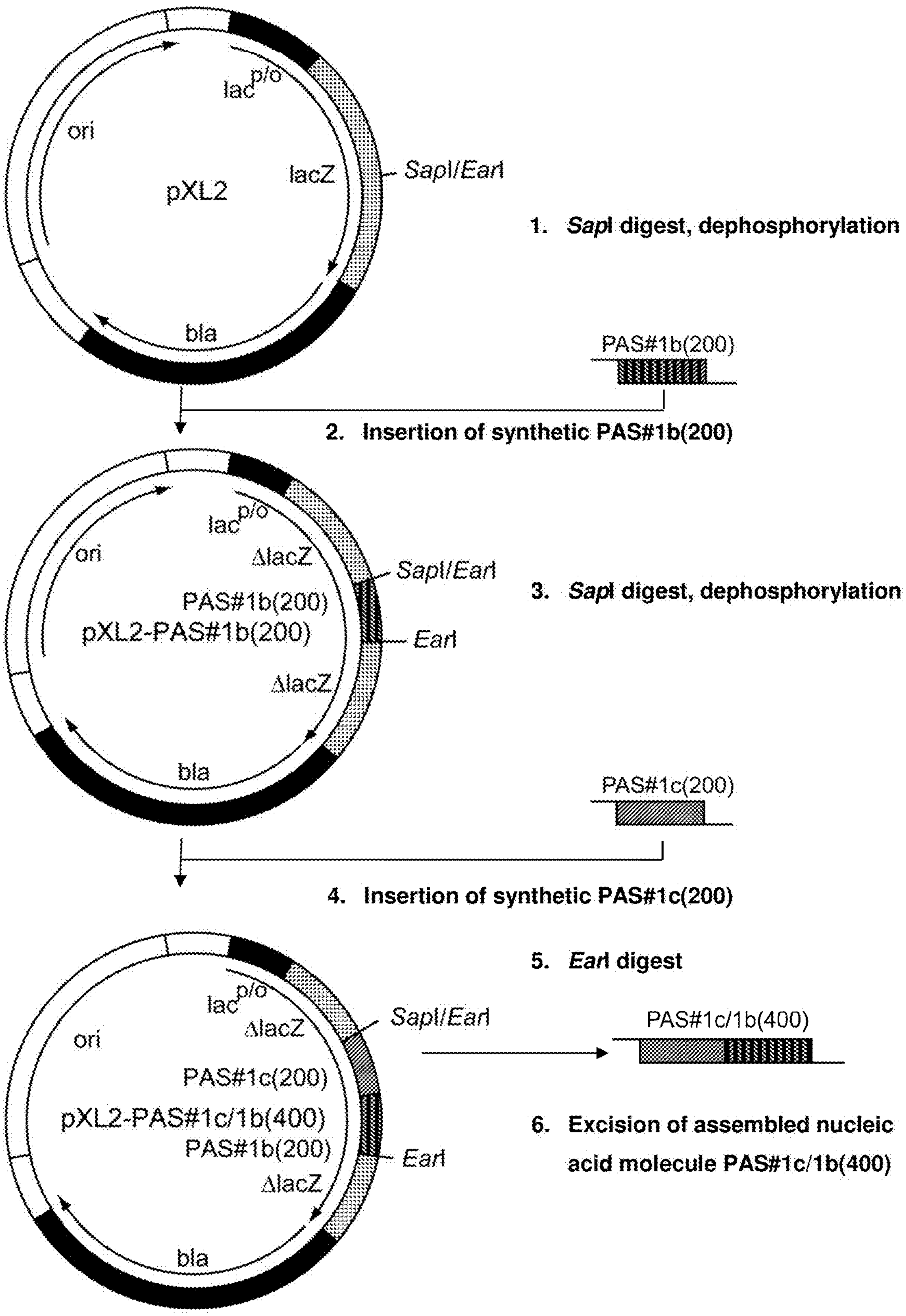

Assembly of Low Repetitive Nucleotide Sequence Units to Longer Nucleotide Sequences Encoding Proline/Alanine-Rich Amino Acid Repeat Sequences Plasmids obtained from commercial vendors, each carrying a cloned synthesized DNA fragment, were digested with SapI and the resulting 600 nucleotide DNA fragment was purified via agarose gel electrophoresis according to standard procedures (Sambrook (2001) loc. cit.) The individual nucleotide sequence units were assembled to longer nucleotide sequences using the plasmid pXL2 (SEQ ID NO: 48), a derivative of pUC19 (Yanisch-Perron (1985). Gene. 33, 103-119) shown in FIG. 1A. pXL2 contains a single SapI restriction site, and digest with this type IIS restriction enzyme generates a 5'-GCC/5'-GGC-overhang coding for alanine, which is compatible with the sticky ends of the synthesized purified DNA fragments (FIG. 1C). After insertion/ligation of one nucleotide sequence unit, the plasmid can be opened at one end, here upstream, of the cloned sequence unit by another SapI restriction digest (FIG. 1D). This vector design allows the stepwise insertion of identical or different low repetitive nucleotide sequence units, yielding longer cloned gene cassettes encoding proline/alanine-rich amino acid repeat sequences (FIG. 1E).

As an example, first the nucleotide sequence unit PAS #1b(200) (SEQ ID NO: 19), then the sequence unit PAS #1c(200) (SEQ ID NO: 20), and subsequently the sequence unit PAS #1f(200) (SEQ ID NO: 23) were inserted into pXL2 via the SapI restriction site in the described manner, resulting in the plasmid pXL2-PAS #1f/1c/1b(600) (SEQ ID NO: 38). In a subsequent step, the sequence unit PAS #1d(200) (SEQ ID NO: 19) was additionally inserted in the same manner using the SapI restriction site. The resulting plasmid contained the assembled 2400 bp DNA cassette PAS #1d/1f/1c/1b(800) which in total revealed nucleotide sequence repeats with a maximum length of 14 nucleotides (SEQ ID NO: 39). As the recognition sequence of EarI (5'-CTCTTC-3') downstream of the low repetitive DNA cassette cloned on pXL2 is also part of the recognition sequence of SapI, the entire assembled DNA cassette can be easily excised via restriction digest with EarI, thus cutting twice, allowing subsequent use for further subcloning.

In the same manner, the low repetitive nucleotide sequence PA #1e/1d/1c/1b(800) (SEQ ID NO: 44) was assembled from the nucleotide sequence units PA #1b(200) (SEQ ID NO: 28), PA #1c(200) (SEQ ID NO: 29), PA #1d(200) (SEQ ID NO: 30) and PA #1e(200) (SEQ ID NO: 31) in the stated order. The described assembled nucleotide sequences as well as further exemplary low repetitive nucleic acid molecules encoding proline/alanine-rich amino acid repeat sequences according to this invention, also with codon usage optimized for host organisms different from *E. coli*, are summarized in Table 1. The disclosed cloning strategy offers a simple, stepwise assembly of complex gene cassettes comprising long low repetitive nucleic acid molecules encoding proline/alanine-rich amino acid repeat sequences, which cannot be directly obtained by common gene synthesis methods.

Example 3

Figure 2A:
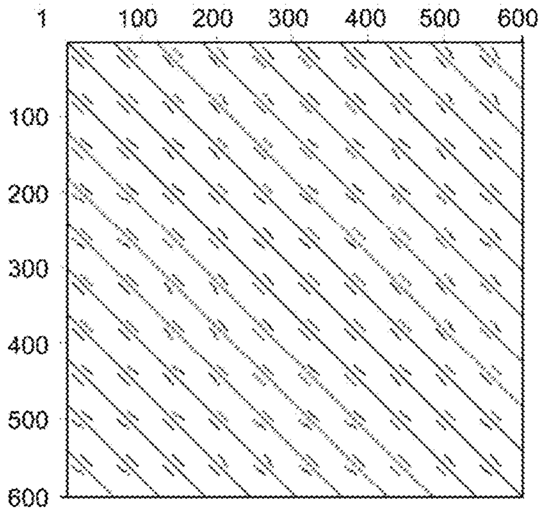
FIGS. 2A-2E: Repeat Analysis of Proline/Alanine-Rich Sequences.
Figure 2A:
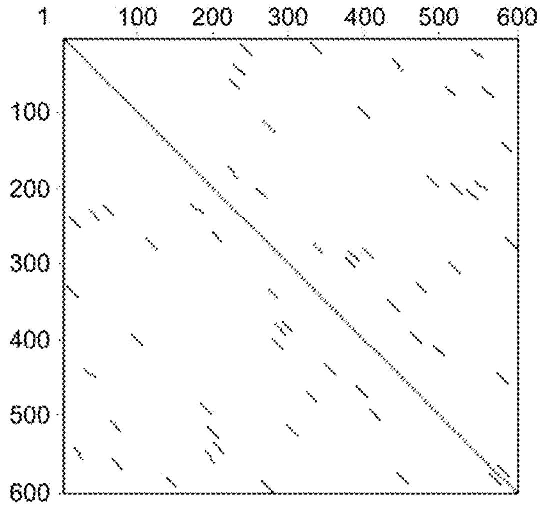
Figure 2A:
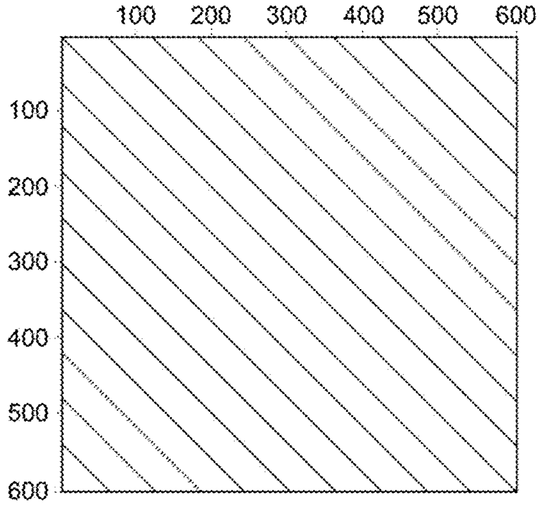
Figure 2A:
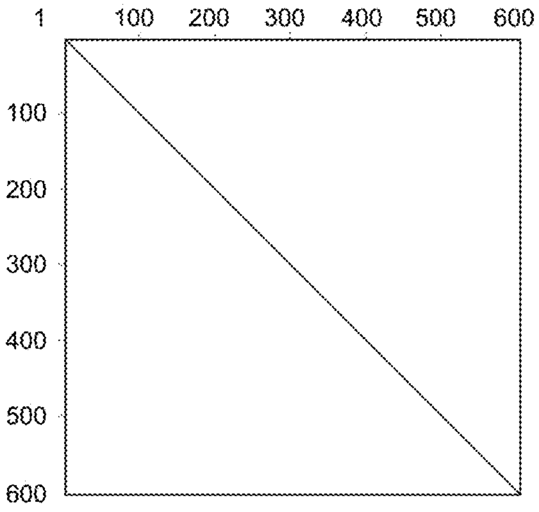
Figure 2B:
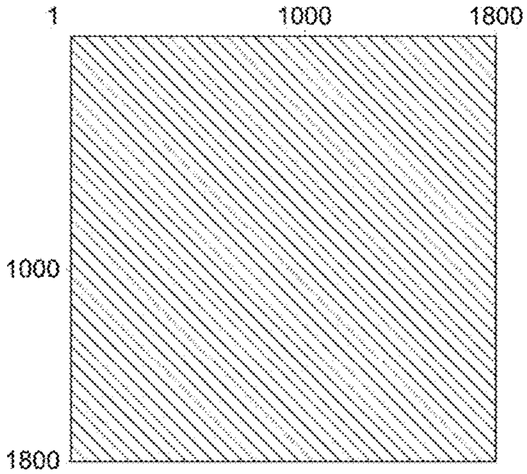
Figure 2B:
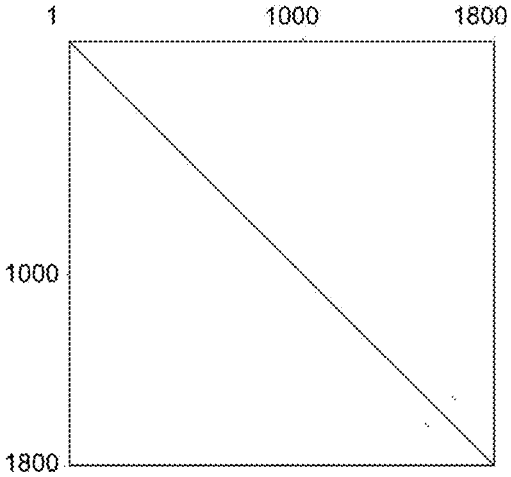
Figure 2B:
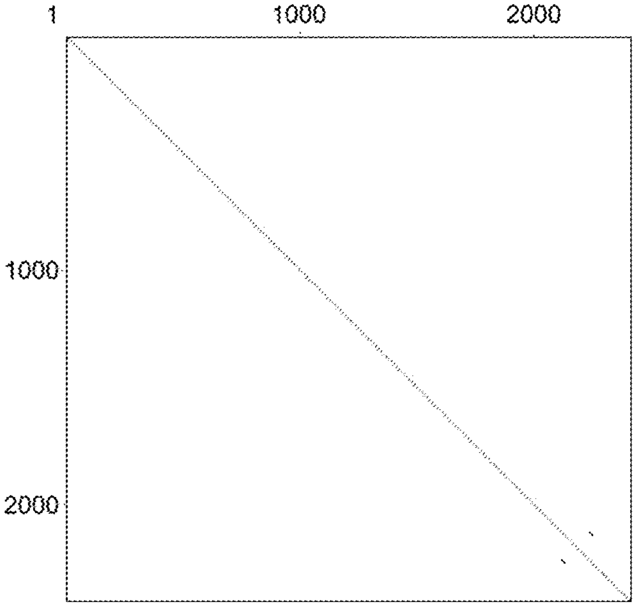
Figure 2C:
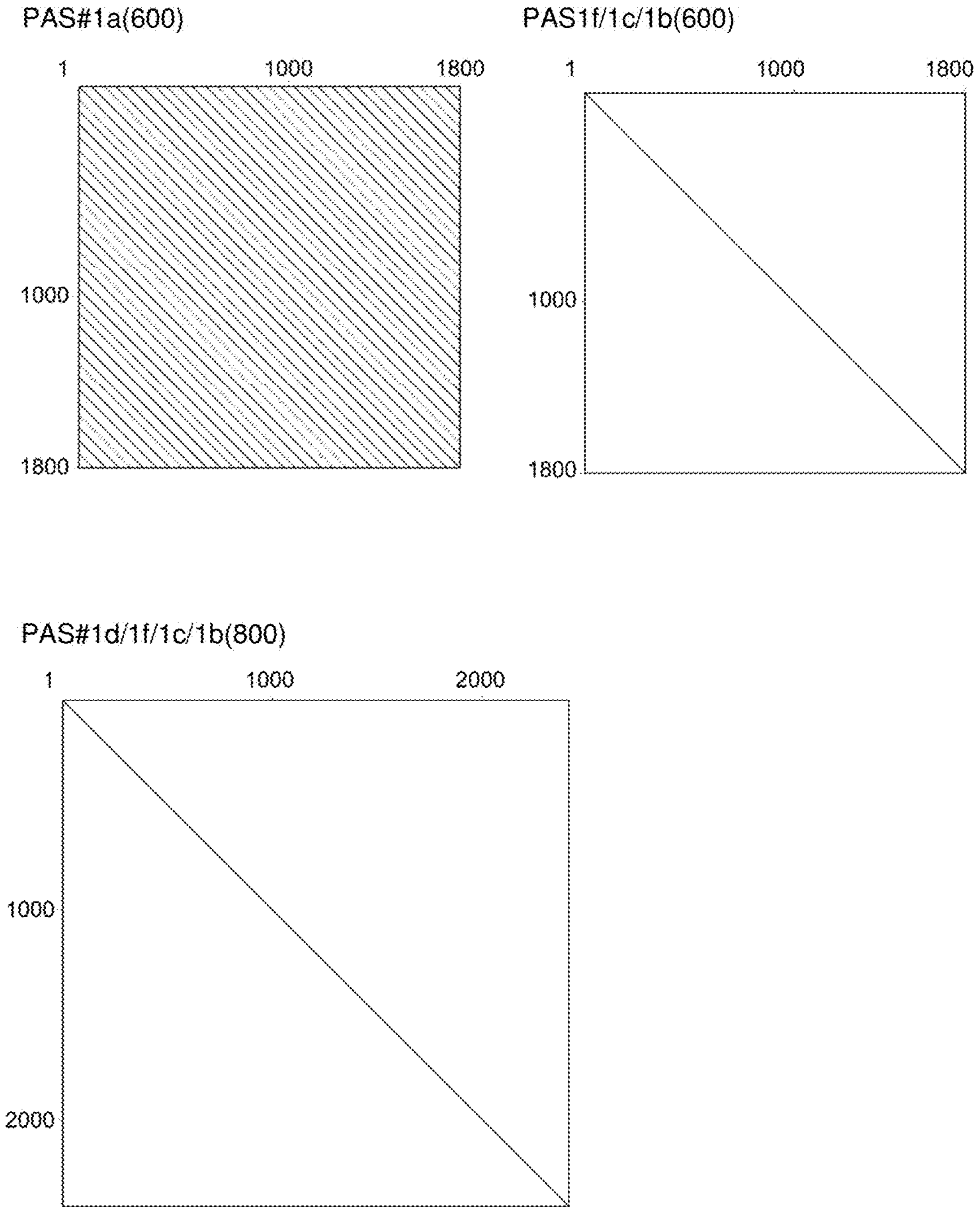
Figure 2D:
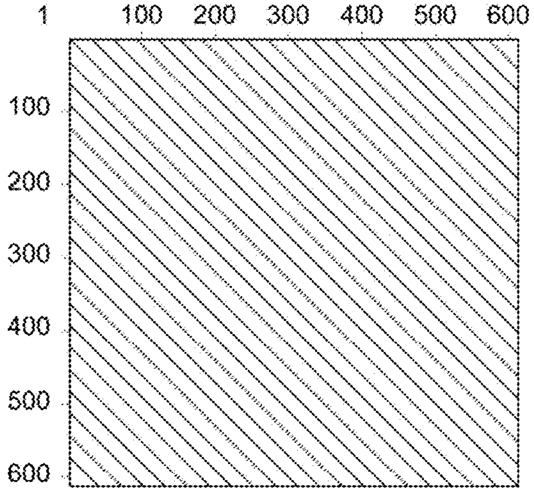
Figure 2D:
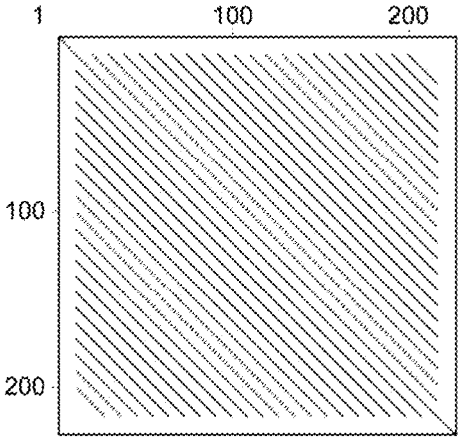
Figure 2D:
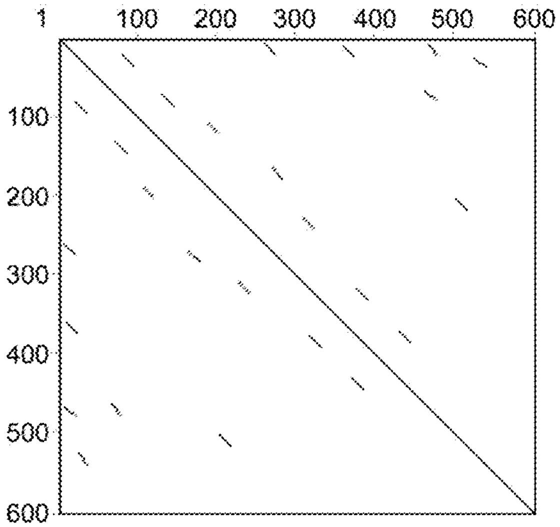
Figure 2E:
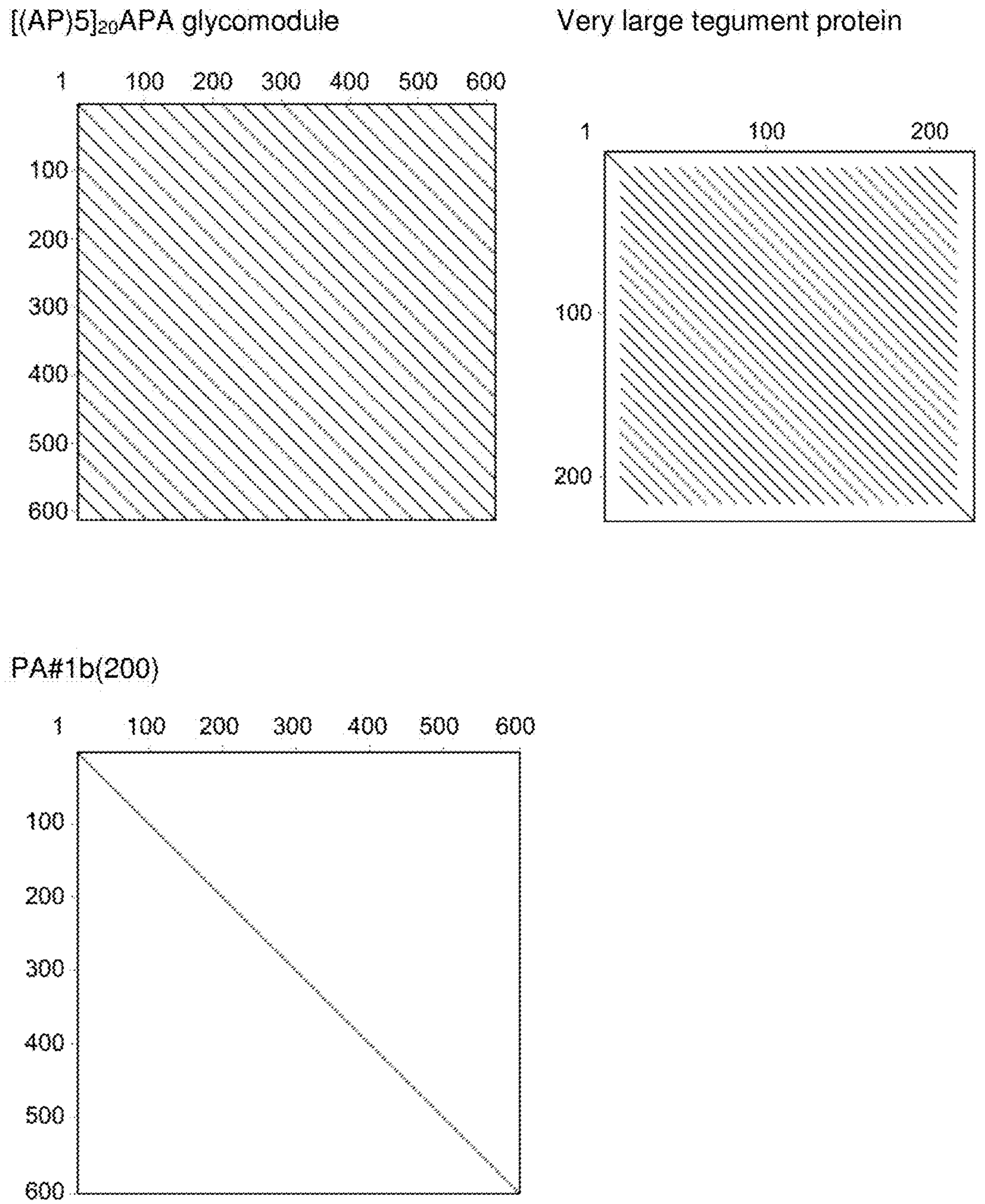

Repetitivity Analysis of Nucleotide Sequences Encoding Proline/Alanine-Rich Amino Acid Repeat Sequences A dot plot analysis was performed for different nucleotide sequences encoding the proline/alanine-rich amino acid repeat sequences PA #3 (SEQ ID NO: 15) (FIG. 2A) as disclosed in WO 2011144756, PAS #1 (SEQ ID NO: 11) (FIGS. 2B-2C) as disclosed in WO2008155134, a $[(AP)_5]_n$ multimer (SEQ ID NO: 16) as disclosed in WO2004094590, and a repetitive proline/alanine-rich amino acid sequence region of the very large tegument protein of Macacine herpesvirus 1 gene, published under the GenBank accession number AAP41454.1 (SEQ ID NO: 18) (FIGS. 2D-2E). The analysis was performed by aligning each nucleotide sequence to itself using the dot plot tool "dottup" of the Geneious software package version 8.1 (Biomatters, Auckland, New Zealand) and applying a repeat window of 14 or 15 nucleotides. The algorithm of this software is based on the freely available EMBOSS 6.5.7 tool "dottup" (Sanger Institute, Cambridge, UK). Resulting two-dimensional dot plot graphs obtained for the prior art nucleotide sequences were compared to dot plots of the low repetitive nucleotide sequence units PA #3b(200) (SEQ ID NO: 36), PA #1b(200) (SEQ ID NO: 28) and the assembled nucleotide sequences PAS #1f/1c/1b(600) (SEQ ID NO: 38) and PAS #1d/1f/1c/1b(800) (SEQ ID NO: 39) which encode longer proline/alanine-rich amino acid repeat sequences. Whereas all analyzed prior art nucleotide sequences revealed a highly repetitive nature on the nucleotide sequence level, as illustrated by black diagonal lines (FIG. 2 A, B, C, D, E), dot plots of the optimized nucleotide sequences encoding proline/alanine-rich amino acid repeat sequences according to this invention showed only a few scattered or short 14 nucleotide repeats (black lines) within the entire analyzed nucleotide sequence of 600 nucleotides of the PA #3b(200) and PA #1b(200) cassettes (FIGS. 2 A, 2D, 2E), the 1800 nucleotide PAS #1f/1c/1b(600) cassette (FIGS. 2B-2C) or the 2400 nucleotide PAS #1d/1f/1c/1b(800) cassette (FIGS. 2 B-2C).

Example 4

Figure 3:
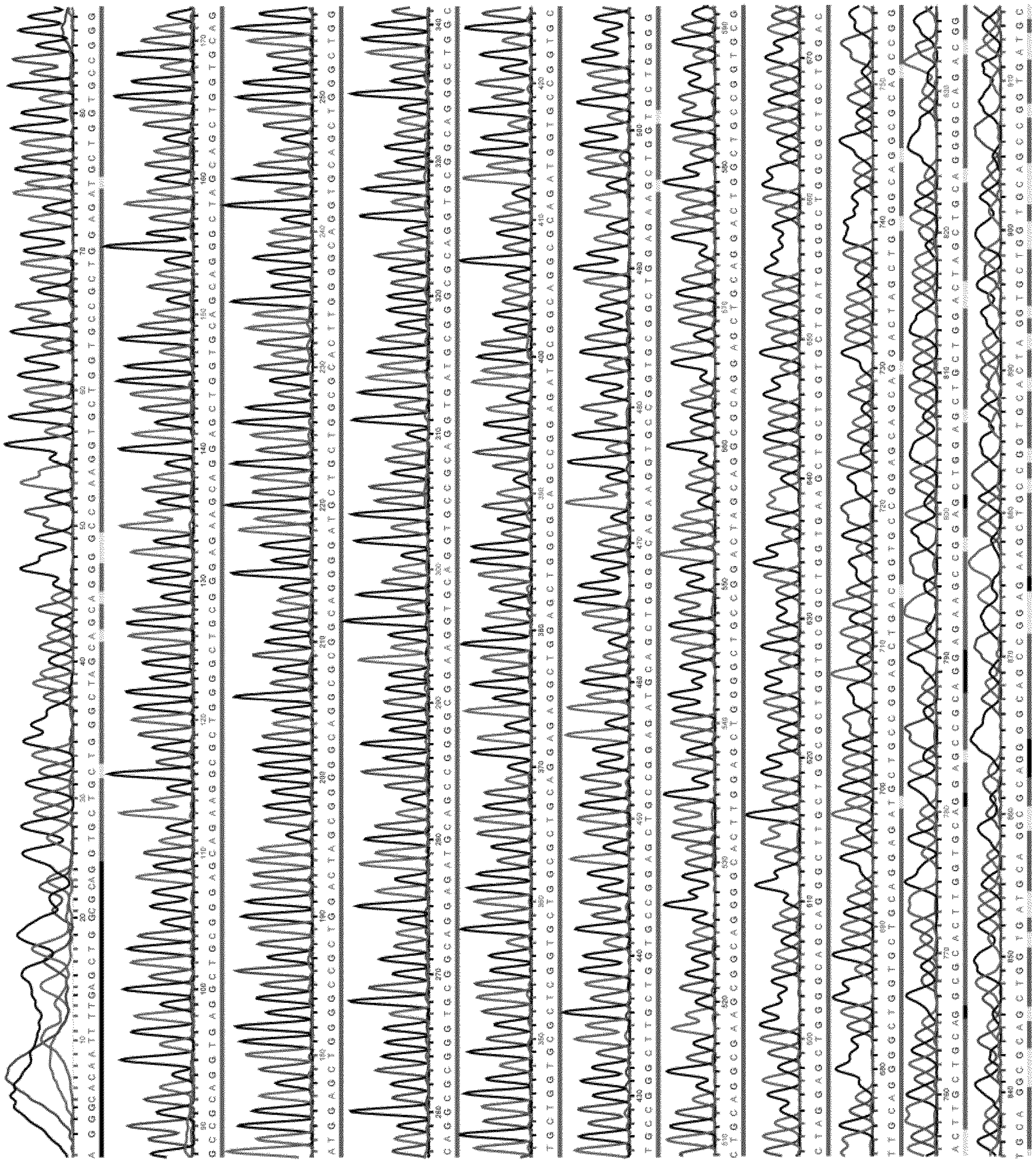
FIG. 3: Electropherogram from DNA Sequencing of a Low Repetitive Nucleic Acid Molecule Encoding Proline/Alanine-Rich Amino Acid Sequences.

DNA-Sequencing of Low Repetitive Nucleic Acid Molecules Encoding Long Proline/Alanine-Rich Amino Acid Repeat Sequences The low repetitive PAS #1f/1c/1b(600) DNA cassette (SEQ ID NO: 38) cloned on the plasmid pXL2 and described in Example 2 was sequenced by a DNA-sequencing service provider (Eurofins Genomics, Ebersberg, Germany) using Sanger cycle sequencing on an ABI 3730XL instrument (Thermo Fisher Scientific, Waltham, Mass.). To this end, 8 μl (150 ng/μl) of pXL2-PAS #1f/1c/1b(600) plasmid DNA, isolated from transformed *E. coli* XL1-blue cells using the QIAprep Spin Miniprep kit (Qiagen, Hilden, Germany) was mixed with 5 μl doubly distilled $H_2O$ and 2 μl primer XLP-1 (10 μM) (SEQ ID NO: 3), which hybridizes within the coding region of the PAS #1b(200) nucleotide sequence unit and submitted to the DNA-sequencing service provider. As result, an error-free electropherogram comprising more than 900 assignable nucleotides (FIG. 3) was obtained, which showed no signs of unspecific or multiple primer binding. Thus, in contrast to long repetitive nucleotide sequences, which can only be partially sequenced using primers hybridizing to vector nucleotide sequences upstream or downstream of the cloned DNA, long low repetitive nucleic acid molecules according to this invention encoding proline/alanine-rich amino acid repeat sequences can be easily sequenced also using primers that specifically hybridize internally, within the cloned nucleotide sequence. This enables multiple overlapping sequence reads using different suitable primers, thus allowing full sequence coverage even of very long nucleic acid molecules according to the invention.

Example 5

Construction of pASK75-PAS #1f/1c/1b(600), a Genetically Stable Expression Vector for the Bacterial Production of a Therapeutic PAS #1(600)-IL1Ra Fusion Protein For the construction of an expression plasmid encoding the interleukin-1 receptor antagonist (IL-1Ra) as fusion with a 600 residue PAS #1 amino acid repeat sequence (SEQ ID NO: 38), the vector pASK75-IL1Ra (FIG. 4 A) (SEQ ID NO: 49) was cut with SapI, dephosphorylated with shrimp alkaline phosphatase (Thermo Fisher Scientific, Waltham, Mass.) and ligated with a DNA fragment corresponding to the low repetitive nucleotide sequence cassette encoding the 600 residue PAS #1 polypeptide, which was excised from the plasmid pXL2-PAS #1f/1c/1b(600) by restriction digest with EarI. After transformation of *E. coli* XL1-Blue (Bullock (1987) Biotechniques 5:376-378), plasmid DNA was prepared and the presence of the inserted DNA fragment was confirmed by restriction analysis and DNA sequencing. The resulting plasmid was designated pASK75-PAS #1f/1c/1b (600)-IL1Ra (SEQ ID NO: 50) and is shown in FIG. 4 B.

Example 6

Long-Term Genetic Stability Testing of a Plasmid Harboring a Low Repetitive Nucleic Acid Molecule Encoding a Proline/Alanine-Rich Amino Acid Repeat Sequence The genetic stability of the plasmid pASK75-PAS #1f/1c/1b(600)-IL1Ra (SEQ ID NO: 50) was compared to the genetic stability of pASK75-PAS #1a(600)-IL1Ra (SEQ ID NO: 51), a derivative wherein the PAS #1f/1c/1b(600) DNA cassette was substituted by the repetitive nucleic acid PAS #1a(600) (SEQ ID NO: 12). To this end, *E. coli* KS272 (Strauch (1988) Proc. Natl. Acad. Sci. USA 85:1576-1580) was transformed with the respective plasmid using the calcium chloride method (Sambrook (2001) loc. cit.) and cultured for 7 days at 37° C., 170 rpm, in 50 ml Luria Bertani (LB) medium supplemented with 100 mg/mL ampicillin in a 100 mL shake flask without induction of gene expression. During this period, bacterial cells were twice daily (in the morning and in the evening) transferred into fresh medium using a 1:1000 dilution. On day 7, after a continuous growth over approximately 70 generations, the culture was finally grown to stationary phase and cells were plated on LB/Amp agar. Then, individual clones were picked, used for inoculation of 50 mL cultures in LB medium and, after growth to stationary phase over night, plasmid DNA from five clones for each of the two plasmids was prepared using the Qiagen Miniprep Kit (Qiagen, Hilden, Germany) and analyzed by a XbaI/HindIII restriction digest (FIG. 5).

Only 1 out of 5 analyzed clones of pASK75-PAS #1a (600)-IL1Ra showed the expected bands corresponding to 3093 bp and 2377 bp (FIG. 5, lane 1). Two clones (FIG. 5, lanes 3 and 5) revealed a band at 573 bp, the approximate size of the combined gene sequences encoding OmpA and IL1Ra, indicating a more or less complete loss of the repetitive PAS #1a(600) sequence cassette, possibly by recombination. Two other clones showed significantly shortened DNA fragments (FIG. 5, lanes 2 and 4), also indicating deletion events within the repetitive PAS #1a(600) sequence cassette and, hence, genetic instability. In contrast, all five analyzed clones of pASK75-PAS #1f/1c/1b(600)-IL1Ra revealed the expected bands at 3093 bp and 2377 bp (FIG. 5, lanes 6-10), indicating an intact gene cassette encoding proline/alanine-rich amino acid repeat sequences and, thus, high genetic plasmid stability of the low repetitive nucleic acid molecules according to this invention.

Example 7

Seamless and Directed Cloning of a Low Repetitive Nucleotide Sequence Encoding Proline/Alanine-Rich Amino Acid Repeat Sequences on an Expression Plasmid Encoding the Biologically Active Protein IL-1Ra With the goal of pharmaceutical application, fusion proteins comprising solely the biologically active protein and a proline/alanine-rich amino acid repeat sequence are desired. The absence of additional amino acid linkers, e.g., introduced in order to provide or utilize restriction sites for cloning, may prevent potential immune responses during clinical use and/or avoid unintended interactions on the protein level. Therefore, a seamless cloning strategy was developed (FIGS. 6A-6C) for the directed insertion of low repetitive nucleotide sequences, here exemplified for the DNA fragment comprising PA #1b(200) (SEQ ID NO: 28), on a derivative of the generic expression plasmid pASK75 (Skerra (1994) loc. cit.) encoding the biologically active protein IL1-Ra (Molto (2010) Joint Bone Spine. 77:102-107).

At first, a synthetic DNA fragment encoding the mature amino acid sequence of IL1-Ra (UniProt ID P18510) was obtained from a gene synthesis provider (Thermo Fisher Scientific, Regensburg, Germany). This gene fragment (SEQ ID NO: 46) comprised an XbaI restriction site, followed by a ribosomal binding site, the nucleotide sequence encoding the OmpA signal peptide, followed by a GCC alanine codon, a first SapI recognition sequence GCTCTTC on the non-coding strand, a GC dinucleotide spacer, and a second SapI restriction sequence in reverse complementary orientation, with its recognition sequence GCTCTTC on the coding strand, followed by a GCC alanine codon directly linked to the coding sequence for mature IL1Ra (UniProt ID P18510), which was finally followed by a HindIII restriction site.

This gene fragment was cloned on pASk75 via the flanking restriction sites XbaI and HindIII according to standard procedures (Sambrook (2001) loc. cit.). The resulting plasmid (cf. FIG. 6A) was digested with SapI, which led to the liberation of a small (24 bp) DNA insert containing both SapI recognition sites and a cleaved vector backbone with compatible 5'-GCC/5'-GGC sticky ends at the position directly in front of the encoded mature N-terminus of IL-1Ra, which is ideally suited for insertion of the low repetitive nucleic acid molecule encoding the proline/alanine-rich amino acid repeat sequence (FIG. 6B). After isolation of the vector fragment using the QIAquick gel extraction kit (Qiagen, Hilden, Germany) and dephosphorylation with the thermosensitive alkaline phosphatase FastAP (Thermo Fisher Scientific, Waltham, Mass.), both according to the manufacturer's instructions, it was ligated with the PA #1b(200) gene cassette excised from pXL2-PA #1b(200) (SEQ ID NO: 54) via EarI restriction digest (FIG. 6C). The resulting plasmid (SEQ ID NO: 56) allows the bacterial expression of a fusion protein (SEQ ID NO: 10) consisting solely of a proline/alanine-rich amino acid repeat sequence fused with the biologically active protein IL-1Ra (after in vivo processing of the OmpA signal peptide upon periplasmic secretion in *E. coli*).

Example 8

Bacterial Production and Purification of a Fusion Protein Between the PAS #1(600) Sequence and IL-1Ra Encoded on the Genetically Stable Plasmid pASK75-PAS #1f/1c/1b(600)-IL1Ra The PAS #1(600)-IL1-Ra fusion protein (calculated mass: 68 kDa) was produced at 25° C. in *E. coli* KS272 harboring the genetically stable expression plasmid pASK75-PAS #1f/1c/1b(600)-IL1Ra from Example 6 and the folding helper plasmid pTUM4 (Schlapschy (2006) Protein Eng. Des. Sel. 20:273-284) using an 8 L bench top fermenter with a synthetic glucose mineral medium supplemented with 100 mg/L ampicillin and 30 mg/L chloramphenicol according to a published procedure (Schiweck (1995) Proteins 23:561-565). Recombinant gene expression was induced by addition of 500 µg/L anhydrotetracycline (Skerra (1994) loc. cit.) as soon as the culture reached $OD_{550}$=28. After an induction period of 2.5 h, cells were harvested by centrifugation and resuspended during 10 min in ice-cold periplasmic fractionation buffer (500 mM sucrose, 1 mM EDTA, 100 mM Tris/HCl pH 8.0; 2 ml per L and $OD_{550}$). After adding 15 mM EDTA and 250 µg/mL lysozyme, the cell suspension was incubated for 20 min on ice, centrifuged several times, and the cleared supernatant containing the recombinant protein was recovered.

The periplasmic extract was dialyzed four times at 4° C. against 5 L 40 mM Na-phosphate pH 7.5, 500 mM NaCl, respectively and purified by means of the $His_6$-tag using an 80 ml HisTrap HP column (GE Healthcare, Freiburg, Germany). The protein was eluted with an imidazole/HCl pH 7.5 concentration gradient from 0 to 200 mM in 40 mM Na-phosphate pH 7.5, 0.5 M NaCl. The purified protein was pooled and dialyzed twice against 5 L 20 mM Tris/HCl pH 8.0, 1 mM EDTA at 4° C. for at least 6 h, respectively. The dialyzed protein solution was subjected to anion exchange chromatography using a 60 ml XK column (GE Healthcare, Freiburg, Germany) packed with Source15Q resin, connected to an Äkta purifier system (GE Healthcare, Freiburg, Germany), using 20 mM Tris/HCl pH 8.0, 1 mM EDTA as running buffer. The protein was eluted using an NaCl concentration gradient from 0 to 200 mM in running buffer.

Eluted fractions were dialyzed twice against 10 mM MES/HCl pH 6.0, 1 mM EDTA at 4° C. for at least 6 h, respectively, and subsequently subjected to a cation exchange chromatography using an XK column packed with 36 ml Source15S resin (GE Healthcare, Freiburg, Germany). The cation exchange chromatography was performed on an Äkta purifier system using 10 mM MES/HCl pH 6.0, 1 mM EDTA as running buffer and a NaCl concentration gradient from 0 to 500 mM in running buffer over 4 column volumes to elute the protein. The eluted protein fractions containing PAS #1(600)-IL1-Ra were again pooled, dialyzed against 5 L phosphate-buffered saline (PBS: 115 mM NaCl, 4 mM $KH_2PO_4$ and 16 mM $Na_2HPO_4$ pH 7.4) at 4° C. overnight, concentrated to 5 mg/ml using an Amicon Ultra centrifugal filter device (30000 MWCO; 15 mL; Millipore, Billerica, Mass.) and further purified via size exclusion chromatography using a HiLoad 26/60 Superdex 200 prepgrade column (GE Healthcare, Freiburg, Germany) equilibrated with PBS.

A homogeneous protein preparation without signs of aggregation was obtained with a final yield of 70 mg from one 8 L fermenter. Protein concentration was determined by measuring the absorption at 280 nm using a calculated extinction coefficient (Gill (1989) Anal. Biochem. 182:319-326) of 15720 $M^{-1}$ $cm^{-1}$. SDS-PAGE was performed using a high molarity Tris buffer system (Fling (1986) Anal. Biochem. 155:83-88) (FIG. 7A).

Example 9

ESI-MS Analysis of the PAS #1(600)-IL1Ra Fusion Protein

PAS #1(600)-IL1Ra produced and purified as described in Example 8 was dialyzed twice against a 1000-fold volume of 10 mM ammonium acetate pH 6.8 and analyzed via ESI mass spectrometry on a Q-Tof Ultima instrument (Waters, Eschbronn, Germany) using the positive ion mode. The deconvoluted spectrum of the PA #1(600)-IL1Ra fusion protein revealed a mass of 67994.8 Da, which essentially coincides with the calculated mass of 67994.8 Da (FIG. 7B). This clearly demonstrates that the entire PA #1(600)-IL1Ra fusion protein can be efficiently produced in *E. coli* using the genetically stable expression plasmid pASK75-PAS #1f/1c/1 b(600)-IL1Ra.

Example 10

Construction of pASK37-MP-PA #1d/1c/1b(600), a Genetically Stable Plasmid for the Production of a Proline/Alanine-Rich Amino Acid Repeat Polypeptide in *E. coli*

For the construction of a stable expression plasmid encoding the pure PA #1(600) polypeptide, 100 pmol of the primers NdeI-MP-SapI-HindIIIfw (SEQ ID NO: 4) and NdeI-MP-SapI-HindIIIrev (SEQ ID NO: 5) were phosphorylated, mixed, heated up to 80° C. for 10 min and slowly cooled down to room temperature overnight to allow hybridization. The resulting double stranded DNA fragment exhibited sticky ends compatible to NdeI and HindIII overhangs. The plasmid pASK37 (Skerra (1991) loc. cit) was cut with NdeI and HindIII and the backbone fragment was ligated with the hybridized primers.

The resulting plasmid was digested with SapI, which led to the liberation of a small (24 bp) insert containing two SapI recognition sites and a cleaved vector backbone with compatible sticky 5'-GCC/5'-GGC ends. These sticky ends are ideally suited for insertion of the low repetitive nucleotide sequence encoding the proline/alanine-rich amino acid repeat sequence at the position directly downstream of the N-terminal start methionine codon (ATG) followed by the proline codon CCA, which was found to allow efficient translational initiation. After isolation of the vector fragment using the QIAquick gel extraction kit and dephosphorylation with the thermosensitive alkaline phosphatase FastAP according to the manufacturer's instructions, it was ligated with the low repetitive gene cassette PA #1d/1c/1b(600) (SEQ ID NO: 42) excised from pXL2-PA #1d/1c/1b(600) via EarI restriction digest. The resulting plasmid (SEQ ID NO: 53) permits expression of a polypeptide comprising solely a proline/alanine-rich amino acid repeat sequence (FIG. 8A).

Example 11

Bacterial Expression and Purification of a PA #1(600) Polypeptide Encoded on the Genetically Stable Plasmid pASK37-MP-PA #1d/1c/1b(600)

The PA #1(600) polypeptide, with an additional Pro residue at the N-terminus and an additional Ala residue at the C-terminus (calculated mass: 48302 Da), was produced in the cytoplasm of *E. coli* KS272 harboring the expression plasmid pASK37-PA #1d/1c/1b(600) described in Example 10. 4 ml LB medium in a sterile 13 mL polypropylene tube (Sarstedt, Nümbrecht, Germany), substituted with 1% w/v glucose and 100 mg/L ampicillin, were inoculated with a colony of *E. coli* KS272 transformed with pASK37-PA #1d/1c/1b(600) and grown overnight at 37° C., 170 rpm. Bacterial protein production was performed at 30° C. in a 5 L shake flask with 2 L terrific broth (TB) medium (Sambrook (2001) loc. cit.) supplemented with 2.5 g/L D-glucose and 100 mg/L ampicillin.

*E. coli* cultures were inoculated with 2 ml overnight culture, cells were grown overnight and recombinant gene expression was induced at $OD_{550}$=5 by addition of isopropyl-β-D-thiogalactopyranoside (IPTG) to a final concentration of 0.5 mM. Bacteria were harvested 3 h after induction, resuspended in 20 ml 40 mM Na-phosphate pH 7.2, 1 mM EDTA and lysed using a French pressure cell (Thermo Scientific, Waltham, Mass.). After centrifugation (17,000 rpm, 1 h, 4° C.) of the lysate, no inclusion bodies were observed. The supernatant containing the soluble PA #1(600) polypeptide was subjected to an ammonium sulfate precipitation by stepwise addition of solid $(NH_4)_2SO_4$ to a final concentration of 20% w/v under continuous stirring at room temperature. The supernatant was centrifuged at 17,000 rpm at room temperature for 20 min. The sediment containing the precipitated PA #1(600) polypeptide was dissolved in 20 mM Tris/HCl pH 8.0 and the solution was centrifuged (13,000 rpm, 10 min, room temperature) to remove insoluble contaminants.

Pure acetic acid (Sigma-Aldrich, Steinheim, Germany) was added to a final concentration of 1% v/v and impurities were sedimented by centrifugation at 13,000 rpm for 10 min. The supernatant containing the almost pure PA #1(600) polypeptide was dialyzed against a 100-fold volume of 1% v/v acetic acid overnight at 4° C. To remove residual impurities, the dialysed protein was subjected to a subtractive cation exchange chromatography using a 1 ml Source15S column (GE Healthcare, Freiburg, Germany) connected to an Äkta purifier system using 1% v/v acetic acid as running buffer.

Samples from each purification step were analyzed by SDS-PAGE using a high molarity Tris buffer system (Fling (1986) loc. cit.). After SDS-PAGE, the gel was first stained with barium iodide as described for the analysis of PEG (Kurfurst (1992) Anal. Biochem. 200:244-248). Briefly, the polyacrylamide gel was rinsed with water and then incubated in a 2.5% w/v $BaI_2$ (barium iodide dihydrate; Sigma-Aldrich, Steinheim, Germany) solution in water for 5 min. After rinsing with water, the gel was transferred into Lugol solution (10% w/v p.a. grade KI (AppliChem, Darmstadt, Germany 5% p.a. grade $I_2$ (Riedel de Haen AG, Seelze, Germany) in water) for 5 min. After destaining in 10% v/v acetic acid, orange PA #1(600) polypeptide bands became visible (FIG. 8B). Subsequently, the gel was destained with water and subjected to a second staining with Coomassie brilliant blue R250 (Applichem), dissolved in 10% acetic acid (Honeywell Specialty Chemicals, Seelze, Germany), 65% $H_2O$ and 25% isopropanol (CLN, Niederhummel, Germany). After destaining in 10% v/v acetic acid blue protein bands (for host cell proteins) became visible (FIG. 8C).

Example 12

ESI-MS Analysis of a Pure PA #1(600) Polypeptide

200 μl of the isolated PA #1(600) polypeptide from Example 11 at a concentration of 5 mg/mL was applied to a 1 mL Resource RPC column (GE Healthcare, Freiburg, Germany) connected to an Äkta purifier system using 2% v/v acetonitrile, 1% v/v formic acid as running buffer. The protein was eluted using an acetonitrile gradient from 2% v/v acetonitrile, 1% v/v formic acid to 80% v/v acetonitrile, 0.1% v/v formic acid over 20 column volumes. The eluted protein was directly analyzed via ESI mass spectrometry on a Q-Tof Ultima instrument using the positive ion mode. The deconvoluted spectrum of the PA #1(600) polypeptide revealed a mass of 48301.78 Da, which essentially coincides with the calculated mass of the PA #1(600) polypeptide, with an additional Pro residue at the N-terminus and an additional Ala residue at the C-terminus but devoid of the start methionine (48301.4 Da) (FIG. 8D). This clearly demonstrates that a pure PA #1(600) polypeptide (without an affinity tag), encoded by a genetically stable nucleotide sequence, can be produced in *E. coli* in its intact form.

Example 13

Repeat Analysis of Nucleotide Sequences Encoding Proline/Alanine-Rich Amino Acid Sequences As a measure to assess the quality of nucleic acid molecules encoding proline/alanine-rich sequences with regard to the frequency (occurrence) of nucleotide sequence repeats we have devised the Nucleotide Repeat Score (NRS), which is calculated according to the following formula:

$$NRS = \frac{\sum_{n=4}^{N_{tot}-1} n^2 \sqrt{\sum_{i=1}^{k(n)} f_i(n)}}{N_{tot}}$$

In this formula, $N_{tot}$ is the total length of the nucleotide sequence analyzed, n is the length of a sequence repeat within the nucleotide sequence analyzed and the frequency $f_i(n)$ is the number of occurrences of this sequence repeat. In case there are several different sequence repeats with the same length n, these different sequence repeats are distinguished by the index i and the number of different sequence repeats with the same length n is k(n). If there is just one type of sequence repeat with length n, k(n) equals 1. The NRS is defined as the sum of the squared repeat length multiplied with the root of the respective overall frequency, divided through the total length of the analyzed nucleotide sequence. The minimal repeat length considered for the calculation of NRS comprises 4 nucleotides, which includes all nucleotide sequences longer than one codon triplet, and it ranges up to $N_{tot}-1$, that is the length of the longest nucleotide sequence repeat that can occur more than once in the analyzed nucleotide sequence.

In this context the term repeat means that a nucleotide sequence occurs at least twice within the nucleotide sequence analyzed. When counting the frequencies we have considered both nucleotide stretches with identical sequence that occur at least twice as well as different sequences of the same length which each also occur at least twice. For example, if the overall frequency of a 14mer repeat is five, this can mean either that the same 14mer nucleotide stretch occurs 5 times, or one 14mer nucleotide sequence occurs twice and a different 14 nucleotide sequence occurs three times in the analyzed nucleotide sequence.

Furthermore, each shorter repeat contained within a longer nucleotide sequence repeat is counted separately. For example, if the analyzed nucleotide sequence contains two GCACC nucleotide stretches (i.e., repeats), GCAC and CACC repeats are also counted individually, regardless if they occur within said GCACC nucleotide stretch or, possibly, in addition elsewhere within the analyzed nucleotide sequence. Of note, only repeats on the coding strand of the nucleic acid molecule are considered.

A person skilled in the art can identify nucleotide sequence repeats either manually or with the aid of generic software programs such as the Visual Gene Developer (Jung (2011) loc. cit.), available for download at visualgenedeveloper.net, or the Repfind tool (Betley (2002) loc. cit), available at zlab.bu.edu/repfind. However, not every algorithm detects each kind of repeat, e.g., the result of the Visual Gene Developer does not include overlapping repeats. Thus, results of software tools have to be checked and, if necessary, manually corrected. Alternatively, the algorithm termed NRS-Calculator described in Example 14 can be used to unambiguously identify nucleotide sequence repeats and to calculate the NRS automatically.

Natural as well as certain synthetic nucleic acids encoding proline/alanine-rich amino acid sequences are known in the art. However, all those sequences are highly repetitive on the genetic level as it becomes clearly evident from the NRS analysis described below and, thus, their use for biotechnological and/or biopharmaceutical applications is limited.

Several prior art nucleotide sequences encoding proline/alanine-rich amino acid sequences were compared to low repetitive nucleic acid molecules encoding proline/alanine-rich amino acid repeat sequences according to this invention using the NRS-Calculator described in Example 14: the nucleotide sequence PAS #1a(200) (SEQ ID NO: 11) disclosed in WO 2008/155134 (FIG. 9A), the nucleotide sequence PA #1a(200) (SEQ ID NO: 14) disclosed in WO2011144756 (FIG. 9B), the nucleotide sequence encoding a $[(AP)_5]_{20}APA$ glycomodule (SEQ ID NO: 16) disclosed in US 20060252120 (FIG. 9C), the nucleotide sequence of a synthetic gene construct encoding the glycomodule $[AAPAPAPAP]_{10}AS$ (SEQ ID NO: 17) published under GenBank accession number DQ399411.1 (FIG. 9D), the 225 nucleotide sequence encoding a proline/alanine-rich sequence within the large tegument protein of the macacine herpesvirus 1 (SEQ ID NO: 18) published under GenBank accession number NP 851896 (FIG. 9E), the low repetitive nucleotide sequence PAS #1b(200) (SEQ ID NO: 19) according to this invention (FIG. 9F,G) and the low repetitive nucleotide sequence PA #1e/1d/1c/1b(800) (SEQ ID NO: 44) according to this invention (FIG. 9H,I).

The calculated repeat frequencies were plotted against the respective repeat length using Kaleidagraph V3.6 software (Synergy Software, Reading, Pa.) (FIGS. 9A-9I). All histograms of the prior art nucleotide sequences reveal a highly repetitive nature as illustrated by a large number of high bars with broad distribution of repeat lengths, up to very long repeats. Notably, in these cases the repeat frequency decreases only slowly with increasing repeat length (FIG. 9A-E). In contrast, the histograms of the low repetitive nucleotide sequences PAS #1b(200) and PA #1e/1d/1c/1b (800) according to this invention show only a few repeats with a maximum length of 14 nucleotides, whose frequencies rapidly decrease to zero when going from shorter to longer repeats (FIG. 9F,G,H,I).

The difference in repetitivity between the prior art nucleotide sequences and the low repetitive nucleotide sequences of the invention becomes even more evident when comparing their Nucleotide Repeat Scores. Whereas all prior art sequences reveal an NRS above 80000 (Table 2), the 600 nucleotide sequence PAS #1b(200) and the 2400 nucleotide sequence PA #1e/1d/1c/1b(800) show NRS values of just 13 and 14, respectively (Table 1). This clearly demonstrates that the repeat quality of the low repetitive nucleotide sequences encoding proline/alanine-rich amino acid repeat sequences according to this invention is much higher compared to prior art sequences, with both fewer and shorter nucleotide sequence repeats.

TABLE 1

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| A: Nucleotide sequence units (building blocks) | | | | | | | |
| 1 | PAS#1b(200) | 19 | *E. coli* | ASPAAPAPASPA APAPSAPA (SEQ ID NO: 1) | 14 | 600 | 13 |
| 2 | PAS#1c(200) | 20 | *E. coli* | ASPAAPAPASPA APAPSAPA (SEQ ID NO: 1) | 12 | 600 | 12 |
| 3 | PAS#1d(200) | 21 | *E. coli* | ASPAAPAPASPA APAPSAPA (SEQ ID NO: 1) | 12 | 600 | 11 |
| 4 | PAS#1e(200) | 22 | CHO (*C. griseus*) | ASPAAPAPASPA APAPSAPA (SEQ ID NO: 1) | 12 | 600 | 12 |
| 5 | PAS#1f(200) | 23 | *E. coli* | ASPAAPAPASPA APAPSAPA (SEQ ID NO: 1) | 12 | 600 | 11 |
| 6 | PAS#1g(200) | 24 | *Pichia pastoris* | ASPAAPAPASPA APAPSAPA (SEQ ID NO: 1) | 14 | 600 | 24 |
| 7 | PAS#1h(200) | 25 | CHO (*C. griseus*) | ASPAAPAPASPA APAPSAPA (SEQ ID NO: 1) | 12 | 600 | 20 |
| 8 | PAS#1i(200) | 26 | CHO (*C. griseus*) | ASPAAPAPASPA APAPSAPA (SEQ ID NO: 1) | 14 | 600 | 17 |
| 9 | PAS#1j(200) | 27 | CHO (*C. griseus*) | ASPAAPAPASPA APAPSAPA (SEQ ID NO: 1) | 14 | 600 | 16 |
| 10 | PA#1b(200) | 28 | *E. coli* | AAPAAPAPAAP AAPAPAAPA (SEQ ID NO: 2) | 14 | 600 | 21 |
| 11 | PA#1c(200) | 29 | *E. coli* | AAPAAPAPAAP AAPAPAAPA (SEQ ID NO: 2) | 14 | 600 | 18 |
| 13 | PA#1d(200) | 30 | *E. coli* | AAPAAPAPAAP AAPAPAAPA (SEQ ID NO: 2) | 14 | 600 | 19 |
| 14 | PA#1e(200) | 31 | *E. coli* | AAPAAPAPAAP AAPAPAAPA (SEQ ID NO: 2) | 14 | 600 | 22 |
| 15 | PA#1f(200) | 32 | CHO (*C. griseus*) | AAPAAPAPAAP AAPAPAAPA (SEQ ID NO: 2) | 14 | 600 | 24 |
| 16 | PA#1g(200) | 33 | CHO (*C. griseus*) | AAPAAPAPAAP AAPAPAAPA (SEQ ID NO: 2) | 14 | 600 | 24 |
| 17 | PA#1h(200) | 34 | CHO (*C. griseus*) | AAPAAPAPAAP AAPAPAAPA (SEQ ID NO: 2) | 17 | 600 | 32 |
| 18 | PA#1i(200) | 35 | CHO (*C. griseus*) | AAPAAPAPAAP AAPAPAAPA (SEQ ID NO: 2) | 17 | 600 | 17 |
| 19 | PA#3b(200) | 36 | *E. coli* | AAAPAAAPAAA PAAAPAAAP (SEQ ID NO: 57) | 14 | 600 | 26 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 20 | PA#5b(198) | 37 | *E. coli* | AAAAAPAAAAA PAAAAAP (SEQ ID NO: 58) | 14 | 594 | 27 |
| 101 | PA#1j(200) | 87 | *P. pastoris* | AAPAAPAPAAP AAPAPAAPA (SEQ ID NO: 2) | 17 | 600 | 39 |
| 102 | PA#1k(200) | 88 | *P. pastoris* | AAPAAPAPAAP AAPAPAAPA (SEQ ID NO: 2) | 17 | 600 | 29 |
| 103 | PA#1l(200) | 89 | *P. pastoris* | AAPAAPAPAAP AAPAPAAPA (SEQ ID NO: 2) | 17 | 600 | 31 |
| 104 | PA#1m(200) | 90 | *P. pastoris* | AAPAAPAPAAP AAPAPAAPA (SEQ ID NO: 2) | 14 | 600 | 24 |
| 105 | PA#1n(200) | 91 | *S. cerevisiae* | AAPAAPAPAAP AAPAPAAPA (SEQ ID NO: 2) | 17 | 600 | 38 |
| 106 | PA#1o(200) | 92 | *S. cerevisiae* | AAPAAPAPAAP AAPAPAAPA (SEQ ID NO: 2) | 14 | 600 | 20 |
| 107 | PA#1p(200) | 93 | *S. cerevisiae* | AAPAAPAPAAP AAPAPAAPA (SEQ ID NO: 2) | 14 | 600 | 19 |
| 108 | PA#1q(200) | 94 | *K. lactis* | AAPAAPAPAAP AAPAPAAPA (SEQ ID NO: 2) | 17 | 600 | 28 |
| 109 | PA#1r(200) | 95 | *K. lactis* | AAPAAPAPAAP AAPAPAAPA (SEQ ID NO: 2) | 14 | 600 | 23 |
| 110 | PA#1s(200) | 96 | *K. lactis* | AAPAAPAPAAP AAPAPAAPA (SEQ ID NO: 2) | 17 | 600 | 34 |
| 111 | PA#1t(200) | 97 | *H. sapiens* (HEK cells) | AAPAAPAPAAP AAPAPAAPA (SEQ ID NO: 2) | 14 | 600 | 25 |
| 112 | PA#1u(200) | 98 | *H. sapiens* (HEK cells) | AAPAAPAPAAP AAPAPAAPA (SEQ ID NO: 2) | 17 | 600 | 29 |
| 114 | PA#1v(200) | 99 | *H. sapiens* (HEK cells) | AAPAAPAPAAP AAPAPAAPA (SEQ ID NO: 2) | 17 | 600 | 31 |
| 114 | PA#1w(200) | 100 | *Bacillus subtilis* | AAPAAPAPAAP AAPAPAAPA (SEQ ID NO: 2) | 14 | 600 | 23 |
| 115 | PA#1x(200) | 101 | *Bacillus subtilis* | AAPAAPAPAAP AAPAPAAPA (SEQ ID NO: 2) | 16 | 600 | 27 |
| 116 | PA#1y(200) | 102 | *Bacillus subtilis* | AAPAAPAPAAP AAPAPAAPA (SEQ ID NO: 2) | 17 | 600 | 32 |
| 117 | PA#1z(200) | 103 | *E. coli* | AAPAAPAPAAP AAPAPAAPA (SEQ ID NO: 2) | 18 | 600 | 45 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 118 | PA#1aa(200) | 104 | *E. coli* | AAPAAPAPAAP AAPAPAAPA (SEQ ID NO: 2) | 14 | 600 | 18 |
| 119 | PA#1ab(200) | 105 | *E. coli* | AAPAAPAPAAP AAPAPAAPA (SEQ ID NO: 2) | 17 | 600 | 25 |
| 120 | PA#1ac(200) | 106 | *E. coli* | AAPAAPAPAAP AAPAPAAPA (SEQ ID NO: 2) | 14 | 600 | 18 |
| 121 | PA#1ad(200) | 107 | *E. coli* | AAPAAPAPAAP AAPAPAAPA (SEQ ID NO: 2) | 17 | 600 | 24 |
| 122 | PA#1ae(100) | 108 | *E. coli* | AAPAAPAPAAP AAPAPAAPA (SEQ ID NO: 2) | 14 | 300 | 27 |
| 123 | PA#1af(200) | 109 | *C. glutamicum* | AAPAAPAPAAP AAPAPAAPA (SEQ ID NO: 2) | 14 | 600 | 20 |
| 124 | PA#1ag(200) | 110 | *C. glutamicum* | AAPAAPAPAAP AAPAPAAPA (SEQ ID NO: 2) | 17 | 600 | 24 |
| 125 | PA#1ah(200) | 111 | *C. glutamicum* | AAPAAPAPAAP AAPAPAAPA (SEQ ID NO: 2) | 17 | 600 | 25 |
| 126 | PA#1ai(200) | 112 | *C. glutamicum* | AAPAAPAPAAP AAPAPAAPA (SEQ ID NO: 2) | 16 | 600 | 21 |
| 127 | PA#1aj(200) | 113 | *P. patens* | AAPAAPAPAAP AAPAPAAPA (SEQ ID NO: 2) | 17 | 600 | 30 |
| 128 | PA#1ak(200) | 114 | *P. patens* | AAPAAPAPAAP AAPAPAAPA (SEQ ID NO: 2) | 17 | 600 | 31 |
| 129 | PA#1al(200) | 115 | *P. patens* | AAPAAPAPAAP AAPAPAAPA (SEQ ID NO: 2) | 15 | 600 | 24 |
| 130 | PA#1am(200) | 116 | *P. fluorescens* | AAPAAPAPAAP AAPAPAAPA (SEQ ID NO: 2) | 17 | 600 | 32 |
| 131 | PA#1an(200) | 117 | *P. fluorescens* | AAPAAPAPAAP AAPAPAAPA (SEQ ID NO: 2) | 17 | 600 | 35 |
| 132 | PA#1ao(200) | 118 | *P. fluorescens* | AAPAAPAPAAP AAPAPAAPA (SEQ ID NO: 2) | 18 | 600 | 41 |
| 133 | PA#1ap(200) | 119 | *T. thermophila* | AAPAAPAPAAP AAPAPAAPA (SEQ ID NO: 2) | 17 | 600 | 37 |
| 134 | PA#1aq(200) | 120 | *T. thermophila* | AAPAAPAPAAP AAPAPAAPA (SEQ ID NO: 2) | 17 | 600 | 34 |
| 135 | PA#1ar(200) | 121 | *T. thermophila* | AAPAAPAPAAP AAPAPAAPA (SEQ ID NO: 2) | 14 | 600 | 22 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 136 | PA#1as(200) | 122 | *T. thermophila* | AAPAAPAPAAP AAPAPAAPA (SEQ ID NO: 2) | 17 | 600 | 35 |
| 137 | PAS#1k(200) | 123 | *E. coli* | ASPAAPAPASPA APAPSAPA (SEQ ID NO: 1) | 14 | 600 | 14 |
| 138 | PAS#1l(200) | 124 | *E. coli* | ASPAAPAPASPA APAPSAPA (SEQ ID NO: 1) | 15 | 600 | 17 |
| 139 | PAS#1m(200) | 125 | *E. coli* | ASPAAPAPASPA APAPSAPA (SEQ ID NO: 1) | 14 | 600 | 16 |
| 140 | PAS#1n(100) | 126 | *E. coli* | ASPAAPAPASPA APAPSAPA (SEQ ID NO: 1) | 14 | 300 | 15 |
| 141 | PAS#1o(200) | 127 | *P. pastoris* | ASPAAPAPASPA APAPSAPA (SEQ ID NO: 1) | 14 | 600 | 17 |
| 142 | PAS#1p(200) | 128 | *P. pastoris* | ASPAAPAPASPA APAPSAPA (SEQ ID NO: 1) | 17 | 600 | 29 |
| 143 | PAS#1q(200) | 129 | *P. Fluorescens* | ASPAAPAPASPA APAPSAPA (SEQ ID NO: 1) | 17 | 600 | 25 |
| 144 | PAS#1r(200) | 130 | *P. Fluorescens* | ASPAAPAPASPA APAPSAPA (SEQ ID NO: 1) | 14 | 600 | 14 |
| 145 | PAS#1s(200) | 131 | *P. Fluorescens* | ASPAAPAPASPA APAPSAPA (SEQ ID NO: 1) | 17 | 600 | 24 |
| 146 | PAS#1t(200) | 132 | *C. glutamicum* | ASPAAPAPASPA APAPSAPA (SEQ ID NO: 1) | 14 | 600 | 15 |
| 147 | PAS#1u(200) | 133 | *C. glutamicum* | ASPAAPAPASPA APAPSAPA (SEQ ID NO: 1) | 14 | 600 | 12 |
| 148 | PAS#1v(200) | 134 | *C. glutamicum* | ASPAAPAPASPA APAPSAPA (SEQ ID NO: 1) | 14 | 600 | 11 |
| 149 | PAS#1w(200) | 135 | *P. patens* | ASPAAPAPASPA APAPSAPA (SEQ ID NO: 1) | 14 | 600 | 15 |
| 150 | PAS#1x(200) | 136 | *P. patens* | ASPAAPAPASPA APAPSAPA (SEQ ID NO: 1) | 12 | 600 | 12 |
| 151 | PAS#1y(200) | 137 | *P. patens* | ASPAAPAPASPA APAPSAPA (SEQ ID NO: 1) | 11 | 600 | 10 |
| 152 | PAS#1z(200) | 138 | *K. lactis* | ASPAAPAPASPA APAPSAPA (SEQ ID NO: 1) | 14 | 600 | 15 |
| 153 | PAS#1aa(200) | 139 | *K. lactis* | ASPAAPAPASPA APAPSAPA (SEQ ID NO: 1) | 15 | 600 | 17 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 154 | PAS#1ab(200) | 140 | *K. lactis* | ASPAAPAPASPA APAPSAPA (SEQ ID NO: 1) | 14 | 600 | 16 |
| 155 | PAS#1ac(200) | 141 | *S. cerevisiae* | ASPAAPAPASPA APAPSAPA (SEQ ID NO: 1) | 14 | 600 | 14 |
| 156 | PAS#1ad(200) | 142 | *S. cerevisiae* | ASPAAPAPASPA APAPSAPA (SEQ ID NO: 1) | 14 | 600 | 14 |
| 157 | PAS#1ae(200) | 143 | *S. cerevisiae* | ASPAAPAPASPA APAPSAPA (SEQ ID NO: 1) | 14 | 600 | 14 |
| 158 | PAS#1af(200) | 144 | *T. thermophila* | ASPAAPAPASPA APAPSAPA (SEQ ID NO: 1) | 17 | 600 | 25 |
| 159 | PAS#1ag(200) | 145 | *T. thermophila* | ASPAAPAPASPA APAPSAPA (SEQ ID NO: 1) | 17 | 600 | 25 |
| 160 | PAS#1ah(200) | 146 | *T. thermophila* | ASPAAPAPASPA APAPSAPA (SEQ ID NO: 1) | 15 | 600 | 20 |
| 161 | PAS#1ai(200) | 147 | *H. sapiens* (HEK cells) | ASPAAPAPASPA APAPSAPA (SEQ ID NO: 1) | 14 | 600 | 13 |
| 162 | PAS#1aj(200) | 148 | *H. sapiens* (HEK cells) | ASPAAPAPASPA APAPSAPA (SEQ ID NO: 1) | 12 | 600 | 10 |
| 163 | PAS#1ak(200) | 149 | *H. sapiens* (HEK cells) | ASPAAPAPASPA APAPSAPA (SEQ ID NO: 1) | 14 | 600 | 11 |
| 164 | PAS#1al(200) | 150 | *B. subtilis* | ASPAAPAPASPA APAPSAPA (SEQ ID NO: 1) | 12 | 600 | 11 |
| 165 | PAS#1am(200) | 151 | *B. subtilis* | ASPAAPAPASPA APAPSAPA (SEQ ID NO: 1) | 14 | 600 | 13 |
| 166 | PAS#1an(200) | 152 | *B. subtilis* | ASPAAPAPASPA APAPSAPA (SEQ ID NO: 1) | 14 | 600 | 14 |
| 167 | PA#1at(200) | 192 | *E. coli* | AAPAAPAPAAP AAPAPAAPA (SEQ ID NO: 2) | 31 | 600 | 190 |
| 168 | PA#1au(200) | 193 | *E. coli* | AAPAAPAPAAP AAPAPAAPA (SEQ ID NO: 2) | 26 | 600 | 105 |
| 169 | PAS#1ao(200) | 194 | *E. coli* | ASPAAPAPASPA APAPSAPA (SEQ ID NO: 1) | 32 | 600 | 211 |
| 170 | PAS#1ap(200) | 195 | *E. coli* | ASPAAPAPASPA APAPSAPA (SEQ ID NO: 1) | 26 | 600 | 105 |
| | B: Assembled low-repetitive nucleotide sequences | | | | | | |
| 21 | PAS#1f/1c/1b(600) | 38 | *E. coli* | ASPAAPAPASP AAPAPSAPA (SEQ ID NO: 1) | 14 | 1800 | 9 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 22 | PAS#1d/1f/1c/1b(800) | 39 | *E. coli* | ASPAAPAPASP AAPAPSAPA (SEQ ID NO: 1) | 14 | 2400 | 8 |
| 23 | PAS#1h/1e/1i(600) | 40 | CHO (*C. griseus*) | ASPAAPAPASP AAPAPSAPA (SEQ ID NO: 1) | 14 | 1800 | 14 |
| 24 | PAS#1j/1h/1e/1i(800) | 41 | CHO (*C. griseus*) | ASPAAPAPASP AAPAPSAPA (SEQ ID NO: 1) | 14 | 2400 | 13 |
| 25 | PA#1d/1c/1b(600) | 42 | *E. coli* | AAPAAPAPAAP AAPAPAAPA (SEQ ID NO: 2) | 14 | 1800 | 15 |
| 26 | PA#1i/1h/1g/1f(800) | 43 | CHO (*C. griseus*) | AAPAAPAPAAP AAPAPAAPA (SEQ ID NO: 2) | 17 | 2400 | 22 |
| 27 | PA#1e/1d/1c/1b(800) | 44 | *E. coli* | AAPAAPAPAAP AAPAPAAPA (SEQ ID NO: 2) | 14 | 2400 | 14 |
| 28 | PA#1i/1h/1g/1f/ 1e/1d/1c/1b(1600) | 45 | *E. coli*/ CHO (*C. griseus*) | AAPAAPAPAAP AAPAPAAPA (SEQ ID NO: 2) | 27 | 4800 | 24 |
| 171 | PA#1ae/1c(300) | 153 | *E. coli* | AAPAAPAPAAP AAPAPAAPA (SEQ ID NO: 2) | 14 | 900 | 18 |
| 172 | PA#1ae/1d(300) | 154 | *E. coli* | AAPAAPAPAAP AAPAPAAPA (SEQ ID NO: 2) | 14 | 900 | 17 |
| 173 | PA#1d/1c(400) | 155 | *E. coli* | AAPAAPAPAAP AAPAPAAPA (SEQ ID NO: 2) | 14 | 1200 | 17 |
| 174 | PA#1b/1c/1d(600) | 156 | *E. coli* | AAPAAPAPAAP AAPAPAAPA (SEQ ID NO: 2) | 14 | 1800 | 15 |
| 175 | PA#1d/1b/1c(600) | 157 | *E. coli* | AAPAAPAPAAP AAPAPAAPA (SEQ ID NO: 2) | 20 | 1800 | 17 |
| 176 | PA#1c/1b/1d(600) | 158 | *E. coli* | AAPAAPAPAAP AAPAPAAPA (SEQ ID NO: 2) | 17 | 1800 | 16 |
| 177 | PA#1c/1d/1b(600) | 159 | *E. coli* | AAPAAPAPAAP AAPAPAAPA (SEQ ID NO: 2) | 20 | 1800 | 17 |
| 178 | PA#1b/1d/1c(600 | 160 | *E. coli* | AAPAAPAPAAP AAPAPAAPA (SEQ ID NO: 2) | 17 | 1800 | 16 |
| 179 | PA#1aa/1e/1d/1c/ 1b(1000) | 161 | *E. coli* | AAPAAPAPAAP AAPAPAAPA (SEQ ID NO: 2) | 20 | 3000 | 17 |
| 180 | PA#1ab/1aa/1e/ 1d/1c/1b(1200) | 162 | *E. coli* | AAPAAPAPAAP AAPAPAAPA (SEQ ID NO: 2) | 20 | 3600 | 17 |
| 181 | PA#1ac/1ab/1aa/1e/ 1d/1c/1b(1400) | 163 | *E. coli* | AAPAAPAPAAP AAPAPAAPA (SEQ ID NO: 2) | 20 | 4200 | 16 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 182 | PA#1ad/1ac/1ab/1aa/1e/1d/1c/1b(1600) | 164 | *E. coli* | AAPAAPAPAAP AAPAPAAPA (SEQ ID NO: 2) | 20 | 4800 | 16 |
| 183 | PA#1ao/1an/1am(600) | 165 | *P. fluorescens* | AAPAAPAPAAP AAPAPAAPA (SEQ ID NO: 2) | 19 | 1800 | 27 |
| 184 | PA#1ai/1ah/1ag/1af(800) | 166 | *C. glutamicum* | AAPAAPAPAAP AAPAPAAPA (SEQ ID NO: 2) | 17 | 2400 | 17 |
| 185 | PA#1y/1x/1w(600) | 167 | *B. subtilis* | AAPAAPAPAAP AAPAPAAPA (SEQ ID NO: 2) | 17 | 1800 | 24 |
| 186 | PA#1j/1k/1l/1m(800) | 168 | *P. pastoris* | AAPAAPAPAAP AAPAPAAPA (SEQ ID NO: 2) | 17 | 2400 | 23 |
| 187 | PA#1p/1o/1n(600) | 169 | *S. cerevisiae* | AAPAAPAPAAP AAPAPAAPA (SEQ ID NO: 2) | 18 | 1800 | 21 |
| 188 | PA#1s/1r/1q(600) | 170 | *K. lactis* | AAPAAPAPAAP AAPAPAAPA (SEQ ID NO: 2) | 17 | 1800 | 23 |
| 189 | PA#1as/1ar/1aq/1ap(800) | 171 | *T. thermophila* | AAPAAPAPAAP AAPAPAAPA (SEQ ID NO: 2) | 20 | 2400 | 30 |
| 190 | PA#1v/1u/1t(600) | 172 | *H. sapiens* (HEK cells) | AAPAAPAPAAP AAPAPAAPA (SEQ ID NO: 2) | 19 | 1800 | 28 |
| 191 | PA#1al/1ak/1j(600) | 173 | *P. patens* | AAPAAPAPAAP AAPAPAAPA (SEQ ID NO: 2) | 18 | 1800 | 24 |
| 192 | PAS#1n/1b(300) | 174 | *E. coli* | ASPAAPAPASP AAPAPSAPA (SEQ ID NO: 1) | 14 | 900 | 12 |
| 193 | PAS#1n/1c(300) | 175 | *E. coli* | ASPAAPAPASP AAPAPSAPA (SEQ ID NO: 1) | 14 | 900 | 13 |
| 194 | PAS#1b/1f/1c(600) | 176 | *E. coli* | ASPAAPAPASP AAPAPSAPA (SEQ ID NO: 1) | 14 | 1800 | 9 |
| 195 | PAS#1b/1c/1f(600) | 177 | *E. coli* | ASPAAPAPASP AAPAPSAPA (SEQ ID NO: 1) | 14 | 1800 | 9 |
| 196 | PAS#1c/1b/1f(600) | 178 | *E. coli* | ASPAAPAPASP AAPAPSAPA (SEQ ID NO: 1) | 14 | 1800 | 9 |
| 197 | PAS#1f/1b/1c(600) | 179 | *E. coli* | ASPAAPAPASP AAPAPSAPA (SEQ ID NO: 1) | 14 | 1800 | 9 |
| 198 | PAS#1c/1f/1b(600) | 180 | *E. coli* | ASPAAPAPASP AAPAPSAPA (SEQ ID NO: 1) | 14 | 1800 | 9 |
| 199 | PAS#1k/1d/1f/1c/1b(1000) | 181 | *E. coli* | ASPAAPAPASP AAPAPSAPA (SEQ ID NO: 1) | 20 | 3000 | 11 |

TABLE 1-continued

Characteristics of nucleic acid molecules according to this invention

| | Low repetitive nucleotide sequence no. | SEQ ID: | Codon-optimized for: | Encoded amino acid repeat | $n_{max}$ | $N_{tot}$ | NRS |
|---|---|---|---|---|---|---|---|
| 200 | PAS#1l/1k/1d/1f/1c/1b(1200) | 182 | *E. coli* | ASPAAPAPASP AAPAPSAPA (SEQ ID NO: 1) | 20 | 3600 | 12 |
| 201 | PAS#1s/1q/1r(600) | 183 | *P. fluorescens* | ASPAAPAPASP AAPAPSAPA (SEQ ID NO: 1) | 20 | 1800 | 21 |
| 202 | PAS#1v/1t/1u(600) | 184 | *C. glutamicum* | ASPAAPAPASP AAPAPSAPA (SEQ ID NO: 1) | 17 | 1800 | 13 |
| 203 | PAS#1an/am/1l(600) | 185 | *B. subtilis* | ASPAAPAPASP AAPAPSAPA (SEQ ID NO: 1) | 14 | 1800 | 11 |
| 204 | PAS#1p/1o/1g(600) | 186 | *P. pastoris* | ASPAAPAPASP AAPAPSAPA (SEQ ID NO: 1) | 17 | 1800 | 20 |
| 205 | PAS#1ae/1ad/1ac(600) | 187 | *S. cerevisiae* | ASPAAPAPASP AAPAPSAPA (SEQ ID NO: 1) | 15 | 1800 | 12 |
| 206 | PAS#1ab/1aa/1z(600) | 188 | *K. lactis* | ASPAAPAPASP AAPAPSAPA (SEQ ID NO: 1) | 17 | 1800 | 15 |
| 207 | PAS#1ah/1ag/1af(600) | 189 | *T. thermophila* | ASPAAPAPASP AAPAPSAPA (SEQ ID NO: 1) | 17 | 1800 | 19 |
| 208 | PAS#1ak/aj/ah(600) | 190 | *H. sapiens* (HEK cells) | ASPAAPAPASP AAPAPSAPA (SEQ ID NO: 1) | 14 | 1800 | 10 |
| 209 | PAS#1y/1x/1w(600) | 191 | *P. patens* | ASPAAPAPASP AAPAPSAPA (SEQ ID NO: 1) | 17 | 1800 | 14 |

TABLE 2

Characteristics of prior art nucleotide sequences

| | Sequence name | Organism | SEQ ID: | GenBank entry/ patent no. | $n_{max}$ | $N_{tot}$ | NRS |
|---|---|---|---|---|---|---|---|
| 1 | PAS#1a(200) | synthetic | 11 | WO 2008155134 | 540 | 600 | 1 127 680 |
| 2 | PA#1a(200) | synthetic | 14 | WO2011144756 | 540 | 600 | 1 127 680 |
| 3 | PA#3a(200) | synthetic | 15 | WO2011144756 | 540 | 600 | 1 127 680 |
| 4 | $[(AP)_5]_{20}$APA | synthetic | 16 | US2006/0252120 | 579 | 609 | 1 315 159 |
| 5 | $[AAPAPAPAP]_{10}$AS module of pBI-SS-(Tom)(AP)51-EGFP | synthetic | 17 | DQ399411.1 | 243 | 276 | 150 961 |
| 6 | Large tegument protein | Macacine Herpes virus 1 | 18 | NP_851896.1 | 197 | 225 | 81 858 |

Example 14

NRS-Calculator, an Algorithm to Unambiguously Identify Nucleotide Sequence Repeats and to Calculate the Nucleotide Repeat Score Generally available software programs such as the Visual Gene Developer (Jung (2011) loc. cit) or the Repfind tool (Betley (2002) loc. cit) do not always work reliably and may require manual corrections in order to calculate all sequence repeats within an analyzed nucleotide sequence properly. In addition, repeats have to be counted manually and the NRS must be calculated separately according to the formula described in Example 13. To provide an algorithm that yields unambiguous results and to facilitate the calculation of the NRS, a simple Python script termed NRS-Calculator is described here. This script, executed on the runtime environment Python 2.7.10 (python.org), is based on a dot matrix sequence comparison and identifies all forward repeats within a potentially long nucleotide sequence, including overlapping repeats, without considering gaps. The dot matrix sequence comparison is a method well known by a person skilled in the art and is described in common bioinformatics text books such as, e.g., Mount (2004) Bioinformatics: Sequence and Genome Analysis, Cold Spring Harbor Laboratory Press, $2^{nd}$ edition, New York.

NRS-Calculator counts the frequencies for each repeat length and automatically calculates the NRS according to the formula described in Example 13. To execute the NRS-Calculator script the runtime environment Python version 2.7.10 was downloaded from python.org/downloads and installed on a ThinkPad L530 notebook (Lenovo, Stuttgart, Germany) running a Windows 7 operating system. The NRS-Calculator script listed below was saved as plain text file designated NRScalculator.py using Microsoft Windows Editor Version 6.1. The nucleotide sequence to be analyzed was saved as FASTA file named sequence.fas within the same folder. Subsequently, the command line shell was opened and the directory containing both the NRScalculator.py and the sequence.fas file was selected. To start the calculation, the following command line was executed:

user\admin\NRSfolder>c:\Python27\python.exe NRScalculator.py sequence.fas

This command resulted in a screen output of two rows: the left row indicating the repeat length (Length) and the right (second) row indicating the respective repeat frequency (Frequency). In addition, $N_{tot}$ and NRS (number rounded as integer) were stated at the beginning and the end of the output, respectively.

NRS-Calculator Script:

```
import math
import sys
class NRSCalculator:
  def __init__(self):
    self.repeats = dict( )
    self.sums = dict( )
    self.seq = None
    self.range_min = None
    self.range_max = None
  def _match_at(self, row, column):
    return self.seq[row] == self.seq[column]
  def _get_repeats_at(self, row, column):
    length = 1
    search_row = row
    search_column = column
    while True:
      if not 0 <= search_row < len(self.seq):
        break
      if not 0 <= search_column < search_row:
        break
      if length > self.range_max:
        break
      if not self._match_at(search_row, search_column):
        break
      if length >= self.range_min:
        repeats =
self.repeats.setdefault(self.seq[row:row + length], set( ))
        repeats.add(row)
        repeats.add(column)
      search_row += 1
      search_column += 1
      length += 1
```

-continued

```
  def _get_repeats(self):
    self.repeats = dict( )
    for row in xrange(len(self.seq)):
      for column in xrange(row):
        self._get_repeats_at(row, column)
  def _get_sums(self):
    self.sums = dict( )
    for (seq, repeats) in self.repeats.iteritems( ):
      length = len(seq)
      self.sums[length] = self.sums.get(length, 0) +
len(repeats)
  def set_range(self, range_min, range_max):
    self.range_min = range_min
    self.range_max = range_max
  def set_sequence(self, seq):
    self.seq = seq
  def work(self):
    if not self.seq and not self.range_min and not
self.range_max:
      raise RuntimeError('Can not work without
initialization')
    self._get_repeats( )
    self._get_sums( )
  def print_repeats(self):
    print('Sequence (Length bp) : NumRepeats
(Positions)')
    for seq, repeats in sorted(self.repeats.iteritems( ),
key=lambda t: len(t[0])):
      list = [seq, len(seq), len(repeats)]
      list.extend(map(lambda value: value + 1,
sorted(repeats)))
      print('%s Ntot = %u : %u (%s)' % (seq, len(seq),
len(repeats), ', '.join(map(lambda value: str(value + 1),
sorted(repeats)))))
  def print_sums(self):
    print('Length\tFrequency')
    for item in self.sums.iteritems( ):
      print('%u\t%u' % item)
  def print_score(self):
    sum = 0
    for length, count in self.sums.iteritems( ):
      sum += (length ** 2) * math.sqrt(count)
    print('NRS = %.0f' % (sum / len(self.seq)))
def handle_sequence(finder, name, sequence):
  finder.set_range(4 , len(sequence))
  finder.set_sequence(sequence)
  finder.work( )
  print('%s: Ntot = %u' % (name, len(sequence)))
  #finder.print_repeats( )
  finder.print_sums( )
  finder.print_score( )
if len(sys.argv) != 2:
  print('Usage: %s FILENAME' % sys.argv[0])
  sys.exit(1)
finder = NRSCalculator( )
with open(sys.argv[1], 'r') as infile:
  name = 'Unnamed'
  seq = ' '
  for line in infile:
    line = line.strip( )
    if line.startswith('>'):
      if len(seq) > 0:
        handle_sequence(finder, name, seq)
      name = line
      seq = ' '
      continue
    seq += line.upper( )
  handle_sequence(finder, name, seq)
```

Exemplary Output from NRS-Calculator:

| >PAS#1b(200): Ntot = 600 | |
|---|---|
| Length | Frequency |
| 4 | 587 |
| 5 | 547 |

-continued

| >PAS#1b(200): Ntot = 600 | |
|---|---|
| Length | Frequency |
| 6 | 478 |
| 7 | 388 |
| 8 | 281 |
| 9 | 158 |
| 10 | 90 |
| 11 | 45 |
| 12 | 6 |
| 13 | 4 |
| 14 | 2 |

NRS = 13

Example 15

Construction of pASK75-PA #1d/1c/1b(600)-IL1Ra, a Genetically Stable Expression Vector for the Bacterial Production of a Therapeutic PA #1(600)-IL1Ra Fusion Protein For the construction of an expression plasmid encoding the interleukin-1 receptor antagonist (IL-1Ra) as fusion with a 600 residue PA #1 amino acid repeat sequence, the vector pASK75-IL1Ra (FIG. 4 A) (SEQ ID NO: 49) was cut with SapI, dephosphorylated with shrimp alkaline phosphatase (Thermo Fisher Scientific, Waltham, Mass.) and ligated with a DNA fragment corresponding to the low repetitive nucleotide sequence cassette encoding the 600 residue PA #1 polypeptide, which was excised from the plasmid pXL1-PA #1d/1c/1b(600) (SEQ ID NO: 79) by restriction digest with SapI. After transformation of *E. coli* XL1-Blue (Bullock (1987) loc. cit.), plasmid DNA was prepared and the presence of the inserted DNA fragment was confirmed by restriction analysis and DNA sequencing. The resulting plasmid was designated pASK75-PA #1d/1c/1b(600)-IL1Ra (SEQ ID NO: 77) and is shown in FIG. 10.

Example 16

Long-Term Genetic Stability Testing of the Plasmid pASK75-PA #1b/1c/1b(600)-IL1Ra Harboring the Low Repetitive Nucleic Acid Molecule PA #1d/1c/1b(600) Encoding a Proline/Alanine-Rich Amino Acid Repeat Sequence The genetic stability of the plasmid pASK75-PA #1d/1c/1b(600)-IL1Ra (SEQ ID NO: 77) was compared to the genetic stability of pASK75-PA #1a(600)-IL1Ra (SEQ ID NO: 78), a derivative wherein the PA #1d/1c/1b(600) DNA cassette was replaced by the repetitive nucleic acid PA #1a(600) (SEQ ID NO: 80). To this end, *E. coli* JM83 (Yanisch-Perron C. (1985) loc. cit.) was transformed with the respective plasmid using the calcium chloride method (Sambrook (2001) loc. cit.) and cultured for 7 days at 37° C., 170 rpm, in 50 ml Luria Bertani (LB) medium supplemented with 100 mg/L ampicillin in a 100 mL shake flask without induction of gene expression. During this period, bacterial cells were twice daily (in the morning and in the evening) transferred into fresh medium using a 1:1000 dilution. On day 7, after a continuous growth over approximately 70 generations, the culture was finally grown to stationary phase and cells were plated on LB/Amp agar. Then, ten individual colonies for each of the two plasmids were picked, each used for inoculation of a 50 mL culture in LB/Amp medium and, after growth to stationary phase over night, plasmid DNA was prepared using the Qiagen Miniprep Kit (Qiagen, Hilden, Germany) and analyzed via XbaI/HindIII restriction digest (FIGS. 11A-11B).

Only 6 out of 10 analyzed clones of pASK75-PA #1a(600)-IL1Ra showed the expected bands corresponding to 3093 bp and 2377 bp (FIG. 11A, lanes 1, 3, 4, 5, 7 and 8). Four clones showed significantly shortened DNA fragments (FIG. 11A, lanes 2, 6, 9 and 10), indicating deletions within the repetitive PA #1a(600) sequence cassette and, hence, genetic instability. In contrast, all ten analyzed clones of pASK75-PA #1d/1c/1b(600)-IL1Ra revealed the expected bands at 3093 bp and 2377 bp (FIG. 11B, lanes 1-10), indicating an intact gene cassette encoding proline/alanine-rich amino acid repeat sequences and, thus, high genetic plasmid stability of the low repetitive nucleic acid molecule according to this invention.

Example 17

Construction of Genetically Stable Expression Vectors for the Bacterial Production of Human Leptin Fused with Proline/Alanine-Rich Amino Acid Repeat Sequences For the construction of an expression plasmid encoding human Leptin (huLeptin) N-terminally fused with a 600 residue PA #1 amino acid repeat sequence (SEQ ID NO: 82), the vector pASK37-MP-huLeptin (FIG. 12 A) (SEQ ID NO: 81) was cut with SapI, which led to the excision of a small (24 bp) DNA insert containing both SapI recognition sites and a cleaved vector backbone with compatible 5'-GCC/5'-GGC sticky ends at the position directly upstream of the encoded mature N-terminus of human Leptin. These sticky ends are ideally suited for insertion of the low repetitive nucleotide sequence encoding the proline/alanine-rich amino acid repeat sequence at the position directly downstream of the N-terminal start methionine codon (ATG) followed by the proline codon CCA, which was found to allow efficient translational initiation. After isolation of the vector fragment using the QIAquick gel extraction kit (Qiagen, Hilden, Germany) and dephosphorylation with the thermosensitive alkaline phosphatase FastAP (Thermo Fisher Scientific, Waltham, Mass.), both according to the manufacturers' instructions, the plasmid was ligated with a DNA fragment corresponding to the low repetitive nucleotide sequence cassette encoding the 600 residue PA #1 polypeptide, which was excised from the plasmid pXL1-PA #1d/1c/1b(600) (SEQ ID NO: 79) by restriction digest with SapI. After transformation of *E. coli* XL1-Blue (Bullock (1987) loc. cit.), plasmid DNA was prepared and the presence of the inserted DNA fragment was confirmed by restriction analysis and DNA sequencing. The resulting plasmid was designated pASK37-MP-PA #1d/1c/1b(600)-huLeptin (SEQ ID NO: 82) and is depicted in FIG. 12 B. In the same manner, pASK37-MP-PAS #1f/1c/1b(600)-huLeptin (SEQ ID NO: 83), an expression plasmid encoding human Leptin (huLeptin) N-terminally fused with a 600 residue PAS #1 amino acid repeat sequence shown in FIG. 12 C, was constructed by insertion of the low repetitive nucleotide sequence PAS #1f/1c/1b (SEQ ID No: 38) excised from pXL1-PAS #1f/1c/1b (SEQ ID No: 84) into the plasmid pASK37-MP-huLeptin (FIG. 12 A) (SEQ ID NO: 81). A similar cloning strategy can be applied to construct Leptin versions with C-terminally fused proline/alanine-rich amino acid repeat sequences.

Example 18

Bacterial Production, Purification and Characterization of a Fusion Protein Between a Proline/Alanine-Rich Amino Acid Repeat Sequence and a Human Leptin Mutant Encoded on the Genetically Stable Plasmid pASK37-PA #1d/1c/1b(600)hu-Leptin(W100Q)

PA #1(600)-huLeptin(W100Q) a fusion protein between a human Leptin mutant with a tryptophan to glutamine substitution at position 100 of the mature amino acid sequence (UniProtKB accession code P41159) and the proline/alanine-rich amino acid repeat sequence PA #1(600) (SEQ ID NO: 85) (calculated mass: 64.25 kDa) was produced at 30° C. in the cytoplasm of Origami B (Novagene/Merck Millipore, Billerica, Mass.), an *E. coli* strain which has an oxidizing cytoplasm due to trxB, gor and ahpC mutations (Bessette (1999) Proc. Natl. Acad. Sci. USA 96:13703-13708). To this end, 4 ml LB medium in a sterile 13 mL polypropylene tube (Sarstedt, Nümbrecht, Germany), supplemented with 1% w/v D-glucose and 100 mg/L ampicillin, was inoculated with a colony of *E. coli* Origami B transformed with the genetically stable expression plasmid pASK37-MP-PA #1d/1c/1b(600)-huLep(W100Q) (SEQ ID NO: 86). Bacterial cells were grown overnight at 30° C. in a shaker at 170 rpm.

Bacterial protein production was performed at 30° C. in a 5 L baffle flask with 2 L terrific broth (TB) medium (Sambrook (2001) loc. cit.) supplemented with 2.5 g/L D-glucose and 100 mg/L ampicillin, which was inoculated with 2 ml of the *E. coli* overnight culture. Bacterial cells were grown at 30° C. and recombinant gene expression was induced at $OD_{550}$=0.85 by addition of isopropyl-β-D-thiogalactopyranoside (IPTG) to a final concentration of 0.5 mM. Bacteria were harvested 19 h after induction, resuspended in 3 ml PBS/E (PBS supplemented with 10 mM EDTA) per 1 g bacterial cell wet weight and lysed using a Panda cell homogenizer (GEA, Parma, Italy). After centrifugation (20,000 rpm, 30 min, 4° C.) of the lysate, no inclusion bodies were observed. 1 mM 2,2'-dithiodipyridine was added to the supernatant to boost disulfide bridge formation in the recombinant Leptin. The supernatant containing the soluble Leptin fusion protein was dialyzed over night at 4° C. against a 100-fold volume of PBS. Subsequently, the fusion protein was precipitated at room temperature by dropwise addition of 4 M $(NH_4)_2SO_4$ (dissolved in water) under continuous stirring until a final concentration of 1 M $(NH_4)_2SO_4$ was reached. After centrifugation for 20 min at 17,000 rpm at room temperature the sediment containing the precipitated PA #1(600)-hu-Leptin(W100/Q) fusion protein was dissolved in PBS and the solution was centrifuged (13,000 rpm, 10 min, room temperature) to remove insoluble contaminants.

The PA #1(600)-hu-Leptin(W100Q) fusion protein was dialyzed twice against 5 L 20 mM Tris/HCl pH 8.5 at 4° C., each for at least 6 h. Then, the protein solution was subjected to anion exchange chromatography using a 6 ml ResourceQ column (GE Healthcare, Freiburg, Germany) connected to an Äkta purifier system (GE Healthcare, Freiburg, Germany), using 20 mM Tris/HCl pH 8.5 as running buffer. The fusion protein was subsequently eluted using a NaCl concentration gradient. Eluted fractions were collected and further purified via size exclusion chromatography using a Superdex 200 HR10/300 column (GE Healthcare, Freiburg, Germany) equilibrated with PBS.

By this procedure a homogeneous protein preparation without signs of aggregation was obtained with a final yield of 0.8 mg/L bacterial culture. Protein concentration was determined by measuring the absorption at 280 nm using a calculated extinction coefficient (Gill (1989) loc. cit.) of 8605 $M^{-1}$ $cm^{-1}$. SDS-PAGE was performed using a 10% high molarity Tris buffer system (Fling (1986) loc. cit.) (FIG. 13A). The eluted protein was dialyzed twice against the 10000-fold volume of 10 mM ammonium acetate pH 5.5 and analyzed via ESI mass spectrometry on an maXis Q-TOF instrument (Bruker Daltonics, Bremen, Germany) using the positive ion mode. The deconvoluted spectrum of PA #1(600)-hu-Leptin(W100Q) revealed a mass of 64249.53 Da (FIG. 13B), which essentially coincides with the calculated mass of this fusion protein (64249.80 Da). This clearly demonstrates that a PA #1(600)-hu-Leptin (W100Q) fusion protein, encoded by a genetically stable low repetitive nucleic acid molecule according to this invention, can be produced in *E. coli* in its intact form.

The invention claimed is:

1. A nucleic acid molecule, comprising a nucleotide sequence encoding a polypeptide consisting of proline and alanine or a polypeptide consisting of proline, alanine, and serine, wherein the nucleotide sequence of said nucleic acid has a length of at least 300 nucleotides, wherein said nucleotide sequence has a Nucleotide Repeat Score (NRS) lower than 1,000, wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}},$$

wherein $N_{tot}$ is the length of said nucleotide sequence, n is the length of a repeat within said nucleotide sequence, and $f_i(n)$ is the frequency of said repeat of length n, wherein if there is more than one repeat of length n, k(n) is the number of different repeats of length n, otherwise k(n) is 1 for said repeat of length n.

2. The nucleic acid molecule of claim 1, wherein said encoded polypeptide consists of proline and alanine.

3. The nucleic acid molecule of claim 2, wherein proline constitutes more than about 10% and less than about 75% of said encoded polypeptide.

4. The nucleic acid molecule of claim 1, wherein said encoded polypeptide consists of proline, alanine, and serine.

5. The nucleic acid molecule of claim 4, wherein proline constitutes more than 4% and less than 40% of said encoded polypeptide.

6. The nucleic acid molecule of claim 1, wherein said Nucleotide Repeat Score (NRS) is lower than 100.

7. The nucleic acid molecule of claim 1, wherein said Nucleotide Repeat Score (NRS) is lower than 50.

8. The nucleic acid molecule of claim 1, wherein said Nucleotide Repeat Score (NRS) is lower than 35.

9. The nucleic acid molecule of claim 1, wherein the nucleotide sequence of said nucleic acid has a length of at least 900 nucleotides.

10. The nucleic acid molecule of claim 1, wherein said nucleotide sequence comprises said repeats, wherein said repeats have a maximum length $n_{max}$, wherein $n_{max}$ is determined according to the formula:

$$n_{max} \leq 17 + \frac{N_{tot}}{600}$$

and wherein $N_{tot}$ is the length of said nucleotide sequence.

11. The nucleic acid molecule of claim 1, wherein said repeats have a maximum length of about 14, 15, 16, or 17 nucleotides to about 55 nucleotides.

12. The nucleic acid molecule of claim 1, wherein said encoded polypeptide comprises a repetitive amino acid sequence with a plurality of amino acid repeats, wherein no more than 9 consecutive amino acid residues are identical and wherein said polypeptide forms a random coil.

13. The nucleic acid molecule of claim 1, wherein said nucleic acid molecule is selected from the group consisting of:

(a) a nucleic acid molecule comprising at least one nucleotide sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 192 and SEQ ID NO: 193;

(b) a nucleic acid molecule comprising the nucleotide sequence consisting of SEQ ID NO: 42, SEQ ID NO: 43, SEQ ID NO: 44, SEQ ID NO: 45, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, or SEQ ID NO: 173;

(c) a nucleic acid molecule that hybridizes under stringent conditions to the complementary strand of a nucleotide sequence as defined in (a) or (b);

(d) a nucleic acid molecule comprising a nucleotide sequence having at least 66.7% identity to a nucleotide sequence as defined in any one of (a), (b) and (c); and (e) a nucleic acid molecule being degenerate as a result of the genetic code to a nucleotide sequence as defined in (a) or (b).

14. The nucleic add molecule of claim 1, wherein said nucleic add molecule k selected from the group consisting of:

(a) a nucleic add molecule comprising at least one nucleotide sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 194 and SEQ ID NO: 195;

(b) a nucleic add molecule comprising the nucleotide sequence selected from the group consisting of SEQ ID NO: 38, SEQ ID NO: 39, SEQ ID NO: 40, SEQ ID NO: 41, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 184, SEQ ID NO: 185, SEQ ID NO: 186, SEQ ID NO: 187, SEQ ID NO: 188, SEQ ID NO: 189, SEQ ID NO: 190, and SEQ ID NO: 191;

(c) a nucleic add molecule that hybridizes under stringent conditions to the complementary strand of the nucleotide sequence as defined in (a) or (b);

(d) a nucleic add molecule comprising a nucleotide sequence having at least 60% identity to the nucleotide sequence as defined in any one of (a), (b) and (c); and (e) a nucleic add molecule being degenerate as a result of the genetic code to a nucleotide sequence as defined in (a) or (b).

15. The nucleic acid molecule of claim 1 operably linked in the same reading frame to a nucleic acid encoding a biologically active protein.

16. The nucleic acid molecule of claim 15, wherein said biologically active protein is a therapeutically effective protein.

17. The nucleic acid molecule of claim 15, wherein said biologically active protein is selected from the group consisting of a binding protein, an antibody fragment, a cytokine, a growth factor, a hormone, an enzyme, a protein vaccine, a peptide vaccine, a peptide which consists of up to 50 amino acid residues, and a peptidomimetic.

18. The nucleic acid molecule of claim 17, wherein said binding protein is selected from the group consisting of antibodies, Fab fragments, Fab' fragments, $F(ab')_2$ fragments, single chain variable fragments (scFv), (single) domain antibodies, isolated variable regions of antibodies (VL and/or VH regions), CDRs, immunoglobulin domains, CDR-derived peptidomimetics, lectins, protein scaffolds, fibronectin domains, tenascin domains, protein A domains, SH3 domains, ankyrin repeat domains, and lipocalins.

19. The nucleic acid molecule of claim 15, wherein said biologically active protein is selected from the group consisting of interleukin 1 receptor antagonist, leptin, acid sphingomyelinase, adenosine deaminase, agalsidase alfa, alpha-1 antitrypsin, alpha atrial natriuretic peptide, alpha-galactosidase, alpha-glucosidase, alpha-N-acetylglucosaminidase, alteplase, amediplase, amylin, amylin analog, anti-HIV peptide fusion inhibitor, arginine deiminase, asparaginase, B domain deleted factor VIII, bone morphogenetic protein, bradykinin antagonist, B-type natriuretic peptide, bouganin, growth hormone, chorionic gonadotropin, CD3 receptor antagonist, CD19 antagonist, CD20 antagonist, CD40 antagonist, CD40L antagonist, cerebroside sulfatase, coagulation factor VIIa, coagulation factor XIII, coagulation factor IX, coagulation factor X, complement component C3 inhibitor, complement component 5a antagonist, C-peptide, CTLA-4 antagonist, C-type natriuretic peptide, defensin, deoxyribonuclease I, EGFR receptor antagonist, epidermal growth factor, erythropoietin, exendin-4, ezrin peptide 1, FcγIIB receptor antagonist, fibroblast growth factor 21, follicle-stimulating hormone, gastric inhibitory polypeptide (GIP), GIP analog, glucagon, glucagon receptor agonist, glucagon-like peptide 1 (GLP-1), GLP-1 analog, glucagon-like peptide 2 (GLP-2), GLP-2 analog, gonadorelin, gonadotropin-releasing hormone agonist, gonadotropin-releasing hormone antagonist, gp120, gp160, granulocyte colony stimulating factor (G-CSF), granulocyte macrophage colony stimulating factor (GM-CSF), grehlin, grehlin analog, growth hormone, growth hormone-releasing hormone, hematide, hepatocyte growth factor, hepatocyte growth factor receptor (HGFR) antagonist, hepcidin antagonist, hepcidin mimetic, Her2/neu receptor antagonist, histrelin, hirudin, hsp70 antagonist, humanin, hyaluronidase, hydrolytic lysosomal glucocerebroside-specific enzyme, iduronate-2-sulfatase, IgE antagonists, insulin, insulin analog, insulin-like growth factor 1, insulin-like growth factor 2, interferon-alpha, interferon-alpha antagonist, interferon-alpha superagonist, interferon-alpha-n3, interferon-beta, interferon-gamma, interferon-lambda, interferon tau, interleukin, interleukin 2 fusion protein, interleukin-22 receptor subunit alpha (IL-22ra) antagonist, irisin, islet neogenesis associated protein, keratinocyte growth factor, Kv1.3 ion channel antagonists, lanthipeptide, lipase, luteinizing hormone, lutropin alpha, lysostaphin, mannosidase, N-acetylgalactosamine-6-sulfatase, N-acetylglucosaminidase, neutrophil gelatinase-associated lipocalin, octreotide, ω-conotoxin, *Ornithodoros moubata* complement inhibitor, osteogenic protein-1, osteoprotegerin, oxalate decarboxylase, P128, parathyroid hormone, Phylomer, PD-1 antagonist, PDGF antagonist, phenylalanine ammonia lyase, platelet derived growth factor, proinsulin, protein C, relaxin, relaxin analog, secretin, RGD peptide, ribonuclease, senrebotase, serine protease inhibitor, soluble complement receptor type 1, soluble DCC receptor, soluble TACI receptor, soluble tumor necrosis factor I receptor (sTNF-RI), soluble tumor necrosis factor II receptor (sTNF-RII), soluble VEGF receptor Flt-1, soluble FcγIIB receptor, somatostatin, somatostatin analog, streptokinase, T-cell receptor ligand, tenecteplase, teriparatide, thrombomodulin alpha, thymosin alpha 1, toll like receptor inhibitor, tumor necrosis factor (TNFα), tumor necrosis factor α antagonist, uricase, vasoactive intestinal peptide, vasopressin, vasopressin analog, VEGF antagonist, and von Willebrand factor.

20. A vector comprising the nucleic acid molecule of claim 1.

21. An isolated host cell comprising the nucleic acid molecule of claim 1 or a vector comprising the nucleic acid molecule of claim 1.

22. A method for preparing the nucleic add molecule of claim 1, wherein the method comprises culturing a host or host cell comprising the nucleic acid molecule of claim 1, a host or host cell comprising a vector comprising the nucleic acid molecule of claim 1, or a host or host cell transformed with a vector comprising the nucleic acid molecule of claim 1 and optionally isolating the produced nucleic acid molecule.

23. A method for preparing a vector comprising the nucleic acid molecule of claim 1, wherein the method comprises culturing a host or host cell comprising a vector comprising the nucleic acid molecule of claim 1, or a host or host cell transformed with a vector comprising the nucleic acid molecule of claim 1, and optionally isolating the produced vector.

24. A method for preparing a polypeptide encoded by the nucleic acid molecule of claim 1, wherein the method comprises culturing/raising a host or host cell comprising the nucleic acid molecule of claim 1, a host or host cell comprising a vector comprising the nucleic acid molecule of claim 1, or a host or host cell transformed with a vector comprising the nucleic acid molecule of claim 1, and optionally isolating the produced polypeptide.

25. A method for preparing a drug conjugate, wherein said drug conjugate comprises a polypeptide encoded by the nucleic acid molecule of claim 1 and further comprises (i) a biologically active protein and/or (ii) a small molecule and/or (iii) carbohydrate, wherein the method further comprises culturing a host or host cell comprising the nucleic acid molecule of claim 1, a host or host cell comprising a vector comprising the nucleic acid molecule of claim 1, or a host or host cell transformed with a vector comprising the nucleic acid molecule of claim 1 and optionally isolating the produced polypeptide and/or drug conjugate.

26. The method of claim 25, wherein said biologically active protein is a therapeutically effective protein.

27. The method of claim 25, wherein said biologically active protein is selected from the group consisting of a binding protein, an antibody fragment, a cytokine, a growth factor, a hormone, an enzyme, a protein vaccine, a peptide vaccine, a peptide which consists of up to 50 amino acid residues and a peptidomimetic.

28. The method of claim 27, wherein said binding protein is selected from the group consisting of antibodies, Fab fragments, Fab' fragments, F(ab')2 fragments, single chain variable fragments (scFv), single domain antibodies, isolated variable regions of antibodies CDRs, immunoglobulin domains, CDR-derived peptidomimetics, lectins, protein scaffolds, fibronectin domains, tenascin domains, protein A domains, SH3 domains, ankyrin repeat domains, and lipocalins.

29. The method of claim 25, wherein said biologically active protein is selected from the group consisting of interleukin 1 receptor antagonist, leptin, acid sphingomyelinase, adenosine deaminase, agalsidase alfa, alpha-1 antitrypsin, alpha atrial natriuretic peptide, alpha-galactosidase, alpha-glucosidase, alpha-N-acetylglucosaminidase, alteplase, amediplase, amylin, amylin analog, anti-HIV peptide fusion inhibitor, arginine deiminase, asparaginase, B domain deleted factor VIII, bone morphogenetic protein, bradykinin antagonist, B-type natriuretic peptide, bouganin, growth hormone, chorionic gonadotropin, CD3 receptor antagonist, CD19 antagonist, CD20 antagonist, CD40 antagonist, CD40L antagonist, cerebroside sulfatase, coagulation factor VIIa, coagulation factor XIII, coagulation factor IX, coagulation factor X, complement component C3 inhibitor, complement component 5a antagonist, C-peptide, CTLA-4 antagonist, C-type natriuretic peptide, defensin, deoxyribonuclease I, EGFR receptor antagonist, epidermal growth factor, erythropoietin, exendin-4, ezrin peptide 1, FcγIIB receptor antagonist, fibroblast growth factor 21, follicle-stimulating hormone, gastric inhibitory polypeptide (GIP), GIP analog, glucagon, glucagon receptor agonist, glucagon-like peptide 1 (GLP-1), GLP-1 analog, glucagon-like peptide 2 (GLP-2), GLP-2 analog, gonadorelin, gonadotropin-releasing hormone agonist, gonadotropin-releasing hormone antagonist, gp120, gp160, granulocyte colony stimulating factor (G-CSF), granulocyte macrophage colony stimulating factor (GM-CSF), grehlin, grehlin analog, growth hormone, growth hormone-releasing hormone, hematide, hepatocyte growth factor, hepatocyte growth factor receptor (HGFR) antagonist, hepcidin antagonist, hepcidin mimetic, Her2/neu receptor antagonist, histrelin, hirudin, hsp70 antagonist, humanin, hyaluronidase, hydrolytic lysosomal glucocerebroside-specific enzyme, iduronate-2-sulfatase, IgE antagonists, insulin, insulin analog, insulin-like growth factor 1, insulin-like growth factor 2, interferon-alpha, interferon-alpha antagonist, interferon-alpha superagonist, interferon-alpha-n3, interferon-beta, interferon-gamma, interferon-lambda, interferon tau, interleukin, interleukin 2 fusion protein, interleukin-22 receptor subunit alpha (IL-22ra) antagonist, irisin, islet neogenesis associated protein, keratinocyte growth factor, Kv1.3 ion channel antagonists, lanthipeptide, lipase luteinizing hormone, lutropin alpha, lysostaphin, mannosidase, N-acetylgalactosamine-6-sulfatase, N-acetylglucosaminidase, neutrophil gelatinase-associated lipocalin, octreotide, ω-conotoxin, *Ornithodoros moubata* complement inhibitor, osteogenic protein-1, osteoprotegerin, oxalate decarboxylase, P128, parathyroid hormone, Phylomer, PD-1 antagonist, PDGF antagonist, phenylalanine ammonia lyase, platelet derived growth factor, proinsulin, protein C, relaxin, relaxin analog, secretin, RGD peptide, ribonuclease, senrebotase, serine protease inhibitor, soluble complement receptor type 1, soluble DCC receptor, soluble TACI receptor, soluble tumor necrosis factor I receptor (sTNF-RI), soluble tumor necrosis factor II receptor (sTNF-RII), soluble VEGF receptor Flt-1, soluble FcγIIB receptor, somatostatin, somatostatin analog, streptokinase, T-cell receptor ligand, tenecteplase, teriparatide, thrombomodulin alpha, thymosin alpha 1, toll like receptor inhibitor, tumor necrosis factor (TNFα), tumor necrosis factor α antagonist, uricase, vasoactive intestinal peptide, vasopressin, vasopressin analog, VEGF antagonist, and von Willebrand factor.

30. The method of claim 25, wherein said small molecule is selected from the group consisting of angiogenesis inhibitors, anti-allergic drugs, anti-emetic drugs, anti-depressant drugs, anti-hypertensive drugs, anti-inflammatory drugs, anti-infective drugs, anti-psychotic drugs, anti-proliferative cytotoxic and cytostatic drugs, calcium antagonists and other circulatory organ drugs, cholinergic agonists, drugs acting on the central nervous system, drugs acting on the respiratory system, hormones, steroids, polyketides, carbohydrates, oligosaccharides, nucleic acids, nucleic acid derivatives, antisense nucleic acids, small interference RNAs (siRNAs), micro RNA (miR) inhibitors, microRNA mimetics, DNA aptamers and RNA aptamers.

31. A method for selecting a genetically stable nucleic acid molecule, comprising a nucleotide sequence encoding a polypeptide consisting of proline and alanine or a polypeptide consisting of proline, alanine, and serine, wherein said nucleotide sequence has a length of at least 300 nucleotides, the method comprising selecting a nucleic acid molecule comprising a nucleotide sequence having a Nucleotide Repeat Score (NRS) lower than 1,000, wherein said Nucleotide Repeat Score (NRS) is determined according to the formula:

$$NRS = \frac{\sum_{n=4}^{N_{tot}-1} n^2 \sqrt{\sum_{i=1}^{k(n)} f_i(n)}}{N_{tot}},$$

wherein $N_{tot}$ is the length of said nucleotide sequence, n is the length of a repeat within said nucleotide sequence, and $f_i(n)$ is the frequency of said repeat of length n, wherein if there is more than one repeat of length n, k(n) is the number of different repeats of length n, otherwise k(n) is 1 for said repeat of length n.

* * * * *

UNITED STATES PATENT AND TRADEMARK OFFICE

CERTIFICATE OF CORRECTION

PATENT NO. : 11,401,305 B2
APPLICATION NO. : 16/064951
DATED : August 2, 2022
INVENTOR(S) : Binder et al.

It is certified that error appears in the above-identified patent and that said Letters Patent is hereby corrected as shown below:

In the Claims

Claim 14, Column 389, Lines 51-54:
Please delete:
"The nucleic add molecule of claim 1, wherein said nucleic add molecule k selected from the group consisting of:
(a) a nucleic add molecule comprising at least one nucleo-"
Please replace with:
"The nucleic acid molecule of claim 1, wherein said nucleic acid molecule is selected from the group consisting of:
(a) a nucleic acid molecule comprising at least one nucleo-"

Claim 14, Column 390, Line 3:
Please delete:
"(b) a nucleic add molecule comprising the nucleotide"
Please replace with:
"(b) a nucleic acid molecule comprising the nucleotide"

Claim 14, Column 390, Line 12:
Please delete:
"(c) a nucleic add molecule that hybridizes under stringent"
Please replace with:
"(c) a nucleic acid molecule that hybridizes under stringent"

Claim 14, Column 390, Line 15:
Please delete:
"(d) a nucleic add molecule comprising a nucleotide"
Please replace with:
"(d) a nucleic acid molecule comprising a nucleotide"

Signed and Sealed this
Eighteenth Day of October, 2022

Katherine Kelly Vidal

Katherine Kelly Vidal
*Director of the United States Patent and Trademark Office*

Claim 14, Column 390, Line 18:
Please delete:
"(e) a nucleic add molecule being degenerate as a result of"
Please replace with:
"(e) a nucleic acid molecule being degenerate as a result of"

Claim 22, Column 391, Line 43:
Please delete:
"A method for preparing the nucleic add molecule of"
Please replace with:
"A method for preparing the nucleic acid molecule of"

Claim 28, Column 392, Line 22:
Please delete:
"lated variable regions of antibodies CDRs, immunoglobulin"
Please replace with:
"lated variable regions of antibodies, CDRs, immunoglobulin"